US 11,459,338 B2

(12) United States Patent
Vadivelu et al.

(10) Patent No.: US 11,459,338 B2
(45) Date of Patent: Oct. 4, 2022

(54) HETEROCYCLIC COMPOUNDS AS PRMT5 INHIBITORS

(71) Applicant: JUBILANT EPISCRIBE LLC, Yardley, PA (US)

(72) Inventors: Saravanan Vadivelu, Bangalore (IN); Sridharan Rajagopal, Bangalore (IN); Raghunadha Reddy Burri, Bangalore (IN); Shivani Garapaty, Bangalore (IN); Dhanalakshmi Sivanandhan, Bangalore (IN); Manish Kumar Thakur, Bangalore (IN); Tamizharasan Natarajan, Bangalore (IN); Indu N Swamy, Bangalore (IN); Nagendra Nagaraju, Bangalore (IN); Subramaniam Kanagaraj, Bangalore (IN); Zainuddin Mohd, Bangalore (IN); Sayantani Sarkar, Bangalore (IN); Swapan Kumar Samanta, Bangalore (IN); Hariprakash, Noida (IN)

(73) Assignee: JUBILANT EPISCRIBE LLC, Yardley, PA (US)

( * ) Notice: Subject to any disclaimer, the term of this patent is extended or adjusted under 35 U.S.C. 154(b) by 0 days.

(21) Appl. No.: 16/766,413

(22) PCT Filed: Nov. 23, 2018

(86) PCT No.: PCT/IN2018/050778
§ 371 (c)(1),
(2) Date: May 22, 2020

(87) PCT Pub. No.: WO2019/102494
PCT Pub. Date: May 31, 2019

(65) Prior Publication Data
US 2021/0371431 A1 Dec. 2, 2021

(30) Foreign Application Priority Data

Jan. 11, 2018 (IN) .............................. 201841001334
Nov. 24, 2018 (IN) .............................. 201741042307

(51) Int. Cl.
*C07D 471/04* (2006.01)
*C07D 519/00* (2006.01)
*C07D 487/04* (2006.01)
*C07D 498/04* (2006.01)

(52) U.S. Cl.
CPC ......... *C07D 519/00* (2013.01); *C07D 471/04* (2013.01); *C07D 487/04* (2013.01); *C07D 498/04* (2013.01)

(58) Field of Classification Search
CPC .. C07D 471/04; C07D 519/00; C07D 487/04; C07D 498/04
(Continued)

(56) References Cited

U.S. PATENT DOCUMENTS 3,565,896 A 2/1971 Ghielmetti et al.
3,970,753 A 7/1976 Durant
(Continued)

FOREIGN PATENT DOCUMENTS

CN 101838264 9/2010
CN 105461693 A 4/2016
(Continued)

OTHER PUBLICATIONS

Acharya et al., "Neuronal PAD4 expression and protein citrullination: Possible role in production of autoantibodies associated with neurodegenerative disease", J. Autoimmun., vol. 38, pp. 369-380, 2012.
(Continued)

*Primary Examiner* — Niloofar Rahman
(74) *Attorney, Agent, or Firm* — Knobbe, Martens, Olson & Bear LLP

(57) ABSTRACT

The compounds of Formula I, Formula Ia, and Formula Ib are described herein along with their analogs, tautomeric forms, stereoisomers, polymorphs, hydrates, solvates, pharmaceutically acceptable salts, pharmaceutical compositions, metabolites, and prodrugs thereof. These compounds inhibit PRMT5 and are useful as therapeutic or ameliorating agent for diseases that are involved in cellular growth such as malignant tumors, schizophrenia, Alzheimer's disease, Parkinson's disease and the like.

16 Claims, No Drawings

(58) Field of Classification Search
USPC .................................................. 514/210.16
See application file for complete search history.

(56) References Cited

U.S. PATENT DOCUMENTS

| | | | |
|---|---|---|---|
| 3,985,881 | A | 10/1976 | Mehrhof et al. |
| 4,246,274 | A | 1/1981 | Regel et al. |
| 4,315,855 | A | 2/1982 | Schefczik |
| 4,495,191 | A | 1/1985 | Ehrhardt et al. |
| 4,703,056 | A | 10/1987 | Hideg et al. |
| 4,757,081 | A | 7/1988 | Yonekura et al. |
| 4,871,735 | A | 10/1989 | Heider et al. |
| 4,871,751 | A | 10/1989 | Yonekura et al. |
| 4,962,113 | A | 10/1990 | Tsushima et al. |
| 5,001,132 | A | 3/1991 | Manoury et al. |
| 5,010,094 | A | 4/1991 | Schade et al. |
| 5,047,411 | A | 9/1991 | Takasugi et al. |
| 5,100,890 | A | 3/1992 | Siegal et al. |
| 5,179,125 | A | 1/1993 | Mimura et al. |
| 5,210,266 | A | 5/1993 | Mimura et al. |
| 5,229,516 | A | 7/1993 | Messer et al. |
| 5,244,908 | A | 9/1993 | Takatani et al. |
| 5,273,980 | A | 12/1993 | Frenette et al. |
| 5,330,989 | A | 7/1994 | Soll et al. |
| 5,420,289 | A | 5/1995 | Musser et al. |
| 5,541,033 | A | 7/1996 | Blakeney et al. |
| 5,547,814 | A | 8/1996 | Blakeney et al. |
| 5,550,162 | A | 8/1996 | Frost et al. |
| 5,554,621 | A | 9/1996 | Poindexter et al. |
| 5,587,383 | A * | 12/1996 | Takatani ............. C07D 471/04 546/121 |
| 5,663,183 | A | 9/1997 | Frost et al. |
| 6,844,445 | B2 | 1/2005 | Wierzbicki et al. |
| 6,887,868 | B2 | 5/2005 | Fu |
| 8,148,408 | B2 | 4/2012 | Bunnelle et al. |
| 8,642,660 | B2 | 2/2014 | Goldfarb |
| 9,067,898 | B1 | 6/2015 | Illig |
| 2002/0094989 | A1 | 7/2002 | Hale et al. |
| 2002/0173531 | A1 | 11/2002 | Wierzbicki et al. |
| 2003/0018025 | A1 | 1/2003 | Thurkauf et al. |
| 2004/0229160 | A1 | 11/2004 | Naiini et al. |
| 2005/0159334 | A1 | 7/2005 | Gluck et al. |
| 2005/0228014 | A1 | 10/2005 | Marquess et al. |
| 2006/0270686 | A1 | 11/2006 | Kelly et al. |
| 2007/0191371 | A1 | 8/2007 | Bennett et al. |
| 2007/0219218 | A1 | 9/2007 | Yu et al. |
| 2008/0280891 | A1 | 11/2008 | Kelly et al. |
| 2010/0249127 | A1 | 9/2010 | Namdev et al. |
| 2017/0105971 | A1 | 4/2017 | Catrina et al. |
| 2017/0174672 | A1 | 6/2017 | Amberg et al. |
| 2021/0015810 | A1 | 1/2021 | Venkateshappa et al. |

FOREIGN PATENT DOCUMENTS

| | | |
|---|---|---|
| CN | 107056630 A | 8/2017 |
| CN | 107163044 A | 9/2017 |
| CN | 108358917 A | 8/2018 |
| CN | 110105299 A | 8/2019 |
| CN | 110963997 A | 9/2019 |
| CN | 107056630 B | 1/2020 |
| CN | 111606904 A | 9/2020 |
| DE | 1961595 A | 6/1970 |
| DE | 2832677 A1 | 2/1980 |
| DE | 3210570 A1 | 10/1983 |
| DE | 3628545 A1 | 4/1987 |
| DE | 3901723 A1 | 7/1990 |
| DE | 4227522 A1 | 2/1994 |
| DE | 19717371 A1 | 10/1998 |
| DE | 19834751 | 2/2000 |
| EP | 0090269 A1 | 10/1983 |
| EP | 0218118 A1 | 4/1987 |
| EP | 0239391 A2 | 9/1987 |
| EP | 0259793 A1 | 3/1988 |
| EP | 0301751 A1 | 2/1989 |
| EP | 0370852 A1 | 5/1990 |
| EP | 0218118 B1 | 9/1991 |
| EP | 0471236 A1 | 2/1992 |
| EP | 0259793 B1 | 7/1992 |
| EP | 0301751 B1 | 3/1993 |
| EP | 0533056 A2 | 3/1993 |
| EP | 0535924 A1 | 4/1993 |
| EP | 0533056 A3 | 6/1993 |
| EP | 0666250 A1 | 8/1995 |
| EP | 0747378 A1 | 12/1996 |
| EP | 0764640 A1 | 3/1997 |
| EP | 0819977 A1 | 1/1998 |
| EP | 0666250 B1 | 2/1998 |
| EP | 1245565 A1 | 10/2002 |
| EP | 1245565 B1 | 9/2003 |
| EP | 1388342 A1 | 2/2004 |
| EP | 2194035 A2 | 6/2010 |
| EP | 2194035 A3 | 6/2010 |
| EP | 2194035 B1 | 11/2011 |
| EP | 3 112 362 A1 | 1/2017 |
| FR | 2102082 A2 | 4/1972 |
| FR | 2102082 B2 | 10/1974 |
| FR | 2706895 A1 | 12/1994 |
| FR | 2706895 B1 | 8/1995 |
| GB | 1230663 A | 5/1971 |
| GB | 1356789 A | 6/1974 |
| JP | 62187452 A | 8/1987 |
| JP | H 02215809 A | 8/1990 |
| JP | 06184076 | 12/1992 |
| JP | 07304770 | 5/1994 |
| JP | 11119379 A1 | 4/1999 |
| JP | 2001233712 A | 8/2001 |
| JP | 2005060247 A | 3/2005 |
| JP | 2008280344 A | 11/2008 |
| JP | 2009209090 A | 9/2009 |
| JP | 2009274984 | 11/2009 |
| JP | 2011063589 A | 3/2011 |
| JP | 2011207765 | 10/2011 |
| JP | 2019156770 A | 9/2019 |
| JP | 2021054909 | 4/2021 |
| RU | 2371444 C1 | 10/2009 |
| WO | WO 86/05519 | 9/1986 |
| WO | WO 9106537 A2 | 5/1991 |
| WO | WO 9106537 A3 | 10/1991 |
| WO | WO 9301157 A1 | 1/1993 |
| WO | WO 9312094 A1 | 6/1993 |
| WO | WO 9320099 A2 | 10/1993 |
| WO | WO 9320099 A3 | 11/1993 |
| WO | WO 9401407 A2 | 1/1994 |
| WO | WO 9401407 A3 | 3/1994 |
| WO | WO 9422829 A2 | 10/1994 |
| WO | WO 9422834 A1 | 10/1994 |
| WO | WO 9427971 A1 | 12/1994 |
| WO | WO 9422829 A3 | 1/1995 |
| WO | WO 9509843 A1 | 4/1995 |
| WO | WO 9511226 A1 | 4/1995 |
| WO | WO 9521164 A1 | 8/1995 |
| WO | WO 9521832 A1 | 8/1995 |
| WO | WO 9610012 A1 | 4/1996 |
| WO | WO 9616040 A1 | 5/1996 |
| WO | WO 9709066 A1 | 3/1997 |
| WO | WO 9724119 A1 | 7/1997 |
| WO | WO 9740051 A1 | 10/1997 |
| WO | WO 9817648 A1 | 4/1998 |
| WO | WO 9824766 A1 | 6/1998 |
| WO | WO 9834609 A1 | 8/1998 |
| WO | WO 9836749 A1 | 8/1998 |
| WO | WO 9838156 A1 | 9/1998 |
| WO | WO 9906387 A2 | 2/1999 |
| WO | WO 9906387 A3 | 4/1999 |
| WO | WO 9932447 A2 | 7/1999 |
| WO | WO 9932447 A3 | 10/1999 |
| WO | WO 2000007978 A1 | 2/2000 |
| WO | WO 2000023420 A1 | 4/2000 |
| WO | WO 2000026203 A1 | 5/2000 |
| WO | WO 2001070731 A1 | 9/2001 |
| WO | WO 2001077075 A2 | 10/2001 |
| WO | WO 2001087293 A1 | 11/2001 |
| WO | WO 2002002518 A2 | 1/2002 |
| WO | WO 2002002520 A2 | 1/2002 |

(56) References Cited

FOREIGN PATENT DOCUMENTS

| | | |
|---|---|---|
| WO | WO 2002083673 A1 | 1/2002 |
| WO | WO 2001077075 A3 | 3/2002 |
| WO | WO 2002002518 A3 | 8/2002 |
| WO | WO 2002002520 A3 | 8/2002 |
| WO | WO 2002066478 A1 | 8/2002 |
| WO | WO 2002070510 A2 | 9/2002 |
| WO | WO 2002076964 A1 | 10/2002 |
| WO | WO 2002076979 A1 | 10/2002 |
| WO | WO 2002088089 A1 | 11/2002 |
| WO | WO 2002098869 A2 | 12/2002 |
| WO | WO 2002100813 A2 | 12/2002 |
| WO | WO 2002070510 A3 | 1/2003 |
| WO | WO 2008000408 A1 | 1/2003 |
| WO | WO 2003035076 A1 | 5/2003 |
| WO | WO 2003037887 A1 | 5/2003 |
| WO | WO 2003044016 A1 | 5/2003 |
| WO | WO 2003044017 A1 | 5/2003 |
| WO | WO 2003066613 A1 | 8/2003 |
| WO | WO 2003084916 A2 | 10/2003 |
| WO | WO 2002100813 A3 | 11/2003 |
| WO | WO 2003084916 A3 | 12/2003 |
| WO | WO 2002098869 A3 | 2/2004 |
| WO | WO 2004011430 A1 | 2/2004 |
| WO | WO 2004014372 A1 | 2/2004 |
| WO | WO 2004022558 A2 | 3/2004 |
| WO | WO 2004035579 A1 | 4/2004 |
| WO | WO 2004022558 A3 | 5/2004 |
| WO | WO 2004/052846 A1 | 6/2004 |
| WO | WO 2004048363 A1 | 6/2004 |
| WO | WO 2004058679 A2 | 7/2004 |
| WO | WO 2004058679 A3 | 8/2004 |
| WO | WO 2004078731 A1 | 9/2004 |
| WO | WO 2004109400 A2 | 12/2004 |
| WO | WO 2002034716 A2 | 5/2005 |
| WO | WO 2005058823 A1 | 6/2005 |
| WO | WO 2005092899 A1 | 10/2005 |
| WO | WO 2005100350 A1 | 10/2005 |
| WO | WO 2005105805 A1 | 11/2005 |
| WO | WO 2005105805 A9 | 1/2006 |
| WO | WO 2006048330 A1 | 5/2006 |
| WO | WO 2006062224 A1 | 6/2006 |
| WO | WO 2006069125 A1 | 6/2006 |
| WO | WO 2006102588 A1 | 9/2006 |
| WO | WO 2006105971 A1 | 10/2006 |
| WO | WO 2004109400 A3 | 11/2006 |
| WO | WO 2006125119 A1 | 11/2006 |
| WO | WO 2006130707 A2 | 12/2006 |
| WO | WO 2006133104 A2 | 12/2006 |
| WO | WO 2006130707 A3 | 1/2007 |
| WO | WO 2006133104 A3 | 4/2007 |
| WO | WO 2007073503 A2 | 6/2007 |
| WO | WO 2007087548 A2 | 8/2007 |
| WO | WO 2007105989 A2 | 9/2007 |
| WO | WO 2007106469 A2 | 9/2007 |
| WO | WO 2007073503 A3 | 11/2007 |
| WO | WO 2007105989 A3 | 11/2007 |
| WO | WO 2007133108 A1 | 11/2007 |
| WO | WO 2007106469 A3 | 12/2007 |
| WO | WO 2008008059 A1 | 1/2008 |
| WO | WO 20082022945 A1 | 2/2008 |
| WO | WO 2008051757 A1 | 5/2008 |
| WO | WO 2008064320 A2 | 5/2008 |
| WO | WO 2008065500 A2 | 6/2008 |
| WO | WO 2008065500 A3 | 6/2008 |
| WO | WO 2008066789 A2 | 6/2008 |
| WO | WO 2008079988 A2 | 7/2008 |
| WO | WO 2008104077 A1 | 9/2008 |
| WO | WO 2008112715 A2 | 9/2008 |
| WO | WO 2008064320 A3 | 10/2008 |
| WO | WO 2008121687 A2 | 10/2008 |
| WO | WO 2008123582 A1 | 10/2008 |
| WO | WO 2008112715 A3 | 11/2008 |
| WO | WO 2008135526 A1 | 11/2008 |
| WO | WO 2008156142 A1 | 12/2008 |
| WO | WO 2009010925 A2 | 1/2009 |
| WO | WO 2009023179 A2 | 2/2009 |
| WO | WO 2009038842 A2 | 3/2009 |
| WO | WO 2009048152 A2 | 4/2009 |
| WO | WO 2009054914 A1 | 4/2009 |
| WO | WO 2009010925 A3 | 7/2009 |
| WO | WO 2009080351 A1 | 7/2009 |
| WO | WO 2009104819 A1 | 8/2009 |
| WO | WO 2009048152 A3 | 9/2009 |
| WO | WO 2009112651 A1 | 9/2009 |
| WO | WO 2009137309 A2 | 11/2009 |
| WO | WO 2009140101 A2 | 11/2009 |
| WO | WO 2005123703 A2 | 12/2009 |
| WO | WO 2009038842 A3 | 12/2009 |
| WO | WO 2009153313 A1 | 12/2009 |
| WO | WO 2010048207 A2 | 4/2010 |
| WO | WO 2010075973 A1 | 7/2010 |
| WO | WO 2010077680 A2 | 7/2010 |
| WO | WO 2010091409 A1 | 8/2010 |
| WO | WO 2010098495 A1 | 9/2010 |
| WO | WO 2010151799 A2 | 12/2010 |
| WO | WO 2011023989 A1 | 3/2011 |
| WO | WO 2011086178 A1 | 7/2011 |
| WO | WO 2011100380 A1 | 8/2011 |
| WO | WO 2011123751 A2 | 10/2011 |
| WO | WO 2012006202 A1 | 1/2012 |
| WO | WO 2012006203 A1 | 1/2012 |
| WO | WO 2012022265 A1 | 2/2012 |
| WO | WO 2021028810 A1 | 2/2012 |
| WO | WO 20122022045 A1 | 2/2012 |
| WO | WO 2012058133 A1 | 5/2012 |
| WO | WO 2012087833 A1 | 6/2012 |
| WO | WO 2013000994 A1 | 1/2013 |
| WO | WO 2013002879 A1 | 1/2013 |
| WO | WO 2013002880 A1 | 1/2013 |
| WO | WO 2013018371 A1 | 2/2013 |
| WO | WO 2013025733 A1 | 2/2013 |
| WO | WO 2013068470 A1 | 5/2013 |
| WO | WO 2013096049 A1 | 6/2013 |
| WO | WO 2013096055 A1 | 6/2013 |
| WO | WO 2013096059 A1 | 6/2013 |
| WO | WO 2013096060 A1 | 6/2013 |
| WO | WO 2013096681 A1 | 6/2013 |
| WO | WO 2013120464 A1 | 8/2013 |
| WO | WO 2013127729 A1 | 9/2013 |
| WO | WO 2010077680 A3 | 10/2013 |
| WO | WO 2013174895 A1 | 11/2013 |
| WO | WO 2013178810 A1 | 12/2013 |
| WO | WO 2013192430 A2 | 12/2013 |
| WO | WO 2014013182 A1 | 1/2014 |
| WO | WO 2014015905 A1 | 1/2014 |
| WO | WO 2014031872 A2 | 2/2014 |
| WO | WO 2014031986 A1 | 2/2014 |
| WO | WO 2014031872 A3 | 4/2014 |
| WO | WO 2014077321 A1 | 5/2014 |
| WO | WO 2014/100719 A2 | 6/2014 |
| WO | WO 2014100764 A2 | 6/2014 |
| WO | WO 2014100764 A3 | 9/2014 |
| WO | WO 2014152018 A1 | 9/2014 |
| WO | WO 2015011397 A1 | 1/2015 |
| WO | WO 2015031295 A1 | 3/2015 |
| WO | WO 2015034820 A1 | 3/2015 |
| WO | WO 2015086512 A1 | 6/2015 |
| WO | WO 2015086527 A1 | 6/2015 |
| WO | WO 2015108038 A1 | 7/2015 |
| WO | WO 2015140051 A1 | 9/2015 |
| WO | WO 2015197028 A1 | 12/2015 |
| WO | WO 2016008433 A1 | 1/2016 |
| WO | WO 2016031815 A1 | 3/2016 |
| WO | WO 2016034675 A1 | 3/2016 |
| WO | WO 2016036636 A1 | 3/2016 |
| WO | WO 2016051306 A2 | 4/2016 |
| WO | WO 2016102727 A1 | 6/2016 |
| WO | WO 2006126939 A1 | 11/2016 |
| WO | WO 2016185279 A1 | 11/2016 |
| WO | WO 2017024180 A1 | 2/2017 |
| WO | WO 2017025510 A1 | 2/2017 |
| WO | WO 2017/042182 | 3/2017 |
| WO | WO 2017068412 A1 | 4/2017 |
| WO | WO 2017106634 A1 | 6/2017 |

(56) References Cited

FOREIGN PATENT DOCUMENTS

| | | |
|---|---|---|
| WO | WO 2017109095 A1 | 6/2017 |
| WO | WO 2017/118762 | 7/2017 |
| WO | WO 2017/147102 | 8/2017 |
| WO | WO 2017216281 A1 | 12/2017 |
| WO | WO 2018002848 A1 | 1/2018 |
| WO | WO 2018019204 A1 | 2/2018 |
| WO | WO 2018026971 A1 | 2/2018 |
| WO | WO 2018112843 A1 | 6/2018 |
| WO | WO 2018119036 A1 | 6/2018 |
| WO | WO 2018121610 A1 | 7/2018 |
| WO | WO 2018183411 A1 | 10/2018 |
| WO | WO 2018208985 A2 | 11/2018 |
| WO | WO 2018234342 A1 | 12/2018 |
| WO | WO 2019007696 A1 | 1/2019 |
| WO | WO 2019/058393 A1 | 3/2019 |
| WO | WO 2019/077631 A1 | 4/2019 |
| WO | WO 2019079783 A1 | 4/2019 |
| WO | WO 2019/087214 A1 | 5/2019 |
| WO | WO 2019/102494 A1 | 5/2019 |
| WO | WO 2019126081 A1 | 6/2019 |
| WO | WO 2019154047 A1 | 8/2019 |
| WO | WO 2019160014 A1 | 8/2019 |
| WO | WO 2019175897 A1 | 9/2019 |
| WO | WO 2019205147 A1 | 10/2019 |
| WO | WO 2019213234 A1 | 11/2019 |
| WO | WO 2020028723 A1 | 2/2020 |
| WO | WO 2020029980 A1 | 2/2020 |
| WO | WO 2020045216 A1 | 3/2020 |
| WO | WO 2020083971 A2 | 4/2020 |
| WO | WO 2020092394 A1 | 5/2020 |
| WO | WO 2020201773 A1 | 10/2020 |
| WO | WO 2020246910 A1 | 12/2020 |
| WO | WO 2021014949 A1 | 1/2021 |
| WO | WO 2021018858 A1 | 2/2021 |
| WO | WO 2021060432 A1 | 4/2021 |
| WO | WO 2021096238 A1 | 5/2021 |
| WO | WO 2021096241 A1 | 5/2021 |

OTHER PUBLICATIONS

Arisan, et al., "Putative Roles for Peptidylarginine Deiminases in COVID-19", International Journal of Molecular Sciences, vol. 21, No. 13, in 29 pages, 2020.
Barber, et al., "Restoring function in exhausted CD8 T cells during chronic viral infection", Nature, vol. 439, No. 7077, pp. 682-687, 2005.
Bardhan, et al., "The PD1 :PD-L1/2 Pathway from Discovery to Clinical Implementation", Frontiers In Immunology, vol. 7, No. 550, pp. 1-17, 2016.
Barnes, et al., "Targeting potential drivers of COVID-19: Neutrophil extracellular traps", Journal of Experimental Medicine, vol. 217, No. 6, in 7 pages, 2020.
Bertini, et al., "Carbazole-containing arylcarboxamides as BACE1 inhibitors," Bioorganic & Medicinal Chemistry Letters (2011), 21 (22), 6657-6661.
Borregaard, "Neutrophils, from Marrow to Microbes", Immunity, vol. 33, No. 5, pp. 657-670, 2010.
Brinkmann, et al., "Neutrophil Extracellular Traps Kill Bacteria", Science, vol. 303, No. 5663, pp. 1532-1535, 2004.
Candi et al., "The Cornified Envelope: A Model of Cell Death in the Skin", Nat. Rev. Mol. Cell Biol., vol. 6, pp. 328-340, 2005.
Cedervall et al., NETosis in Cancer, Oncoscience, vol. 2, No. 11, pp. 900-901, 2015.
Chen, et al., "Anti-PD-1/PD-L1 therapy of human cancer: past, present, and future", Journal of Clinical Investigation, vol. 125, No. 9, pp. 3384-3391, 2015.
Chang et al., "Increased PADI4 expression in blood and tissues of patients with malignant tumors", BMC Cancer, vol. 9, pp. 40, 2009.
Christophorou et al., Citrullination regulated pluripotency and histone H1 binding to chromatin, Nature, vol. 507, pp. 104-108, 2014.
Chiummiento, et a;.., "New indolic non-peptidic HIV protease inhibitors from (S)-glycidol: synthesis and preliminary biological activity," Tetrahedron (2009), 65(31), 5984-5989.
Chumanevich et al., "Suppression of colitis in mice by C1-amidine: a novel peptidylarginine deiminase inhibitor", Am. J. Physiol. Gastrointest. Liver Physiol., vol. 300, No. 6, pp. G929-G938, 2011.
Curiel, et al., "Blockade of B7-H1 improves myeloid dendritic cell-mediated antitumor or immunity", Nature Medicine, vol. 9, No. 5, pp. 562-567, 2003.
DiMauro et al., Discovery of Aminoquinazolines as Potent, Orally Bioavailable Inhibitor of Lek: Synthesis, SAR, and in Vivo Anti-inflammatory Activity, Journal of Medical Chemistry, vol. 49, No. 19, pp. 5671-5686, 2006.
Dong, et al., "Tumor-associated B7-H1 promotes T-cell apoptosis: A potential mechanism of immune evasion", Nature Medicine, vol. 8, No. 8, pp. 793-800, 2002.
Dong, et al., "PD-1 and its ligands are important immune checkpoints in cancer", Oncotarget, vol. 8, No. 2, pp. 2171-2186, 2017.
First Examination Report dated Sep. 8, 2021 received in Indian Patent Application No. 201741033768.
Flies, et al., "The New B7S: Playing a Pivotal Rose in Tumor Immunity", Immunotherapy, vol. 30, No. 3, pp. 251-260, 2007.
Flies, et al., "Blockade of the B7-H1/PD-1 Pathway for Cancer Immunotherapy", Yale J. Biology Medicine, vol. 84, No. 4, pp. 409-421, 2011.
Fuhrmann, Jakob, et al., "Chemical Biology of Protein Arginine Modifications in Epigenetic Regulation," Chemical Reviews, 2015, 115, 5413-5461.
Francisco, et al., "PD-L1 regulates the development, maintenance, and function of induced regulatory T cells", Journal of Experimental Medicine, vol. 206, No. 13, pp. 3015-3029, 2009.
Guo, et al., "Development of Benzophenone-Alkyne Bifunctional Sigma Receptor Ligands," ChemBioChem (2012), 13(15), 2277-2289.
Gyorgy et al., "Citrullination: A posttranslational modification in health and disease", Int. J. Biochem. Cell Biol., vol. 38, pp. 1662-1677, 2006.
Hamanishi, et al., "PD-1/PD-L1 blockade in cancer treatment: perspectives and issues", Int. J. Clin. Oncol., vol. 21, pp. 462-473, 2016.
He, et al., "Development of PD-1/PD-L1 Pathway in Tumor Immune Microenvironment and Treatment for Non-Small Cell Lung Cancer", Scientific Reports, vol. 5, pp. 1-9, 2015.
International Search Report and WritTen Opinion dated Nov. 12, 2018 for PCT/IN2018/050614.
International Search Report & written opinion, dated Feb. 14, 2019, in International Application No. PCT/IN2018/050671.
International Search Report & Written Opinion, dated Feb. 20, 2019, in International Application No. PCT/IN2018/050671.
International Search Report & Written Opinion, dated May 20, 2019 in International Application No. PCT/IN2019/050203.
Ireland et al., "Autophagy in antigen-presenting cells results in presentation of citrullinated peptides to CD4 T cells", J. Exp. Med., vol. 208, pp. 2625-2632, 2011.
Jones et al., "Protein arginine deiminase 4 (PAD4): current understanding and future therapeutic potential", Curr. Opin. Drug Discov. Devel., vol. 12, pp. 616-627, 2009.
Knight et al., "Peptidylarginine Deiminase Inhibition Reduces Vascular Damage and Modulates Innate Immune Responses in Murine Models of Atherosclerosis", Circ. Res., vol. 114, No. 6, pp. 947-956, 2014.
Kochi et al., "PADI4 polymorphism predisposes male smokers to rheumatoid arthritis", Ann. Rheum. Dis., vol. 70, pp. 512-515, 2011.
Lai, et al., "A Novel PD-L1-targeting Antagonistic DNA Aptamer With Antitumor Effects", Mol. Therapy—Nucl. Acids, vol. 5, pp. e397, 2016.
Lakshmann, et al.,"Synthesis and evaluation of novel N-substituted-6 methoxynaphthalene-2-carboxamides as potential chemosensitizing agents for cancer," Chemical & Pharmaceutical Bulletin (2008), 56(7), 894-896.
Lange et al., "Protein deiminases: New players in the developmentally regulated loss of neural regenerative ability", Dev. Biol., vol. 355, No. 2, pp. 205-214, 2011.

(56) References Cited

OTHER PUBLICATIONS

Lee, et al., Interferon regulatory factor-1 is prerequisite to the constitutive expression and IFN-γ-induced upregulation of B7-H1 (CD274), FEBS Letters, vol. 580, pp. 755-762, 2006.
"Letter to the Editors-in-Chief", Thrombosis Research 191, pp. 26-27, 2020.
Leung, et al., "The CD28-B7 Family in Anti-Tumor Immunity: Emerging Concepts in Cancer Immunotherapy", Immune Network, vol. 14, No. 6, pp. 265-276, 2014.
Lewis et al., "Inhibition of PAD4 activity is sufficient to disrupt mouse and human NET formation", Nature Chemical Biology 11 (3), 189-191. 10.1038/nchembio.1735, 2015.
Li et al., "Regulation of p53 Target Gene Expression by Peptidylarginine Deiminase 4", Mol. Cell Biol., vol. 28, pp. 4745-4758, 2008.
Liu, G.-Y, et al., "Overexpression of peptidylarginine deiminase IV features in apoptosis of haematopoietic cells", Apoptosis, vol. 11, pp. 183-196, 2006.
Loos et al., "Citrullination of CXCL10 and CXCL11 by peptidylarginine deiminase: a naturally occurring posttranslational modification of chemokines and new dimension of immunoregulation", Blood, vol. 112, pp. 2648-2656, 2008.
Makrygiannakis et al., "Citrullination is an inflammation-dependent process", Ann. Rheum. Dis., vol. 65, pp. 1219-1222, 2006.
Mastronardi et al., "Increased Citrullination of Histone H3 in Multiple Sclerosis Brain and Animal Models of Demyelination: A Role for Tumor Necrosis Factor-Induced Peptidylarginine Deiminase 4 Translocation", The Journal of Neurosciences, vol. 26, pp. 11387-11396, 2006.
Mohanan, Sunish, et al., "Potential Role of Peptidylarginine Deiminase Enzymes and Protein Citrullination in Cancer Pathogenesis," Biochemistry Research International, vol. 2012, article ID 895343.
Muenst, et al., "Expression of programmed death ligand 1 (PD-L1) is associated with poor prognosis in human breast cancer", Breast Cancer Res. Treat., vol. 146, No. 1, pp. 15-24, 2014.
Nakashima et al., "Molecular Characterization of Peptidylarginine Deiminase in HL-60 Cells Induced by Retinoic Acid and 1α,25-Dihydroxyvitamin D3", J. Biol. Chem., vol. 274, pp. 27786-27792, 1999.
Nathan, "Neutrophils and COVID-19: Nots, NETs, and knots", The Journal of Experimental Medicine, vol. 217, No. 9, in 3 pages, 2020.
Neeli et al., "Histone Deimination As a Response to Inflammatory Stimuli in Neutrophils", J. Immunol., vol. 180, pp. 1895-1902, 2008.
Omran, et al., "Synthesis and biological evaluation of new Donepezil-like Thiaindanones as AChE inhibitors," Journal of Enzyme Inhibition and Medicinal Chemistry (2008), 23(5), 696-703.
Patsoukis, et al., "PD-1 inhibits T cell proliferation by upregulating p27 and p15 and suppressing Cdc25A", Cell Cycle, vol. 11, No. 23, pp. 4305-4309, 2012.
Schönrich, et al., "Neutrophil Extracellular Traps Go Viral", Frontiers in Immunology, vol. 7, No. 366 in 7 pages, 2016.
Sheppard, et al., "PD-1 inhibits T-cell receptor induced phosphorylation of the ZAP70/CD3 signalosome and downstream signaling to PKCθ", FEBS Letters, vol. 574, pp. 37-41, 2004.
Slack et al., "Protein arginine deiminase 4: a target for an epigenetic cancer therapy", Cellular And Molecular Life Sciences, vol. 68, No. 4, pp. 709-720, 2011.
Smahel, Michal, "PD-1/PD-L1 Blockade Therapy for Tumors with Downregulated MHC Class I Expression", Int. J. Mol. Sci., vol. 18, No. 6, pp. 1331, 2017.
Topalian, et al., "Targeting the PD-1/B7-H1 (PD-L1) pathway to activate anti-tumor immunity", Curr. Opin. Immunol., vol. 24, No. 2, pp. 207-212, 2012.
Vinay, et al., "Immune evasion in cancer: Mechanistic basis and therapeutic strategies", Seminars In Cancer Biology, vol. 35, pp. S185-S198, 2015.
Wang et al., "Histone hypercitrullination mediates chromatin decondensation and neutrophil extracellular trap formation", J. Cell Biol., vol. 184, pp. 205-213, 2009.

Wang, Shu, et al., "Peptidylarginine deiminases in citrullination, gene regulation, health and pathogenesis," Biochim Biophys Acta, Oct. 2013; 1829 (10): 1126-1135.
Wang, et al., "Prognostic significance of PD-L1 in solid tumor", Medicine Baltimore, vol. 96, No. 18, pp. e6369, 2017.
Wang, et al., "PD-LI expression in human cancers and its association with clinical outcomes", Oncotargets and Therapy, vol. 9, pp. 5023-5039, 2016.
Wei, Lianhu, et al., "Novel Inhibitors of Protein Arginine Deiminase with Potential Activity in Multiple Sclerosis Animal Model," Journal of Medicinal Chemistry, 2013, 56, 1715-1722.
Willis et al., N-α-Benzoyl-N5-(2-Chloro-1-lminoethyl)-1-Ornithine Amine, a Protein Arginine Deiminase Inhibitor, Reduces the Severity of Murine Collagen-Induced Arthritis, J. Immunol., vol. 186, No. 7, pp. 4396-4404, 2011.
Zamarron, et al., "Dual Roles of Immune Cells and Their Factors in Cancer Development and Progression", Intl. J. Biol. Sciences, vol. 7, No. 5, pp. 651-658, 2011.
Zawrotniak, et al., "Neutrophil extracellular traps (NETs) - formation and implications", ACTA Biochimica Polonica, vol. 60, No. 3, pp. 277-284, 2013.
Zhuravel, et al., "Solution-phase synthesis of a combinatorial library of 3-[4-(Coumarin-3-yl)-1,3-thiazol-2-ylcarbamoyl]propanoic acid amides," Molecules (2005), 10(2), 444-456.
Zou, et al., "Neutrophil extracellular traps in COVID-19", JCI Insight, vol. 5, No. 11, pp. 1-11, 2020.
Zou, et al., "PD-L1 (B7-H1) and PD-1 pathway blockade for cancer therapy: Mechanisms, response biomarkers, and combinations", Sci. Transl. Med., vol. 8, No. 328, pp. 328rv4, 2016.
Chemical Abstracts, STN Registry Database, Record for RN 1648388-87-7, Entered into STN Feb. 16, 2015.
Cromwell, et al., "Amino ketones. III. B-Tetrahydroisoquinolino ketones and derivatives. Reaction with Grignard reagents," Journal of the American Chemical Society (1944), 66, 872-3.
Evans, et al. "Phenoxyacetic acids as PPAR☐ partial agonists: Synthesis, optimization, and in vivo efficacy," Bioorganic & Medicinal Chemistry Letters (2011), 21(8), 2345-2350.
Fukagawa, Tomokichi," The biuret reaction. VII. Primary-quaternary bases which give the biuret reaction," Z. physiol. Chem. (1931), 201, 40-6.
Goi, et al.," Synthesis and pharmacological properties of pyridinecarbonyl derivatives of 7-substituted theophyllines," Chimica Therapeutica (1973), 8(6), 634-7.
Hankovsky, et al., "New antiarrhythmic agents. 2,2,5,5-Tetramethyl-3-pyrroline-3-carboxamides and 2,2,5,5 tetramethylpyrrolidine-3-carboxamides," Journal of Medicinal Chemistry (1986), 29(7), 1138-52.
Hwang, et al.," Synthesis and evaluation of methylsulfonylnitrobenzamides (MSNBAs) as inhibitors of the thyroid hormone receptor-coactivator interaction," Bioorganic & Medicinal Chemistry Letters (2013), 23(6), 1891-1895.
Ivaschenko, et al., "Synthesis, biological evaluation and in silico modeling of novel integrase strand transfer inhibitors (INSTIs)," European Journal of Medicinal Chemistry (2020), 189, 112064.
Nicolaou, et al., "Synthesis of imides, N-acyl vinylogous carbamates and ureas, and nitriles by oxidation of amides and amines with Dess-Martin periodinane," Angewandte Chemie, International Edition (2005), 44(37), 5992-5997.
Piper, et al., "Synthesis of potential inhibitors of hypoxanthine-guanine phosphoribosyltransferase for testing as antiprotozoal agents. 1. 7-Substituted 6-oxopurines," Journal of Medicinal Chemistry (1980), 23(4), 357-64.
Spassova, et al., "Synthesis of N-(3-azido-2 hydroxypropyl), N-(3-phthalimido-2-hydroxypropyl) and N-(3-amino-2 hydroxypropyl) derivatives of heterocyclic bases," Collection of Czechoslovak Chemical Communications (1994), 59(5), 1153-74.
Uenishi, et al., "Structural effects of diazonaphthoquinone-photoactivecompound backbone on resist lithographic properties," Proceedings of SPIE—The International Society for Optical Engineering (1991), 1466(Adv. Resist Technol. Process. 8), 102-16.
Vooturi, et al.," Solution-phase parallel synthesis of novel membrane-targeted antibiotics," Journal of Combinatorial Chemistry (2010), 12(1), 151-160.

(56) References Cited

OTHER PUBLICATIONS

Zajdel, et al., "Solid-phase synthesis of aryl-alkylamine derivatives using protected aminoalcohol building blocks on SynPhase lanterns," QSAR & Combinatorial Science (2007), 26(2), 215-219.

* cited by examiner

HETEROCYCLIC COMPOUNDS AS PRMT5 INHIBITORS

PRIORITY AND CROSS REFERENCE TO RELATED APPLICATIONS

This application is the U.S. National Stage Application under 35 U.S.C. § 371 of International Application No. PCT/IN2018/050778, filed Nov. 23, 2018, designating the U.S. and published in English as WO 2019/102494 A1 on May 31, 2019, which claims the benefit of Indian Patent Application No. IN 201841001334, filed Jan. 11, 2018, and Indian Patent Application No. IN 201741042307, filed Nov. 24, 2017. Any and all applications for which a foreign or a domestic priority is claimed is/are identified in the Application Data Sheet filed herewith and is/are hereby incorporated by reference in their entireties under 37 C.F.R. § 1.57.

TECHNICAL FIELD OF THE INVENTION

The present disclosure relates to the field of pharmaceutical chemistry in general. In particular, the present disclosure relates to the development of PRMT5 inhibitory compounds of Formula I, Formula Ia, or Formula Ib their analogs, tautomeric forms, stereoisomers, geometrical isomers, polymorphs, hydrates, solvates, pharmaceutically acceptable salts, pharmaceutical compositions, metabolites and prodrugs thereof, active against the PRMT5 protein.

It further relates to the synthesis and characterization of aforementioned compounds to exhibit PRMT5 inhibitory activity.

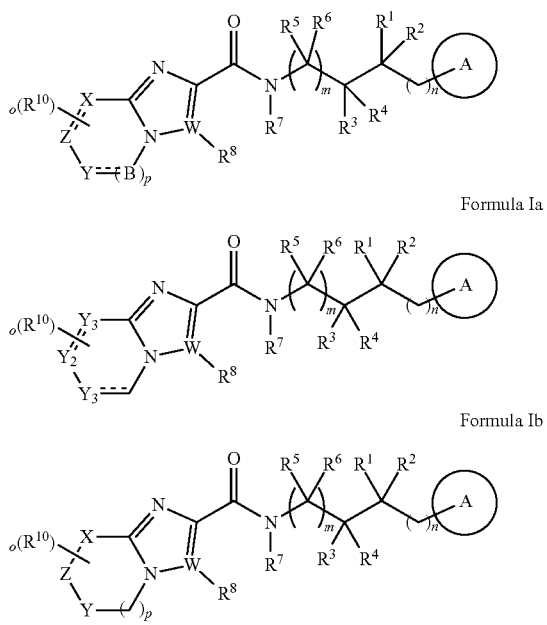

The compounds described herein are substituted heterocyclic compounds that inhibit PRMT5 enzyme and may be used in the treatment of a condition mediated by PRMT5 or a proliferative disorder or cancer.

BACKGROUND OF THE INVENTION

The methylation of arginine, carried out by argininemethyltransferases (PRMTs), is a modification which is as common as phosphorylation and ubiquitination (Larsen S C et al., Science Signaling, 2016, 9(443): RS9). The family of PRMTs is a group of nine proteins, which are responsible for the catalytic transfer of a methyl group from S-adenosyl-methionine (SAM) to the guanidine nitrogen atoms of arginine (Bedford M. T. et al., Molecular Cell, 2009, 33:1-13; Yang Y et al., Nature Review Cancer, 2013, 13:37-50).

There are three main categories according to the catalytic activity of PRMTs: Type I (PRMT1, PRMT2, PRMT3, PRMT4, PRMT6 and PRMT8), Type II (PRMT5 and PRMT9), and Type III (PRMT7). Among these enzymes, PRMT5 is the major enzyme responsible for mono- and symmetric dimethylation of arginine. This protein is the regulatory protein possessing critical biological function in a wide range of cellular processes. The methylation by PRMT5 is known to regulate genome organization, transcription, stem cells, primordial germ cells, differentiation, the cell cycle, and spliceosome assembly. It forms an active complex with MEP50 and transfers methyl groups from S-adenosylmethoinine (SAM) to histone proteins and transcription factors. These methylations form mono and symmetrically di-methylated arginine residues.

Human PRMT5 was first identified as Jak-binding protein 1 (JBP1) (Pollack B. P. et al., J. Biological Chemistry, 1999, 274(44):31531-42; Branscombe T. L. et al., J. Biological Chemistry, 2001, 276(35):32971-6) and shown to methylate Histones H2A, H4 on Arg3 (H2AR3, H4R3), and H3 on Arg8 (H3R8) along with a number of non-histone proteins including P53 (Jansson et al., Nature Cell Biology, 2008, 10(12):1431-9), and epidermal growth factor receptor (EGFR) (Hsu J. M. et al., Nature Cell Biology, 2011, 13(2):174-81), NF-κB (Wei H. et al., Proc. Natl. Acad. Sci, 2013, 110(13):13516-21).

The activity of PRMT5 has an important role in cell signaling, chromatin remodeling, and control of gene expression and thus in diseases like cancer, kidney and heart diseases, and neurological disorders. It mainly functions as a co-repressor (transcriptional repressor), wherein H4R3me2s antibody is recognized by the DNA methyltransferase DNMT3a. Once recruited, DNMT3a methylates neighboring DNA to further strengthen the associated gene repression by PMRT5 (Fabbrizo E. et al., EMBO Reports, 2002, 3(7):641-5; Zhao Q. et al., Nature Structural and Molecular Biology, 2009, 16:304-11). Besides being a transcriptional repressor, PRMT5, along with PRMT7, plays an important role in the splicing of mRNA through methylatingspliceosomal proteins (Sm proteins D1, D3, B/B' etc.), which are then assembled into small nuclear ribonucleoproteins (snRNPs). Due to this reason, the PRMT5-deficient cells harbor numerous defects in splicing (Brahms H et al., RNA, 2001, 7(11):1531-42; Meister G et al., EMBO J, 2002, 21(21):5853-63; Stopa N. et al., Cellular and Molecular Life Sciences, 2015, 72(11):2014-59).

PRMT5 is emerging as an important enzyme involved in tumorigenesis and stem cell maintenance, as it is highly expressed in several cancer types, including ovarian, lung, lymphoid, glioblastoma, colon, melanoma, gastric, bladder cancers and germ cell tumors (Eckert D. et al., BMC Developmental Biology, 2008, 8(106):1-11; Gu Z. et al., Biochemistry J, 2012, 446(2):235-41; Bao X. et al., J. Histochem Cytochem, 2013, 61(3):206-17; Nicholas C. et al., PLoS ONE, 2013, 8(9):e74710; Stopa N. et al., Cellular and Molecular Life Sciences, 2015, 72(11):2014-59).

PRMT5 is therefore considered to be a clinically relevant target and potential. PRMT5 inhibitors are under development as specified in the applications, such as, WO 2017153518A1, WO 2017153186A1, WO2016034671A1, WO216034673A1, WO2016034675A1, WO2016022605A1, and WO2015200677A2. However, there is still a need for novel, potent, PRMT5 inhibitors as anti-cancer therapies.

SUMMARY OF INVENTION

In an aspect of the present disclosure, there is provided compounds of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein Formula I

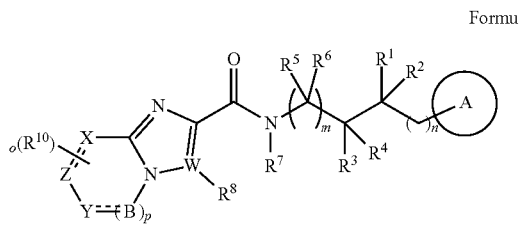

wherein A is selected from

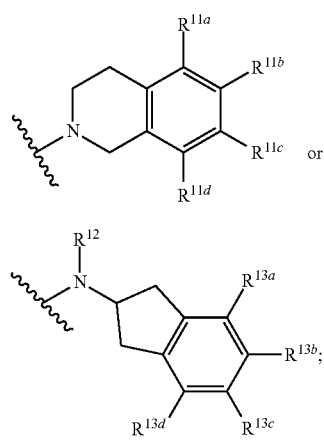

---- represents optional single or double bond; n is 0 or 1; m is 0-2; p is 1 or 2; o is 1-3; $R^1$, $R^2$, $R^3$, $R^4$, $R^5$, and $R^6$ are independently selected from hydrogen, halogen, hydroxyl or $C_{1-6}$ alkyl, wherein $C_{1-6}$ alkyl is optionally substituted with one or more groups selected from hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O, or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$alkyl, $C_{1-6}$haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)$ $NR_aR_b$, $C(S)NR_aR_b$, $NR_aC(O)NR_bR_c$, $N(R_a)SOR_b$, $N(R_a)$ $SO_2R_b$, $NR_aC(O)OR_b$, $NR_aR_b$, $NR_aC(S)NR_bR_c$, $NR_aC(O)$ $R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an aspect of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein Formula Ia

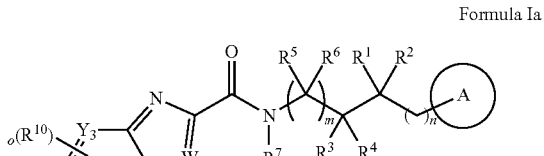

A is selected from

Ia

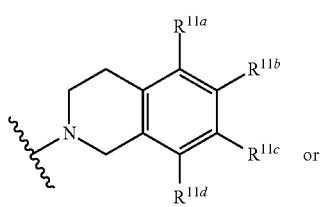

Ib

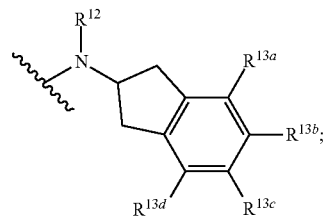

n is 0 or 1; m is 0-2; o is 1-3; $R^1$, $R^2$, $R^3$, $R^4$, $R^5$, and $R^6$ are independently selected from the group consisting of hydrogen, halogen, hydroxyl, or $C_{1-6}$ alkyl, wherein $C_{1-6}$ alkyl is optionally substituted with one or more groups selected from hydroxyl, or halogen; $R^7$ and $R^{12}$ are independently selected from hydrogen, and $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{11a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_a$-$C(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, or $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{3-6}$ cycloalkyl, $C_{1-6}$ alkyl, $C_{1-6}$ haloalkyl, $C_{1-6}$alkoxy, $C_{3-6}$cycloalkyl, $C(O)R_b$, 3-6 membered saturated or unsaturated heterocyclyl or heteroaryl ring with 1-5 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or or $R_a$ and $R_b$ can be taken together to form a 5-10 membered monocyclic or bicyclic, saturated or unsaturated heterocyclic ring with 1-3 heteroatoms selected from N, S or O.

In an aspect of the present disclosure, there is provided compounds of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein Formula Ib

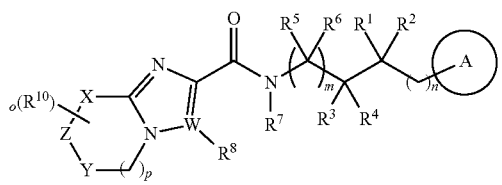

wherein A is selected from

Ia

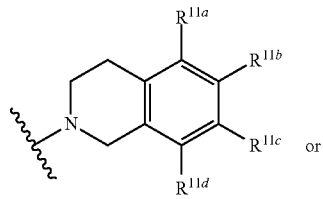

Ib

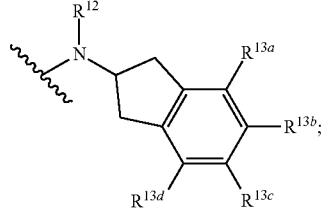

n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

The present disclosure further describes the process of preparation of compounds of Formula I, Formula Ia, or Formula Ib, their analogs, tautomeric forms, stereoisomers, geometrical isomers, polymorphs, hydrates, solvates, pharmaceutically acceptable salts, pharmaceutical compositions, metabolites, and prodrugs thereof.

The present disclosure further relates to a pharmaceutical composition comprising a compound of Formula I, Formula Ta, or Formula Tb or a pharmaceutically acceptable salt thereof together with a pharmaceutically acceptable carrier, optionally in combination with one or more other pharmaceutical compositions.

The present disclosure further relates to a method for the treatment and/or prevention of various diseases, including cancer and infectious diseases, comprising administering to a subject suffering from the proliferative disorder or cancer a therapeutically effective amount of the compound of Formula I, Formula Ta, or Formula Tb or the pharmaceutical composition, with other clinically relevant cytotoxic agents or non-cytotoxic agents to a subject in need thereof.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a" "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

The term "effective amount" refers to an amount or concentration of the compound of Formula Ib, Formula Ia, and Formula I that produces a biological response either individually or when present in a pharmaceutical composition. The term effective amount or effective dose can be used interchangeably when measurements are taken either in vivo, or in vitro.

The term "cytotoxic agents" or "inhibitors" is used to identify any agents or drugs which is capable of killing cells including cancer cells. These agents or inhibitors may stop cancer cells from growing and dividing and may cause tumors to shrink in size.

The term "non-cytotoxic agents" or "inhibitors" is used to identify any agents or inhibitors are which does not directly kill cells, but instead affects cellular transport and metabolic functions to ultimately produce cell death.

The term "immune checkpoint inhibitors agents" or "immune modulators agents" are used to identify any agents or inhibitors that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. The immune checkpoint inhibitors include inhibitors against immune checkpoint molecules such as CD27, CD28, CD40, CD122, CD96, CD73, CD47, 0X40, GITR, CSF1R, JAK, PI3K delta, PI3K gamma, TAM, aiginase, CD137 (also known as 4-1BB), ICOS, A2AR, B7-H3, B7-H4, BTLA, CTLA-4, LAG3, TIM3, VISTA, PD-1, PD-L1 and PD-L2. The terms "immune modulators agents" and "immune checkpoint inhibitors" are used interchangeably throughout the present disclosure.

The term "alkyl" refers to straight or branched aliphatic hydrocarbon groups having the specified number of carbon atoms, which are attached to the rest of the molecule by a single atom, which may be optionally substituted by one or more substituents as described hereinafter in the disclosure. For example, which are not limited, $C_{1-6}$ alkyl refers to an alkyl group having from 1-6 carbon atoms, or 1-5, or 1-4 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, isobutyl, t-butyl, pentyl, hexyl, heptyl, octyl, and the like.

The term "alkenyl" refers to an aliphatic hydrocarbon group containing a carbon-carbon double bond and which may be straight or branched chain having about 2-6 carbon atoms, which may be optionally substituted by one or more substituents as as described hereinafter in the disclosure. Preferred alkenyl groups include, without limitation, ethenyl, 1-propenyl, 2-propenyl, iso-propenyl, 2-methyl-1-propenyl, 1-butenyl, 2-butenyl, and the like.

The term "alkynyl" refers to a straight or branched hydrocarbyl radicals having at least one carbon-carbon triple bond and having in the range of 2-6 carbon atoms, which may be optionally substituted by one or more substituents as described hereinafter in the disclosure. Preferred alkynyl groups include, without limitation, ethynyl, propynyl, butynyl, and the like.

The term "alkoxy" refers to an alkyl group as defined above attached via an oxygen linkage to the rest of the molecule, which may be optionally substituted by one or more substituents as described hereinafter in the disclosure. For example, $C_{1-6}$ alkoxy refers to an alkyl group having from 1-6 carbon atoms, or 1-4, or 1-3 carbon atoms attached via an oxygen linkage to the rest of the molecule. Preferred alkoxy groups include, without limitation, —OCH$_3$ (methoxy), —OC$_2$H$_5$ (ethoxy), and the like.

The term "alkylamino" refers to an alkyl group as defined above attached via amino linkage to the rest of the molecule, which may be optionally substituted by one or more substituents as described hereinafter in the disclosure. For example, $C_{1-6}$ alkylamino refers to an alkyl group having from 1-6 carbon atoms, or 1-4 carbon atoms attached via amino linkage to the rest of the molecule. Preferred alkylamino groups include, without limitation, —NHCH$_3$, —N(CH$_3$)$_2$, and the like.

The term "haloalkyl" refers to a halogen in an alkyl group as defined above attached via alkyl linkage to the rest of the molecule. For example, $C_{1-6}$ haloalkyl refers to an alkyl group having from 1-6 carbon atoms, or 1-4 carbon atoms attached via halo linkage to the rest of the molecule. Preferred haloalkyl groups include, without limitation, —CH$_2$Cl, —CHCl$_2$, trifluoromethyl, 2,2,2-trifluoroethyl, and the like.

The term "haloalkoxy" refers to a halogen in an alkoxy group as defined above attached via oxygen linkage to the rest of the molecule. For example, C$_{1-6}$ haloalkoxy refers to an alkoxy group having from 1-6 carbon atoms, or 1-4 carbon atoms attached via oxygen linkage of the alkoxy group to the rest of the molecule. Preferred haloalkoxy groups include, without limitation, —OCH$_2$Cl, —OCHCl$_2$, and the like.

The term "halogen" refers to a halogen radical, for example, fluoro, chloro, bromo, or iodo.

The term "cycloalkyl" refers to non-aromatic mono or polycyclic ring system of about 3 to 6 carbon atoms, which may be optionally substituted by one or more substituents as described hereinafter in the disclosure. The polycyclic ring denotes hydrocarbon systems containing two or more ring systems with one or more ring carbon atoms in common i.e. a spiro, fused or bridged structures. For example, which are not limited, C$_{3-6}$ cycloalkyl refers to a cycloalkyl group having from 3 to 6 membered atoms. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g. spiro [4.4] non-2-yl, and the like.

The term "aryl" refers to aromatic ring having a specified number (5 to 6) of carbon atoms, which may be optionally substituted by one or more substituents as described hereinafter in the disclosure. For example, C$_{5-6}$ aryl refers to an aryl group having 5 or 6 membered atoms, or 6 membered atoms. Preferred aryl groups include, without limitation, phenyl, naphthyl, indanyl, biphenyl, and the like.

The term "heteroaryl" refers to an aromatic heterocyclic ring radical as defined above which may be optionally substituted by one or more substituents as described hereinafter in the disclosure. The heteroaryl ring radical may be attached to the main structure at any heteroatom or carbon atom that results in the creation of stable structure. The "heteroaryl" includes pyridinyl, tetrazolyl, and pyrazolyl.

The term "heterocyclyl" refers to a heterocyclic ring radical which may be optionally substituted by one or more substituents as described hereinafter in the disclosure. The heterocyclyl ring radical may be attached to the main structure at any heteroatom or carbon atom that results in the creation of a stable structure. Furthermore, the term "heterocyclyl" refers to a stable 3 to 15 membered rings radical, which consists of carbon atoms and from one to five heteroatoms selected from nitrogen, phosphorus, oxygen and sulfur. For purposes of this disclosure the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Preferred heterocyclyl groups include, without limitation, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinylsulfoxide, furyl, tetrahydrofuryl, tetrahydropyranyl, chromanyl and isochromanyl.

Furthermore, the compound of Formula I, Formula Ia, or Formula Ib can be its derivatives, analogs, stereoisomer's, diastereomers, geometrical isomers, polymorphs, solvates, co-crystals, intermediates, hydrates, metabolites, prodrugs or pharmaceutically acceptable salts and compositions.

It is understood that included in the family of compounds of Formula I, Formula Ta, or Formula Tb are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers and geometrical isomers can be separated by physical and/or chemical methods by those skilled in the art.

Compounds disclosed herein may exist as single stereoisomers, racemates and or mixtures of enantiomers and/or diastereomers. All such single stereoisomers, racemates and mixtures thereof are intended to be within the scope of the subject matter described.

Compounds disclosed herein include isotopes of hydrogen, carbon, oxygen, fluorine, chlorine, iodine and sulfur which can be incorporated into the compounds, such as, but not limited to, $^2$H (D), $^3$H (T), $^{11}$C, $^{13}$C, $^{14}$C, $^{15}$N, $^{18}$F, $^{35}$S, $^{36}$Cl, and $^{125}$I. Compounds of this disclosure wherein atoms were isotopically labeled for example radioisotopes such as $^3$H, $^{13}$C, $^{14}$C, and the like can be used in metabolic studies, kinetic studies, and imaging techniques such as positron emission tomography used in understanding the tissue distribution of the drugs. Compounds of the disclosure where hydrogen is replaced with deuterium may improve the metabolic stability, and pharmacokinetics properties of the drug such as in vivo half-life. Compounds of the disclosure where isotopically labeled $^{18}$F can be useful as PET imaging studies.

The compounds of Formula I, Formula Ta, or Formula Tb and their analogs, tautomeric forms, stereoisomers, geometrical isomers, polymorphs, hydrates, solvates, pharmaceutically acceptable salts, pharmaceutical compositions, metabolites, and prodrugs thereof can also be referred as "compounds of the present disclosure".

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The compounds described herein may also exhibit polymorphism. This disclosure further includes different polymorphs of the compounds of the present disclosure. The term polymorph refers to a particular crystalline state of a substance, having particular physical properties such as X-ray diffraction, IR spectra, melting point, and the like.

The term "substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

The term "prodrugs" refers to the precursor of the compound of Formula I which on administration undergoes chemical conversion by metabolic processes before becoming active pharmacological substances. Described herein are prodrugs of the compound of Formula I, Formula Ia, or Formula Ib, which on administration undergoes chemical conversion by metabolic processes before becoming active pharmacological substances. In general, such prodrugs will be functional derivatives of a compound of the disclosure, which are readily convertible in vivo into a compound of the disclosure.

The compounds described herein can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

The phrase "pharmaceutically acceptable" refers to compounds or compositions that are physiologically tolerable and do not typically produce allergic or similar untoward reactions, including but not limited to gastric upset or dizziness when administered to mammal.

As used herein, the term "pharmaceutically acceptable salts" refers to salts that retain the desired biological activity of the subject compound and exhibit minimal undesired toxicological effects. Pharmaceutically acceptable salts forming part of this disclosure include salts derived from inorganic bases such as Li, Na, K, Ca, Mg, Fe, Cu, Zn, Mn, ammonium, substituted ammonium salts, aluminum salts and the like; salts of organic bases such as N,N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, and the like. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates, and the like.

The terms "Protein arginine methyl transferase" and "PRMT" are intended to refer to any one of a family of enzymes that transfer methyl group to the arginines of histone or proteins.

The term "Protein arginine methyl transferase inhibitor" or "inhibitor of protein arginine methyl transferase" is used to identify a compound, which is capable of interacting with a protein arginine methyl transferase and inhibiting its activity, more particularly its enzymatic activity. Inhibiting protein arginine methyl transferase enzymatic activity means reducing the ability of a protein arginine methyl transferase for methylation of arginine residue of histone or other proteins.

The term "Protein arginine methyl transferase inhibitor-5" or "inhibitor of protein arginine methyl transferase-5 or inhibitors of PRMT5" is used to identify a compound, which is capable of interacting with a protein arginine methyl transferase and inhibiting its activity, more particularly its enzymatic activity. Inhibiting protein arginine methyl transferase-5 enzymatic activity means reducing the ability of a protein arginine methyl transferase-5 for symmetrical dimethylation of arginine residue of histone or other proteins.

The disclosure also provides a method of treatment of cancer in patients including administration of a therapeutically effective amount of a compound of Formula I, Formula Ia, or Formula Ib. The disclosure also provides a method for treatment of proliferative conditions or cancer, comprising administering to a subject suffering from proliferative conditions or cancer, a therapeutically effective amount of a compound of Formula I, Formula Ia, or Formula Ib, in the presence or absence of other clinically relevant cytotoxic agents or non-cytotoxic agents need thereof.

The present disclosure provides a method of treatment of a disorder caused by, associated with or accompanied by disruptions of cell proliferation and/or angiogenesis and the subsequent metastasis including administration of a therapeutically effective amount of a compound of Formula I, Formula Ia, or Formula Ib.

The disclosure provides a method of treatment of cancer in patient including administration of effective amount of compounds of Formula I, Formula Ta, or Formula Tb. The cancer can be either a hematologic malignancy or solid tumor. Hematological malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer, and brain cancer.

As discussed above, the compounds of the present disclosure are useful for treating proliferative diseases. Proliferative diseases include, for example, a tumor disease and/or metastates. Compounds of the present disclosure are useful for treating a proliferative disease that is refractory to the treatment with other chemotherapeutics; or a tumor that is refractory to treatment with other therapeutics due to multidrug resistance.

Compounds of the present disclosure are able to slow tumor growth, stop tumor growth or bring about the regression of tumors and to prevent the formation of tumor metastates (including micrometastates) and the growth of metastates (including micrometastates). In addition, they can be used in epidermal hyperproliferation.

The compound of Formula I of the present disclosure can be used as a prophylactic or therapeutic agent for cancer. Examples of the cancer include but are not restricted to, breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder, skin cancer, hemangioma, malignant lymphoma, malignant melanoma, thyroid cancer, bone tumor, vascular fibroma, retinoblastoma, penile cancer, pediatric solid cancer, lymphoma, myeloma and leukemia (including, for example acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL) or hairy cell leukemia).

"Combination therapy" includes the administration of the subject compounds in further combination with other biologically active ingredients (such as, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the disclosure. The compounds can be administered simultaneously or sequentially to the other drug therapy.

In an embodiment, the disclosure provides a method of inhibiting PRMT5 activity comprising administering, to a patient in need of treatment, an amount of a composition comprising a compound of Formula I, Formula Ia, or Formula Ib and a pharmaceutically acceptable carrier sufficient to inhibit PRMT5 activity.

In one aspect of this embodiment, the disclosure provides a compound of Formula I for use in inhibiting PRMT5. In a related aspect, the disclosure provides for the use of a compound of Formula I, Formula Ia, or Formula Ib for the manufacture of a medicament for inhibiting PRMT5.

In an embodiment, the disclosure provides a method of treating and/or preventing a neurodegenerative disease or disorder comprising administering, to a patient in need of treatment, a therapeutically effectively amount of a composition comprising a compound of Formula I, Formula Ia, or Formula Ib and a pharmaceutically acceptable carrier.

In an aspect of this embodiment, the disclosure provides a compound of Formula I for use in treating and/or preventing a neurodegenerative disorder or condition. In a related aspect, the disclosure provides for the use of a compound of Formula I, Formula Ia, or Formula Ib for the manufacture of a medicament for treating and/or preventing a neurodegenerative disorder or condition.

In another aspect, the compound may be administered in combination therapy by combining the compound of Formula I, Formula Ia, or Formula Ib with one or more separate agents, not limited to targets such as DNA methyltransferase, heat shock proteins (e.g. HSP90), kinase, epigenetic and other matrix metalloproteinases.

In another aspect, the subject compounds may be combined with the antineoplastic agents (e.g. small molecules, cytotoxic reagents, non-cytotoxic reagents, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In yet another aspect, the subject compounds may be combined with immunoncology drugs not restricting to PDL-1, IDO, TDO, CTLA4 or any other drugs which is involved in the immune modulation.

As discussed in the background section, PRMT5 enzymes play an important role in cancer and other related diseases. Therefore, there is a requirement for PRMT5 inhibitors for treating cancer and other diseases or conditions associated with the over expression of PRMT5.

In an embodiment of the present disclosure, there is provided compounds of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein

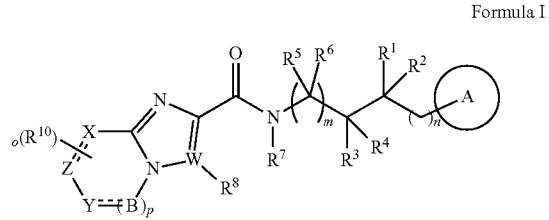

Formula I wherein A is selected from

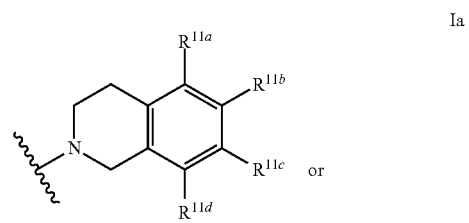

Ia

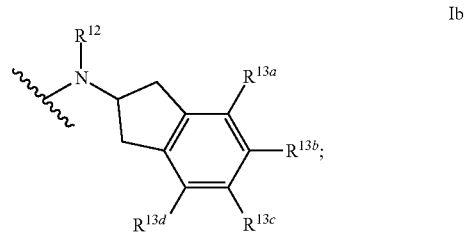

Ib

---- represents optional single or double bond; n is 0 or 1; m is 0-2; p is 1 or 2; o is 1-3; $R^1$, $R^2$, $R^3$, $R^4$, $R^5$, and $R^6$ are independently selected from hydrogen, halogen, hydroxyl or $C_{1-6}$ alkyl, wherein $C_{1-6}$ alkyl is optionally substituted with one or more groups selected from hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O, or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein
A is

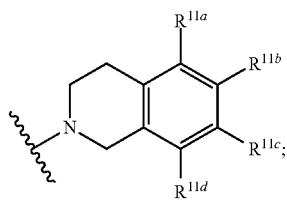

Ia

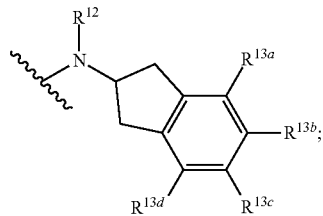

Ib

---- represents optional single or double bond; n is 0 or 1; m is 0-2; p is 1 or 2; o is 1-3; $R^1$, $R^2$, $R^3$, $R^4$, $R^5$, and $R^6$ are independently selected from hydrogen, halogen, hydroxyl or $C_{1-6}$ alkyl, wherein $C_{1-6}$ alkyl is optionally substituted with one or more groups selected from hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, and $R^{11d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O, or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein
A is ---- represents optional single or double bond; n is 0 or 1; m is 0-2; p is 1 or 2; o is 1-3; $R^1$, $R^2$, $R^3$, $R^4$, $R^5$, and $R^6$ are independently selected from hydrogen, halogen, hydroxyl or $C_{1-6}$ alkyl, wherein $C_{1-6}$ alkyl is optionally substituted with one or more groups selected from hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O, or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

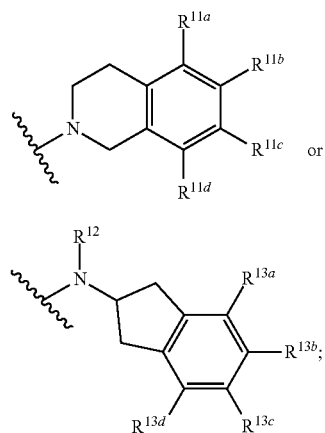

---- represents optional single or double bond; n is 0 or 1; m is 0-2; p is 1; o is 1 or 2; $R^1$, $R^2$, $R^3$, $R^4$, $R^5$, and $R^6$ are independently selected from hydrogen, halogen, hydroxyl, or $C_{1-6}$ alkyl, wherein $C_{1-6}$ alkyl is optionally substituted with one or more groups selected from hydroxyl and halogen; $R^7$, and $R^{12}$ are independently selected from hydrogen, or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SF_5$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-6}$ cycloalkyl, $C_{3-15}$ heterocyclyl, or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein

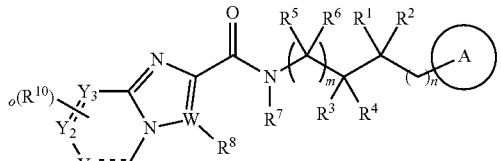

A is selected from

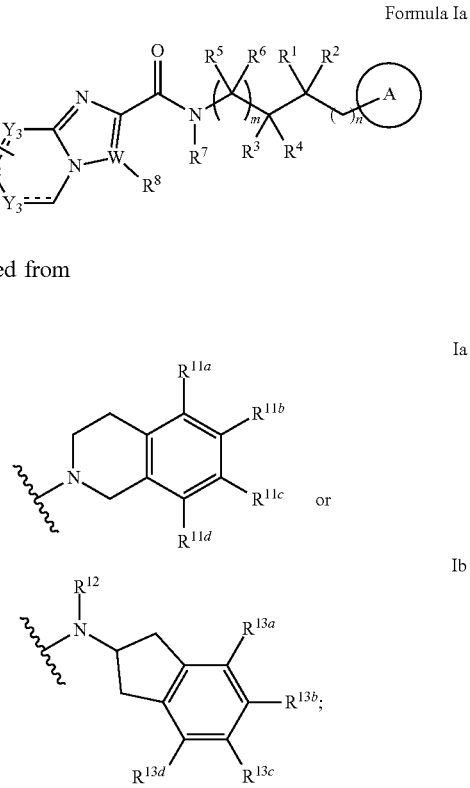

n is 0 or 1; m is 0-2; o is 1-3; $R^1$, $R^2$, $R^3$, $R^4$, $R^5$, and $R^6$ are independently selected from the group consisting of hydrogen, halogen, hydroxyl, or $C_{1-6}$ alkyl, wherein $C_{1-6}$ alkyl is optionally substituted with one or more groups selected from hydroxyl, or halogen; $R^7$ and $R^{12}$ are independently selected from hydrogen, and $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, or $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{3-6}$ cycloalkyl, $C_{1-6}$ alkyl, $C_{1-6}$haloalkyl, $C_{1-6}$alkoxy, $C_{3-6}$cycloalkyl, $C(O)R_b$, 3-6 membered saturated or unsaturated heterocyclyl or heteroaryl ring with 1-5 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

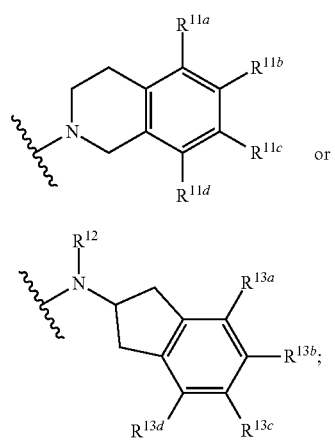

Ia or

Ib n is 0 or 1; m is 0-2; o is 1-3; $R^1$, $R^2$, $R^3$, $R^4$, $R^5$, and $R^6$ are independently selected from the group consisting of hydrogen, halogen, hydroxyl, and $C_{1-5}$ alkyl, wherein $C_{1-5}$ alkyl is optionally substituted with one or more groups selected from hydroxyl, or halogen; $R^7$ and $R^{12}$ are independently selected from hydrogen, and $C_{1-6}$ alkyl, wherein $C_{1-6}$ alkyl is optionally substituted with $C_{5-6}$ aryl, wherein $C_{5-6}$ aryl is optionally substituted with one or more groups selected from the group consisting of $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

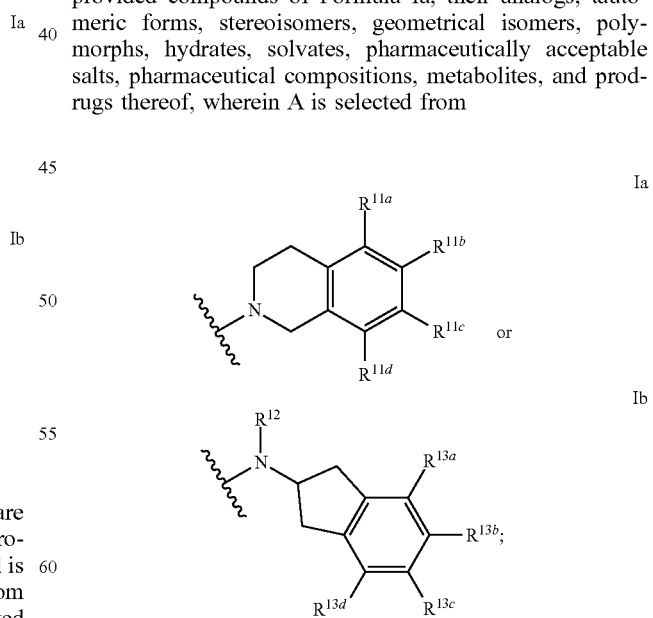

n is 0 or 1; m is 0-2; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, or halogen; $R^7$ and $R^{12}$ are independently selected from hydrogen, and $C_{1-6}$ alkyl, wherein $C_{1-6}$ alkyl is optionally substituted with $C_{5-6}$ aryl, wherein $C_{5-6}$ aryl is optionally substituted with one or more groups selected from the group consisting of $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

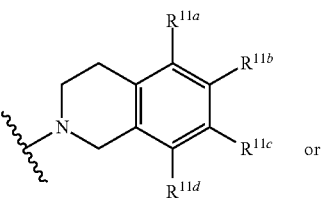

Ia

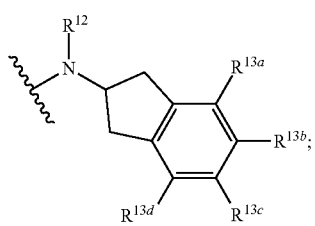

Ib n is 0 or 1; m is 0-2; o is 1-3; $R^1$, $R^2$, $R^3$ $R^4$, $R^5$, and $R^6$ are independently selected from the group consisting of hydrogen, halogen, hydroxyl, or $C_{1-4}$ alkyl, wherein $C_{1-4}$ alkyl is optionally substituted with one or more groups selected from hydroxyl, or halogen; $R^7$ and $R^{12}$ are independently selected from hydrogen, or $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, and wherein 3-6 membered saturated or unsaturated heterocyclyl or heteroaryl ring with 1-3 heteroatoms selected from N, S or O is optionally substituted with $C(O)R_b$, wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

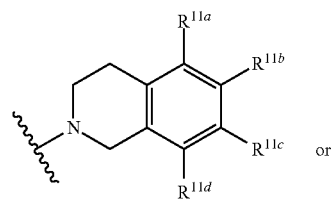

Ia

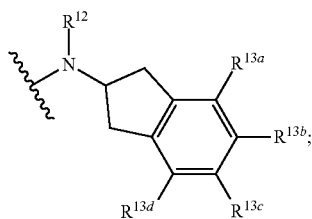

Ib

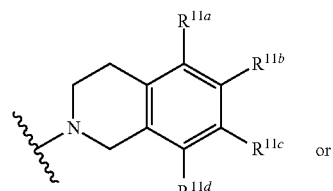

Ia

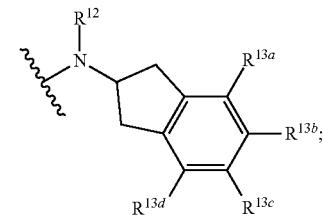

Ib n is 0 or 1; m is 0 or 1; o is 1-3; $R^1$, $R^2$, $R^3$ $R^4$, $R^5$, and $R^6$ are independently selected from the group consisting of hydrogen, halogen, hydroxyl, or $C_{1-4}$ alkyl, wherein $C_{1-4}$ alkyl is optionally substituted with one or more groups selected from hydroxyl, or halogen; $R^7$ and $R^{12}$ are independently selected from hydrogen, or $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, and wherein 3-6 membered saturated or unsaturated heterocyclyl or heteroaryl ring with 1-3 heteroatoms selected from N, S or O is optionally substituted with $C(O)R_b$, wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from n is 0 or 1; m is 0 or 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$ alkylamino, $COOR_a$, $C(O)R_b$, $C(S)R_a$, $C(O)NR_aR_b$, $C(S)NR_aR_b$, $NR_aC(O)NR_bR_c$, $NR_a C(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

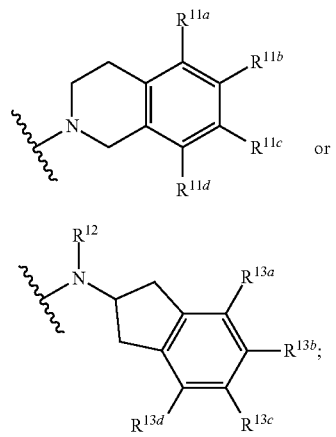

Ia or

Ib

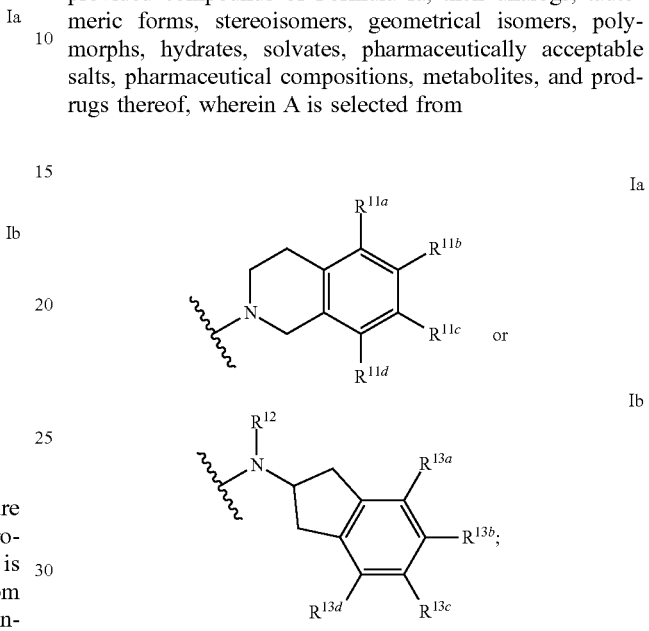

n is 0; m is 0; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$haloalkyl, $C_{3-6}$cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, COOR$_a$, C(O)R$_b$, C(S)R$_a$, C(O)NR$_a$R$_b$, C(S)NR$_a$R$_b$, NR$_a$C(O)NR$_b$R$_c$, NR$_a$C(S)NR$_b$R$_c$, N(R$_a$)SOR$_b$, N(R$_a$)SO$_2$R$_b$, NR$_a$C(O)OR$_b$, NR$_a$R$_b$, NR$_a$C(O)R$_b$, NR$_a$C(S)R$_b$, SF$_5$, SONR$_a$R$_b$, SO$_2$NR$_a$R$_b$, OR$_a$, OR$_a$-C(O)OR$_b$, OC(O)NR$_a$R$_b$, OC(O)R$_a$, OC(O)NR$_a$R$_b$, R$_a$NR$_b$R$_c$, R$_a$OR$_b$, SR$_a$, SOR$_a$ and SO$_2$R$_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, C(O)R$_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with C(O)R$_b$, and wherein R$_a$, R$_b$, and R$_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or R$_a$ and R$_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from Ia or Ib n is 1; m is 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$haloalkyl, $C_{3-6}$cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, COOR$_a$, C(O)R$_b$, C(S)R$_a$, C(O)NR$_a$R$_b$, C(S)NR$_a$R$_b$, NR$_a$C(O)NR$_b$R$_c$, NR$_a$C(S)NR$_b$R$_c$, N(R$_a$)SOR$_b$, N(R$_a$)SO$_2$R$_b$, NR$_a$C(O)OR$_b$, NR$_a$R$_b$, NR$_a$C(O)R$_b$, NR$_a$C(S)R$_b$, SF$_5$, SONR$_a$R$_b$, SO$_2$NR$_a$R$_b$, OR$_a$, OR$_a$-C(O)OR$_b$, OC(O)NR$_a$R$_b$, OC(O)R$_a$, OC(O)NR$_a$R$_b$, R$_a$NR$_b$R$_c$, R$_a$OR$_b$, SR$_a$, SOR$_a$ and SO$_2$R$_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, C(O)R$_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

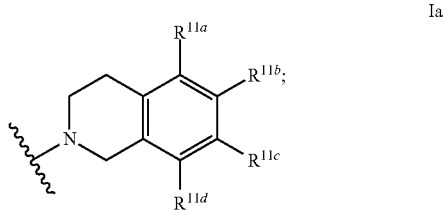

Ia n is 0; m is 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ is selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{11a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$ alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

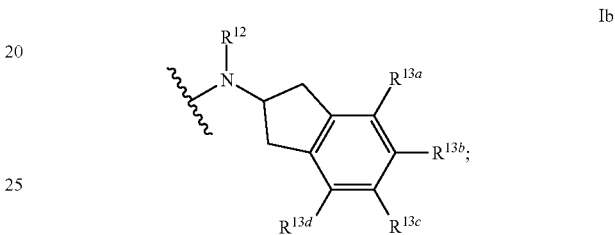

Ib n is 0; m is 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$ alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

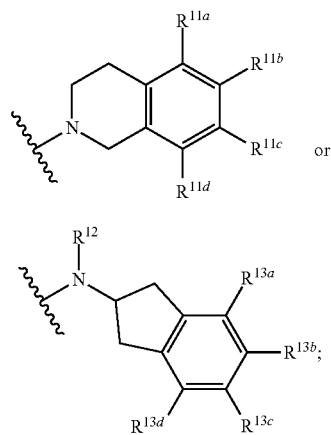

n is 0 or 1; m is 0 or 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{11a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is C; $R^8$ is absent or is selected from hydrogen, halogen, $C_{1-4}$ alkyl, $C_{1-4}$ alkenyl, $C_{1-4}$ alkynyl, $C_{1-4}$haloalkyl, $C_{3-6}$cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_a$-$C(O)OR_b$, $OC(O)NR_aR_b$, $OC(O)R_a$, $OC(O)NR_aR_b$, $R_a$ $NR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

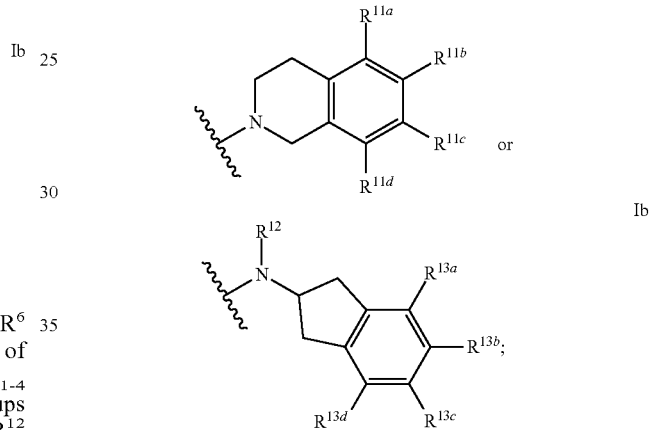

n is 0 or 1; m is 0 or 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, or bromo; $R^7$ and $R^{12}$ are independently selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_a$-$C(O)OR_b$, $OC(O)NR_aR_b$, $OC(O)R_a$, $OC(O)NR_aR_b$, $R_a$ $NR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

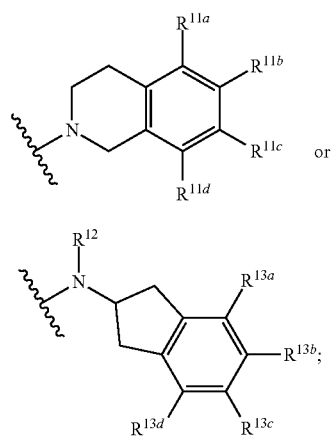

Ia

Ib n is 0 or 1; m is 0 or 1; o is 1-3; $R^1$, $R^2$, $R^3$, $R^4$, $R^5$, and $R^6$ are independently selected from the group consisting of hydrogen, halogen, hydroxyl, and $C_{1-4}$ alkyl, wherein $C_{1-4}$ alkyl is optionally substituted with one or more groups selected from hydroxyl, fluoro, chloro, or bromo; $R^7$ is selected from hydrogen, or $C_{1-4}$ alkyl; $R^{12}$ is selected from hydrogen, and $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano; $R^{11a}$, $R^{11b}$, $R^{11c}$, $R^{13a}$, $R^{13a}$, $R^{13b}$, $R^{13c}$, and $R^{13d}$ are independently selected from the group consisting of hydrogen, halogen, cyano, $C_{1-6}$ alkyl, $C_{1-6}$ haloalkyl, or $C_{1-6}$ alkoxy; $Y^1$, $Y^2$, and $Y^3$ are independently selected from N or CH; W is selected from N or C; $R^8$ is absent or is selected from hydrogen, halogen, $C_{1-4}$ alkyl, $C_{1-4}$ alkenyl, $C_{1-4}$ alkynyl, $C_{1-4}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$alkoxy, $C_{1-4}$haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$ and $SO_2R_a$, wherein $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided compounds of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein

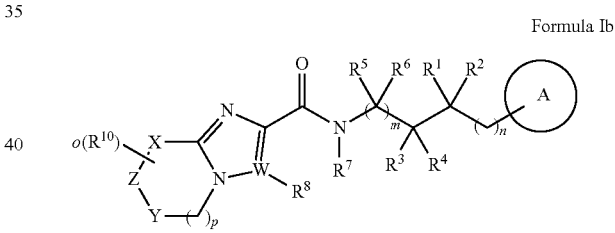

Formula Ib wherein A is selected from

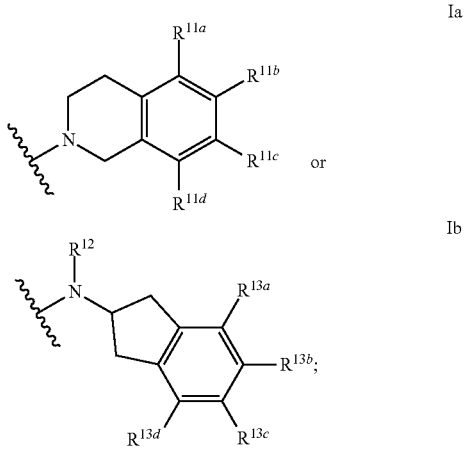

Ia

Ib n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{11a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

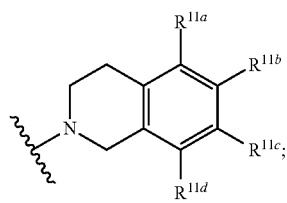

Ia n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, and $R^{11d}$ are independently selected from hydrogen, halogen, cyano, $C_{1-6}$ alkyl, $C_{1-6}$haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

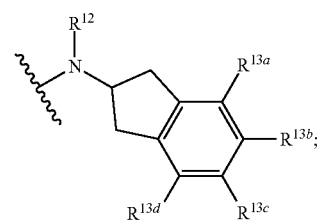

Ib n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

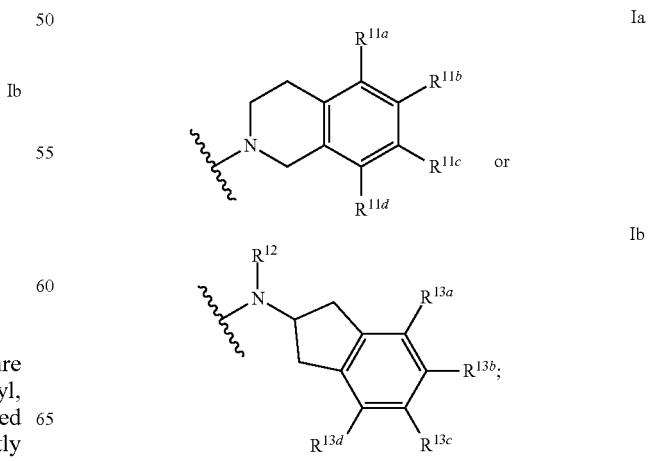

n is 0; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

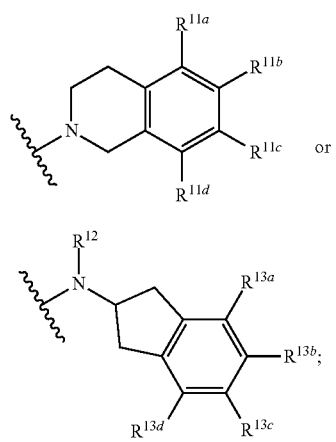

n is 0 or 1; m is 1; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13a}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SON-R_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from n is 0 or 1; m is 0-2; p is 1; o is 1-3; $R^1$, $R^2$, $R^3$, $R^4$, $R^5$, and $R^6$ are independently selected from hydrogen, halogen, hydroxyl or $C_{1-6}$ alkyl; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SON-R_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

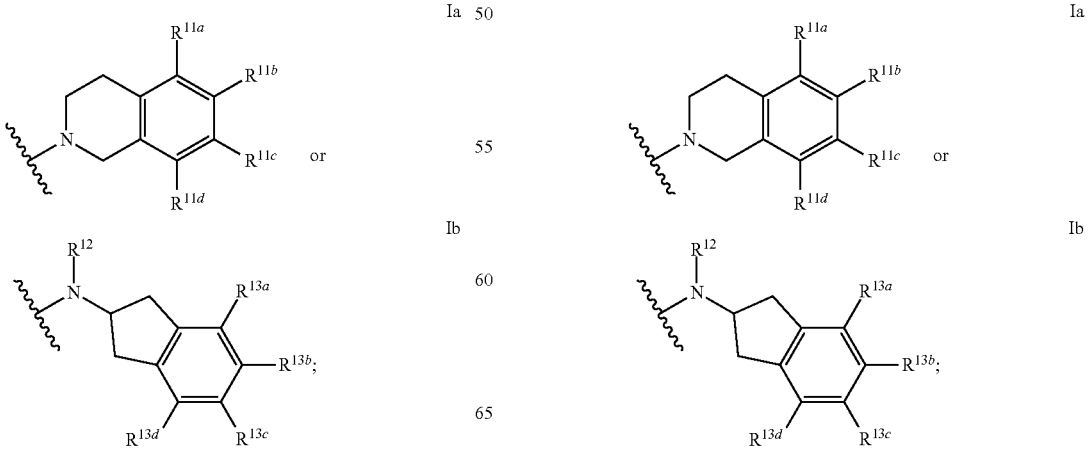

n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13a}$ are independently selected from hydrogen, halogen, cyano, $C_{1-6}$ alkyl, $C_{1-6}$ haloalkyl, or $C_{1-6}$ alkoxy; X is $CH_2$, Y, and Z are independently selected from $CR^{10}$, $NR^{10}$, or O; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from n is 0 or 1; m is 0-2; p is 1; o is 1-3; $R^1$, $R^2$, $R^3$, and $R^4$ are independently selected from hydrogen, halogen, hydroxyl, or $C_{1-6}$ alkyl, wherein $C_{1-6}$ alkyl is optionally substituted with hydroxyl, or halogen; $R^5$, and $R^6$ are independently selected from hydrogen, $C_{1-6}$ alkyl, or halogen, wherein $C_{1-6}$ alkyl is optionally substituted with hydroxyl, or halogen; $R^7$, and $R^{12}$ are independently selected from hydrogen, or $C_{1-6}$ alkyl; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

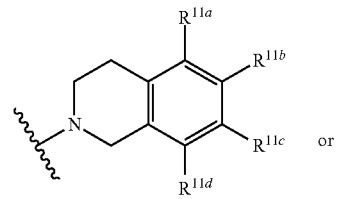

Ia

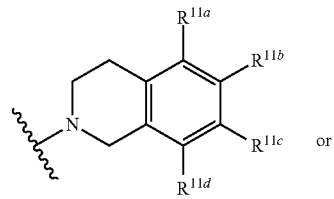

Ia

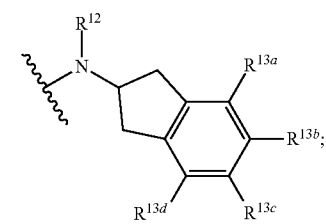

Ib

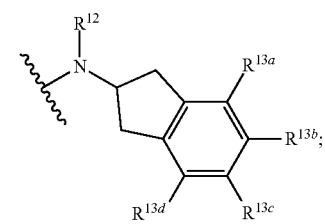

Ib n is 0 or 1; m is 0 or 1; p is 1; o is 1-3; $R^1$, $R^2$, $R^3$, and $R^4$ are independently selected from hydrogen, halogen, hydroxyl, or $C_{1-5}$ alkyl, wherein $C_{1-5}$ alkyl is optionally substituted with hydroxyl, or halogen; $R^5$, and $R^6$ are independently selected from hydrogen, $C_{1-5}$ alkyl, or halogen, wherein $C_{1-5}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13a}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^9$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

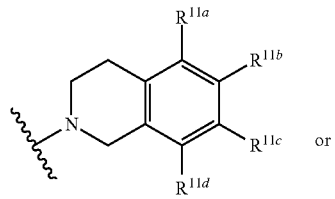

Ia

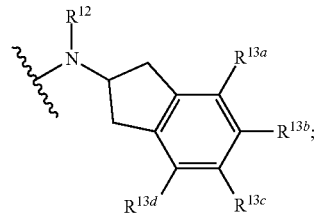

Ib n is 0 or 1; m is 0 or 1; p is 1; o is 1-3; $R^1$, $R^2$, $R^3$, and $R^4$ are independently selected from hydrogen, halogen, hydroxyl, or $C_{1-5}$ alkyl, wherein $C_{1-5}$ alkyl is optionally substituted with hydroxyl, or halogen; $R^5$, and $R^6$ are independently selected from hydrogen, $C_{1-5}$ alkyl, or halogen, wherein $C_{1-5}$ alkyl is optionally substituted with hydroxyl, or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13a}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^9$, $NR^{10}$, O, or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

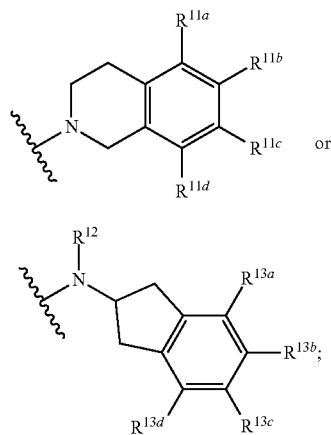

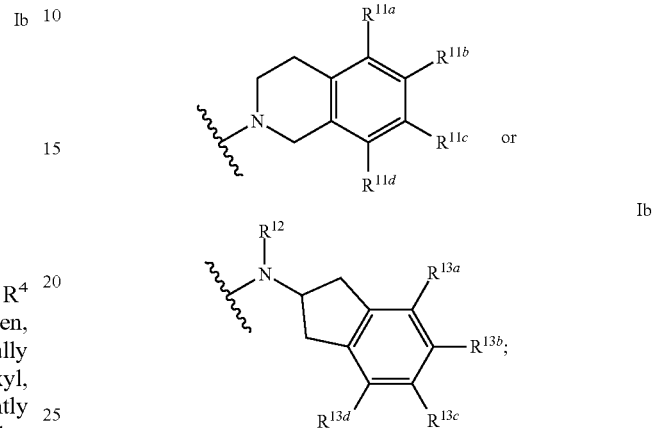

n is 0 or 1; m is 0 or 1; p is 1; o is 1-3; $R^1$, $R^2$, $R^3$, and $R^4$ are independently selected from hydrogen, halogen, hydroxyl, or $C_{1-4}$ alkyl, wherein $C_{1-4}$ alkyl is optionally substituted with one or more groups selected from hydroxyl, chloro, bromo, fluoro, or iodo; $R^5$, and $R^6$ are independently selected from hydrogen, $C_{1-4}$ alkyl, or halogen, wherein $C_{1-4}$ alkyl is optionally substituted with one or more groups selected from hydroxyl, chloro, bromo, fluoro, or iodo; $R^7$, and $R^{12}$ are independently selected from hydrogen or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from n is 0 or 1; m is 0 or 1; p is 1; o is 1-3; $R^1$, $R^2$, $R^3$, $R^4$, $R^5$, and $R^6$ are independently selected from hydrogen, halogen, hydroxyl, or $C_{1-4}$ alkyl; $R^7$, and $R^{12}$ are independently selected from hydrogen or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$ and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O or S; W is selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

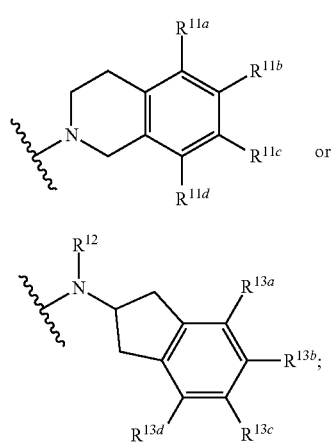

n is 0 or 1; m is 0 or 1; p is 1; o is 1-3; $R^1$, $R^2$, $R^3$, and $R^4$ are independently selected from hydrogen, halogen, hydroxyl, or $C_{1-4}$ alkyl, wherein $C_{1-4}$ alkyl is optionally substituted with one or more groups selected from hydroxyl, chloro, bromo, fluoro, or iodo; $R^5$, and $R^6$ are independently selected from hydrogen, $C_{1-4}$ alkyl, or halogen, wherein $C_{1-4}$ alkyl is optionally substituted with one or more groups selected from hydroxyl, chloro, bromo, fluoro, or iodo; $R^7$, and $R^{12}$ are independently selected from hydrogen or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$, O or S; W is C; $R^8$ is is selected from hydrogen, halogen, or $C_{1-6}$ alkyl; $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

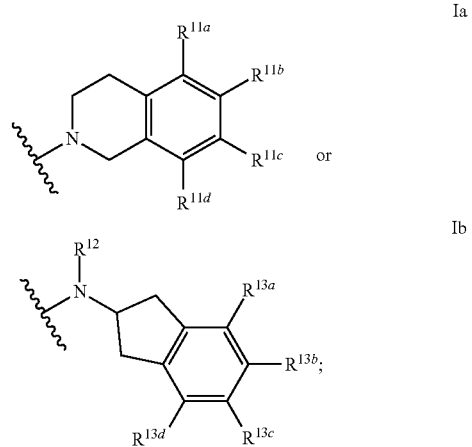

n is 0 or 1; m is 0 or 1; p is 1; o is 1-3; $R^1$, $R^2$, $R^3$, and $R^4$ are independently selected from hydrogen, halogen, hydroxyl, or $C_{1-4}$ alkyl, wherein $C_{1-4}$ alkyl is optionally substituted with one or more groups selected from hydroxyl, fluoro, or chloro; $R^5$, and $R^6$ are independently selected from hydrogen, $C_{1-4}$ alkyl or halogen, wherein $C_{1-4}$ alkyl is optionally substituted with one or more groups selected from hydroxyl, chloro, bromo, fluoro, or iodo; $R^7$, and $R^{12}$ are independently selected from hydrogen or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O or S; W is selected from N or C; $R^8$ is absent or is selected from hydrogen, halogen, $C_{1-4}$ alkyl, $C_{2-4}$ alkenyl, $C_{2-4}$ alkynyl, $C_{1-4}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, $C_{1-4}$ alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, cyano, $C_{1-4}$ alkyl, $C_{1-4}$ haloalkyl, $C_{1-4}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-4}$ alkyl, $C_{3-6}$cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

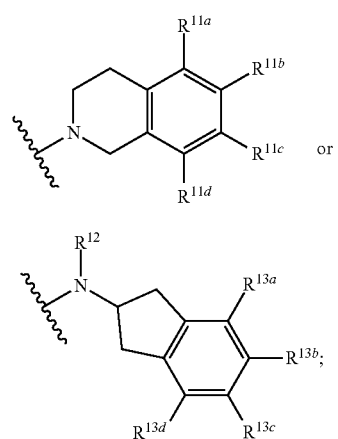

n is 0 or 1; m is 0 or 1; p is 1; o is 1-3; $R^1$, $R^2$, $R^3$, and $R^4$ are independently selected from hydrogen, or hydroxyl; $R^5$, and $R^6$ are independently selected from hydrogen, $C_{1-4}$ alkyl, or halogen, wherein $C_{1-4}$ alkyl is optionally substituted with hydroxyl, chloro, bromo, fluoro, or iodo; $R^7$, and $R^{12}$ are independently selected from hydrogen, or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O, or S; W is selected from N or C; $R^8$ is absent or is selected from hydrogen, halogen, $C_{1-4}$ alkyl, $C_{2-4}$ alkenyl, $C_{2-4}$ alkynyl, $C_{1-4}$haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SON-R_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

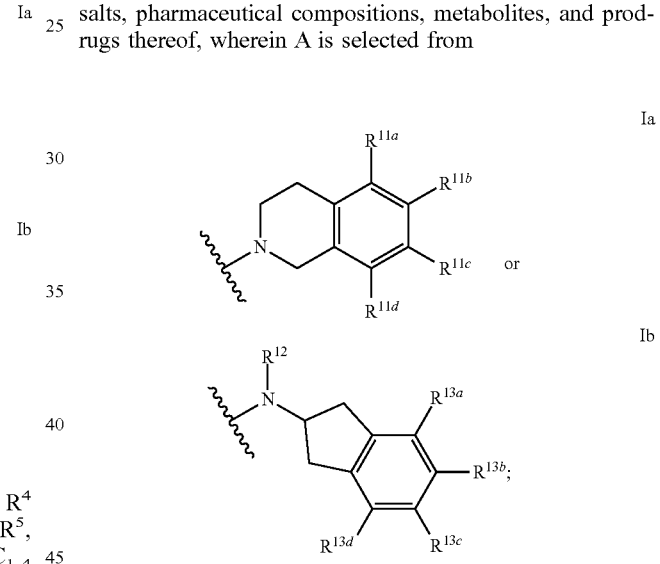

n is 0 or 1; m is 0 or 1; p is 1; o is 1-3; $R^1$, $R^2$, $R^3$, and $R^4$ are independently selected from hydrogen, halogen, hydroxyl or $C_{1-4}$ alkyl, wherein $C_{1-4}$ alkyl is optionally substituted with one or more substituents selected from hydroxyl, fluoro, or chloro; $R^5$, and $R^6$ are independently selected from hydrogen, $C_{1-4}$ alkyl, or halogen, wherein $C_{1-4}$ alkyl is optionally substituted with one or more substituents selected from hydroxyl, chloro, bromo, fluoro, or iodo; $R^7$, and $R^{12}$ are independently selected from hydrogen, or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen, hydroxyl, or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy; X, Y, and Z are independently selected from $CR^{10}$, $NR^{10}$ or O or S; W is C; $R^8$ is selected from hydrogen, halogen, $C_{1-4}$ alkyl, $C_{2-4}$ alkenyl, $C_{2-4}$ alkynyl, $C_{1-4}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

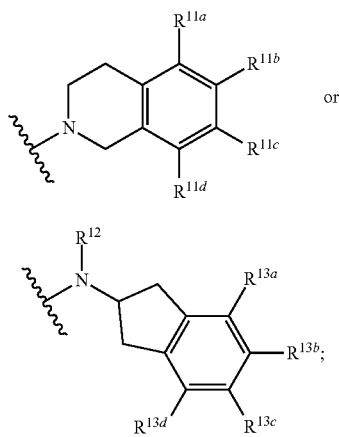

n is 0 or 1; m is 0 or 1; p is 1; o is 1-3; $R^1$, $R^2$, $R^3$, $R^4$, $R^5$, and $R^6$ are independently selected from group consisting of hydrogen, hydroxyl, or $C_{1-4}$ alkyl; $R^7$, and $R^{12}$ are independently selected from hydrogen, or $C_{1-4}$ alkyl, wherein $C_{1-4}$ alkyl is optionally substituted with $C_6$ aryl, and wherein $C_6$ aryl is optionally substituted with one or more groups selected from $C_{1-4}$ alkyl, $C_{1-4}$ alkoxy, halogen or hydroxyl; $R^{11a}$, $R^{11b}$, $R^{11c}$, $R^{11d}$, $R^{13a}$, $R^{13b}$, $R^{13c}$, and $R^{13d}$ are independently selected from hydrogen; X, and Y are independently selected from $CR^{10}$, $NR^{10}$ or O; Z is O; W is C; $R^8$ is hydrogen; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

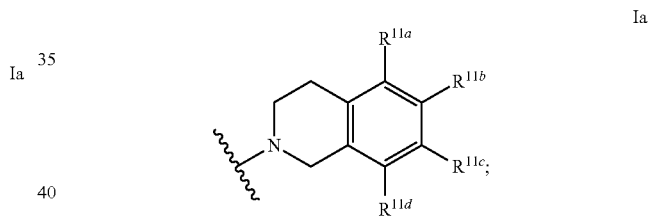

n is 0 or 1; m is 1; p is 1; o is 1-3; $R^1$, $R^2$, $R^3$, $R^4$, $R^5$, and $R^6$ are independently selected from group consisting of hydrogen, hydroxyl, or $C_{1-4}$ alkyl; $R^7$ is from hydrogen, or $C_{1-4}$ alkyl; $R^{11a}$, $R^{11b}$, $R^{11c}$, and $R^{11d}$ are independently selected from hydrogen; X is $CR^{10}$; Y is selected from $CR^{10}$, or O; Z is selected from $CR^{10}$, $NR^{10}$ or O; W is C; $R^8$ is hydrogen; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, $C_{3-6}$ cycloalkyl, $C(O)R_b$, cyano, $C_{1-6}$ alkyl, $C_{1-6}$ haloalkyl, $C_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with C(O)R$_b$, and wherein R$_a$, R$_b$, and R$_c$ are independently selected from hydrogen, C$_{1-6}$ alkyl, C$_{3-6}$ cycloalkyl, C$_{5-6}$ aryl, C$_{3-15}$ heterocyclyl or C$_{3-15}$ heteroaryl, wherein C$_{5-6}$ aryl, and C$_{3-15}$ heteroaryl are optionally substituted with one or more substituents selected from halogen, cyano, or C$_{1-6}$ alkyl; or R$_a$ and R$_b$ can be taken together to form a 5-10 membered monocyclic or bicyclic, saturated or unsaturated heterocyclic ring with 1-3 heteroatoms selected from N, S, or O.

In an embodiment of the present disclosure, there is provided a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is

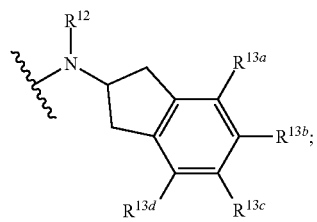

Ib n is 0 or 1; m is 1; p is 1; o is 1-3; R$^1$, R$^2$, R$^3$, R$^4$, R$^5$, and R$^6$ are independently selected from group consisting of hydrogen, hydroxyl, or C$_{1-4}$ alkyl; R$^7$, and R$^{12}$ are independently selected from hydrogen, or C$_{1-4}$ alkyl, wherein C$_{1-4}$ alkyl is optionally substituted with C$_6$ aryl, and wherein C$_6$ aryl is optionally substituted with one or more groups selected from C$_{1-4}$ alkyl, C$_{1-4}$ alkoxy, halogen or hydroxyl; R$^{13a}$, R$^{13b}$, R$^{13c}$, and R$^{13d}$ are independently selected from hydrogen; X is CR$^{10}$; Y is selected from CR$^{10}$, or O; Z is selected from CR$^{10}$, NR$^{10}$ or O; W is C; R$^8$ is hydrogen; and R$^{10}$ is selected from hydrogen, halogen, hydroxyl, oxo, nitro, cyano, azido, nitroso, amino, hydrazino, formyl, C$_{1-6}$ alkyl, C$_{1-6}$ haloalkyl, C$_{1-6}$ alkoxy, C$_{1-6}$ haloalkoxy, C$_{3-6}$ cycloalkyl, C$_{5-6}$ aryl, C$_{1-6}$ alkylamino, COOR$_a$, C(O)R$_b$, C(S)R$_a$, C(O)NR$_a$R$_b$, C(S)NR$_a$R$_b$, NR$_a$C(O)NR$_b$R$_c$, N(R$_a$)SOR$_b$, N(R$_a$)SO$_2$R$_b$, NR$_a$C(O)OR$_b$, NR$_a$R$_b$, NR$_a$C(S)NR$_b$R$_c$, NR$_a$C(O)R$_b$, NR$_a$C(S)R$_b$, SONR$_a$R$_b$, SO$_2$NR$_a$R$_b$, OC(O)NR$_a$R$_b$, OR$_a$C(O)OR$_b$, OC(O)NR$_a$R$_b$, OC(O)R$_a$, OR$_a$, R$_a$NR$_b$R$_c$, R$_a$OR$_b$, SR$_a$, SOR$_a$, SO$_2$R$_a$ or 3-15 membered saturated or unsaturated heterocyclyl or heteroaryl ring with 1-5 heteroatoms selected from N, S or O, wherein C$_{5-6}$ aryl, C$_{3-6}$ cycloalkyl, and 3-15 membered saturated or unsaturated heterocyclyl or heteroaryl ring are optionally substituted with one or more groups selected from halogen, hydroxyl, oxo, C$_{3-6}$ cycloalkyl, C(O)R$_b$, cyano, C$_{1-6}$ alkyl, C$_{1-6}$ haloalkyl, C$_{1-6}$ alkoxy, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with C(O)R$_b$, and wherein R$_a$, R$_b$, and R$_c$ are independently selected from hydrogen, C$_{1-6}$ alkyl, C$_{3-6}$ cycloalkyl, C$_{5-6}$ aryl, C$_{3-15}$ heterocyclyl or C$_{3-15}$ heteroaryl, wherein C$_{5-6}$ aryl, and C$_{3-15}$ heteroaryl are optionally substituted with one or more substituents selected from halogen, cyano, or C$_{1-6}$ alkyl; or R$_a$ and R$_b$ can be taken together to form a 5-10 membered monocyclic or bicyclic, saturated or unsaturated heterocyclic ring with 1-3 heteroatoms selected from N, S, or O.

In an embodiment, the present disclosure relates to a compound of Formula I, Formula Ia, or Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, which is selected from a group consisting of:
N-(3-(3,4-dihydroisoquinolin-2(1H)-yl)-2-hydroxypropyl)-6-(trifluoromethyl)imidazo[1,2-a]pyridine-2-carboxamide (Example 1),
N-(3-(3,4-dihydroisoquinolin-2(1H)-yl)-2-hydroxypropyl)-6-methylimidazo[1,2-a]pyridine-2-carboxamide (Example 2),
N-(2-(3,4-dihydroisoquinolin-2(1H)-yl)-1-hydroxyethyl)-7-(4-fluorophenyl) imidazo[1,2-a]pyridine-2-carboxamide (Example 3),
(S)—N-(3-(3,4-dihydroisoquinolin-2(1H)-yl)-2-hydroxypropyl)-6-(1-ethyl-1H-pyrazol-4-yl)imidazo[1,2-a]pyridine-2-carboxamide (Example 4),
(S)—N-(3-(3,4-dihydroisoquinolin-2(1H)-yl)-2-hydroxypropyl)-6-(5-propyl-1,2,4-oxadiazol-3-yl)imidazo[1,2-a]pyridine-2-carboxamide (Example 5),
(S)—N-(3-(3,4-dihydroisoquinolin-2(1H)-yl)-2-hydroxypropyl)-6-(5-methyl-1,2,4-oxadiazol-3-yl)imidazo[1,2-a]pyridine-2-carboxamide (Example 6)
(S)—N-(3-(3,4-dihydroisoquinolin-2(1H)-yl)-2-hydroxypropyl)-6-(5-(trifluoromethyl)-1,2,4-oxadiazol-3-yl)imidazo[1,2-a]pyridine-2-carboxamide (Example 7),
(S)—N-(3-(3,4-dihydroisoquinolin-2(1H)-yl)-2-hydroxypropyl)-6(trifluoromethyl) imidazo[1,2-a]pyridine-2-carboxamide (Example 8),
N-(3-(3,4-dihydroisoquinolin-2(1H)-yl)-2-hydroxypropyl)-6-methoxyimidazo [1,2a]pyridine-2-carboxamide (Example 9),
N-(3-(3,4-dihydroisoquinolin-2(1H)-yl)-2-hydroxypropyl)-6-phenylimidazo[1,2-a]pyridine-2-carboxamide (Example 10),
N-(3-(3,4-dihydroisoquinolin-2(1H)-yl)-2-hydroxypropyl)-6-(4-fluorophenyl) imidazo[1,2-a]pyridine-2-carboxamide (Example 11),
(S)—N-(3-(3,4-dihydroisoquinolin-2(1H)-yl)-2-hydroxypropyl)-6-isopropylimidazo [1,2-a]pyridine-2-carboxamide (Example 12),
(S)—N-(3-(3,4-dihydroisoquinolin-2(1H)-yl)-2-hydroxypropyl)-6-(1-methyl-1H-pyrazol-4-yl)imidazo[1,2-a] pyridine-2-carboxamide (Example 13),
(S)-6-(4-cyanophenyl)-N-(3-(3,4-dihydroisoquinolin-2(1H)-yl)-2-hydroxypropyl) imidazo[1,2-a]pyridine-2-carboxamide (Example 14),
(S)—N-(3-(3,4-dihydroisoquinolin-2(1H)-yl)-2-hydroxypropyl)-6-(3,5-dimethyl isoxazol-4-yl)imidazo[1,2-a]pyridine-2-carboxamide (Example 15),
(S)-6-(3,5-difluorophenyl)-N-(3-(3,4-dihydroisoquinolin-2(1H)-yl)-2-hydroxypropyl)imidazo[1,2-a]pyridine-2-carboxamide (Example 16),
(S)—N-(3-(3,4-dihydroisoquinolin-2(1H)-yl)-2-hydroxypropyl)-6-(4fluorophenyl) imidazo[1,2-a]pyridine-2-carboxamide (Example 17),
(S)—N-(3-(3,4-dihydroisoquinolin-2(1H)-yl)-2-hydroxypropyl)-6-(1-isobutyl-1H-pyrazol-4-yl)imidazo[1,2-a]pyridine-2-carboxamide (Example 18),
(S)-6-(3,6-dihydro-2H-pyran-4-yl)-N-(3-(3,4-dihydroisoquinolin-2(1H)-yl)-2-hydroxypropyl)imidazo[1,2-a]pyridine-2-carboxamide (Example 19),
N—((S)-3-(3,4-dihydroisoquinolin-2(1H)-yl)-2-hydroxypropyl)-6-(1-((R)-tetrahydrofuran-3-yl)-1H-pyrazol-4-yl) imidazo[1,2-a]pyridine-2-carboxamide (Example 20), (S)—N-(3-(3,4-dihydroisoquinolin-2(1H)-yl)-2-hydroxypropyl)-6-(1H-pyrazol-4-yl)imidazo[1,2-a]pyridine-2-carboxamide (Example 21), (S)—N-(3-(3,4-dihydroisoquinolin-2(1H)-yl)-2-hydroxypropyl)-6-(1-(oxetan-3-yl)-1H-pyrazol-4-yl)imidazo[1,2-a]pyridine-2-carboxamide (Example 22), (S)-6-(1-(1-acetylazetidin-3-yl)-1H-pyrazol-4-yl)-N-(3-(3,4-dihydroisoquinolin-2(1H)-yl)-2-hydroxypropyl)imidazo[1,2-a]pyridine-2-carboxamide (Example 23), (S)—N-(3-(3,4-dihydroisoquinolin-2(1H)-yl)-2-hydroxypropyl)-6-(5-isopropyl-1,2,4-oxadiazol-3-yl)imidazo[1,2-a]pyridine-2-carboxamide (Example 24), (S)-6-(5-cyclopropyl-1,2,4-oxadiazol-3-yl)-N-(3-(3,4-dihydroisoquinolin-2(1H)-yl)-2-hydroxypropyl)imidazo[1,2-a]pyridine-2-carboxamide (Example 25), (S)—N-(3-(3,4-dihydroisoquinolin-2(1H)-yl)-2-hydroxypropyl)-6-(tetrahydro-2H-pyran-4-yl)imidazo[1,2-a]pyridine-2-carboxamide (Example-26), (S)-6-(1-acetylpiperidin-4-yl)-N-(3-(3,4-dihydroisoquinolin-2(1H)-yl)-2-hydroxypropyl)imidazo[1,2-a]pyridine-2-carboxamide (Example 27), (S)—N-(3-(3,4-dihydroisoquinolin-2(1H)-yl)-2-hydroxypropyl)-6-(2-methylpyrimidin-5-yl)imidazo[1,2-a]pyridine-2-carboxamide (Example 28), (S)—N-(3-(3,4-dihydroisoquinolin-2(1H)-yl)-2-hydroxypropyl)-6-(6-methylpyridin-3-yl)imidazo[1,2-a]pyridine-2-carboxamide (Example 29), (S)—N-(3-(3,4-dihydroisoquinolin-2(1H)-yl)-2-hydroxypropyl)-6-(6-methylpyridazin-3-yl)imidazo[1,2-a]pyridine-2-carboxamide (Example 30), (S)—N-(3-(3,4-dihydroisoquinolin-2(1H)-yl)-2-hydroxypropyl)-6-(2-methylthiazol-5-yl)imidazo[1,2-a]pyridine-2-carboxamide (Example 31), (S)—N-(3-(3,4-dihydroisoquinolin-2(1H)-yl)-2-hydroxypropyl)-6-(4,5-dimethylthiazol-2-yl)imidazo[1,2-a]pyridine-2-carboxamide (Example 32), (S)-6-(5-chloropyridin-2-yl)-N-(3-(3,4-dihydroisoquinolin-2(1H)-yl)-2-hydroxypropyl)imidazo[1,2-a]pyridine-2-carboxamide (Example 33), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyridine-2-carboxamide (Example 34), (S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyridine-2-carboxamide (Example 35), (S)—N-(3-(3,4-dihydroisoquinolin-2(1H)-yl)-2-hydroxypropyl)-6-(1-methyl-1H-1,2,3-triazol-4-yl)imidazo[1,2-a]pyridine-2-carboxamide (Example 36), (S)—N-(3-(3,4-dihydroisoquinolin-2(1H)-yl)-2-hydroxypropyl)-6-(1-isopropyl-1H-1,2,3-triazol-4-yl)imidazo[1,2-a]pyridine-2-carboxamide (Example 37), (S)—N2-(3-(3,4-dihydroisoquinolin-2(1H)-yl)-2-hydroxypropyl)-N6-methylimidazo[1,2-a]pyridine-2,6-dicarboxamide (Example 38), (S)-6-acetamido-N-(3-(3,4-dihydroisoquinolin-2(1H)-yl)-2-hydroxypropyl)imidazo[1,2-a]pyridine-2-carboxamide (Example 39), (S)—N-(3-(3,4-dihydroisoquinolin-2(1H)-yl)-2-hydroxypropyl)-6-sulfamoylimidazo[1,2-a]pyridine-2-carboxamide (Example 40), (S)—N-(3-(3,4-dihydroisoquinolin-2(1H)-yl)-2-hydroxypropyl)-6-(methylsulfonamido)imidazo[1,2-a]pyridine-2-carboxamide (Example 41), ((S)—N-(3-(3,4-dihydroisoquinolin-2(1H)-yl)-2-hydroxypropyl)-6-(trifluoromethyl)imidazo[1,2-a]pyrimidine-2-carboxamide (Example 42), (S)—N-(3-(3,4-dihydroisoquinolin-2(1H)-yl)-2-hydroxypropyl)-6-(1-methyl-1H-pyrazol-4-yl)imidazo[1,2-a]pyrimidine-2-carboxamide (Example 43), (S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyrimidine-2-carboxamide (Example 44), (S)—N-(3-(3,4-dihydroisoquinolin-2(1H)-yl)-2-hydroxypropyl)-6-(1-methyl-1H-pyrazol-4-yl)imidazo[1,2-a]pyrazine-2-carboxamide (Example 45), (S)—N-(3-(3,4-dihydroisoquinolin-2(1H)-yl)-2-hydroxypropyl)-6-(1-methyl-1H-pyrazol-4-yl)imidazo[1,2-b]pyridazine-2-carboxamide (Example 46), (S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyrazine-2-carboxamide (Example 47), (S)—N-(3-(3,4-dihydroisoquinolin-2(1H)-yl)-2-hydroxypropyl)-6-(1-methyl-2-oxo-1,2-dihydropyridin-4-yl)imidazo[1,2-b]pyridazine-2-carboxamide (Example 48), (S)-6-(1-acetylpiperidin-4-yl)-N-(3-(3,4-dihydroisoquinolin-2(1H)-yl)-2-hydroxypropyl)imidazo[1,2-b]pyridazine-2-carboxamide (Example 49), (S)—N-(3-(3,4-dihydroisoquinolin-2(1H)-yl)-2-hydroxypropyl)-6-(trifluoromethyl)imidazo[1,2-b]pyridazine-2-carboxamide (Example 50), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 51), (S)-6-(1-acetylpiperidin-4-yl)-N-(3-(3,4-dihydroisoquinolin-2(1H)-yl)-2-hydroxypropyl)imidazo[1,2-a]pyrazine-2-carboxamide (Example 52), (S)—N-(3-(3,4-dihydroisoquinolin-2(1H)-yl)-2-hydroxypropyl)-6-(trifluoromethyl)imidazo[1,2-a]pyrazine-2-carboxamide (Example 53), (S)—N-(3-(3,4-dihydroisoquinolin-2(1H)-yl)-2-hydroxypropyl)-3-methyl-6-(trifluoromethyl)imidazo[1,2-b]pyridazine-2-carboxamide (Example 54), (S)—N-(3-(3,4-dihydroisoquinolin-2(1H)-yl)-2-hydroxypropyl)-3,6-dimethylimidazo[1,2-a]pyrazine-2-carboxamide (Example 55), (S)—N-(3-(3,4-dihydroisoquinolin-2(1H)-yl)-2-hydroxypropyl)-6-methylimidazo[1,2-b]pyridazine-2-carboxamide (Example 56), (S)—N-(3-(3,4-dihydroisoquinolin-2(1H)-yl)-2-hydroxypropyl)-6-(trifluoromethyl)imidazo[1,2-a]pyrazine-2-carboxamide (Example 57), (S)-6-(3,3-difluoroazetidin-1-yl)-N-(3-(3,4-dihydroisoquinolin-2(1H)-yl)-2-hydroxypropyl)imidazo[1,2-a]pyrazine-2-carboxamide (Example 58), (S)-6-(3,3-difluoroazetidin-1-yl)-N-(3-(3,4-dihydroisoquinolin-2(1H)-yl)-2-hydroxypropyl)imidazo[1,2-a]pyridine-2-carboxamide (Example 59), (S)—N-(3-(3,4-dihydroisoquinolin-2(1H)-yl)-2-hydroxypropyl)-5-(trifluoromethyl)pyrazolo[1,5-a]pyrimidine-2-carboxamide (Example 60), (S)—N-(3-(3,4-dihydroisoquinolin-2(1H)-yl)-2-hydroxypropyl)-6-(3-hydroxyoxetan-3-yl)imidazo[1,2-a]pyridine-2-carboxamide (Example 61), (S)—N-(3-(3,4-dihydroisoquinolin-2(1H)-yl)-2-hydroxypropyl)-5-(1-methyl-1H-pyrazol-4-yl)pyrazolo[1,5-a]pyrimidine-2-carboxamide (Example 62), (S)—N-(3-(3,4-dihydroisoquinolin-2(1H)-yl)-2-hydroxypropyl)-5-(1-methyl-2-oxo-1,2-dihydropyridin-4-yl)pyrazolo[1,5-a]pyrimidine-2-carboxamide (Example 63), (S)—N-(3-(3,4-dihydroisoquinolin-2(1H)-yl)-2-hydroxypropyl)-3-methyl-6-(1-methyl-1H-pyrazol-4-yl)imidazo[1,2-a]pyrazine-2-carboxamide (Example 64), (S)—N-(3-(3,4-dihydroisoquinolin-2(1H)-yl)-2-hydroxypropyl)-3-methyl-6-(1-methyl-2-oxo-1,2-dihydropyridin-4-yl)imidazo[1,2-a]pyrazine-2-carboxamide (Example 65), (S)—N-(3-(3,4-dihydroisoquinolin-2(1H)-yl)-2-hydroxypropyl)-3-methyl-6-(1-methyl-6-oxo-1,6-dihydropyridin-3-yl)imidazo[1,2-a]pyrazine-2-carboxamide (Example 66), (S)—N-(3-(3,4-dihydroisoquinolin-2(1H)-yl)-2-hydroxypropyl)-5-methylpyrazolo[1,5-a]pyrimidine-2-carboxamide (Example 67), (S)—N-(3-(3,4-dihydroisoquinolin-2(1H)-yl)-2-hydroxypropyl)-3-fluoro-5-(trifluoromethyl)pyrazolo[1,5-a]pyrimidine-2-carboxamide (Example 68), (S)-6-(azetidin-1-yl)-N-(3-(3,4-dihydroisoquinolin-2(1H)-yl)-2-hydroxypropyl)imidazo[1,2-a]pyridine-2-carboxamide (Example 69), N—((S)-3-(3,4-dihydroisoquinolin-2(1H)-yl)-2-hydroxypropyl)-6-(3-fluoropyrrolidin-1-yl)imidazo[1,2-a]pyridine-2-carboxamide (Example 70), (S)—N-(3-(3,4-dihydroisoquinolin-2(1H)-yl)-2-hydroxypropyl)-6-(4-methylpiperazin-1-yl)imidazo[1,2-a]pyridine-2-carboxamide (Example 71), (S)—N-(3-(3,4-dihydroisoquinolin-2(1H)-yl)-2-hydroxypropyl)-6-morpholinoimidazo[1,2-a]pyridine-2-carboxamide (Example 72), N—((S)-3-(3,4-dihydroisoquinolin-2(1H)-yl)-2-hydroxypropyl)-6-(3-fluoropyrrolidin-1-yl)imidazo[1,2-a]pyrazine-2-carboxamide (Example 73), (S)-6-(4-cyanophenyl)-N-(3-(3,4-dihydroisoquinolin-2(1H)-yl)-2-hydroxypropyl)imidazo[1,2-a]pyrazine-2-carboxamide (Example 74), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 75, N-((2S,3S)-4-(3,4-dihydroisoquinolin-2(1H)-yl)-2,3-dihydroxybutyl)-6-(trifluoromethyl)imidazo[1,2-a]pyridine-2-carboxamide (Example 76), N-((2R,3R)-4-(3,4-dihydroisoquinolin-2(1H)-yl)-2,3-dihydroxybutyl)-6-(trifluoromethyl)imidazo[1,2-a]pyridine-2-carboxamide (Example 77), N-((2S,3S)-4-(3,4-dihydroisoquinolin-2(1H)-yl)-2,3-dihydroxybutyl)-6-(5-methyl-1,2,4-oxadiazol-3-yl)imidazo[1,2-a]pyridine-2-carboxamide (Example-78), N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide (Example 79), N-((2S,3S)-4-(3,4-dihydroisoquinolin-2(1H)-yl)-2,3-dihydroxybutyl)-6-(1-methyl-2-oxo-1,2-dihydropyridin-4-yl)imidazo[1,2-a]pyridine-2-carboxamide (Example 80), N-((2S,3S)-4-(3,4-dihydroisoquinolin-2(1H)-yl)-2,3-dihydroxybutyl)-6-(1-methyl-1H-pyrazol-4-yl)imidazo[1,2-a]pyridine-2-carboxamide (Example 81), (S)—N-(3-(6-fluoro-3,4-dihydroisoquinolin-2(1H)-yl)-2-hydroxypropyl)-6-(1-methyl-1H-pyrazol-4-yl)imidazo[1,2-a]pyridine-2-carboxamide (Example 82), (S)—N-(3-(6-fluoro-3,4-dihydroisoquinolin-2(1H)-yl)-2-hydroxypropyl)-6-(trifluoromethyl)imidazo[1,2-b]pyridazine-2-carboxamide (Example 83), (S)—N-(3-(6-fluoro-3,4-dihydroisoquinolin-2(1H)-yl)-2-hydroxypropyl)-6-(trifluoromethyl)imidazo[1,2-a]pyrazine-2-carboxamide (Example 84), (S)—N-(3-(6-fluoro-3,4-dihydroisoquinolin-2(1H)-yl)-2-hydroxypropyl)-6-(1-methyl-2-oxo-1,2-dihydropyridin-4-yl)imidazo[1,2-a]pyrazine-2-carboxamide (Example 85), (S)-6-(difluoromethyl)-N-(3-(3,4-dihydroisoquinolin-2(1H)-yl)-2-hydroxypropyl)imidazo[1,2-a]pyridine-2-carboxamide (Example 86), 6-(difluoromethyl)-N—((S)-3-(3,4-dihydroisoquinolin-2(1H)-yl)-2-hydroxypropyl)-5,6,7,8-tetrahydroimidazo[1,2-a]pyridine-2-carboxamide (Example 87), (R)—N-(3-(3,4-dihydroisoquinolin-2(1H)-yl)-2-hydroxypropyl)-N-methyl-6-(trifluoromethyl)imidazo[1,2-a]pyridine-2-carboxamide (Example 88), (R)—N-(3-(3,4-dihydroisoquinolin-2(1H)-yl)-2-hydroxypropyl)-N-methyl-6-(trifluoromethyl)imidazo[1,2-a]pyrazine-2-carboxamide (Example 89), (R)—N-(3-(3,4-dihydroisoquinolin-2(1H)-yl)-2-hydroxypropyl)-N-methyl-5-(trifluoromethyl)pyrazolo[1,5-a]pyrimidine-2-carboxamide (Example 90), (R)—N-(3-(3,4-dihydroisoquinolin-2(1H)-yl)-2-hydroxypropyl)-N-methyl-6-(trifluoromethyl)imidazo[1,2-b]pyridazine-2-carboxamide (Example 91), (R)—N-(3-(3,4-dihydroisoquinolin-2(1H)-yl)-2-hydroxypropyl)-N-methyl-6-(1-methyl-1H-pyrazol-4-yl)imidazo[1,2-a]pyrazine-2-carboxamide (Example 92), (R)—N-(3-(3,4-dihydroisoquinolin-2(1H)-yl)-2-hydroxypropyl)-N-methyl-6-(1-methyl-2-oxo-1,2-dihydropyridin-4-yl)imidazo[1,2-a]pyrazine-2-carboxamide (Example 93), (R)—N-(3-(3,4-dihydroisoquinolin-2(1H)-yl)-2-hydroxypropyl)-N-methyl-6-(1-methyl-6-oxo-1,6-dihydropyridin-3-yl)imidazo[1,2-a]pyrazine-2-carboxamide (Example 94), (R)-6-(4-cyanophenyl)-N-(3-(3,4-dihydroisoquinolin-2(1H)-yl)-2-hydroxypropyl)-N-methylimidazo[1,2-a]pyrazine-2-carboxamide (Example 95), N-(3-((2,3-dihydro-1H-inden-2-yl)amino)-2-hydroxypropyl)-6-trifluoromethyl)imidazo[1,2-a]pyridine-2-carboxamide (Example 96), N-(3-((2,3-dihydro-1H-inden-2-yl)amino)-2-hydroxypropyl)-6-(tetrahydro-2H-pyran-4-yl)imidazo[1,2-a]pyridine-2-carboxamide (Example 97), 6-(1-acetylpiperidin-4-yl)-N-(3-((2,3-dihydro-1H-inden-2-yl)amino)-2-hydroxypropyl)imidazo[1,2-a]pyridine-2-carboxamide (Example 98), N-(3-((2,3-dihydro-1H-inden-2-yl)amino)-2-hydroxypropyl)-6-(1-methyl-2-oxo-1,2-dihydropyridin-4-yl)imidazo[1,2-a]pyridine-2-carboxamide (Example 99), N-(4-(3,4-dihydroisoquinolin-2(1H)-yl)-1-hydroxybutan-2-yl)-6-(trifluoromethyl)imidazo[1,2-a]pyridine-2-carboxamide (Example 100), N-(3-(3,4-dihydroisoquinolin-2(1H)-yl)-2-hydroxypropyl)-5,6,7,8 tetrahydroimidazo[1,2-a]pyridine-2-carboxamide (Example 101), N-(3-(3,4-dihydroisoquinolin-2(1H)-yl)-2-hydroxypropyl)-6-methyl-5,6,7,8-tetrahydroimidazo[1,2-a]pyridine-2-carboxamide (Example 102), N-(3-(3,4-dihydroisoquinolin-2(1H)-yl)-2-hydroxypropyl)-7-methyl-5,6,7,8-tetrahydroimidazo[1,2-a]pyridine-2-carboxamide (Example 103), 6-cyclopropyl-N—((S)-3-(3,4-dihydroisoquinolin-2(1H)-yl)-2-hydroxypropyl)-5,6,7,8-tetrahydroimidazo[1,2-a]pyridine-2-carboxamide (Example 104), N-(3-(3,4-dihydroisoquinolin-2(1H)-yl)-2-hydroxypropyl)-7-propyl-5,6,7,8 tetrahydroimidazo[1,2-a]pyridine-2-carboxamide (Example 105), N-(3-(3,4-dihydroisoquinolin-2(1H)-yl)-2-hydroxypropyl)-6-propyl-5,6,7,8-tetrahydroimidazo[1,2-a]pyridine-2-carboxamide (Example 106), (R)—N—((S)-3-(3,4-dihydroisoquinolin-2(1H)-yl)-2-hydroxypropyl)-6-methoxy-5,6,7,8-tetrahydroimidazo[1,2- a]pyridine-2-carboxamide (Example 7a) and (S)—N—((S)-3-(3,4-dihydroisoquinolin-2(1H)-yl)-2-hydroxypropyl)-6-methoxy-5,6,7,8-tetrahydroimidazo[1,2-a]pyridine-2-carboxamide (Example 107b) (Examples 107a and 7b), N—((S)-3-(3,4-dihydroisoquinolin-2(1H)-yl)-2-hydroxypropyl)-6-isopropyl-5,6,7,8-tetrahydroimidazo[1,2-a]pyridine-2-carboxamide (Example 108), N-(2-(3,4-dihydroisoquinolin-2(1H)-yl)-1-hydroxyethyl)-7-phenyl-5,6,7,8-tetrahydroimidazo[1,2-a]pyridine-2-carboxamide (Example 109), N-(3-(3,4-dihydroisoquinolin-2(1H)-yl)-2-hydroxypropyl)-6-phenyl-5,6,7,8-tetrahydroimidazo[1,2-a]pyridine-2-carboxamide (Example 110), N-(3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 111), N—((S)-3-(3,4-dihydroisoquinolin-2(1H)-yl)-2-hydroxypropyl)-6-phenyl-5,6-dihydro-8H-imidazo[2,1-c][1,4]oxazine-2-carboxamide (Example 112), N-(3-(3,4-dihydroisoquinolin-2(1H)-yl)-2-hydroxypropyl)-7-isopropyl-5,6,7,8-tetrahydroimidazo [1,2-a] pyrazine-2-carboxamide (Example 113), N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 114), N—((S)-3-(3,4-dihydroisoquinolin-2(1H)-yl)-2-hydroxypropyl)-6-(4-fluorophenyl)-5,6,7,8-tetrahydroimidazo[1,2-a]pyridine-2-carboxamide (Example 115), N—((S)-3-(3,4-dihydroisoquinolin-2(1H)-yl)-2-hydroxypropyl)-6-(4-fluorophenyl)-5,6-dihydro-8H-imidazo[2,1-c][1,4]oxazine-2-carboxamide (Example 116), N-((2S,3S)-4-(3,4-dihydroisoquinolin-2(1H)-yl)-2,3-dihydroxybutyl)-6-(trifluoromethyl)-5,6,7,8-tetrahydroimidazo[1,2-a]pyridine-2-carboxamide (Example 117), (R)-6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide (-Example 118A), (S)-6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide (Example 118B), N-3-(3,4-dihydroisoquinolin-2(1H)-yl)-2-hydroxypropyl)-N-methyl-6-(trifluoromethyl)-5,6,7,8-tetrahydroimidazo[1,2-a]pyridine-2-carboxamide (Example-119), (R)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 120A), (S)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (-Example 120B), (S)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121A), (R)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121B), (R)-6-bromo-N-(3-(3,4-dihydroisoquinolin-2(1H)-yl)-2-hydroxypropyl)imidazo[1,2-a]pyridine-2-carboxamide (Example 122), (S)-6-cyano-N-(3-(3,4-dihydroisoquinolin-2(1H)-yl)-2-hydroxypropyl)imidazo[1,2-a]pyridine-2-carboxamide (Example 123), (R)—N-(3-(3,4-dihydroisoquinolin-2(1H)-yl)-2-hydroxypropyl)imidazo[1,2-a]pyridine-2-carboxamide (Example 124), (R)-N-(3-(3,4-dihydroisoquinolin-2(1H)-yl)-2-hydroxypropyl)-6-fluoroimidazo[1,2-a]pyridine-2-carboxamide (Example 125), (R)-2-((3-(3,4-dihydroisoquinolin-2(1H)-yl)-2-hydroxypropyl)carbamoyl)imidazo[1,2-a]pyridine-6-carboxylic acid (Example 126), (S)—N-(3-(3,4-dihydroisoquinolin-2(1H)-yl)-2-hydroxypropyl)-6-(piperidine-1-carbonyl)imidazo[1,2-a]pyridine-2-carboxamide (Example 127), (S)—N6-(3,3-difluorocyclobutyl)-N2-(3-(3,4-dihydroisoquinolin-2(1H)-yl)-2-hydroxypropyl)imidazo[1,2-a]pyridine-2,6-dicarboxamide (Example 128), (S)—N-(3-(3,4-dihydroisoquinolin-2(1H)-yl)-2-hydroxypropyl)-6-(piperazine-1-carbonyl)imidazo[1,2-a]pyridine-2-carboxamide (Example 129), (S)—N6-cyclohexyl-N2-(3-(3,4-dihydroisoquinolin-2(1H)-yl)-2-hydroxypropyl)imidazo[1,2-a]pyridine-2,6-dicarboxamide (Example 130), (R)—N-(3-(3,4-dihydroisoquinolin-2(1H)-yl)-2-hydroxypropyl)-6-(2,6-diazaspiro[3.3]heptane-2-carbonyl)imidazo[1,2-a]pyridine-2-carboxamide (Example 131), N—((R)-3-(3,4-dihydroisoquinolin-2(1H)-yl)-2-hydroxypropyl)-6-(octahydropyrrolo[3,4-c]pyrrole-2-carbonyl)imidazo[1,2-a]pyridine-2-carboxamide (Example 132), N—((S)-3-(3,4-dihydroisoquinolin-2(1H)-yl)-2-hydroxypropyl)-6-(piperidine-1-carbonyl)-5,6,7,8-tetrahydroimidazo[1,2-a]pyridine-2-carboxamide (Example 133), N6-(3,3-difluorocyclobutyl)-N2-((S)-3-(3,4-dihydroisoquinolin-2(1H)-yl)-2-hydroxypropyl)-5,6,7,8-tetrahydroimidazo[1,2-a]pyridine-2,6-dicarboxamide (Example 134), N—((S)-3-(3,4-dihydroisoquinolin-2(1H)-yl)-2-hydroxypropyl)-6-(piperazine-1-carbonyl)-5,6,7,8-tetrahydroimidazo[1,2-a]pyridine-2-carboxamide (Example 135), N—((R)-3-(3,4-dihydroisoquinolin-2(1H)-yl)-2-hydroxypropyl)-6-(2,6-diazaspiro[3.3]heptane-2-carbonyl)-5,6,7,8-tetrahydroimidazo[1,2-a]pyridine-2-carboxamide (Example 136), N—((R)-3-(3,4-dihydroisoquinolin-2(1H)-yl)-2-hydroxypropyl)-6-(octahydropyrrolo[3,4-c]pyrrole-2-carbonyl)-5,6,7,8-tetrahydroimidazo[1,2-a]pyridine-2-carboxamide (Example 137), (S)-6-benzamido-N-(3-(3,4-dihydroisoquinolin-2(1H)-yl)-2-hydroxypropyl)imidazo[1,2-a]pyridine-2-carboxamide (Example 138), (S)—N-(3-(3,4-dihydroisoquinolin-2(1H)-yl)-2-hydroxypropyl)-6-(2-fluorobenzamido)imidazo[1,2-a]pyridine-2-carboxamide (Example 139), (S)-6-(cyclohexanecarboxamido)-N-(3-(3,4-dihydroisoquinolin-2(1H)-yl)-2-hydroxypropyl)imidazo[1,2-a]pyridine-2-carboxamide (Example 140), (S)—N-(3-(3,4-dihydroisoquinolin-2(1H)-yl)-2-hydroxypropyl)-6-(tetrahydro-2H-pyran-4-carboxamido)imidazo[1,2-a]pyridine-2-carboxamide (Example 141), (S)-6-(cyclopropanecarboxamido)-N-(3-(3,4-dihydroisoquinolin-2(1H)-yl)-2-hydroxypropyl)imidazo[1,2-a]pyridine-2-carboxamide (Example 142), (S)-6-(cyclobutanecarboxamido)-N-(3-(3,4-dihydroisoquinolin-2(1H)-yl)-2-hydroxypropyl)imidazo[1,2-a]pyridine-2-carboxamide (Example 143), (S)-6-(4-cyanobenzamido)-N-(3-(3,4-dihydroisoquinolin-2(1H)-yl)-2-hydroxypropyl)imidazo[1,2-a]pyridine-2-carboxamide (Example 144), 6-(4-cyanobenzamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 145), 6-benzamido-N—((S)-3-(3,4-dihydroisoquinolin-2(1H)-yl)-2-hydroxypropyl)-5,6,7,8-tetrahydroimidazo[1,2-a]pyridine-2-carboxamide (Example 146), N—((S)-3-(3,4-dihydroisoquinolin-2(1H)-yl)-2-hydroxypropyl)-6-(isonicotinamido)-5,6,7,8-tetrahydroimidazo[1,2-a]pyridine-2-carboxamide (Example 147), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-4-carboxamide (Example 148), N—((R)-3-(3,4-dihydroisoquinolin-2(1H)-yl)-2-hydroxypropyl)-6-(tetrahydro-2H-pyran-4-carboxamido)-5,6,7,8-tetrahydroimidazo[1,2-a]pyridine-2-carboxamide (Example 149), 6-(cyclopentanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 150), 6-(cyclopropanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 151), 6-(cyclohexanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 152), 6-(cyclobutanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 153), (R)—N-(3-(3,4-dihydroisoquinolin-2(1H)-yl)-2-hydroxypropyl)-6-(phenylsulfonamido)imidazo[1,2-a]pyridine-2-carboxamide (Example 154), N—((R)-3-(3,4-dihydroisoquinolin-2(1H)-yl)-2-hydroxypropyl)-6-(phenylsulfonamido)-5,6,7,8-tetrahydroimidazo[1,2-a]pyridine-2-carboxamide (Example 155), rac-(R)-6-(azetidine-1-carbonyl)-N-(3-(3,4-dihydroisoquinolin-2(1H)-yl)-2-hydroxypropyl)imidazo[1,2-a]pyridine-2-carboxamide (Example 156), (S)—N-(2-((3-(3,4-dihydroisoquinolin-2(1H)-yl)-2-hydroxypropyl)carbamoyl)imidazo[1,2-a]pyridin-6-yl)isoxazole-3-carboxamide (Example 157), 6-(bicyclo[2.2.1]heptane-2-carboxamido)-N—((S)-3-(3,4-dihydroisoquinolin-2(1H)-yl)-2-hydroxypropyl)imidazo[1,2-a]pyridine-2-carboxamide (Example 158), (S)—N-(2-((3-(3,4-dihydroisoquinolin-2(1H)-yl)-2-hydroxypropyl)carbamoyl)imidazo[1,2-a]pyridin-6-yl)oxazole-2-carboxamide (Example 159), (S)—N-(2-((3-(3,4-dihydroisoquinolin-2(1H)-yl)-2-hydroxypropyl)carbamoyl)imidazo[1,2-a]pyridin-6-yl)thiazole-5-carboxamide (Example 160), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)isoxazole-3-carboxamide (Example 161), 6-(bicyclo[2.2.1]heptane-2-carboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 162), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-2-carboxamide (Example 163), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)thiazole-5-carboxamide (Example 164), (S)—N-(3-(3,4-dihydroisoquinolin-2(1H)-yl)-2-hydroxypropyl)-6-ethylimidazo[1,2-a]pyridine-2-carboxamide (Example 165), (S)-6-(1,1-difluoroethyl)-N-(3-(3,4-dihydroisoquinolin-2(1H)-yl)-2-hydroxypropyl)imidazo[1,2-a]pyridine-2-carboxamide (Example 166), and (S)—N-(3-(3,4-dihydroisoquinolin-2(1H)-yl)-2-hydroxypropyl)-6-(pentafluoro-I6-sulfaneyl)imidazo[1,2-a]pyridine-2-carboxamide (Example 167).

In an embodiment, the present disclosure relates to a process of preparation of compounds of Formula I or its analogs, tautomeric forms, stereoisomers, geometrical isomers, polymorphs, hydrates, solvates, pharmaceutically acceptable salts, pharmaceutical compositions, metabolites and prodrugs thereof as described herein, wherein the process comprises reacting compounds of Formula II with Formula III in presence of a coupling reagent and a solvent to obtain the compounds of Formula I

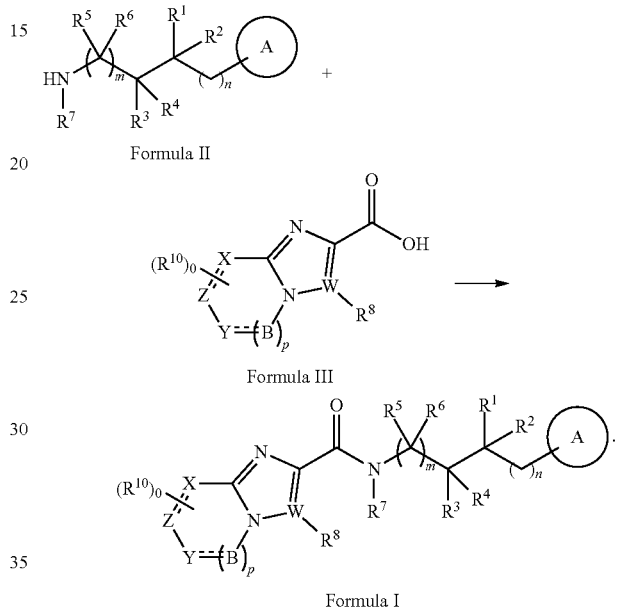

In an embodiment, the present disclosure relates to a process of preparation of compounds of Formula I or its analogs, tautomeric forms, stereoisomers, geometrical isomers, polymorphs, hydrates, solvates, pharmaceutically acceptable salts, pharmaceutical compositions, metabolites and prodrugs thereof as described herein, wherein the process comprises reacting compounds of Formula II with Formula III in presence of a coupling reagent and a solvent to obtain the compounds of Formula I, wherein X, Y, and Z of Formula III are independently selected from $CR^{10}$, $NR^{10}$, O or S; W and B are independently selected from N or C, p is 1 or 2; o is 1-3; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl, and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, cyano, $C_{1-6}$ alkyl, $C_{1-6}$ haloalkyl, $C_{1-6}$ alkoxy or 3-15 membered saturated or unsaturated heterocyclyl or heteroaryl ring with 1-5 heteroatoms selected from N, S or O, wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, and $C_{3-15}$ heteroaryl are optionally substituted with $C_{1-6}$ alkyl; n is 0-1; A of Formula II is selected from

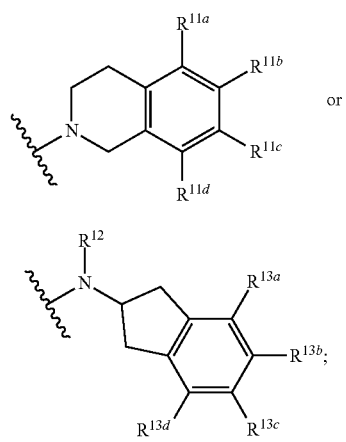

n is 0-1; m is 0-2; $R^1$, $R^2$, $R^3$, and $R^4$ are independently selected from hydrogen, halogen, hydroxyl or $C_{1-6}$ alkyl, wherein $C_{1-6}$ alkyl is optionally substituted with hydroxyl, halogen, and combinations thereof; $R^5$, and $R^6$ are independently selected from hydrogen, $C_{1-6}$ alkyl or halogen, wherein $C_{1-6}$ alkyl is optionally substituted with hydroxyl, halogen, and combinations thereof; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl or cyano; $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl or $C_{1-6}$ alkoxy; A of Formula I is selected from

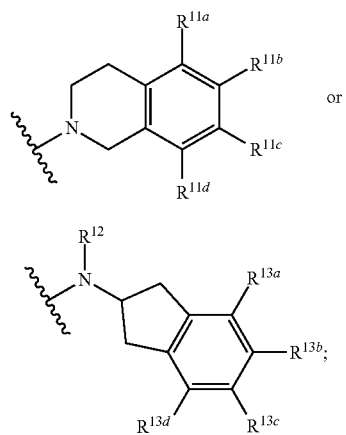

---- represents optional single or double bond; n is 0 or 1; m is 0-2; p is 1 or 2; o is 1-3; $R^1$, $R^2$, $R^3$, $R^4$, $R^5$, and $R^6$ are independently selected from hydrogen, halogen, hydroxyl or $C_{1-6}$ alkyl, wherein $C_{1-6}$ alkyl is optionally substituted with one or more groups selected from hydroxyl or halogen; $R^7$, and $R^{12}$ are independently selected from hydrogen or $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano; $R^{11a}$, $R^{11b}$, $R^{11c}$, $R^{11d}$, $R^{13a}$, $R^{13b}$, $R^{13c}$ and $R^{13d}$ are independently selected from hydrogen, halogen, cyano, $C_{1-6}$ alkyl, $C_{1-6}$ haloalkyl or $C_{1-6}$ alkoxy; X, Y, and Z are independently selected from $CR^{10}$, $NR^{10}$, O or S; W, and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment, the present disclosure relates to a process of preparation of compounds of Formula I as described herein, wherein the coupling reagent is selected from the group consisting of N-(3-dimethylaminopropyl)-N'-ethylcarbodiimide hydrochloride, hydroxybenzotriazole, propane phosphonic acid anhydride, and combinations thereof.

In an embodiment, the present disclosure relates to a process of preparation of compounds of Formula I as described herein, wherein the solvent is a polar aprotic solvent selected from the group consisting of DMF, dioxane, acetonitrile, THF, and combinations thereof.

In an embodiment, the present disclosure relates to pharmaceutical composition comprising a compound of Formula I, Formula Ia, or Formula Ib as described herein, or a pharmaceutically acceptable salt thereof together with a pharmaceutically acceptable carrier, optionally in combination with one or more other pharmaceutical compositions.

In another embodiment, the present disclosure relates to the pharmaceutical composition as described herein, wherein the composition is in the form selected from the group consisting of a tablet, capsule, powder, syrup, solution, aerosol and suspension.

In an embodiment, the present disclosure relates to a method for the treatment and/or prevention of various diseases, including cancer and infectious diseases, comprising administering to a subject suffering from the proliferative disorder or cancer a therapeutically effective amount of the compounds of Formula I, Formula Ia, or Formula Ib or a pharmaceutically acceptable salt thereof or together with a pharmaceutically acceptable carrier, with other clinically relevant cytotoxic agents or non-cytotoxic agents to a subject in need thereof.

In an embodiment, the present disclosure relates to the use of compounds of Formula I, Formula Ia, or Formula Ib or pharmaceutically acceptable salts thereof together with a pharmaceutically acceptable carrier, for the treatment and/or prevention of various diseases including proliferative disorder or cancer; or treatment of cancer together with other clinically relevant cytotoxic agents or non-cytotoxic agents.

In an embodiment, the present disclosure relates to the use of compounds of Formula Ib, Formula Ia, Formula I or pharmaceutically acceptable salts thereof together with a pharmaceutically acceptable carrier, for the treatment and/or prevention of various diseases including proliferative disorder or cancer; or treatment of cancer together with other clinically relevant cytotoxic agents or non-cytotoxic agents such as carboplatin, bortezomib, carfilzomib, lenalidomide, pomalidomide, doxorubicin, daunorubicin, decitabine, denileukin, denileukin diftitox, dexrazoxane, docetaxel, doxorubicin, dromostanolone propionate cyclophosphamide, 5-fluroruracil, imatinib, methotrexate, irinotecan, toptecan, vinblastine, etoposide, vincristine, carmustine, paclitaxel, vorinostat, belinostat, panbinostat, romidepsin, chiadamide, entinostat, mocetinostat, afatinib, bosutinib, cetuximab, enterctinib, lapatinib, nilotinib, pazopanib, ruxlotinib, sorafeenib, sunitinib, vermurafenib, axitinib, gefitinib, cobimetinib, carbozantinib, temozolomide, idarubicin, abarelix, aldesleukin, alemtuzumab, allopurinol, altretamine, anastrozole, asparaginase, bexarotene, baricitinib, bleomycin, busulfan, capecitabine, cladribine, clofarabine, cytarabine, dacarbazine, dactinomycin, sodium, dasatinib, letrozole, tamoxifen, oxaliplatin, procarbazine and zoleronate.

In an embodiment, the present disclosure relates to a method for the treatment of cancer as described herein, wherein said method comprising administering a combination of the compounds of Formula I or pharmaceutically acceptable salts thereof, together with a pharmaceutically acceptable carrier, with other clinically relevant cytotoxic agents or non-cytotoxic agents to a subject in need thereof.

In an embodiment, the present disclosure relates to a method of treatment of cancer as described herein, wherein said method comprising administering a combination of the compounds of Formula I or the pharmaceutical composition with other clinically relevant immune modulator agents to a subject in need of thereof.

In an embodiment, the present disclosure relates to a method of treatment of cancer as described herein, wherein said method comprising administering a combination of the compounds of Formula I, Formula Ia, or Formula Ib or the pharmaceutical composition with other clinically relevant immune checkpoint inhibitors. In another embodiment of the present disclosure, the immune checkpoint inhibitors are selected from the group consisting of CD27, CD28, CD40, CD122, CD96, CD73, CD47, 0X40, GITR, CSF1R, JAK, PI3K delta, PI3K gamma, TAM, aiginase, CD137 (also known as 4-1BB), ICOS, A2AR, B7-H3, B7-H4, BTLA, CTLA-4, LAG3, TIM3, VISTA, PD-1, PD-L1, PD-L2, and combinations thereof.

In an embodiment, the present disclosure relates to a method of treatment of cancer as described herein, wherein said method comprising administering a combination of the compounds of Formula I, Formula Ia, or Formula Ib or the pharmaceutical composition with other clinically relevant immune checkpoint inhibitors such as nivolumab, pembrolizumab, pidilimumab, bms-986016, epacadostat, tremelimumab, CD73 inhibitors and arginase inhibitors to a subject in need of thereof.

In an embodiment, the present disclosure relates to the use of compounds of Formula I or the pharmaceutical composition for treatment of a condition mediated by PRMT5; treatment and/or prevention of a proliferative disorder or cancer; or treatment of cancer together with other clinically relevant cytotoxic agents or non-cytotoxic agents.

In an embodiment, the present disclosure relates to a method for the treatment and/or prevention of a condition mediated by PRMT5 or a proliferative disorder or cancer as described herein, wherein said method comprising administering to a subject suffering from the condition mediated by PRMT5 or the proliferative disorder or cancer, a therapeutically effective amount of the compound of Formula I or the pharmaceutical composition.

In an embodiment, the present disclosure relates to a compound of Formula I, Formula Ia, or Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein A is selected from

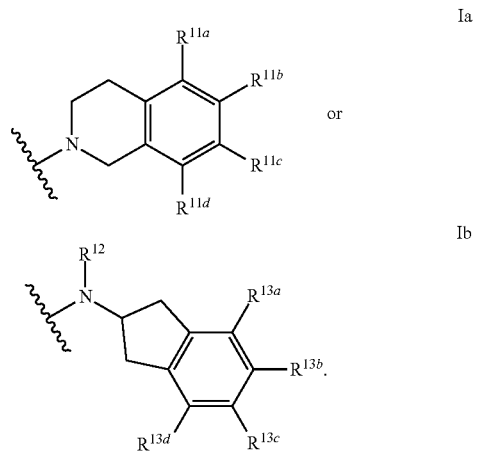

In an embodiment, the present disclosure relates to a compound of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein n is 0 or 1; m is 0-2; p is 1 or 2; and o is 1-3.

In an embodiment, the present disclosure relates to a compound of Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein n is 0 or 1; and m is 0-2.

In an embodiment, the present disclosure relates to a compound of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein n is 0 or 1; m is 0-2; and p is 1.

In an embodiment, the present disclosure relates to a compound of Formula I, or Formula Ia, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^1$, $R^2$, $R^3$, $R^4$, $R^5$, and $R^6$ are independently selected from hydrogen, halogen, hydroxyl, or $C_{1-6}$ alkyl, wherein $C_{1-6}$ alkyl is optionally substituted with one or more groups selected from hydroxyl, or halogen.

In an embodiment, the present disclosure relates to a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^1$, $R^2$, $R^3$, and $R^4$ are independently selected from hydrogen, halogen, hydroxyl, or $C_{1-6}$ alkyl, wherein $C_{1-6}$ alkyl is optionally substituted with one or more groups selected from hydroxyl, or halogen; and $R^5$, and $R^6$ are independently selected from hydrogen, $C_{1-6}$ alkyl, or halogen, wherein $C_{1-6}$ alkyl is optionally substituted with one or more groups selected from hydroxyl, or halogen.

In an embodiment, the present disclosure relates to a compound of Formula I, Formula Ta, or Formula Tb, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^7$ is selected from hydrogen, or $C_{1-4}$ alkyl.

In an embodiment, the present disclosure relates to a compound of Formula I, Formula Ia, or Formula Tb, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^{12}$ is absent or is selected from hydrogen, or $C_{1-4}$ alkyl, wherein $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl, or cyano.

In an embodiment, the present disclosure relates to a compound of Formula I, Formula Ia, or Formula Tb, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^{11a}$, $R^{11b}$, $R^{11c}$, $R^{11d}$, $R^{13a}$, $R^{13b}$, $R^{13c}$, and $R^{13d}$ are independently selected from hydrogen, halogen, cyano, $C_{1-6}$ alkyl, $C_{1-6}$ haloalkyl, or $C_{1-6}$ alkoxy.

In an embodiment, the present disclosure relates to a compound of Formula I, Formula Ia, or Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein X, Y, and Z are independently selected from $CR^{10}$, $NR^{10}$, O, or S.

In an embodiment, the present disclosure relates to a compound of Formula I, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)$ $SOR_b$, $N(R_a)SO_2R_b$, $NR_aC(O)OR_b$, $NR_aR_b$, $NR_aC(S)$ $NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, or $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

In an embodiment, the present disclosure relates to a compound of Formula Ta, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, or $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{3-6}$ cycloalkyl, $C_{1-6}$ alkyl, $C_{1-6}$ haloalkyl, $C_{1-6}$ alkoxy, $C_{3-6}$ cycloalkyl, $C(O)R_b$, 3-6 membered saturated or unsaturated heterocyclyl or heteroaryl ring with 1-5 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or or $R_a$ and $R_b$ can be taken together to form a 5-10 membered monocyclic or bicyclic, saturated or unsaturated heterocyclic ring with 1-3 heteroatoms selected from N, S or O.

In an embodiment, the present disclosure relates to a compound of Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, C(S)R$_a$, C(O)NR$_a$R$_b$, C(S)NR$_a$R$_b$, NR$_a$C(O)NR$_b$R$_c$, N(R$_a$)SOR$_b$, N(R$_a$)SO$_2$R$_b$, NR$_a$C(O)OR$_b$, NR$_a$R$_b$, NR$_a$C(S)NR$_b$R$_c$, NR$_a$C(O)R$_b$, NR$_a$C(S)R$_b$, SONR$_a$R$_b$, SO$_2$NR$_a$R$_b$, OC(O)NR$_a$R$_b$, OR$_a$C(O)OR$_b$, OC(O)NR$_a$R$_b$, OC(O)R$_a$, OR$_a$, R$_a$NR$_b$R$_c$, R$_a$OR$_b$, SR$_a$, SOR$_a$, SO$_2$R$_a$, or 3-15 membered saturated or unsaturated heterocyclyl or heteroaryl ring with 1-5 heteroatoms selected from N, S or O, wherein C$_{5-6}$ aryl, C$_{3-6}$ cycloalkyl, and 3-15 membered saturated or unsaturated heterocyclyl or heteroaryl ring are optionally substituted with one or more groups selected from halogen, hydroxyl, cyano, oxo, C$_{1-6}$ alkyl, C$_{1-6}$ haloalkyl, C$_{1-6}$ alkoxy, C$_{3-6}$ cycloalkyl, C(O)R$_b$, or 3-6 membered saturated or unsaturated heterocyclyl or heteroaryl ring with 1-3 heteroatoms selected from N, S or O, wherein 3-6 membered saturated or unsaturated heterocyclyl or heteroaryl ring is optionally substituted with C(O)R$_b$, and wherein R$_a$, R$_b$, and R$_c$ are independently selected from hydrogen, C$_{1-6}$ alkyl, C$_{3-6}$ cycloalkyl, C$_{5-6}$ aryl, C$_{3-15}$ heterocyclyl or C$_{3-15}$ heteroaryl, wherein C$_{5-6}$ aryl, C$_{3-6}$ cycloalkyl, and C$_{3-15}$ heteroaryl are optionally substituted with one or more substituents selected from halogen, cyano, or C$_{1-6}$ alkyl; or R$_a$ and R$_b$ can be taken together to form a 5-10 membered monocyclic or bicyclic, saturated or unsaturated heterocyclic ring with 1-3 heteroatoms selected from N, S or O.

In an embodiment, the present disclosure relates to a compound of Formula I, Formula Ia, or Formula Ib, their analogs, tautomeric forms, stereoisomers, geometrical isomers, polymorphs, hydrates, solvates, pharmaceutically acceptable salts, pharmaceutical compositions, metabolites, and prodrugs thereof, wherein W is selected from N or C.

In an embodiment, the present disclosure relates to a compound of Formula I, Formula Ta or Formula Tb, their analogs, tautomeric forms, stereoisomers, geometrical isomers, polymorphs, hydrates, solvates, pharmaceutically acceptable salts, pharmaceutical compositions, metabolites, and prodrugs thereof, wherein R$^8$ is absent or is selected from hydrogen, halogen, C$_{1-4}$ alkyl, C$_{2-4}$ alkenyl, C$_{2-4}$ alkynyl, C$_{1-4}$ haloalkyl, C$_{3-6}$ cycloalkyl, C$_{5-6}$ aryl, C$_{3-15}$ heteroaryl, and C$_{3-15}$ heterocyclyl.

EXAMPLES

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Abbreviations:
BSA Bovine serum albumin;
DCE 1,2-Dichloroethane;
DCM Dichloromethane;
DME 1,2-Dimethoxyethane;
DMF Dimethyl formamide;
Hünig's base N-ethyl-N-(1-methylethyl)-2-propanamine;
Dioxane 1,4-Dioxane;
DMSO Dimethylsulfoxide;
DTT Dithiothreitol;
N-(3-Dimethylaminopropyl)-N'-ethylcarbodiimide hydrochloride;
HPLC High pressure liquid chromatography;
HOBT Hydroxybenzotriazole;
LiOH.H$_2$O Lithium hydroxide monohydrate;
NMR Nuclear magnetic resonance;
DCMComplex[1,1'-Bis(diphenylphosphino)ferrocene]dichloropalladium(II). dichloromethane complex; tetrakis(triphenylphosphine)palladium(0); (1-[Bis(dimethylamino)methylene]-1H-1,2,3-triazolo[4,5-b]pyridinium 3-oxid hexafluorophosphate);
RT Room temperature;
TCEP (Tris(2-carboxyethyl)phosphine)
TLC Thin layer chromatography;
TMS Tetramethyl silane;
T$_3$P Propane phosphonic acid anhydride;
TFA Trifluoroacetic acid; and
THF Tetrahydrofuran.

The following examples provide the details about the synthesis, activities, and applications of the compounds of the present disclosure. It should be understood the following is representative only, and that the disclosure is not limited by the details set forth in these examples.

The compounds of the disclosure may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the disclosure.

There is also provided a process as shown in the following Scheme-1, for the preparation of compounds of the Formula I, wherein all the groups are as defined earlier.

Example 1

General Procedure for Synthesis of Compounds of Formula I

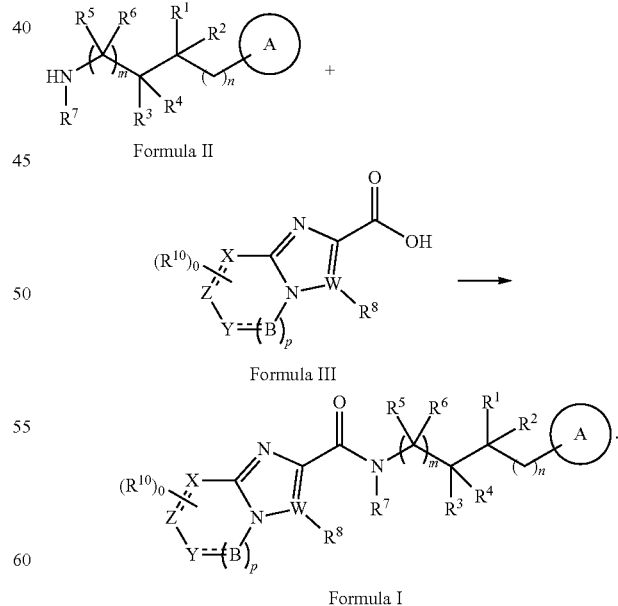

The said process for the preparation of the compounds of Formula I comprises: (a) Reacting compounds of Formula II with compounds of Formula III in the presence of a coupling reagent such as EDCI.HCl, HOBT, T$_3$P and the like in solvents like polar aprotic solvents such as DMF, dioxane and the like gives compound of Formula I.

Compounds of Formula I when isotopically labeled can be synthesized using the general protocol given in Scheme 1 by using the corresponding isotopically labeled starting materials.

General Considerations and Analytical Methods:

The compounds used in the reaction processes, if not mentioned otherwise, were commercially available and purchased from Aldrich. NMR data were obtained on Varian 400 MHz spectrometer. All compounds were characterized by $^1$H NMR, HPLC and mass spectrometry (LCMS (ES)), Liquid chromatography-Mass spectrometry). All $^1$H chemical shifts were reported in parts per million (ppm) and were measured relative to TMS or residual deuterated DMSO as solvent. LCMS (ES) measurements were performed on Agilent and WatersMass spectrometers. The yields of the compounds provided refer to isolated compounds.

The examples given below are provided by the way of illustration only and therefore should not be construed to limit the scope of the disclosure.

General Procedure for Synthesis of Intermediates

Synthesis of 1-amino-3-(3,4-dihydroisoquinolin-2(1H)-yl)propan-2-ol (I-1)

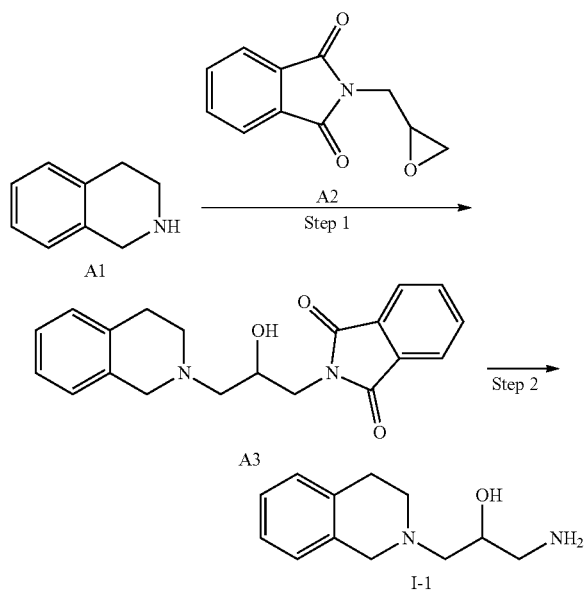

Step-1: Preparation of 2-(3-(3,4-dihydroisoquinolin-2(1H)-yl)-2-hydroxypropyl)isoindoline-1,3-dione (A3)

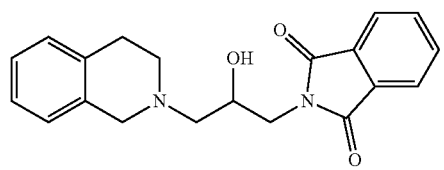

A3

To a stirred suspension of compound 2-(oxiran-2-yl-methyl) isoindoline-1, 3-dione (A2, 20.0 g, 98.0 mmol) in ethanol (200 mL) was added 1, 2, 3, 4-tetrahydroisoquinoline (A1, 13.1 g, 98.0 mmol). The reaction mixture was heated at 80° C. for 16 h and cooled to room temperature. The solvent was evaporated to afford the crude product A3 (32.8 g) which was taken for the next step as such. MS (ESI) m/z=337.2 [M+H]$^+$.

Step-2: Preparation of 1-amino-3-(3,4-dihydroisoquinolin-2(1H)-yl)propan-2-ol (I-1)

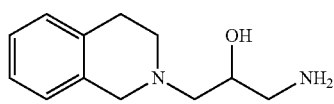

I1

To a stirred solution of crude compound 2-(3-(3,4-dihydroisoquinolin-2(1H)-yl)-2 hydroxypropyl)isoindoline-1,3-dione (A3, 32.8 g, 97 mmol) in ethanol 200 mL was added hydrazine hydrate (24 mL, 488 mmol). An additional 800 mL of ethanol was added. The reaction mixture was stirred at 23-25° C. until the disappearance of starting material. The solvent was filtered and the residue washed with dichloromethane (DCM). The filtrate was concentrated to dryness. The residue was taken in DCM and minimum amount of water was added (~50 mL). The organic and aqueous layers were separated. The DCM layer was dried over anhydrous Na$_2$SO$_4$, filtered and evaporated to dryness to get compound 1-amino-3-(3,4-dihydroisoquinolin-2(1H)-yl)propan-2-ol I-1 as a yellow syrupy liquid. Yield: 24.4 g (90%). MS (ESI) m/z=207.1 [M+H]$^+$.

Synthesis of (S)-1-amino-3-(3,4-dihydroisoquinolin-2(1H)-yl)propan-2-ol (I-2)

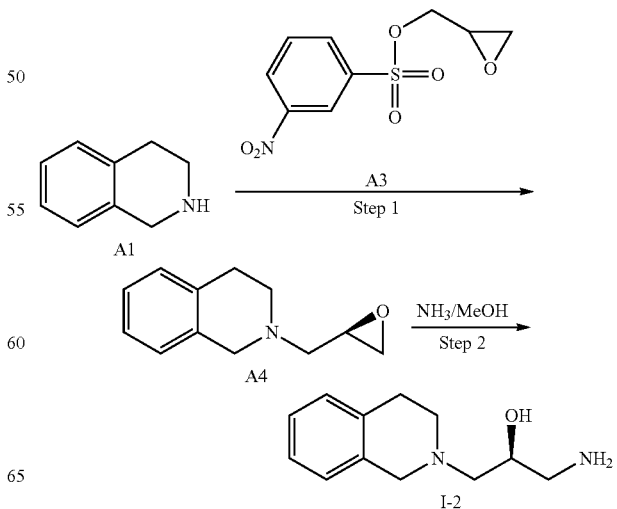

Step-1: Preparation of (R)-2-(oxiran-2-ylmethyl)-1,2,3,4-tetrahydroisoquinoline (A4)

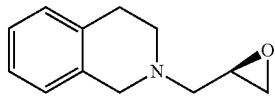

A4

To a solution of 1,2,3,4-tetrahydroquinoline (A1, 1 g, 7.5 mmol) in THF (10 mL) at 0° C. was added KF (0.87 g, 15 mmol). After 1 h (S)-oxiran-2yl-methyl-3-nitro benzenesulfonate (A3, 2.2 g, 8.49 mmol) was added and the resulting solution was stirred at room temperature for 16 h. The solid was removed by filtration and washed with THF. The solution was concentrated to afford to compound A4 (1 g) was used for next step without further purification. MS (ESI) m/z=190.2 [M+H]$^+$.

Step-2: Preparation of(S)-1-amino-3-(3,4-dihydroisoquinolin-2(1H)-yl)propan-2-ol (I-2)

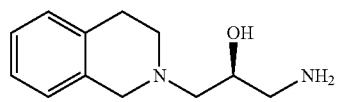

I-2

To a solution of crude (R)-2-(Oxiran-2-yl methyl)-1,2,3,4-tetrahydroisoquinoline (A4, 1 g, 4.85 mmol) in ethanol (20 mL) at −78° C. was slowly bubbled ammonia for 30 min. The reaction mixture was sealed and heated at 80° C. for 3 h. The reaction mixture was concentrated and crude product I-2 (1 g, purity 80%) was used for next step without further purification. MS (ESI) m/z=207.2 [M+H]$^+$.

Synthesis of 1-amino-3-((2,3-dihydro-1H-inden-2-yl)(4-methoxybenzyl)amino) propan-2-ol (I-3)

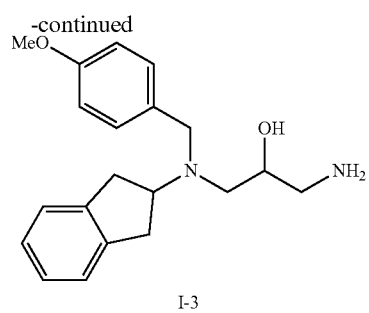

I-3

Step 1: Preparation of 2-(3-((2,3-dihydro-1H-inden-2-yl)(4-methoxybenzyl)amino)-2-hydroxypropyl)isoindoline-1,3-dione (B3)

To a stirred solution of N-(4-methoxybenzyl)-2,3-dihydrobenzofuran-2-amine (A4, 7.1 g, 28.4 mmol) in EtOH (60 mL) was added 2-(oxiran-2-ylmethyl)-1H-indene-1,3(2H)-dione (A2, 5.7 g, 28.4 mmol). The reaction mixture was stirred for 16 h at 80° C. The solvent was evaporated to get the product B3 as a brown liquid (10.1 g, 78%). MS (ESI) m/z=457.2 [M+H]$^+$.

Step 2: Preparation of 1-amino-3-((2,3-dihydro-1H-inden-2-yl)(4-methoxybenzyl)amino)propan-2-ol (I-3)

To a stirred solution 2-(3-((2,3-dihydro-1H-inden-2-yl)(4-methoxybenzyl)amino)-2-hydroxypropyl)isoindoline-1,3-dione (B3, 11 g, 2.41 mmol) in EtOH was added hydrazine hydrate (50 mL, 6.03 mmol). Reaction mixture was stirred for 16 h at room temperature. The reaction mixture was concentrated. The residue was dissolved in ethylacetate/H$_2$O mixture. Organic layer was separated and dried over anhydrous Na$_2$SO$_4$. The organic layer was concentrated to afford yellow oily product I-3 (5.6 g, 65%). MS (ESI) m/z=327.1 [M+H]$^+$.

Synthesis of tert-butyl (4-(3,4-dihydroisoquinolin-2(1H)-yl)-1-hydroxybutan-2-yl)carbamate (I-4)

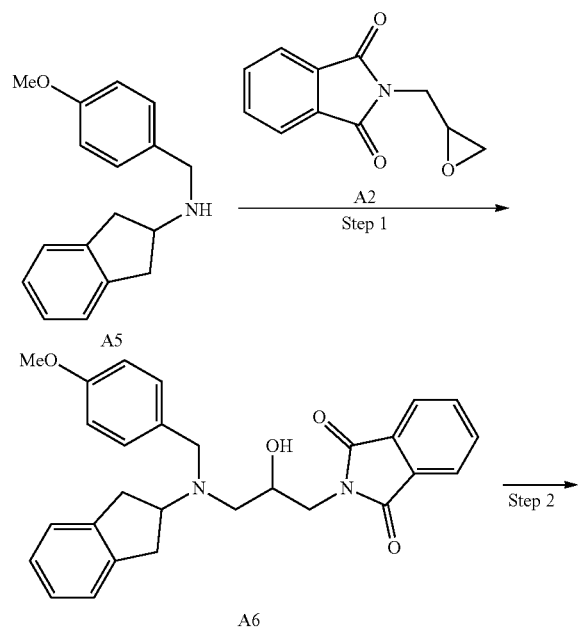

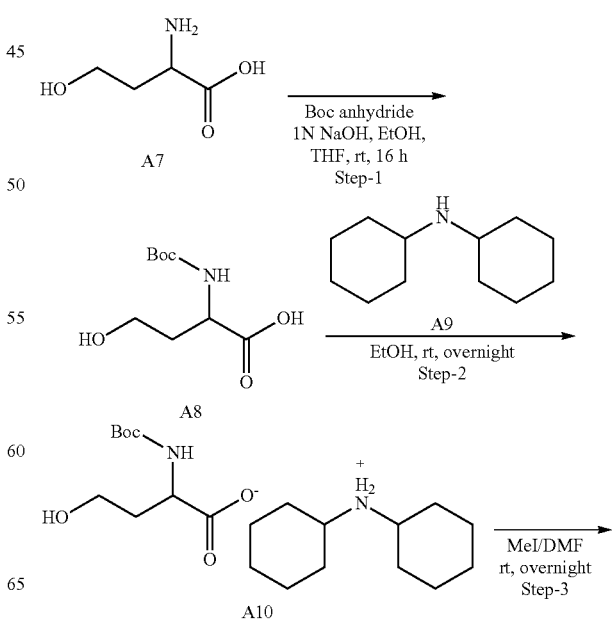

-continued

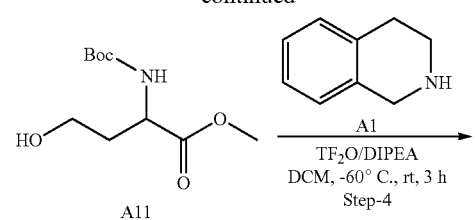

Step 2: Preparation of (tert-butoxycarbonyl)homoserinedicyclohexyl amine complex (A10)

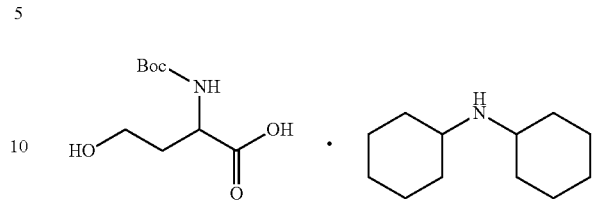

To a solution of (tert-butoxycarbonyl)homoserine (A8, 5.9 g, 26.9 mmol) in EtOH (41 mL) was added drop wise dicyclohexylamine (A9, 5.82 mL, 29.3 mmol). The mixture was stirred for 12 h at room temperature and then concentrated under reduced pressure. The white solid was dried under high vacuum and then triturated with ether (1000 mL). The fine white powder was collected by filtration, washed with ether and dried under high vacuum. (6.37 g, 59% yield). The crude material A10 was as such taken for next step.

Step 3: Preparation of Methyl (tert-butoxycarbonyl)homoserinate (A11)

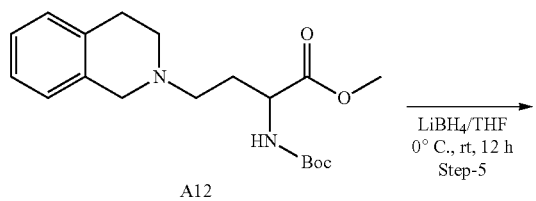

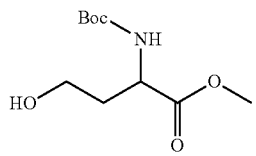 [SMILES: COC(=O)C(CCO)NC(=O)OC(C)(C)C]

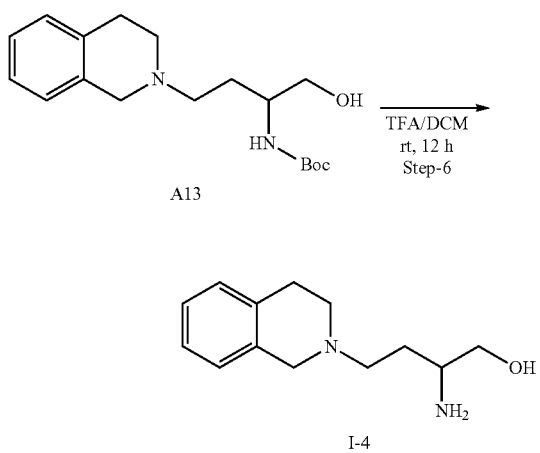

To a suspension of (tert-butoxycarbonyl)homoserinedicyclohexyl amine complex (A10, 6.37 g, 15.9 mmol) in DMF (52 mL) was added iodomethane (1.18 mL, 19.1 mmol). The mixture was stirred at room temperature for 16 h. The clear solution was concentrated under reduced pressure. The residue was diluted with water (200 mL) and extracted with ethyl acetate (2×100 mL) and stirred for 2 h before the layers were separated. The combined extracts were washed with brine (250 mL), dried over anhydrous sodium sulfate, filtered and concentrated under reduced pressure to provide yellow oil. The crude was purified by column chromatography using silica gel eluting with ethyl acetate/hexane to afford methyl (tert-butoxycarbonyl)homoserinate A11 as a colorless oil (2 g, 54% yield). The crude material was as such taken for next step.

Step 4: Preparation of Methyl 2-((tert-butoxycarbonyl)amino)-4-(3,4-dihydroisoquinolin-2(1H)-yl)butanoate (A12)

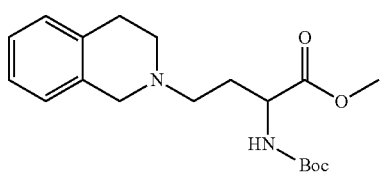 [SMILES: COC(=O)C(CCN1CCc2ccccc2C1)NC(=O)OC(C)(C)C]

To a solution of methyl (tert-butoxycarbonyl)homoserinate (A11, 0.2 g, 0.86 mmol) in dry dichloromethane (5 mL),

Step 1: Preparation of (tert-butoxycarbonyl)homoserine (A8)

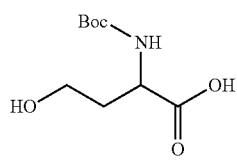

To a solution of DL-homoserine (A7, 12.12 g, 101.89 mmol) in 1N NaOH (111 mL) and EtOH (97 mL) was added a solution of Boc anhydride (24.43 g, 112 mmol) in THF (97 mL) over 15 minutes. The reaction mixture was stirred at room temperature for 16 h. The mixture was then washed with ether (3×200 mL), acidified with 1N HCl to pH 2 and extracted with ethyl acetate (6×250 mL). The combined organic extracts were washed with brine (250 mL), dried over anhydrous sodium sulfate, filtered and concentrated under reduced pressure. To afford 5.9 g of A8 as a colourless liquid. MS (ESI) m/z=218.9 [M+H]$^+$.

diisopropyl ethyl amine (0.75 mL, 4.2 mmol) was added and cooled to −60° C., triflic anhydride (0.21 mL, 1.28 mmol) was added to the reaction mixture slowly and allowed to stirred at room temperature for 3 h. Reaction mixture was quenched with water and extracted with dichloromethane. The combined organic layers were washed with brine, dried over sodium sulfate, filtered and concentrated under reduced pressure. The crude material was purified by column chromatography using silica gel eluting with ethyl acetate/hexane to afford methyl 2-((tert-butoxycarbonyl)amino)-4-(3,4-dihydroisoquinolin-2(1H)-yl)butanoate A11 as a colorless liquid (0.18 g, 60%). MS (ESI) m/z=349.2 [M+H]$^+$.

Step 5: Preparation of tert-butyl (4-(3,4-dihydroisoquinolin-2(1H)-yl)-1-hydroxybutan-2-yl)carbamate (A13)

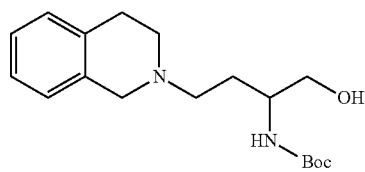 [SMILES: CC(C)(C)OC(=O)NC(CO)CCN1CCc2ccccc2C1]

A solution of methyl 2-((tert-butoxycarbonyl)amino)-4-(3,4-dihydroisoquinolin-2(1H)-yl)butanoate methyl ester (A12, 0.18 g, 0.51 mmol) in 7 mL of THF was cooled to 0° C. in an ice bath. (1.29 mL, 1.29 mmol) of a 1M solution of LiBH$_4$ in THF was then added at once. The ice bath was removed 2 min. later. The solution was allowed to warm to room temperature and stirred for 22 h. Reaction mixture was quenched with sat. NH$_4$Cl solution was then added carefully due to the resulting evolution of hydrogen. Once effervescence had ceased, the resulting mixture was extracted with dichloromethane and then an additional (3×20 mL) of dichloromethane. The organic extracts were dried over sodium sulfate and then filtered and concentrated. Purified by column chromatography using ethyl acetate/hexane to afford A13 as a colorless liquid (0.14 g, 84.8%). MS (ESI) m/z=321.2 [M+H]$^+$.

Step 6: Preparation of TFA salt of 2-amino-4-(3,4-dihydroisoquinolin-2(1H)-yl)butan-1-ol (I-4)

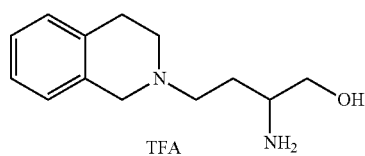 [SMILES: NC(CO)CCN1CCc2ccccc2C1]

To a solution of tert-butyl (4-(3,4-dihydroisoquinolin-2(1H)-yl)-1-hydroxybutan-2-yl)carbamate (A13, 0.14 g, 0.43 mmol) in DCM (5 mL), cooled to 0° C., Trifluoro acetic acid (1 mL) and stirred at room temperature for 12 h. Reaction mixture was concentrated. The crude material 1-4 was as such taken for next step. MS (ESI) m/z=221.1 [M+H]$^+$.

Synthesis of (S)-1-(3,4-dihydroisoquinolin-2(1H)-yl)-3-(methylamino)propan-2-ol (I-5)

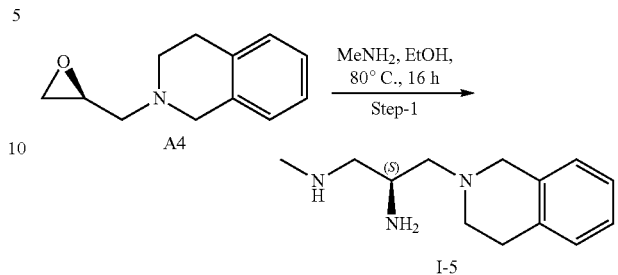

Step-1: (S)-1-(3,4-dihydroisoquinolin-2(1H)-yl)-3-(methylamino)propan-2-ol (I5)

To a stirred solution of (S)-2-(oxiran-2-ylmethyl)-1,2,3,4-tetrahydroisoquinoline (B2, 1.0 g, 5.28 mmol) in EtOH (10 mL) and methylamine (2.0 M solution THF) (3.96 mL, 7.92 mmol) was added drop wise at room temperature and the reaction was stirred for 16 h at 80° C. The reaction mixture was concentrated under reduced pressure to afford (S)-1-(3,4-dihydroisoquinolin-2(1H)-yl)-3-(methylamino)propan-2-ol I-5 as a light yellow liquid. Yield: 1.0 g (crude) LC-MS (ES) m/z: 221.16 [M+H]$^+$ Synthesis of Ethyl 6-bromoimidazo[1,2-a]pyridine-2-carboxylate (I-6)

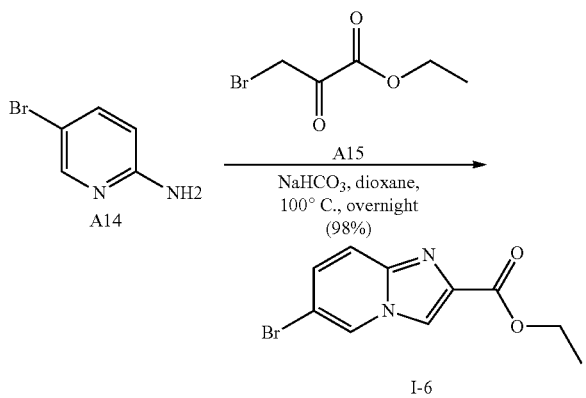

To a stirred solution of 5-bromopyridin-2-amine (A14, 10 g, 57.8 mmol) in 1,4-dioxane (120 mL) was added ethyl 3-bromo pyruvate (A15, 10.83 mL, 86.71 mmol), followed by NaHCO$_3$ (9.71 g, 115.6 mmol). The reaction mixture was heated for 12 h at 100° C. and then concentrated under reduced pressure. The crude product was washed with ethyl acetate/water 2:1 mixture (3×75 mL) and the combined organic layer was concentrated. Purified by column chromatography using ethyl acetate/hexane to afford 16 as blackish brown solid (15.3 g, 98%). MS (ESI) m/z=271 [M+H]$^+$.

Further, the following intermediates were synthesized using the protocol exemplified for I-6.

| Intermediate No | Structure | LC/MS_m/z_ [M + H]+ |
|---|---|---|
| I-7 | 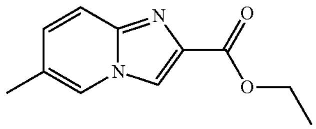 | 205.2 |
| I-8 | 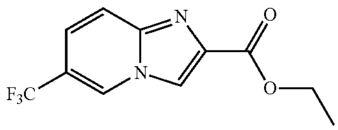 [SMILES: CCOC(=O)c1cn2cc(C(F)(F)F)ccc2n1] | 259.0 |
| I-9 | 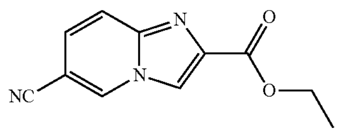 [SMILES: CCOC(=O)c1cn2cc(C#N)ccc2n1] | 216.9 |
| I-10 | 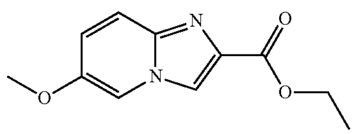 [SMILES: CCOC(=O)c1cn2cc(OC)ccc2n1] | 193.1 |
| I-11 | 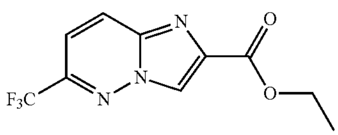 [SMILES: CCOC(=O)c1cn2nc(C(F)(F)F)ccc2n1] | 260.1 |
| I-12 | 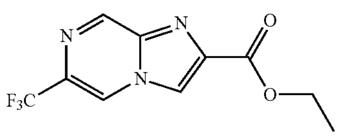 [SMILES: CCOC(=O)c1cn2cc(C(F)(F)F)ncc2n1] | 260.1 |
| I-13 | 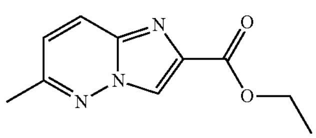 | 206.04 |
| I-14 | 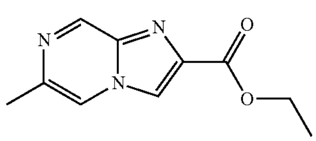 | 206.04 |
| I-15 | 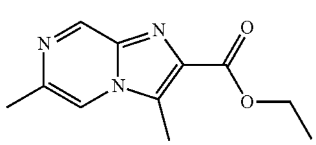 [SMILES: CCOC(=O)c1nc2cnc(C)cn2c1C] | 206.2 |

-continued

| Intermediate No | Structure | LC/MS_m/z_ [M + H]+ |
|---|---|---|
| I-16 | 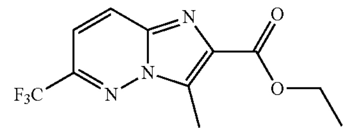 [SMILES: CCOC(=O)c1nc2ccc(C(F)(F)F)nn2c1C] | 260.1 |

Synthesis of Ethyl 6-(4-fluorophenyl)imidazo[1,2-a]pyridine-2-carboxylate (I-17)

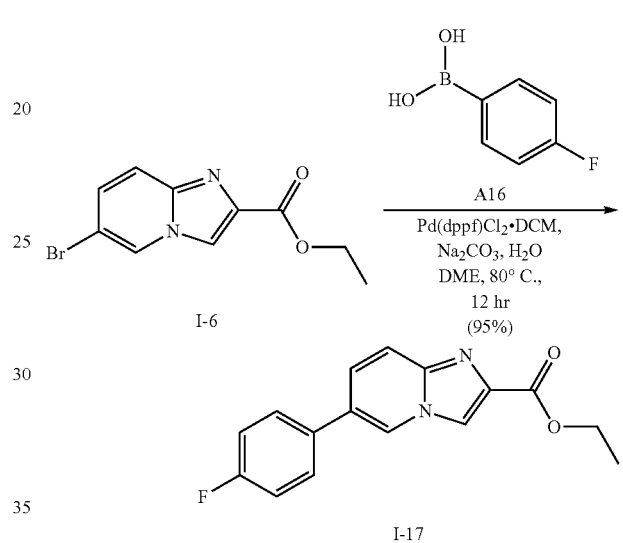

To a solution of ethyl 6-bromoimidazo[1,2-a]pyridine-2-carboxylate (I-6, 2 g, 7.43 mmol) in 1,2-DME (50 mL) was added (4-fluorophenyl)boronic acid (A16, 1.56 g, 11.15 mmol), followed by addition of $Na_2CO_3$ (2.34 g, 22.29 mmol) dissolved in $H_2O$ (12 mL). The reaction mixture was purged with $N_2$ gas for 20 min followed by the addition of Pd(dppf)$Cl_2$.DCM (0.54 g, 0.743 mmol). It was further purged with $N_2$ gas for 10 more minutes and stirred for 16 h at 80° C. The reaction mixture was filtered through celite and extracted with ethyl acetate/water mixture. The combined organic layer was washed with brine, dried over anhydrous $Na_2SO_4$ and concentrated under reduced pressure. Purified using column chromatography using ethyl acetate/hexane to afford I-17 as a blackish brown solid product (2.0 g, 95%). MS (ESI) m/z=285.1 [M+H]+.

The following intermediates were synthesized using the protocol exemplified for I-17.

| Intermediate No | Structure | LC/MS_m/z_ [M + H]+ |
|---|---|---|
| I-18 | 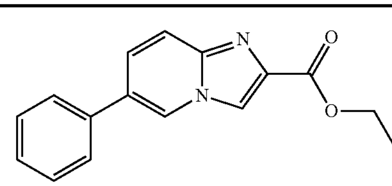 | 267.1 |

-continued

| Intermediate No | Structure | LC/MS_m/z_ [M + H]+ |
|---|---|---|
| I-19 | 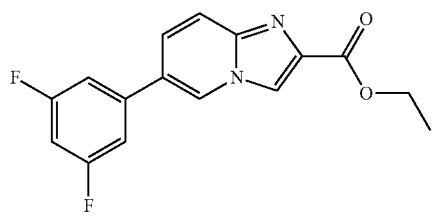 [SMILES: CCOC(=O)c1cn2cc(-c3cc(F)cc(F)c3)ccc2n1] | 303.2 |
| I-20 | 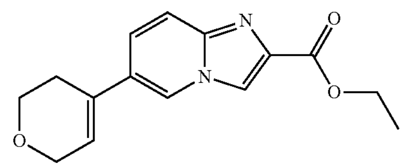 [SMILES: CCOC(=O)c1cn2cc(C3=CCOCC3)ccc2n1] | 273.1 |
| I-21 | 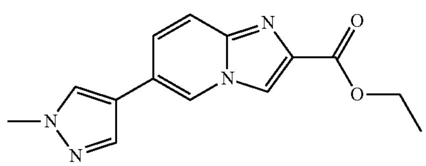 [SMILES: CCOC(=O)c1cn2cc(-c3cnn(C)c3)ccc2n1] | 271.1 |
| I-22 | 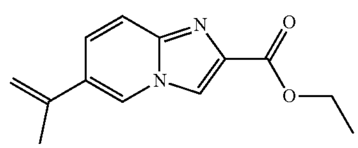 [SMILES: C=C(C)c1ccc2nc(C(=O)OCC)cn2c1] | 231.2 |
| I-23 | 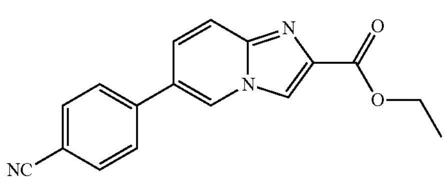 [SMILES: CCOC(=O)c1cn2cc(-c3ccc(C#N)cc3)ccc2n1] | 292.1 |
| I-24 | 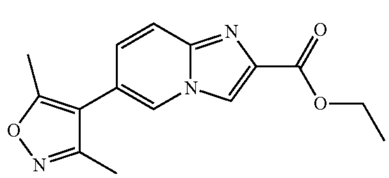 [SMILES: CCOC(=O)c1cn2cc(-c3c(C)noc3C)ccc2n1] | 286.1 |
| I-25 | 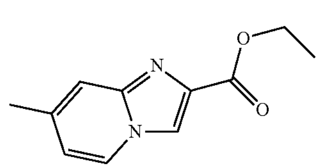 | 372.1 |

| Intermediate No | Structure | LC/MS_m/z_ [M + H]+ |
|---|---|---|
| I-26 | 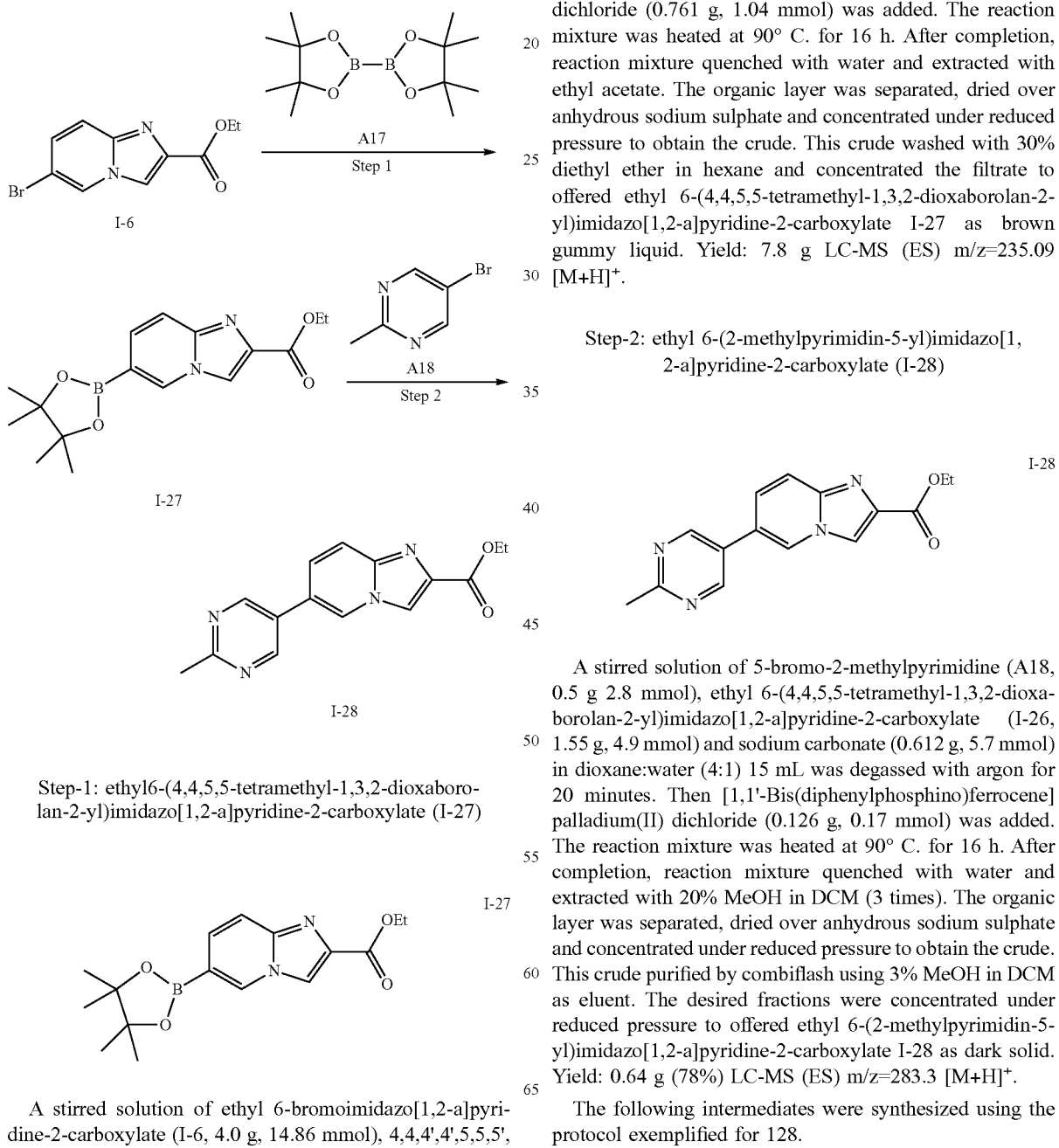 | 283.2 |

Synthesis of ethyl 6-(2-methylpyrimidin-5-yl)imidazo[1,2-a]pyridine-2-carboxylate I-28

Step-1: ethyl6-(4,4,5,5-tetramethyl-1,3,2-dioxaborolan-2-yl)imidazo[1,2-a]pyridine-2-carboxylate (I-27)

A stirred solution of ethyl 6-bromoimidazo[1,2-a]pyridine-2-carboxylate (I-6, 4.0 g, 14.86 mmol), 4,4,4',4',5,5,5', 5'-octamethyl-2,2'-bi(1,3,2-dioxaborolane) (A17, 6.42 g, 25.27 mmol) and KOAc (2.47 gm, 25.27 mmol) in dioxane (100 mL) was degassed with argon for 30 minutes. Then [1,1'-Bis(diphenylphosphino)ferrocene]palladium(II) dichloride (0.761 g, 1.04 mmol) was added. The reaction mixture was heated at 90° C. for 16 h. After completion, reaction mixture quenched with water and extracted with ethyl acetate. The organic layer was separated, dried over anhydrous sodium sulphate and concentrated under reduced pressure to obtain the crude. This crude washed with 30% diethyl ether in hexane and concentrated the filtrate to offered ethyl 6-(4,4,5,5-tetramethyl-1,3,2-dioxaborolan-2-yl)imidazo[1,2-a]pyridine-2-carboxylate I-27 as brown gummy liquid. Yield: 7.8 g LC-MS (ES) m/z=235.09 [M+H]+.

Step-2: ethyl 6-(2-methylpyrimidin-5-yl)imidazo[1,2-a]pyridine-2-carboxylate (I-28)

A stirred solution of 5-bromo-2-methylpyrimidine (A18, 0.5 g 2.8 mmol), ethyl 6-(4,4,5,5-tetramethyl-1,3,2-dioxaborolan-2-yl)imidazo[1,2-a]pyridine-2-carboxylate (I-26, 1.55 g, 4.9 mmol) and sodium carbonate (0.612 g, 5.7 mmol) in dioxane:water (4:1) 15 mL was degassed with argon for 20 minutes. Then [1,1'-Bis(diphenylphosphino)ferrocene] palladium(II) dichloride (0.126 g, 0.17 mmol) was added. The reaction mixture was heated at 90° C. for 16 h. After completion, reaction mixture quenched with water and extracted with 20% MeOH in DCM (3 times). The organic layer was separated, dried over anhydrous sodium sulphate and concentrated under reduced pressure to obtain the crude. This crude purified by combiflash using 3% MeOH in DCM as eluent. The desired fractions were concentrated under reduced pressure to offered ethyl 6-(2-methylpyrimidin-5-yl)imidazo[1,2-a]pyridine-2-carboxylate I-28 as dark solid. Yield: 0.64 g (78%) LC-MS (ES) m/z=283.3 [M+H]+.

The following intermediates were synthesized using the protocol exemplified for 128.

| Intermediate No | Structure | LC/MS_m/z_ [M + H]+ |
|---|---|---|
| I-29 | 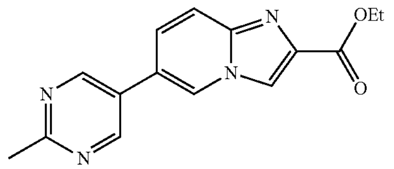 [SMILES: CCOC(=O)c1cn2cc(-c3cnc(C)nc3)ccc2n1] | 283.3 |
| I-30 | 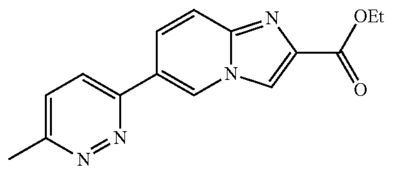 [SMILES: CCOC(=O)c1cn2cc(-c3ccc(C)nn3)ccc2n1] | 283.2 |
| I-31 | 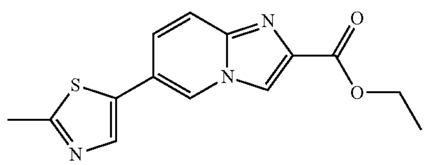 [SMILES: CCOC(=O)c1cn2cc(-c3cnc(C)s3)ccc2n1] | 287.9 |
| I-32 | 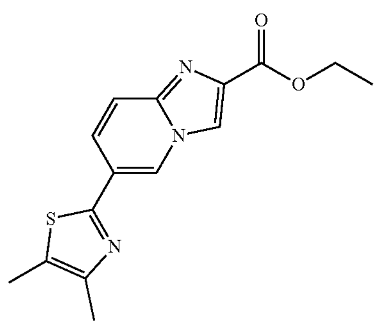 [SMILES: CCOC(=O)c1cn2cc(-c3nc(C)c(C)s3)ccc2n1] | 302.2 |
| I-33 | 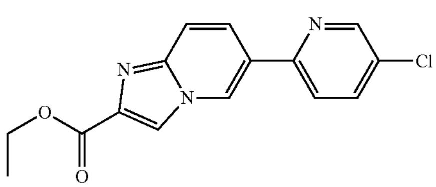 [SMILES: CCOC(=O)c1cn2cc(-c3ccc(Cl)cn3)ccc2n1] | 302.2 |
| I-34 | 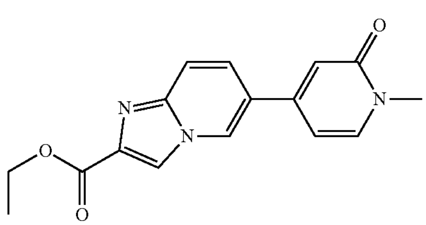 | 298.08 |
| I-35 | 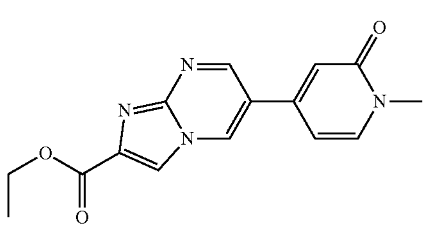 [SMILES: CCOC(=O)c1cn2cc(-c3ccn(C)c(=O)c3)cnc2n1] | 299.1 |

Synthesis of (S)—N-(3-(3,4-dihydroisoquinolin-2(1H)-yl)-2-hydroxypropyl)-6-(1-isobutyl-1H-pyrazol-4-yl)imidazo[1,2-a]pyridine-2-carboxamide (I-37)

Step 1: Preparation of Ethyl 6-(1H-pyrazol-4-yl)imidazo[1,2-a]pyridine-2-carboxylate (I-36)

A solution of ethyl 6-bromoimidazo[1,2-a]pyridine-2-carboxylate (I-6, 3 g, 11.15 mmol), cesium carbonate (7.3 g, 25.09 mmol) and boronic acid compound A19 (4.92 g, 16.72 mmol) in DMF (60 mL) was purged with argon gas for 30 minutes at room temperature, tetrakis (0.427 g, 0.55 mmol) was added to the reaction mixture and purged argon for another 10 min. The reaction mixture was then heated to 100° C. for 18 h. The reaction mixture was filtered through celite pad and the filtrate was diluted with ice cold water and extracted with ethyl acetate. The organic layer was then washed with ice cold water (2×50 mL) and brine solution. Finally, the organic layer was dried over sodium sulfate and concentrated under reduced pressure to get the crude product. The crude product was then purified by column chromatography with 70% ethyl acetate/hexane as eluent to afford the compound I-36 as white solid (0.9 g, 32%). MS (ESI) m/z=256.9 [M+H]$^+$.

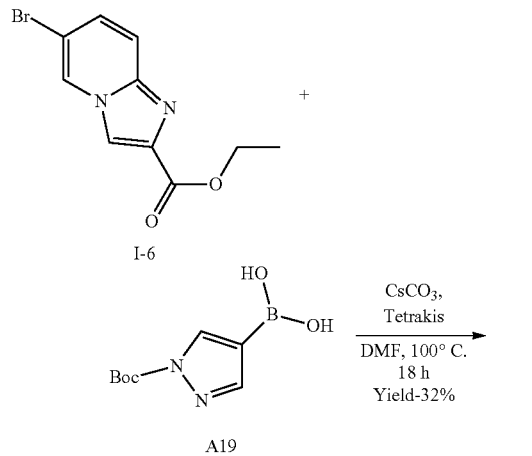

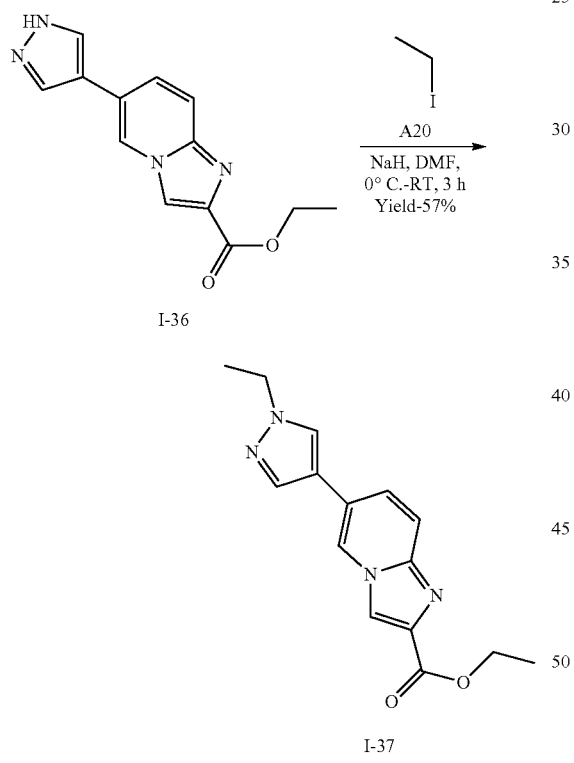

Step 2: Preparation of Ethyl 6-(1-ethyl-1H-pyrazol-4-yl)imidazo[1,2-a]pyridine-2-carboxylate (I-37)

To a solution of ethyl 6-(1H-pyrazol-4-yl)imidazo[1,2-a]pyridine-2-carboxylate (I28, 0.75 g, 2.9 mmol) in DMF (6 mL) at 0° C. was added sodium hydride (0.13 g, 3.4 mmol) under inert atmosphere. To the reaction mixture was added ethyl iodide (A20, 0.28 mL, 3.5 mmol). The reaction mixture was stirred for 12 h, then quenched with ice and extracted with ethyl acetate/ice water, followed by brine, dried over Na$_2$SO$_4$ and concentrated under reduced pressure. The compound was purified using column chromatography using ethyl acetate/hexane to afford I-37 brown solid product (0.35 g, 95%). MS (ESI) m/z=285.3 [M+H]$^+$.

The following intermediates were synthesized using the protocol exemplified for I-37. For intermediates I-39-I-41 cycloalkyl tosylates were used in place of cycloalkyl bromide.

| Intermediate No | Structure | LC/MS_m/z_ [M + H]$^+$ |
|---|---|---|
| I-38 | 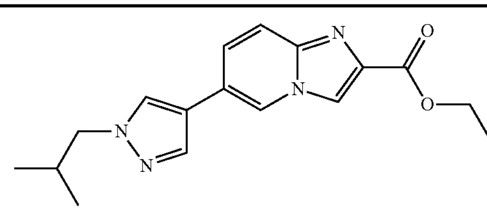 | 285.0 |

-continued

| Intermediate No | Structure | LC/MS_m/z_ [M + H]+ |
|---|---|---|
| I-39 | 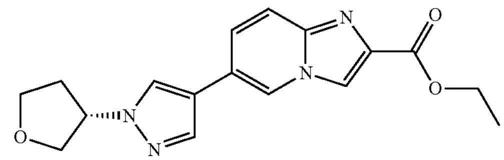 [SMILES: CCOC(=O)c1cn2cc(-c3cnn([C@H]4CCOC4)c3)ccc2n1] | 327.1 |
| I-40 | 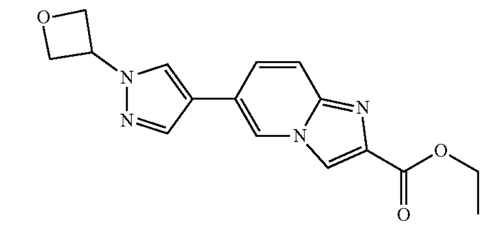 [SMILES: CCOC(=O)c1cn2cc(-c3cnn(C4COC4)c3)ccc2n1] | 313.3 |
| I-41 | 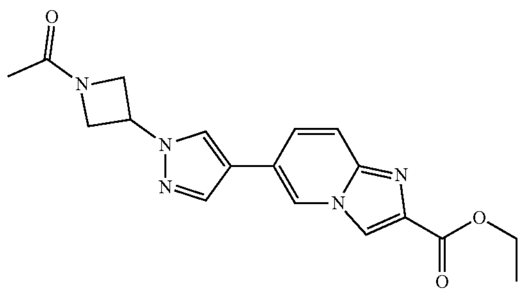 [SMILES: CCOC(=O)c1cn2cc(-c3cnn(C4CN(C(C)=O)C4)c3)ccc2n1] | 354.3 |

Synthesis of ethyl 7-(4-fluorophenyl)imidazo[1,2-a]pyridine-2-carboxylate (I-42)

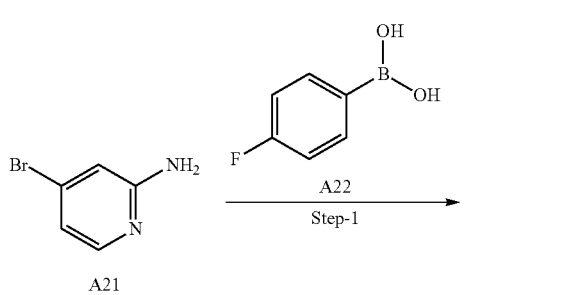

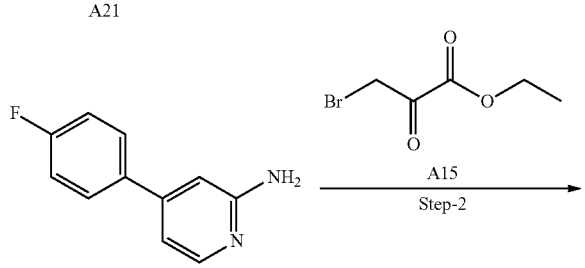

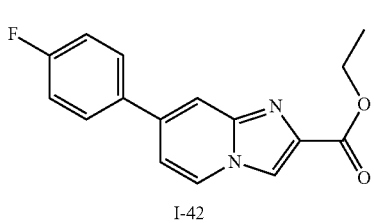

Step 1: Preparation of 4-(4-fluorophenyl)pyridin-2-amine (A23)

To a stirred solution of 4-bromopyridin-2-amine (A21, 3 g, 17.4 mmol) in 1,2-DME (80 mL) and (4-fluorophenyl) boronic acid (A22, 3.0 g, 20.9 mmol) was added $Na_2CO_3$ (3.7 g, 34.90 mmol) dissolved in $H_2O$ (30 mL). The reaction mixture was purged with N2 gas for 20 min. To the above reaction mixture was added $Pd(PPh_3)_4$ and the resulting solution was further purged with $N_2$ gas for 10 min then stirred for 1 h at 80-85° C. The reaction mixture was filtered over celite bed and washed with ethyl acetate/water mixture. The filtrate was washed with water, brine solution, dried over anhydrous $Na_2SO_4$ and concentrated under reduced pressure. The compound was purified by column chromatography using 30% ethyl acetate/hexane as the eluent to afford the title product A23 as a yellow solid (2.5 g, 76%). MS (ESI) m/z=189.1 $[M+H]^+$.

Step 2: Preparation of Ethyl 7-(4-fluorophenyl)imidazo[1,2-a]pyridine-2-carboxylate (I-42)

To a stirred solution of 4-(4-fluorophenyl)pyridin-2-amine (B9, 2.5 g, 13.2 mmol) in 1,2-DME (30 mL) was added ethyl 3-bromo pyruvate (A8, 3.4 mL, 26.5 mmol) and stirred at room temperature for 16 h. A white precipitate was observed and was filtered. The precipitate was washed with diethylether (10 mL×2). The solid was taken in EtOH and heated for 4 h at 70-75° C. Reaction mixture was cooled to room temperature and concentrated to remove ethanol. The crude I-42 was a brown oil and used for the next step without further purification (2.0 g). MS (ESI) m/z=285.1 $[M+H]^+$.

Synthesis of ethyl 6-(5-methyl-1,2,4-oxadiazol-3-yl)imidazo[1,2-a]pyridine-2-carboxylate (I-43)

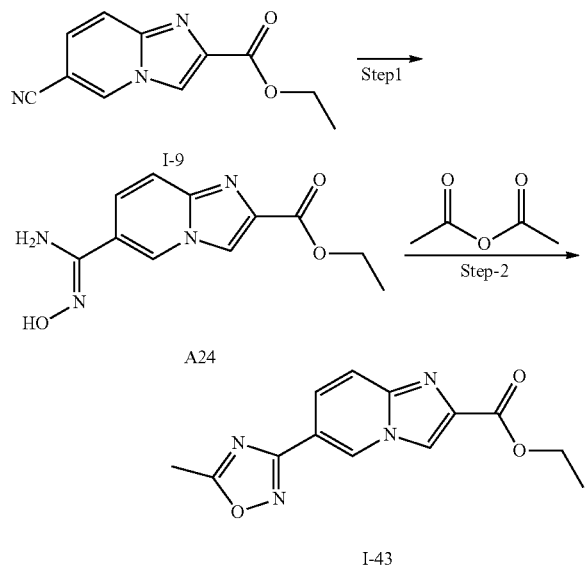

Step-1: ethyl(Z)-6-(N'-hydroxycarbamimidoyl)imidazo[1,2-a]pyridine-2-carboxylate (A24)

To a suspension of ethyl 6-cyanoimidazo[1,2-a]pyridine-2-carboxylate (I9, 0.3 g, 1.39 mmol) in isopropanol (25 mL) were added triethylamine (1.35 mL, 9.76 mmol) and hydroxylamine hydrochloride (0.579 g, 8.34 mmol). The reaction mixture was stirred at 90° C. for 16 h. The solvent was evaporated and the crude residue was diluted with sodium bicarbonate solution and extracted with ethyl acetate. The combined organic layer was washed with brine solution, dried over anhydrous sodium sulphate and concentrated under reduced pressure to give the title compound B10 as light yellow solid (0.13 g, 37.5%). MS (ESI) m/z=249 (M+H)+.

Step-2: ethyl 6-(5-methyl-1,2,4-oxadiazol-3-yl)imidazo[1,2-a]pyridine-2-carboxylate (I-43)

A suspension of ethyl (Z)-6-(N'-hydroxycarbamimidoyl)imidazo[1,2-a]pyridine-2-carboxylate B10 (0.1 g, 0.402 mmol) in acetic anhydride (A16, 3 mL) was stirred at 100° C. for 16 h. The reaction mixture was concentrated under reduced pressure to give crude residue and purified by column chromatography using 3% methanol/dichloromethane mixture as eluent to give the title compound I-43 as oily mass (0.091 g, 83%). $^1$H NMR (CDCl$_3$, 400 MHz, ppm) δ 8.91 (s, 1H), 8.25 (s, 1H), 7.89 (d, J=9.2 Hz, 1H), 7.78 (d, J=9.6 Hz, 1H), 4.50-4.45 (q, 2H), 2.68 (s, 3H), 1.45 (t, J=7.2 Hz, 3H); MS (ESI) m/z=273.1 (M+H)$^+$.

The following intermediates were synthesized using the protocol exemplified for I-43.

| Intermediate No | Structure | LC/MS_m/z_ [M + H] |
|---|---|---|
| I-44 | 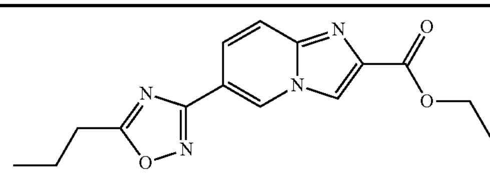 | 301.1 |
| I-45 | 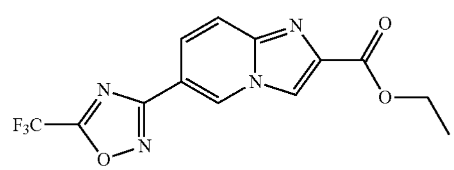 [SMILES: CCOC(=O)c1cn2cc(-c3noc(C(F)(F)F)n3)ccc2n1] | 327.9 |
| I-46 | 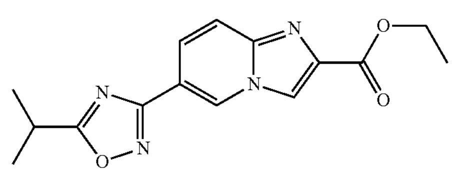 [SMILES: CCOC(=O)c1cn2cc(-c3noc(C(C)C)n3)ccc2n1] | 301.82 |
| I-47 | 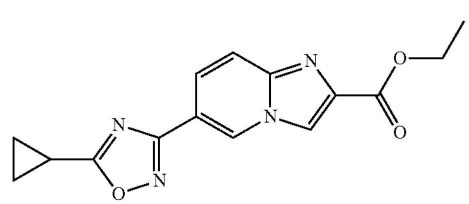 [SMILES: CCOC(=O)c1cn2cc(-c3noc(C4CC4)n3)ccc2n1] | 299.3 |

Synthesis of ethyl 6-isopropylimidazo[1,2-a]pyridine-2-carboxylate (I-48)

Ethyl 6-(1-acetylpiperidin-4-yl)imidazo[1,2-a]pyridine-2-carboxylate (I-50)

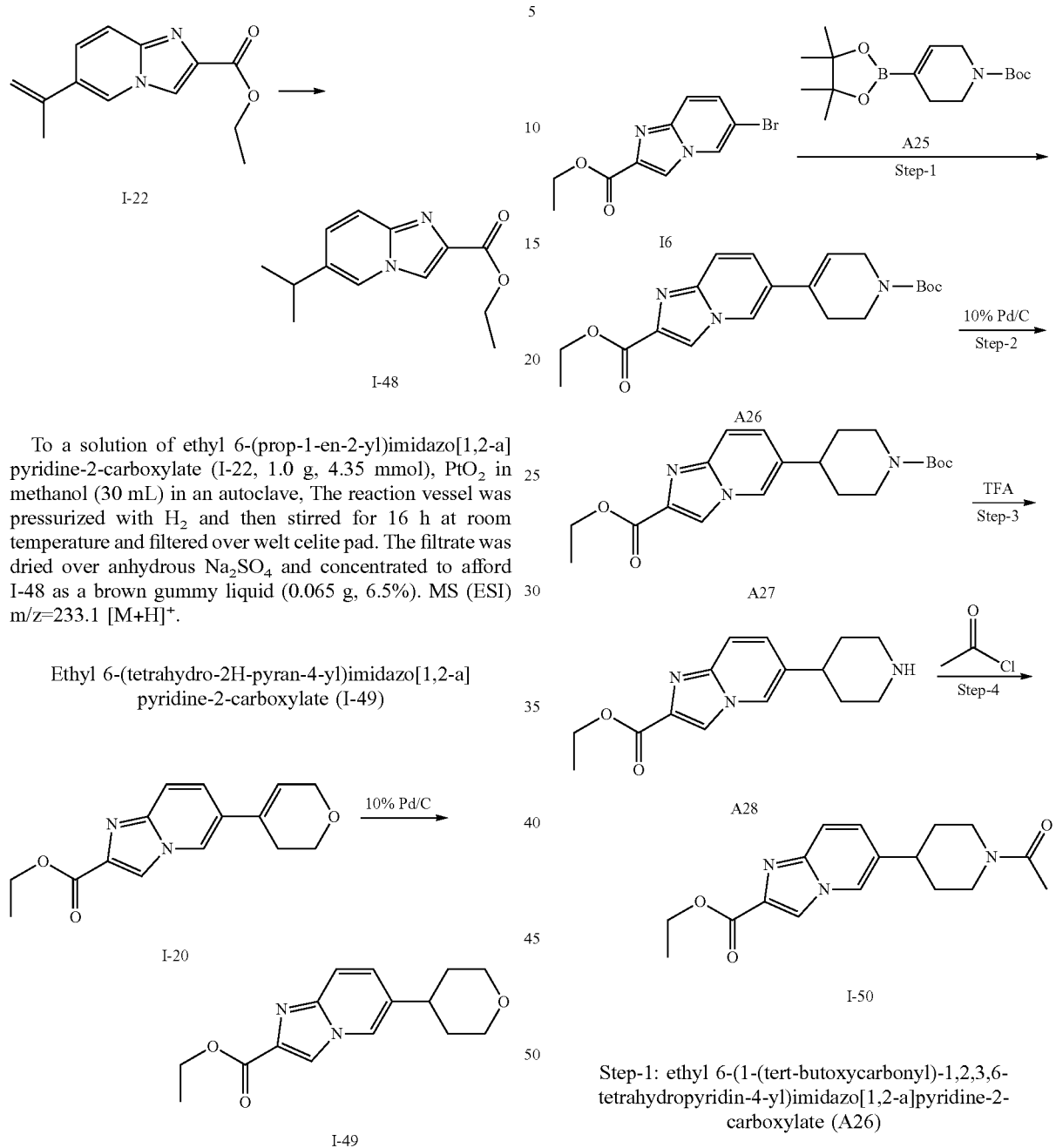

To a solution of ethyl 6-(prop-1-en-2-yl)imidazo[1,2-a]pyridine-2-carboxylate (I-22, 1.0 g, 4.35 mmol), PtO$_2$ in methanol (30 mL) in an autoclave, The reaction vessel was pressurized with H$_2$ and then stirred for 16 h at room temperature and filtered over welt celite pad. The filtrate was dried over anhydrous Na$_2$SO$_4$ and concentrated to afford I-48 as a brown gummy liquid (0.065 g, 6.5%). MS (ESI) m/z=233.1 [M+H]$^+$.

Ethyl 6-(tetrahydro-2H-pyran-4-yl)imidazo[1,2-a]pyridine-2-carboxylate (I-49)

To a stirred solution of ethyl 6-(3,6-dihydro-2H-pyran-4-yl)imidazo[1,2-a]pyridine-2-carboxylate (I14, 0.40 g, 1.46 mmol) in methanol (10 mL) was added Pd/C (0.08 g, 0.471 mmol) under N2 atmosphere and the reaction mixture was stirred under H$_2$ balloon pressure at room temperature for 4 h. After completion of reaction mixture filtered through celite bed and washed with EtOAc. The filtrate was concentrated to dryness. The residue was washed with n-pentane dried to get ethyl 6-(tetrahydro-2H-pyran-4-yl)imidazo[1,2-a]pyridine-2-carboxylate I-49 as a pale yellow solid. Yield: 0.30 g (75%) LC-MS (ES) m/z: 274.74 [M+H]$^+$.

Step-1: ethyl 6-(1-(tert-butoxycarbonyl)-1,2,3,6-tetrahydropyridin-4-yl)imidazo[1,2-a]pyridine-2-carboxylate (A26)

To a stirred solution of ethyl 6-bromoimidazo[1,2-a]pyridine-2-carboxylate (I-6, 0.50 g, 1.85 mmol) in 1,2-dimethoxyethane (10 mL) and tert-butyl 4-(4,4,5,5-tetramethyl-1,3,2-dioxaborolan-2-yl)-3,6-dihydropyridine-1(2H)-carboxylate (A25, 0.86 g, 2.78 mmol) was added Na$_2$CO$_3$ (0.59 g, 5.57 mmol) dissolved in H$_2$O (2 mL). The reaction mixture was purged with N2 gas for 20 min. To the above reaction mixture was added [1,1'-Bis(diphenylphosphino)ferrocene]dichloropalladium(II) with dichloromethane PdCl$_2$(dppf).DCM (0.15 g, 0.185 mmol), and the resulting solution was further purged with N2 gas for 10 min then stirred for 16 h at 80° C. The reaction mixture was filtered over celite bed and washed with ethylacetate/water mixture.

The filtrate was washed with water, brine solution, dried over anhydrous Na₂SO₄ and concentrated under reduced pressure. The compound was purified by column chromatography using 0-10% methanol/dichloromethane as the eluent to afford ethyl 6-(1-(tert-butoxycarbonyl)-1,2,3,6-tetrahydropyridin-4-yl)imidazo[1,2-a]pyridine-2-carboxylate A26 as a white solid. Yield: 0.50 g (72%) LC-MS (ES) m/z: 372.06 [M+H]⁺.

Step-2: ethyl 6-(1-(tert-butoxycarbonyl)piperidin-4-yl)imidazo[1,2-a]pyridine-2-carboxylate (A27)

To a stirred solution of ethyl 6-(1-(tert-butoxycarbonyl)-1,2,3,6-tetrahydropyridin-4-yl)imidazo[1,2-a]pyridine-2-carboxylate (A26, 0.35 g, 0.942 mmol) in methanol (10 mL) was added Pd/C (0.05 g, 0.471 mmol) under N2 atmosphere and the reaction mixture was stirred under H₂ balloon pressure at room temperature for 4 h. After completion of reaction mixture filtered through celite bed and washed with EtOAc. The filtrate was concentrated to dryness. The residue was washed with n-pentane dried to get ethyl 6-(1-(tert-butoxycarbonyl)piperidin-4-yl)imidazo[1,2-a]pyridine-2-carboxylate B12 as a pale yellow solid. Yield: 0.27 g (77%) LC-MS (ES) m/z: 374.74 [M+H]⁺.

Step-3: ethyl 6-(piperidin-4-yl)imidazo[1,2-a]pyridine-2-carboxylate (A27)

To a solution of ethyl 6-(1-(tert-butoxycarbonyl)piperidin-4-yl)imidazo[1,2-a]pyridine-2-carboxylate (A26, 0.25 g, 0.669 mmol) in DCM (5 mL) at 0° C. was added TFA (2.5 mL) and the resulting solution was stirred at room temperature for 2 h. After completion of reaction mixture concentrated under reduced pressure and washed with ether and dried to afford compound ethyl 6-(piperidin-4-yl)imidazo[1,2-a]pyridine-2-carboxylate A27 as a brown solid. Yield: 0.25 g (crude) LC-MS (ES) m/z: 274.03 [M+H]⁺.

Step-4: ethyl 6-(1-acetylpiperidin-4-yl)imidazo[1,2-a]pyridine-2-carboxylate (I-50)

To a solution of ethyl 6-(piperidin-4-yl)imidazo[1,2-a]pyridine-2-carboxylate (A27, 0.250 g, 0.914 mmol) in DCM (10 mL) at 0° C. was added TEA (0.31 mL, 2.28 mmol) and acetyl chloride (0.10 mL, 1.37 mmol) was added and the resulting solution was stirred at room temperature for 4 h. After completion of reaction diluted with DCM and washed with water the organic layer was dried over anhydrous sodium sulfate, filtered and concentrated under reduced pressure to afford ethyl 6-(1-acetylpiperidin-4-yl)imidazo[1,2-a]pyridine-2-carboxylate I-50 as a brown solid. Yield: 0.21 g (98%) LC-MS (ES) m/z: 316.12 [M+H]⁺.

Ethyl 6-(1-methyl-1H-1,2,3-triazol-4-yl)imidazo[1,2-a]pyridine-2-carboxylate (I-51)

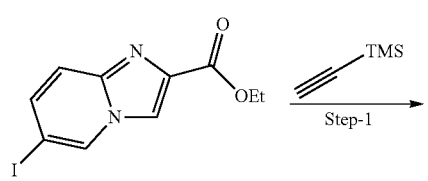

A28

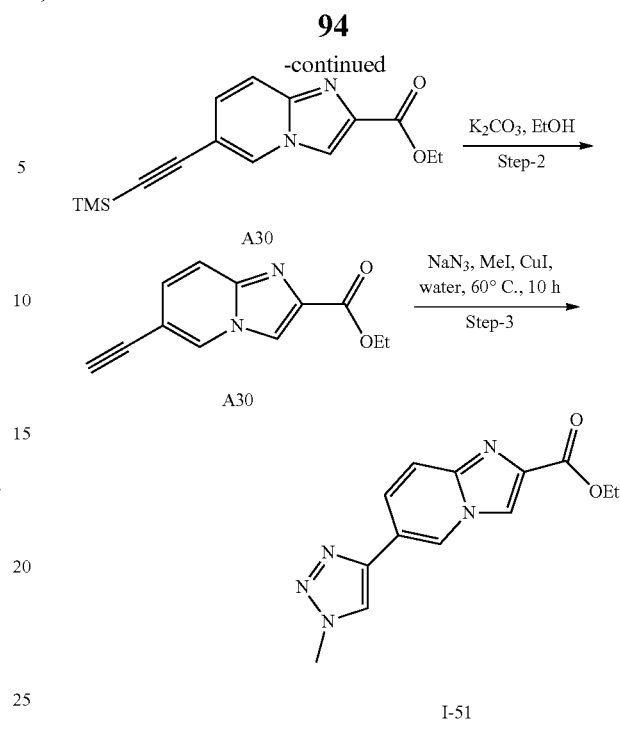

I-51

Step-1: ethyl 6-((trimethylsilyl)ethynyl)imidazo[1,2-a]pyridine-2-carboxylate (A29)

To a stirred solution of ethyl 6-iodoimidazo[1,2-a]pyridine-2-carboxylate (A28, 3.0 g, 9.49 mmol) in 1,4-dioxane (60 mL) was added ethynyltrimethylsilane (2.02 ml, 14.23 mmol), triethylamine (6.31 mL, 47.45 mmol), followed by CuI (9.03 g, 64.74 mmol) and PdCl₂(PPh₃)₂ (0.66 g, 0.949 mmol). The reaction mixture was stirred at room temperature for 16 h. After completion of reaction, the mixture was filtered through celite bed and washed with EtOAc. The filtrate was diluted with water, organic layer separated, dried over sodium sulphate and concentrated under reduced pressure. The obtained crude was purified by column chromatography using 30% ethyl acetate in hexane as eluent to afford ethyl 6-((trimethylsilyl)ethynyl)imidazo[1,2-a]pyridine-2-carboxylate A29 the desired product as yellow solid (2.2 g, 81%). LC-MS m/z: 286.99 [M+H]⁺.

Step-2: ethyl 6-ethynylimidazo[1,2-a]pyridine-2-carboxylate (A30)

To a stirred solution of ethyl 6-((trimethylsilyl)ethynyl) imidazo[1,2-a]pyridine-2-carboxylate (A29, 2.20 g, 7.68 mmol) in THF (20 mL) was added tetra butyl ammonium fluoride (4.44 mL, 15.36 mmol) and the reaction mixture was stirred at room temperature for 2 h. After completion of reaction mixture quenched with water and extracted with ethyl acetate. The organic layer was dried over sodium sulphate and concentrated under reduced pressure. The obtained crude was purified by column chromatography using 40% ethyl acetate in hexane as eluent to get compound ethyl 6-ethynylimidazo[1,2-a]pyridine-2-carboxylate A30 as a brown solid. Yield: 1.2 g (83%) LC-MS (ES) m/z: 214.99 [M+H]⁺.

Step-3: ethyl 6-(1-methyl-1H-1,2,3-triazol-4-yl) imidazo[1,2-a]pyridine-2-carboxylate (I-51)

To a solution of 6-ethynylimidazo[1,2-a]pyridine-2-carboxylate (A30, 1 g, 4.66 mmol) in EtOH:H2O (1:1) (15 mL)

was added NaN3 (0.36, 5.60 mmol), CuI (0.08, 0.466 mmol) and Iodomethane (0.46 mL, 4.67 mmol). The resulting solution was stirred in microwave for 1 h. After completion of reaction diluted with DCM and washed with water. The organic layer was dried over anhydrous sodium sulphate, filtered and concentrated under reduced pressure. The obtained crude was purified by column chromatography 5.0% MeOH in DCM as eluent to afford ethyl 6-(1-methyl-1H-1,2,3-triazol-4-yl)imidazo[1,2-a]pyridine-2-carboxylate I-51 as a white solid. Yield: 0.30 g (18%) LC-MS (ES) m/z: 271.22 [M+H]⁺.

Synthesis of ethyl 6-(1-isopropyl-1H-1,2,3-triazol-4-yl)imidazo[1,2-a]pyridine-2-carboxylate (I-52)

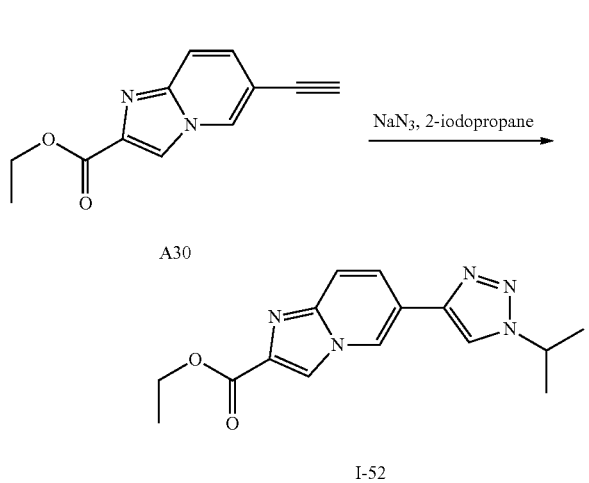

To a solution of ethyl 6-ethynylimidazo[1,2-a]pyridine-2-carboxylate (A30, 1.0 g, 4.66 mmol) in EtOH:H₂O (1:1) (15 mL) was added NaN₃ (0.36 g, 5.60 mmol), CuI (0.08 g, 0.466 mmol) and 2-iodopropane (0.46 mL, 4.67 mmol) and the resulting solution was stirred in microwave for 1 h. After completion of reaction diluted with DCM and washed with water the organic layer was dried over anhydrous sodium sulfate, filtered and concentrated under reduced pressure. The obtained crude was purified by column chromatography using 0-60% ethyl acetate in hexanes to afford compound ethyl 6-(1-isopropyl-1H-1,2,3-triazol-4-yl)imidazo[1,2-a]pyridine-2-carboxylate I-52 as a white solid. Yield: 0.30 g (18%) LC-MS (ES) m/z: 271.22 [M+H]⁺.

Synthesis of ethyl 6-(methylcarbamoyl)imidazo[1,2-a]pyridine-2-carboxylate (I-53)

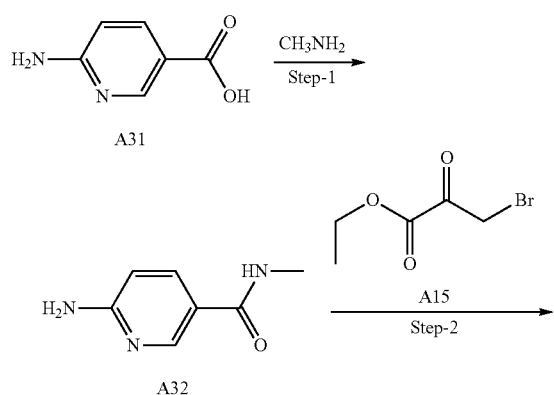

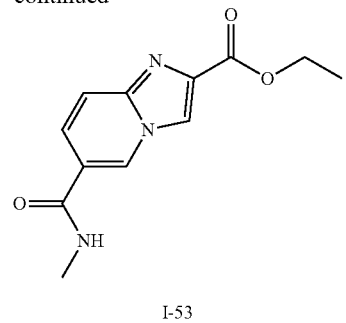

Step-1; 6-amino-N-methylnicotinamide (A32)

To a solution of 6-aminonicotinic acid (A31, 1.0 g, 7.24 mmol) in DMF (10 mL) was added DIPEA (3.89 mL, 21.73 mmol) followed by HATU (4.1 g, 10.86 mmol). The reaction mixture was stirred for 10 min followed by addition methyl amine (2.0 M in THF) (5.43 mL, 10.86 mmol). The reaction mixture was stirred at room temperature for 16 h. The reaction was monitored till the completion of starting materials (LC/MS) and then concentrated under reduced pressure. The obtained crude was purified by column chromatography using 10% methanol in dichloromethane as eluent to afford 6-amino-N-methylnicotinamide B18 as white solid, Yield: 0.12 g (13%) LC-MS (ES) m/z: 150.12 [M+H]⁺.

Step-2: ethyl 6-(methylcarbamoyl)imidazo[1,2-a]pyridine-2-carboxylate (I-53)

To a stirred solution of 6-amino-N-methylnicotinamide (A31, 0.9 g, 5.96 mmol) in 1,4-dioxane (10 mL) was added Ethyl 3-bromo pyruvate (A15, 1.12 mL, 8.94 mmol), followed by NaHCO₃ (1.0 g, 11.92 mmol). The reaction mixture was heated for 12 h at 100° C. and then concentrated under reduced pressure. The crude product was triturated with water and washed with n-pentane and dried to afford ethyl 6-(methylcarbamoyl)imidazo[1,2-a]pyridine-2-carboxylate I-53 as white solid Yield: 0.7 g, (50%). LC-MS m/z: 246.12 [M−H]⁻.

Synthesis of ethyl 6-acetamidoimidazo[1,2-a]pyridine-2-carboxylate (I-54)

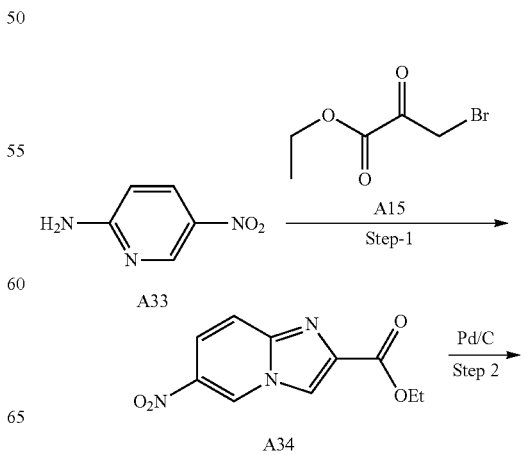

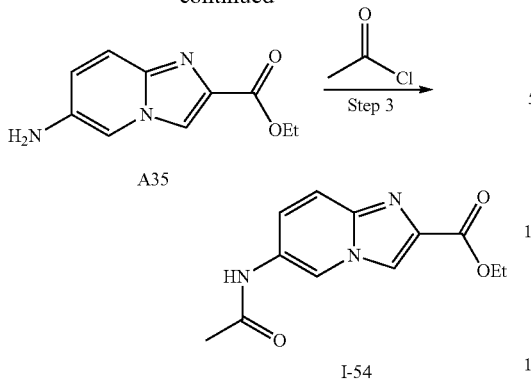

Step-1: ethyl 6-nitroimidazo[1,2-a]pyridine-2-carboxylate (A34)

To a stirred solution of 5-nitropyridin-2-amine (A33, 4.50 g, 32.37 mmol) in 1,4-dioxane (100 mL) was added ethyl 3-bromo pyruvate (A15, 6.31 mL, 48.56 mmol), followed by NaHCO$_3$ (5.43 g, 64.74 mmol). The reaction mixture was heated for 12 h at 100° C. and then concentrated under reduced pressure. The crude product was triturated with water and washed with n-pentane and dried to afford ethyl 6-nitroimidazo[1,2-a]pyridine-2-carboxylate A34 as off white solid. Yield: 7.30 g, (96%). LC-MS m/z 236.23 [M+H]$^+$.

Step-2: ethyl 6-aminoimidazo[1,2-a]pyridine-2-carboxylate (A35)

To a stirred solution of ethyl 6-nitroimidazo[1,2-a]pyridine-2-carboxylate (A34, 7.30 g, 31.73 mmol) in methanol (100 mL) was added Pd/C (1.6 g, 15.86 mmol) under N2 atmosphere and the reaction mixture was stirred under H$_2$ balloon pressure at room temperature for 4 h. after completion of reaction mixture filtered through celite bed and washed with EtOAc. The filtrate was concentrated to dryness. The residue was washed with n-pentane dried to get compound ethyl 6-aminoimidazo[1,2-a]pyridine-2-carboxylate A35 as a green solid. Yield: 4.50 g (70%) LC-MS (ES) m/z: 205.99 [M+H]$^+$.

Step-3: ethyl 6-acetamidoimidazo[1,2-a]pyridine-2-carboxylate (I-54)

To a solution of ethyl 6-aminoimidazo[1,2-a]pyridine-2-carboxylate (A35, 0.50 g, 2.43 mmol) in DCM (10 mL) at 0° C. was added TEA (1.01 mL, 7.31 mmol) and acetyl chloride (0.26 mL, 3.65 mmol) was added and the resulting solution was stirred at room temperature for 4 h. after completion of reaction diluted with DCM and washed with water the organic layer was dried over anhydrous sodium sulfate, filtered and concentrated under reduced pressure to afford compound ethyl 6-acetamidoimidazo[1,2-a]pyridine-2-carboxylate I-55 as a brown solid. Yield: 0.40 g (66%) LC-MS (ES) m/z: 248.11 [M+H]$^+$.

Synthesis of ethyl 6-sulfamoylimidazo[1,2-a]pyridine-2-carboxylate (I-55)

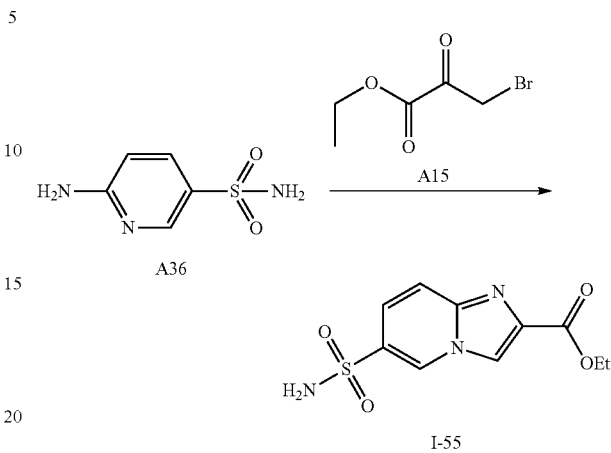

To a stirred solution of 6-aminopyridine-3-sulfonamide (A36, 0.80 g, 4.62 mmol) and NaHCO$_3$ (0.776 g, 9.24 mmol) in 1,4-dioxane, ethyl 3-bromo-2-oxopropanoate (2, 0.87 mL, 6.93 mmol) was added and reaction mixture heated to 100° C. for 16 h. After completion, reaction mixture quenched with water and extracted with ethyl acetate. The organic layer was separated, dried over anhydrous sodium sulphate and concentrated under reduced pressure to offered ethyl 6-sulfamoylimidazo[1,2-a]pyridine-2-carboxylate (I-55) as brown solid. Yield: 0.61 g (49%) LC-MS (ES) m/z=270.08 [M+H]$^+$.

Synthesis of ethyl 6-(methylsulfonamido)imidazo[1,2-a]pyridine-2-carboxylate (I-56)

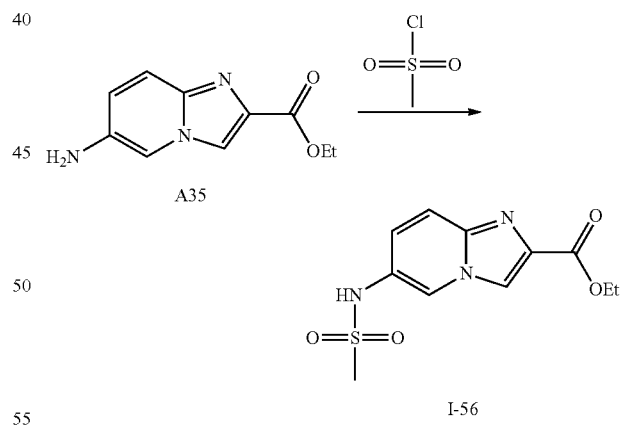

Synthesis of ethyl 6-(methylsulfonamido)imidazo[1,2-a]pyridine-2-carboxylate (I-56)

To a solution of ethyl 6-aminoimidazo[1,2-a]pyridine-2-carboxylate (A35, 1.0 g, 4.87 mmol) in pyridine (10 mL) methane sulphonyl chloride (0.37 mL, 4.87 mmol) was added and the resulting solution was stirred at room temperature for 2 h. After completion of reaction concentrated under reduced pressure to get crude. The crude was dissolved in DCM and washed with water and dried with anhydrous Na$_2$SO$_4$, filtered and concentrated to afford ethyl 6-(methylsulfonamido)imidazo[1,2-a]pyridine-2-carboxylate I-56 as a Light green solid. Yield: 0.70 g (crude) LC-MS (ES) m/z: 284.08 [M+H]$^+$.

Synthesis of methyl 6-(trifluoromethyl)imidazo[1,2-a]pyrimidine-2-carboxylate (I-57 & I-58)

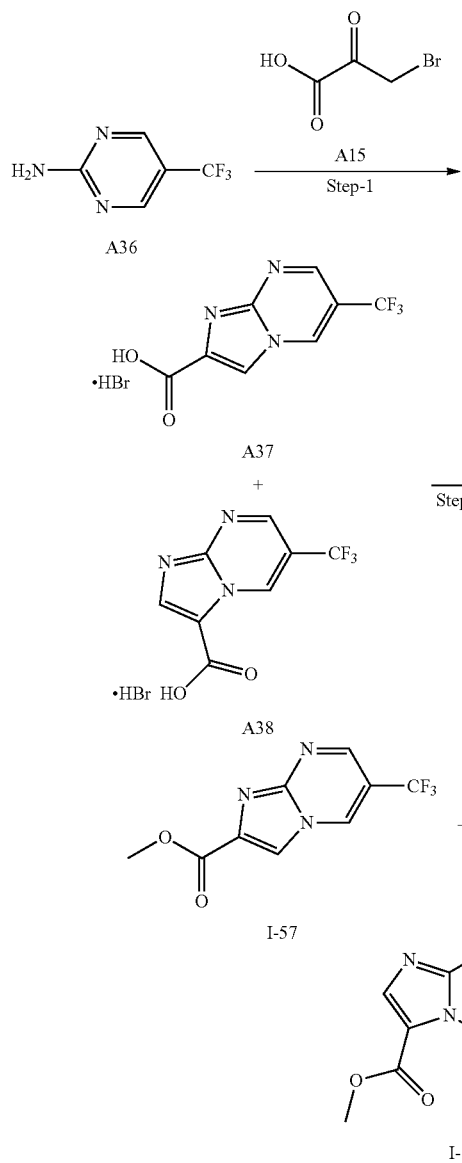

Step-1: 6-(trifluoromethyl)imidazo[1,2-a]pyrimidine-2-carboxylic acid (A37 and A38)

To a stirred solution of 5-(trifluoromethyl)pyrimidin-2-amine (A36, 4.5 g, 27.60 mmol) in 1,4-dioxane (80 mL) was added 3-bromo-2-oxopropanoic acid (A15, 6.87 g, 41.4 mmol). The reaction mixture was heated at 100° C. for 16 h. After completion of reaction mixture was concentrated under reduced pressure. The crude product was triturated with ethyl acetate and dried to afford 6-(trifluoromethyl) imidazo[1,2-a]pyrimidine-2-carboxylic acid A37 and A38 as dark brown mixture Yield: 7.0 g, (crude). LC-MS m/z: 229.96 [M−H]$^−$.

Step-2: methyl 6-(trifluoromethyl)imidazo[1,2-a]pyrimidine-2-carboxylate (I-57 and I-58)

To a stirred solution of the mixture A37 and A38 (3, 4.5 g, 19.4 mmol) in methanol (100 mL) was added drop wise H$_2$SO$_4$ (10 mL) and the reaction mixture was stirred at 80° C. temperature for 16 h. After completion of reaction organic solvent was evaporated and the aqueous layer was basified with Sat.NaHCO$_3$ up to pH 8 to 9 and aqueous layer was extracted with 10% MeOH in DCM and then concentrated under reduced pressure. The obtained crude was purified by column chromatography using 10% methanol in dichloromethane as eluent to afford methyl 6-(trifluoromethyl) imidazo[1,2-a]pyrimidine-2-carboxylate I-57 and I-58 as pink solid Yield: 0.5 g, (10%). LC-MS m/z: 245.97 [M+H]$^+$.

Synthesis of ethyl 6-(1-methyl-1H-pyrazol-4-yl)imidazo[1,2-a]pyrimidine-2-carboxylate (I-59)

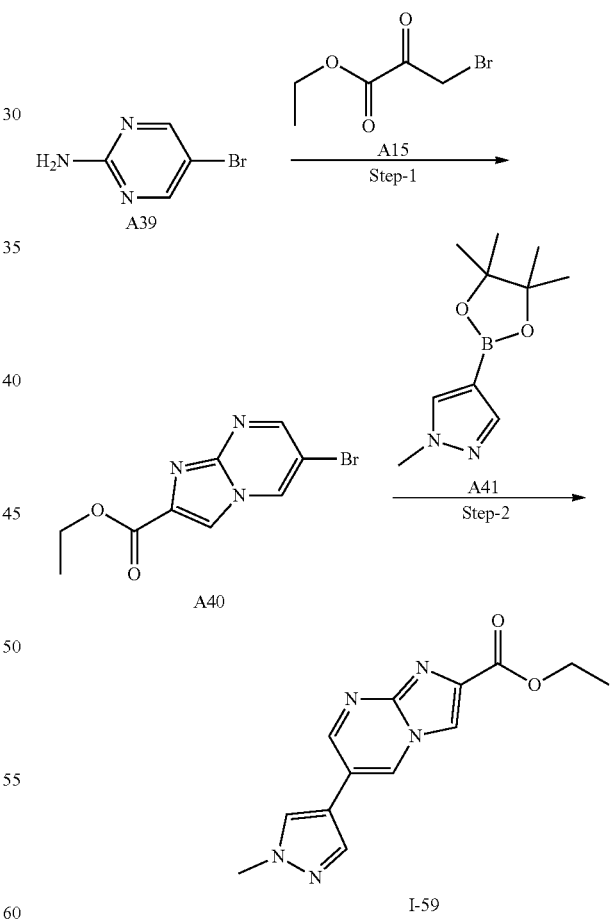

Step-1: ethyl 6-bromoimidazo[1,2-a]pyrimidine-2-carboxylate (A40)

To a stirred solution of 5-bromopyrimidin-2-amine (A39, 1.0 g, 5.74 mmol) in DMF (20 mL) was added ethyl 3-bromo pyruvate (A15, 0.86 mL, 6.89 mmol). The reaction mixture was Stirred for 16 h at Room temp. and then concentrated under reduced pressure. The crude product was triturated with water and washed with n-pentane and dried to afford ethyl 6-bromoimidazo[1,2-a]pyrimidine-2-carboxylate A40 as light brown solid Yield: 1.50 g, (87%). LC-MS m/z: 268.20 [M−H]⁻.

Step-2: ethyl 6-(1-methyl-1H-pyrazol-4-yl)imidazo [1,2-a]pyrimidine-2-carboxylate (I-59)

To a stirred solution of ethyl 6-bromoimidazo[1,2-a]pyrimidine-2-carboxylate (A40, 0.5 g, 1.85 mmol) in 1,4-dioxane (300 mL) and tert-butyl 4-(4,4,5,5-tetramethyl-1,3,2-dioxaborolan-2-yl)-1H-pyrazole-1-carboxylate (A41, 0.57 g, 2.78 mmol) was added Na$_2$CO$_3$ (0.58 g, 5.57 mmol) dissolved in H$_2$O (2 mL). The reaction mixture was purged with N2 gas for 20 min. To the above reaction mixture was added Pd(PPh$_3$)$_4$ (0.21 g, 0.185 mmol), and the resulting solution was further purged with N2 gas for 10 min then stirred for 16 h at 80° C. The reaction mixture was filtered over celite bed and washed with ethylacetate/water mixture. The filtrate was washed with water, brine solution, dried over anhydrous Na$_2$SO$_4$ and concentrated under reduced pressure. The compound was purified by column chromatography using 0-10% methanol/dichloromethane as the eluent to afford ethyl 6-(1H-pyrazol-4-yl)imidazo[1,2-a]pyridine-2-carboxylate I-59 as a brown solid. Yield: 0.4 g (86%) LC-MS (ES) m/z: 272.31 [M+H]⁺.

Synthesis of (6-(1-methyl-2-oxo-1,2-dihydropyridin-4-yl)imidazo[1,2-a] pyrimidine-2-carboxylic acid (I61)

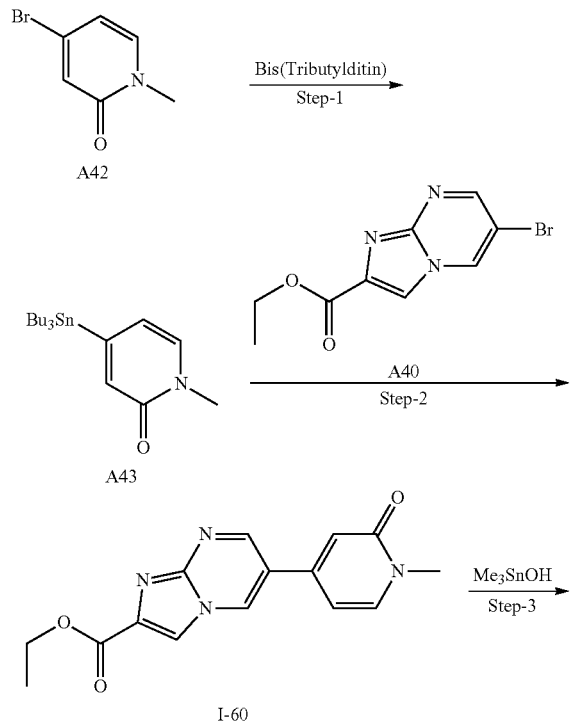

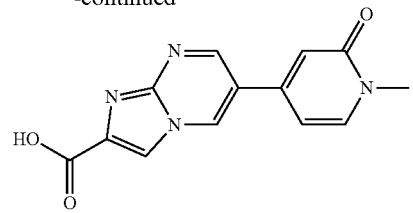

I-142

Step-1: 1-methyl-4-(tributylstannyl)pyridin-2(1H)-one (A43)

To a stirred solution of 4-bromo-1-methylpyridin-2(1H)-one (A-42, 7.0 g, 37.23 mmol) in 1,4-dioxane (140 mL) and Bis(Tributylditin) (28.72 mL, 55.85 mmol). The reaction mixture was purged with N2 gas for 20 min. To the above reaction mixture was added [1,1'-Bis(diphenylphosphino)ferrocene]dichloropalladium(II) PdCl$_2$(dppf) (2.71 g, 3.72 mmol), and the resulting solution was further purged with N$_2$ gas for 10 min then stirred for 16 h at 80° C. The reaction mixture was filtered over celite bed and washed with ethylacetate. The filtrate was washed with water, brine solution, dried over anhydrous Na$_2$SO$_4$ and concentrated under reduced pressure. The compound was purified by column chromatography using 0-10% methanol/dichloromethane as the eluent to afford 1-methyl-4-(tributylstannyl)pyridin-2(1H)-one A43 as a black liquid. Yield: 8.0 g (53%) LC-MS (ES) m/z: 400.17 [M+H]⁺.

Step-2: ethyl 6-(1-methyl-2-oxo-1,2-dihydropyridin-4-yl)imidazo[1,2-a]pyrimidine-2-carboxylate (I-60)

To a stirred solution of ethyl 6-bromoimidazo[1,2-a]pyrimidine-2-carboxylate (A40, 1.0 g, 3.70 mmol) in 1,4-dioxane (20 mL) and 1-methyl-4-(tributylstannyl)pyridin-2(1H)-one (A43, 2.20 g, 5.55 mmol). The reaction mixture was purged with N2 gas for 20 min. To the above reaction mixture was added Bis(triphenylphosphine)palladium (II) dichloride PdCl2(PPh$_3$)$_2$ (0.25 g, 0.372 mmol), and the resulting solution was further purged with N$_2$ gas for 10 min then stirred for 16 h at 80° C. The reaction mixture was filtered over celite bed and washed with ethylacetate. The filtrate was washed with water, brine solution, dried over anhydrous Na$_2$SO$_4$ and concentrated under reduced pressure. The compound was purified by column chromatography using 0-10% methanol/dichloromethane as the eluent to afford ethyl 6-(1-methyl-2-oxo-1,2-dihydropyridin-4-yl)imidazo[1,2-a]pyrimidine-2-carboxylate I-141 as a brown solid. Yield: 0.45 g (63%) LC-MS (ES) m/z: 299.20 [M+H]⁺.

Step-3: (6-(1-methyl-2-oxo-1,2-dihydropyridin-4-yl)imidazo[1,2-a]pyrimidine-2-carboxylic acid (I61)

To a stirred solution of ethyl 6-(1-methyl-2-oxo-1,2-dihydropyridin-4-yl)imidazo[1,2-a]pyrimidine-2-carboxylate (I-60, 0.45 g, 1.51 mmol) in 1,2 dichloroethane (10 mL) was added trimethyl tin hydroxide Me$_3$SnOH (0.81 g, 4.53 mmol). The reaction mixture was stirred at 100° C. for 16 h. After completion of reaction washed with saturated KF solution and the organic solvent was dried with Na$_2$SO$_4$, filtered and evaporated and the crude was acidified with 1N HCl up to pH 3 to 4 and concentrated to get desired product as a 6-(1-methyl-2-oxo-1,2-dihydropyridin-4-yl)imidazo[1,2-a]pyrimidine-2-carboxylic acid I-61 as a white solid. Yield: 0.45 g (crude) LC-MS (ES) m/z: 271.09 [M+H]$^+$.

Synthesis of ethyl 6-(1-methyl-1H-pyrazol-4-yl)imidazo[1,2-a]pyrazine-2-carboxylate (I-62)

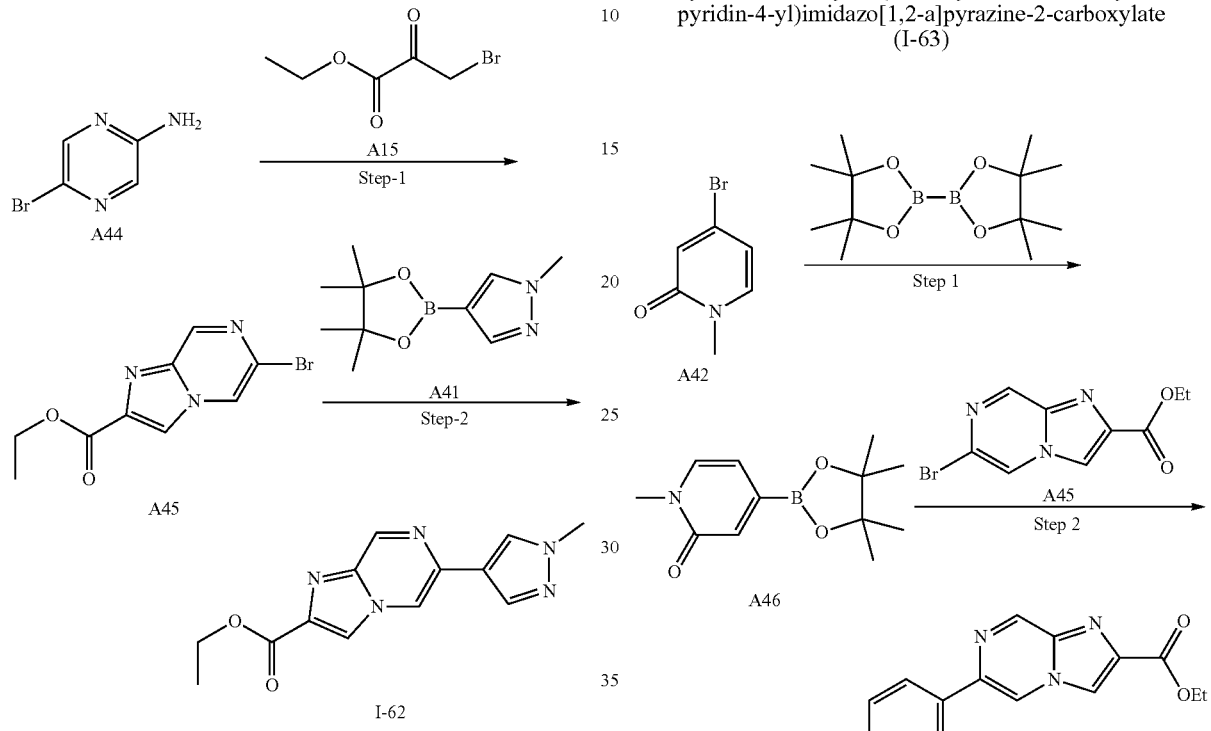

Step-1: ethyl 6-bromoimidazo[1,2-a]pyrazine-2-carboxylate (A45)

To a stirred solution of 5-bromopyrazin-2-amine (A44, 2.0 g, 11.49 mmol) in 1,4-dioxane (40 mL) was added ethyl 3-bromo pyruvate (A15, 2.16 mL, 17.24 mmol), followed by NaHCO$_3$ (1.93 g, 22.98 mmol). The reaction mixture was heated for 12 h at 100° C. After completion of reaction mixture concentrated under reduced pressure. The crude product was triturated with water and washed with n-pentane and dried to afford ethyl 6-bromoimidazo[1,2-a]pyrazine-2-carboxylate A45 as Off white solid Yield: 2.20 g, (71%). LC-MS m/z: 270.05 [M+H]$^+$.

Step-2: ethyl 6-(1-methyl-1H-pyrazol-4-yl)imidazo[1,2-a]pyrazine-2-carboxylate (I-62)

To a stirred solution of ethyl 6-bromoimidazo[1,2-a]pyrazine-2-carboxylate (A45, 1 g, 3.70 mmol) in 1,4-dioxane (20 mL) and DMF (1 mL) and 1-methyl-4-(4,4,5,5-tetramethyl-1,3,2-dioxaborolan-2-yl)-1H-pyrazole, (1.15 g, 5.55 mmol) was added Na$_2$CO$_3$ (1.17 g, 11.10 mmol) dissolved in H$_2$O (2 mL). The reaction mixture was purged with N2 gas for 20 min. To the above reaction mixture was added [1,1'-Bis(diphenylphosphino)ferrocene]dichloropalladium(II) PdCl$_2$(dppf) (0.27 g, 0.37 mmol), and the resulting solution was further purged with N2 gas for 10 min then stirred for 16 h at 80° C. The reaction mixture was filtered over celite bed and washed with ethylacetate/water mixture. The filtrate was washed with water, brine solution, dried over anhydrous Na$_2$SO$_4$ and concentrated under reduced pressure. The compound was purified by column chromatography using 0-10% methanol/dichloromethane as the eluent to afford ethyl 6-(1-methyl-1H-pyrazol-4-yl)imidazo[1,2-a]pyrazine-2-carboxylate I-62 as a brown solid. Yield: 0.70 g (70%) LC-MS (ES) m/z: 272.26 [M+H]$^+$.

Synthesis of ethyl 6-(1-methyl-2-oxo-1,2-dihydropyridin-4-yl)imidazo[1,2-a]pyrazine-2-carboxylate (I-63)

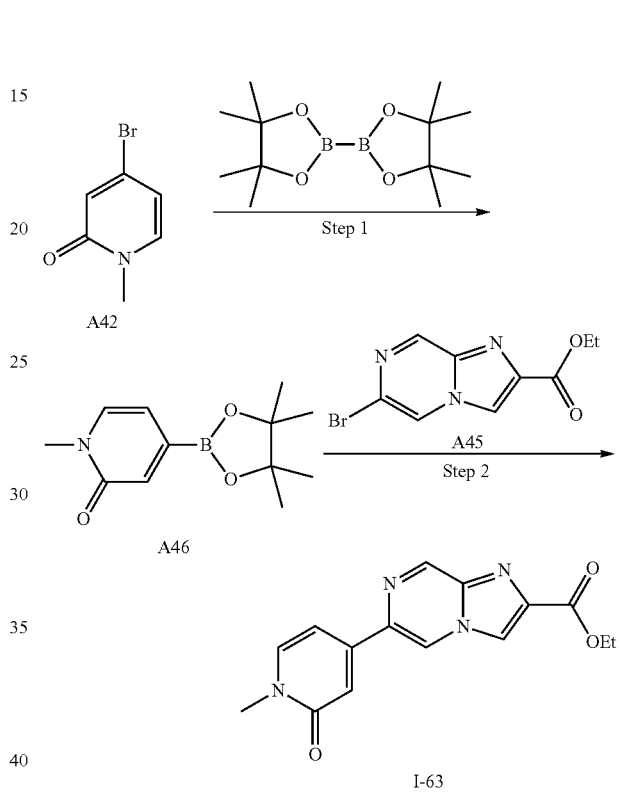

Step-1: 1-methyl-4-(4,4,5,5-tetramethyl-1,3,2-dioxaborolan-2-yl)pyridin-2(1H)-one (B27)

To a stirred solution of 4-boraneyl-1-methylpyridin-2(1H)-one (A42, 5.0 g, 41.33 mmol) in 1,4-dioxane (100 mL) and 4,4,4',4',5,5,5',5'-octamethyl-2,2'-bi(1,3,2-dioxaborolane) (15.74 g, 62.00 mmol) was added KOAc (8.10 g, 82.66 mmol). The reaction mixture was purged with N2 gas for 20 min. To the above reaction mixture was added [1,1'-Bis(diphenylphosphino)ferrocene]dichloropalladium(II) PdCl$_2$(dppf) (3.02 g, 4.13 mmol), and the resulting solution was further purged with N2 gas for 10 min then stirred for 16 h at 80° C. The reaction mixture was filtered over celite bed and washed with ethylacetate. The filtrate was washed with water, brine solution, dried over anhydrous Na$_2$SO$_4$ and concentrated under reduced pressure. to afford 1-methyl-4-(4,4,5,5-tetramethyl-1,3,2-dioxaborolan-2-yl)pyridin-2(1H)-one A46 as a brown solid. Yield: 8.0 g (crude) LC-MS (ES) m/z: 154.18 [M+H]$^+$ (corresponding boronic acid).

Step-2: ethyl 6-(1-methyl-2-oxo-1,2-dihydropyridin-4-yl)imidazo[1,2-a]pyrazine-2-carboxylate (I-63)

To a stirred solution of ethyl 6-bromoimidazo[1,2-a]pyrazine-2-carboxylate (A45, 0.60 g, 2.22 mmol) in 1,4- dioxane (12 mL) and 1-methyl-4-(4,4,5,5-tetramethyl-1,3,2-dioxaborolan-2-yl)pyridin-2(1H)-one (A46, 1.04 g, 4.44 mmol) was added Na$_2$CO$_3$ (0.705 g, 6.66 mmol) dissolved in H$_2$O (2 mL). The reaction mixture was purged with N$_2$ gas for 20 min. To the above reaction mixture was added [1,1'-Bis(diphenylphosphino)ferrocene]dichloropalladium (II) PdCl2(dppf) (0.16 g, 0.22 mmol), and the resulting solution was further purged with N2 gas for 10 min then stirred for 16 h at 80° C. The reaction mixture was filtered over celite bed and washed with ethylacetate. The filtrate was washed with water, brine solution, dried over anhydrous Na$_2$SO$_4$ and concentrated under reduced pressure. The compound was purified by column chromatography using 0-10% methanol/dichloromethane as the eluent to afford ethyl 6-(1-methyl-2-oxo-1,2-dihydropyridin-4-yl)imidazo[1,2-a]pyrazine-2-carboxylate I-63 as a off white solid. Yield: 0.50 g (45%) LC-MS (ES) m/z: 299.16 [M+H]$^+$.

Synthesis of ethyl 6-(1-methyl-6-oxo-1,6-dihydropyridin-3-yl)imidazo[1,2-a]pyrazine-2-carboxylate (I-64)

pressure. The compound was purified by column chromatography using 0-5% methanol/dichloromethane as the eluent to afford 1-methyl-5-(tributylstannyl)pyridin-2(1H)-one A48 as colorless liquid. Yield: 0.90 g (42%) LC-MS (ES) m/z: 400.16 [M+H]$^+$.

Step-2: ethyl 6-(1-methyl-6-oxo-1,6-dihydropyridin-3-yl)imidazo[1,2-a]pyrazine-2-carboxylate (I64)

To a stirred solution of ethyl 6-bromoimidazo[1,2-a]pyrazine-2-carboxylate (A45, 1.0 g, 3.70 mmol) in N,N-dimethylformamide (10 mL) and 1-methyl-5-(tributylstannyl)pyridin-2(1H)-one (A48, 2.21 g, 5.55 mmol). The reaction mixture was purged with N2 gas for 20 min. to the above reaction mixture was added Bis(triphenylphosphine) dichloropalladium(II) PdCl$_2$(PPh$_3$)$_2$ (0.23 g, 0.37 mmol), and the resulting solution was further purged with N$_2$ gas for 10 min then stirred for 6 h at 100° C. The reaction mixture was filtered over celite bed and washed with ethylacetate. The filtrate was washed with water, brine solution, dried over anhydrous Na$_2$SO$_4$ and concentrated under reduced pressure. The compound was purified by column chromatography using 0-5% methanol/dichloromethane as the eluent to afford ethyl 6-(1-methyl-6-oxo-1,6-dihydropyridin-3-yl)imidazo[1,2-a]pyrazine-2-carboxylate I-64 as brown solid, Yield: 0.19 g (18%) LC-MS (ES) m/z: 299.16 [M+H]$^+$.

Synthesis of ethyl 6-(1-methyl-1H-pyrazol-4-yl)imidazo[1,2-b]pyridazine-2-carboxylate (I-67)

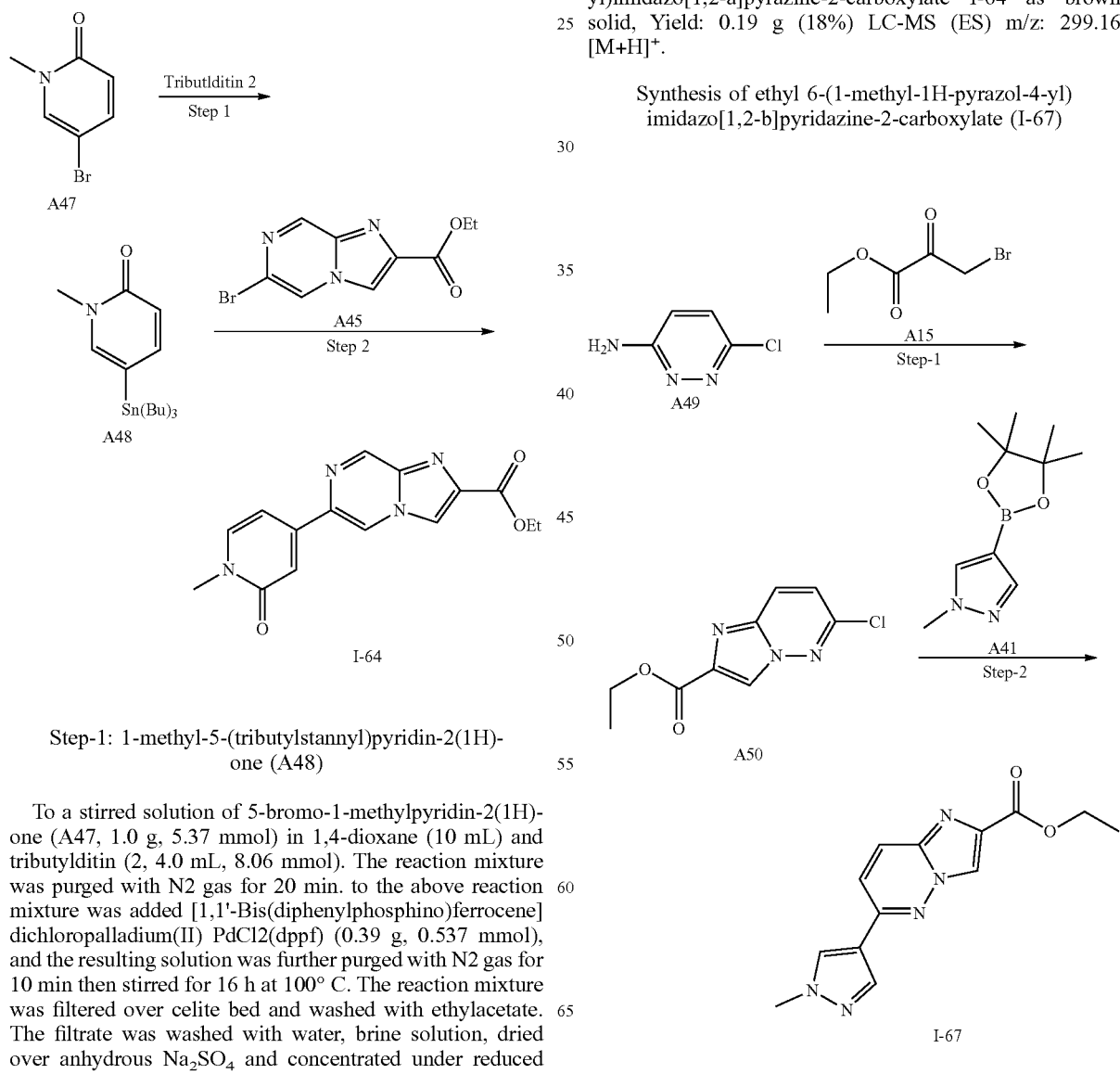

Step-1: 1-methyl-5-(tributylstannyl)pyridin-2(1H)-one (A48)

To a stirred solution of 5-bromo-1-methylpyridin-2(1H)-one (A47, 1.0 g, 5.37 mmol) in 1,4-dioxane (10 mL) and tributylditin (2, 4.0 mL, 8.06 mmol). The reaction mixture was purged with N2 gas for 20 min. to the above reaction mixture was added [1,1'-Bis(diphenylphosphino)ferrocene]dichloropalladium(II) PdCl2(dppf) (0.39 g, 0.537 mmol), and the resulting solution was further purged with N2 gas for 10 min then stirred for 16 h at 100° C. The reaction mixture was filtered over celite bed and washed with ethylacetate. The filtrate was washed with water, brine solution, dried over anhydrous Na$_2$SO$_4$ and concentrated under reduced

Step-1: ethyl 6-chloroimidazo[1,2-b]pyridazine-2-carboxylate (A50)

To a stirred solution of 6-chloropyridazin-3-amine (A49, 2.0 g, 15.43 mmol) in 1,4-dioxane (40 mL) was added ethyl 3-bromo pyruvate (A15, 2.32 mL, 18.51 mmol), followed by NaHCO$_3$ (1.94 g, 23.14 mmol). The reaction mixture was heated for 12 h at 100° C. After completion of reaction mixture concentrated under reduced pressure. The crude product was triturated with water and washed with n-pentane and dried to afford ethyl 6-chloroimidazo[1,2-b]pyridazine-2-carboxylate 3 as Off white solid Yield: 2.20 g, (64%). LC-MS m/z: 226.05 [M+H]$^+$.

Step-2: ethyl 6-(1-methyl-1H-pyrazol-4-yl)imidazo[1,2-b]pyridazine-2-carboxylate (I-67)

To a stirred solution of ethyl 6-chloroimidazo[1,2-b]pyridazine-2-carboxylate (A50, 1 g, 4.43 mmol) in 1,4-dioxane (20 mL) and DMF (1 mL) and 1-methyl-4-(4,4,5,5-tetramethyl-1,3,2-dioxaborolan-2-yl)-1H-pyrazole (A41, 1.38 g, 6.64 mmol) was added Na$_2$CO$_3$ (1.40 g, 13.29 mmol) dissolved in H$_2$O (2 mL). The reaction mixture was purged with N$_2$ gas for 20 min. To the above reaction mixture was added [1,1'-Bis(diphenylphosphino)ferrocene]dichloropalladium(II) PdCl2(dppf) (0.32 g, 0.44 mmol), and the resulting solution was further purged with N$_2$ gas for 10 min then stirred for 16 h at 80° C. The reaction mixture was filtered over celite bed and washed with ethylacetate/water mixture. The filtrate was washed with water, brine solution, dried over anhydrous Na$_2$SO$_4$ and concentrated under reduced pressure. The compound was purified by column chromatography using 0-10% methanol/dichloromethane as the eluent to afford ethyl 6-(1-methyl-1H-pyrazol-4-yl)imidazo[1,2-b]pyridazine-2-carboxylate I-67 as a brown solid. Yield: 0.70 g (59%) LC-MS (ES) m/z: 272.26 [M+H]$^+$.

Synthesis of ethyl 6-(1-methyl-2-oxo-1,2-dihydropyridin-4-yl)imidazo[1,2-b]pyridazine-2-carboxylate (I-68)

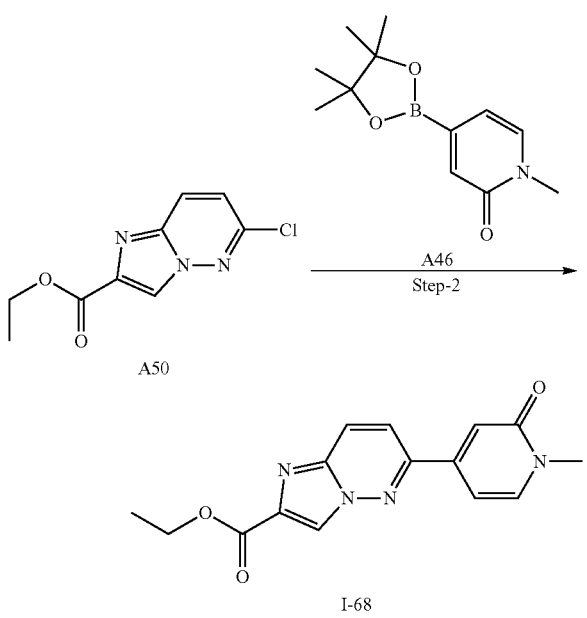

Step-2: ethyl 6-(1-methyl-2-oxo-1,2-dihydropyridin-4-yl)imidazo[1,2-b]pyridazine-2-carboxylate (I-68)

To a solution of ethyl 6-chloroimidazo[1,2-b]pyridazine-2-carboxylate (A50, 1 g, 4.43 mmol) in 1,4-Dioxane (8 mL) was added 1-methyl-4-(4,4,5,5-tetramethyl-1,3,2-dioxaborolan-2-yl)pyridin-2(1H)-one (A48, 2.08 g, 8.86 mmol), Na$_2$CO$_3$ (1.16 g, 13.29 mmol) dissolved in H$_2$O (2 mL). The reaction mixture was purged with N$_2$ gas for 20 min. To the above reaction mixture was added [1,1'-Bis(diphenylphosphino)ferrocene]dichloropalladium(II) with dichloromethane PdCl$_2$(dppf).DCM (0.15 g, 0.185 mmol), and the resulting solution was further purged with N$_2$ gas for 10 min then stirred for 16 h at 80° C. The reaction mixture was filtered over celite bed and washed with ethylacetate/water mixture. The filtrate was washed with water, brine solution, dried over anhydrous Na$_2$SO$_4$ and concentrated under reduced pressure. The obtained crude was purified by column chromatography using 0-10% MeOH-DCM as eluent to afford ethyl 6-(1-methyl-2-oxo-1,2-dihydropyridin-4-yl)imidazo[1,2-b]pyridazine-2-carboxylate 5 as white solid Yield: 0.32 g, (18%). LC-MS (ES) m/z: 299.16 [M+H]$^+$.

Synthesis of ethyl 6-(1-acetylpiperidin-4-yl)imidazo[1,2-b]pyridazine-2-carboxylate (I-69)

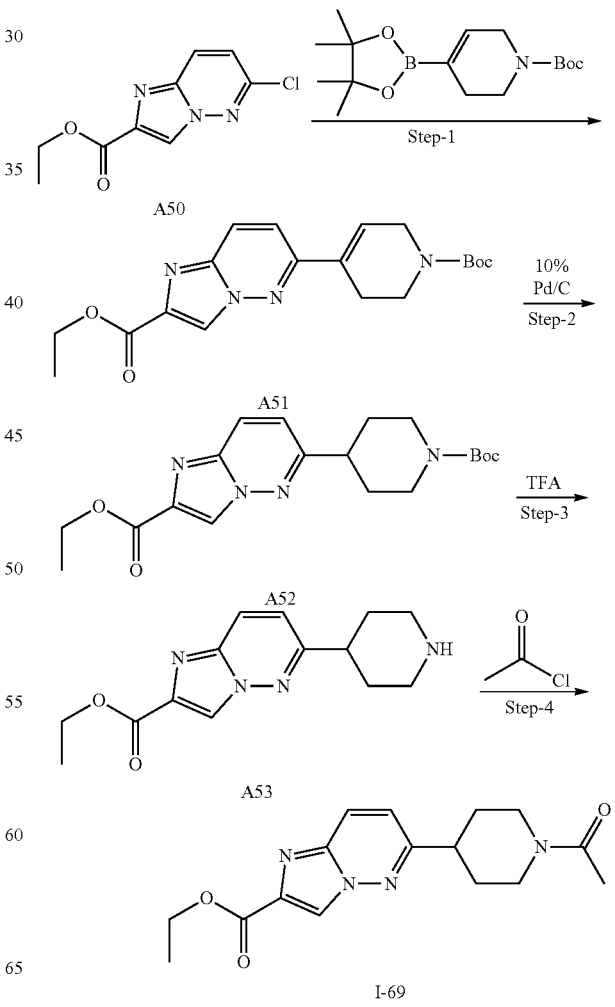

Step-1: ethyl 6-(1-(tert-butoxycarbonyl)-1,2,3,6-tetrahydropyridin-4-yl)imidazo[1,2-b]pyridazine-2-carboxylate (A51)

To a stirred solution of ethyl 6-chloroimidazo[1,2-b]pyridazine-2-carboxylate (A50, 1.5 g, 6.64 mmol) in 1,2-dimethoxy ethane (30 mL) and H₂O (6 mL) was added tert-butyl 4-(4,4,5,5-tetramethyl-1,3,2-dioxaborolan-2-yl)-3,6-dihydropyridine-1(2H)-carboxylate (1, 3.08 g, 9.97 mmol) and Na₂CO₃ (2.11 g, 19.94 mmol). The reaction mixture was purged with N₂ gas for 20 min. To the above reaction mixture was added [1,1'-Bis(diphenylphosphino)ferrocene]dichloropalladium(II) with dichloromethane PdCl₂(dppf).DCM (0.54 g, 0.664 mmol), and the resulting solution was further purged with N₂ gas for 10 min then stirred for 16 h at 80° C. The reaction mixture was filtered over celite bed and washed with ethylacetate/water mixture. The filtrate was washed with water, brine solution, dried over anhydrous Na₂SO₄ and concentrated under reduced pressure. The obtained crude was purified by column chromatography using 0-10% MeOH in DCM as eluent to afford ethyl 6-(1-(tert-butoxycarbonyl)-1,2,3,6-tetrahydropyridin-4-yl)imidazo[1,2-b]pyridazine-2-carboxylate A51 as a brown solid. Yield: 2.0 g (81%). LC-MS m/z: 370.98 [M−H]⁻.

Step-2: ethyl 6-(1-(tert-butoxycarbonyl)piperidin-4-yl)imidazo[1,2-b]pyridazine-2-carboxylate (A52)

To a stirred solution of ethyl 6-(1-(tert-butoxycarbonyl)-1,2,3,6-tetrahydropyridin-4-yl)imidazo[1,2-b]pyridazine-2-carboxylate (A51, 1.0 g, 2.68 mmol) in MeOH was added 10% Pd/C (0.20 g) and the resulting solution was stirred under H₂ gas atmosphere for 16 h at room temperature. The reaction mixture was filtered over celite bed and washed with ethyl acetate. The filtrate was concentrated under reduced pressure. The crude was triturated with diethyl ether, decant and dried to afford ethyl 6-(1-(tert-butoxycarbonyl)piperidin-4-yl)imidazo[1,2-b]pyridazine-2-carboxylate A52 as a yellow liquid. Yield: 1.0 g (95%) LC-MS (ES) m/z: 375.27 [M+H]⁺.

Step-3: ethyl 6-(piperidin-4-yl)imidazo[1,2-b]pyridazine-2-carboxylate (A53)

To a solution of ethyl 6-(1-(tert-butoxycarbonyl)piperidin-4-yl)imidazo[1,2-b]pyridazine-2-carboxylate (A52, 1.0 g, 2.67 mmol) in DCM:TFA (1:1 10 mL) the resulting solution was stirred for 2 h at room temperature The reaction mixture was basified with aqueous sodium bicarbonate solution and extracted with ethyl acetate. The organic layer was washed with water, brine solution, dried over anhydrous Na₂SO₄, filtered, and concentrated under reduced pressure. The obtained crude washed with diethyl ether and dried to afford ethyl 6-(piperidin-4-yl)imidazo[1,2-b]pyridazine-2-carboxylate A53 as white solid Yield: 0.8 g, (crude). LC-MS (ES) m/z: 275.22 [M+H]⁺.

Step-4 ethyl 6-(1-acetylpiperidin-4-yl)imidazo[1,2-b]pyridazine-2-carboxylate (I-69)

To a stirred solution of ethyl 6-(piperidin-4-yl)imidazo[1,2-b]pyridazine-2-carboxylate (A53, 0.8 g, 2.91 mmol) in (10 mL) was added TEA (2.03 mL, 14.58 mmol) and acetyl chloride (0.312 mL, 4.37 mmol) at 0° C. The reaction mixture was stirred for 1 h at room temp. After completion of reaction diluted with H₂O and extracted with DCM. The organic layer was dried over over anhydrous Na₂SO₄, filtered and concentrated under reduced pressure to get crude. Which was triturate with n-pentane and dried to afford ethyl 6-(1-acetylpiperidin-4-yl)imidazo[1,2-b]pyridazine-2-carboxylate I-69 as off white solid. Yield: 0.65 g (crude) LC-MS (ES) m/z: 317.23 [M+H]⁺.

Synthesis of ethyl 6-(1-acetylpiperidin-4-yl)imidazo[1,2-a]pyrazine-2-carboxylate (I-70)

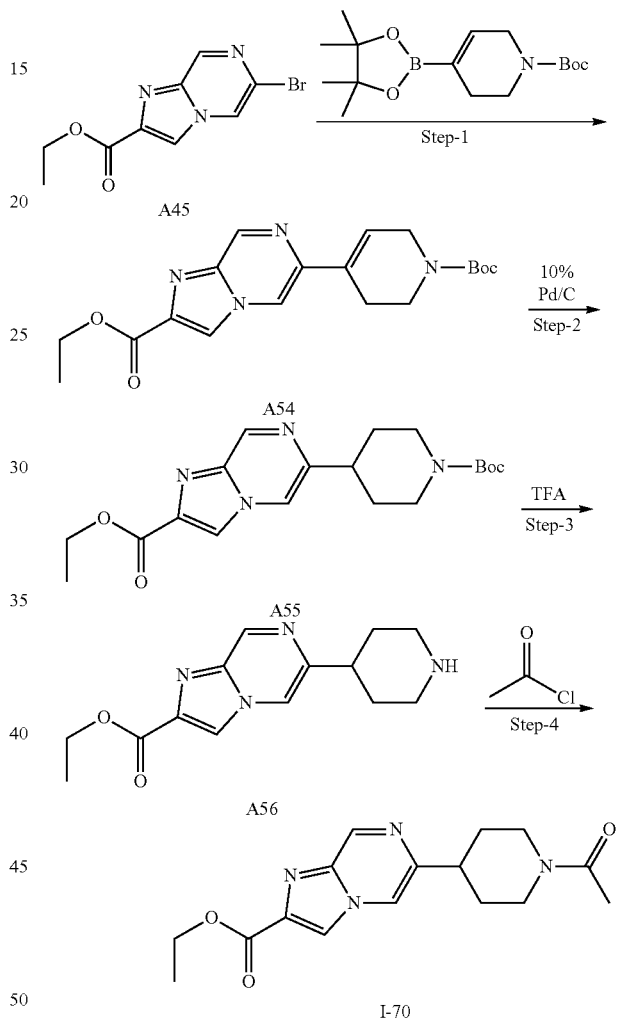

Step-1: ethyl 6-(1-(tert-butoxycarbonyl)-1,2,3,6-tetrahydropyridin-4-yl)imidazo[1,2-a]pyrazine-2-carboxylate (A54)

To a stirred solution of ethyl 6-bromoimidazo[1,2-a]pyrazine-2-carboxylate (A45, 0.50 g, 1.85 mmol) in 1,2-dimethoxyethane (10 mL) and tert-butyl 4-(4,4,5,5-tetramethyl-1,3,2-dioxaborolan-2-yl)-3,6-dihydropyridine-1(2H)-carboxylate (0.86 g, 2.78 mmol) was added Na₂CO₃ (0.59 g, 5.57 mmol) dissolved in H₂O (2 mL). The reaction mixture was purged with N₂ gas for 20 min. To the above reaction mixture was added [1,1'-Bis(diphenylphosphino)ferrocene]dichloropalladium(II) with dichloromethane PdCl₂(dppf).DCM (0.15 g, 0.185 mmol), and the resulting solution was further purged with N₂ gas for 10 min then stirred for 16 h at 80° C. The reaction mixture was filtered over celite bed and washed with ethylacetate/water mixture. The filtrate was washed with water, brine solution, dried over anhydrous Na₂SO₄ and concentrated under reduced pressure. The compound was purified by column chromatography using 0-10% methanol/dichloromethane as the eluent to afford ethyl 6-(1-(tert-butoxycarbonyl)-1,2,3,6-tetrahydropyridin-4-yl)imidazo[1,2-a]pyrazine-2-carboxylate A54 as a white solid. Yield: 0.50 g (72%) LC-MS (ES) m/z: 373.06 [M+H]⁺.

Step-2: ethyl 6-(1-(tert-butoxycarbonyl)piperidin-4-yl)imidazo[1,2-a]pyrazine-2-carboxylate (A55)

To a stirred solution of ethyl 6-(1-(tert-butoxycarbonyl)-1,2,3,6-tetrahydropyridin-4-yl)imidazo[1,2-a]pyrazine-2-carboxylate (A54, 0.35 g, 0.942 mmol) in methanol (10 mL) was added Pd/C (0.05 g, 0.471 mmol) under N₂ atmosphere and the reaction mixture was stirred under H₂ balloon pressure at room temperature for 4 h. After completion of reaction mixture filtered through celite bed and washed with EtOAc. The filtrate was concentrated to dryness. The residue was washed with n-pentane dried to get ethyl 6-(1-(tert-butoxycarbonyl)piperidin-4-yl)imidazo[1,2-a]pyrazine-2-carboxylate A55 as a pale yellow solid. Yield: 0.27 g (77%) LC-MS (ES) m/z: 375.74 [M+H]⁺.

Step-3: ethyl 6-(piperidin-4-yl)imidazo[1,2-a]pyrazine-2-carboxylate (AA56)

To a solution of ethyl 6-(1-(tert-butoxycarbonyl)piperidin-4-yl)imidazo[1,2-a]pyrazine-2-carboxylate (A55, 0.25 g, 0.669 mmol) in DCM (5 mL) at 0° C. was added TFA (2.5 mL) and the resulting solution was stirred at room temperature for 2 h. After completion of reaction mixture concentrated under reduced pressure and washed with ether and dried to afford compound ethyl 6-(piperidin-4-yl)imidazo[1,2-a]pyrazine-2-carboxylate B36 as a brown solid. Yield: 0.25 g (crude) LC-MS (ES) m/z: 275.03 [M+H]⁺.

Step-4: ethyl 6-(1-acetylpiperidin-4-yl)imidazo[1,2-a]pyrazine-2-carboxylate (I-70)

To a solution of ethyl 6-(piperidin-4-yl)imidazo[1,2-a]pyrazine-2-carboxylate (A56, 0.250 g, 0.914 mmol) in DCM (10 mL) at 0° C. was added TEA (0.31 mL, 2.28 mmol) and acetyl chloride (0.10 mL, 1.37 mmol) was added and the resulting solution was stirred at room temperature for 4 h. After completion of reaction diluted with DCM and washed with water the organic layer was dried over anhydrous sodium sulfate, filtered and concentrated under reduced pressure to afford ethyl 6-(1-acetylpiperidin-4-yl)imidazo[1,2-a]pyrazine-2-carboxylate I-70 as a brown solid. Yield: 0.21 g (98%) LC-MS (ES) m/z: 317.12 [M+H]⁺.

Synthesis of ethyl 6-(1-methyl-1H-pyrazol-4-yl)imidazo[1,2-a]pyrazine-2-carboxylate (I-71)

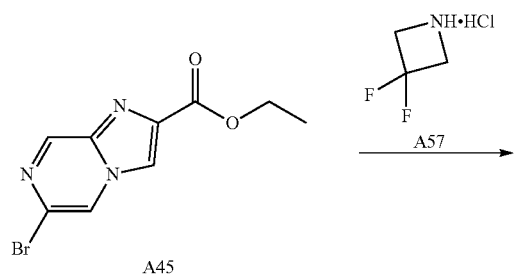

To a stirred solution of ethyl 6-bromoimidazo[1,2-a]pyrazine-2-carboxylate (A45, 1 g, 3.70 mmol) in 1,4-dioxane (20 mL) and 3,3-difluoroazetidine hydrochloride (A56, 0.95 g, 7.40 mmol) was added Cs₂CO₃ (3.60 g, 11.10 mmol). The reaction mixture was purged with N₂ gas for 20 min. To the above reaction mixture was added Tris(dibenzylideneacetone)dipalladium(0) Pd₂(dba)₃ (0.16 g, 0.18 mmol), and 4,5-Bis(diphenylphosphino)-9,9-dimethylxanthene (xantphos) (0.10 g, 0.018 mmol) and the resulting solution was further purged with N₂ gas for 10 min then stirred for 16 h at 80° C. The reaction mixture was filtered over celite bed and washed with ethylacetate/water mixture. The filtrate was washed with water, brine solution, dried over anhydrous Na₂SO₄ and concentrated under reduced pressure. The compound was purified by column chromatography using 0-10% methanol/dichloromethane as the eluent to afford ethyl 6-(3,3-difluoroazetidin-1-yl)imidazo[1,2-a]pyrazine-2-carboxylate I-71 as a brown solid. Yield: 0.60 g (59%) LC-MS (ES) m/z: 283.26 [M+H]⁺

The following intermediates were synthesized using the protocol exemplified for I-71.

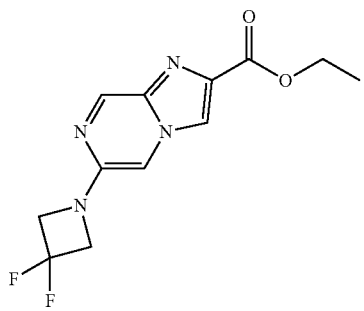 [SMILES: CCOC(=O)c1cn2cc(N3CC(F)(F)C3)ccc2n1]

| Intermediate | Structure | Mass |
| --- | --- | --- |
| I-72 | 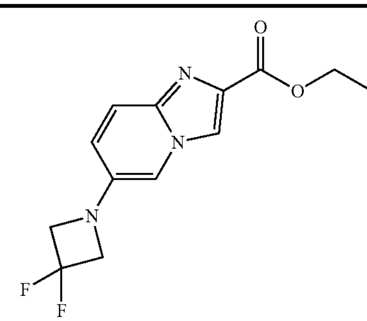 | 282.3 |
| I-73 | 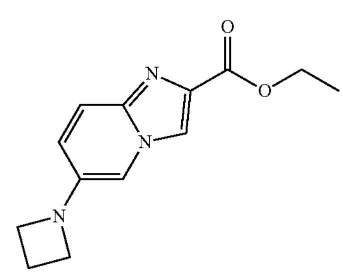 [SMILES: CCOC(=O)c1cn2cc(N3CCC3)ccc2n1] | 246.3 |

113
-continued

| Intermediate | Structure | Mass |
|---|---|---|
| I-74 | 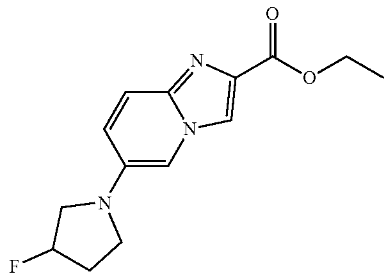 [SMILES: CCOC(=O)c1cn2cc(N3CCC(F)C3)ccc2n1] | 278.3 |
| I-75 | 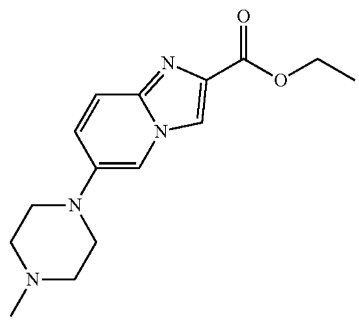 [SMILES: CCOC(=O)c1cn2cc(N3CCN(C)CC3)ccc2n1] | 289.3 |
| I-76 | 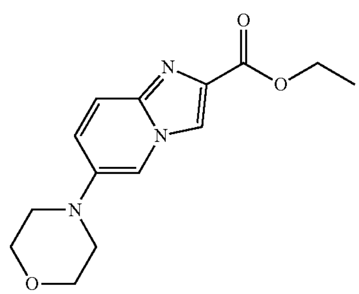 [SMILES: CCOC(=O)c1cn2cc(N3CCOCC3)ccc2n1] | 276.3 |
| I-77 | 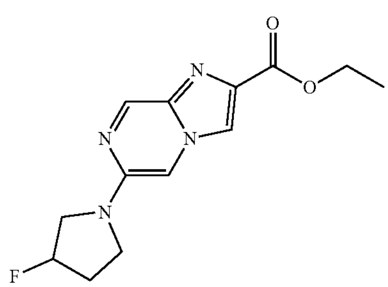 [SMILES: CCOC(=O)c1cn2cc(N3CCC(F)C3)ncc2n1] | 279.3 |

Synthesis of methyl 5-(trifluoromethyl)pyrazolo[1,5-a]pyrimidine-2-carboxylate (I-78)

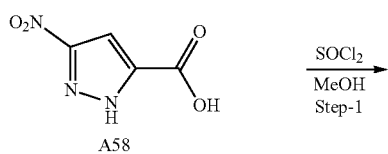

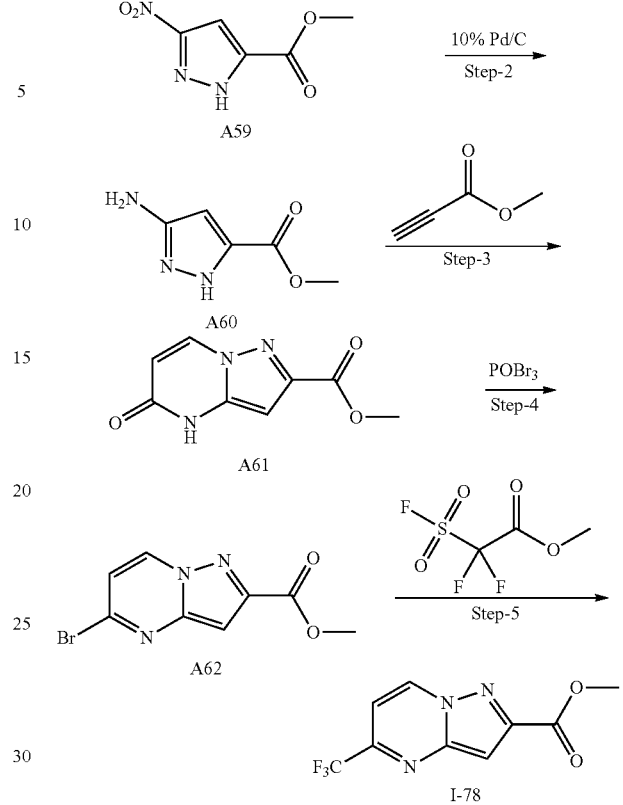

Step-1: methyl 3-nitro-1H-pyrazole-5-carboxylate (BA59)

To a stirred solution of 3-nitro-1H-pyrazole-5-carboxylic acid (A58, 25.0 g, 159.14 mmol) in Methanol (250 mL) was added dropwise $SOCl_2$ (23.09 mL, 318.28 mmol) mL). The reaction mixture was stirred for 16 h at 80° C. After completion, addition of n-hexane (500 mL) solid precipitated, filtered and dried under reduced pressure to afford methyl 3-nitro-1H-pyrazole-5-carboxylate A59 as a white solid. Yield: 26.0 g (95%) LC-MS (ES) m/z: 170.14 [M+H]+.

Step-2: methyl 3-amino-1H-pyrazole-5-carboxylate (A60)

To a stirred solution of methyl 3-nitro-1H-pyrazole-5-carboxylate (A59, 25.0 g, 146.19 mmol) in methanol (500 mL) was added Pd/C (3.80 g, 36.54 mmol) under $N_2$ atmosphere and the reaction mixture was stirred under $H_2$ balloon pressure at room temperature for 4 h. After completion of reaction mixture filtered through celite bed and washed with EtOAc. The filtrate was concentrated to dryness. The residue was washed with n-pentane dried to get methyl 3-amino-1H-pyrazole-5-carboxylate A60 as a pale yellow solid. Yield: 18.0 g (87%) LC-MS (ES) m/z: 142.16 [M+H]+.

Step-3: methyl 5-oxo-4,5-dihydropyrazolo[1,5-a]pyrimidine-2-carboxylate (A61)

To a stirred solution of methyl 3-amino-1H-pyrazole-5-carboxylate (A60, 22.0 g, 124.92 mmol) in 1,4-dioxane (440 mL) was added methyl propiolate (13.30 mL, 149.90 mmol) under N₂ atmosphere and the reaction mixture was stirred at 90° C. for 16 h. After completion of reaction mixture, the solvent was concentrated to dryness. The residue was purified by column chromatography using silica gel (100-200 mesh) 0-50% EtOAc/n-Hexnes as the eluent to afford methyl 5-oxo-4,5-dihydropyrazolo[1,5-a]pyrimidine-2-carboxylate A61 as a yellow solid. Yield: 7.0 g (29%) LC-MS (ES) m/z: 194.13 [M+H]⁺.

Step-4: methyl 5-bromopyrazolo[1,5-a]pyrimidine-2-carboxylate (A62)

To a stirred solution of methyl 5-oxo-4,5-dihydropyrazolo[1,5-a]pyrimidine-2-carboxylate (A61, 7.0 g, 36.25 mmol) in 1,4-dioxane (140 mL) was added phosphorous oxybromide (51.90 g, 181.26 mmol) under N₂ atmosphere and the reaction mixture was stirred at 90° C. for 4 h. After completion of reaction mixture, the solvent was concentrated to dryness and basified with 1M Na₂CO₃ solution upto Ph-8, then extract with EtOAc the organic layer was dried over anhydrous Na₂SO₄ filtered, and concentrated under reduced pressure. The crude was purified by column chromatography using 0-10% methanol/dichloromethane as the eluent to afford methyl 5-bromopyrazolo[1,5-a]pyrimidine-2-carboxylate A62 as a light yellow solid. Yield: 3.0 g (32%) LC-MS (ES) m/z: 255.97 [M+H]⁺.

Step-5: methyl 5-(trifluoromethyl)pyrazolo[1,5-a]pyrimidine-2-carboxylate (I-78)

To a stirred solution of methyl 5-bromopyrazolo[1,5-a]pyrimidine-2-carboxylate (A62, 1.0 g, 3.92 mmol) in N,N-dimethyl formamide (20 mL) was added methyl 2,2-difluoro-2-(fluorosulfonyl)acetate (7, 1.10 mL, 7.84 mmol) and copper (I) iodide (0.074 g, 0.39 mmol), under N₂ atmosphere and the reaction mixture was stirred at 90° C. for 16 h. After completion of reaction mixture, quenched with water and extracted with EtOAc the organic layer was dried over anhydrous Na₂SO₄ filtered, and concentrated under reduced pressure. The crude was purified by column chromatography using 0-50% EtOAc/n-Hexnes as the eluent to afford methyl 5-(trifluoromethyl)pyrazolo[1,5-a]pyrimidine-2-carboxylate I-78 as a light yellow solid. Yield: 0.25 g (26%) LC-MS (ES) m/z: No ionization. ¹H NMR (DMSO-d₆, 400 MHz, ppm) δ 9.55 (d, J=7.08 Hz, 1H), 7.68 (d, J=7.0 Hz, 1H), 7.51 (s, 1H), 3.93 (s, 3H).

Synthesis of 1methyl 5-(1-methyl-1H-pyrazol-4-yl)pyrazolo[1,5-a]pyrimidine-2-carboxylate (I-79)

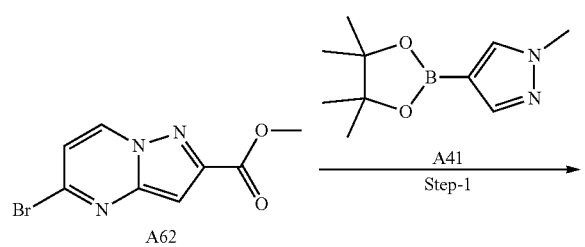

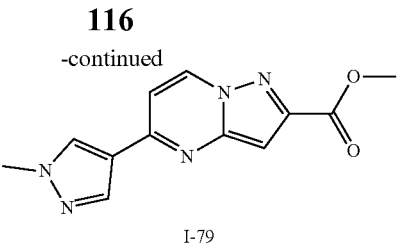

To a stirred solution of methyl 5-bromopyrazolo[1,5-a]pyrimidine-2-carboxylate (A62, 1 g, 3.90 mmol) in 1,4-dioxane (20 mL) and DMF (1 mL) and 1-methyl-4-(4,4,5,5-tetramethyl-1,3,2-dioxaborolan-2-yl)-1H-pyrazole (A41, 1.21 g, 5.85 mmol) was added Na₂CO₃ (1.24 g, 11.70 mmol) dissolved in H₂O (2 mL). The reaction mixture was purged with N₂ gas for 20 min. To the above reaction mixture was added [1,1'-Bis(diphenylphosphino)ferrocene]dichloropalladium(II) PdCl₂(dppf) (0.28 g, 0.39 mmol), and the resulting solution was further purged with N₂ gas for 10 min then stirred for 16 h at 80° C. The reaction mixture was filtered over celite bed and washed with ethylacetate/water mixture. The filtrate was washed with water, brine solution, dried over anhydrous Na₂SO₄ and concentrated under reduced pressure. The compound was purified by column chromatography using 0-10% methanol/dichloromethane as the eluent to afford methyl 5-(1-methyl-1H-pyrazol-4-yl)pyrazolo[1,5-a]pyrimidine-2-carboxylate I-79 as a brown solid. Yield: 0.51 g (51%) LC-MS (ES) m/z: 258.26 [M+H]⁺.

Synthesis of methyl 5-(1-methyl-2-oxo-1,2-dihydropyridin-4-yl)pyrazolo[1,5-a]pyrimidine-2-carboxylate (I-80)

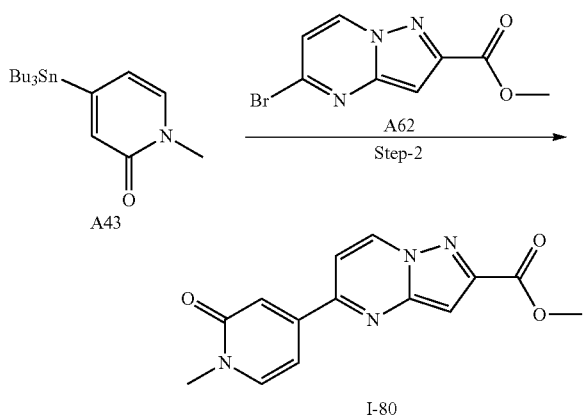

To a stirred solution of methyl 5-bromopyrazolo[1,5-a]pyrimidine-2-carboxylate (A62, 1.0 g, 3.90 mmol) in 1,4-dioxane (20 mL) and 1-methyl-4-(tributylstannyl)pyridin-2(1H)-one (A43, 2.33 g, 5.85 mmol). The reaction mixture was purged with N₂ gas for 20 min. To the above reaction mixture was added Bis(triphenylphosphine)palladium (II) dichloride PdCl₂(PPh₃)₂ (0.28 g, 0.392 mmol), and the resulting solution was further purged with N₂ gas for 10 min then stirred for 16 h at 80° C. The reaction mixture was filtered over celite bed and washed with ethyl acetate. The filtrate was washed with water, brine solution, dried over anhydrous Na₂SO₄ and concentrated under reduced pressure. The compound was purified by column chromatography using 0-10% methanol/dichloromethane as the eluent to afford methyl 5-(1-methyl-2-oxo-1,2-dihydropyridin-4-yl)

pyrazolo[1,5-a]pyrimidine-2-carboxylate I-80 as a brown solid. Yield: 0.35 g (32%) LC-MS (ES) m/z: 285.20 [M+H]+.

Synthesis of methyl 3-methyl-6-(1-methyl-1H-pyrazol-4-yl)imidazo[1,2-a]pyrazine-2-carboxylate (I-81)

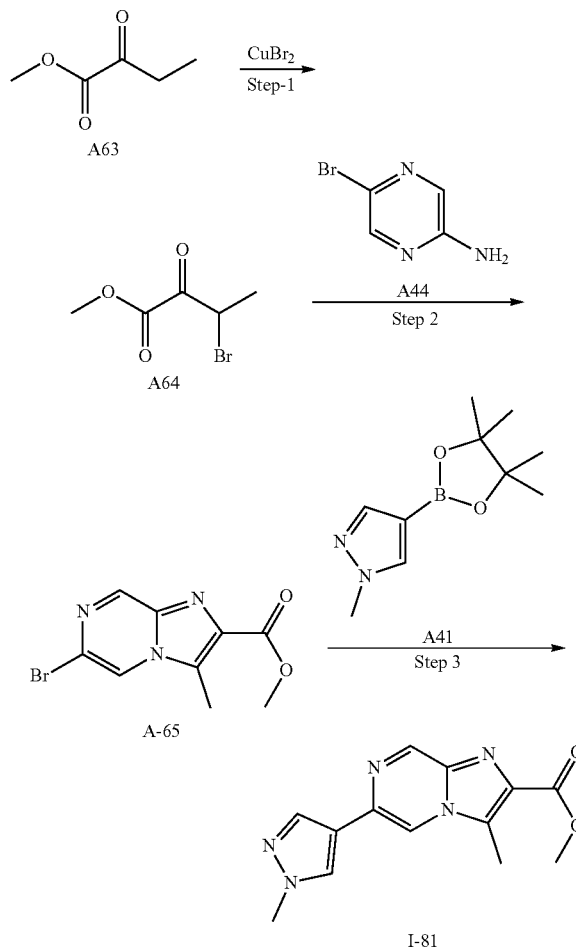

Step-1: methyl 3-bromo-2-oxobutanoate (A64)

To a stirred solution of CuBr2 (57.67 g, 258.6 mmol) in ethyl acetate, methyl 2-oxobutanoate (A63, 15.0 g, 9.17 mmol) was added dissolving in chloroform and reaction mixture heated to 80° C. for 1.5 h. After completion, reaction mixture cooled to room temperature and filtered through celite and silica bed. Then concentrated the filtrate to obtain the crude. This crude diluted with dichloromethane and filtered through celite bed and concentrated the filtrate under reduced pressure to offered methyl 3-bromo-2-oxobutanoate (2) as brown liquid. Yield: 23.0 g (85%) 1H NMR (400 MHz, DMSO-d6) δ 5.31-5.26 (m, 1H), 3.84 (s, 3H), 1.69 (d, J=6.4 Hz, 1H).

Step-2: methyl 6-bromo-3-methylimidazo[1,2-a]pyrazine-2-carboxylate (65)

To a stirred solution of 5-bromopyrazin-2-amine (3, 4.0 g, 22.98 mmol) and NaHCO3 (5.79 g, 68.96 mmol) in 1,4-dioxane, methyl 3-bromo-2-oxobutanoate (A44, 26.89 g, 137.93 mmol) was added and reaction mixture heated to 100° C. for 16 h. After completion, reaction mixture quenched with water and extracted with ethyl acetate. The organic layer was separated, dried over anhydrous sodium sulphate and concentrated to obtain the crude. This crude purified by combiflash using 25% ethyl acetate in hexane as eluent. The desired fractions concentrated under reduced pressure to offered methyl 6-bromo-3-methylimidazo[1,2-a]pyrazine-2-carboxylate A65 as brown solid. Yield: 1.3 g (20%) LC-MS (ES) m/z=269.96 [M+H]+.

Step-3: methyl 3-methyl-6-(1-methyl-1H-pyrazol-4-yl)imidazo[1,2-a]pyrazine-2-carboxylate (I-81)

A stirred solution of methyl 6-bromo-3-methylimidazo[1,2-a]pyrazine-2-carboxylate (4, 0.7 g 2.59 mmol), 1-methyl-4-(4,4,5,5-tetramethyl-1,3,2-dioxaborolan-2-yl)-1H-pyrazole (5, 0.808 g, 3.88 mmol) and sodium carbonate (0.824 g, 7.77 mmol) in dioxane:water (3:1) 17 mL was degassed with argon for 20 minutes. Then [1,1'-Bis(diphenylphosphino)ferrocene]palladium(II) dichloride (0.189 g, 0.25 mmol) was added. The reaction mixture was heated at 100° C. for 6 h. After completion, reaction mixture quenched with water and extracted with 10% MeOH in DCM (3 times). The organic layer was separated, dried over anhydrous sodium sulphate and concentrated under reduced pressure to obtain the crude. This crude purified by combiflash using 3.5% MeOH in DCM as eluent. The desired fractions were concentrated under reduced pressure to offered methyl 3-methyl-6-(1-methyl-1H-pyrazol-4-yl)imidazo[1,2-a]pyrazine-2-carboxylate I-81 as brown solid. Yield: 0.36 g (50%) LC-MS (ES) m/z=272.19 [M+H]+.

Synthesis of methyl 3-methyl-6-(1-methyl-2-oxo-1,2-dihydropyridin-4-yl)imidazo[1,2-a]pyrazine-2-carboxylate (I-82)

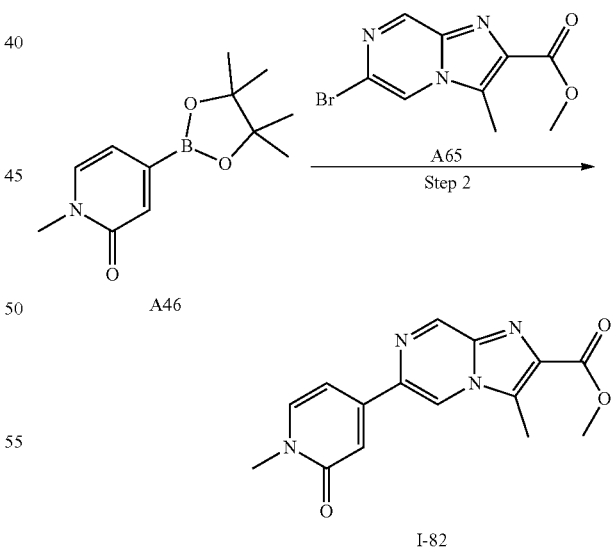

Synthesis of methyl 3-methyl-6-(1-methyl-2-oxo-1,2-dihydropyridin-4-yl)imidazo[1,2-a]pyrazine-2-carboxylate (I-82)

A stirred solution of methyl 6-bromo-3-methylimidazo[1,2-a]pyrazine-2-carboxylate (4, 0.7 g 2.59 mmol), 1-methyl- 4-(4,4,5,5-tetramethyl-1,3,2-dioxaborolan-2-yl)pyridin-2(1H)-one (3, 3.04 g, 12.96 mmol) and Tripotassium phosphate (1.64 g, 7.7 mmol) in DMF: water (3:1) 12 mL was degassed with argon for 20 minutes. Then Bis(triphenylphosphine)palladium(II) dichloride (0.145 g, 0.2 mmol) was added. The reaction mixture was heated at 90° C. for 16 h. After completion, evaporated the solvent from reaction mixture to obtain the residue. This residue quenched with water and extracted with 10% IPA in CHCl3 (3 times). The organic layer was separated, dried over anhydrous sodium sulphate and concentrated under reduced pressure to obtain the crude. This crude purified by combiflash using 4.3% MeOH in DCM as eluent. The desired fractions were concentrated under reduced pressure to offered methyl 3-methyl-6-(1-methyl-2-oxo-1,2-dihydropyridin-4-yl)imidazo[1,2-a]pyrazine-2-carboxylate I-82 as brown solid. Yield: 0.61 g (79%) LC-MS (ES) m/z=299.15 [M+H]+.

Synthesis if methyl 3-methyl-6-(1-methyl-6-oxo-1,6-dihydropyridin-3-yl)imidazo[1,2-a]pyrazine-2-carboxylate (I-83)

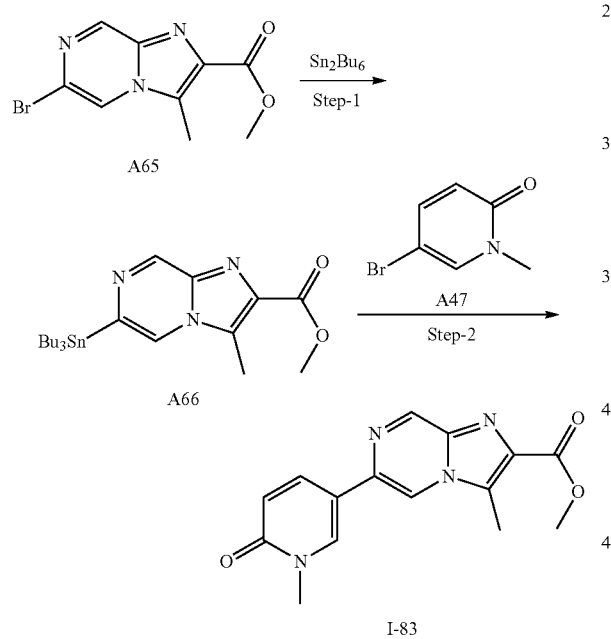

Step-1: methyl 3-methyl-6-(tributylstannyl)imidazo[1,2-a]pyrazine-2-carboxylate (2)

A stirred solution of methyl 6-bromo-3-methylimidazo[1,2-a]pyrazine-2-carboxylate (A65, 1.0 g, 3.7 mmol), hexabutylditin (2.83 mL, 5.5 mmol) in dioxane (10 mL), was degassed with argon for 30 minutes. Then tetrakis(triphenylphosphine)palladium(0) (0.429 g, 0.37 mmol) was added. The reaction mixture was heated at 100° C. for 2 h. After completion, reaction mixture quenched with water and extracted with ethyl acetate. The organic layer was dried over sodium sulphate and concentrated under reduced pressure to obtain the crude. This crude purified by combiflash using 2.3% MeOH in DCM as eluent. The desired fractions were concentrated under reduced pressure to offered methyl 3-methyl-6-(tributylstannyl)imidazo[1,2-a]pyrazine-2-carboxylate A66 as light brown gummy liquid. Yield: 0.3 g (16.6%) LC-MS (ES) m/z=482.25 [M+H]+.

Step-2: methyl 3-methyl-6-(1-methyl-6-oxo-1,6-dihydropyridin-3-yl)imidazo[1,2-a]pyrazine-2-carboxylate (I-83)

A stirred solution of methyl 3-methyl-6-(tributylstannyl)imidazo[1,2-a]pyrazine-2-carboxylate (2, 0.3 g, 0.62 mmol) and 5-bromo-1-methylpyridin-2(1H)-one (3, 0.141 g, 0.75 mmol) in dioxane 15 mL was degassed with argon for 20 minutes. Then [1,1'-Bis(diphenylphosphino)ferrocene]palladium(II) dichloride (0.045 g, 0.062 mmol) was added. The reaction mixture was heated at 100° C. for 16 h. After completion, reaction mixture quenched with water and extracted with ethyl acetate. The organic layer was dried over sodium sulphate and concentrated under reduced pressure to offered methyl 3-methyl-6-(1-methyl-6-oxo-1,6-dihydropyridin-3-yl)imidazo[1,2-a]pyrazine-2-carboxylate I-83 as brown solid. Yield: 0.2 g (71%) LC-MS (ES) m/z=299.01 [M+H]+.

Synthesis of ethyl 6-(4-cyanophenyl)imidazo[1,2-a]pyrazine-2-carboxylate (I-84)

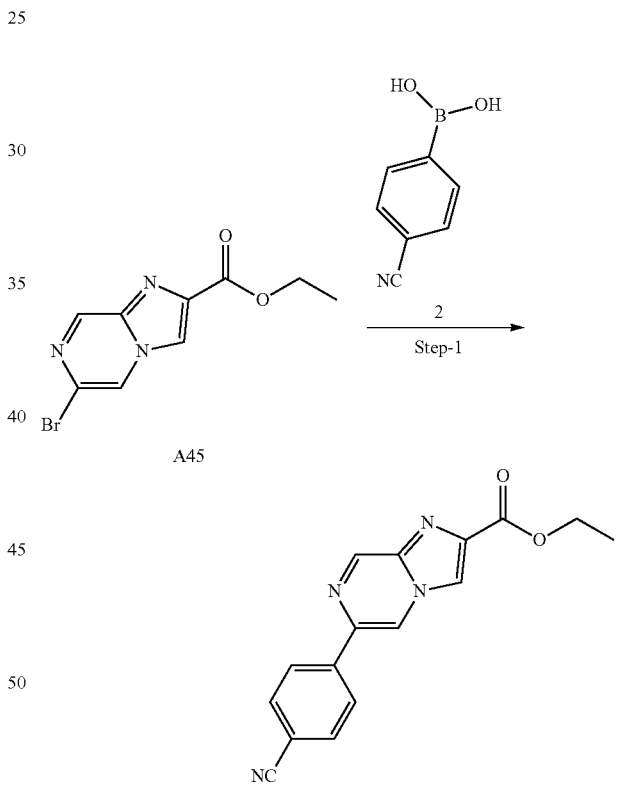

Step-1: ethyl 6-(4-cyanophenyl)imidazo[1,2-a]pyrazine-2-carboxylate (3)

To a stirred solution of ethyl 6-bromoimidazo[1,2-a]pyrazine-2-carboxylate (3, 1 g, 3.70 mmol) in 1,4-dioxane (20 mL) and DMF (1 mL) and (4-cyanophenyl)boronic acid (2, 0.816 g, 5.55 mmol) was added K3PO4 (2.35 g, 11.10 mmol) dissolved in H2O (2 mL). The reaction mixture was purged with N2 gas for 20 min. To the above reaction mixture was added [1,1'-Bis(diphenylphosphino)ferrocene]

dichloropalladium(II) PdCl2 (dppf) (0.27 g, 0.37 mmol), and the resulting solution was further purged with N₂ gas for 10 min then stirred for 16 h at 80° C. The reaction mixture was filtered over celite bed and washed with ethylacetate/water mixture. The filtrate was washed with water, brine solution, dried over anhydrous Na₂SO₄ and concentrated under reduced pressure. The compound was purified by column chromatography using 0-10% methanol/dichloromethane as the eluent to afford ethyl 6-(4-cyanophenyl)imidazo[1,2-a]pyrazine-2-carboxylate 3 as a brown solid. Yield: 0.50 g (50%) LC-MS (ES) m/z: 293.26 [M+H]⁺.

Synthesis of ethyl 6-(3-hydroxyoxetan-3-yl)imidazo[1,2-a]pyridine-2-carboxylate (I-84)

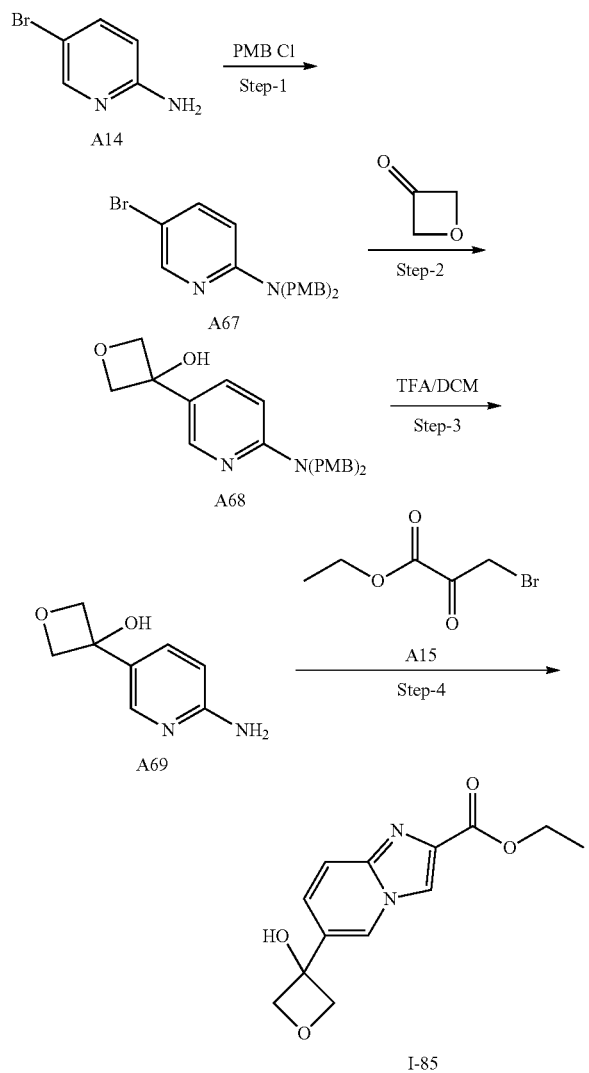

Step-1: 5-bromo-N,N-bis(4-methoxybenzyl)pyridin-2-amine (A67)

To a stirred solution of 5-bromopyridin-2-amine (A14, 2.0 g, 11.56 mmol) in N,N-dimethylformamide (40 mL) was added NaH (60% paraffin oil) (1.38 g, 34.68 mmol) at 0° C. The reaction mixture stirred at room temperature for 1 h.

4-methoxy benzyl chloride (3.10 mL, 23.12 mmol) was added at 0° C. The reaction mixture was stirred for 16 h at room temperature. After completion of reaction, quenched with ice water extracted with EtOAc. The organic layer was washed with water, brine solution, dried over anhydrous Na₂SO₄, filtered and concentrated under reduced pressure. The crude was purified by column chromatography using 0-30% EtOAc/n-hexanes as the eluent to afford 5-bromo-N,N-bis(4-methoxybenzyl)pyridin-2-amine A67 as a white solid. Yield: 4.0 g (85%) LC-MS (ES) m/z: 413.08 [M+H]⁺.

Step-2: 3-(6-(bis(4-methoxybenzyl)amino)pyridin-3-yl)oxetan-3-ol (A-68)

To a stirred solution of 5-bromo-N,N-bis(4-methoxybenzyl)pyridin-2-amine (A-67, 3.0 g, 7.28 mmol) in dry THF (60 mL) was added drop wise n-BuLi (1.6 M solution) (5.46 mL, 8.736 mmol) at −78° C. under N₂ atmosphere. The reaction mixture was stirred at −78° C. for 1 h. A solution of in THF was added drop wise oxetan-3-one (0.65 g, 8.736 mmol) at −78° C. The reaction mixture was stirred at −78° C. for 1 h and slowly raised to temperature at room temperature then stirred for 3 h. After completion of reaction mixture, quenched with ice water and extracted with EtOAc. The organic layer was washed with water, brine solution, dried over anhydrous Na₂SO₄, filtered and concentrated under reduced pressure. The crude was purified by column chromatography using 0-30% EtOAc/n-hexanes as the eluent to afford 3-(6-(bis(4-methoxybenzyl)amino)pyridin-3-yl)oxetan-3-ol A-68 as a yellow sticky solid. Yield: 1.40 g (48%) LC-MS (ES) m/z: 407.16 [M+H]⁺

Step-3: 3-(6-aminopyridin-3-yl)oxetan-3-ol (A69)

To a solution of 3-(6-(bis(4-methoxybenzyl)amino)pyridin-3-yl)oxetan-3-ol (A68, 5.30 g, 13.05 mmol) in DCM (20 mL) at 0° C. was added TFA (20 mL) and the resulting solution was stirred at room temperature for 16 h. After completion of reaction mixture concentrated under reduced pressure and washed with ether and dried to afford 3-(6-aminopyridin-3-yl)oxetan-3-ol A69 as off white solid. Yield: 2.10 g (92%) LC-MS (ES) m/z: 167.18 [M+H]⁺.

Step-4: ethyl 6-(3-hydroxyoxetan-3-yl)imidazo[1,2-a]pyridine-2-carboxylate (I-85)

To a stirred solution of 3-(6-aminopyridin-3-yl)oxetan-3-ol (B45, 2.1 g, 12.64 mmol) in 1,4-dioxane (40 mL) was added ethyl 3-bromo-2-oxopropanoate (2, 3.31 mL, 18.96 mmol), followed by NaHCO₃ (1.59 g, 18.96 mmol), The reaction mixture was heated at 100° C. for 16 h. after completion of reaction mixture, the solvent was concentrated under reduced pressure. The crude product was triturated with water and washed with n-pentane and dried to afford ethyl 6-(3-hydroxyoxetan-3-yl)imidazo[1,2-a]pyridine-2-carboxylate I-85 as brown solid. Yield: 3.10 g, (67%). LC-MS m/z: 263.07 [M+H]⁺.

Synthesis of methyl 3-fluoro-5-methylpyrazolo[1,5-a]pyrimidine-2-carboxylate (I-87)

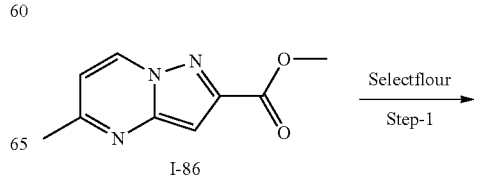

-continued

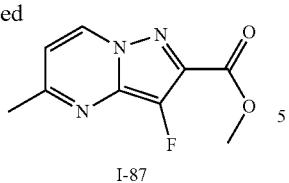
I-87

To a stirred solution of methyl 5-methylpyrazolo[1,5-a]pyrimidine-2-carboxylate (I-86, 1.0 g, 5.23 mmol) in acetonitrile (25 mL), was added 1-chloromethyl-4-fluoro-1,4-diazoniabicyclo[2.2.2]octane bis (4.63 g, 13.07 mmol) at room temperature. The reaction mixture was heated at 70° C. for 36 h. after completion of reaction diluted with water and extracted with EtOAc. The organic layer was dried over sodium sulphate, filtered and concentrated under reduced pressure to get crude. The crude was purified by column chromatography using 0-30% ethyl acetate in hexanes as eluent to afford methyl 3-fluoro-5-methylpyrazolo[1,5-a]pyrimidine-2-carboxylate I-87 yellow solid Yield:0.3 g, (27%). LC-MS m/z: 210.07 [M+H]$^+$.

Synthesis of methyl 3-fluoro-5-(trifluoromethyl)pyrazolo[1,5-a]pyrimidine-2-carboxylate (I-88)

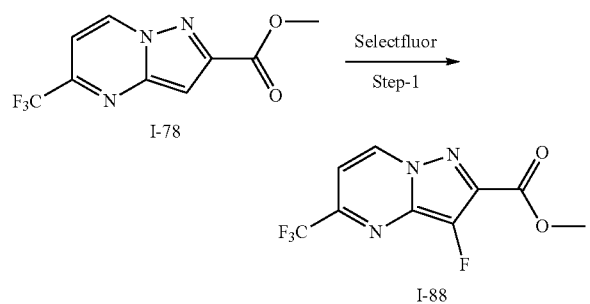

To a stirred solution of methyl 5-(trifluoromethyl)pyrazolo[1,5-a]pyrimidine-2-carboxylate (I-78, 0.60 g, 2.44 mmol) in acetonitrile (15 mL), was added 1-chloromethyl-4-fluoro-1,4-diazoniabicyclo[2.2.2]octane bis (2.59 g, 7.32 mmol) at room temperature. The reaction mixture was heated at 70° C. for 36 h. after completion of reaction diluted with water and extracted with EtOAc. The organic layer was dried over sodium sulphate, filtered and concentrated under reduced pressure to get crude. The crude was purified by column chromatography using 0-60% ethyl acetate in hexanes as eluent to afford methyl 3-fluoro-5-(trifluoromethyl)pyrazolo[1,5-a]pyrimidine-2-carboxylate I-88 yellow solid Yield:0.2 g, (31%). LC-MS m/z: 262.04 [M−H]$^-$.

Synthesis of ethyl 6-(4-fluorophenyl)-5,6,7,8-tetrahydroimidazo[1,2-a]pyridine-2-carboxylate (I-89)

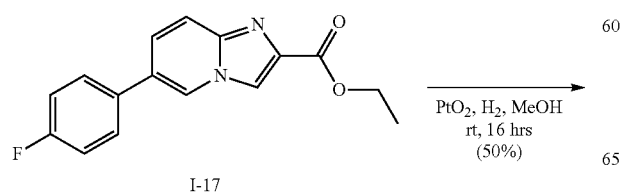

-continued

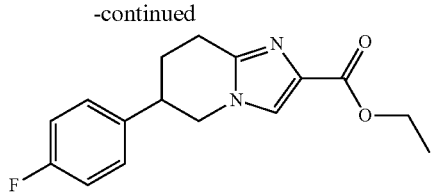
I-89

To an argon purged solution of ethyl 6-(4-fluorophenyl)imidazo[1,2-a]pyridine-2-carboxylate (I-17 0.1 g, 0.35 mmol) in methanol (30 mL) was added PtO$_2$ (10 wt %, 10 mg). The resulting mixture was stirred for 16 h in an autoclave at room temperature under hydrogen atmosphere. The reaction mixture was then filtered through celite and concentrated. The crude product was purified by combi-flash purifier with 5% MeOH in DCM as eluent to afford of intermediate I-89 as a brown oily liquid (50%). MS (ESI) m/z=289.1 [M+H]$^+$.

The following ester intermediates were synthesized using the protocol exemplified for I-89.

| Intermediate No | Structure | LC/MS_m/z_ [M + H]$^+$ |
|---|---|---|
| I-90 | 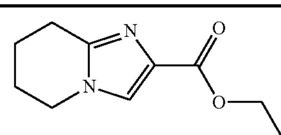 | 195.1 |
| I-91 | 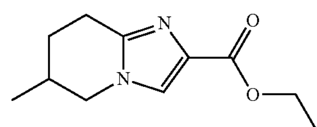 | 209.2 |
| I-92 | 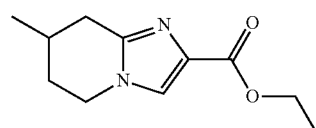 | 209.2 |
| I-93 | 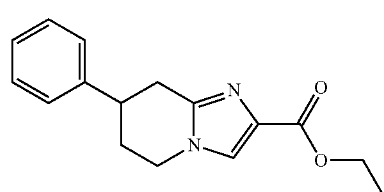 | 271.2 |
| I-94 | 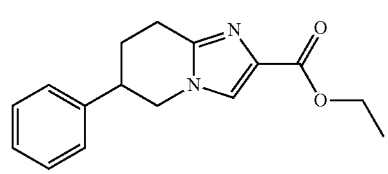 [SMILES: CCOC(=O)c1cn2c(n1)CCC(c1ccccc1)C2] | 271.2 |
| I-95 | 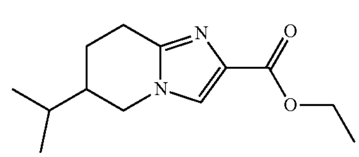 [SMILES: CCOC(=O)c1cn2c(n1)CCC(C(C)C)C2] | 237.2 |

125
-continued

| Intermediate No | Structure | LC/MS_m/z_ [M + H]+ |
|---|---|---|
| I-96 | ethyl 6-(trifluoromethyl)-5,6,7,8-tetrahydroimidazo[1,2-a]pyridine-2-carboxylate | 262.9 |
| I-97 | ethyl 6-(1-methyl-1H-pyrazol-4-yl)-5,6,7,8-tetrahydroimidazo[1,2-a]pyridine-2-carboxylate | 275.2 |
| I-98 | ethyl 6-cyclopropyl-5,6,7,8-tetrahydroimidazo[1,2-a]pyridine-2-carboxylate | 235.2 |
| I-99 | ethyl 6-methoxy-5,6,7,8-tetrahydroimidazo[1,2-a]pyridine-2-carboxylate | 225.1 |

126

Synthesis of 6-(4-fluorophenyl)imidazo[1,2-a]pyridine-2-carboxylic acid (I-100)

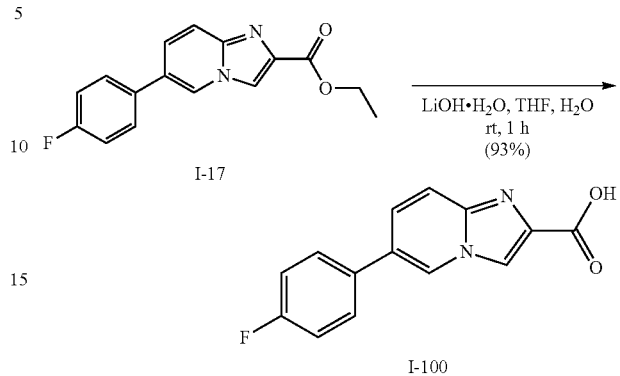

To a stirred solution of ethyl 6-(4-fluorophenyl)imidazo[1,2-a]pyridine-2-carboxylate (I56, 0.5 g, 1.76 mmol) in 10 mL of THF:H$_2$O (1:1) was added LiOH.H$_2$O (0.15 g, 3.52 mmol). The reaction mixture was stirred for 1 h at room temperature. Then pH of reaction mixture was brought in the range of 3 to 4 with 2N HCl and extracted with DCM/methanol mixture. The combined organic layer dried over anhydrous Na$_2$SO$_4$ and concentrated under reduced pressure to afford I-100 as a white solid (0.42 g, 93%). MS (ESI) m/z=257.1 [M+H]+.

The following acid intermediates were synthesized using the protocol exemplified for I98.

| Intermediate No | Structure | LC/MS_m/z_ [M + H]+ |
|---|---|---|
| I-101 | 6-methylimidazo[1,2-a]pyridine-2-carboxylic acid | 177.1 |
| I-102 | 6-(trifluoromethyl)imidazo[1,2-a]pyridine-2-carboxylic acid | 231.1 |
| I-103 | 6-phenylimidazo[1,2-a]pyridine-2-carboxylic acid | 239.1 |
| I-104 | 6-(3,5-difluorophenyl)imidazo[1,2-a]pyridine-2-carboxylic acid | 275.1 |
| I-105 | 6-(3,6-dihydro-2H-pyran-4-yl)imidazo[1,2-a]pyridine-2-carboxylic acid | 244.9 |

-continued
| Intermediate No | Structure | LC/MS_m/z_ [M + H]+ |
|---|---|---|
| I-106 | 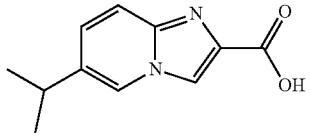 | 205.1 |
| I-107 | 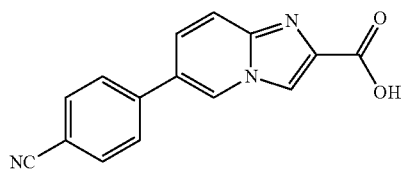 [SMILES: N#Cc1ccc(-c2ccc3nc(C(=O)O)cn3c2)cc1] | 264.1 |
| I-108 | 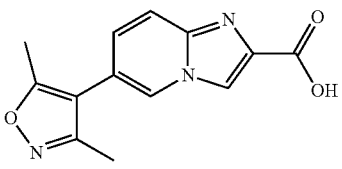 [SMILES: Cc1noc(C)c1-c1ccc2nc(C(=O)O)cn2c1] | 258.1 |
| I-109 | 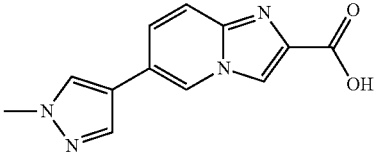 [SMILES: Cn1cc(-c2ccc3nc(C(=O)O)cn3c2)cn1] | 243.1 |
| I-110 | 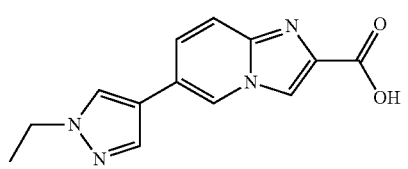 [SMILES: CCn1cc(-c2ccc3nc(C(=O)O)cn3c2)cn1] | 257.1 |
| I-111 | 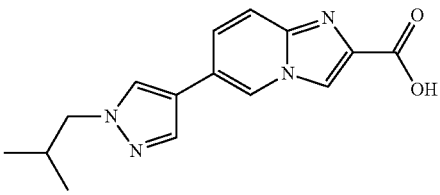 [SMILES: CC(C)Cn1cc(-c2ccc3nc(C(=O)O)cn3c2)cn1] | 285.0 |
| I-112 | 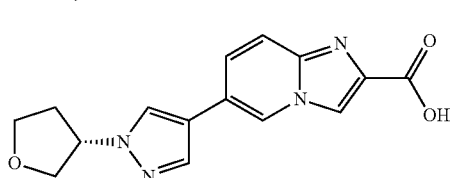 | 299.1 |
| I-113 | 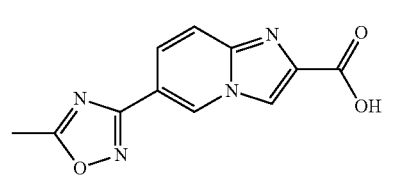 [SMILES: Cc1nc(-c2ccc3nc(C(=O)O)cn3c2)no1] | 245.0 |
| I-114 | 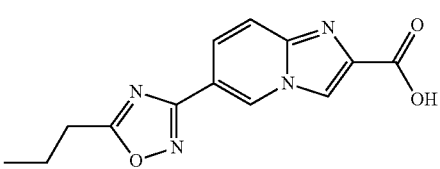 [SMILES: CCCc1nc(-c2ccc3nc(C(=O)O)cn3c2)no1] | 271.1 |

-continued

| Intermediate No | Structure | LC/MS_m/z_ [M + H]+ |
|---|---|---|
| I-115 | 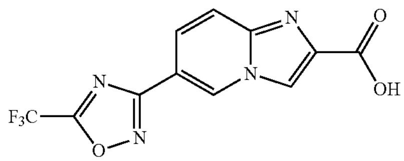 [SMILES: O=C(O)c1cn2cc(-c3noc(C(F)(F)F)n3)ccc2n1] | — |
| I-116 | 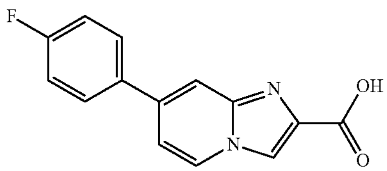 [SMILES: O=C(O)c1cn2ccc(-c3ccc(F)cc3)cc2n1] | 257.1 |
| I-117 | 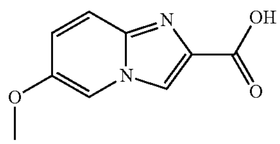 | 193.1 |
| I-118 | 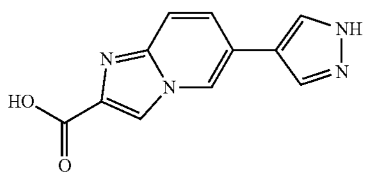 [SMILES: O=C(O)c1cn2cc(-c3cn[nH]c3)ccc2n1] | 229.3 |
| I-119 | 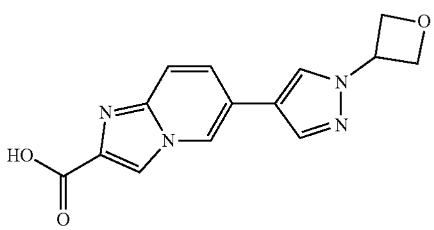 [SMILES: O=C(O)c1cn2cc(-c3cnn(C4COC4)c3)ccc2n1] | 285.1 |
| I-120 | 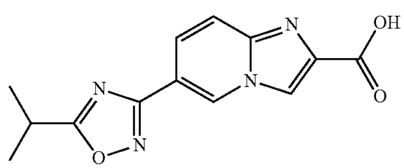 [SMILES: CC(C)c1nc(-c2ccc3nc(C(=O)O)cn3c2)no1] | 271 |
| I-121 | 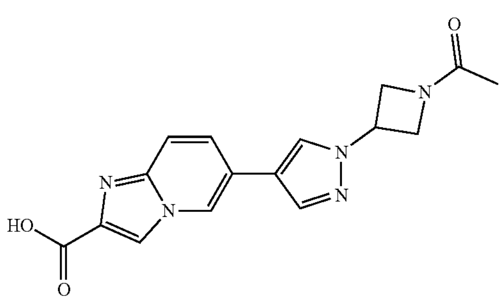 [SMILES: CC(=O)N1CC(n2cc(-c3ccc4nc(C(=O)O)cn4c3)cn2)C1] | 326.3 |
| I-122 | 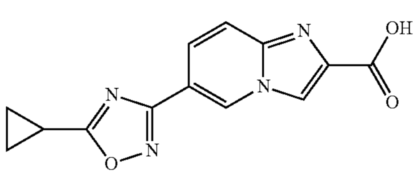 [SMILES: O=C(O)c1cn2cc(-c3noc(C4CC4)n3)ccc2n1] | 271.3 |

-continued

| Intermediate No | Structure | LC/MS_m/z_ [M + H]+ |
|---|---|---|
| I-123 | 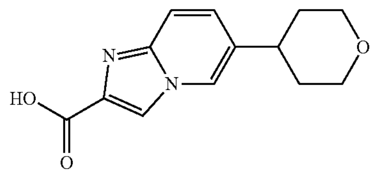 [SMILES: O=C(O)c1cn2cc(C3CCOCC3)ccc2n1] | 247.3 |
| I-124 | 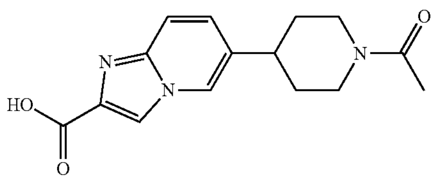 [SMILES: CC(=O)N1CCC(c2ccc3nc(C(=O)O)cn3c2)CC1] | 288.3 |
| I-125 | 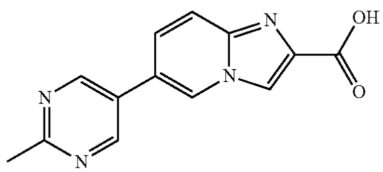 [SMILES: Cc1ncc(-c2ccc3nc(C(=O)O)cn3c2)cn1] | 255.2 |
| I-126 | 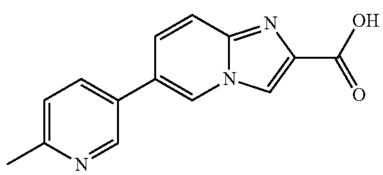 [SMILES: Cc1ccc(-c2ccc3nc(C(=O)O)cn3c2)cn1] | 254.2 |
| I-127 | 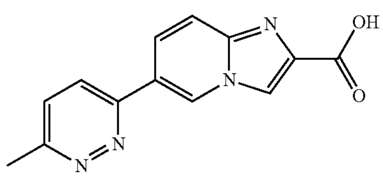 | 255.2 |
| I-128 | 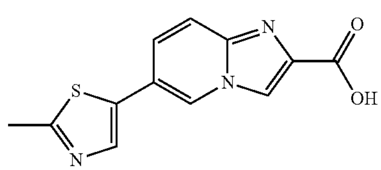 [SMILES: Cc1ncc(-c2ccc3nc(C(=O)O)cn3c2)s1] | 260.2 |
| I-129 | 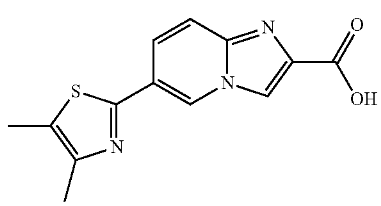 [SMILES: Cc1nc(-c2ccc3nc(C(=O)O)cn3c2)sc1C] | 274 |
| I-130 | 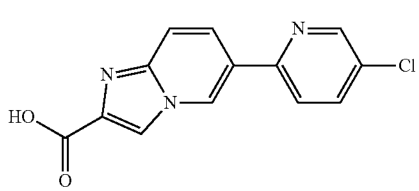 [SMILES: O=C(O)c1cn2cc(-c3ccc(Cl)cn3)ccc2n1] | 274 |

-continued

| Intermediate No | Structure | LC/MS_m/z_ [M + H]+ |
|---|---|---|
| I-131 | 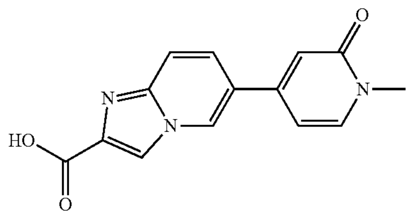 | 270.2 |
| I-132 | 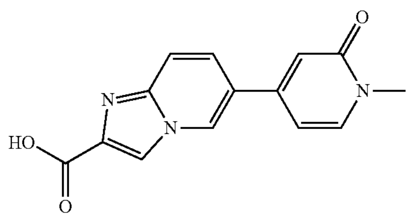 | 270.1 |
| I-133 | 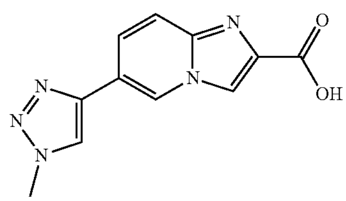 [SMILES: Cn1cc(-c2ccc3nc(C(=O)O)cn3c2)nn1] | 243.8 |
| I-134 | 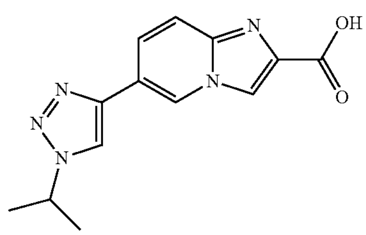 [SMILES: CC(C)n1cc(-c2ccc3nc(C(=O)O)cn3c2)nn1] | 272.8 |
| I-135 | 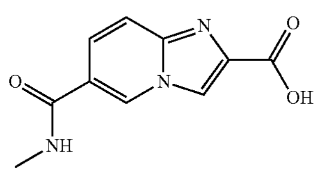 [SMILES: CNC(=O)c1ccc2nc(C(=O)O)cn2c1] | 220.1 |
| I-136 | 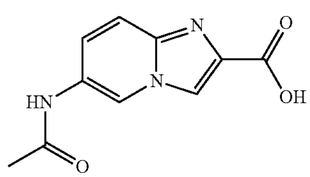 [SMILES: CC(=O)Nc1ccc2nc(C(=O)O)cn2c1] | 220.2 |
| I-137 | 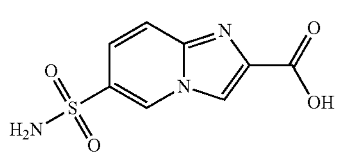 | 241.8 |

-continued
| Intermediate No | Structure | LC/MS_m/z_ [M + H]+ |
|---|---|---|
| I-138 | 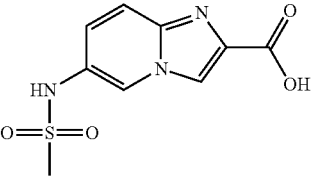 [SMILES: CS(=O)(=O)Nc1ccc2nc(C(=O)O)cn2c1] | 254.2 |
| I-139 | 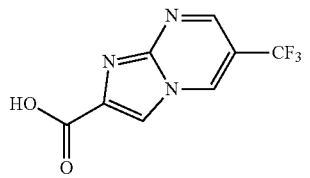 [SMILES: O=C(O)c1cn2cc(C(F)(F)F)cnc2n1] | 229.9 |
| I-140 | 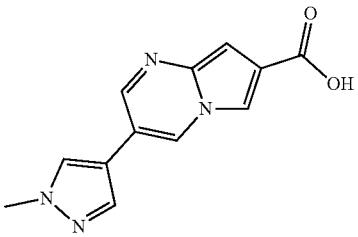 [SMILES: Cn1cc(-c2cnc3cc(C(=O)O)cn3c2)cn1] | 242.1 |
| I-141 | 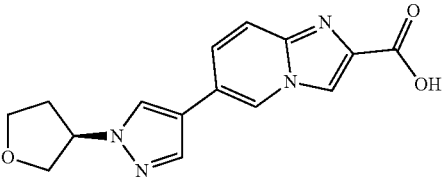 [SMILES: O=C(O)c1cn2cc(-c3cnn([C@@H]4CCOC4)c3)ccc2n1] | 299.1 |
| I-142 | 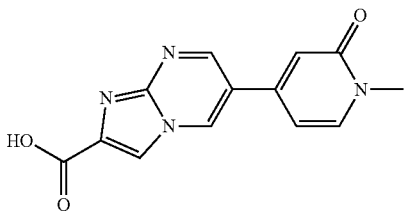 | 271.1 |
| I-144 | 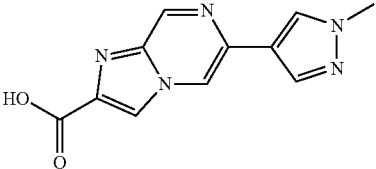 [SMILES: Cn1cc(-c2cn3cc(C(=O)O)nc3cn2)cn1] | 244.08 |
| I-145 | 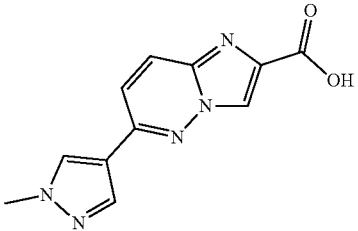 [SMILES: Cn1cc(-c2ccc3nc(C(=O)O)cn3n2)cn1] | 244.08 |

-continued

| Intermediate No | Structure | LC/MS_m/z_ [M + H]+ |
|---|---|---|
| I-146 | 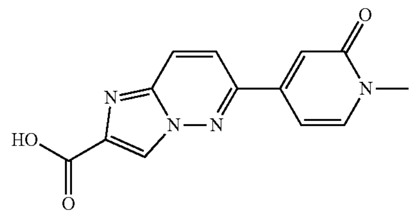 [SMILES: Cn1ccc(-c2ccc3nc(C(=O)O)cn3n2)cc1=O] | 271.2 |
| I-147 | 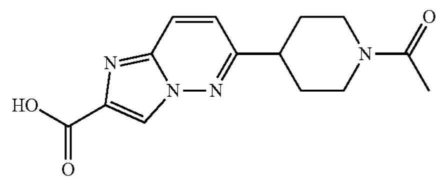 [SMILES: CC(=O)N1CCC(c2ccc3nc(C(=O)O)cn3n2)CC1] | 289.2 |
| I-148 | 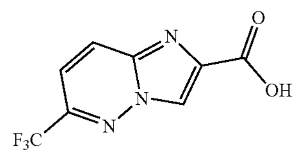 [SMILES: O=C(O)c1cn2nc(C(F)(F)F)ccc2n1] | 232.1 |
| I-149 | 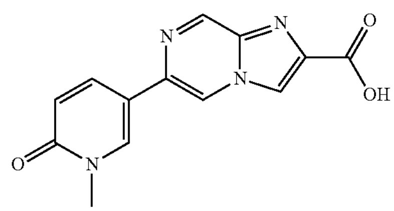 [SMILES: Cn1cc(-c2cn3cc(C(=O)O)nc3cn2)ccc1=O] | 270.1 |
| I-150 | 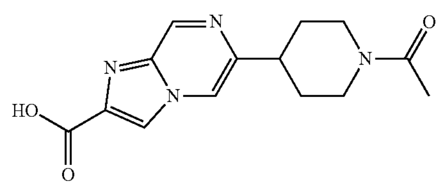 [SMILES: CC(=O)N1CCC(c2cn3cc(C(=O)O)nc3cn2)CC1] | 289.3 |
| I-151 | 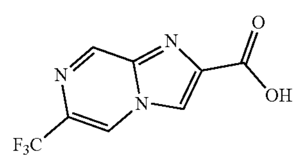 | 232.2 |
| I-152 | 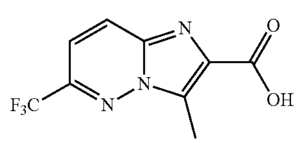 [SMILES: Cc1c(C(=O)O)nc2ccc(C(F)(F)F)nn12] | 244.1 |
| I-153 | 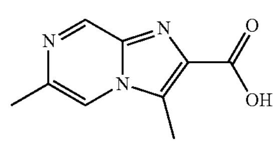 | 190.1 |
| I-154 | 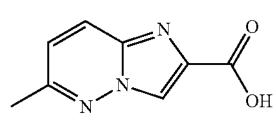 | 178.1 |

-continued
| Intermediate No | Structure | LC/MS_m/z_ [M + H]+ |
|---|---|---|
| I-155 | 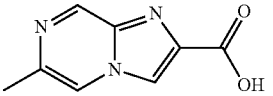 | 178.1 |
| I-156 | 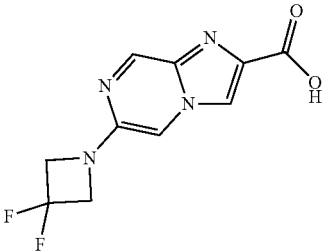 [SMILES: O=C(O)c1cn2cc(N3CC(F)(F)C3)ncc2n1] | 255.1 |
| I-157 | 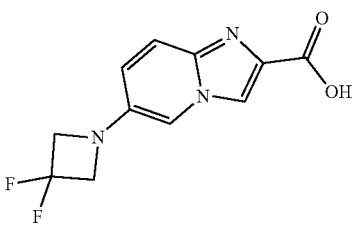 [SMILES: O=C(O)c1cn2cc(N3CC(F)(F)C3)ccc2n1] | 252.1 |
| I-158 | 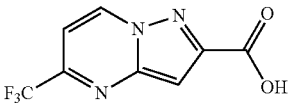 | 222.9 |
| I-159 | 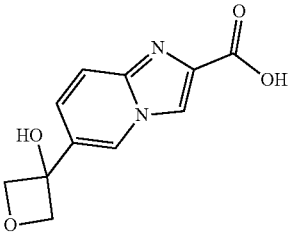 [SMILES: O=C(O)c1cn2cc(C3(O)COC3)ccc2n1] | 235.1 |
| I-160 | 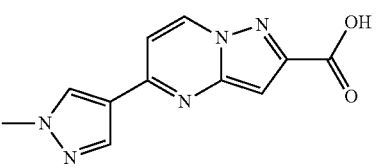 [SMILES: Cn1cc(-c2ccn3nc(C(=O)O)cc3n2)cn1] | 241.1 |
| I-161 | 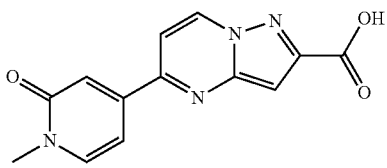 [SMILES: Cn1ccc(-c2ccn3nc(C(=O)O)cc3n2)cc1=O] | 269.1 |
| I-162 | 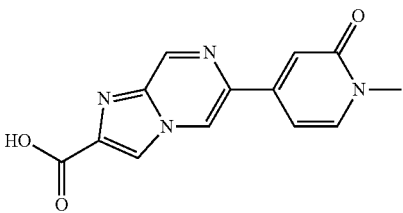 | 271.1 |

| Intermediate No | Structure | LC/MS_m/z_ [M + H]+ |
|---|---|---|
| I-163 | 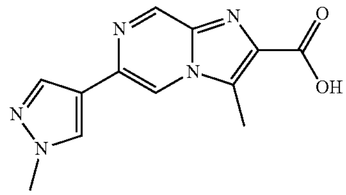 [SMILES: Cc1c(C(=O)O)nc2cnc(-c3cnn(C)c3)cn12] | 258.1 |
| I-164 | 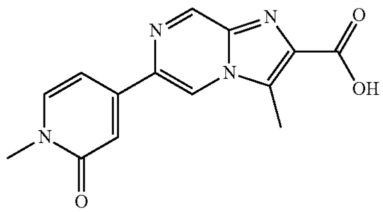 [SMILES: Cc1c(C(=O)O)nc2cnc(-c3ccn(C)c(=O)c3)cn12] | 285.1 |
| I-165 | 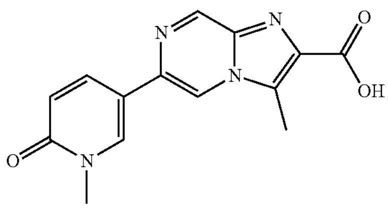 [SMILES: Cc1c(C(=O)O)nc2cnc(-c3ccc(=O)n(C)c3)cn12] | 285.1 |
| I-166 | 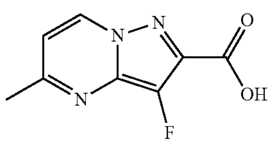 | 194.2 |
| I-167 | 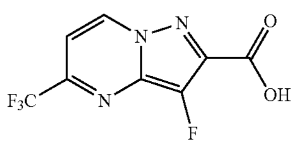 [SMILES: O=C(O)c1nn2ccc(C(F)(F)F)nc2c1F] | 248.1 |
| I-168 | 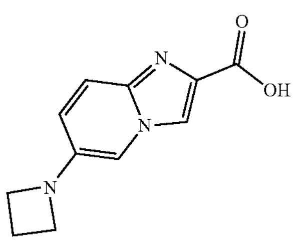 [SMILES: O=C(O)c1cn2cc(N3CCC3)ccc2n1] | 218.1 |
| I-169 | 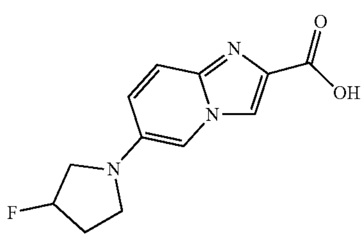 [SMILES: O=C(O)c1cn2cc(N3CCC(F)C3)ccc2n1] | 250.1 |
| I-170 | 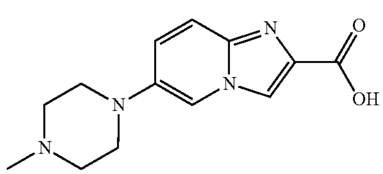 [SMILES: CN1CCN(c2ccc3nc(C(=O)O)cn3c2)CC1] | 261.1 |

-continued
| Intermediate No | Structure | LC/MS_m/z_ [M + H]+ |
|---|---|---|
| I-171 | 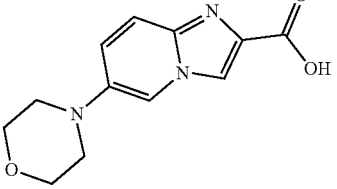 | 248.1 |
| I-172 | 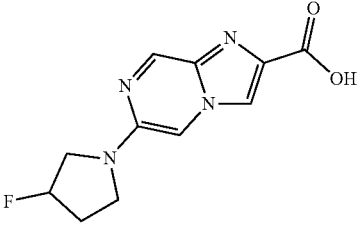 [SMILES: O=C(O)c1cn2cc(N3CCC(F)C3)ncc2n1] | 251.1 |
| I-173 | 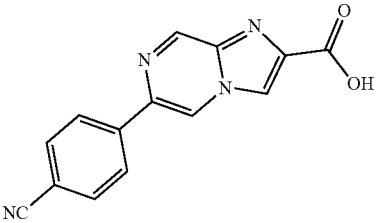 [SMILES: N#Cc1ccc(-c2cn3cc(C(=O)O)nc3cn2)cc1] | 265.1 |
| I-175 | 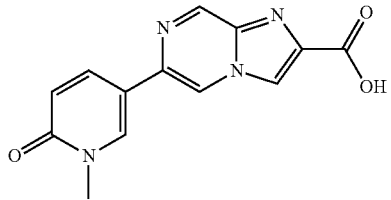 [SMILES: Cn1cc(-c2cn3cc(C(=O)O)nc3cn2)ccc1=O] | 269.2 |
| I-176 | 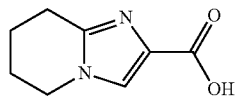 [SMILES: O=C(O)c1cn2c(n1)CCCC2] | 167.1 |
| I-177 | 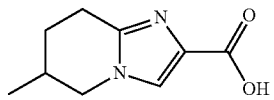 | 181.1 |
| I-178 | 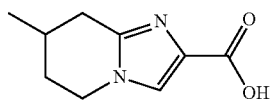 | 181.1 |
| I-180 | 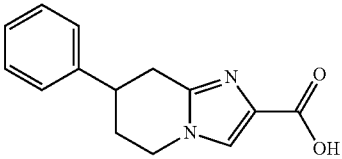 [SMILES: O=C(O)c1cn2c(n1)CC(c1ccccc1)CC2] | 243.1 |
| I-181 | 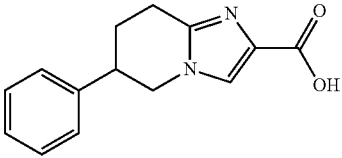 [SMILES: O=C(O)c1cn2c(n1)CCC(c1ccccc1)C2] | 243.2 |

-continued

| Intermediate No | Structure | LC/MS_m/z_ [M + H]+ |
|---|---|---|
| I-182 | 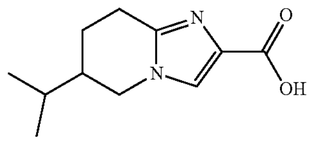 | 209.1 |
| I-183 | 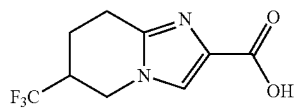 [SMILES: O=C(O)c1cn2c(n1)CCC(C(F)(F)F)C2] | 235.1 |
| I-184 | 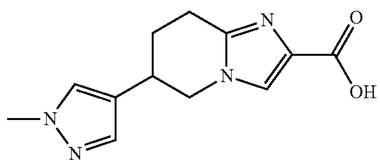 [SMILES: Cn1cc(C2CCc3nc(C(=O)O)cn3C2)cn1] | 247.2 |
| I-185 | 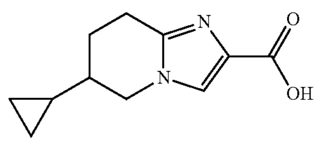 [SMILES: O=C(O)c1cn2c(n1)CCC(C1CC1)C2] | 207.1 |
| I-186 | 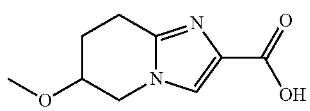 | 197.1 |
| I-187 | 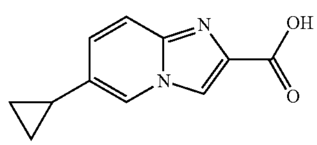 [SMILES: O=C(O)c1cn2cc(C3CC3)ccc2n1] | 203.1 |
| I-188 | 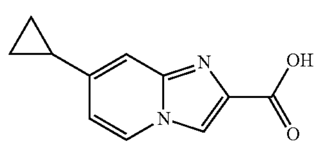 [SMILES: O=C(O)c1cn2ccc(C3CC3)cc2n1] | 203.1 |
| I-192 | 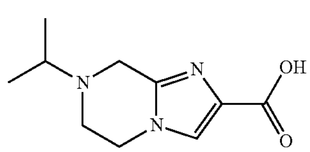 | 210.2 |

Synthesis of 6-propyl-5,6,7,8-tetrahydroimidazo[1,2-a]pyridine-2-carboxylic acid (I-189)

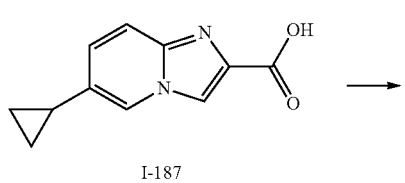

I-187

-continued

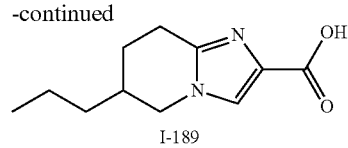

I-189

To a solution of 6-cyclopropylimidazo[1,2-a]pyridine-2-carboxylic acid (I-187, 0.05 g, 0.24 mmol) in ethanol (8 mL) was added 10% Pd—C (0.03 g) and the resulting reaction mixture was stirred for 1 h under hydrogen atmosphere at room temperature. After completion of the reaction [monitored by LCMS], reaction mixture was filtered through diatomaceous earth and separated the organic layer. Organic layer was concentrated under reduced pressure to afford the desired product I-189 as yellow semi solid (0.055 g) which was used for the next step without further purification. MS (ESI) m/z=209.2 (M+H)⁺.

Synthesis of 7-propyl-5,6,7,8-tetrahydroimidazo[1,2-a]pyridine-2-carboxylic acid (I-190)

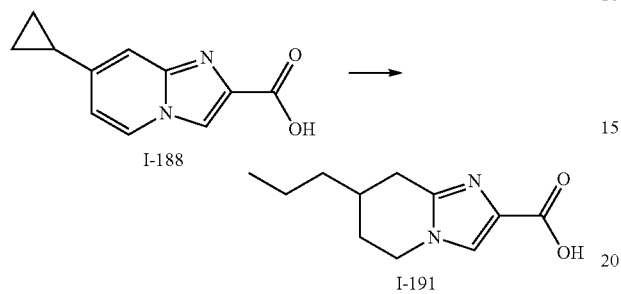

To a solution of 7-cyclopropylimidazo[1,2-a]pyridine-2-carboxylic acid (I188, 0.1 g, 0.49 mmol) in ethanol (10 mL) was added 10% Pd—C (0.03 g) and the resulting reaction mixture was stirred for 1 h under hydrogen atmosphere at room temperature. After completion of the reaction [monitored by LCMS], reaction mixture was filtered through diatomaceous earth and separated the organic layer. Organic layer was concentrated under reduced pressure to afford the desired crude product I-191 as yellow semi solid which was used for the next step without further purification (0.09 g). MS (ESI) m/z=209.1 (M+H)⁺.

Synthesis of 7-isopropyl-5,6,7,8-tetrahydroimidazo[1,2-a]pyrazine-2-carboxylic acid (I-192)

Step 1: Ethyl imidazo [1,2-a]pyrazine-2-carboxylate (A71)

To a solution of pyrazin-2-amine (A70, 2.0 g, 2.10 mmol) and ethyl 3-bromo-2-oxopropanoate (A15, 3.0 mL, 2.30 mmol) in ethanol (15.0 mL) was added Conc., HCl (1.0 mL) at 0° C. and stirred for 12 h at 95° C. The reaction mixture was concentrated under reduced pressure followed by addition of water (10 mL), the mixture was then extracted with DCM and the organic layer was washed with saturated NaHCO₃ solution and brine, dried over sodium sulphate, filtered and concentrated under reduced pressure. The obtained crude was purified by combi-flash purifier with 3% methanol in dichloromethane as eluent to afford the desired product A71 as yellow solid (0.4 g, 10%). ¹H NMR (DMSO-d₆, 400 MHz) δ 1.31 (t, J=7.2 Hz, 3H), 4.33 (q, J=7.2 Hz, 2H), 7.96 (d, J=4.4 Hz, 1H), 8.57 (d, J=4.0 Hz, 1H), 8.66 (s, 1H), 9.15 (s, 1H); MS (ESI) m/z=192.1 (M+H)⁺.

Step 2: Ethyl 5,6,7,8-tetrahydroimidazo [1,2-a]pyrazine-2-carboxylate (A-72)

To a solution of ethyl imidazo [1,2-a] pyrazine-2-carboxylate (A71, 0.25 g, 1.30 mmol) in methanol (15.0 mL) was added PtO₂ (0.1 g). The reaction mixture was then stirred 12 hours under H₂ atmosphere. After completion of the reaction (monitored by TLC), the reaction mixture was filtered through a celite pad and the organic layer was concentrated under reduced pressure to afford the desired product A-72 as a viscous oil (0.22 g, 88%). ¹H NMR (DMSO-d₆, 400 MHz) δ 1.22 (t, J=7.2 Hz, 3H), 2.71 (bs, 1H), 3.00 (t, J=6.0 Hz, 2H), 3.80 (s, 2H), 3.90 (t, J=6.0 Hz, 2H), 4.16 (q, J=7.2 Hz, 2H), 7.71 (s, 1H), 9.15 (s, 1H); MS (ESI) m/z=196.2 (M+H)⁺.

Synthesis of ethyl 7-isopropyl-5,6,7,8-tetrahydroimidazo [1,2-a] pyrazine-2-carboxylate (A73)

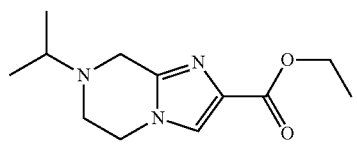

A73

To a solution of ethyl 5,6,7,8-tetrahydroimidazo [1,2-a] pyrazine-2-carboxylate (A72, 0.2 g, 1.02 mmol) in methanol (10.0 mL) was added acetone (0.11 mL, 1.55 mmol) followed by catalytic amount of acetic acid (0.1 mL) at 0° C. and stirred at the same temperature for 30 mins. Sodium cyano borohydride (0.13 g, 2.05 mmol) was added slowly and it was further stirred for 12 h at room temperature. The reaction mixture was concentrated under reduced pressure followed by addition of water (10 mL) and then extracted in to EtOAc. The organic layer was washed with saturated NaHCO₃ solution and brine, dried over sodium sulphate, filtered and concentrated under reduced pressure. The obtained crude was purified by combi-flash purifier with 3% methanol in dichloromethane as eluent to afford the desired product A73 as yellow oil (0.21 g, 86%). $^1$H NMR (DMSO-d$_6$, 400 MHz) δ 1.03 (d, J=7.6 Hz, 6H), 1.22 (t, J=4.0 Hz, 3H), 2.81-2.87 (m, 3H), 3.62 (s, 2H), 3.95 (t, J=6.0 Hz, 2H), 4.17 (q, J=7.2 Hz, 2H), 7.73 (s, 1H); MS (ESI) m/z=238.2 (M+H)$^+$.

Synthesis of 6-phenyl-5,6-dihydro-8H-imidazo[2,1-c][1,4]oxazine-2-carboxylic acid (I-193)

Step 1: 6-phenylmorpholine-3-thione (A75)

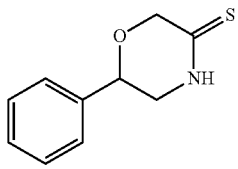

A75

To a stirred solution of 6-phenylmorpholin-3-one (A11, 3.5 g, 20.0 mmol) in 100 mL of dry THF was added Lawsson's reagent (4.86 g, 12.0 mmol). The reaction mixture was stirred for 1.5 h at room temperature then 6N HCl (22.0 mL) was added and further stirred for another 10 min. The reaction mixture was concentrated and the concentrate was stirred with a mixture of DCM/sat. NaHCO₃. The separated organic layer was dried with anhydrous Na₂SO₄ and evaporated under reduced pressure. The crude product was purified by combiflash using 25% ethylacetate/hexane to afford product B51 as an off white solid (2.5 g, 65.7%). MS (ESI) m/z=194.0[M+H]$^+$.

Step 2: 5-(methylthio)-2-phenyl-3,6-dihydro-2H-1,4-oxazine (A76)

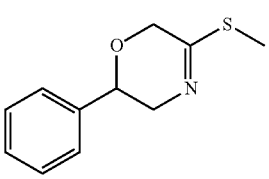

A76

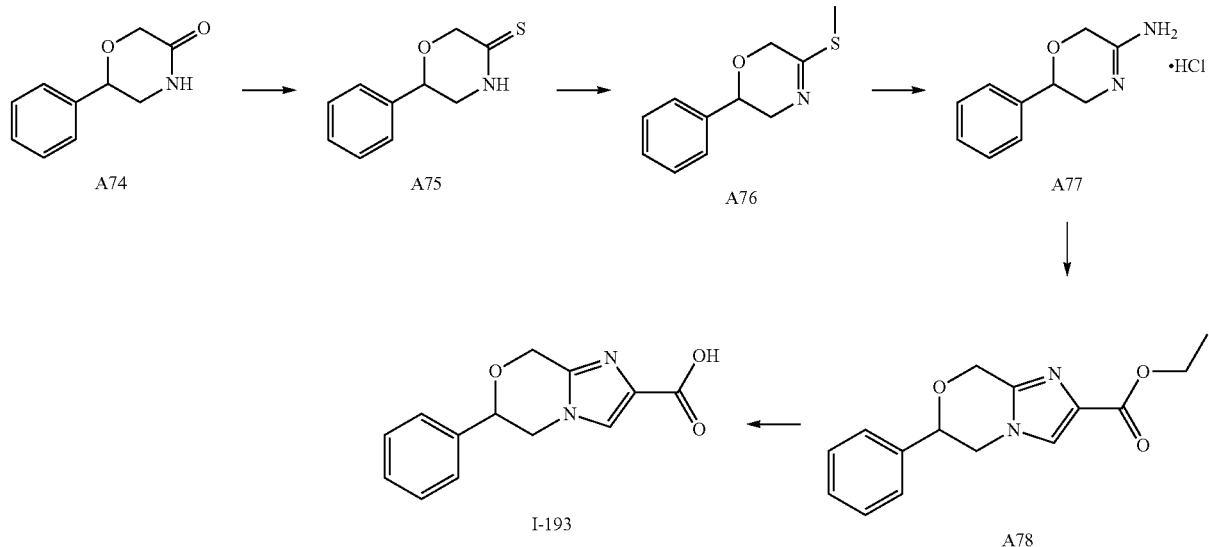

To a stirred solution of 6-phenylmorpholine-3-thione (B51, 1.0 g, 5.0 mmol) in 50 mL of dry DCM was added trimethyloxonium tetrafluoroborate (1.3 g, 8.6 mmol) at 0° C. The reaction mixture was stirred for 1 h at room temperature and quenched with saturated solution of K₂CO₃ (22.0 mL) at −10° C. and extracted with DCM. The separated organic layer was dried with anhydrous Na₂SO₄ and evaporated under reduced pressure to afford product B52 as a yellow solid (0.950 g, 88.78%). MS (ESI) m/z=208.1[M+H]⁺.

Step 3: 6-phenyl-5,6-dihydro-2H-1,4-oxazin-3-amine hydrochloride (B53)

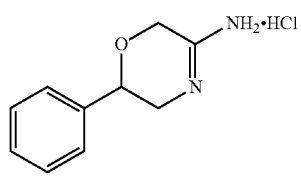
A77

To a stirred solution of 5-(methylthio)-2-phenyl-3,6-dihydro-2H-1,4-oxazine (B52, 0.950 g, 0.45 mmol) in 20 mL of MeOH (1.3 g, 8.6 mmol) was added ammonium chloride (0.294 g, 0.55 mmol). The reaction mixture was refluxed for 2 h. After the completion of reaction, it was concentrated to afford A77 as an off white solid product (1.05 g) which was used with out further purification in the next step. MS (ESI) m/z=177.1[M+H]⁺.

Step 4: ethyl 6-phenyl-5,6-dihydro-8H-imidazo[2,1-c][1,4]oxazine-2-carboxylate (A78)

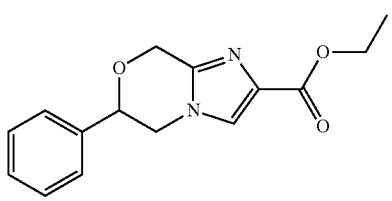
A78

To a stirred solution of 6-phenyl-5,6-dihydro-2H-1,4-oxazin-3-amine hydrochloride (A77, 0.65 g 0.30 mmol) in EtOH:dioxane (10:10 mL) was added ethyl bromopyruvate A15 (0.5 mL, 0.36 mmol), followed by NaHCO₃ (0.772 g, 10.0 mmol). The reaction mixture was heated for 16 h at 100° C. and then concentrated. The concentrate was washed three times with 30 mL of ethyl acetate/water (8:2). The separated organic layer was dried with anhydrous Na₂SO₄ and evaporated under reduced pressure. The crude product was purified by combiflash using 25% ethyl acetate/hexane to afford A78 as a brown sticky solid (0.2 g). MS (ESI) m/z=273.1[M+H]⁺.

Step 5: 6-phenyl-5,6-dihydro-8H-imidazo[2,1-c][1,4]oxazine-2-carboxylic acid (I-193)

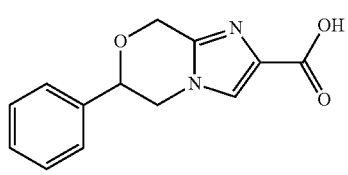
I-193

To a stirred solution of ethyl 6-phenyl-5,6-dihydro-8H-imidazo[2,1-c][1,4]oxazine-2-carboxylate (A78, 0.2 g, 0.08 mmol) in 30 mL of MeOH:THF:H₂O (1:1:1) was added LiOH.H₂O (0.041 g, 10.0 mmol). The reaction mixture was stirred for 16 h at room temperature and then evaporated to dryness. The pH of the aqueous solution was adjusted to 4 using dil HCl and then extracted with ethyl acetate. The organic layer was washed with water and brine, dried over sodium sulphate, filtered and concentrated under reduced pressure to afford the desired product I-192 as pale yellow solid (0.2 g). MS (ESI): m/z=245.0 [M+H]⁺.

Synthesis of 6-(4-fluorophenyl)-5,6-dihydro-8H-imidazo[2,1-c][1,4]oxazine-2-carboxylic acid (I193)

Using the procedure for the synthesis of I193, the compound I194 was synthesized

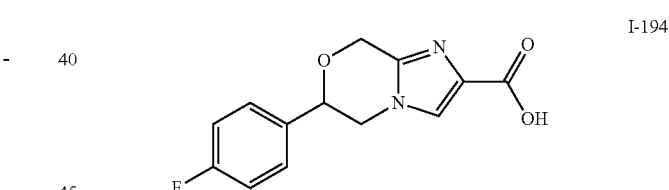
I-194

Synthesis of (S)-1-amino-3-(3,4-dihydroisoquinolin-2(1H)-yl)propan-2-ol (I-195)

Prepared according to the protocols followed for compound I-2

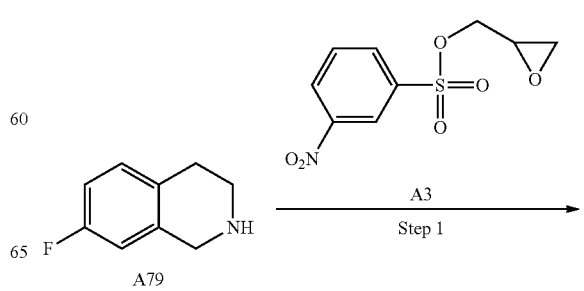

153

-continued

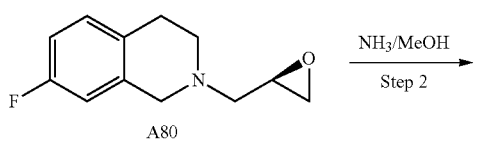

Further, the compounds of Formula I were prepared utilizing the intermediates above.

N-(3-(3,4-dihydroisoquinolin-2(1H)-yl)-2-hydroxy-propyl)-6-(trifluoromethyl)imidazo[1,2-a]pyridine-2-carboxamide (Example 1)

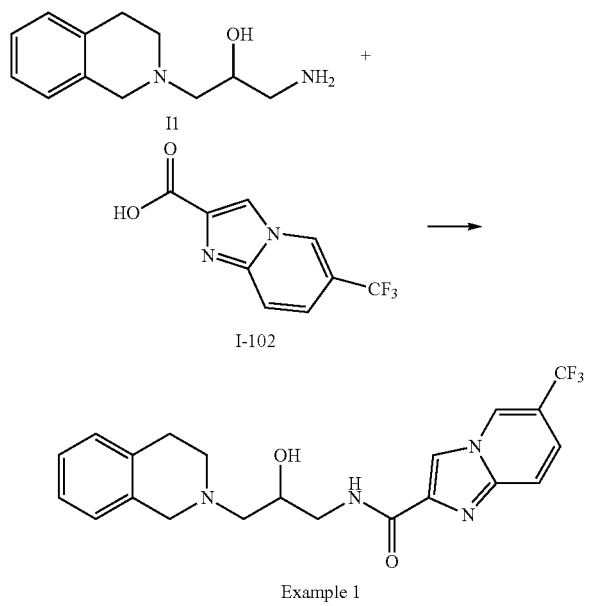

To a solution of carboxylic acid (I-102, 0.2 g, 0.86 mmol) in DMF (8 mL) was added DIPEA (0.45 mL, 2.60 mmol) followed by EDC.HCl (0.333 g, 1.73 mmol) and HOBt (0.266 g, 1.73 mmol). The reaction mixture was stirred for 1 h followed by addition of 1-amino-3-(3,4-dihydroisoquinolin-2(1H)-yl)propan-2-ol (I1, 0.179 g, 0.86 mmol). The reaction mixture was stirred for 16 h. The reaction was monitored till the completion of starting materials (LC/MS) and then concentrated under reduced pressure. The obtained crude was purified by column chromatography using 10% methanol in dichloromethane as eluent to afford the desired product as white solid (27 mg, 8%). $^1$H NMR (DMSO-d$_6$, 400 MHz, ppm)-δ 9.23 (s, 1H), 8.42 (s, 1H), 8.36 (s, 1H), 7.68 (d, J=9.2 Hz, 1H), 7.54 (d, J=10 Hz, 1H), 7.12-7.04 (m, 3H), 6.99 (d, J=5.6 Hz, 1H), 4.92 (d, J=4.4 Hz, 1H), 3.90 (d, J=5.2 Hz, 1H), 3.61 (s, 2H), 3.47-3.43 (m, 2H), (2 protons are merged with water-DMSO peak), 2.81 (d, J=4.8 Hz, 2H), 2.77-2.73 (m, 1H), 2.69-2.65 (m, 1H); MS (ESI) m/z=419.2 [M+H]$^+$.

154

N-(3-(3,4-dihydroisoquinolin-2(1H)-yl)-2-hydroxy-propyl)-6-methylimidazo[1,2-a]pyridine-2-carboxamide (Example 2)

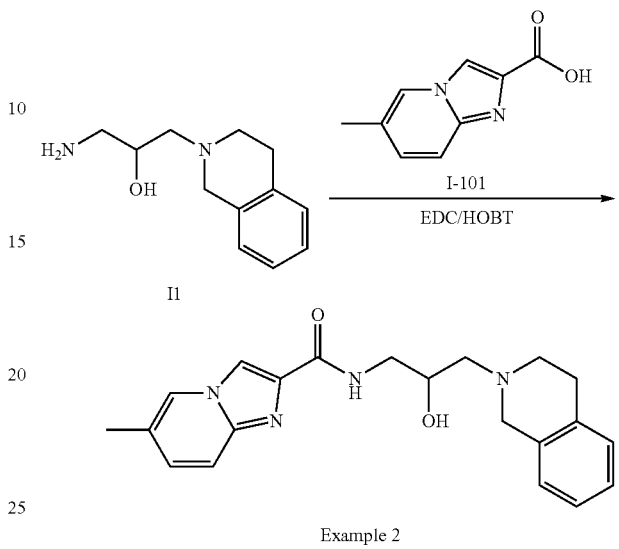

$^1$H NMR (DMSO-d$_6$, 400 MHz, ppm)-(TFA salt): δ 8.33 (bs, 1H), 8.16-8.23 (m, 1H, excluded the TFA proton), 7.40 (d, J=9.2 Hz, 1H), 7.17 (d, J=8.4 Hz, 1H), 7.01-7.09 (m, 3H), 6.96-7.04 (m, 1H), 6.42-6.46 (m, 1H), 4.89-4.91 (m, 1H), 3.83-3.89 (m, 1H), 3.55-3.61 (m, 2H), 3.41-3.47 (m, 1H), 2.78-2.84 (m, 2H), 2.65-2.73 (m, 2H), 2.25 (s, 3H) & 3 of the aliphatic protons merged underneath the DMSO/H$_2$O peak; MS (ESI) m/z=365.3 [M+H]$^+$.

N-(2-(3,4-dihydroisoquinolin-2(1H)-yl)-1-hydroxy-ethyl)-7-(4-fluorophenyl) imidazo[1,2-a]pyridine-2-carboxamide (Example 3)

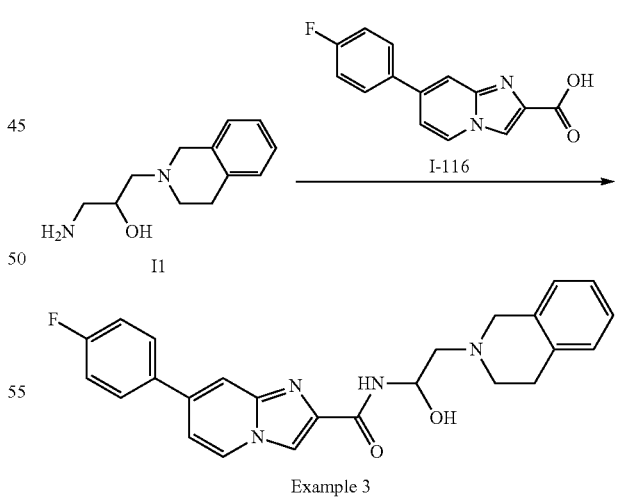

Yield 5.8%. $^1$H NMR (DMSO-d$_6$, 400 MHz, ppm): δ 8.60 (d, J=6.8 Hz, 1H), 8.28-8.37 (m, 2H), 7.82-7.85 (m, 2H), 7.69 (s, 1H), 7.32-7.36 (m, 3H), 7.04-7.12 (m, 3H), 7.00-7.02 (m, 1H), 4.94 (bs, 1H), 3.86-3.91 (m, 1H), 3.55-3.62 (m, 2H), 3.43-3.49 (m, 1H), 3.27-3.35 (m, 1H), 2.74-2.84 (m, 2H), 2.69-2.74 (m, 2H) & 2 of the aliphatic protons merged with the DMSO/H$_2$O peak; MS (ESI) m/z=445.2 [M+H]$^+$.

(S)—N-(3-(3,4-dihydroisoquinolin-2(1H)-yl)-2-hydroxypropyl)-6-(1-ethyl-1H-pyrazol-4-yl)imidazo[1,2-a]pyridine-2-carboxamide (Example 4)

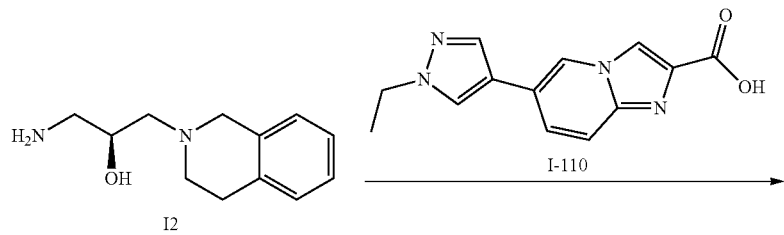

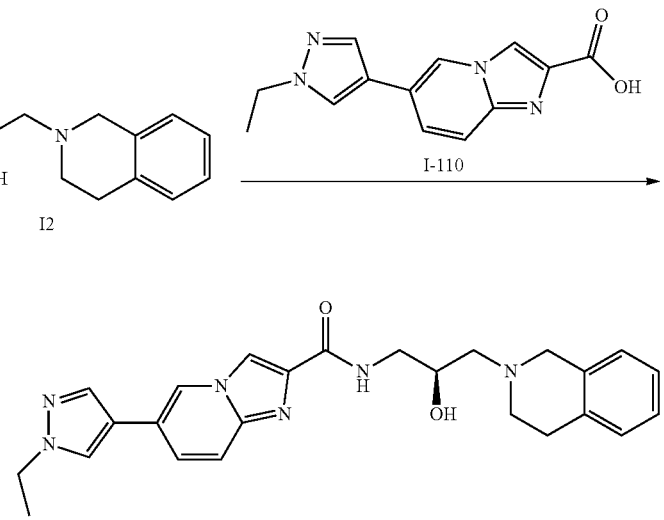

Example 4

Yield 6%). $^1$H NMR (DMSO-d$_6$, 400 MHz, ppm): δ 8.80 (s, 1H), 8.22 (d, 2H, J=6.4 Hz), 7.86 (s, 1H), 7.60 (d, 1H, J=9.2 Hz), 7.54-7.50 (m, 1H), 7.14-7.06 (m, 3H), 7.06-6.98 (m, 2H), 4.20-4.10 (m, 2H), 3.70-3.64 (m, 1H), 3.48-3.40 (m, 1H), 2.82-2.75 (m, 2H), 2.91-2.87 (m, 1H), 1.42-1.38 (m, 3H), 1.30-1.20 (m, 3H), 1.15-1.10 (m, 1H), 0.90-0.80 (m, 3H); MS (ESI) m/z=445.2 [M+H]$^+$.

(S)—N-(3-(3,4-dihydroisoquinolin-2(1H)-yl)-2-hydroxypropyl)-6-(5-propyl-1,2,4-oxadiazol-3-yl)imidazo[1,2-a]pyridine-2-carboxamide (Example 5)

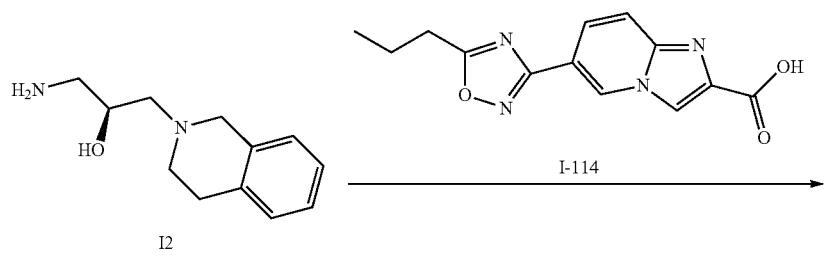

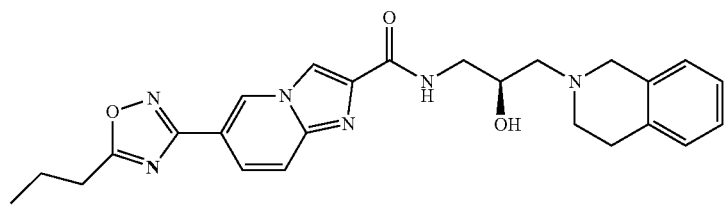

Example 5

13.75%). $^1$H NMR (DMSO-d$_6$, 400 MHz, ppm): δ 9.34 (s, 1H), 8.51 (s, 1H), 7.80 (d, J=9.2 Hz, 1H), 7.64 (d, J=9.2 Hz, 1H), −7.08 (bs, 3H), 7.00 (s, 1H), 4.92 (s, 1H), 3.90-3.89 (m, 1H), 3.61 (s, 2H), 3.47-3.43 (m, 1H), 2H proton merged with DMSO/H$_2$O peak), 2.99 (t, J=6.8 Hz, 2H), 2.82 (s, 2H), 2.73-2.64 (m, 3H), 1.84-1.78 (q, 2H), 0.98 (t, J=7.2 Hz, 3H); MS (ESI) m/z=461.1 [M+H]$^+$.

(S)—N-(3-(3,4-dihydroisoquinolin-2(1H)-yl)-2-hydroxypropyl)-6-(5-methyl-1,2,4-oxadiazol-3-yl)imidazo[1,2-a]pyridine-2-carboxamide (Example 6)

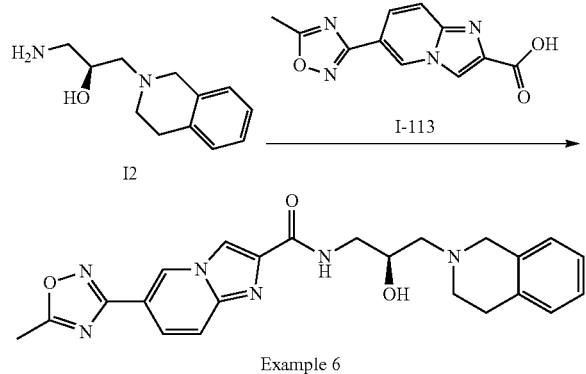

Example 6

25%). $^1$H NMR (DMSO-d$_6$, 400 MHz, ppm): δ 9.34 (s, 1H), 8.51 (s, 1H), 8.33 (bs, 1H), 7.79 (d, J=9.6 Hz, 1H), 7.64 (d, J=9.6 Hz, 1H), 7.08-7.06 (m, 3H), 7.01 (d, J=6.8 Hz, 1H), 4.93 (d, J=4.0 Hz, 1H), 3.91-3.90 (m, 1H), 3.61 (s, 2H), 3.47-3.44 (m, 1H) (4H, proton merged with DMSO peak), 2.83 (s, 2H), 2.77-2.74 (m, 1H), 2.67 (s, 3H); MS (ESI) m/z=433.0 [M+H]$^+$.

(S)—N-(3-(3,4-dihydroisoquinolin-2(1H)-yl)-2-hydroxypropyl)-6-(5-(trifluoromethyl)-1,2,4-oxadiazol-3-yl)imidazo[1,2-a]pyridine-2-carboxamide Example 7

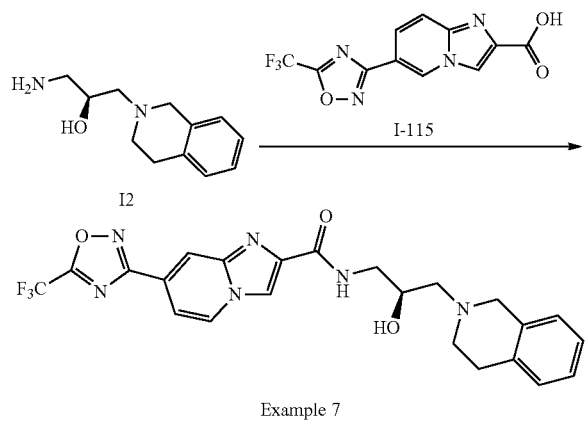

Example 7

3.2%). $^1$H NMR (DMSO-d$_6$, 400 MHz, ppm): δ 9.50 (s, 1H), 8.52 (s, 1H), 8.36 (t, J=7.6 Hz, 1H), 7.84 (d, J=9.2 Hz, 1H), 7.69 (d, J=9.2 Hz, 1H), 7.08-7.06 (m, 3H), 7.00 (d, J=6.8 Hz, 1H), 4.92 (d, J=4.4 Hz, 1H), 3.91-3.90 (m, 1H), 3.61 (s, 2H), 3.47-3.44 (m, 1H), 3.4 (m, 3H, proton merged with DMSO/H$_2$O peak), 2.82-2.77 (m, 2H), 2.73-2.64 (m, 2H); MS (ESI) m/z=487.1 [M+H]$^+$.

(S)—N-(3-(3,4-dihydroisoquinolin-2(1H)-yl)-2-hydroxypropyl)-6(trifluoromethyl) imidazo[1,2-a]pyridine-2-carboxamide (Example 8)

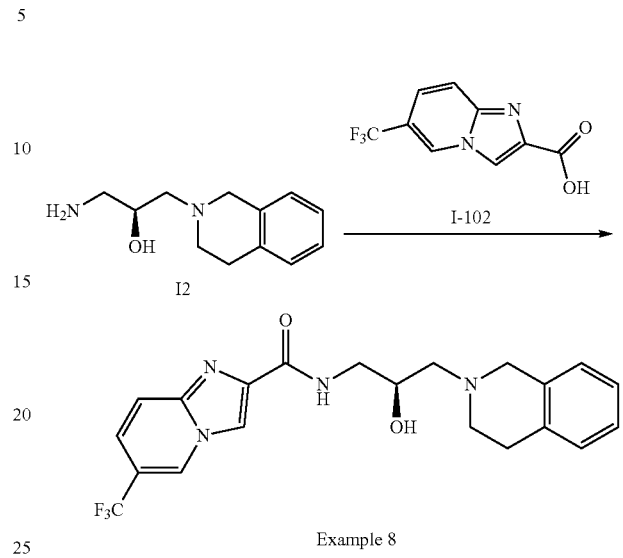

Example 8

10%). $^1$H NMR (DMSO-d$_6$, 400 MHz, ppm)-δ 9.24 (s, 1H), 8.42 (s, 1H), 8.38 (bs, 1H), 7.68 (d, J=9.6 Hz, 1H), 7.54 (d, J=9.2 Hz, 1H), 7.12-7.04 (m, 3H), 7.02-6.97 (m, 1H), 4.94 (bs, 1H), 3.96-3.87 (m, 1H), 3.66-3.55 (m, 2H), 3.50-3.42 (m, 2H), 2.87-2.80 (m, 2H), 2.78-2.72 (m, 2H), 2.70-2.64 (m, 2H); MS (ESI) m/z=419.2.

N-(3-(3,4-dihydroisoquinolin-2(1H)-yl)-2-hydroxypropyl)-6-methoxyimidazo[1,2a]pyridine-2-carboxamide (Example 9)

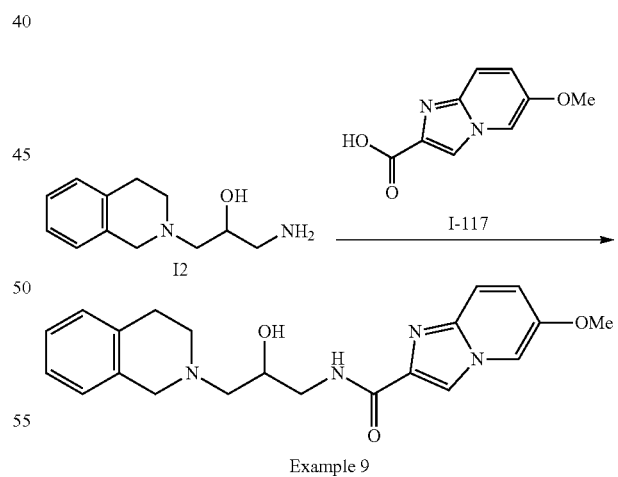

Example 9

25%). $^1$H NMR (DMSO-d$_6$, 400 MHz, ppm): δ 8.246-8.241 (m, 1H), 8.21 (s, 1H), 8.19-8.16 (m, 1H), 7.40 (d, J=8 Hz, 1H), 7.10-7.04 (m, 4H), 7.00-6.99 (m, 1H), 4.91 (d, J=8 Hz, 1H), 3.90-3.86 (m, 1H), 3.77 (s, 3H), 3.58-3.60 (m, 2H), 3.48-3.41 (m, 1H), 3.30-3.24 (m, 1H) (1 proton is merged with water/DMSO peak), 2.88-2.82 (m, 2H), 2.76-2.71 (m, 1H), 2.69-2.63 (m, 1H), 2.50-2.40 (m, 1H); MS (ESI) m/z=381.2 [M+H]$^+$.

N-(3-(3,4-dihydroisoquinolin-2(1H)-yl)-2-hydroxypropyl)-6-phenylimidazo[1,2-a]pyridine-2-carboxamide (Example 10)

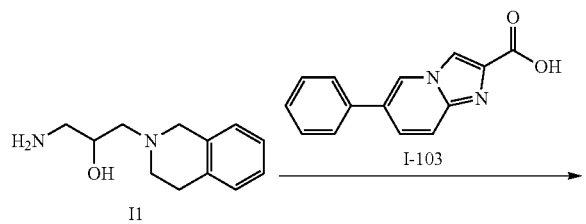

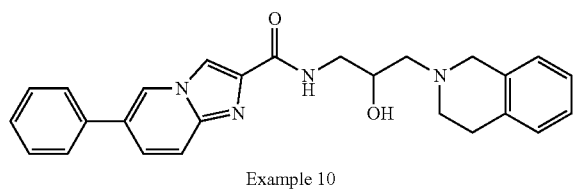

Example 10

To a stirred solution of 6-phenylimidazo[1,2-a]pyridine-2-carboxylic acid (I31, 0.1 g, 0.42 mmol) in DMF was added compound (I1, 0.095 g, 0.46 mmol) followed by DIPEA (0.3 mL, 1.72 mmol), HATU (0.18 g, 0.46 mmol). The reaction mixture was stirred for 16 h at room temperature. The reaction mixture was diluted with ethyl acetate, washed with water, brine, dried over anhydrous sodium sulfate, filtered and concentrated. Purification was done by preparative HPLC in to afford Example 10 as white solid (0.02 g, 11%). $^1$H NMR (DMSO-$d_6$, 400 MHz, ppm): δ 8.94 (s, 1H), 8.54 (br, 1H), 8.42 (s, 1H), 7.76 (d, J=9.6 Hz, 1H), 7.69 (d, J=6.8 Hz, 3H), 7.50 (t, J=7.6 Hz, 2H), 7.44-7.38 (m, 1H), 7.29-7.20 (m, 3H), 7.18-7.14 (m, 1H), 4.92 (d, J=5.2 Hz, 1H), 4.58-4.47 (m, 21H), 4.40-4.30 (m, 1H), 4.27-4.17 (m, 1H), 3.45-3.38 (m, 3H), 3.36-3.28 (m, 1H), 3.24-3.12 (m, 2H), 3.11-2.94 (m, 2H); MS (ESI) m/z=427.2 [M+H]$^+$.

N-(3-(3,4-dihydroisoquinolin-2(1H)-yl)-2-hydroxypropyl)-6-(4-fluorophenyl)imidazo[1,2-a]pyridine-2-carboxamide (Example 11)

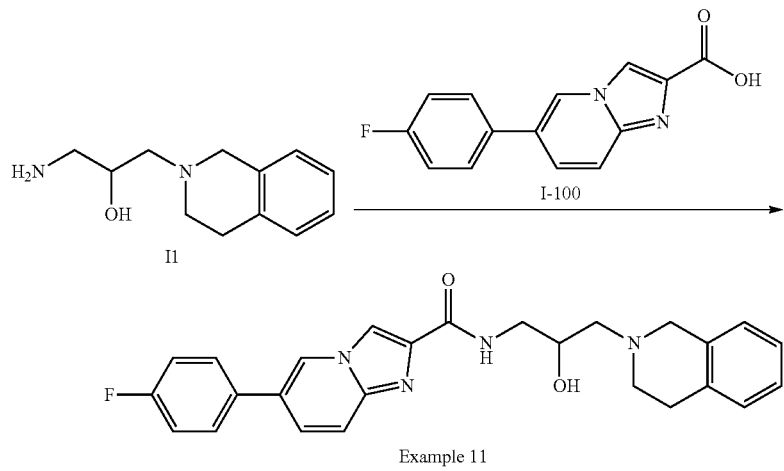

Example 11

15%). $^1$H NMR (DMSO-$d_6$, 400 MHz, ppm): δ 8.90 (br, 1H), 8.33-8.26 (m, 2H), 7.77-7.71 (m, 2H), 7.66 (d, J=9.2 Hz, 1H), 7.57 (d, J=9.2 Hz, 1H), 7.34 (t, J=8.6 Hz, 2H), 7.11-7.05 (m, 3H), 7.04-6.99 (m, 1H), 4.93 (d, J=4.4 Hz, 1H), 3.94-3.87 (m, 1H), 3.58-3.62 (m, 2H), 3.66-3.58 (m, 2H), 3.51-3.44 (m, 1H), 3.36-3.23 (m, 1H), 2.87-2.81 (m, 3H), 2.79-2.73 (m, 2H), 2.72-2.64 (m, 1H); MS (ESI) m/z=445.2 [M+H]$^+$.

(S)—N-(3-(3,4-dihydroisoquinolin-2(1H)-yl)-2-hydroxypropyl)-6-isopropylimidazo[1,2-a]pyridine-2-carboxamide (Example 12)

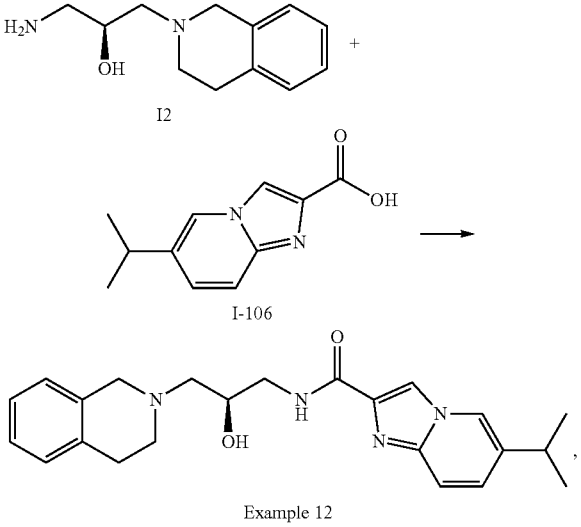

Example 12

7%). $^1$H NMR (DMSO-$d_6$, 400 MHz, ppm): δ 8.38 (s, 1H), 8.24 (bs, 2H), 7.43 (d, J=9.2 Hz, 1H), 7.30 (d, J=8.8 Hz, 1H), 7.11-7.04 (m, 3H), 7.03-6.98 (m, 1H), 4.92 (s, 1H), 3.89 (bs, 1H), 3.68-3.57 (m, 2H), 3.50-3.40 (m, 3H), 2.96-2.88 (m, 1H), 2.87-2.80 (m, 2H), 2.79-2.72 (m, 2H), 2.70-2.62 (m, 1H), 1.23 (d, J=5.6 Hz, 6H); MS (ESI) m/z=393.1 [M+H]$^+$.

(S)—N-(3-(3,4-dihydroisoquinolin-2(1H)-yl)-2-hydroxypropyl)-6-(1-methyl-1H-pyrazol-4-yl)imidazo[1,2-a]pyridine-2-carboxamide (Example 13)

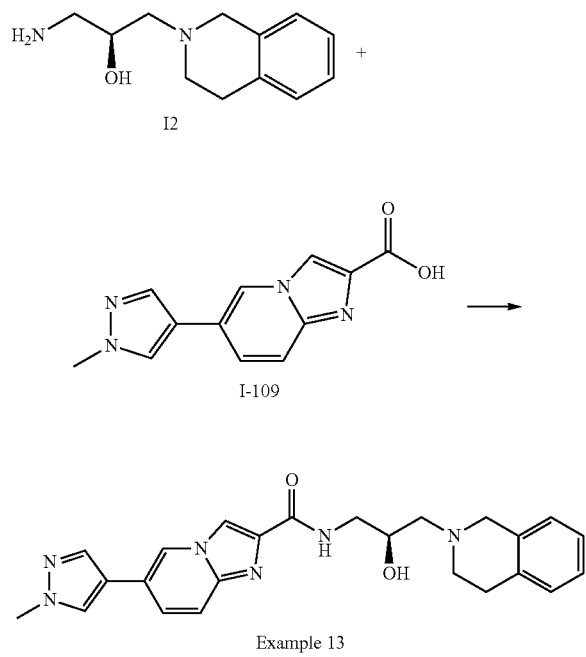

22%). ¹H NMR (DMSO-d₆, 400 MHz, ppm): δ 8.21 (s, 1H), 8.13 (s, 1H), 7.85 (bs, 1H), 7.73 (s, 1H), 7.62 (s, 1H), 7.56 (d, J=9.2 Hz, 1H), 7.35 (d, J=9.2 Hz, 1H), 7.20-7.10 (m, 3H), 7.02 (d, J=6.8 Hz, 1H), 4.23 (bs, 1H), 4.03 (d, J=14.8 Hz, 1H), 3.97 (s, 3H), 3.87 (d, J=15.2 Hz, 1H), 3.78-3.69 (m, 1H), 3.58-3.50 (m, 1H), 3.18-3.09 (m, 1H), 3.06-2.96 (m, 3H), 2.88-2.78 (m, 2H); MS (ESI) m/z=431.2 [M+H]⁺.

(S)-6-(4-cyanophenyl)-N-(3-(3,4-dihydroisoquinolin-2(1H)-yl)-2-hydroxypropyl) imidazo[1,2-a]pyridine-2-carboxamide (Example 14)

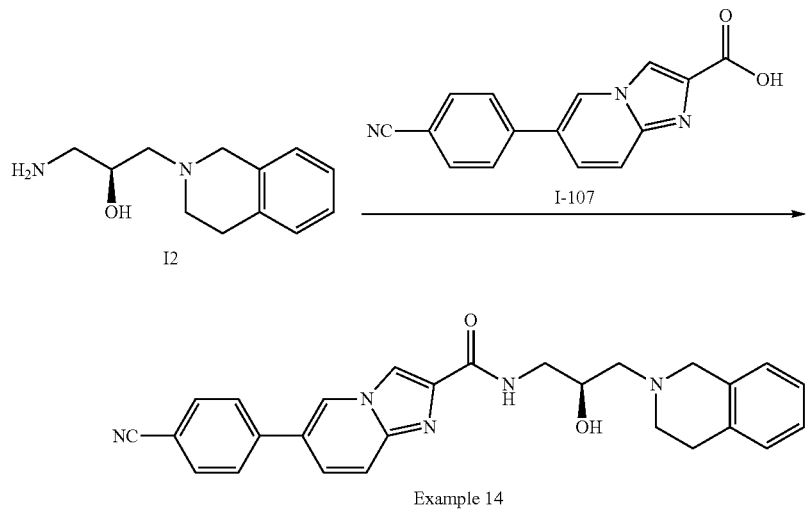

21%). ¹H NMR (CDCl₃-d₆, 400 MHz, ppm): δ 8.37 (s, 1H), 8.22 (s, 1H), 7.92 (bs, 1H), 7.78 (d, J=8.0 Hz, 1H), 7.68 (d, J=8.4 Hz, 2H), 7.47 (d, J=9.2 Hz, 1H), 7.28-7.24 (m, 2H), 7.21-7.12 (m, 3H), 7.04 (d, J=7.2 Hz, 1H), 4.29 (bs, 1H), 4.10 (d, J=14.8 Hz, 1H), 3.94 (d, J=14.8 Hz, 1H), 3.80-3.72 (m, 1H), 3.60-3.51 (m, 1H), 3.24-3.16 (m, 1H), 3.12-3.02 (m, 3H), 2.94-2.82 (m, 2H); MS (ESI) m/z=452.2[M+H]⁺.

(S)—N-(3-(3,4-dihydroisoquinolin-2(1H)-yl)-2-hydroxypropyl)-6-(3,5-dimethyl isoxazol-4-yl)imidazo[1,2-a]pyridine-2-carboxamide (Example 15)

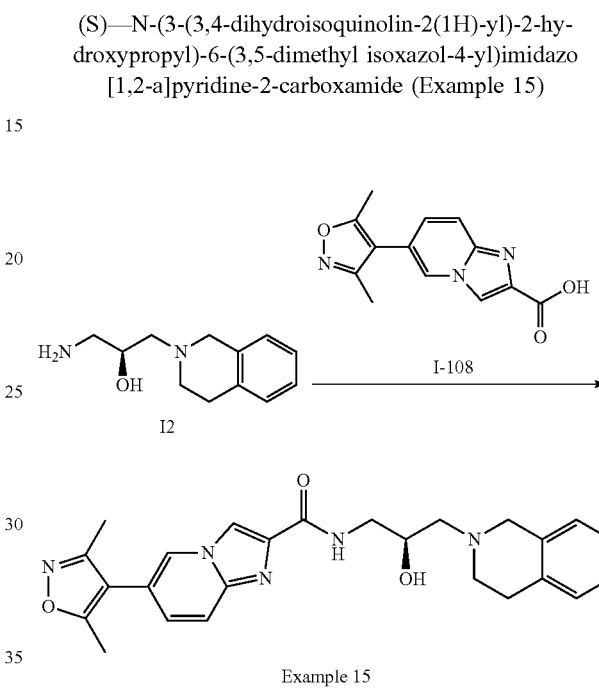

19.29%). ¹H NMR (DMSO-d₆, 400 MHz, ppm): δ 8.64 (s, 2H), 8.30 (s, 1H), 7.57 (d, J=8 Hz, 1H), 7.36 (d, J=8.8 Hz, 1H), 7.06-7.08 (m, 2H), 6.99-6.97 (m, 1H), 4.95-4.94 (m, 1H), 3.91-3.90 (m, 1H), 3.61 (s, 2H), 3.57-3.44 (m, 1H), (1 protons are merged with water-DMSO peak) 2.83 (bs, 2H), 2.48 (s, 4H), 2.25 (s, 3H); MS (ESI) m/z=446.2 [M+H]⁺.

(S)-6-(3,5-difluorophenyl)-N-(3-(3,4-dihydroisoquinolin-2(1H)-yl)-2-hydroxypropyl)imidazo[1,2-a]pyridine-2-carboxamide (Example 16)

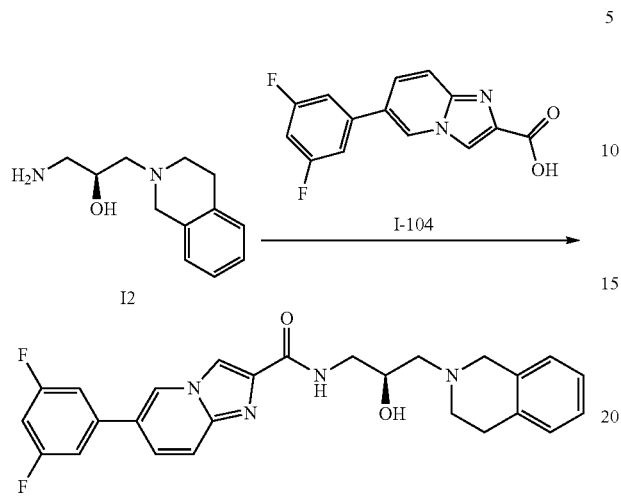

Example 16

9%). $^1$H NMR (DMSO-d$_6$, 400 MHz, ppm): δ 8.65-8.34 (m, 2H), 7.73 (d, 1H, J=8 Hz), 7.61 (d, 1H, J=12 Hz), 7.51 (d, 2H, J=8.1 Hz), 7.30-7.25 (m, 1H), 7.12-7.04 (m, 3H), 7.02-6.98 (m, 1H), 4.85-4.81 (m, 1H), 3.85-3.79 (m, 1H), 3.68-3.58 (m, 2H), 3.51-3.42 (m, 1H), 3.34-3.25 (m, 1H), 2.88-2.80 (m, 2H), 2.78-2.72 (m, 1H), 2.71-2.62 (m, 1H); MS (ESI) m/z=445.2 [M+H]$^+$.

(S)—N-(3-(3,4-dihydroisoquinolin-2(1H)-yl)-2-hydroxypropyl)-6-(4fluorophenyl) imidazo[1,2-a]pyridine-2-carboxamide (Example 17)

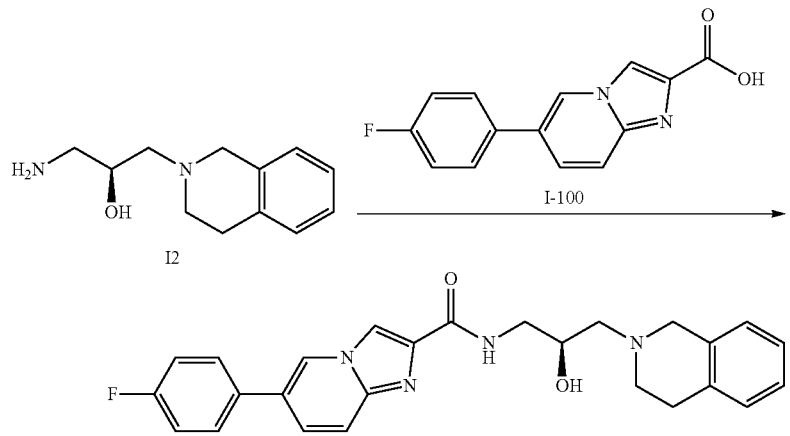

Example 17

10%). $^1$H NMR (DMSO-d$_6$, 400 MHz, ppm): δ 8.90 (s, 1H), 8.33-8.26 (m, 2H), 7.78-7.71 (m, 2H), 7.66 (d, J=9.6 Hz, 1H), 7.57 (d, J=9.6 Hz, 1H), 7.34 (t, J=8.8 Hz, 2H), 7.13-7.05 (m, 3H), 7.03-6.98 (m, 1H), 4.94 (d, J=4.4 Hz, 1H), 3.98-3.86 (m, 1H), 3.68-3.58 (m, 2H), 3.50-3.42 (m, 2H), 3.36-3.24 (m, 1H), 2.84 (s, 2H), 2.80-2.72 (m, 1H), 2.70-2.62 (m, 2H); MS (ESI) m/z=445.2 [M+H]$^+$.

(S)—N-(3-(3,4-dihydroisoquinolin-2(1H)-yl)-2-hydroxypropyl)-6-(1-isobutyl-1H-pyrazol-4-yl)imidazo[1,2-a]pyridine-2-carboxamide (Example 18)

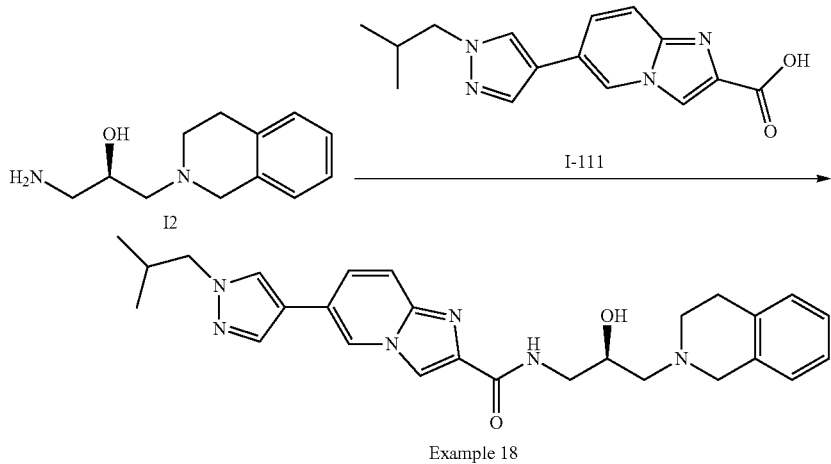

Example 18

To a stirred solution of 6-(1-isobutyl-1H-pyrazol-4-yl)imidazo[1,2-a]pyridine-2-carboxylic acid (I39, 0.10 g, 0.35 mmol) in DCM (10 mL) was added compound I2 (0.093 g, 0.45 mmol) and triethylamine (0.16 g, 1.65 mmol). Then reaction mixture was cooled to 0° C. and T$_3$P (0.28 g, 0.881 mmol) was added at the same temperature. The reaction mixture was then stirred at RT for 3 h. After completion of reaction, the reaction mixture was washed with water and brine. The organic layer was dried over anhydrous Na$_2$SO$_4$, filtered and concentrated under reduced pressure. The crude product was purified by column chromatography with silica-gel column using methanol in DCM as the eluent to afford Example 18 as an off white solid. Yield: 15.5 mg (9%). $^1$H NMR (DMSO-d$_6$, 400 MHz, ppm): δ 8.80 (s, 1H), 8.27 (bs, 1H), 8.22 (s, 1H), 8.18 (s, 1H), 7.87 (s, 1H), 7.58-7.49 (m, 2H), 7.09 (s, 3H), 7.02 (s, 1H), 4.94 (bs, 1H), 3.93 (d, J=6.8 Hz, 3H), 3.63 (s, 2H), 3.49-3.43 (m, 1H), 2.84 (s, 4H), 2.16-2.09 (m, 2H), 0.85 (d, J=6 Hz, 6H) (3 protons are merged with DMSO/H$_2$O peak); MS (ESI) m/z=473.3 [M+H]$^+$.

(S)-6-(3,6-dihydro-2H-pyran-4-yl)-N-(3-(3,4-dihydroisoquinolin-2(1H)-yl)-2-hydroxypropyl)imidazo[1,2-a]pyridine-2-carboxamide (Example 19)

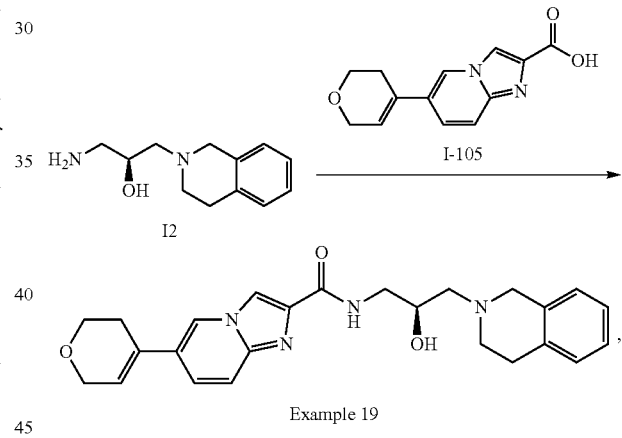

Example 19

3.2%). $^1$H NMR (CD$_3$OD-d$_6$, 400 MHz, ppm): δ 8.44 (s, 1H), 8.21 (s, 1H), 7.62-7.57 (m, 1H), 7.44 (d, 1H, J=9.6 Hz), 7.10-7.07 (m, 3H), 7.01 (d, 1H, J=6.8 Hz), 4.32 (s, 2H), 4.13-4.10 (m, 1H), 3.94 (t, 2H, J=10.4 Hz), 3.78 (s, 2H), 3.62-3.58 (m, 1H), 3.52-3.47 (m, 1H), 2.93-2.91 (m, 3H), 2.72-2.71 (m, 2H), 1.44-1.40 (m, 1H), 1.34-1.28 (m, 1H), 0.94-0.89 (m, 1H). MS (ESI) m/z=433.2 [M+H]$^+$.

N—((S)-3-(3,4-dihydroisoquinolin-2(1H)-yl)-2-hydroxypropyl)-6-(1-((R)-tetrahydrofuran-3-yl)-1H-pyrazol-4-yl)imidazo[1,2-a]pyridine-2-carboxamide (Example 20)

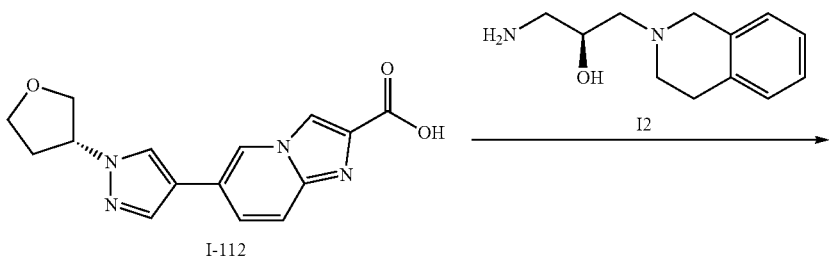

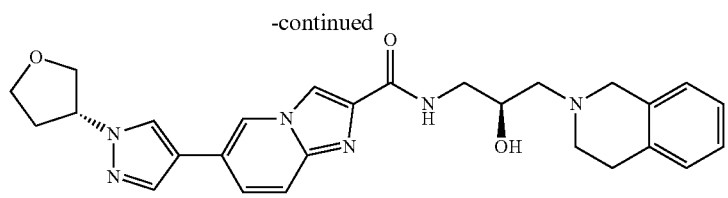

Example 20

(3.2%). $^1$H NMR (CD$_3$OD, 400 MHz) δ 8.68 (s, 1H), 8.22 (s, 1H), 8.12 (s, 1H), 7.90 (s, 1H), 7.60 (d, J=9.6 Hz, 1H), 7.49 (d, J=9.2 Hz, 1H), 7.08-7.06 (m, 3H), 7.01-7.00 (m, 1H), 5.09-05.06 (m, 1H), 4.17-4.11 (m, 2H), 4.09-4.06 (m, 2H), 3.95-3.90 (m, 1H), 3.74 (s, 2H), 3.63-3.58 (m, 1H), 3.52-3.47 (m, 1H), 2.93-2.91 (m, 2H), 2.88-2.87 (m, 2H), 2.68-2.64 (m, 2H), 2.53-2.47 (m, 1H), 2.40-2.36 (m, 1H); MS (ESI) m/z=487.2 [M+H]$^+$.

(S)—N-(3-(3,4-dihydroisoquinolin-2(1H)-yl)-2-hydroxypropyl)-6-(1H-pyrazol-4-yl)imidazo[1,2-a]pyridine-2-carboxamide (Example 21)

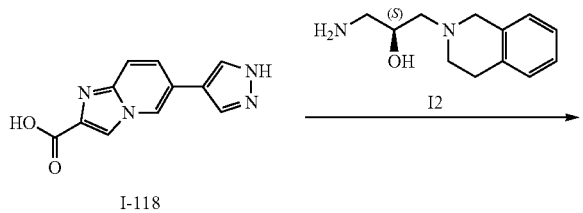 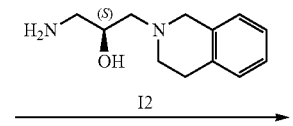

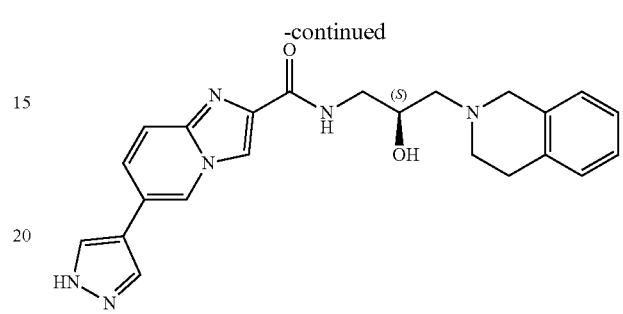

Example 21

$^1$H NMR (DMSO-d$_6$, 400 MHz, ppm)-δ 13.05 (s, 1H), 8.84 (s, 1H), 8.29-8.23 (m, 3H), 7.94 (bs, 1H), 7.63 (d, 1H, J=9.96 Hz), 7.52 (d, 1H, J=9.36 Hz), 7.11-7.04 (m, 4H), 4.97 (bs, 1H), 3.93 (s, 1H), 3.64 (s, 1H), 3.48-3.45 (m, 2H), 3.40-3.30 (m, 2H), 2.86-2.77 (m, 5H). MS (ES) m/z: 417.12 [M+H]$^+$ (S)—N-(3-(3,4-dihydroisoquinolin-2(1H)-yl)-2-hydroxypropyl)-6-(1-(oxetan-3-yl)-1H-pyrazol-4-yl)imidazo[1,2-a]pyridine-2-carboxamide (Example 22)

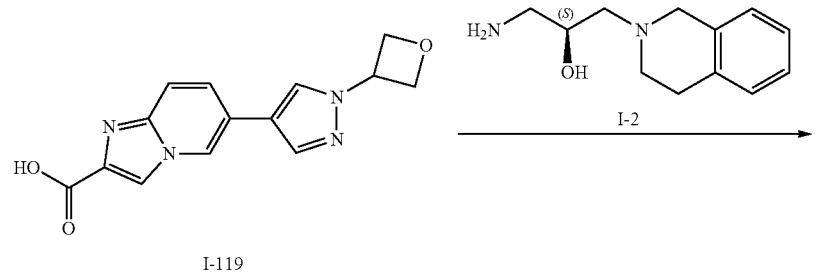 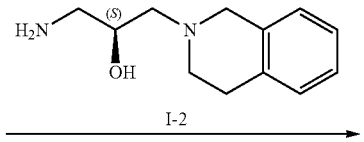

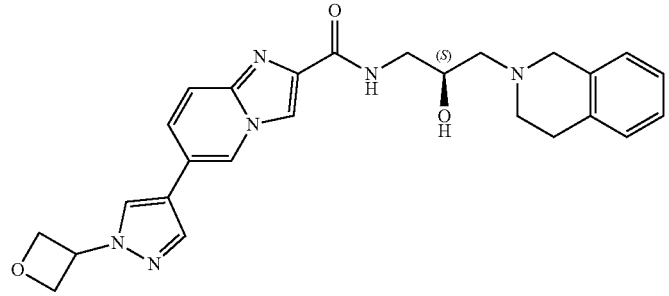

Example 22

¹H NMR (DMSO-d₆, 400 MHz, ppm)-δ 8.86 (s, 1H), 8.43 (s, 1H), 8.3 (bs, 1H), 8.25 (s, 1H), 8.05 (s, 1H), 7.62 (d, J=8.2 Hz, 1H), 7.53 (d, J=9.3 Hz, 1H), 7.1 (bs, 3H), 7.03 (bs, 1H), 5.61 (t, J=6.7 Hz, 1H), 4.97-4.9 (m, 5H), 3.92 (d, J=5.0 Hz, 1H), 3.63 (bs, 2H), 3.5-3.44 (m, 1H), 3.29 (s, 1H), 2.85 (bs, 2H), 2.75-2.66 (m, 2H). LC-MS (ES) m/z: 473.19 [M+H]⁺.

(S)-6-(1-(1-acetylazetidin-3-yl)-1H-pyrazol-4-yl)-N-(3-(3,4-dihydroisoquinolin-2(1H)-yl)-2-hydroxypropyl)imidazo[1,2-a]pyridine-2-carboxamide (Example 23)

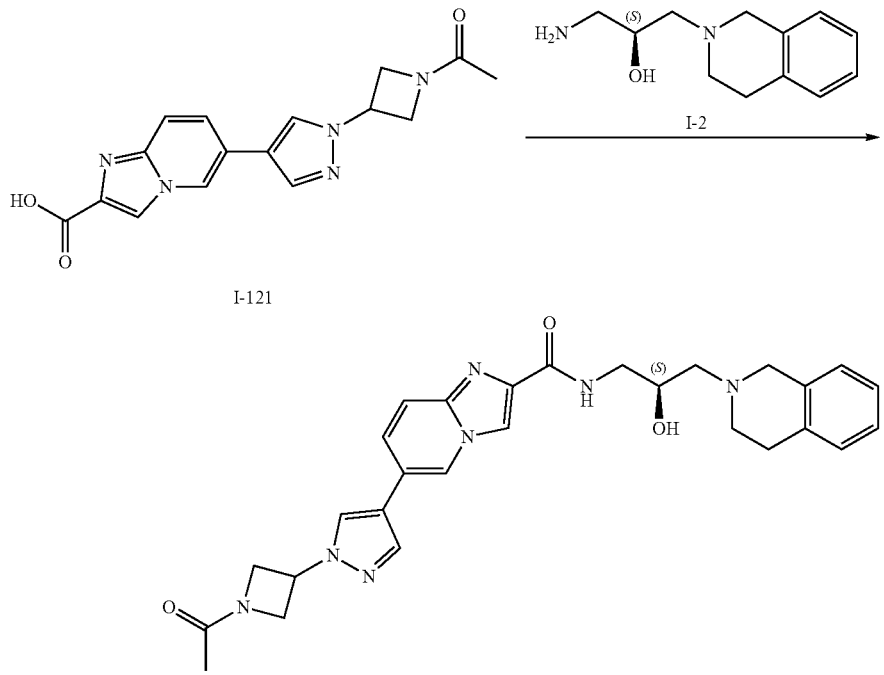

Example 23

¹H NMR (DMSO-d₆, 400 MHz, ppm) δ 9.82 (s, 1H), 8.89 (s, 1H), 8.57-8.52 (m, 1H), 8.46 (s, 1H), 8.31 (s, 1H), 8.05 (s, 1H), 7.64 (s, 1H), 7.26-7.19 (m, 4H), 5.92 (bs, 1H), 5.31-5.25 (m, 1H), 4.62-4.52 (m, 2H), 4.43-4.30 (m, 3H), 4.23-4.11 (m, 2H), 3.55-3.43 (m, 3H), 3.32-2.94 (m, 5H), 1.83 (s, 3H). LC-MS (ES) m/z: 514.26 [M+H]⁺.

(S)—N-(3-(3,4-dihydroisoquinolin-2(1H)-yl)-2-hydroxypropyl)-6-(5-isopropyl-1,2,4-oxadiazol-3-yl)imidazo[1,2-a]pyridine-2-carboxamide (Example 24)

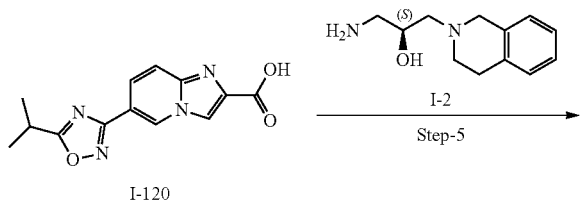

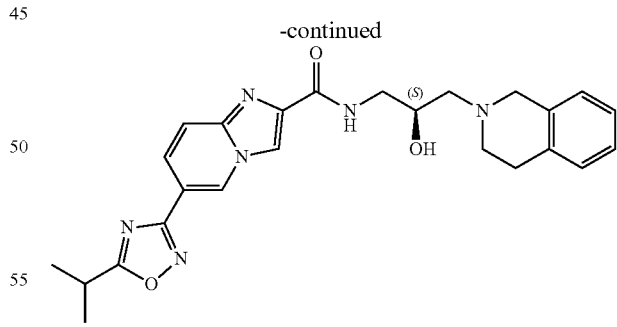

Example 24

¹H NMR (DMSO-d₆, 400 MHz, ppm)-δ 9.79 (bs, 1H), 9.40 (s, 1H), 8.60 (bs, 2H), 7.85 (dd, J=9.4, 1.2 Hz, 1H), 7.76 (d, J=9.4 Hz, 1H), 7.28-7.17 (m, 4H), 5.9 (bs, 1H), 4.6-4.52 (m, 2H), 4.43-4.33 (m, 2H), 4.25 (bs, 2H), 3.75-3.69 (m, 1H), 3.43-3.36 (m, 2H), 3.23-3.19 (m, 1H), 3.06-3.02 (m, 1H), 1.4 (d, J=6.9 Hz, 6H). LC-MS (ES) m/z: 461.16 [M+H]⁺.

(S)-6-(5-cyclopropyl-1,2,4-oxadiazol-3-yl)-N-(3-(3,4-dihydroisoquinolin-2(1H)-yl)-2-hydroxypropyl)imidazo[1,2-a]pyridine-2-carboxamide (Example 25)

(S)—N-(3-(3,4-dihydroisoquinolin-2(1H)-yl)-2-hydroxypropyl)-6-(tetrahydro-2H-pyran-4-yl)imidazo[1,2-a]pyridine-2-carboxamide (Example-26)

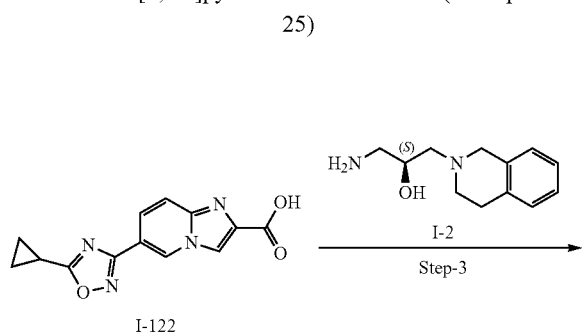

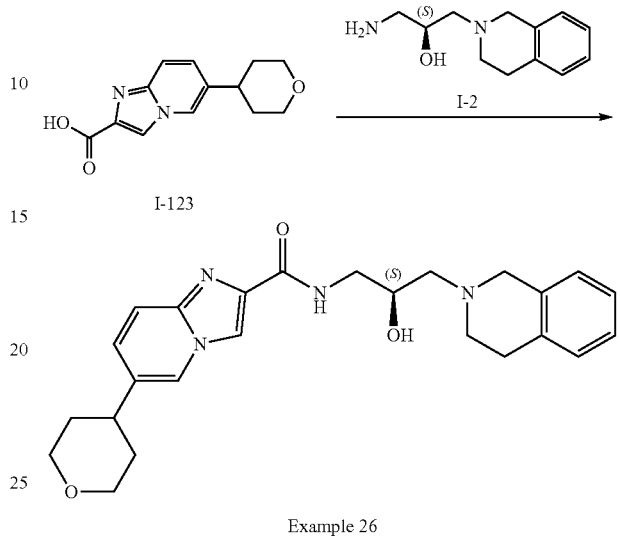

$^1$H NMR (400 MHz, DMSO-d6) δ 9.31 (s, 1H), 8.52 (s, 1H), 8.36 (t, J=5.4 Hz, 1H), 7.77 (dd, J=9.4, 1.3 Hz, 1H), 7.63 (d, J=9.4 Hz, 1H), 7.1-7.01 (m, 4H), 4.95 (d, J=3.8 Hz, 1H), 3.91 (d, J=4.8 Hz, 1H), 3.62 (bs, 2H), 3.49-3.43 (m, 1H), 3.35-3.31 (m, 1H), 2.84 (s, 2H), 2.85-2.66 (m, 3H), 2.41-2.35 (m, 2H), 1.35-1.3 (m, 2H), 1.23-1.19 (m, 2H). LC-MS (ES) m/z=459.14 [M+H]$^+$.

$^1$H NMR (DMSO-d$_6$, 400 MHz, ppm) δ 8.42 (s, 1H), 8.26 (s, 2H), 7.46 (d, J=8.96 Hz, 1H), 7.33 (d, J=9.20 Hz, 1H), 7.12-7.05 (m, 4H), 4.99 (bs, 1H), 3.99-3.96 (dd, J=7.28 Hz, 3.32 Hz, 3H), 3.78 (bs, 2H), 3.53-3.39 (m, 4H), 3.05-2.66 (m, 7H), 1.80 (d, J=11.40 Hz, 2H), 1.74-1.64 (m, 2H). LC-MS (ES) m/z: 435.19 [M+H]$^+$.

(S)-6-(1-acetylpiperidin-4-yl)-N-(3-(3,4-dihydroisoquinolin-2(1H)-yl)-2-hydroxypropyl)imidazo[1,2-a]pyridine-2-carboxamide (Example 27)

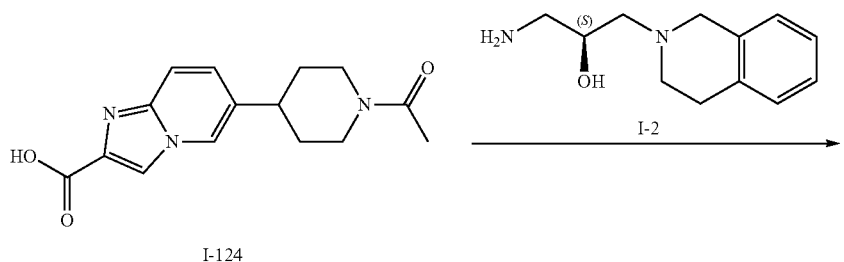

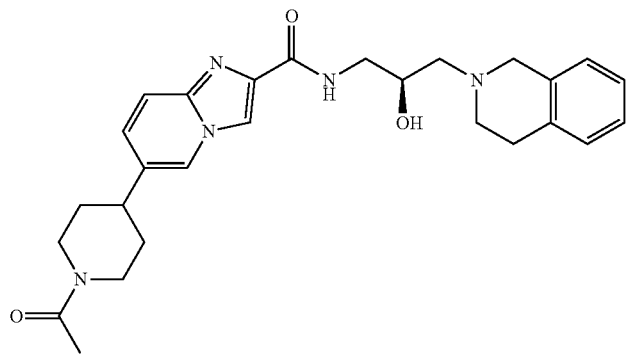

¹H NMR (DMSO-d₆, 400 MHz, ppm) δ 8.40 (s, 1H), 8.24 (s, 1H), 8.17 (bs, 1H), 7.48 (d, 1H, J=9.44 Hz), 7.31 (d, 1H, 9.36 Hz), 7.18-7.04 (m, 4H), 5.16 (bs, 1H), 4.54 (m, 4H), 3.52-3.41 (m, 1H), 3.40-3.38 (m, 1H), 3.05-3.00 (m, 3H), 3.00-2.87 (m, 3H), 2.86-2.76 (m, 3H), 2.73-2.66 (m, 1H), 2.08 (s, 3H), 1.69-1.49 (m, 2H). LC-MS (ES) m/z: 476.18 [M+H]⁺.

(S)—N-(3-(3,4-dihydroisoquinolin-2(1H)-yl)-2-hydroxypropyl)-6-(2-methylpyrimidin-5-yl)imidazo[1,2-a]pyridine-2-carboxamide (Example 28)

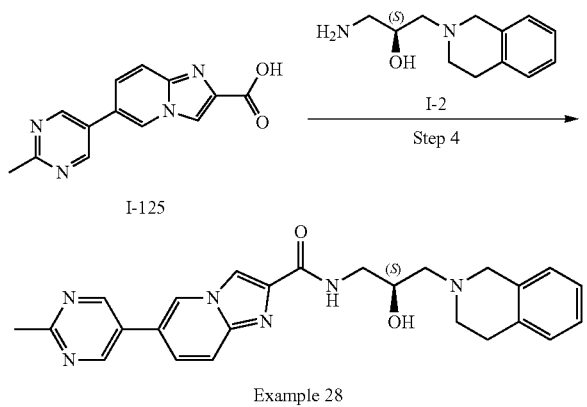

Example 28

¹H NMR (400 MHz, DMSO-d6) δ 9.07 (m, 2H), 8.34 (m, 2H), 7.77 (dd, J₁₋₃=9.4 Hz, J₁₋₂=1.4 Hz, 1H), 7.64 (d, J=9.4 Hz, 1H), 7.09 (m, 3H), 7.03 (bs, 1H), 4.96 (d, J=4.6 Hz, 1H), 3.92 (m, 1H), 3.63 (s, 2H), 3.48 (m, 1H), 3.35 (m, 1H), 2.85 (bs, 2H), 2.76 (m, 1H), 2.68 (bs, 5H), 2.54 (m, 1H). LC-MS (ES) m/z= 443.14 [M+H]⁺.

(S)—N-(3-(3,4-dihydroisoquinolin-2(1H)-yl)-2-hydroxypropyl)-6-(6-methylpyridin-3-yl)imidazo[1,2-a]pyridine-2-carboxamide (Example 29)

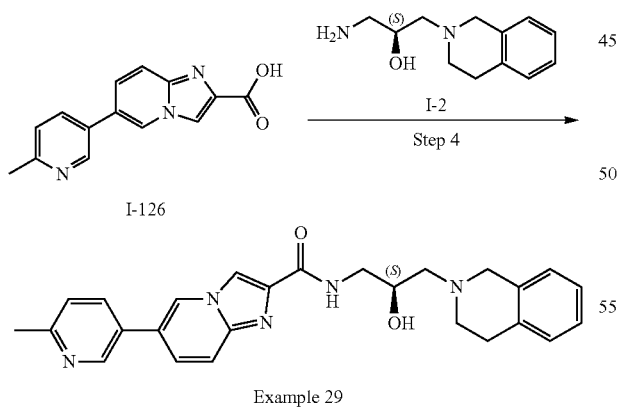

Example 29

¹H NMR (400 MHz, DMSO-d6) δ 8.99 (s, 1H), 8.8 (d, J=1.9 Hz, 1H), 8.32 (bs, 2H), 8.01 (dd, J₁₋₃=8.0 Hz, J₁₋₂=2.2 Hz, 1H), 7.71 (dd, J₁₋₃=9.4 Hz, J₁₋₂=1.4 Hz, 1H), 7.61 (d, J=9.4 Hz, 1H), 7.39 (d, J=8.1 Hz, 1H), 7.09 (m, 3H), 7.02 (bs, 1H), 5.0 (bs, 1H), 3.92 (t, J=5.6 Hz, 1H), 3.63 (s, 2H), 3.5 (m, 1H), 3.35 to 3.25 (m, 3H), 2.85 (bs, 1H), 2.75-2.68 (m, 2H), 2.53 (s, 3H). LC-MS (ES) m/z=442.16 [M+H]⁺.

(S)—N-(3-(3,4-dihydroisoquinolin-2(1H)-yl)-2-hydroxypropyl)-6-(6-methylpyridazin-3-yl)imidazo[1,2-a]pyridine-2-carboxamide (Example 30)

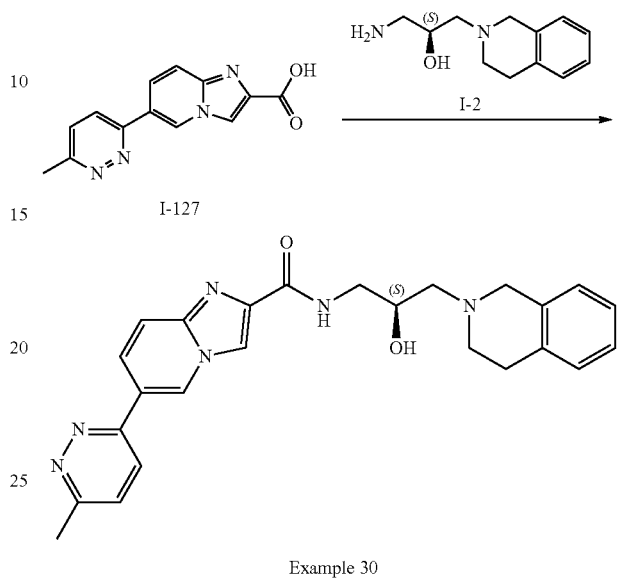

Example 30

¹H NMR (400 MHz, DMSO-d6) δ 9.46 (s, 1H), 8.45 (s, 1H), 8.4 (s, 1H), 8.16 (d, J=8.7 Hz, 1H), 8.1 (d, J=9.6 Hz, 1H), 7.73 (d, J=8.8 Hz, 1H), 7.68 (d, J=9.2 Hz, 1H), 7.1 (m, 4H), 5.0 (bs, 1H), 3.98 (bs, 1H), 3.66 (bs, 2H), 3.5-3.3 (m, 4H), 2.89 (bs, 4H), 2.69 (s, 3H). LC-MS (ES) m/z=443.23 [M+H]⁺.

(S)—N-(3-(3,4-dihydroisoquinolin-2(1H)-yl)-2-hydroxypropyl)-6-(2-methylthiazol-5-yl)imidazo[1,2-a]pyridine-2-carboxamide (Example 31)

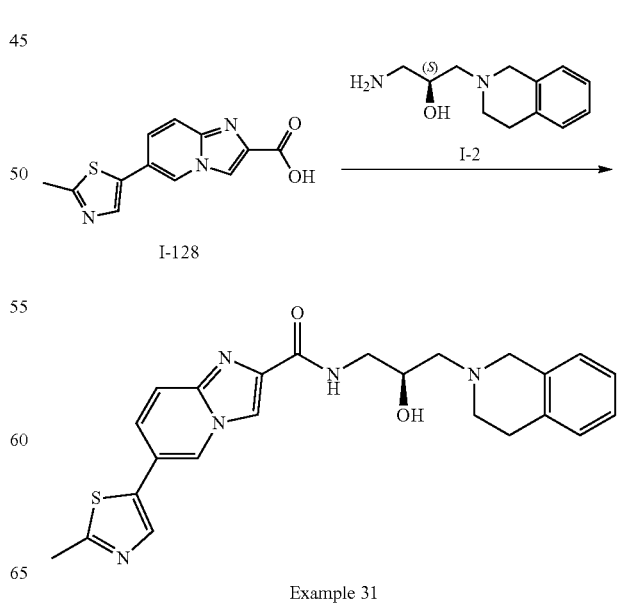

Example 31

Yield: 0.05 g (8.2%); $^1$H NMR (400 MHz, DMSO-d6) δ 8.89 (s, 1H), 8.32 (bs, 2H), 8.29 (s, 1H), 8.08 (s, 1H), 7.67 (d, J=9.4 Hz, 1H), 7.56 (d, J=9.4 Hz, 1H), 7.1 (bs, 3H), 7.02 (bs, 1H), 4.98 (bs, 1H), 3.92 (bs, 1H), 3.64 (bs, 2H), 3.49-3.43 (m, 1H), 3.32 (bs, 2H), 2.85 (bs, 2H), 2.79-2.77 (m, 2H), 2.7-2.66 (m, 4H). LC-MS (ES) m/z=448 [M+H]$^+$.

(S)—N-(3-(3,4-dihydroisoquinolin-2(1H)-yl)-2-hydroxypropyl)-6-(4,5-dimethylthiazol-2-yl)imidazo[1,2-a]pyridine-2-carboxamide (Example 32)

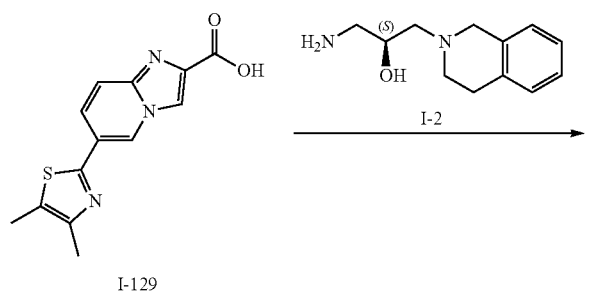

I-129

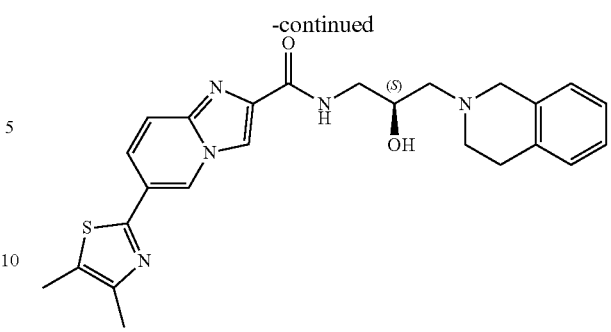

Example 32

LC-MS (ES) m/z: 462.16 [M+H]$^+$ $^1$H NMR (DMSO-d6, 400 MHz, ppm)-δ 9.19 (s, 1H), 8.43 (s, 1H), 8.32 (dd, 1H, J=11.0 Hz, J=5.64), 7.74 (d, 1H, J=9.44 Hz), 7.57 (d, 1H, J=9.48 Hz), 7.10-7.01 (m, 4H), 4.95 (bs, 1H), 3.92 (bs, 1H), 3.67 (s, 2H), 3.44-3.50 (m, 1H), 3.44-3.30 (m, 1H), 2.84-2.79 (m, 2H), 2.71-2.68 (m, 1H), 2.67-2.71 (m, 1H), 2.50-2.41 (m, 2H), 2.41 (s, 3H) 2.33 (s, 3H).

(S)-6-(5-chloropyridin-2-yl)-N-(3-(3,4-dihydroisoquinolin-2(1H)-yl)-2-hydroxypropyl)imidazo[1,2-a]pyridine-2-carboxamide (Example 33)

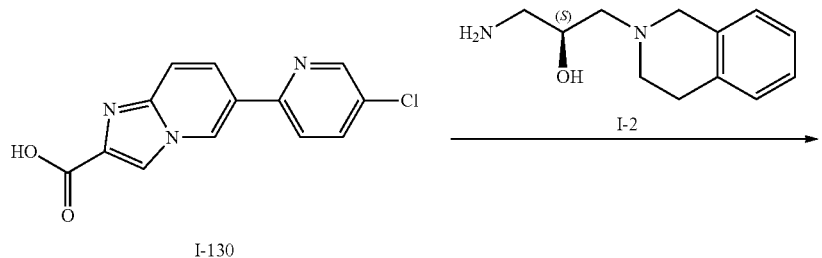

I-130

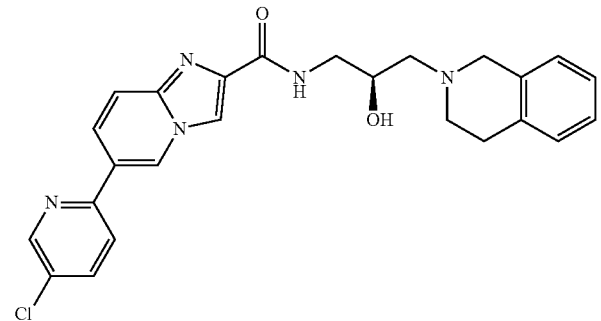

Example 33

LC-MS (ES) m/z: 462.10 [M+H]$^+$ $^1$H NMR (DMSO-d$_6$, 400 MHz, ppm) δ 9.41 (s, 1H), 8.74 (d, 1H, J=2.08 Hz), 8.58 (bs, 1H), 8.49 (s, 1H), 8.12-8.05 (m, 3H), 7.71 (d, 1H, J=9.48 Hz), 7.28-7.17 (m, 4H), 5.93 (bs, 1H), 4.61-4.52 (m, 1H), 4.43-4.34 (m, 1H), 4.33-4.24 (m, 1H), 3.75-3.69 (m, 1H), 3.44-3.33 (m, 3H), 3.24-3.21 (m, 2H), 3.07-2.98 (m, 2H).

(S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyridine-2-carboxamide (Example 34)

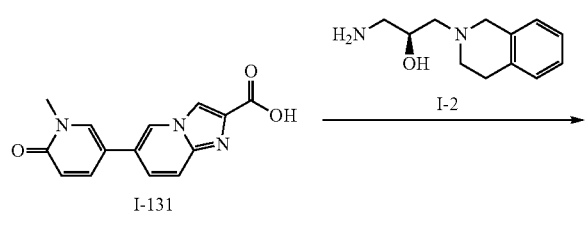

Example 34

LC-MS (ES) m/z=458.17 [M+H]⁺. H NMR (400 MHz, DMSO-d6) δ 8.81 (s, 1H), 8.38 (s, 1H), 8.29 (s, 1H), 8.19 (d, J=2.4 Hz, 1H), 7.81 (dd, J$_{1-3}$=9.4 Hz, J$_{1-2}$=2.6 Hz, 1H), 7.6 (s, 2H), 7.12 (bs, 4H), 6.53 (d, J=9.4 Hz, 1H), 4.02 (bs, 4H), 3.51 (s, 3H), 3.47 (m, 1H), 3.4 (m, 2H), 2.92 (bs, 5H).

(S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyridine-2-carboxamide (Example 35)

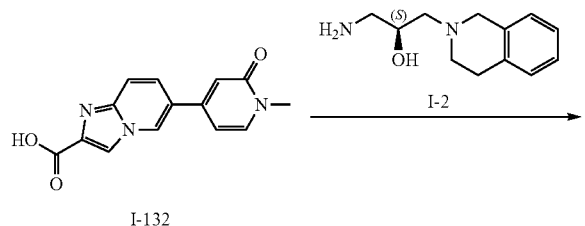

Example 35

LC-MS (ES) m/z: 458.16 [M+H]⁺ ¹H NMR (DMSO-d₆, 400 MHz, ppm) δ 9.10 (s, 1H), 8.34-8.31 (m, 2H), 7.83 (d, J=7.12 Hz, 1H), 7.70 (d, J=1.52 Hz, 1H), 7.57 (d, J=9.52 Hz, 1H), 7.10-7.09 (m, 3H), 7.03 (d, J=5.28 Hz, 1H), 6.78 (s, 1H), 6.61 (d, J=1.84 Hz, 1H), 4.96 (bs, 1H), 3.93 (d, J=4.84 HZ, 1H), 3.63 (s, 2H), 3.49-3.46 (m, 6H), 2.84-2.76 (m, 5H).

(S)—N-(3-(3,4-dihydroisoquinolin-2(1H)-yl)-2-hydroxypropyl)-6-(1-methyl-1H-1,2,3-triazol-4-yl)imidazo[1,2-a]pyridine-2-carboxamide (Example 36)

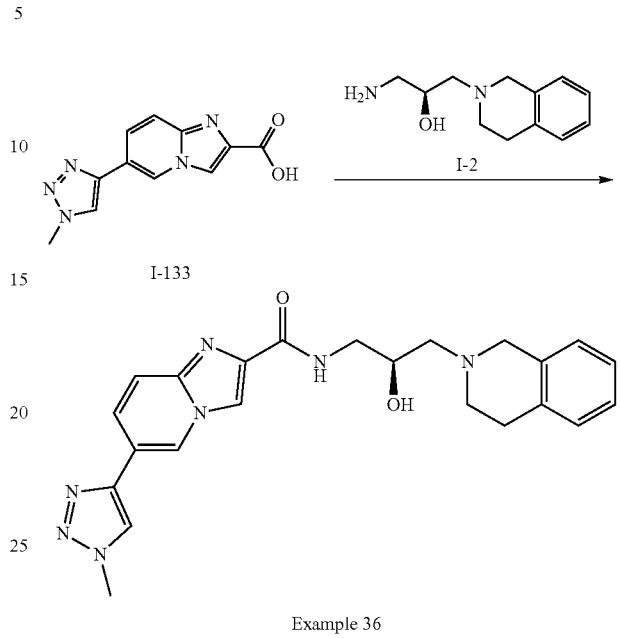

Example 36

LC-MS (ES) m/z: 432.11 [M+H]⁺. ¹H NMR (DMSO-d₆, 400 MHz, ppm)-δ 9.12 (s, 1H), 8.56 (s, 1H), 8.42 (s, 1H), 8.31 (t, J=5.2 Hz, 1H), 7.74 (d, J=9.4 Hz, 1H), 7.6 (d, J=9.4 Hz, 1H), 7.09 (bs, 3H), 7.02 (bs, 1H), 4.96 (d, J=4.6 Hz, 1H), 4.12 (s, 3H), 3.92-3.91 (m, 1H), 3.62 (bs, 2H), 3.49-3.46 (m, 1H), 3.32 (bs, 1H), 2.84 (bs, 2H), 2.77-2.72 (m, 1H), 2.71-2.66 (m, 1H).

(S)—N-(3-(3,4-dihydroisoquinolin-2(1H)-yl)-2-hydroxypropyl)-6-(1-isopropyl-1H-1,2,3-triazol-4-yl)imidazo[1,2-a]pyridine-2-carboxamide (Example 37)

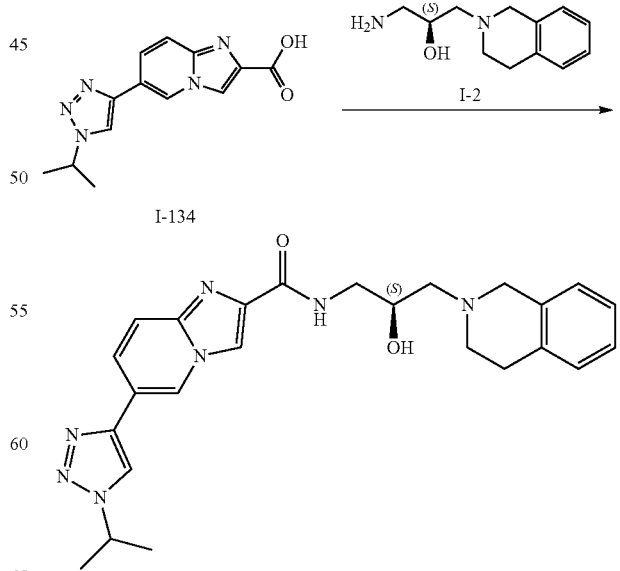

Example 37

LC-MS (ES) m/z: 432.39 [M+H]⁺. ¹H NMR (DMSO-d₆, 400 MHz, ppm)-δ 9.12 (s, 1H), 8.718 (s, 1H), 8.42 (s, 1H), 8.312 (t, J=5.2 Hz, 1H), 7.75 (d, J=9.44 Hz, 1H), 7.60 (d, J=9.4 Hz, 1H), 7.10-7.01 (m, 4H), 4.95 (d, J=4.6 Hz, 1H), 4.91-4.84 (m, 1H), 3.94-3.90 (m, 1H), 3.59 (s, 2H), 3.49-3.44 (m, 2H), 2.84-2.70 (m, 5H), 2.18-2.15 (m, 1H), 1.55 (d, J=6.68 Hz, 6H).

(S)—N₂-(3-(3,4-dihydroisoquinolin-2(1H)-yl)-2-hydroxypropyl)-N₆-methylimidazo[1,2-a]pyridine-2,6-dicarboxamide (Example 38)

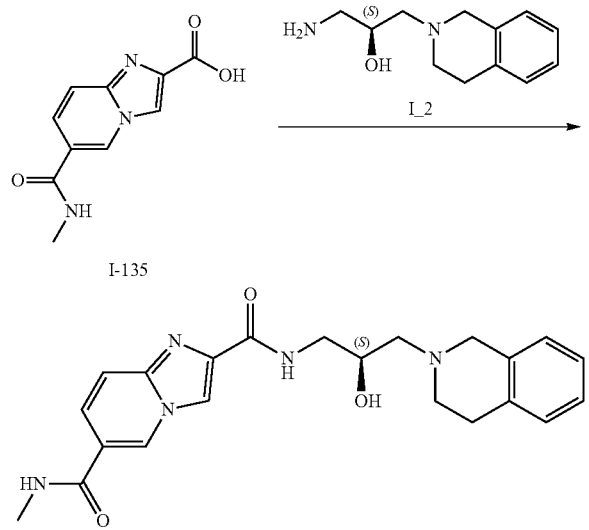

Example 38

LC-MS (ES) m/z: 408.01 [M+H]⁺. ¹H NMR (DMSO-d₆, 400 MHz, ppm) δ 9.11 (s, 1H), 8.59 (dd, J=4.08 Hz, 1H), 8.45 (s, 1H), 8.35 (d, J=4.92 Hz, 1H), 7.70 (d, J=9.44 Hz, 1H), 7.53 (d, J=9.44 Hz, 1H), 7.09-7.01 (m, 4H), 4.95 (d, J=4.0 Hz, 1H), 3.91 (d, J=4.96 Hz, 1H), 3.66-3.58 (m, 2H), 3.49-3.45 (m, 1H), 3.32 (s, 3H), 2.84-2.80 (m, 1H), 2.77-2.73 (m, 3H), 2.69-2.50 (m, 3H).

(S)-6-acetamido-N-(3-(3,4-dihydroisoquinolin-2(1H)-yl)-2-hydroxypropyl)imidazo[1,2-a]pyridine-2-carboxamide (Example 39)

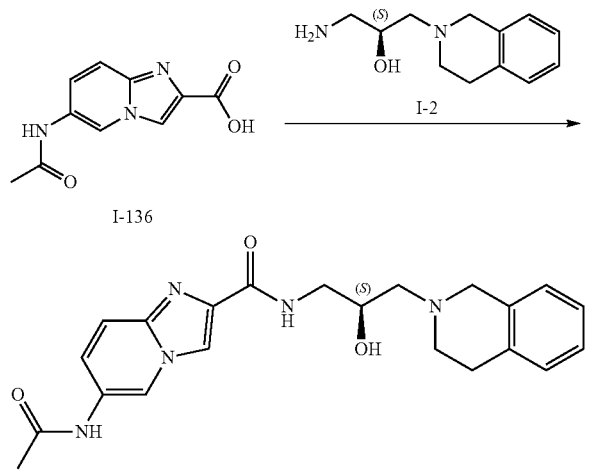

Example 39

LC-MS (ES) m/z: 406.14 [M+H]⁺ ¹H NMR (DMSO-d₆, 400 MHz, ppm)-δ 10.11 (s, 1H), 9.24 (s, 1H), 8.42 (s, 1H), 8.27 (bs, 1H), 7.50 (d, J=9.56 Hz, 1H), 7.22 (d, J=9.64 Hz, 1H), 7.13-7.07 (m, 4H), 5.01 (bs, 1H), 3.97-3.42 (m, 5H), 2.89-2.66 (m, 5H), 2.08 (s, 3H).

(S)—N-(3-(3,4-dihydroisoquinolin-2(1H)-yl)-2-hydroxypropyl)-6-sulfamoylimidazo[1,2-a]pyridine-2-carboxamide (Example 40)

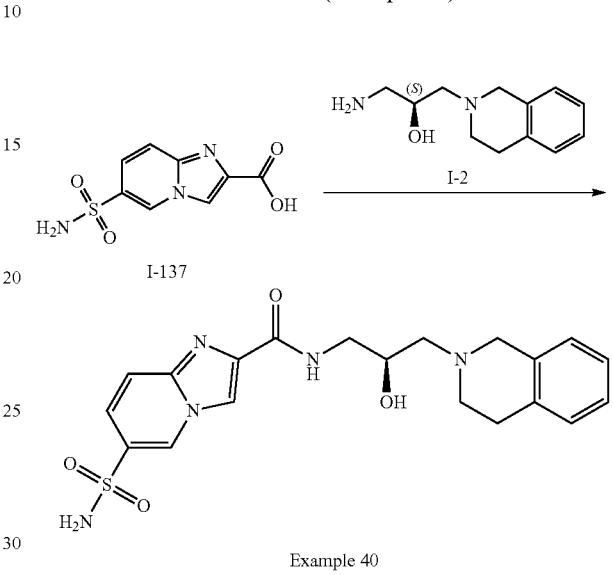

Example 40

LC-MS (ES) m/z=430.17 [M+H]⁺. 1H NMR (400 MHz, DMSO-d6) δ 9.18 (s, 1H), 8.54 (s, 1H), 8.37 (bs, 1H), 7.68-7.59 (m, 4H), 7.09 (bs, 3H), 7.02 (bs, 1H), 4.96 (bs, 1H), 3.92 (bs, 1H), 3.62 (bs, 2H), 3.48-3.45 (m, 1H), 2.84 (bs, 2H), 2.78-2.69 (m, 4H).

(S)—N-(3-(3,4-dihydroisoquinolin-2(1H)-yl)-2-hydroxypropyl)-6-(methylsulfonamido)imidazo[1,2-a]pyridine-2-carboxamide (Example 41)

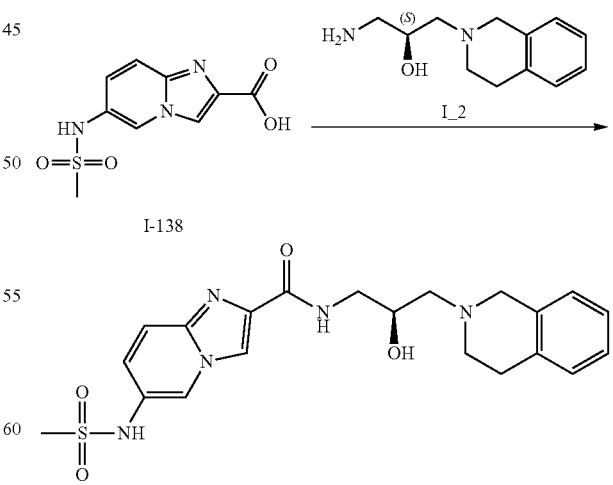

PRMT5_Chemsys_41

LC-MS (ES) m/z: 444.15 [M+H]⁺. ¹H NMR (DMSO-d₆, 400 MHz, ppm) δ 9.77 (s, 1H), 8.50 (s, 1H), 8.40 (s, 1H), 8.28 (bs, 1H), 7.51 (d, J=9.64 Hz, 1H), 7.22 (d, J=8.68 Hz, 1H), 7.11-7.04 (m, 4H), 4.99 (bs, 1H), 3.92 (bs, 1H), 3.65 (bs, 2H), 3.47-3.42 (m, 1H), 3.32-3.30 (m, 1H), 3.04 (s, 3H), 2.85-2.58 (m, 6H).

((S)—N-(3-(3,4-dihydroisoquinolin-2(1H)-yl)-2-hydroxypropyl)-6-(trifluoromethyl)imidazo[1,2-a]pyrimidine-2-carboxamide (Example 42)

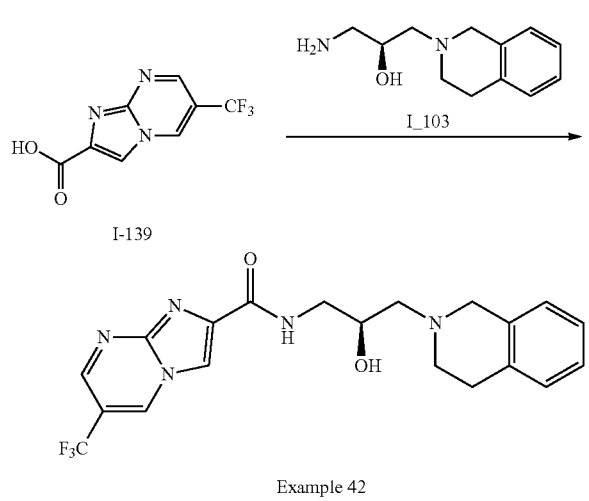

Example 42

LC-MS (ES) m/z: 420.21 [M+H]+. 1H NMR (DMSO-d6, 400 MHz, ppm) δ 9.66 (s, 1H), 8.97 (d, J=2.36 Hz, 1H), 8.47 (dd, J=12.04 Hz, 6.04 Hz, 1H), 8.35 (s, 1H), 7.08-7.02 (m, 4H), 4.97 (bs, 1H), 3.94 (bs, 1H), 3.63 (bs, 2H), 3.53-3.47 (m, 1H), 3.32-3.25 (m, 1H), 2.82-2.66 (m, 6H).

(S)—N-(3-(3,4-dihydroisoquinolin-2(1H)-yl)-2-hydroxypropyl)-6-(1-methyl-1H-pyrazol-4-yl)imidazo[1,2-a]pyrimidine-2-carboxamide (Example 43)

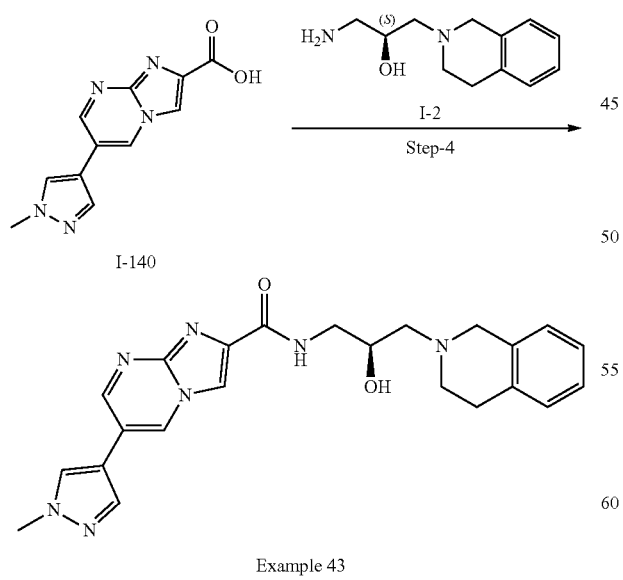

Example 43

LC-MS (ES) m/z: 433.25 [M+H]+. 1H NMR (DMSO-d6, 400 MHz, ppm) δ 9.20 (d, J=2.0 Hz, 1H), 8.95 (d, J=2.24 Hz, 1H), 8.68 (bs, 1H), 8.26 (d, J=11.0 Hz, 2H), 7.96 (s, 1H), 7.28-7.09 (m, 4H), 5.92 (bs, 1H), 4.61-4.56 (m, 1H), 4.52-4.39 (m, 1H), 4.25 (bs, 1H), 3.91 (s, 3H), 3.76-3.69 (m, 1H), 3.40 (m, 2H), 3.24-3.21 (m, 1H), 3.07-2.98 (m, 4H).

(S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyrimidine-2-carboxamide (Example 44)

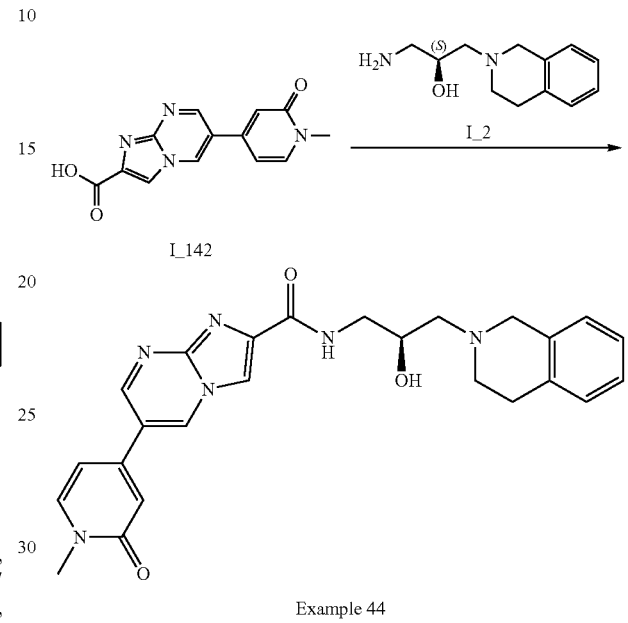

Example 44

LC-MS (ES) m/z: 459.26 [M+H]+ 1H NMR (DMSO-d6, 400 MHz, ppm) δ 9.46 (s, 1H), 9.03 (d, J=1.96 Hz, 1H), 8.39 (bs, 1H), 8.25 (s, 1H), 7.88 (d, J=7.08 Hz, 1H), 7.08-7.02 (m, 4H), 6.89 (s, 1H), 6.65 (d, J=6.96 Hz, 1H), 4.95 (d, J=4.56 Hz, 1H), 3.94 (d, J=5.92 HZ, 1H), 3.62 (d, J=3.16 Hz, 2H), 3.57-3.47 (m, 5H), 3.31-3.26 (m, 2H), 2.82-2.68 (m, 4H).

(S)—N-(3-(3,4-dihydroisoquinolin-2(1H)-yl)-2-hydroxypropyl)-6-(1-methyl-1H-pyrazol-4-yl)imidazo[1,2-a]pyrazine-2-carboxamide (Example 45)

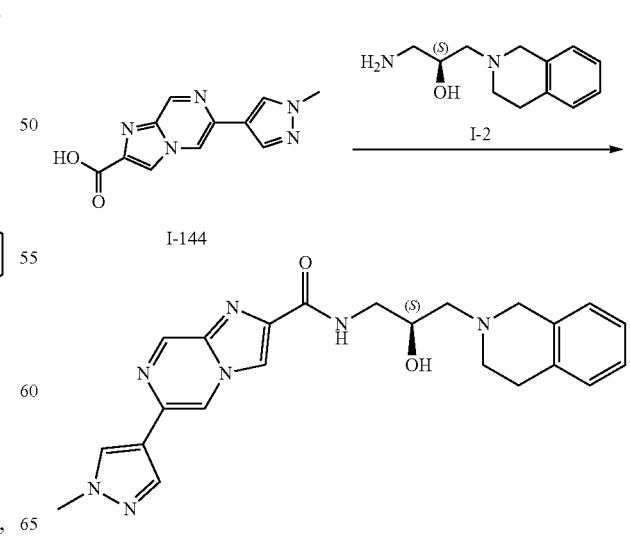

Example 45

183

LC-MS (ES) m/z: 432.17 [M+H]⁺. ¹H NMR (DMSO-d₆, 400 MHz, ppm) δ 8.98 (s, 1H), 8.85 (s, 1H), 8.48 (dd, J=12.24 Hz, J=5.24 Hz, 1H), 8.37 (s, 1H), 8.20 (s, 1H), 7.92 (s, 1H), 7.10-7.00 (m, 4H), 4.97 (d, J=3.72 Hz, 1H), 3.94-3.91 (m, 1H), 3.90 (s, 3H), 3.67-3.62 (m, 2H), 3.58-3.43 (m, 1H), 3.37-3.31 (m, 1H), 2.88-2.83 (m, 2H), 2.79-2.67 (m, 2H), 2.57-2.49 (m, 2H).

(S)—N-(3-(3,4-dihydroisoquinolin-2(1H)-yl)-2-hydroxypropyl)-6-(1-methyl-1H-pyrazol-4-yl)imidazo[1,2-b]pyridazine-2-carboxamide (Example 46)

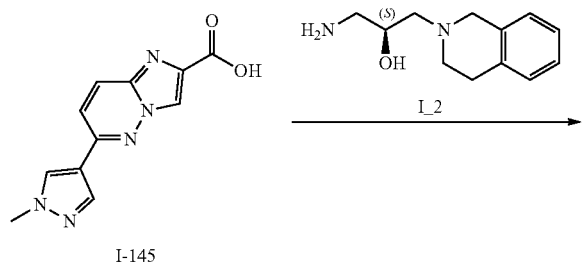

LC-MS (ES) m/z: 432.16 [M+H]⁺. ¹H NMR (DMSO-d₆, 400 MHz, ppm) δ 8.47 (d, J=6.60 Hz, 2H), 8.35 (dd, J=10.24 Hz, 1H), 8.09 (s, 1H), 8.02 (d, J=9.56 Hz, 1H), 7.66 (d, J=9.56 Hz, 1H), 7.10-7.01 (m, 4H), 4.97 (d, J=3.32 Hz, 1H), 3.92 (s, 4H), 3.66-3.59 (m, 2H), 3.51-3.45 (m, 1H), 3.34-3.29 (m, 1H), 2.84-2.79 (m, 2H), 2.75-2.67 (m, 2H), 2.56-2.49 (m, 2H).

(S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyrazine-2-carboxamide (Example 47)

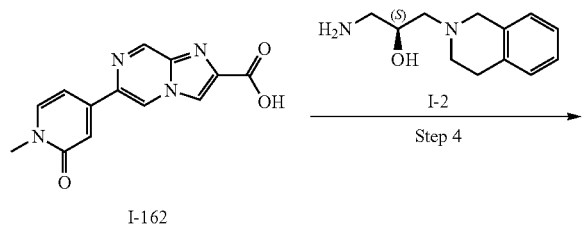

184

-continued

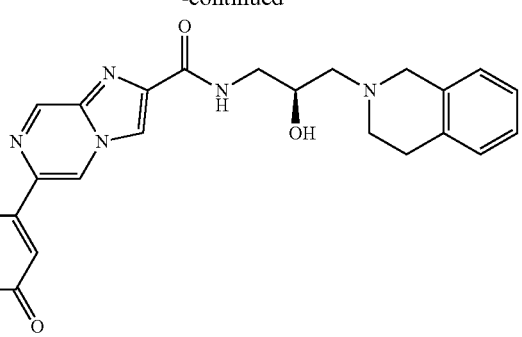

Example 47

LC-MS (ES) m/z: 459.24 [M+H]⁺ ¹H NMR (DMSO-d₆, 400 MHz, ppm) δ 9.33 (s, 1H), 9.09 (s, 1H), 8.54 (dd, J=11.72 Hz, 5.52 Hz, 1H), 8.42 (s, 1H), 7.84 (d, J=7.16 Hz, 1H), 7.10-7.06 (m, 4H), 7.01 (d, J=6.7 Hz, 1H), 6.79 (dd, J=7.12 Hz, 1.52 Hz, 1H), 4.96 (bs, 1H), 3.96-3.91 (m, 1H), 3.67-3.58 (m, 2H), 3.46 (s, 4H), 3.39-3.31 (m, 1H), 2.84 (d, J=4.84 Hz, 2H), 2.76-2.70 (m, 2H), 2.57-2.50 (m, 2H).

(S)—N-(3-(3,4-dihydroisoquinolin-2(1H)-yl)-2-hydroxypropyl)-6-(1-methyl-2-oxo-1,2-dihydropyridin-4-yl)imidazo[1,2-b]pyridazine-2-carboxamide (Example 48)

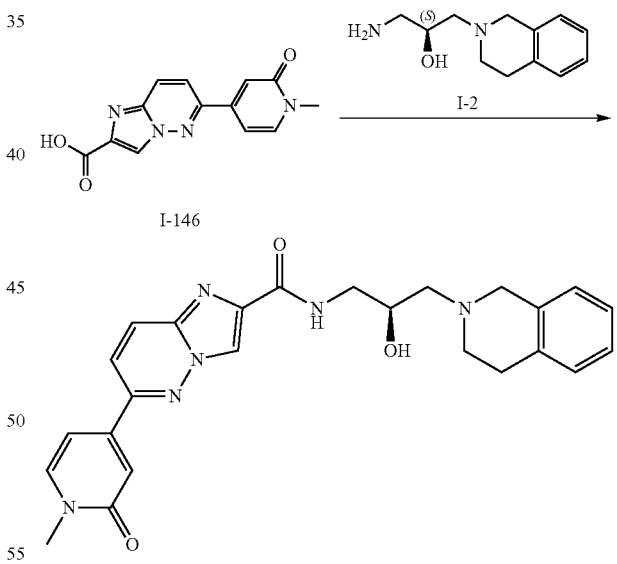

Example 48

LC-MS (ES) m/z: 459.19 [M+H]⁺. ¹H NMR (DMSO-d₆, 400 MHz, ppm)-δ 8.69 (s, 1H), 8.43 (dd, J=10.20 Hz, 1H), 8.15 (d, J=9.68 Hz, 1H), 7.94 (d, J=9.64 Hz, 1H), 7.88 (d, J=7.04 Hz, 1H), 7.15 (s, 1H), 7.09 (s, 3H), 7.02 (d, J=5.80 Hz, 1H), 6.88 (d, J=6.88 Hz, 1H), 4.97 (d, J=4.44 Hz, 1H), 3.94 (d, J=5.52 Hz, 1H), 3.67-3.62 (m, 2H), 3.49 (s, 4H), 3.36-3.28 (m, 1H), 2.84 (d, J=4.88 Hz, 2H), 2.79-2.69 (m, 2H), 2.54-2.5 (m, 2H).

(S)-6-(1-acetylpiperidin-4-yl)-N-(3-(3,4-dihydroiso-quinolin-2(1H)-yl)-2-hydroxypropyl)imidazo[1,2-b]pyridazine-2-carboxamide (Example 49)

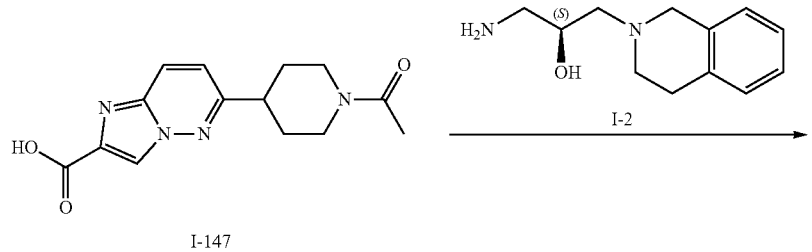

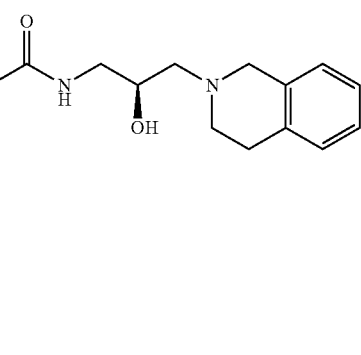

Example 49

LC-MS (ES) m/z: 477.26 [M+H]+ 1H NMR (DMSO-d6, 400 MHz, ppm)-δ 8.50 (s, 1H), 8.34 (t, J=5.56 Hz, 1H), 7.98 (d, J=9.56 Hz, 1H), 7.36 (d, J=9.52 Hz, 1H), 7.09-7.01 (m, 4H), 4.96 (bs, 1H), 4.52 (d, J=12.88 Hz, 1H), 3.95-3.92 (m, 2H), 3.62-3.57 (m, 2H), 3.49-3.44 (m, 1H), 3.31-3.07 m, 3H), 2.83-2.61 (m, 6H), 2.01 (s, 3H), 1.92 (t, J=11.56 Hz, 2H), 1.70-1.64 (m, 1H), 1.52-1.47 (m, 1H), 1.07-1.02 (m, 1H).

(S)—N-(3-(3,4-dihydroisoquinolin-2(1H)-yl)-2-hydroxypropyl)-6-(trifluoromethyl)imidazo[1,2-b]pyridazine-2-carboxamide (Example 50)

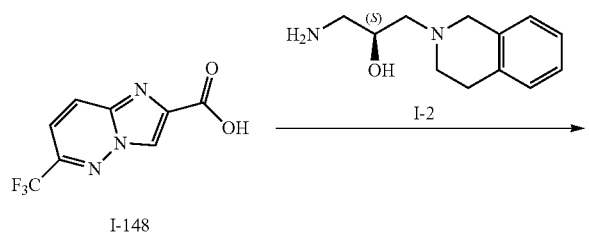

Example 50

LC-MS (ES) m/z=420.14 [M+H]+. 1H NMR (400 MHz, DMSO-d6) δ 9.83 (bs, 1H), 8.96 (s, 1H), 8.74 (d, J=4.2 Hz, 1H), 8.5 (d, J=9.5 Hz, 1H), 7.8 (d, J=9.5 Hz, 1H), 7.28-7.19 (m, 4H), 5.93 (bs, 1H), 4.6-4.52 (m, 1H), 4.41-4.35 (m, 1H), 4.25 (bs, 1H), 3.75-3.69 (m, 1H), 3.33 (bs, 2H), 3.24-3.21 (m, 2H), 3.06-2.98 (m, 2H).

(S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 51)

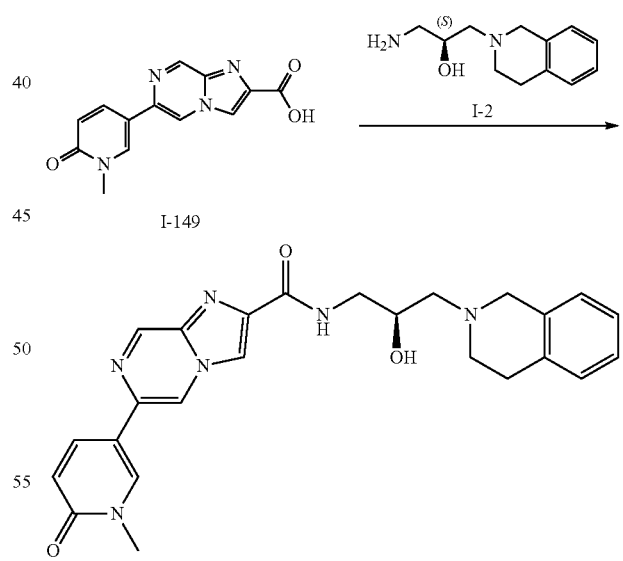

Example 51

LC-MS (ES) m/z: 459.23 [M+H]+ 1H NMR (DMSO-d6, 400 MHz, ppm) δ 8.99 (s, 1H), 8.51 (bs, 1H), 8.43 (s, 1H), 8.39 (s, 1H), 8.01-7.98 (dd, J=9.48 Hz, 2.04 Hz, 1H), 7.10-7.07 (m, 3H), 7.01 (d, J=6.76 Hz, 1H), 6.55 (d, J=9.48 Hz, 1H), 4.98 (bs, 1H), 3.93 (bs, 1H), 3.67-3.62 (m, 2H), 3.58 (s, 3H), 3.48-3.44 (m, 1H), 3.37-3.32 (m, 1H), 2.85-2.67 (m, 4H), 2.55-2.49 (m, 2H).

(S)-6-(1-acetylpiperidin-4-yl)-N-(3-(3,4-dihydroiso-quinolin-2(1H)-yl)-2-hydroxypropyl)imidazo[1,2-a]pyrazine-2-carboxamide (Example 52)

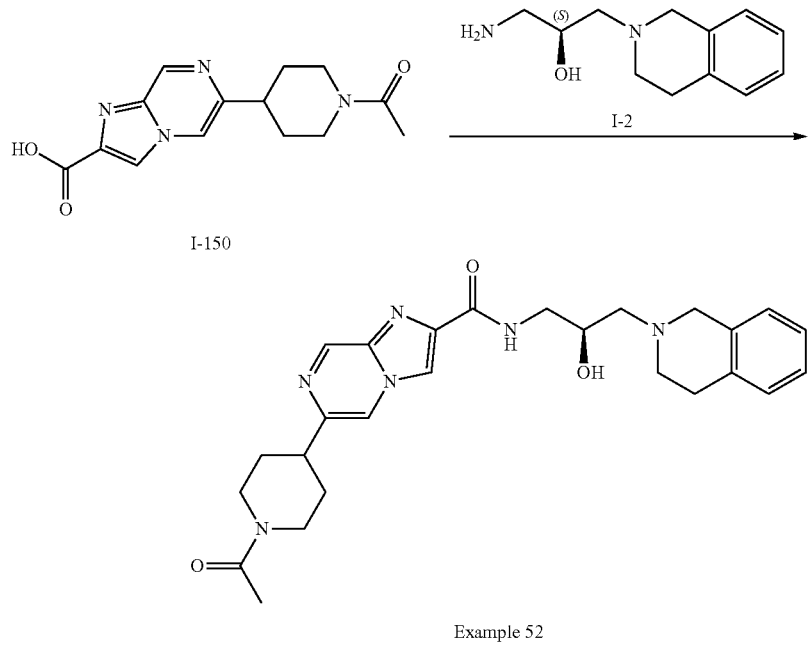

Example 52

LC-MS (ES) m/z: 477.32 [M+H]$^+$ $^1$H NMR (DMSO-d$_6$, 400 MHz, ppm) δ 9.11 (s, 1H), 8.66 (bs, 1H), 8.47 (d, J=4.64 Hz, 2H), 7.26-7.18 (m, 4H), 5.90 (bs, 1H), 4.59-4.38 (m, 2H), 4.23 (bs, 1H), 3.95-3.92 (m, 1H), 3.75-3.68 (m, 1H), 3.34-2.92 (m, 8H), 2.66-2.62 (m, 1H), 2.03 (s, 3H), 1.96-1.89 (m, 2H), 1.69-1.61 (m, 1H), 1.61-1.49 (m, 1H).

(S)—N-(3-(3,4-dihydroisoquinolin-2(1H)-yl)-2-hydroxypropyl)-6-(trifluoromethyl)imidazo[1,2-a]pyrazine-2-carboxamide (Example 53)

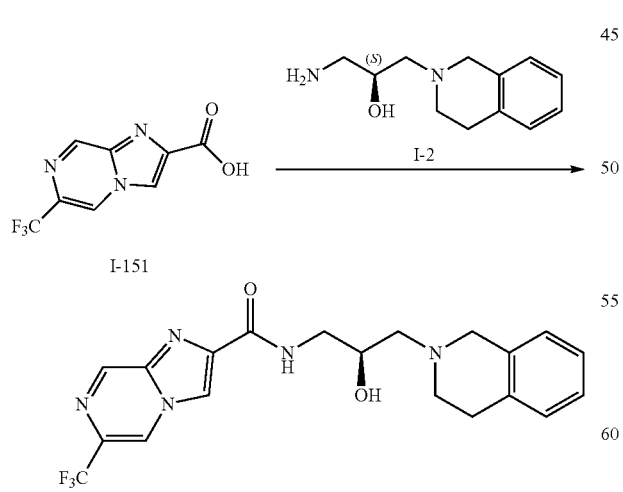

Example 53

LC-MS (ES) m/z=420.2 [M+H]$^+$. 1H NMR (400 MHz, DMSO-d$_6$) δ 9.32 (s, 1H), 9.1 (s, 1H), 8.61 (bs, 1H), 8.56 (s, 1H), 7.1-7.0 (m, 4H), 4.97 (bs, 1H), 3.94 (bs, 1H), 3.63 (bs, 2H), 3.5-3.35 (m, 2H), 2.84 (bs, 2H), 2.76-2.63 (m, 2H), 2.54 (bs, 1H).

(S)—N-(3-(3,4-dihydroisoquinolin-2(1H)-yl)-2-hydroxypropyl)-3-methyl-6-(trifluoromethyl)imidazo[1,2-b]pyridazine-2-carboxamide (Example 54)

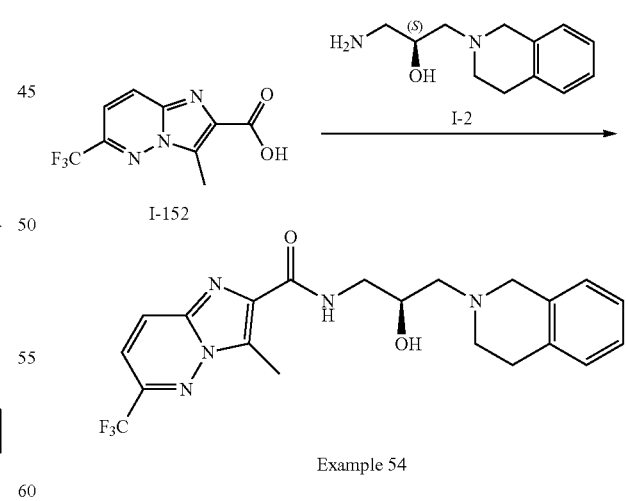

Example 54

LC-MS (ES) m/z: 434.21 [M–H]$^+$ $^1$H NMR (DMSO-d$_6$, 400 MHz, ppm)-δ 8.48 (t, J=5.6 Hz, 1H), 8.29 (d, J=9.52 Hz, 1H), 7.71 (d, J=9.52 Hz, 1H), 7.08-6.99 (m, 4H), 4.97 (d, J=4.64 Hz, 1H), 3.92 (t, J=5.48 Hz, 1H), 3.62 (d, J=2.32 Hz, 2H), 3.50-3.45 (m, 1H), 3.36 (t, J=5.96 Hz, 1H), 2.84-2.67 (m, 7H), 2.58-2.49 (m, 2H).

(S)—N-(3-(3,4-dihydroisoquinolin-2(1H)-yl)-2-hydroxypropyl)-3,6-dimethylimidazo[1,2-a]pyrazine-2-carboxamide (Example 55)

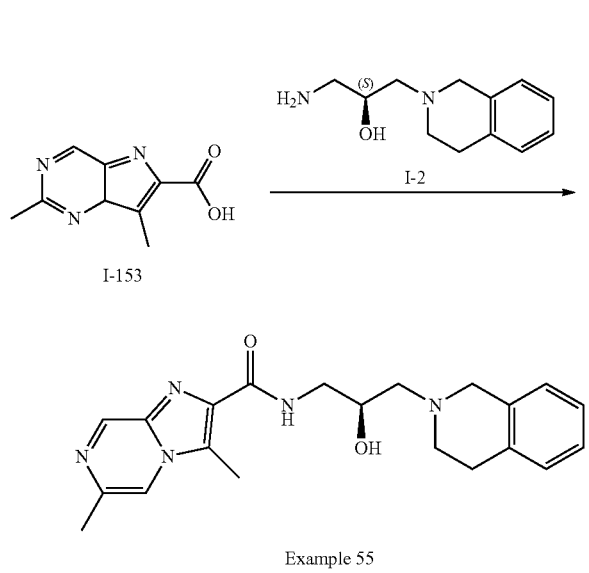

Example 55

LC-MS (ES) m/z: 380.25 [M+H]$^+$. $^1$H NMR (DMSO-d$_6$, 400 MHz, ppm)-δ 8.83 (s, 1H), 8.43 (dd, J=5.44 Hz, 1H), 8.26 (s, 1H), 7.05-7.01 (m, 3H), 7.01 (d, J=6.68 Hz, 1H), 4.96 (d, J=4.68 Hz, 1H), 3.93-3.89 (m, 1H), 3.66-3.58 (m, 2H), 3.48-3.42 (m, 1H), 3.35-3.21 (m, 1H), δ 2.83 (d, J=5.04 Hz, 2H), 2.78-2.66 (m, 5H), 2.61-2.45 (m, 5H).

(S)—N-(3-(3,4-dihydroisoquinolin-2(1H)-yl)-2-hydroxypropyl)-6-methylimidazo[1,2-b]pyridazine-2-carboxamide (Example 56)

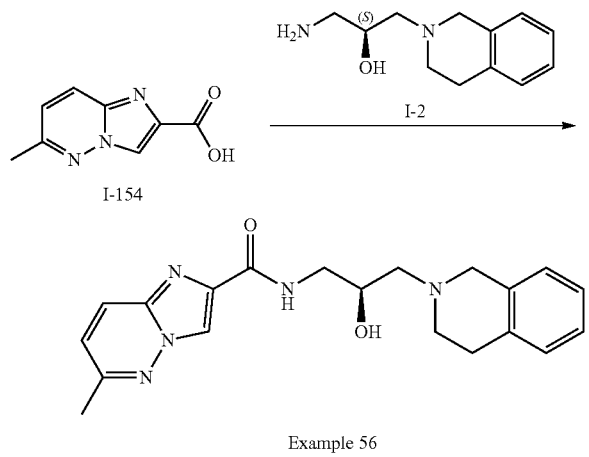

Example 56

LC-MS (ES) m/z=366.22 [M+H]$^+$. 1H NMR (400 MHz, DMSO-d6) δ 8.49 (s, 1H), 8.34 (t, J=6.4 Hz, 1H), 7.94 (d, J=9.3 Hz, 1H), 7.23 (d, J=9.4 Hz, 1H), 7.1 (bs, 3H), 7.03 (bs, 1H), 4.97 (bs, 1H), 3.93 (bs, 1H), 3.64 (bs, 2H), 3.49-3.45 (m, 1H), 2.84 (bs, 4H), 2.72 (bs, 2H), 2.53 (s, 3H).

(S)—N-(3-(3,4-dihydroisoquinolin-2(1H)-yl)-2-hydroxypropyl)-6-(trifluoromethyl)imidazo[1,2-a]pyrazine-2-carboxamide (Example 57)

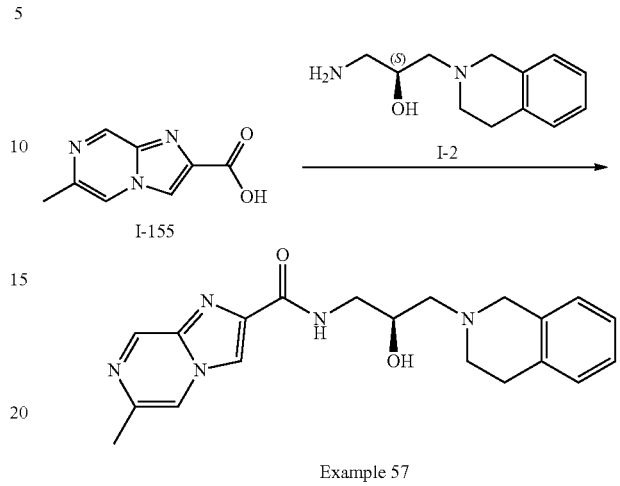

Example 57

LC-MS (ES) m/z=366.19 [M+H]$^+$. 1H NMR (400 MHz, DMSO-d$_6$) δ 8.91 (s, 1H), 8.47 (bs, 1H), 8.41 (s, 1H), 8.4 (s, 1H), 7.11-7.01 (m, 4H), 5.0 (bs, 1H), 3.94 (bs, 1H), 3.67 (bs, 2H), 3.48-3.42 (m, 1H), 3.37-3.34 (m, 1H), 2.85 (bs, 4H), 2.56 (bs, 2H), 2.42 (s, 3H).

(S)-6-(3,3-difluoroazetidin-1-yl)-N-(3-(3,4-dihydroisoquinolin-2(1H)-yl)-2-hydroxypropyl)imidazo[1,2-a]pyrazine-2-carboxamide (Example 58)

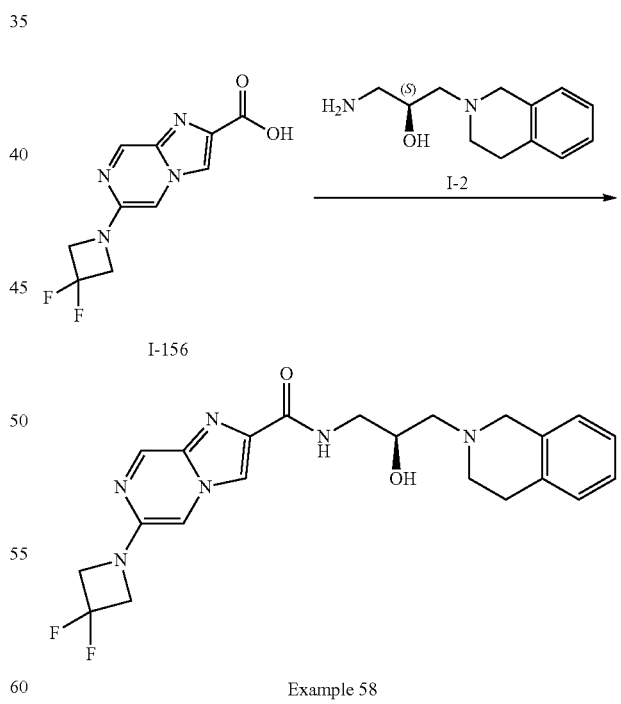

Example 58

LC-MS (ES) m/z: 443.16 [M+H]$^+$. $^1$H NMR (DMSO-d$_6$, 400 MHz, ppm) δ 8.78 (s, 1H), 8.41 (s, 1H), 8.32 (s, 1H), 7.88 (s, 1H), 7.10-7.00 (m, 5H), 4.96 (d, J=4.16 Hz, 1H), 4.34 (t, J=24.6 Hz, 12.32 Hz, 4H), 3.91 (d, J=5.28 Hz, 1H), 3.66-3.62 (m, 2H), 3.48-3.28 (m, 2H), 2.84-2.49 (m, 6H).

(S)-6-(3,3-difluoroazetidin-1-yl)-N-(3-(3,4-dihydroisoquinolin-2(1H)-yl)-2-hydroxypropyl)imidazo[1,2-a]pyridine-2-carboxamide (Example 59)

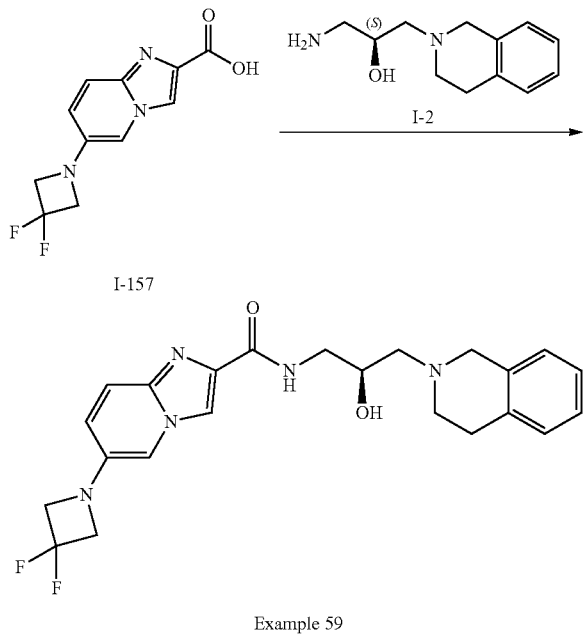

Example 59

LC-MS (ES) m/z: 442.23 [M+H]+. 1H NMR (DMSO-d6, 400 MHz, ppm) δ 8.20 (dd, J=10.96 Hz, 5.56 Hz, 1H), 8.15 (s, 1H), 7.85 (s, 1H), 7.43 (d, J=9.64 Hz, 1H), 7.10-7.08 (m, 4H), 7.02 (d, J=4.56 Hz, 1H), 6.97-6.95 (dd, J=9.72 Hz, 1.96 Hz, 1H), 4.95 (d, J=4.12 Hz, 1H), 4.28 (t, J=24.28 Hz, 12.16 Hz, 4H), 3.90 (d, J=5.64 Hz, 1H), 3.66-3.62 (m, 2H), 3.48-3.44 (m, 1H), 3.31-3.26 (m, 1H), 2.83-2.69 (m, 4H), 2.49-2.43 (m, 2H).

(S)—N-(3-(3,4-dihydroisoquinolin-2(1H)-yl)-2-hydroxypropyl)-5-(trifluoromethyl)pyrazolo[1,5-a]pyrimidine-2-carboxamide (Example 60)

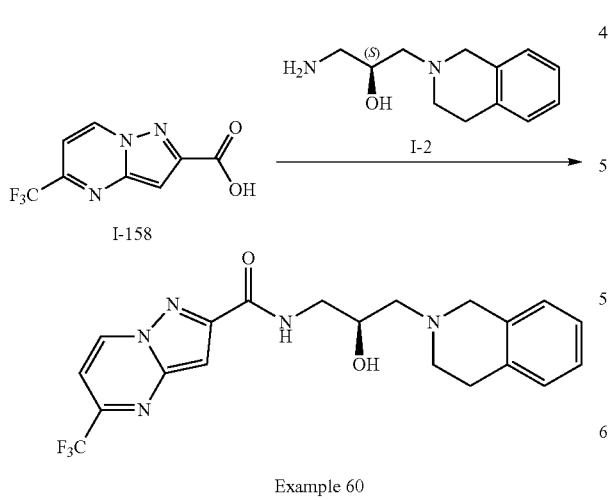

Example 60

LC-MS (ES) m/z: 420.20 [M+H]+ 1H NMR (DMSO-d6, 400 MHz, ppm) δ 9.24 (d, J=7.36 Hz, 1H), 8.58 (dd, J=10.76 Hz, 5.48 Hz, 1H), 7.59 (d, J=7.32 Hz, 1H), 7.34 (s, 1H), 7.08-6.99 (m, 4H), 4.95 (d, J=4.68 Hz, 1H), 3.97-3.93 (m, 1H), 3.62 (d, J=6.16 HZ, 2H), 3.57-3.48 (m, 1H), 3.39-3.34 (m, 1H), 2.82-2.78 (m, 2H), 2.77-2.67 (m, 2H), 2.59-2.32 (m, 2H).

(S)—N-(3-(3,4-dihydroisoquinolin-2(1H)-yl)-2-hydroxypropyl)-6-(3-hydroxyoxetan-3-yl)imidazo[1,2-a]pyridine-2-carboxamide (Example 61)

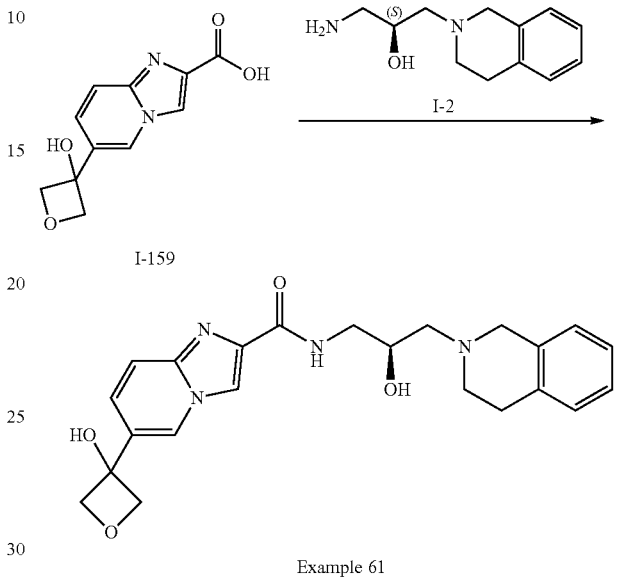

Example 61

LC-MS (ES) m/z: 423.24 [M+H]+ 1H NMR (DMSO-d6, 400 MHz, ppm) δ 8.70 (s, 1H), 8.37 (s, 1H), 8.26 (bs, 1H), 7.57 (d, J=3.56 Hz, 2H), 7.10-7.01 (m, 4H), 4.96 (bs, 1H), 4.79 (d, J=6.84 Hz, 2H), 4.72 (d, J=6.56 Hz, 2H), 3.92 (d, J=4.20 Hz, 1H), 3.62 (bs, 2H), 3.49-3.45 (m, 1H), 2.84 (bs, 2H), 2.79-2.66 (m, 2H).

(S)—N-(3-(3,4-dihydroisoquinolin-2(1H)-yl)-2-hydroxypropyl)-5-(1-methyl-1H-pyrazol-4-yl)pyrazolo[1,5-a]pyrimidine-2-carboxamide (Example 62)

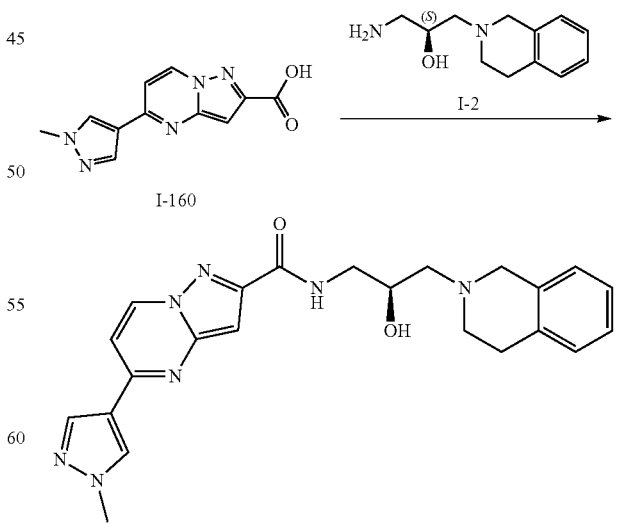

Example 62

LC-MS (ES) m/z: 432.25 [M+H]+ 1H NMR (DMSO-d6, 400 MHz, ppm) δ 8.82 (d, J=7.28 Hz, 1H), 8.53 (s, 1H), 8.38

(bs, 1H), 8.16 (s, 1H), 7.42 (d, J=7.36 Hz, 1H), 7.10-7.01 (m, 4H), 6.85 (s, 1H), 4.94 (bs, 1H), 3.91 (s, 4H), 3.63 (bs, 2H), 3.48-3.43 (m, 1H), 3.37-3.28 (m, 1H), 2.83-2.67 (m, 4H), 2.54-2.50 (m, 2H).

(S)—N-(3-(3,4-dihydroisoquinolin-2(1H)-yl)-2-hydroxypropyl)-5-(1-methyl-2-oxo-1,2-dihydropyridin-4-yl)pyrazolo[1,5-a]pyrimidine-2-carboxamide (Example 63)

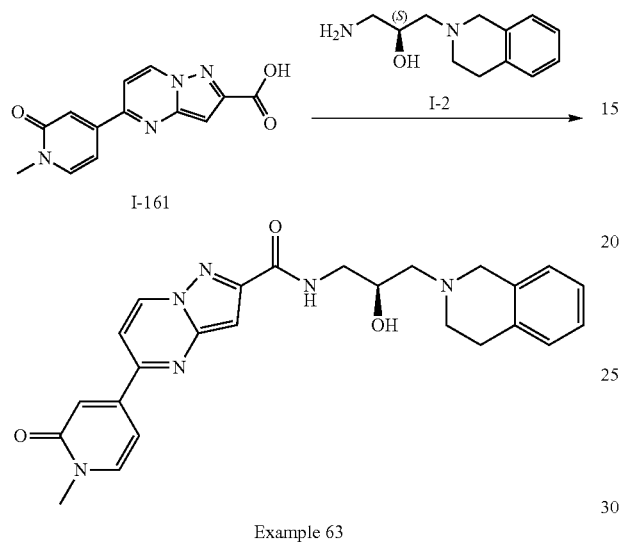

Example 63

LC-MS (ES) m/z: 459.29 [M+H]+ 1H NMR (DMSO-d6, 400 MHz, ppm) δ 9.01 (d, J=7.32 Hz, 1H), 8.49 (dd, J=9.76 Hz, 1H), 7.87-7.78 (dd, J=6.88 Hz, 7.28 Hz, 2H), 7.24-7.00 (m, 7H), 4.95 (s, 1H), 3.95 (d, J=5.20 HZ, 1H), 3.62-3.59 (m, 2H), 3.49-3.31 (m, 5H), 2.76-2.72 (m, 2H), 2.67-2.58 (m, 2H), 2.58-2.50 (m, 2H).

(S)—N-(3-(3,4-dihydroisoquinolin-2(1H)-yl)-2-hydroxypropyl)-3-methyl-6-(1-methyl-1H-pyrazol-4-yl)imidazo[1,2-a]pyrazine-2-carboxamide (Example 64)

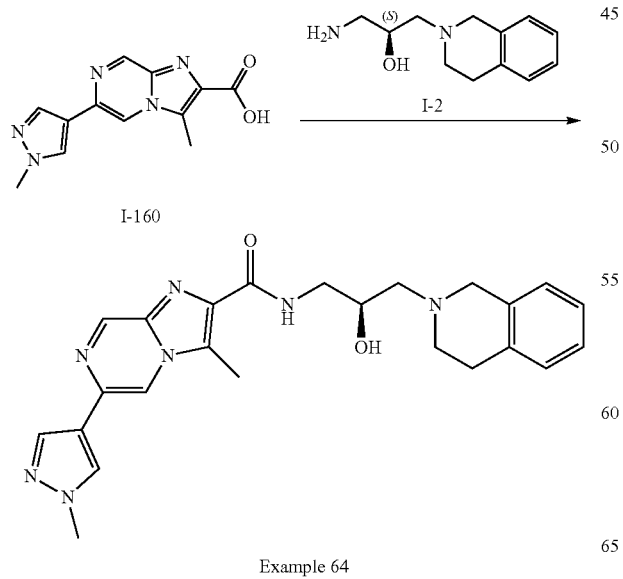

Example 64

LC-MS (ES) m/z=446.34 [M+H]+. 1H NMR (400 MHz, DMSO-d6) δ 8.91 (s, 1H), 8.66 (s, 1H), 8.45 (t, J=8.6 Hz, 1H), 8.26 (s, 1H), 8.05 (s, 1H), 7.1 (bs, 3H), 7.01 (d, J=8.6 Hz, 1H), 4.98 (bs, 1H), 3.95-3.93 (m, 2H), 3.9 (s, 3H), 3.63 (bs, 2H), 3.47-3.44 (m, 1H), 3.35-3.31 (m, 1H), 2.85 (bs, 2H), 2.79 (bs, 4H), 2.71 (bs, 1H), 2.56 (bs, 1H).

(S)—N-(3-(3,4-dihydroisoquinolin-2(1H)-yl)-2-hydroxypropyl)-3-methyl-6-(1-methyl-2-oxo-1,2-dihydropyridin-4-yl)imidazo[1,2-a]pyrazine-2-carboxamide Example 65

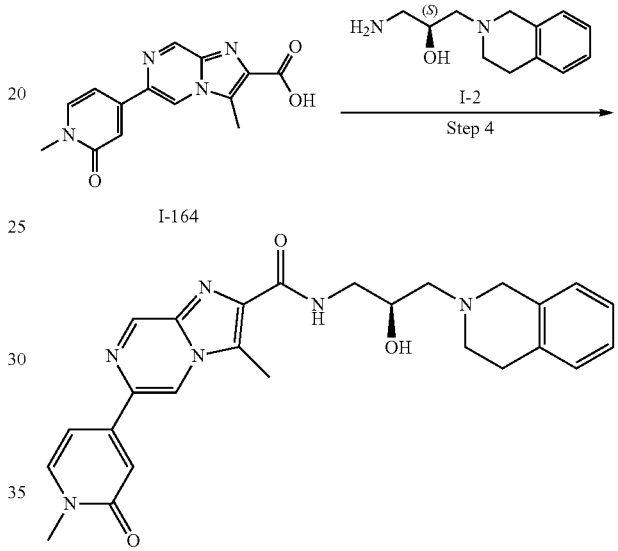

Example 65

LC-MS (ES) m/z=473.38 [M+H]+. 1H NMR (400 MHz, DMSO-d6) δ 9.03 (s, 1H), 9.01 (s, 1H), 8.49 (t, J=5.6 Hz, 1H), 7.83 (d, J=7.2 Hz, 1H), 7.22 (d, J=1.5 Hz, 1H), 7.09-7.05 (m, 4H), 7.01 (d, J=7.0 Hz, 1H), 4.98 (d, J=4.5 Hz, 1H), 3.95-3.91 (m, 1H), 3.67-3.58 (m, 2H), 3.5-3.44 (m, 4H), 3.37-3.35 (m, 1H), 2.84 (bs, 5H), 2.79-2.67 (m, 2H), 2.57-2.53 (m, 2H).

(S)—N-(3-(3,4-dihydroisoquinolin-2(1H)-yl)-2-hydroxypropyl)-3-methyl-6-(1-methyl-6-oxo-1,6-dihydropyridin-3-yl)imidazo[1,2-a]pyrazine-2-carboxamide Example 66

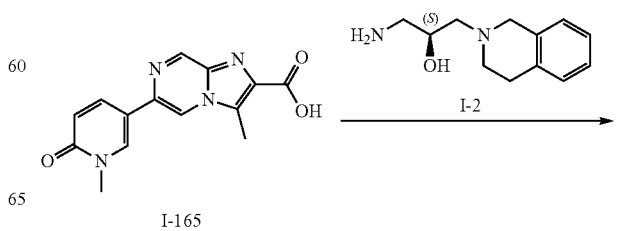

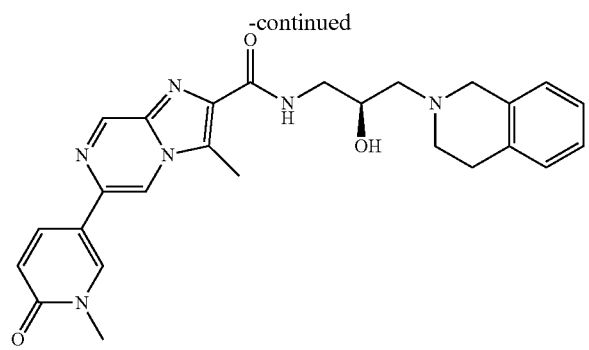

Example 66

LC-MS (ES) m/z=473.35 [M+H]+. 1H NMR (400 MHz, DMSO-d$_6$) δ 8.93 (s, 1H), 8.73 (s, 1H), 8.49-8.45 (m, 2H), 8.2 (dd, J=9.4, 2.4 Hz, 1H), 7.1-7.0 (m, 4H), 6.55 (d, J=9.4 Hz, 1H), 4.98 (d, J=4.6 Hz, 1H), 3.93-3.91 (m, 1H), 3.63 (bs, 2H), 3.55 (s, 3H), 3.49-3.43 (m, 2H), 2.85 (bs, 2H), 2.83 (s, 3H), 2.78-2.67 (m, 2H), 2.55-2.53 (m, 2H).

(S)—N-(3-(3,4-dihydroisoquinolin-2(1H)-yl)-2-hydroxypropyl)-5-methylpyrazolo[1,5-a]pyrimidine-2-carboxamide (Example 67)

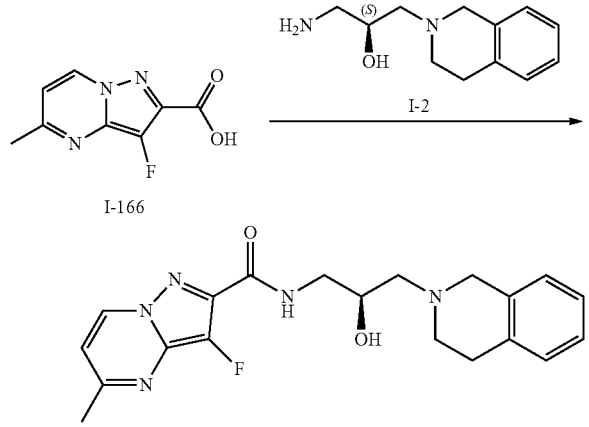

Example 67

LC-MS (ES) m/z: 384.26 [M+H]+. $^1$H NMR (DMSO-d$_6$, 400 MHz, ppm)-δ 8.66 (d, J=7.16 Hz, 1H), 8.34 (d, J=5.52 Hz, 1H), 7.09-7.05 (m, 4H), 7.01-7.00 (d, J=6.20 Hz, 1H), 4.94 (d, J=4.08 Hz, 1H), 3.92 (t, J=11.12 Hz, 5.48 Hz, 1H), 3.67-3.62 (m, 2H), 3.47-3.41 (m, 1H), 3.38-3.31 (m, 1H), 2.82 (d, J=5.16 Hz, 1H), 2.76-2.71 (m, 3H), 2.62 (m, 4H).

(S)—N-(3-(3,4-dihydroisoquinolin-2(1H)-yl)-2-hydroxypropyl)-3-fluoro-5-(trifluoromethyl)pyrazolo[1,5-a]pyrimidine-2-carboxamide (Example 68)

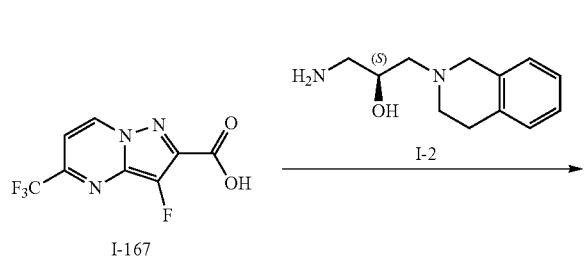

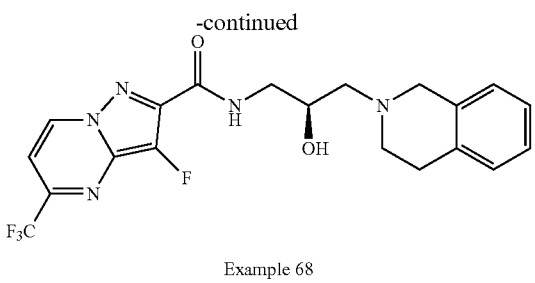

Example 68

LC-MS (ES) m/z: 438.30 [M+H]+ $^1$H NMR (DMSO-d$_6$, 400 MHz, ppm) δ 9.13 (d, J=7.36 Hz, 1H), 8.53 (bs, 1H), 7.60 (d, J=7.44 Hz, 1H), 7.07-6.98 (m, 4H), 4.95 (d, J=4.72 Hz, 1H), 3.97-3.93 (m, 1H), 3.62 (d, J=6.36 HZ, 2H), 3.57-3.43 (m, 1H), 3.40-3.34 (m, 1H), 2.82-2.69 (m, 2H), 2.77-2.67 (m, 4H), 2.59-2.49 (m, 2H).

(S)-6-(azetidin-1-yl)-N-(3-(3,4-dihydroisoquinolin-2 (1H)-yl)-2-hydroxypropyl)imidazo[1,2-a]pyridine-2-carboxamide (Example 69)

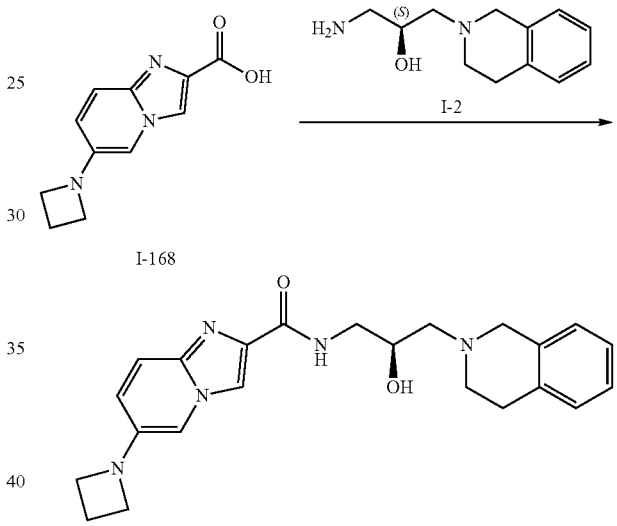

Example 69

LC-MS (ES) m/z: 406.31 [M+H]+. $^1$H NMR (DMSO-d$_6$, 400 MHz, ppm) δ 8.16 (dd, J=11.24 Hz, 1H), 8.12 (s, 1H), 7.62 (s, 1H), 7.36 (d, J=9.60 Hz, 1H), 7.09-7.01 (m, 4H), 6.86-6.83 (dd, J=9.68 Hz, 1.88 Hz, 1H), 4.94 (d, J=4.60 Hz, 1H), 3.88 (t, J=10.80 Hz, 5.20 Hz, 1H), 3.81-3.77 (m, 4H), 3.65-3.61 (m, 2H), 3.48-3.42 (m, 1H), 3.31-3.23 (m, 1H), 2.83-2.65 (m, 4H), 2.56-2.49 (m, 2H), 2.34-2.26 (m, 2H).

N—((S)-3-(3,4-dihydroisoquinolin-2(1H)-yl)-2-hydroxypropyl)-6-(3-fluoropyrrolidin-1-yl)imidazo[1,2-a]pyridine-2-carboxamide (Example 70)

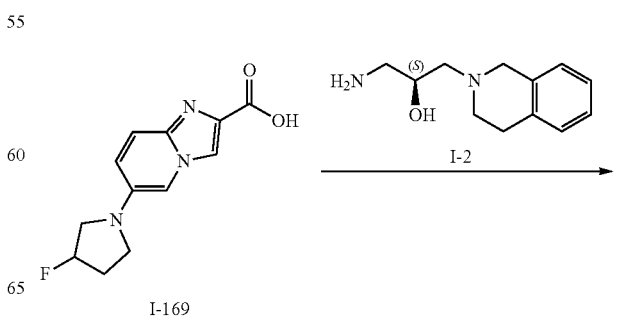

-continued

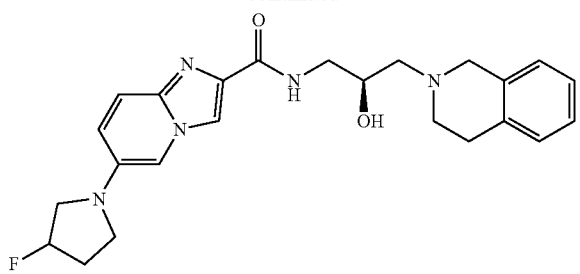

Example 70

LC-MS (ES) m/z: 438.40 [M+H]$^+$. $^1$H NMR (DMSO-d$_6$, 400 MHz, ppm) δ 8.15 (dd, J=10.36 Hz, 1H), 8.13 (s, 1H), 7.73 (s, 1H), 7.39 (d, J=9.76 Hz, 1H), 7.15-7.01 (m, 5H), 5.53-5.39 (m, 1H), 4.95 (d, J=4.56 Hz, 1H), 3.89 (d, J=5.32 Hz, 1H), 3.62-3.55 (m, 3H), 3.49-3.23 (m, 5H), 2.83-2.64 (m, 6H), 2.28 2.17 (m, 2H).

(S)—N-(3-(3,4-dihydroisoquinolin-2(1H)-yl)-2-hydroxypropyl)-6-(4-methylpiperazin-1-yl)imidazo[1,2-a]pyridine-2-carboxamide (Example 71)

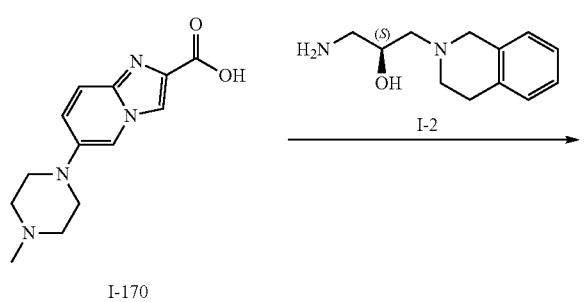

Example 71

LC-MS (ES) m/z: 449.45 [M+H]$^+$. $^1$H NMR (DMSO-d$_6$, 400 MHz, ppm) δ 8.17 (dd, J=12.52 Hz, 2H), 7.98 (s, 1H), 7.38-7.32 (m, 2H), 7.09-7.01 (m, 4H), 4.95 (d, J=4.56 Hz, 1H), 3.89 (d, J=5.68 Hz, 1H), 3.65-3.57 (m, 2H), 3.49-3.43 (m, 1H), 3.31-3.23 (m, 1H), 3.04 (s, 4H), 2.83-2.79 (m, 3H), 2.76-2.64 (m, 3H), 2.49-2.45 (m, 4H), 2.23 (s, 3H).

(S)—N-(3-(3,4-dihydroisoquinolin-2(1H)-yl)-2-hydroxypropyl)-6-morpholinoimidazo[1,2-a]pyridine-2-carboxamide (Example 72)

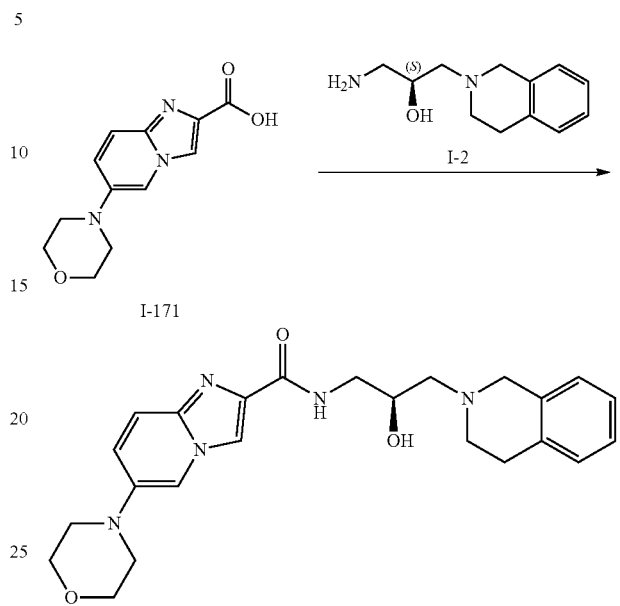

Example 72

LC-MS (ES) m/z: 436.35 [M+H]$^+$. $^1$H NMR (DMSO-d$_6$, 400 MHz, ppm) δ 8.19 (dd, J=8.96 Hz, 2H), 7.40-7.34 (m, 2H), 7.14-7.01 (m, 5H), 4.95 (d, J=4.60 Hz, 1H), 3.89 (t, J=11.0 Hz, 5.40 Hz, 1H), 3.75 (d, J=4.56 Hz, 4H), 3.65-3.57 (m, 2H), 3.49-3.43 (m, 1H), 3.31-3.24 (m, 1H), 3.03 (d, J=4.12 Hz, 4H), 2.83-2.79 (m, 2H), 2.78-2.66 (m, 2H), 2.54-2.44 (m, 2H).

N—((S)-3-(3,4-dihydroisoquinolin-2(1H)-yl)-2-hydroxypropyl)-6-(3-fluoropyrrolidin-1-yl)imidazo[1,2-a]pyrazine-2-carboxamide (Example 73)

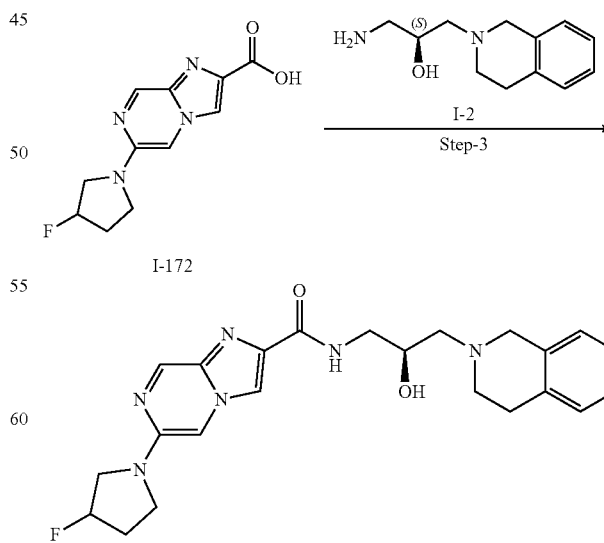

Example 73

LC-MS (ES) m/z: 439.39 [M+H]⁺. ¹H NMR (DMSO-d₆, 400 MHz, ppm) δ 8.76 (s, 1H), 8.35 (dd, J=10.76 Hz, 1H), 8.25 (s, 1H), 7.68 (s, 1H), 7.10-7.00 (m, 4H), 5.52-5.39 (m, 1H), 4.96 (d, J=4.52 Hz, 1H), 3.90 (t, J=10.60 Hz, 3.89 Hz, 2H), 3.69-3.59 (m, 3H), 3.58-3.35 (m, 4H), 2.83 (d, J=5.28 Hz, 2H), 2.78-2.66 (m, 3H), 2.56-2.49 (m, 1H), 2.28-2.23 (m, 2H).

(S)-6-(4-cyanophenyl)-N-(3-(3,4-dihydroisoquinolin-2(1H)-yl)-2-hydroxypropyl)imidazo[1,2-a]pyrazine-2-carboxamide (Example 74)

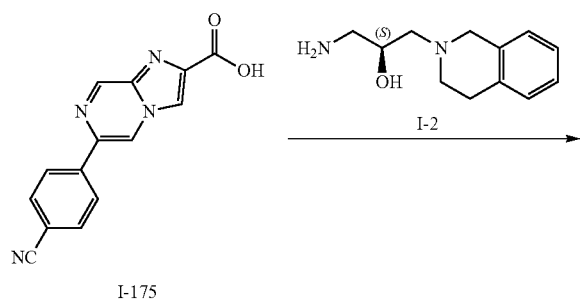

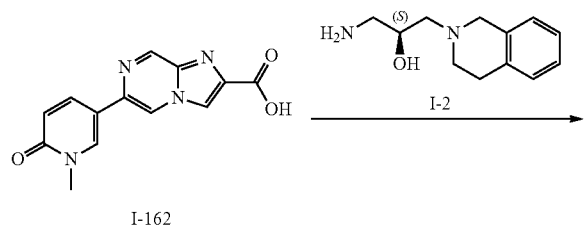

Example 74

LC-MS (ES) m/z: 453.30 [M+H]⁺. ¹H NMR (DMSO-d₆, 400 MHz, ppm) δ 9.37 (s, 1H), 9.12 (s, 1H), 8.55 (dd, J=10.80 Hz, 1H), 8.46 (s, 1H), 8.22 (d, J=8.32 Hz, 2H), 8.00 (d, J=8.32 Hz, 2H), 7.10-7.00 (m, 4H), 4.98 (d, J=4.68 Hz, 1H), 3.95 (d, J=5.80 Hz, 1H), 3.63 (d, J=4.20 Hz, 2H), 3.50-3.48 (m, 1H), 3.46-3.38 (m, 1H), 2.84-2.78 (m, 2H), 2.76-2.66 (m, 2H), 2.55-2.50 (m, 2H).

(S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 75)

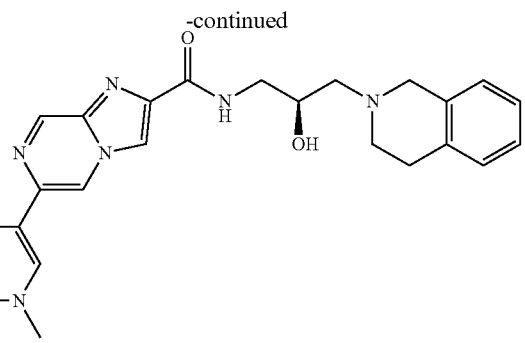

Example 75

LC-MS (ES) m/z: 459.23 [M+H]⁺ ¹H NMR (DMSO-d₆, 400 MHz, ppm) δ 8.99 (s, 1H), 8.51 (bs, 1H), 8.43 (s, 1H), 8.39 (s, 1H), 8.01-7.98 (dd, J=9.48 Hz, 2.04 Hz, 1H), 7.10-7.07 (m, 3H), 7.01 (d, J=6.76 Hz, 1H), 6.55 (d, J=9.48 Hz, 1H), 4.98 (bs, 1H), 3.93 (bs, 1H), 3.67-3.62 (m, 2H), 3.58 (s, 3H), 3.48-3.44 (m, 1H), 3.37-3.32 (m, 1H), 2.85-2.67 (m, 4H), 2.55-2.49 (m, 2H).

N-((2S,3S)-4-(3,4-dihydroisoquinolin-2(1H)-yl)-2,3-dihydroxybutyl)-6-(trifluoromethyl)imidazo[1,2-a]pyridine-2-carboxamide (Example 76)

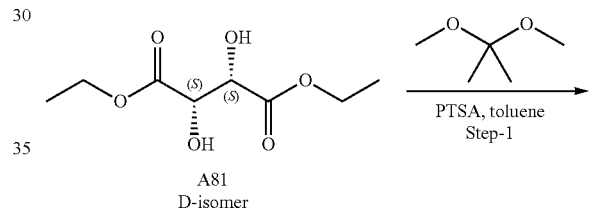

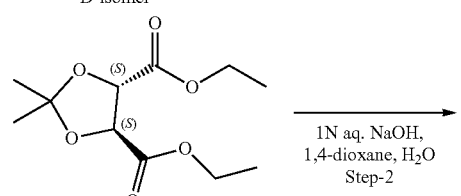

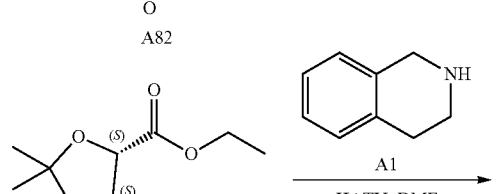

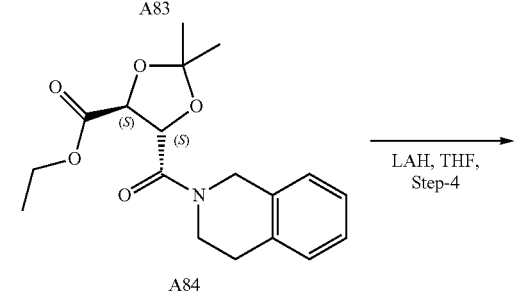

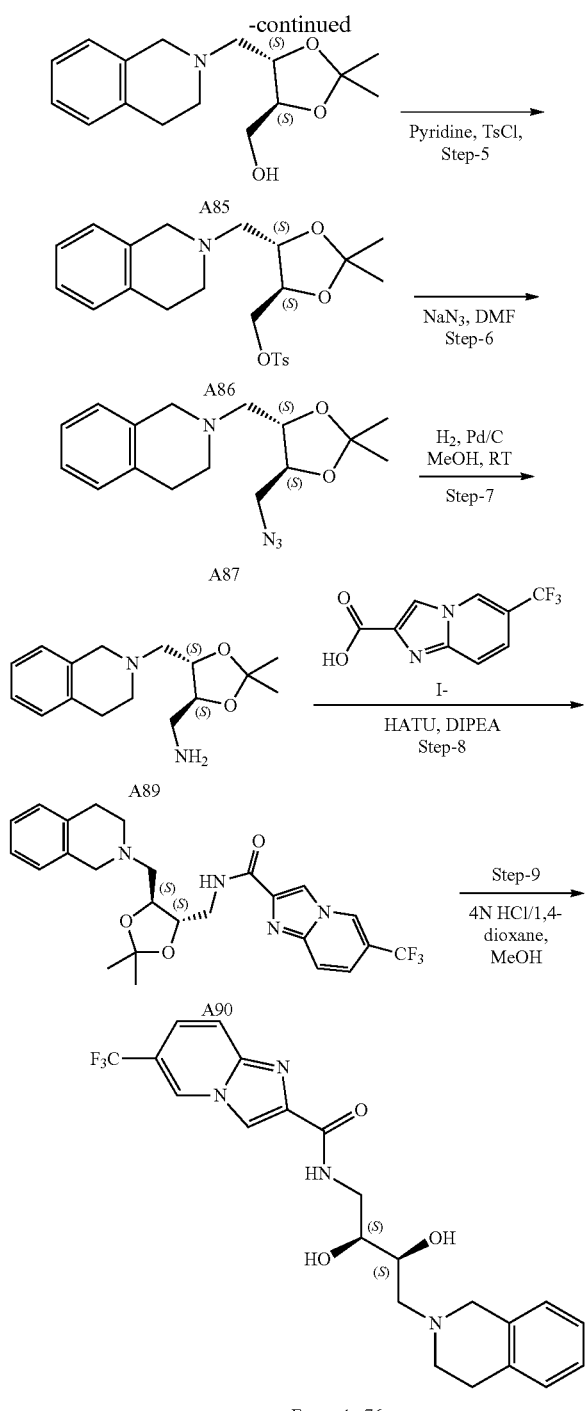

Example-76

Step 1: diethyl (4S,5S)-2,2-dimethyl-1,3-dioxolane-4,5-dicarboxylate (A82)

To the stirred solution of diethyl (2S,3S)-2,3-dihydroxysuccinate (A81, 10.0 g, 48.50 mmol) in toluene was added PTSA (1.84 g, 4.80 mmol), and 2,2-dimethoxypropane (2, 15.4 ml, 63.0 mmol) at room temperature. The reaction mixture was heated at 100° C. for 1 h. The reaction mixture was cooled to room temperature and diluted with EtOAc. The organic layer was washed with sat. NaHCO₃ solution followed by water and brine solution. The organic layer was dried over anhydrous Na₂SO₄, and filtered. The organic layer was concentrated to get diethyl (4S,5S)-2,2-dimethyl-1,3-dioxolane-4,5-dicarboxylate A82 as pale brown oil. Yield: 9.0 g, (75%). LC-MS (ES) m/z: 247.26 [M+H]⁺. ¹H NMR (400 MHz, DMSO-d6) δ 4.87-4.82 (m, 2H), 4.11-4.08 (q, 2H), 1.38 (s, 6H), 1.1 (t, 3H).

Step 2: (4S,5S)-5-(ethoxycarbonyl)-2,2-dimethyl-1,3-dioxolane-4-carboxylic acid (A83)

To the stirred solution of diethyl (4S,5S)-2,2-dimethyl-1,3-dioxolane-4,5-dicarboxylate (A82, 9.0 g, 36.50 mmol), in 1,4-dioxane (60 mL) and water (60 mL) was added dropwise aq. 1N NaOH solution (55.0 mL, 54.80 mmol) at 0° C. The reaction mixture was allowed to stir at room temperature for 4 h. After completion of reaction, reaction mixture was washed with DCM. The aqueous layer was acidified using conc.HCl to pH 2-3. The aqueous layer was extracted with DCM. The organic layer was dried over anhydrous Na₂SO₄, filtered. and concentrated to get (4S,5S)-5-(ethoxycarbonyl)-2,2-dimethyl-1,3-dioxolane-4-carboxylic acid A83 as a pale yellow oil. Yield: 6.0 g, (75%). LC-MS (ES) m/z: 217.10 [M+H]⁺. ¹H NMR (400 MHz, DMSO-d6) δ 13.31 (bs, 1H), 4.71-4.69 (m 2H), 4.19-4.14 (q, 2H), 1.22 (s, 6H), 1.21 (t, 3H).

Step 3: ethyl (4S,5S)-2,2-dimethyl-5-(1,2,3,4-tetrahydroisoquinoline-2-carbonyl)-1,3-dioxolane-4-carboxylate (A84)

To the stirred solution of (4S,5S)-5-(ethoxycarbonyl)-2,2-dimethyl-1,3-dioxolane-4-carboxylic acid (A83, 6.0 g, 27.40 mmol) in DCM (60 mL) at room temperature was added DMAP (0.33 g, 2.70 mmol), and T₃P (24.70 mL, 82.4 mmol). The reaction mixture was stirred for 20 min at room temperature. 1,2,3,4-tetrahydroisoquinoline (A1, 4.4 g, 32.90 mmol) was added at room temperature. Reaction mixture was stirred at room temperature for 16 h. After completion of reaction, diluted with DCM and washed with water and brine solution. The organic layer was dried over anhydrous Na₂SO₄, filtered and concentrated. The crude was purified by combiflash with 0-30% EA/hexanes as eluent. The fractions were concentrated to get ethyl (4S,5S)-2,2-dimethyl-5-(1,2,3,4-tetrahydroisoquinoline-2-carbonyl)-1,3-dioxolane-4-carboxylate A84 as pale yellow oil. Yield: 2.40 g, (26%). LCMS (ESI): m/z: 334.16 [M+H]⁺.

Step 4: ((4S,5S)-5-((3,4-dihydroisoquinolin-2(1H)-yl)methyl)-2,2-dimethyl-1,3-dioxolan-4-yl)methanol (A85)

To the stirred solution of ethyl (4S,5S)-2,2-dimethyl-5-(1,2,3,4-tetrahydroisoquinoline-2-carbonyl)-1,3-dioxolane-4-carboxylate (A84, 2.30 g, 6.80 mmol) in dry THF at 0° C. was added drop wise LAH (5.10 ml, 10.30 mmol). The reaction mixture was heated to 60° C. for 1 h. After completion of reaction, was cooled to room temperature and quenched with ice-cold aq. Rochelle salt solution. The quenched mixture was filtered over celite bed and washed with EtOAc. The organic layer was washed with water, followed by. brine solution. The organic layer was dried over anhydrous Na₂SO₄, filtered and concentrated to get the ((4S,5S)-5-((3,4-dihydroisoquinolin-2(1H)-yl)methyl)-2,2-dimethyl-1,3-dioxolan-4-yl)methanol A85 as pale yellow oil. Yield: 1.3 g, (72%). LCMS (ESI): m/z, 278.19 [M+H]⁺.

Step 5: ((4S,5S)-5-((3,4-dihydroisoquinolin-2(1H)-yl)methyl)-2,2-dimethyl-1,3-dioxolan-4-yl)methyl 4-methylbenzenesulfonate (A86)

To the stirred solution of ((4S,5S)-5-((3,4-dihydroisoquinolin-2(1H)-yl)methyl)-2,2-dimethyl-1,3-dioxolan-4-yl)methanol (A85, 1.3 g, 4.60 mmol) in THF and pyridine at 0° C. was added TsCl (1.30 g, 7.0 mmol). Reaction mixture was stirred at room temperature for 16 h. After completion of reaction was evaporated to get crude. The residue was diluted with EtOAc washed subsequently with cold aqueous 1M HCl solution, saturated aq. NaHCO$_3$ solution and brine solution. The organic layer was dried over anhydrous Na$_2$SO$_4$, filtered and concentrated to get crude. The crude was purified by combiflash over silica gel with gradient using 20-30% EA/hexanes to afford the ((4S,5S)-5-((3,4-dihydroisoquinolin-2(1H)-yl)methyl)-2,2-dimethyl-1,3-dioxolan-4-yl)methanol A86 as a pale yellow oil which changes to a solid at low temperatures. Yield: 0.9 g, (45%). LCMS (ESI): m/z 432.08 [M+H]$^+$.

Step 6: 2-(((4S,5S)-5-(azidomethyl)-2,2-dimethyl-1,3-dioxolan-4-yl)methyl)-1,2,3,4-tetrahydroisoquinoline (A87)

To the stirred solution of 2-(((4S,5S)-5-(azidomethyl)-2,2-dimethyl-1,3-dioxolan-4-yl)methyl)-1,2,3,4-tetrahydroisoquinoline (A86, 0.9 g, 2.0 mmol) in DMF was added NaN$_3$ (0.20 g 3.10 mmol) at room temperature. Reaction was stirred at 70° C. for 16 h. After completion of reaction, reaction mass was diluted with EtOAc washed subsequently with water and brine solution. The organic layer was dried over anhydrous Na$_2$SO$_4$, filtered and concentrated to get crude. The crude was purified by combiflash over silica gel with gradient elution 20-30% EA/hexanes to afford 2-(((4S,5S)-5-(azidomethyl)-2,2-dimethyl-1,3-dioxolan-4-yl)methyl)-1,2,3,4-tetrahydroisoquinoline A87 as a pale yellow oil. Yield: 0.40 g, (66%). LCMS (ESI): m/z, 304.0[M+H]$^+$.

Step 7: ((4S,5S)-5-((3,4-dihydroisoquinolin-2(1H)-yl)methyl)-2,2-dimethyl-1,3-dioxolan-4-yl)methanamine (A88)

To a solution of ((4S,5S)-5-((3,4-dihydroisoquinolin-2(1H)-yl)methyl)-2,2-dimethyl-1,3-dioxolan-4-yl)methyl 4-methylbenzenesulfonate (A87, 0.50 g, 1.60 mmol) in methanol was added Pd/C (50% moisture), and reaction mixture was maintained under hydrogen atmosphere (30 psi) for 1 h. After completion of reaction, reaction mass was filtered through celite and wash with methanol. The filtrate was concentrated to get ((4S,5S)-5-((3,4-dihydroisoquinolin-2(1H)-yl)methyl)-2,2-dimethyl-1,3-dioxolan-4-yl)methanamine A88 as pale yellow oil. Yield: 0.40 g, (90%). LCMS (ESI): m/z 277.06 [M+H]$^+$.

Step 8: N-(((4S,5S)-5-((3,4-dihydroisoquinolin-2(1H)-yl)methyl)-2,2-dimethyl-1,3-dioxolan-4-yl)methyl)-6-(trifluoromethyl)imidazo[1,2-a]pyridine-2-carboxamide (A89)

To a stirred solution of 6-(trifluoromethyl)imidazo[1,2-a]pyridine-2-carboxylic acid (I-102, 0.10 g, 0.46 mmol) in DMF (2.0 mL) was added ((4S,5S)-5-((3,4-dihydroisoquinolin-2(1H)-yl)methyl)-2,2-dimethyl-1,3-dioxolan-4-yl)methanamine (A88, 0.13 g, 0.46 mmol) at 0° C. was added HATU (0.26 g, 0.70 mmol), and DIPEA (0.25 mL, 1.40 mmol). Reaction mixture was stirred at room temperature for 16 h. After completion of reaction diluted with ethyl acetate and washed with water and brine solution. The organic layer was dried over anhydrous Na$_2$SO$_4$, filtered, and concentrated to afford the N-(((4S,5S)-5-((3,4-dihydroisoquinolin-2(1H)-yl)methyl)-2,2-dimethyl-1,3-dioxolan-4-yl)methyl)-6-(trifluoromethyl)imidazo[1,2-a]pyridine-2-carboxamide A89 as a pale yellow oil. Yield: 0.2 g, (90%). LCMS (ESI): m/z 489.18 [M+H]$^+$.

Step-9: N-((2S,3S)-4-(3,4-dihydroisoquinolin-2(1H)-yl)-2,3-dihydroxybutyl)-6-(trifluoromethyl)imidazo[1,2-a]pyridine-2-carboxamide (Example 76)

To the stirred solution of N-(((4S,5S)-5-((3,4-dihydroisoquinolin-2(1H)-yl)methyl)-2,2-dimethyl-1,3-dioxolan-4-yl)methyl)-6-(trifluoromethyl)imidazo[1,2-a]pyridine-2-carboxamide (12, 0.2 g, 0.40 mmol) in MeOH (3 mL) and 1,4-dioxane (2.0 mL) was added dropwise 4N HCl at 0° C. The reaction mixture was stirred at room temperature for 16 h. After completion of reaction concentrated to remove the solvent and basified using aq. ammonia solution. and extracted with 5% MeOH/DCM. The organic layer was dried over anhydrous Na$_2$SO$_4$, filtered, and concentrated and taturate with ether and pentane and dried to afford N-((2S,3S)-4-(3,4-dihydroisoquinolin-2(1H)-yl)-2,3-dihydroxybutyl)-6-(trifluoromethyl)imidazo[1,2-a]pyridine-2-carboxamide as a beige solid Yield: 0.120 g (65%). LCMS (ESI): m/z 449.2, [M+H]$^+$. $^1$H NMR (400 MHz, DMSO-d6) δ 9.27 (s, 1H), 8.45 (s, 1H), 8.29 (s, 1H), 7.79 (d, J=9.36 Hz, 1H), 7.57 (d, J=9.32 Hz, 1H), 7.08-7.01 (m, 4H), 4.87 (bs 1H), 4.60 (bs, 1H), 3.72-3.65 (m, 4H), 3.52 (t, J=13.0 Hz, 1H), 2.79-2.49 (m, 7H).

N-((2R,3R)-4-(3,4-dihydroisoquinolin-2(1H)-yl)-2,3-dihydroxybutyl)-6-(trifluoromethyl)imidazo[1,2-a]pyridine-2-carboxamide (Example 77)

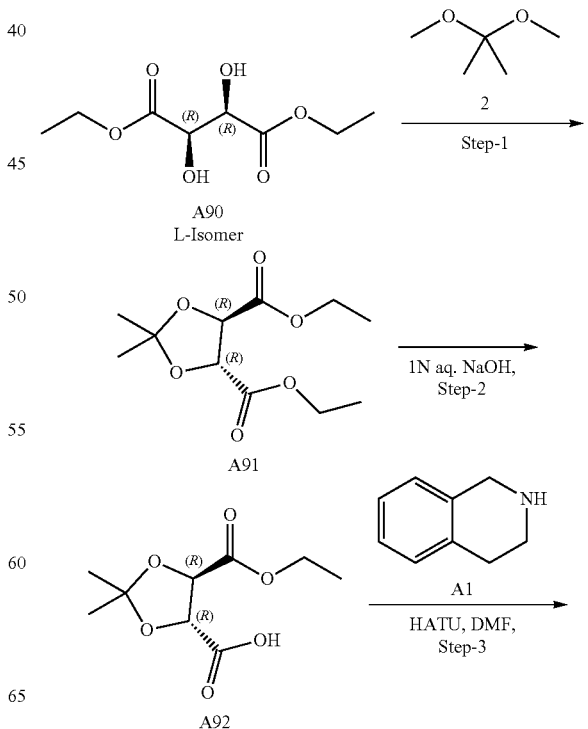

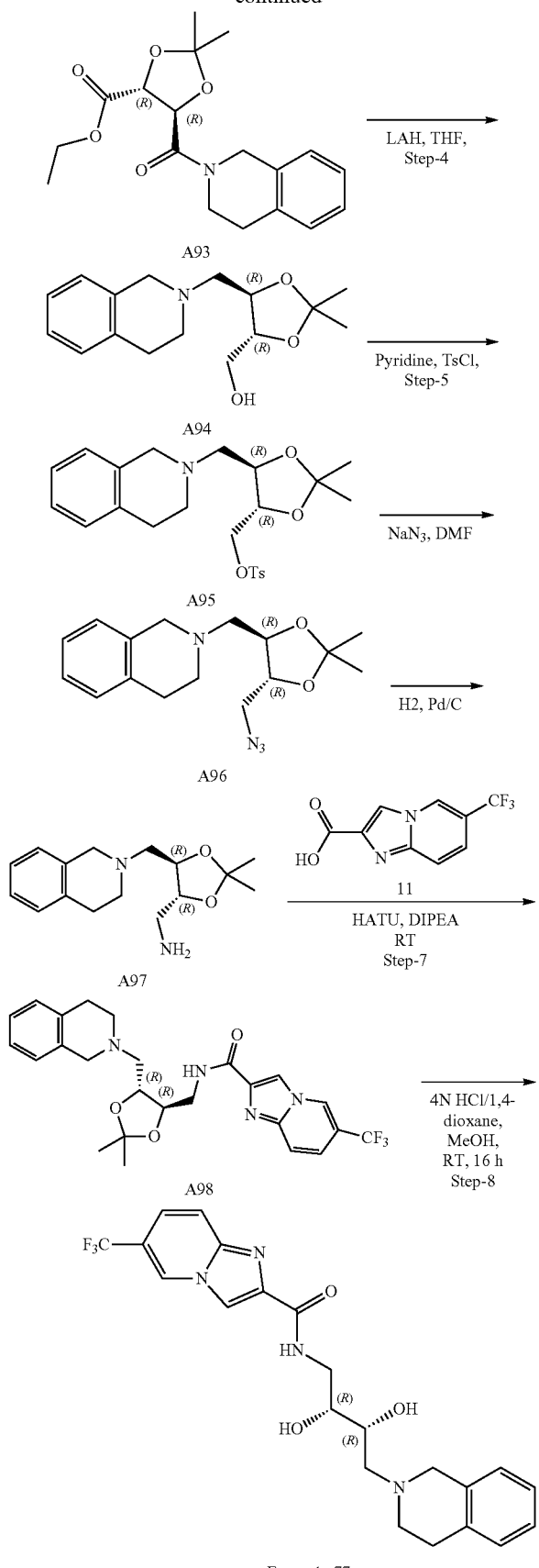

Step 1: diethyl (4R,5R)-2,2-dimethyl-1,3-dioxolane-4,5-dicarboxylate (A91)

To the stirred solution of diethyl (2R,3R)-2,3-dihydroxysuccinate (A90, 20.0 g, 97.0 mmol) in toluene was added PTSA (1.84 g, 9.70 mol), and 2,2-dimethoxypropane (2, 15.4 mL, 126.10 mmol) at room temperature. The reaction mixture was heated to 100° C. for 1 h. The reaction mixture was heated at 100° C. for 1 h. The reaction mixture was cooled to room temperature and diluted with EtOAc. The organic layer was washed with sat. NaHCO₃ solution followed by water and brine solution. The organic layer was dried over anhydrous Na₂SO₄, and filtered. The organic layer was concentrated to get diethyl (4R,5R)-2,2-dimethyl-1,3-dioxolane-4,5-dicarboxylate A91 as pale brown oil. Yield: 18.0 g, (75%). MS (ESI): mass m/z 247.2 [M+H]⁺ ¹H NMR (400 MHz, DMSO-d6) δ 4.87-4.82 (m, 2H), 4.11-4.08 (q, 2H), 1.38 (s, 6H), 1.1 (t, 3H).

Step 2: (4R,5R)-5-(ethoxycarbonyl)-2,2-dimethyl-1,3-dioxolane-4-carboxylic acid (A92)

To the stirred solution of diethyl (4R,5R)-2,2-dimethyl-1,3-dioxolane-4,5-dicarboxylate (A91, 18.0 g, 73.40 mmol), in 1,4-dioxane (130 mL) and water (130 mL) was added dropwise aq. 1N NaOH solution (110.0 mL, 110.0 mmol) at 0° C. The reaction mixture was allowed to stir at room temperature for 4 h. After completion of reaction, reaction mixture was washed with DCM. The aqueous layer was acidified using conc.HCl to pH 2-3. The aqueous layer was extracted with DCM. The organic layer was dried over anhydrous Na₂SO₄, filtered. and concentrated to get (4R,5R)-5-(ethoxycarbonyl)-2,2-dimethyl-1,3-dioxolane-4-carboxylic acid A92 as a pale yellow oil. Yield: 8.0 g, (50%). LC-MS (ES) m/z: 217.10 [M+H]⁺ ¹H NMR (400 MHz, DMSO-d6) δ 13.31 (bs, 1H), 4.71-4.69 (m, 2H), 4.19-4.14 (q, 2H), 1.22 (s, 6H), 1.21 (t, 3H).

Step 3: ethyl (4R,5R)-2,2-dimethyl-5-(1,2,3,4-tetrahydroisoquinoline-2-carbonyl)-1,3-dioxolane-4-carboxylate (A93)

To the stirred solution of (4R,5R)-5-(ethoxycarbonyl)-2,2-dimethyl-1,3-dioxolane-4-carboxylic acid (A92, 5.0 g, 22.9 mmol) in DCM (50 mL) at room temperature was added DMAP (0.27 g, 2.2 mmol), and T₃P (20 mL, 34.3 mmol). The reaction mixture was stirred for 20 min at room temperature. 1,2,3,4-tetrahydroisoquinoline (5, 3, 60 g, 27.4 mmol) was added at room temperature. Reaction mixture was stirred at room temperature for 16 h. After completion of reaction, diluted with DCM and washed with water and brine solution. The organic layer was dried over anhydrous Na₂SO₄, filtered and concentrated. The crude was purified by combiflash with 0-30% EA/hexanes as eluent. The fractions were concentrated to get ethyl (4R,5R)-2,2-dimethyl-5-(1,2,3,4-tetrahydroisoquinoline-2-carbonyl)-1,3-dioxolane-4-carboxylate A93 as pale yellow oil. Yield: 3.0 g, (39%). LCMS (ESI): mass m/z: 334.30 [M+H]⁺.

Step 4: ((4R,5R)-5-((3,4-dihydroisoquinolin-2(1H)-yl)methyl)-2,2-dimethyl-1,3-dioxolan-4-yl)methanol (A94)

To the stirred solution of ethyl (4R,5R)-2,2-dimethyl-5-(1,2,3,4-tetrahydroisoquinoline-2-carbonyl)-1,3-dioxolane-4-carboxylate (A93, 3.8 g, 11.30 mmol) in dry THF at 0° C. was added LAH (8.5 mL, 17.0 mmol). The reaction mixture was heated to 60° C. for 1 h. After completion of reaction, was cooled to room temperature and quenched with ice-cold aq. Rochelle salt solution. The quenched mixture was filtered over celite bed and washed with EtOAc. The organic layer was washed with water, followed by. brine solution. The organic layer was dried over anhydrous $Na_2SO_4$, filtered and concentrated to get the ((4R,5R)-5-((3,4-dihydroisoquinolin-2(1H)-yl)methyl)-2,2-dimethyl-1,3-dioxolan-4-yl) methanol A94 as pale yellow oil. Yield: 2.10 g, (67%). LCMS (ESI): mass m/z 278.30 [M+H]$^+$.

Step 5: ((4R,5R)-5-((3,4-dihydroisoquinolin-2(1H)-yl)methyl)-2,2-dimethyl-1,3-dioxolan-4-yl)methyl 4-methylbenzenesulfonate (A95)

To the stirred solution of ((4R,5R)-5-((3,4-dihydroisoquinolin-2(1H)-yl)methyl)-2,2-dimethyl-1,3-dioxolan-4-yl) methanol (A94, 2.0 g, 7.20 mmol) in pyridine at 0° C. was added TsCl (2.0 g, 10.80 mmol). Reaction mixture was stirred at room temperature for 16 h. After completion of reaction was evaporated to get crude. The residue was diluted with EtOAc washed subsequently with cold aqueous 1M HCl solution, saturated aq. $NaHCO_3$ solution and brine solution. The organic layer was dried over anhydrous $Na_2SO_4$, filtered and concentrated to get crude. The crude was purified by combiflash over silica gel with gradient using 20-30% EA/hexanes to afford to afford the ((4R,5R)-5-((3,4-dihydroisoquinolin-2(1H)-yl)methyl)-2,2-dimethyl-1,3-dioxolan-4-yl)methyl 4-methylbenzenesulfonate A95 as a pale yellow oil which changes to a solid at low temperatures Yield: 0.7 g, (22%). LCMS (ESI): m/z 432.1 [M+H]$^+$.

Step 5: 2-(((4R,5R)-5-(azidomethyl)-2,2-dimethyl-1,3-dioxolan-4-yl)methyl)-1,2,3,4-tetrahydroisoquinoline (A96)

To the stirred solution of 2-(((4R,5R)-5-(azidomethyl)-2,2-dimethyl-1,3-dioxolan-4-yl)methyl)-1,2,3,4-tetrahydroisoquinoline (A945, 0.7 g, 1.62 mmol) in DMF was added $NaN_3$ (0.15 g, 2.40 mmol) at room temperature. Reaction was stirred at 70° C. for 16 h. After completion of reaction, reaction mass was diluted with EtOAc washed subsequently with water and brine solution. The organic layer was dried over anhydrous $Na_2SO_4$, filtered and concentrated to get crude. The crude was purified by combiflash over silica gel with gradient elution 20-30% EA/hexanes to afford 2-(((4R,5R)-5-(azidomethyl)-2,2-dimethyl-1,3-dioxolan-4-yl)methyl)-1,2,3,4-tetrahydroisoquinoline A96 as a pale yellow oil. (0.25 g, 52%). LCMS (ESI): mass; m/z, 304.17 [M+H]$^+$.

Step 6: ((4R,5R)-5-((3,4-dihydroisoquinolin-2(1H)-yl)methyl)-2,2-dimethyl-1,3-dioxolan-4-yl)methanamine (A97)

To a solution of ((4R,5R)-5-((3,4-dihydroisoquinolin-2(1H)-yl)methyl)-2,2-dimethyl-1,3-dioxolan-4-yl)methyl 4-methylbenzenesulfonate (A96, 0.25 g, 0.8 mmol) in methanol was added Pd/C (50% moisture), and reaction mixture was maintained under hydrogen atmosphere (30 psi) for 1 h. after completion of reaction, reaction mass was filtered through celite and washed with methanol. The methanol organic layer concentrated to get ((4R,5R)-5-((3,4-dihydroisoquinolin-2(1H)-yl)methyl)-2,2-dimethyl-1,3-dioxolan-4-yl)methanamine (A97) as pale yellow oil. Yield: 0.2 g, (90%). LCMS (ESI): mass; m/z 277.2[M+H]$^+$.

Step 7: N-(((4R,5R)-5-((3,4-dihydroisoquinolin-2(1H)-yl)methyl)-2,2-dimethyl-1,3-dioxolan-4-yl) methyl)-6-(trifluoromethyl)imidazo[1,2-a]pyridine-2-carboxamide (A98)

To a stirred solution of 6-(trifluoromethyl)imidazo[1,2-a] pyridine-2-carboxylic acid (I-102, 0.16 g, 0.70 mmol) in DMF (3.0 mL) was added ((4R,5R)-5-((3,4-dihydroisoquinolin-2(1H)-yl)methyl)-2,2-dimethyl-1,3-dioxolan-4-yl) methanamine (A97, 0.2 mg, 0.70 mmol). at 0° C. was added HATU (0.41 g, 1.0 mmol), and DIPEA (0.3 mL, 2.10 mmol)). Reaction mixture was stirred at room temperature for 16 h. After completion of reaction diluted with ethyl acetate and washed with water and brine solution. The organic layer was dried over anhydrous $Na_2SO_4$, filtered, and concentrated to afford N-(((4R,5R)-5-((3,4-dihydroisoquinolin-2(1H)-yl)methyl)-2,2-dimethyl-1,3-dioxolan-4-yl) methyl)-6-(trifluoromethyl)imidazo[1,2-a]pyridine-2-carboxamide A98 as a pale yellow oil. Yield: 0.30 g (88%). LCMS (ESI): mass, 488.2; m/z 489.2, [M+H]$^+$.

Step-8: N-((2R,3R)-4-(3,4-dihydroisoquinolin-2 (1H)-yl)-2,3-dihydroxybutyl)-6-(trifluoromethyl) imidazo[1,2-a]pyridine-2-carboxamide (Example 77)

To the stirred solution of N-(((4R,5R)-5-((3,4-dihydroisoquinolin-2(1H)-yl)methyl)-2,2-dimethyl-1,3-dioxolan-4-yl) methyl)-6-(trifluoromethyl)imidazo[1,2-a]pyridine-2-carboxamide (A98, 0.3 g, 0.60 mmol), in MeOH (5 mL) was added dropwise 4N HCl at 0° C. The reaction mixture was stirred at room temperature for 16 h. After completion of reaction concentrated to remove the solvent and basified using aq. ammonia solution. and extracted with 5% MeOH/DCM. The organic layer was dried over anhydrous $Na_2SO_4$, filtered, and taturate with ether and pentane and dried to afford N-((2R,3R)-4-(3,4-dihydroisoquinolin-2 (1H)-yl)-2,3-dihydroxybutyl)-6-(trifluoromethyl)imidazo[1,2-a]pyridine-2-carboxamide as a white solid. Yield: 0.10 g (95% LCMS (ESI): m/z 449.13 [M+H]$^+$. $^1$H NMR (400 MHz, DMSO-d$_6$) δ 9.27 (s, 1H), 8.45 (s, 1H), 8.28 (dd, J=10.64 Hz, 1H), 7.79 (d, J=9.52 Hz, 1H), 7.57 (d, J=8.76 Hz, 1H), 7.08-7.00 (m, 4H), 4.87 (d, J=5.16 Hz, 1H), 4.59 (d, J=5.52 Hz, 1H), 3.70-3.61 (m, 5H), 3.55-3.49 (m, 1H), 2.79-2.49 (m, 6H).

N-((2S,3S)-4-(3,4-dihydroisoquinolin-2(1H)-yl)-2,3-dihydroxybutyl)-6-(5-methyl-1,2,4-oxadiazol-3-yl) imidazo[1,2-a]pyridine-2-carboxamide (Example 78)

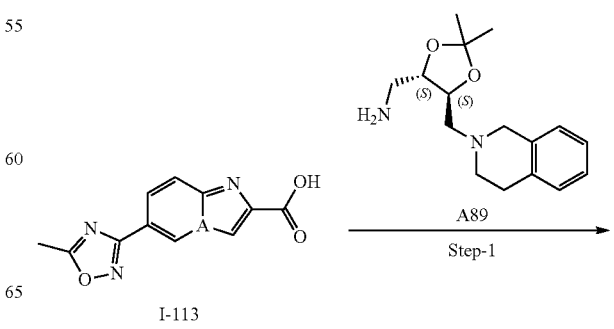

-continued

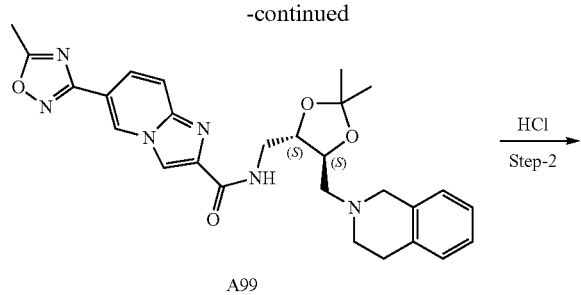

A99

Example 78

Step-1: N-(((4S,5S)-5-((3,4-dihydroisoquinolin-2 (1H)-yl)methyl)-2,2-dimethyl-1,3-dioxolan-4-yl) methyl)-6-(5-methyl-1,2,4-oxadiazol-3-yl)imidazo [1,2-a]pyridine-2-carboxamide (A99)

To a solution of 6-(5-methyl-1,2,4-oxadiazol-3-yl)imidazo[1,2-a]pyridine-2-carboxylic acid (I-113, 0.12 g, 0.49 mmol) in DMF (10 mL) was added DIPEA (0.25 mL, 1.47 mmol) followed by HATU (0.28 g, 0.73 mmol) at 0° C. The reaction mixture was stirred for 10 min followed by addition of ((4S,5S)-5-((3,4-dihydroisoquinolin-2(1H)-yl)methyl)-2, 2-dimethyl-1,3-dioxolan-4-yl)methanamine (A89, 0.13 g, 0.49 mmol). The reaction mixture was stirred at room temperature for 16 h. The reaction was monitored till the completion of starting materials (LC/MS) and then concentrated under reduced pressure. The obtained crude was purified by combi-flash column using 0-10% MeOH/DCM as the eluent to afford N-(((4S,5S)-5-((3,4-dihydroisoquinolin-2(1H)-yl)methyl)-2,2-dimethyl-1,3-dioxolan-4-yl) methyl)-6-(5-methyl-1,2,4-oxadiazol-3-yl)imidazo[1,2-a] pyridine-2-carboxamide A99 as white solid. Yield: 0.20 g, (83%). LC-MS (ES) m/z: 503.23 [M+H]$^+$.

Step-2: N-((2S,3S)-4-(3,4-dihydroisoquinolin-2 (1H)-yl)-2,3-dihydroxybutyl)-6-(5-methyl-1,2,4-oxadiazol-3-yl)imidazo[1,2-a]pyridine-2-carboxamide To a stirred solution of N-(((4S,5S)-5-((3,4-dihydroisoquinolin-2(1H)-yl)methyl)-2,2-dimethyl-1,3-dioxolan-4-yl) methyl)-6-(5-methyl-1,2,4-oxadiazol-3-yl)imidazo[1,2-a] pyridine-2-carboxamide (A99, 0.20 g 0.39 mmol) in MeOH (3 mL) at 0° C., 4N HCl in dioxane was added and reaction mixture stirred at room temperature for 4 h. After completion, evaporated the solvent from reaction mixture to obtain the residue. This residue quenched with NaHCO$_3$ solution and extracted with ethyl acetate (3 times). The organic layer was separated, dried over anhydrous sodium sulphate and concentrated under reduced pressure to obtain the crude. This crude was washed with diethyl ether and dried to afford N-((2S,3S)-4-(3,4-dihydroisoquinolin-2(1H)-yl)-2,3-dihydroxybutyl)-6-(5-methyl-1,2,4-oxadiazol-3-yl)imidazo[1,2-a]pyridine-2-carboxamide as white solid. Yield: 0.011 g (6%) LC-MS (ES) m/z=463.18 [M+H]$^+$ $^1$H NMR (DMSO-d$_6$, 400 MHz, ppm)-δ 9.38 (s, 1H), 8.54 (s, 1H), 8.27 (s, 1H), 7.81 (d, J=8.36 Hz, 1H), 7.74 (d, J=9.52 Hz, 1H), 7.08-7.01 (m, 4H), 4.87 (s, 1H), 4.58 9s, 1H), 3.72-3.50 (m, 5H), 2.80 (s, 2H), 2.68 (d, J=2.72 Hz, 2H), 2.50-2.32 (m, 5H).

N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide (Example 79)

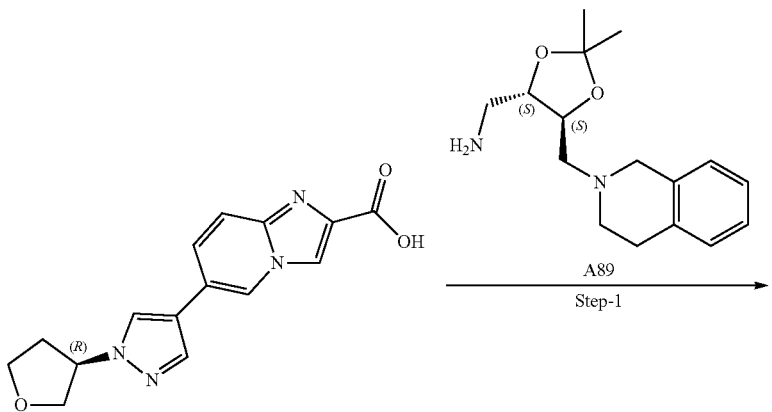

I-141

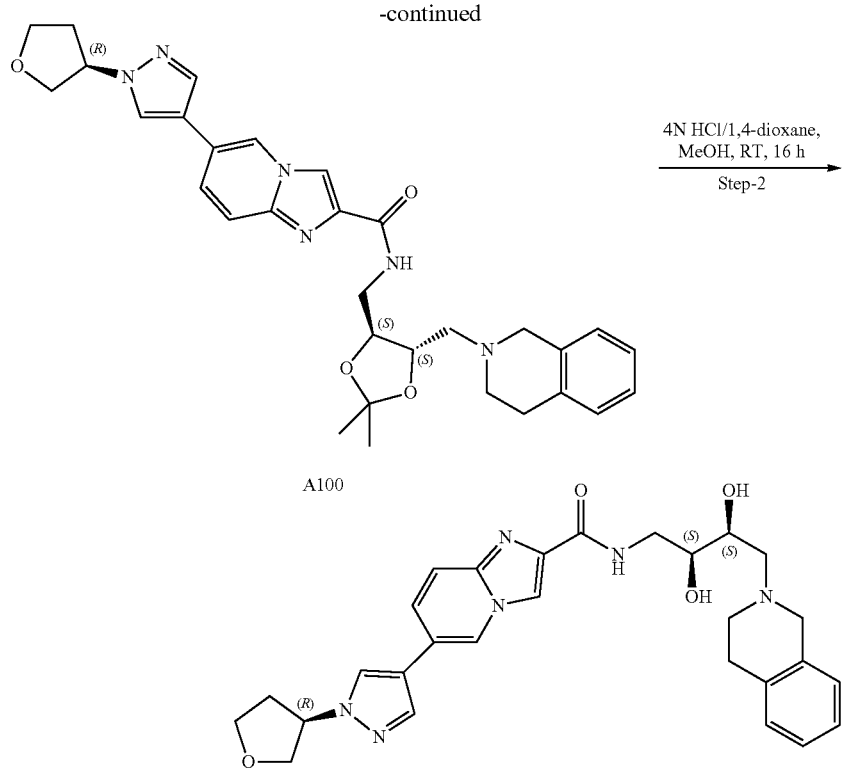

A100

PRMT5_Chemsys_41

Step-1: N-(((4S,5S)-5-((3,4-dihydroisoquinolin-2(1H)-yl)methyl)-2,2-dimethyl-1,3-dioxolan-4-yl)methyl)-6-(1-((R)-tetrahydrofuran-3-yl)-1H-pyrazol-4-yl)imidazo[1,2-a]pyridine-2-carboxamide (3)

To a solution of (R)-6-(1-(tetrahydrofuran-3-yl)-1H-pyrazol-4-yl)imidazo[1,2-a]pyridine-2-carboxylic acid (I-141, 0.13 g, 0.471 mmol) in DMF (3 mL) was added DIPEA (0.25 mL, 1.41 mmol) followed by HATU (0.268 g, 0.706 mmol). The reaction mixture was stirred for 10 min followed by addition of ((4S,5S)-5-((3,4-dihydroisoquinolin-2(1H)-yl)methyl)-2,2-dimethyl-1,3-dioxolan-4-yl)methanamine (A89, 0.140 g, 0.471 mmol). The reaction mixture was stirred at room temperature for 16 h. The reaction was monitored till the completion of starting materials (LC/MS) and then concentrated under reduced pressure. The obtained crude was purified by column chromatography using 0-10% methanol in dichloromethane as eluent to afford N-(((4S,5S)-5-((3,4-dihydroisoquinolin-2(1H)-yl)methyl)-2,2-dimethyl-1,3-dioxolan-4-yl)methyl)-6-(1-((R)-tetrahydrofuran-3-yl)-1H-pyrazol-4-yl)imidazo[1,2-a]pyridine-2-carboxamide A100 as a white solid. Yield: 0.22 g (83%) LC-MS (ES) m/z: 557.53 [M+H]$^+$

Step-2: N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide To a solution of N-(((4S,5S)-5-((3,4-dihydroisoquinolin-2(1H)-yl)methyl)-2,2-dimethyl-1,3-dioxolan-4-yl)methyl)-6-(1-((R)-tetrahydrofuran-3-yl)-1H-pyrazol-4-yl)imidazo[1,2-a]pyridine-2-carboxamide (A100, 0.22 g, 39.49 mmol) in Methanol (4 mL) was added 4M HCL in Dioxane (2 mL) at 0° C. The reaction mixture was stirred at room temperature for 2 h After completion of reaction organic solvent was evaporated and the aqueous layer was basified with sat NaHCO$_3$ up to pH-10 and aqueous layer extracted by DCM and then concentrated under reduced pressure. The obtained crude was purified by column chromatography using 0-10% methanol in dichloromethane as eluent to afford N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide as a white solid. Yield: 0.10 g (49%). LC-MS (ES) m/z: 517.11 [M+H]$^+$ $^1$H NMR (DMSO-d$_6$, 400 MHz, ppm) δ 8.85 (s, 1H), 8.30 (s, 1H), 8.24 (s, 1H), 8.19 (dd, J=11.40 Hz, 5.32 Hz, 1H), 7.93 (s, 1H), 7.64-7.59 (m, 2H), 7.08-7.01 (m, 4H), 5.07-5.03 (m, 1H), 4.88 (bs, 1H), 4.59 (bs, 1H), 4.03-3.99 (m, 2H), 3.98-3.92 (m, 1H), 3.87-3.81 (m, 1H), 3.72-3.50 (m, 5H), 3.32-3.28 (m, 1H), 2.79-2.66 (m, 5H), 2.49-2.32 (m, 3H).

N-((2S,3S)-4-(3,4-dihydroisoquinolin-2(1H)-yl)-2,3-dihydroxybutyl)-6-(1-methyl-2-oxo-1,2-dihydropyridin-4-yl)imidazo[1,2-a]pyridine-2-carboxamide (Example 80)

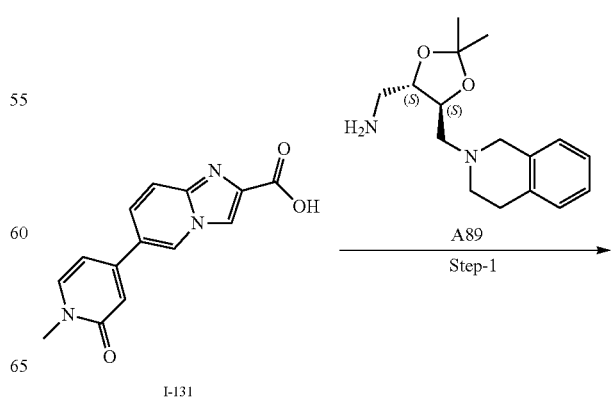

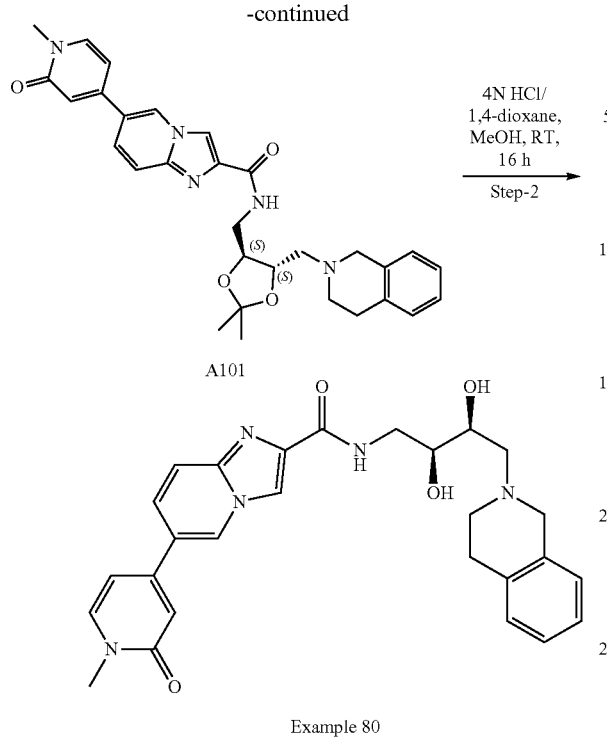

Example 80

Step-1: N-(((4S,5S)-5-((3,4-dihydroisoquinolin-2(1H)-yl)methyl)-2,2-dimethyl-1,3-dioxolan-4-yl)methyl)-6-(1-methyl-2-oxo-1,2-dihydropyridin-4-yl)imidazo[1,2-a]pyridine-2-carboxamide (3)

To a solution of 6-(1-methyl-2-oxo-1,2-dihydropyridin-4-yl)imidazo[1,2-a]pyridine-2-carboxylic acid (I-131, 0.15 g, 0.55 mmol) in DMF (3 mL) was added DIPEA (0.27 mL, 1.67 mmol) followed by HATU (0.250 g, 0.66 mmol). The reaction mixture was stirred for 10 min followed by addition of ((4S,5S)-5-((3,4-dihydroisoquinolin-2(1H)-yl)methyl)-2,2-dimethyl-1,3-dioxolan-4-yl)methanamine (A89, 0.15 g, 0.55 mmol). The reaction mixture was stirred at room temperature for 16 h. The reaction was monitored till the completion of starting materials (LC/MS) and then concentrated under reduced pressure. The obtained crude was purified by column chromatography using 0-10% methanol in dichloromethane as eluent to afford N-(((4S,5S)-5-((3,4-dihydroisoquinolin-2(1H)-yl)methyl)-2,2-dimethyl-1,3-dioxolan-4-yl)methyl)-6-(1-methyl-2-oxo-1,2-dihydropyridin-4-yl)imidazo[1,2-a]pyridine-2-carboxamide A101 as a white solid. Yield: 0.22 g (75%) LC-MS (ES) m/z: 528.53 [M+H]$^+$

Step-2: N-((2S,3S)-4-(3,4-dihydroisoquinolin-2(1H)-yl)-2,3-dihydroxybutyl)-6-(1-methyl-2-oxo-1,2-dihydropyridin-4-yl)imidazo[1,2-a]pyridine-2-carboxamide To a solution of N-(((4S,5S)-5-((3,4-dihydroisoquinolin-2(1H)-yl)methyl)-2,2-dimethyl-1,3-dioxolan-4-yl)methyl)-6-(1-methyl-2-oxo-1,2-dihydropyridin-4-yl)imidazo[1,2-a]pyridine-2-carboxamide (A101, 0.22 g, 0.41 mmol) in Methanol (4 mL) was added 4M HCL in Dioxane (2 mL) at 0° C. The reaction mixture was stirred at room temperature for 2 h After completion of reaction organic solvent was evaporated and the aqueous layer was basified with sat NaHCO$_3$ up to pH-10 and aqueous layer extracted by DCM and then concentrated under reduced pressure. The obtained crude was purified by column chromatography using 0-10% methanol in dichloromethane as eluent to afford N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide as a white solid. Yield: 0.032 g (18%). LC-MS (ES) m/z: 488.0 [M+H]$^+$ $^1$H NMR (DMSO-d$_6$, 400 MHz, ppm) δ 9.11 (s, 1H), 8.32 (s, 1H), 8.25-8.22 (dd, J=11.07 Hz, 5.68 Hz, 1H), 7.84 (d, J=7.12 Hz, 1H), 7.73 (d, J=9.64 Hz, 1H), 7.66 (d, J=9.52 Hz, 1H), 7.08-6.99 (m, 4H), 6.78 (s, 1H), 6.61 (d, J=7.04 Hz, 1H), 4.87 (s, 1H), 4.58 (d, J=4.28 Hz, 1H), 3.71-3.50 (m, 5H), 3.49 (s, 3H), 3.32 (m, 1H), 2.79 (d, J=4.72 Hz, 2H), 2.73 (d, J=4.48 Hz, 2H), 2.63-2.50 (m, 1H).

N-((2S,3S)-4-(3,4-dihydroisoquinolin-2(1H)-yl)-2,3-dihydroxybutyl)-6-(1-methyl-1H-pyrazol-4-yl)imidazo[1,2-a]pyridine-2-carboxamide (Example 81)

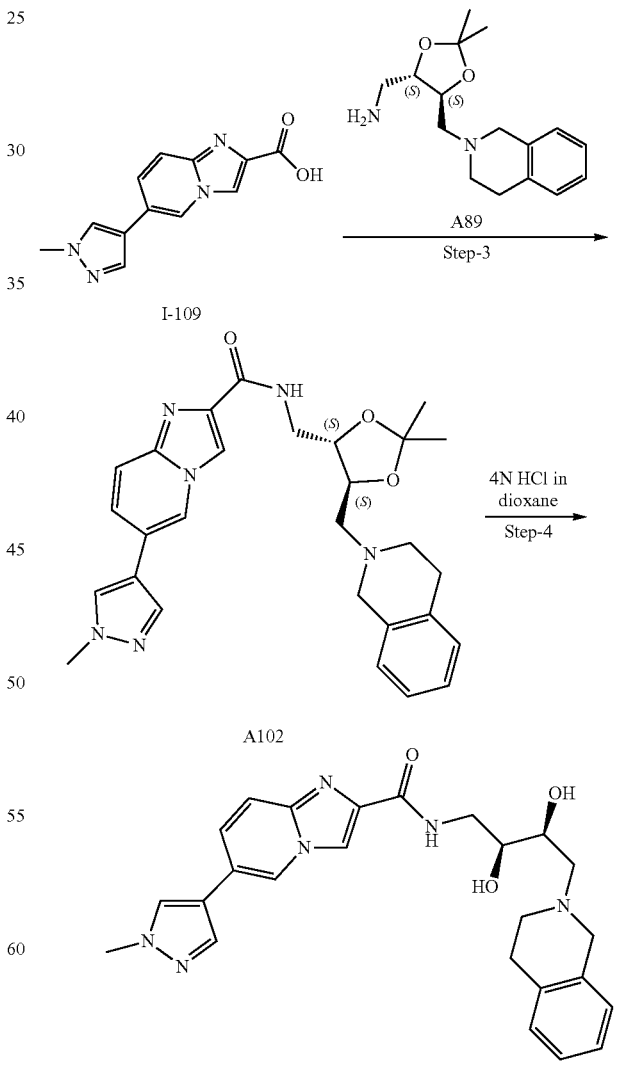

Example 81

Step-3: N-(((4S,5S)-5-((3,4-dihydroisoquinolin-2 (1H)-yl)methyl)-2,2-dimethyl-1,3-dioxolan-4-yl) methyl)-6-(1-methyl-1H-pyrazol-4-yl)imidazo[1,2-a] pyridine-2-carboxamide (A102)

To a solution of 6-(1-methyl-1H-pyrazol-4-yl)imidazo[1,2-a]pyridine-2-carboxylic acid (I-109, 0.20 g, 0.82 mmol) in DMF (3 mL) was added DIPEA (0.43 mL, 2.47 mmol) followed by HATU (0.47 g, 1.23 mmol). The reaction mixture was stirred for 10 min followed by addition of ((4S,5S)-5-((3,4-dihydroisoquinolin-2(1H)-yl)methyl)-2,2-dimethyl-1,3-dioxolan-4-yl)methanamine (A89, 0.27 g, 0.99 mmol). The reaction mixture was stirred at room temperature for 16 h. The reaction was monitored till the completion of starting materials (LC/MS) and then concentrated under reduced pressure. The obtained crude was purified by column chromatography using 0-10% methanol in dichloromethane as eluent to afford N-(((4S,5S)-5-((3,4-dihydroisoquinolin-2(1H)-yl)methyl)-2,2-dimethyl-1,3-dioxolan-4-yl)methyl)-6-(1-methyl-1H-pyrazol-4-yl) imidazo[1,2-a]pyridine-2-carboxamide A102 as a white solid. Yield: 0.30 g (72%) LC-MS (ES) m/z: 501.24 [M+H]$^+$

Step-4: N-((2S,3S)-4-(3,4-dihydroisoquinolin-2 (1H)-yl)-2,3-dihydroxybutyl)-6-(1-methyl-1H-pyrazol-4-yl)imidazo[1,2-a]pyridine-2-carboxamide To a solution of N-(((4S,5S)-5-((3,4-dihydroisoquinolin-2(1H)-yl)methyl)-2,2-dimethyl-1,3-dioxolan-4-yl)methyl)-6-(1-methyl-1H-pyrazol-4-yl)imidazo[1,2-a]pyridine-2-carboxamide (A102, 0.30 g, 0.60 mmol) in Methanol (4 mL) was added 4M HCL in Dioxane (2 mL) at 0° C. The reaction mixture was stirred at room temperature for 4 h. After completion of reaction, organic solvent was evaporated and the aqueous layer was basified with sat NaHCO$_3$ up to pH-10 and aqueous layer extracted by DCM and then concentrated under reduced pressure. The obtained crude was purified by column chromatography using 0-10% methanol in dichloromethane as eluent to afford N-((2S,3S)-4-(3,4-dihydroisoquinolin-2(1H)-yl)-2,3-dihydroxybutyl)-6-(1-methyl-1H-pyrazol-4-yl)pyrazol-4-yl)imidazo[1,2-a]pyridine-2-carboxamide as a white solid. Yield: 0.06 g (21%). LC-MS (ES) m/z: 461.0 [M+H]$^+$ $^1$H NMR (DMSO-d$_6$, 400 MHz, ppm) δ 8.82 (s, 1H), 8.25 (s, 1H), 8.18 (s, 2H), 7.87 (s, 1H), 7.62-7.56 (m, 2H), 7.08-7.01 (m, 4H), 4.87 (d, J=5.68 Hz, 1H), 4.58 (d, J=4.96 Hz, 1H), 3.88 (s, 3H), 3.71 (s, 1H), 3.61 (s, 3H), 3.56-3.50 (m, 2H), 3.32-3.28 (m, 1H), 2.89 (d, J=4.8 Hz, 2H), 2.73 (d, J=5.0 Hz, 2H), 2.66-2.61 (m, 1H).

(S)—N-(3-(6-fluoro-3,4-dihydroisoquinolin-2(1H)-yl)-2-hydroxypropyl)-6-(1-methyl-1H-pyrazol-4-yl) imidazo[1,2-a]pyridine-2-carboxamide (Example 82)

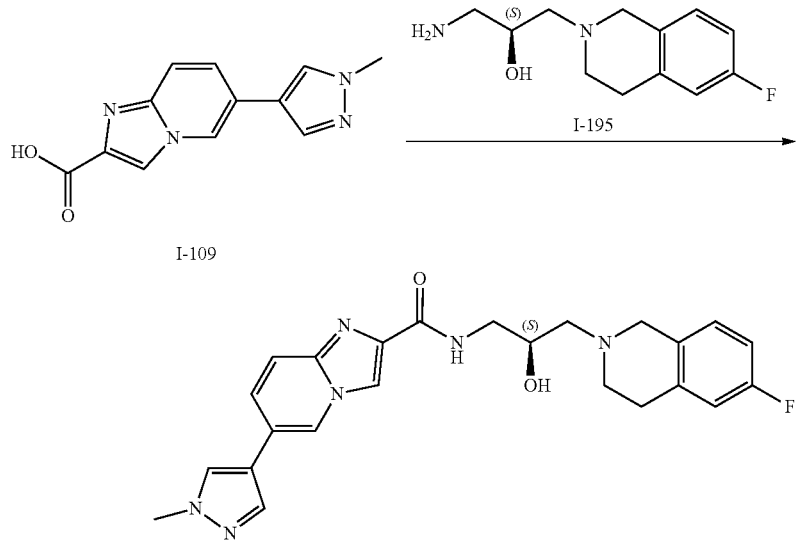

Example 82

LC-MS (ES) m/z: 449.24 [M+H]$^+$ $^1$H NMR (DMSO-d$_6$, 400 MHz, ppm) δ 8.85 (s, 1H), 8.54 (dd, J=5.24 Hz, 1H), 8.31 (s, 1H), 8.19 (s, 1H), 7.88 (s, 1H), 7.62 (s, 2H), 7.26 (d, J=5.64 Hz, 1H), 7.13-7.09 (m, 2H), 5.92 (bs, 1H), 4.55-4.51 (m, 1H), 4.34-4.21 (m, 4H), 3.89 (s, 3H), 3.88-3.77 (m, 2H), 3.23-3.08 (m, 4H).

(S)—N-(3-(6-fluoro-3,4-dihydroisoquinolin-2(1H)-yl)-2-hydroxypropyl)-6-(trifluoromethyl)imidazo[1,2-b]pyridazine-2-carboxamide (Example 83)

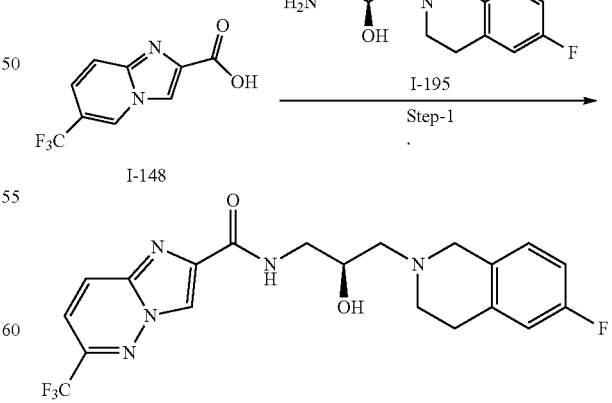

Example 83

LC-MS (ES) m/z=438.18 [M+H]$^+$. 1H NMR (400 MHz, DMSO-d6) δ 8.89 (s, 1H), 8.49 (bs, 1H), 8.39 (d, J=9.5 Hz,

1H), 7.77 (d, J=9.5 Hz, 1H), 7.0 (t, J=6.3 Hz, 1H), 6.93-6.87 (m, 2H), 4.98 (bs, 1H), 3.93 (d, J=4.4 Hz, 1H), 3.58 (bs, 2H), 3.51-3.46 (m, 1H), 3.36 (bs, 1H), 2.84 (bs, 2H), 2.72-2.67 (m, 2H), 2.54 (bs, 2H).

(S)—N-(3-(6-fluoro-3,4-dihydroisoquinolin-2(1H)-yl)-2-hydroxypropyl)-6-(trifluoromethyl)imidazo[1,2-a]pyrazine-2-carboxamide (Example 84)

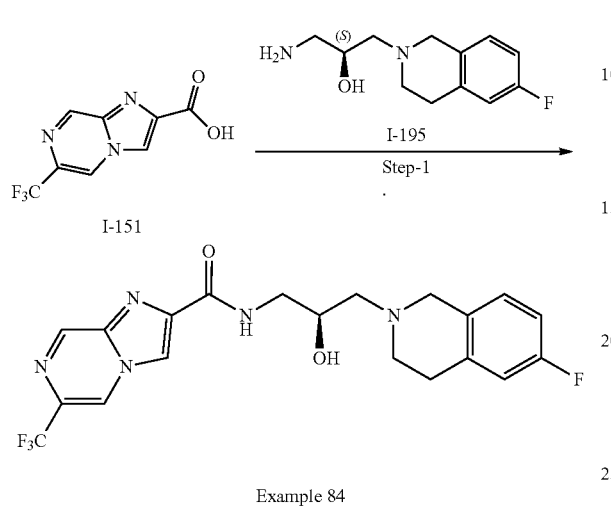

LC-MS (ES) m/z=438.18 [M+H]⁺. 1H NMR (400 MHz, DMSO-d6) δ 9.32 (s, 1H), 9.13 (s, 1H), 8.56 (bs, 2H), 7.03 (t, J=6.3 Hz, 1H), 6.94-6.87 (m, 2H), 4.97 (d, J=4.4 Hz, 1H), 3.92 (t, J=5.4 Hz, 1H), 3.59 (bs, 2H), 3.49-3.43 (m, 1H), 3.38-3.35 (m, 1H), 2.84 (bs, 2H), 2.74-2.67 (m, 2H), 2.55 (bs, 2H).

(S)—N-(3-(6-fluoro-3,4-dihydroisoquinolin-2(1H)-yl)-2-hydroxypropyl)-6-(1-methyl-2-oxo-1,2-dihydropyridin-4-yl)imidazo[1,2-a]pyrazine-2-carboxamide (Example 85)

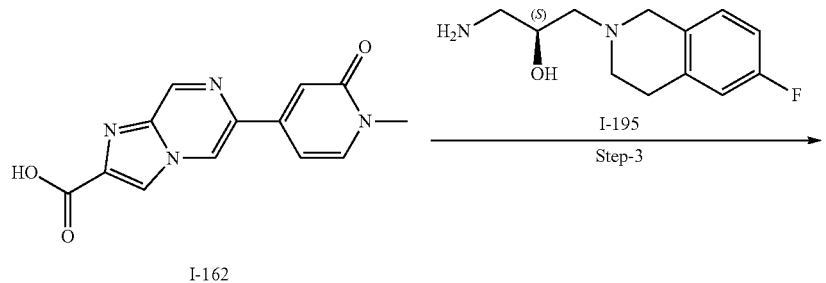

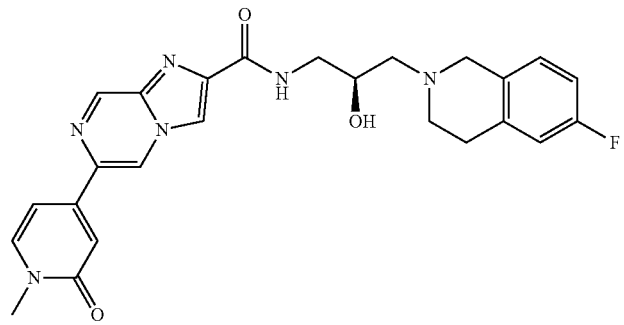

LC-MS (ES) m/z: 477.32 [M+H]⁺

(S)-6-(difluoromethyl)-N-(3-(3,4-dihydroisoquinolin-2(1H)-yl)-2-hydroxypropyl)imidazo[1,2-a]pyridine-2-carboxamide (Example 86)

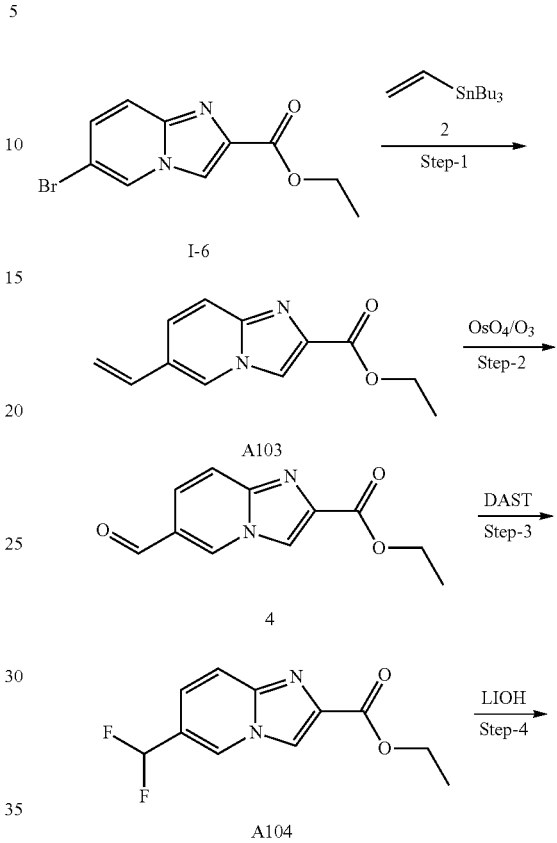

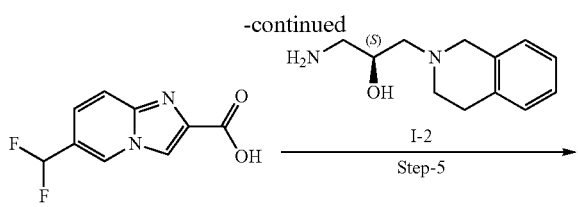

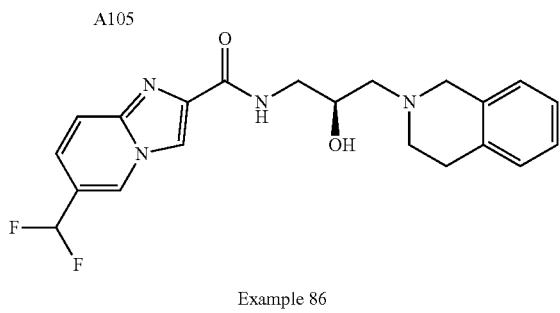

Example 86

LC-MS (ES) m/z: 401.43 [M+H]+

6-(difluoromethyl)-N—((S)-3-(3,4-dihydroisoquinolin-2(1H)-yl)-2-hydroxypropyl)-5,6,7,8-tetrahydroimidazo[1,2-a]pyridine-2-carboxamide (Example 87)

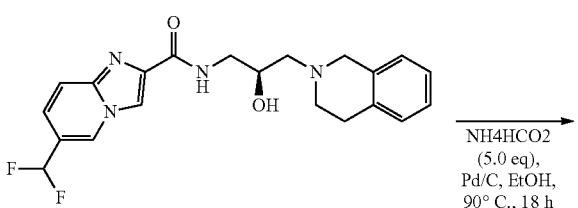

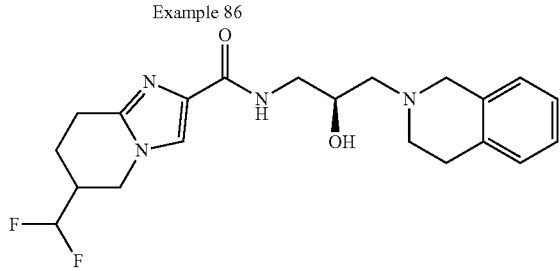

Example 87

LC-MS (ES) m/z: 405.46 [M+H]+

(R)—N-(3-(3,4-dihydroisoquinolin-2(1H)-yl)-2-hydroxypropyl)-N-methyl-6-(trifluoromethyl)imidazo[1,2-a]pyridine-2-carboxamide (Example 88)

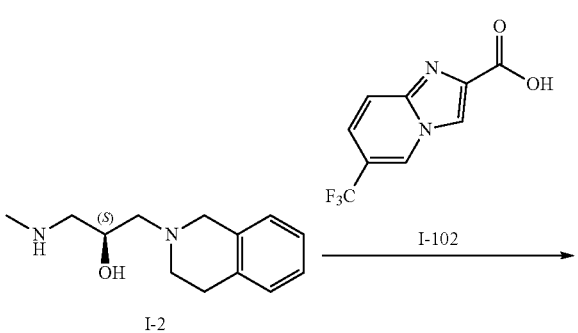

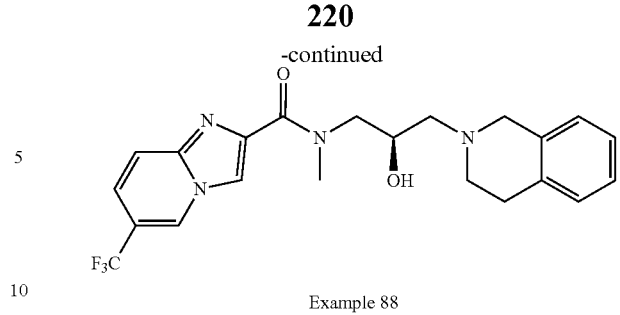

Example 88

LC-MS (ES) m/z: 433.27 [M+H]+ 1H NMR (DMSO-d6, 400 MHz, ppm) δ 9.14 (s, 1H), 8.34 (s, 1H), 7.69 (bs, 1H), 7.45 (d, J=9.44 Hz, 1H), 7.06-6.97 (m, 4H), 4.70 (d, J=15.76 Hz, 1H), 4.06-3.86 (m, 3H), 3.72-3.57 (m, 3H), 2.69-2.32 (m, 6H), 1.89-1.77 (m, 2H).

(R)—N-(3-(3,4-dihydroisoquinolin-2(1H)-yl)-2-hydroxypropyl)-N-methyl-6-(trifluoromethyl)imidazo[1,2-a]pyrazine-2-carboxamide (Example 89)

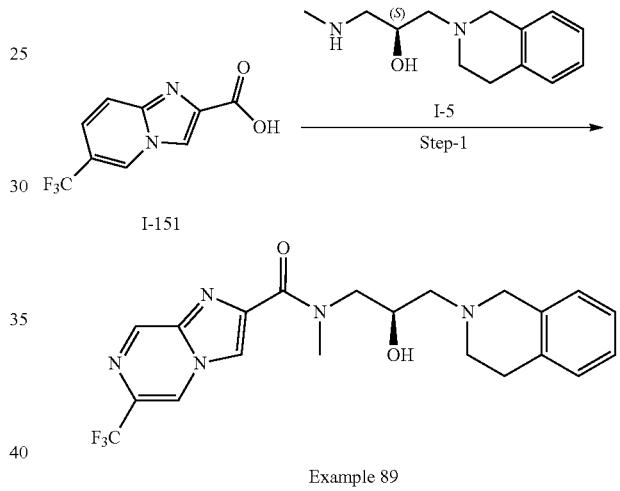

Example 89

LC-MS (ES) m/z=434.21 [M+H]+. Note: compound is rotameric, two sets of peak appeared. 1H NMR (400 MHz, DMSO-d6) δ 9.33 & 9.26 (s, 1H), 9.17 & 9.11 (s, 1H), 8.53 & 8.43 (s, 1H), 7.08 & 7.03 (bs, 3H), 6.94 & 6.91 (bs, 1H), 4.93 & 4.85 (bs, 1H), 4.13 (s, 1H), 4.02-3.99 (m, 2H), 3.83-3.77 (m, 2H), 3.64 (bs, 1H), 3.45-3.42 (m, 4H), 3.26 (bs, 1H), 3.1 (s, 1H), 2.81-2.74 (m, 2H), 2.56 (bs, 3H), 2.37 (bs, 2H). At higher temperature: 1H NMR (400 MHz, DMSO-d6) δ 9.2 (bs, 2H), 8.46 (s, 1H), 7.05 (bs, 4H), 4.63 (bs, 1H), 4.06 (bs, 2H), 3.82-3.35 (m, 6H), 3.19-3.15 (m, 2H), 2.65 (bs, 3H).

(R)—N-(3-(3,4-dihydroisoquinolin-2(1H)-yl)-2-hydroxypropyl)-N-methyl-5-(trifluoromethyl)pyrazolo[1,5-a]pyrimidine-2-carboxamide (Example 90)

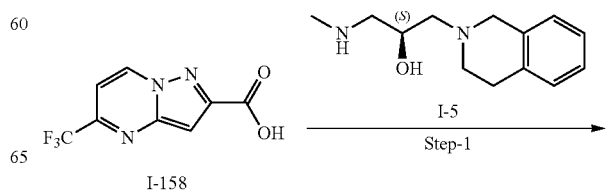

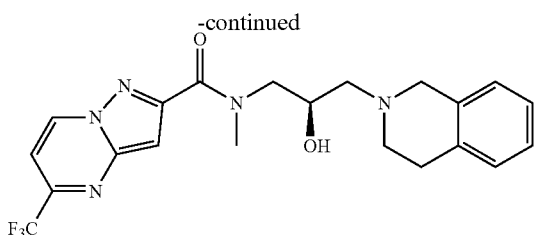

Example 90

LC-MS (ES) m/z: 434.24 [M+H]+ 1H NMR (DMSO-d6, 400 MHz, ppm) δ 9.38 (bs, 1H), 7.52 (d, J=7.16 Hz, 1H), 7.27-7.21 (m, 5H), 5.72 (bs, 1H), 4.40 (bs, 3H), 3.72-3.60 (m, 2H), 3.44-3.15 (m, 9H).

(R)—N-(3-(3,4-dihydroisoquinolin-2(1H)-yl)-2-hydroxypropyl)-N-methyl-6-(trifluoromethyl)imidazo[1,2-b]pyridazine-2-carboxamide (Example 91)

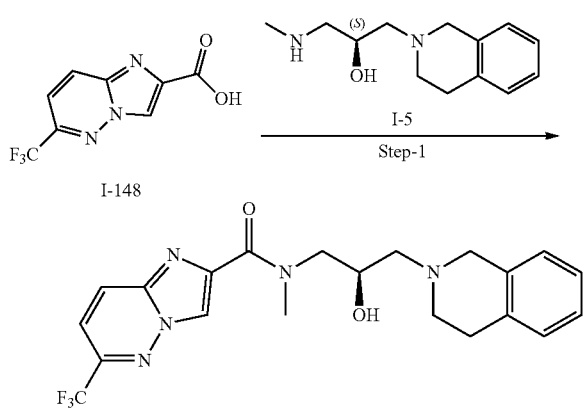

Example 91

LC-MS (ES) m/z=434.24 [M+H]+. Note: compound is rotameric, two sets of peak appeared. 1H NMR (400 MHz, DMSO-d6) δ 8.83 & 8.73 (s, 1H), 8.51 & 8.33 (d, J=9.5 Hz, 1H), 7.74 & 7.62 (d, J=9.5 Hz, 1H), 7.08-6.86 (m, 4H), 4.96 & 4.84 (d, J=4.7 Hz, 1H), 4.12-3.86 (m, 2H), 3.82-3.68 (m, 1H), 3.65-3.41 (m, 4H), 3.23 (bs, 1H), 3.1 (s, 2H), 2.81-2.72 (m, 2H), 2.56 (m, 1H), 2.36-2.34 (m, 1H). At higher temperature: 1H NMR (400 MHz, DMSO-d6) δ 8.67 (s, 1H), 8.35 (bs, 1H), 7.61 (bs, 1H), 7.05-6.9 (bs, 4H), 4.64 (bs, 1H), 4.05 (bs, 2H), 3.75-3.39 (m, 4H), 3.31-3.14 (m, 4H), 2.67 (bs, 3H).

(R)—N-(3-(3,4-dihydroisoquinolin-2(1H)-yl)-2-hydroxypropyl)-N-methyl-6-(1-methyl-1H-pyrazol-4-yl)imidazo[1,2-a]pyrazine-2-carboxamide (Example 92)

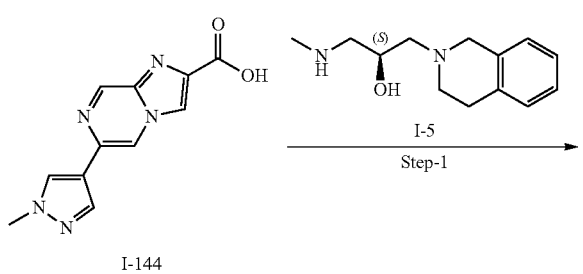

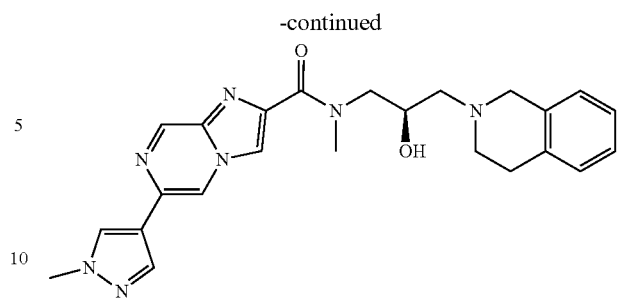

Example 92

LC-MS (ES) m/z: 446.28 [M+H]+ 1H NMR (DMSO-d6, 400 MHz, ppm) δ 9.00 (s, 1H), 8.77 (s, 1H), 8.26 (s, 1H), 8.20 (d, J=4.96 Hz, 1H), 7.92 (d, J=6.80 Hz, 1H), 7.08-0.93 (m, 4H), 5.01 (bs, 1H), 4.11-4.0 (m, 2H), 3.84 (s, 3H), 3.80-3.63 (m, 2H), 3.48 (d, J=7.32 Hz, 3H), 3.37-3.26 (m, 1H), 3.09 (s, 2H), 2.81-2.57 (m, 4H), 2.40-2.32 (m, 2H).

(R)—N-(3-(3,4-dihydroisoquinolin-2(1H)-yl)-2-hydroxypropyl)-N-methyl-6-(1-methyl-2-oxo-1,2-dihydropyridin-4-yl)imidazo[1,2-a]pyrazine-2-carboxamide Example 93

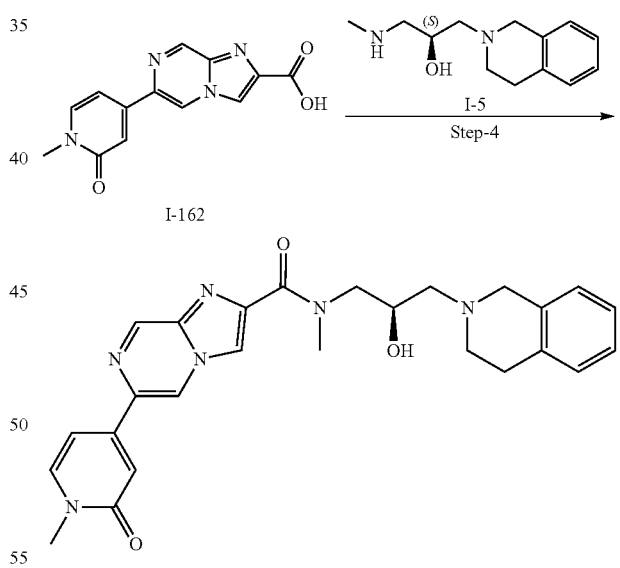

Example 93

LC-MS (ES) m/z=473.38 [M+H]+. Note: compound is rotameric, two sets of peak appeared. 1H NMR (400 MHz, DMSO-d6) δ 9.33 & 9.2 (s, 1H), 9.23 & 9.08 (s, 1H), 8.39 & 8.3 (s, 1H), 7.84 (d, J=7.1 Hz, 1H), 7.19-6.82 (m, 6H), 6.79 (d, J=7.1 Hz, 1H), 4.96 & 4.84 (bs, 1H), 4.12-4.01 (m, 1H), 3.84-3.75 (m, 1H), 3.64-3.58 (m, 1H), 3.47-3.4374 (m, 4H), 3.1 (bs, 2H), 2.82-2.68 (m, 4H), 2.59 (bs, 2H), 2.39-2.37 (m, 2H).

223

(R)—N-(3-(3,4-dihydroisoquinolin-2(1H)-yl)-2-hydroxypropyl)-N-methyl-6-(1-methyl-6-oxo-1,6-dihydropyridin-3-yl)imidazo[1,2-a]pyrazine-2-carboxamide (Example 94)

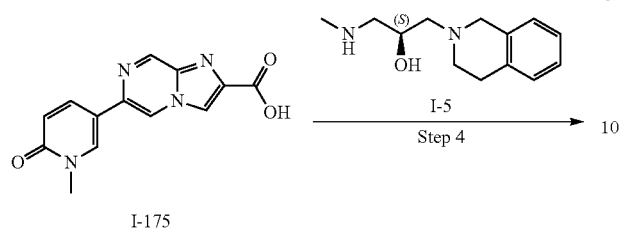

Example 94

LC-MS (ES) m/z=473.38 [M+H]⁺. Note: compound is rotameric, two sets of peak appeared. 1H NMR (400 MHz, DMSO-d6) δ 9.17 & 9.04 (s, 1H), 8.99 & 8.71 (s, 1H), 8.44-8.27 (m, 2H), 7.98 (bs, 1H), 7.08-6.92 (m, 4H), 6.54 (d, J=9.0 Hz, 1H), 5.0 & 4.84 (bs, 1H), 4.11-4.01 (m, 1H), 3.84-3.75 (m, 1H), 3.64 (bs, 1H), 3.55 (s, 3H), 3.49-3.44 (m, 3H), 3.09 (s, 2H), 2.81-2.73 (m, 2H), 2.59 (bs, 2H), 2.39 (bs, 2H).

(R)-6-(4-cyanophenyl)-N-(3-(3,4-dihydroisoquinolin-2(1H)-yl)-2-hydroxypropyl)-N-methylimidazo[1,2-a]pyrazine-2-carboxamide (Example 95)

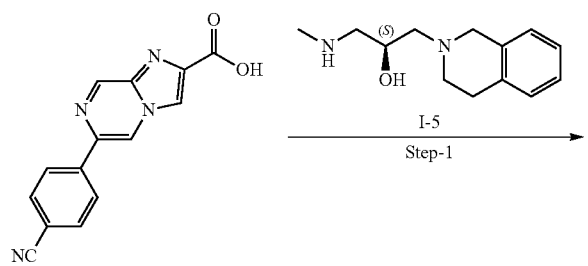

Example 95

224

LC-MS (ES) m/z: 467.36 [M+H]⁺ ¹H NMR (DMSO-d₆, 400 MHz, ppm) δ 9.23-9.13 (bs, 2H), 8.36 (s, 1H), 8.21 (d, J=8.16 Hz, 2H), 7.95 (d, J=8.32 Hz, 2H), 7.08-6.89 (m, 4H), 4.98 (d, J=4.88 Hz, 1H), 4.13-4.03 (m, 2H), 3.86-3.78 (m, 1H), 3.64 (s, 1H), 3.49 (s, 3H), 3.31-3.24 (m, 1H), 3.10 (s, 2H), 2.81-2.58 (m, 5H), 2.39-2.32 (m, 2H).

Synthesis of N-(3-((2,3-dihydro-1H-inden-2-yl)amino)-2-hydroxypropyl)-6-trifluoromethyl)imidazo[1,2-a]pyridine-2-carboxamide (Example 96)

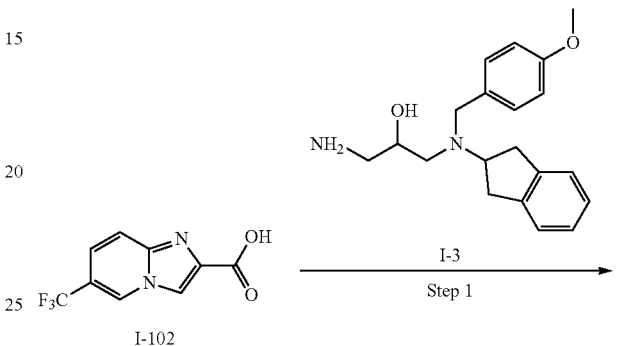

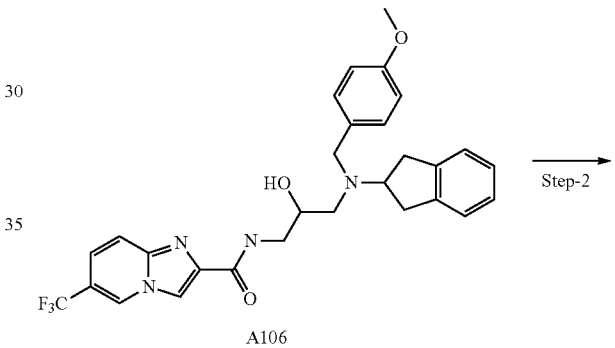

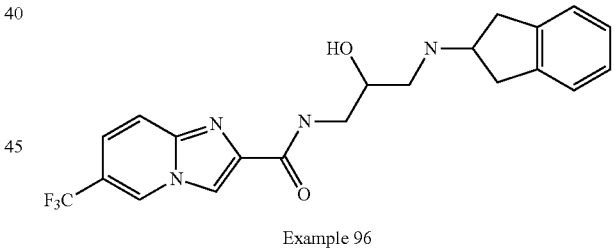

Example 96

Step 1: Preparation of N-(3-((2,3-dihydro-1H-inden-2-yl)(4-methoxybenzyl)amino)-2-hydroxypropyl)-6-(trifluoromethyl)imidazo[1,2-a]pyridine-2-carboxamide (A106)

To a solution of 6-(trifluoromethyl)imidazo[1,2-a]pyridine-2-carboxylic acid (I-102, 0.1 g, 0.43 mmol) in DMF (5 ml) were added 1-amino-3-((2,3-dihydro-1H-inden-2-yl)(4-methoxybenzyl)amino)propan-2-ol (I3, 0.17 g, 0.52 mmol), N-(3-dimethylaminopropyl)-N'-ethylcarbodiimide hydrochloride (0.124 g, 0.651 mmol), N,N-Diisopropylethylamine (0.17 g, 13.03 mmol) and hydroxybenzotriazole (0.088 g, 0.65 mmol). The reaction mixture was stirred at room temperature for 16 h. The reaction mixture was concentrated and basified with sodium bicarbonate solution then extracted with dichloromethane. The combined organic layer was washed with brine solution and dried over anhydrous sodium sulphate, concentrated solvent under reduced pressure to give crude product. The compound was purified using column chromatography using 50% ethyl acetate/hexane as eluent to give A106 as a yellow sticky mass (0.08 g, 34.33%). MS (ESI) m/z=539.2 [M+H]$^+$.

Step 2: Preparation of N-(3-((2,3-dihydro-1H-inden-2-yl)amino)-2-hydroxypropyl)-6-trifluoromethyl)imidazo[1,2-a]pyridine-2-carboxamide (Example 96)

A solution of N-(3-((2,3-dihydro-1H-inden-2-yl)(4-methoxybenzyl)amino)-2-hydroxypropyl)-6-(trifluoromethyl)imidazo[1,2-a]pyridine-2-carboxamide (A102, 0.08 g, 0.148 mmol) in trifluoroacetic acid (1 mL) was heated at 120° C. for 2 h in a microwave. The reaction mixture was concentrated, basified with sodium bicarbonate solution and was extracted with ethyl acetate. The combined organic layer washed with brine solution, dried over anhydrous sodium sulphate and then concentrated under reduced pressure to give crude product. The compound was purified by column chromatography using 7% methanol/dichloromethane as eluent to give the title Example 96 as white solid (0.0085 g, 13.7%). $^1$H NMR (DMSO-d$_6$, 400 MHz, ppm): δ 9.26 (s, 1H), 8.44 (s, 1H), 8.38 (bs, 1H), 7.78 (s, J=9.2 Hz 1H), 7.58 (d, J=9.2 Hz, 1H), 7.14 (s, 2H), 7.08-7.07 (m, 2H), 4.94 (d, J=4.8 Hz, 1H), 3.65-3.64 (m, 1H), 3.47-3.35 (m, 2H), 3.05-3.00 (m, 3H), 2.65 (s, 2H), 2.58-2.54 (m, 2H); MS (ESI) m/z 419.2 [M+H]$^+$.

N-(3-((2,3-dihydro-1H-inden-2-yl)amino)-2-hydroxypropyl)-6-(tetrahydro-2H-pyran-4-yl)imidazo[1,2-a]pyridine-2-carboxamide (Example 97)

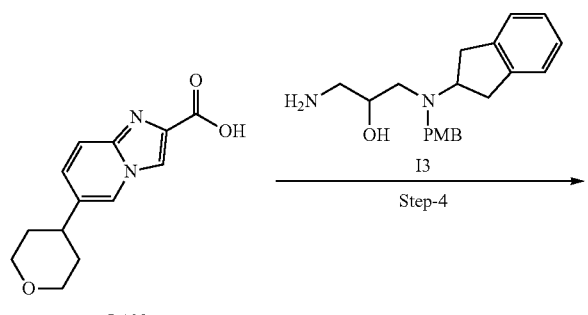

I-123

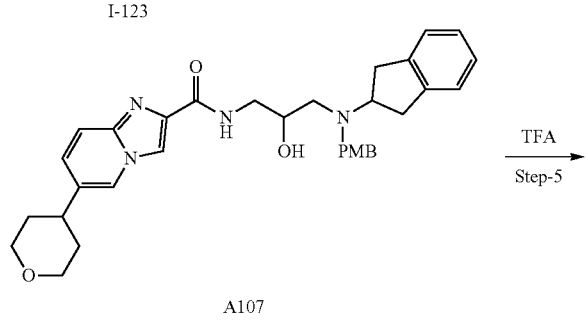

A107

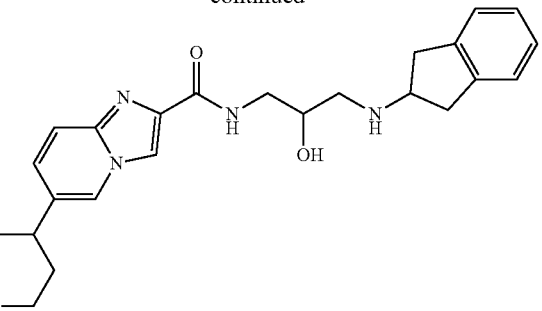

Example 97

Step-4: N-(3-((2,3-dihydro-1H-inden-2-yl)(4-methoxybenzyl)amino)-2-hydroxypropyl)-6-(tetrahydro-2H-pyran-4-yl)imidazo[1,2-a]pyridine-2-carboxamide (7)

To a solution of 6-(tetrahydro-2H-pyran-4-yl)imidazo[1,2-a]pyridine-2-carboxylic acid (I-123, 0.30 g, 1.21 mmol) in DMF (15 mL) was added DIPEA (0.60 mL, 3.63 mmol) followed by HATU (0.55 g, 1.45 mmol). The reaction mixture was stirred for 10 min followed by addition of 1-amino-3-((2,3-dihydro-1H-inden-2-yl)(4-methoxybenzyl)amino)propan-2-ol (I-3, 0.59 g, 1.81 mmol). The reaction mixture was stirred at room temperature for 16 h. The reaction was monitored till the completion of starting materials (LC/MS) and then concentrated under reduced pressure. The obtained crude was purified by column chromatography using 0-10% methanol/dichloromethane as the eluent to afford N-(3-((2,3-dihydro-1H-inden-2-yl)(4-methoxybenzyl)amino)-2-hydroxypropyl)-6-(tetrahydro-2H-pyran-4-yl)imidazo[1,2-a]pyridine-2-carboxamide (A107) White solid Yield: 0.35 g, 53%). LC-MS (ES) m/z: 555.19 [M+H]$^+$ Step-5: N-(3-((2,3-dihydro-1H-inden-2-yl)amino)-2-hydroxypropyl)-6-(tetrahydro-2H-pyran-4-yl)imidazo[1,2-a]pyridine-2-carboxamide To a solution of N-(3-((2,3-dihydro-1H-inden-2-yl)(4-methoxybenzyl)amino)-2-hydroxypropyl)-6-(tetrahydro-2H-pyran-4-yl)imidazo [1,2-a]pyridine-2-carboxamide (A107, 0.20 g, 0.36 mmol) in TFA (4 mL). The reaction mixture was stirred in a microwave at 120° C. After completion of reaction organic solvent was evaporated. The obtained crude was purified by prep-HPLC to afford N-(3-((2,3-dihydro-1H-inden-2-yl)amino)-2-hydroxypropyl)-6-(tetrahydro-2H-pyran-4-yl)imidazo[1,2-a]pyridine-2-carboxamide Example 97 as off white solid Yield: 0.045 g (30%) LC-MS (ES) m/z: 435.20 [M+H]$^+$ $^1$H NMR (DMSO-d$_6$, 400 MHz, ppm) δ 8.43 (s, 1H), 8.32 (bs, 1H), 8.29 (s, 1H), 7.53 (d, J=9.28 Hz, 1H), 7.35 (d, J=9.28 Hz, 1H), 7.18 (d, J=3.08 Hz, 2H), 7.12 (d, J=2.92 Hz, 2H), 5.43 (bs, 1H), 3.96 (d, J=7.72 Hz, 1H), 3.80 (bs, 1H), 3.67 (bs, 1H), 3.44-3.32 (m, 5H), 3.15-3.10 (m, 2H), 2.81-2.67 (m, 5H), 1.77 (d, J=11.36 Hz, 2H), 1.68-1.62 (m, 2H).

6-(1-acetylpiperidin-4-yl)-N-(3-((2,3-dihydro-1H-inden-2-yl)amino)-2-hydroxypropyl)imidazo[1,2-a]pyridine-2-carboxamide (Example 98)

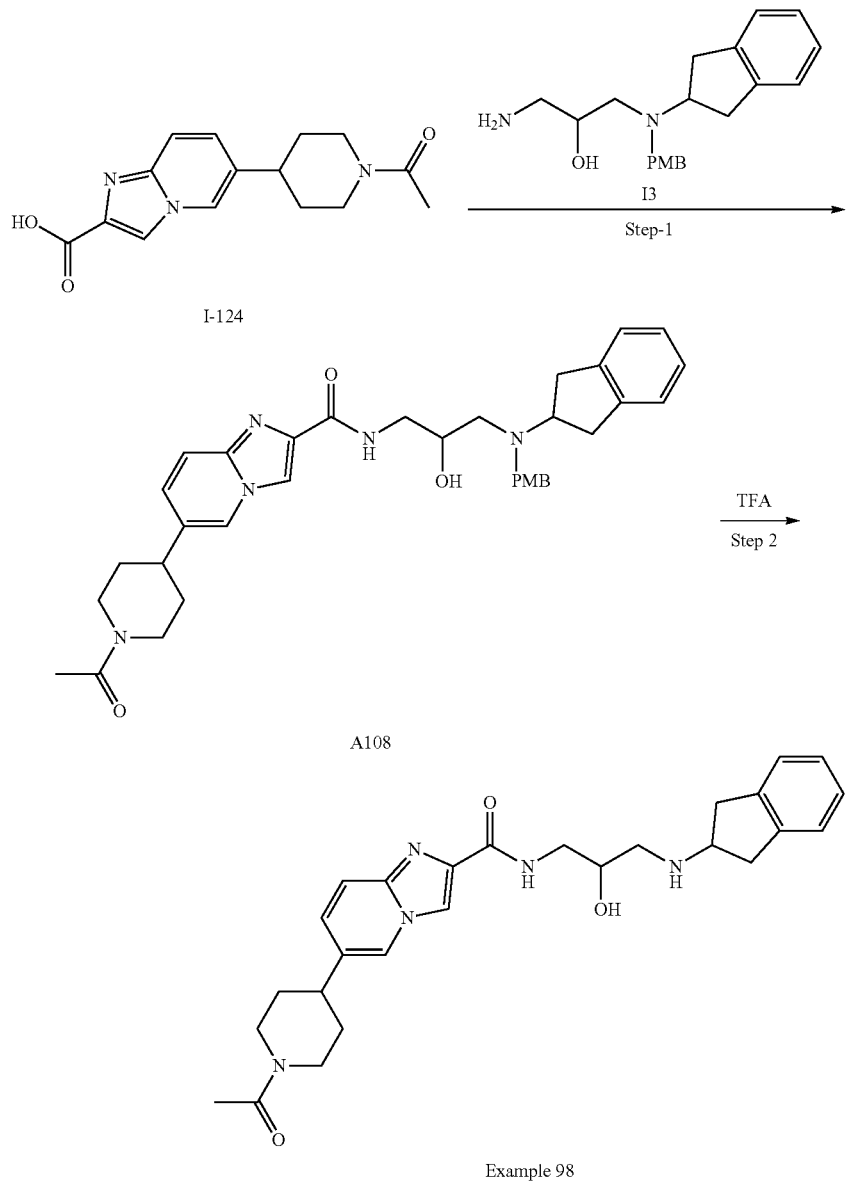

Example 98

Step 1: 6-(1-acetylpiperidin-4-yl)-N-(3-((2,3-dihydro-1H-inden-2-yl)(4-methoxybenzyl)amino)-2-hydroxypropyl)imidazo[1,2-a]pyridine-2-carboxamide (A108)

To a solution of 6-(1-acetylpiperidin-4-yl)imidazo[1,2-a]pyridine-2-carboxylic acid (I-124, 0.75 g, 2.61 mmol) in DMF (15 mL) was added DIPEA (1.4 mL, 7.83 mmol) followed by HATU (1.48 g, 3.91 mmol). The reaction mixture was stirred for 10 min followed by addition of 1-amino-3-((2,3-dihydro-1H-inden-2-yl)(4-methoxybenzyl)amino)propan-2-ol (I-3, 1.28 g, 3.91 mmol). The reaction mixture was stirred at room temperature for 16 h. The reaction was monitored till the completion of starting materials (LC/MS) and then concentrated under reduced pressure. The obtained crude was purified by column chromatography using 0-10% methanol/dichloromethane as the eluent to afford 6-(1-acetylpiperidin-4-yl)-N-(3-((2,3-dihydro-1H-inden-2-yl)(4-methoxybenzyl)amino)-2-hydroxypropyl)imidazo[1,2-a]pyridine-2-carboxamide A108 as Yellow solid (0.80 g, 53%). LC-MS (ES) m/z: 496.24 [M+H]$^+$ Step-2: 6-(1-acetylpiperidin-4-yl)-N-(3-((2,3-dihydro-1H-inden-2-yl)amino)-2-hydroxypropyl)imidazo[1,2-a]pyridine-2-carboxamide To a solution of 6-(1-acetylpiperidin-4-yl)-N-(3-((2,3-dihydro-1H-inden-2-yl)(4-methoxybenzyl)amino)-2-hydroxypropyl)imidazo[1,2-a]pyridine-2-carboxamide (A108, 0.140 g, 0.235 mmol) in TFA (2 mL). The reaction mixture was stirred in a microwave at 120° C. After completion of reaction organic solvent was evaporated. The obtained crude was purified by prep-HPLC to afford 6-(1-acetylpiperidin-4-yl)-N-(3-((2,3-dihydro-1H-inden-2-yl)amino)-2-hydroxypropyl)imidazo[1,2-a]pyridine-2-carboxamide Example 98 as off white solid Yield: 0.035 g (30%) LC-MS (ES) m/z: 476.25 [M+H]+ $^1$H NMR (DMSO-$d_6$, 400 MHz, ppm) δ 8.44 (s, 1H), 8.39 (dd, J=9.02 Hz, 5.04 Hz, 1H), 8.29 (s, 1H), 7.53 (d, J=9.40 Hz, 1H), 7.34 (d, J=9.24 Hz, 1H), 7.20-7.13 (m, 4H), 5.43 (bs, 1H), 4.53 (d, J=12.4 Hz, 1H), 3.93 (d, J=4.84 HZ, 1H), 3.92-3.86 (m, 2H), 3.38-3.11 (m, 5H), 2.89-2.60 (m, 7H), 2.03 (s, 3H), 1.86 (t, J=13.32 Hz, 2H), 1.62-1.49 (m, 2H).

N-(3-((2,3-dihydro-1H-inden-2-yl)amino)-2-hydroxypropyl)-6-(1-methyl-2-oxo-1,2-dihydropyridin-4-yl)imidazo[1,2-a]pyridine-2-carboxamide (Example 99)

Step-3: N-(3-((2,3-dihydro-1H-inden-2-yl)(4-methoxybenzyl)amino)-2-hydroxypropyl)-6-(1-methyl-2-oxo-1,2-dihydropyridin-4-yl)imidazo[1,2-a]pyridine-2-carboxamide (A109)

To a solution of 6-(1-methyl-2-oxo-1,2-dihydropyridin-4-yl)imidazo[1,2-a]pyridine-2-carboxylic acid (I-132, 0.28 g, 1.03 mmol) in DMF (6 mL) was added DIPEA (0.51 mL, 3.11 mmol) followed by HATU (0.46 g, 1.23 mmol). The reaction mixture was stirred for 10 min followed by addition of 1-amino-3-((2,3-dihydro-1H-inden-2-yl)(4-methoxybenzyl)amino)propan-2-ol (5, 0.50 g, 1.54 mmol). The reaction mixture was stirred at room temperature for 16 h. The reaction was monitored till the completion of starting materials (LC/MS) and then concentrated under reduced pressure. The obtained crude was purified by column chromatography using 0-10% methanol/dichloromethane as the eluent to afford to N-(3-((2,3-dihydro-1H-inden-2-yl)(4-methoxybenzyl)amino)-2-hydroxypropyl)-6-(1-methyl-2-

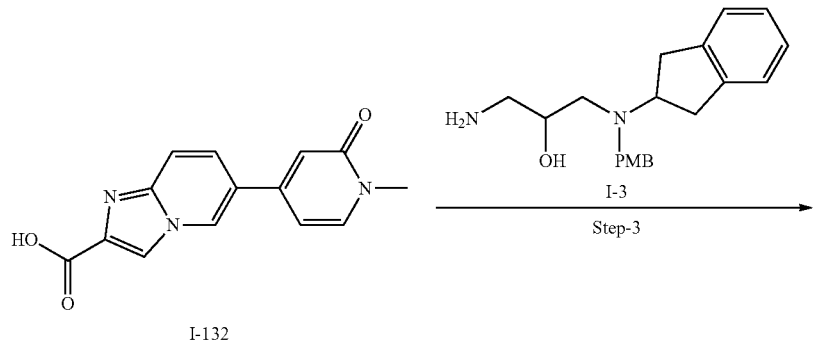

I-132

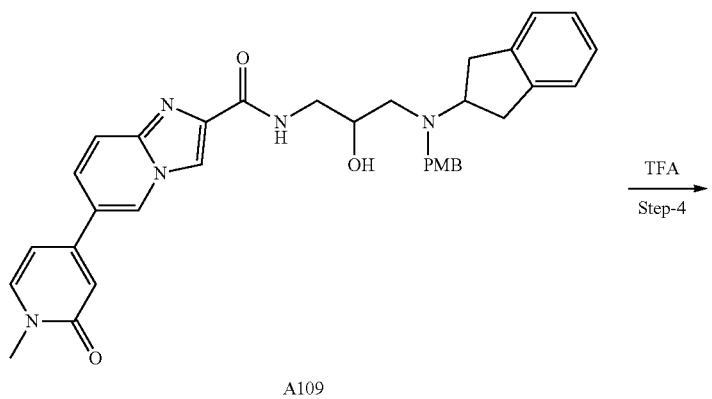

A109

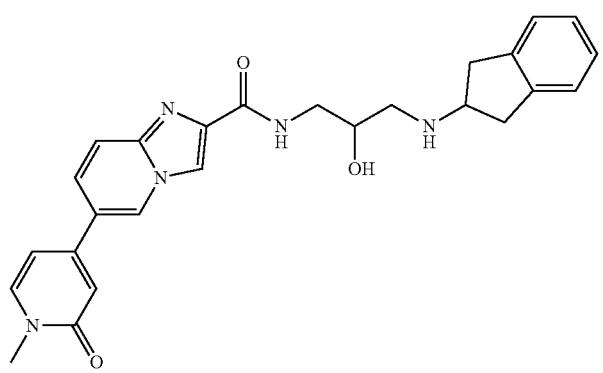

Example 99 oxo-1,2-dihydropyridin-4-yl)imidazo[1,2-a]pyridine-2-carboxamide (A109) as off white solid (0.15 g, 25%).

Step-4: N-(3-((2,3-dihydro-1H-inden-2-yl)amino)-2-hydroxypropyl)-6-(1-methyl-2-oxo-1,2-dihydropyridin-4-yl)imidazo[1,2-a]pyridine-2-carboxamide To a solution of N-(3-((2,3-dihydro-1H-inden-2-yl)(4-methoxybenzyl)amino)-2-hydroxypropyl)-6-(1-methyl-2-oxo-1,2-dihydropyridin-4-yl)imidazo[1,2-a]pyridine-2-carboxamide (A109, 0.150 g, 0.235 mmol) in TFA (4 mL). The reaction mixture was stirred in a microwave at 120° C. After completion of reaction organic solvent was evaporated. The obtained crude was purified by prep-HPLC to afford N-(3-((2,3-dihydro-1H-inden-2-yl)amino)-2-hydroxypropyl)-6-(1-methyl-2-oxo-1,2-dihydropyridin-4-yl)imidazo[1,2-a]pyridine-2-carboxamide Example 99 as off white solid Yield: 0.025 g (21%) LC-MS (ES) m/z: 458.0 [M+H]$^+$ $^1$H NMR (DMSO-d$_6$, 400 MHz, ppm) δ 9.14 (s, 1H), 8.56 (bs, 1H), 8.37 (s, 1H), 7.85 (d, J=7.12 Hz, 1H), 7.75 (d, J=9.48 Hz, 1H), 7.67 (d, J=9.56 Hz, 1H), 7.24 (d, J=3.12 Hz, 2H), 7.18 (dd, J=8.44 Hz, 5.36 Hz, 2H), 6.79 (s, 1H), 6.62-6.60 (dd, J=7.04 Hz, 1.72 Hz, 1H), 5.76 (bs, 1H), 4.01 (bs, 2H), 3.46 (s, 3H), 3.42-3.40 (m, 2H), 3.27-3.21 (m, 2H), 3.13-3.03 (m, 3H), 2.89 (t, J=11.80 Hz, 1H).

Synthesis of N-(4-(3,4-dihydroisoquinolin-2(1H)-yl)-1-hydroxybutan-2-yl)-6-(trifluoromethyl)imidazo[1,2-a]pyridine-2-carboxamide (Example 100)

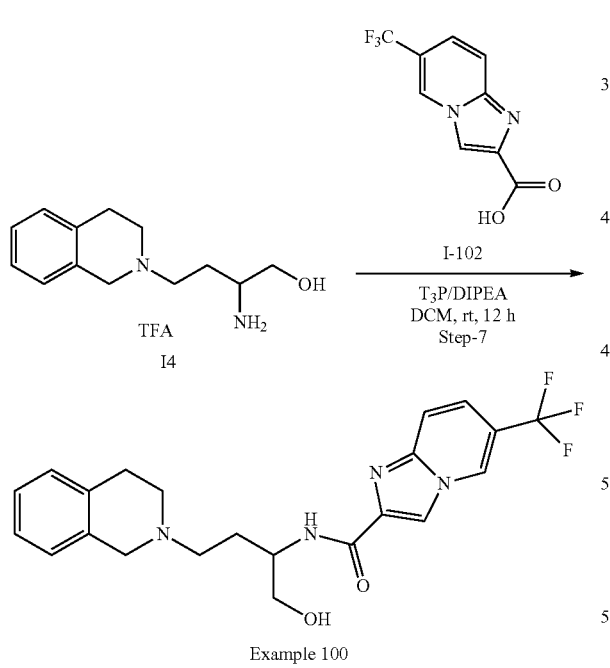

Example 100

To a solution of 6-(trifluoromethyl)imidazo[1,2-a]pyridine-2-carboxylic acid (I-102, 0.043 g, 0.18 mmol) in dichloromethane (5 mL) was added N,N-diisopropylethylamine (0.19 g, 0.6 mmol). The resulting mixture was stirred at 0° C. for 15 minutes. 2,4,6-tripropyl-1,3,5,2,4,6-trioxatriphosphorinane-2,4,6-trioxide (0.07 g, 0.2 mmol) was added into the reaction mixture and further reaction mixture was stirred for 10 minutes at 0° C. TFA salt of 2-amino-4-(3,4-dihydroisoquinolin-2(1H)-yl)butan-1-ol (I4, 0.299 g, 2.475 mmol) was added into the reaction mixture. The resulting mixture was stirred at RT or 16 h. The reaction mixture was diluted with dichloromethane and washed with ice cooled water. The organic layer dried over anhydrous sodium sulfate, concentrated to get crude residue. The crude residue was purified by column chromatography using ethyl acetate/n-hexane as eluent to afford N-(4-(3,4-dihydroisoquinolin-2(1H)-yl)-1-hydroxybutan-2-yl)-6-(trifluoromethyl) imidazo[1,2-a]pyridine-2-carboxamide as off-white solid (0.01 g, 11%). $^1$H NMR (DMSO-d$_6$, 400 MHz, ppm): δ 9.26 (s, 1H), 8.36 (d, 1H, J=4.4 Hz), 8.20-8.09 (m, 1H), 7.76 (t, 1H, J=8.4 Hz), 7.56 (d, 1H, J=9.6 Hz), 7.13-6.99 (m, 4H), 4.86 (s, 1H), 4.12-3.97 (m, 2H), 3.87 (s, 1H), 3.44 (s, 2H), 3.21 (s, 1H), 2.90 (s, 3H), 2.05-1.99 (m, 2H), 1.33 (s, 1H), 0.86 (d, 1H, J=6 Hz); MS (ESI) m/z=433.2 [M+H]$^+$.

N-(3-(3,4-dihydroisoquinolin-2(1H)-yl)-2-hydroxypropyl)-5,6,7,8-tetrahydroimidazo[1,2-a]pyridine-2-carboxamide (Example 101)

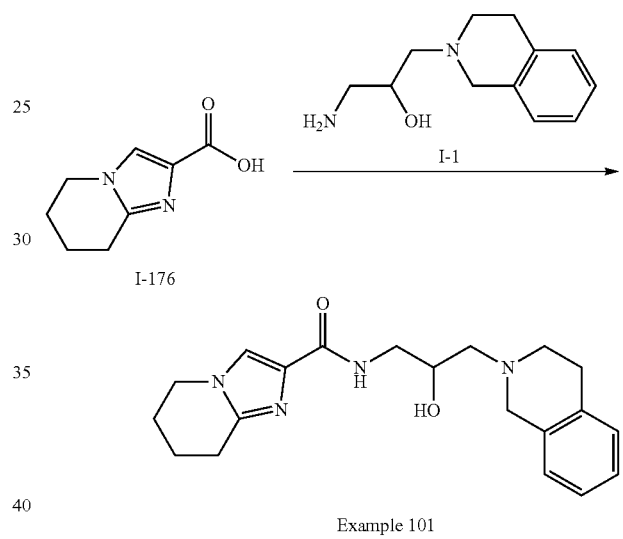

Example 101

Example 101 as an off-white solid (0.025 g, 14.5%). $^1$H NMR (400 MHz, DMSO-d$_6$): δ 7.76 (t, J=5.2 Hz, 1H), 7.42 (s, 1H), 7.04-7.07 (m, 3H), 6.98-7.00 (m, 1H), 4.84 (d, J=4.4 Hz, 1H), 3.94 (t, J=5.6 Hz, 2H), 3.79-3.83 (m, 1H), 3.58 (s, 2H), 3.33-3.39 (m, 1H), 3.16-3.22 (m, 1H), 2.80-2.81 (m, 2H), 2.71-2.76 (m, 1H), 2.64-2.70 (m, 3H), 2.40-2.45 (m, 2H), 1.79-1.85 (m, 4H). LC-MS (ES) m/z=355.5 [M+H]$^+$.

N-(3-(3,4-dihydroisoquinolin-2(1H)-yl)-2-hydroxypropyl)-6-methyl-5,6,7,8-tetrahydroimidazo[1,2-a]pyridine-2-carboxamide (Example 102)

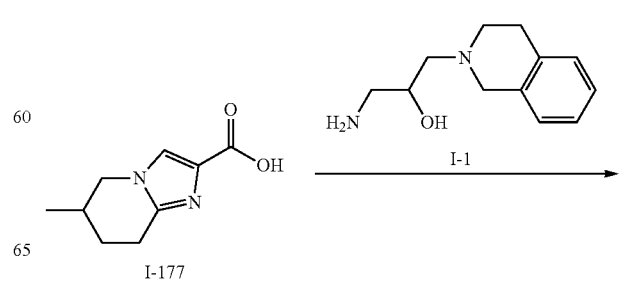

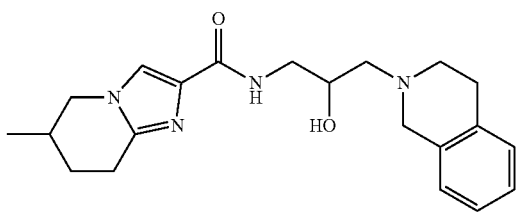

Example 102

Example 102 was prepared according to method exemplified for Example 1 starting from the acid (I-177, 0.15 g, 0.83 mmol) and (I1, 0.15 g, 0.7 mmol) as an off white solid. (0.015 g, 5.8%). $^1$H NMR (400 MHz, DMSO-$d_6$): δ 7.75 (t, J=5.2 Hz, 1H), 7.42 (s, 1H), 7.06-7.07 (m, 3H), 7.00-7.04 (m, 1H), 4.86 (bs, 1H), 4.03-4.06 (m, 1H), 3.81-3.82 (m, 1H), 3.54-3.59 (m, 2H), 3.44-3.49 (m, 1H), 3.33-3.39 (m, 1H), 3.16-3.22 (m, 1H), 2.77-2.80 (m, 2H), 2.59-2.75 (m, 4H), 2.02-2.05 (m, 1H), 1.87-1.91 (m, 1H), 1.44-1.54 (m, 1H), 1.00 (d, J=6.4 Hz, 3H)-2 of the aliphatic protons merged. MS (ESI) m/z=369.3 [M+H]$^+$.

N-(3-(3,4-dihydroisoquinolin-2(1H)-yl)-2-hydroxypropyl)-7-methyl-5,6,7,8-tetrahydroimidazo[1,2-a]pyridine-2-carboxamide (Example 103)

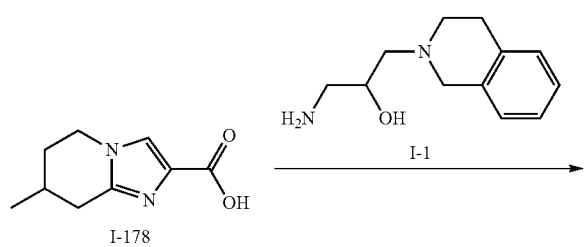

Example 103

Example 103 was prepared according to method exemplified for Example 1 starting from the acid (I-178, 0.15 g, 0.83 mmol) and (I1, 0.15 g, 0.7 mmol) as an off white solid (0.02 g, 6.6%). $^1$H NMR (400 MHz, DMSO-$d_6$): δ 7.76 (bs, 1H), 7.42 (s, 1H), 7.02-7.09 (m, 3H), 7.02-7.09 (m, 1H), 4.83 (bs, 1H), 4.02-4.06 (m, 1H), 3.82 (bs, 2H), 3.59 (bs, 1H), 3.44-3.49 (m, 1H), 3.32-3.37 (m, 1H), 3.18-3.21 (m, 1H), 2.76-2.87 (m, 2H), 2.59-2.72 (m, 5H), 2.02-2.05 (m, 2H), 1.89-1.90 (m, 1H), 1.44-1.54 (m, 1H), 1.00 (d, J=6.4 Hz, 3H). MS (ESI) m/z=369.2 [M+H]$^+$.

6-cyclopropyl-N—((S)-3-(3,4-dihydroisoquinolin-2(1H)-yl)-2-hydroxypropyl)-5,6,7,8-tetrahydroimidazo[1,2-a]pyridine-2-carboxamide (Example 104)

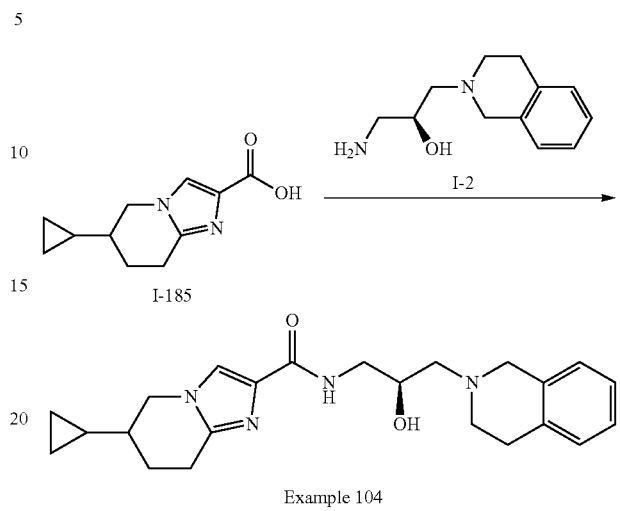

Example 104

Example 104 was prepared according to method exemplified for Example 1 starting from the acid (I-185, 0.29 g, 1.4 mmol) and (I2, 0.29 g, 1.4 mmol) as an off white solid (0.01 g, 8.7%). Compound was isolated as TFA salt since TFA was used as one of the eluent. $^1$H NMR (400 MHz, DMSO-$d_6$): δ 9.79 (br, 1H), 8.2 (br, 1H), 7.75 (br, 1H), 7.27-7.18 (m, 4H), 5.80 (br, 1H), 4.52 (br, 1H), 4.36 (br, 1H), 4.17 (br, 2H), 3.78-3.73 (m, 2H), 3.37 (s, 3H), 3.25-3.32 (m, 1H), 3.14-2.89 (m, 4H), 2.75 (br, 1H), 2.01 (br, 1H), 1.69 (d, 1H, J=6.8 Hz), 1.22 (br, 1H), 0.68 (br, 1H), 0.46 (d, 2H, J=7.2 Hz), 0.21 (t, 2H, J=9.6 Hz). MS (ESI) m/z=395.2 (M+H)$^+$.

N-(3-(3,4-dihydroisoquinolin-2(1H)-yl)-2-hydroxypropyl)-7-propyl-5,6,7,8 tetrahydroimidazo[1,2-a]pyridine-2-carboxamide (Example 105)

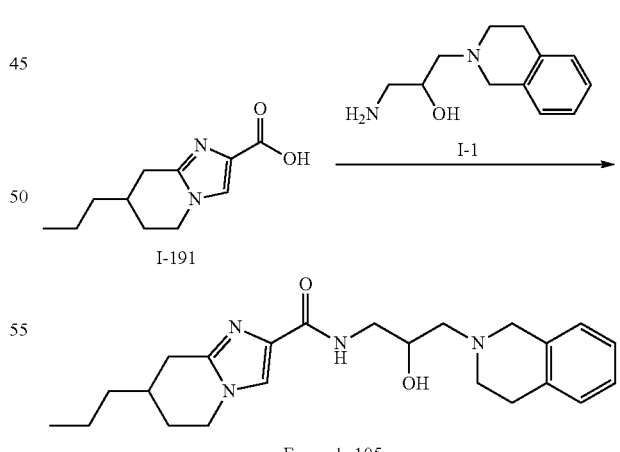

Example 105

To a stirred solution of 7-propyl-5,6,7,8-tetrahydroimidazo[1,2-a]pyridine-2-carboxylic acid (I-191, 0.09 g, 0.43 mmol) in DMF (6 mL) was added compound (I1, 0.095 g, 0.46 mmol) followed by DIPEA (0.22 mL, 1.29 mmol), HATU (0.24 g, 0.64 mmol). The reaction mixture was stirred for 16 h at room temperature. The reaction mixture was diluted with ethyl acetate, washed with water, brine, dried over anhydrous sodium sulfate, filtered and concentrated. Purification was done by preparative HPLC to afford as white solid (0.05 g, 29%). ¹H NMR (400 MHz, DMSO-d₆): δ 7.42 (s, 1H), 7.02-7.08 (m, 4H), 6.98-7.02 (m, 1H), 4.85 (bs, 1H), 4.06-4.09 (m, 1H), 3.75-3.85 (m, 2H), 3.55-3.60 (m, 2H), 3.32-3.33 (m, 1H), 3.20 (m, 1H merged with DMSO-H₂O peak), 2.65-2.82 (m, 5H), 1.95-2.05 (m, 1H), 1.65-1.75 (m, 1H), 1.50-1.65 (m, 2H), 1.25-1.35 (m, 1H), 1.10-1.20 (m, 1H), 0.90-0.92 (m, 3H), 0.65-0.75 (m, 1H), 0.41-0.43 (m, 1H), 0.16-0.17 (m, 1H); MS (ESI) m/z=397.2 (M+H)⁺.

N-(3-(3,4-dihydroisoquinolin-2(1H)-yl)-2-hydroxypropyl)-6-propyl-5,6,7,8-tetrahydroimidazo[1,2-a]pyridine-2-carboxamide (Example 106)

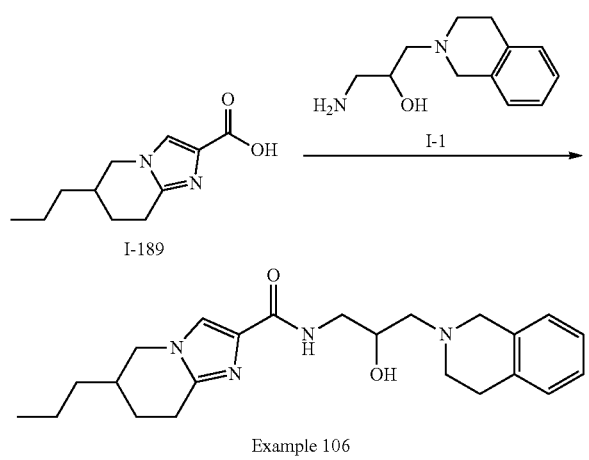

Example 106 was prepared according to method exemplified for Example 105 starting from the acid (I-189, 0.05 g, 0.24 mmol) and (I-1, 0.74 g, 0.36 mmol) as an off white solid (0.007 g, 7%). ¹H NMR (400 MHz, DMSO-d₆): δ 7.91 (bs, 1H), 7.44-7.50 (m, 1H), 7.14-7.24 (m, 3H), 5.40-5.82 (bs, 1H), 3.90-4.30 (m, 3H), 3.52-3.72 (m, 2H), 3.20-3.49 (m, 2H beneath under DMSO-H₂O peak), 2.65-2.83 (m, 5H), 1.81-2.06 (m, 2H), 1.58-1.67 (m, 1H), 1.45-1.55 (m, 1H), 1.30-1.40 (m, 2H), 0.83-0.94 (m, 3H), 0.65-0.75 (m, 1H), 0.41-0.45 (m, 1H), 0.20-0.21 (m, 1H): MS (ESI) m/z=397.3 (M+H)⁺.

(R)—N—((S)-3-(3,4-dihydroisoquinolin-2(1H)-yl)-2-hydroxypropyl)-6-methoxy-5,6,7,8-tetrahydroimidazo[1,2-a]pyridine-2-carboxamide (Example 107a) and (S)—N—((S)-3-(3,4-dihydroisoquinolin-2(1H)-yl)-2-hydroxypropyl)-6-methoxy-5,6,7,8-tetrahydroimidazo[1,2-a]pyridine-2-carboxamide (Example 107b)

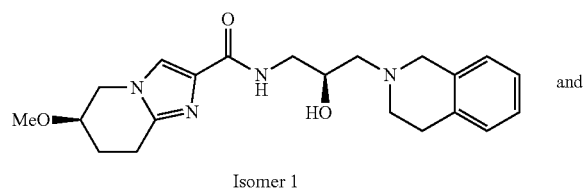

Example 107a and 107b was prepared according to method exemplified for Example 105 starting from the acid (I-186, 0.4 g, 2.0 mmol) and (I2, 0.516 g, 2.0 mmol) as white solids after purification through preparative HPLC using a chiral column Example 107a (0.020 g, 5.1%) and Example 107b (0.045 g, 12.5%).

Example 1077a

¹H NMR (400 MHz, DMSO-d₆) δ 7.77 (t, J=5.4 Hz, 1H), 7.43 (s, 1H), 7.08-7.06 (m, 3H), 7.00-6.99 (m, 1H), 4.86 (s, 1H), 4.08-4.00 (m, 2H), 3.83-3.82 (m, 2H), 3.58 (s, 2H), 3.39-3.18 (m, 4H), 2.86-2.80 (m, 2H), 2.76-2.61 (m, 4H), 2.48-2.41 (m, 2H) 2.11-2.05 (m, 1H), 1.94-1.90 (m, 1H). MS (ESI) m/z=385.2[M+H]⁺.

Example 107b

¹H NMR (400 MHz, DMSO-d₆) δ 7.77 (bs, 1H), 7.43 (s, 1H), 7.07 (bs, 3H), 7.00 (bs, 1H), 4.89 (bs, 1H), 4.04 (bs, 2H), 3.82 (bs, 2H), 3.64 (s, 2H), 3.45-3.18 (m, 6H), 2.84-2.67 (m, 6H), 2.11-2.10 (m, 1H), 1.94-1.87 (m, 1H). MS (ESI) m/z=385.2[M+H]⁺.

N—((S)-3-(3,4-dihydroisoquinolin-2(1H)-yl)-2-hydroxypropyl)-6-isopropyl-5,6,7,8-tetrahydroimidazo[1,2-a]pyridine-2-carboxamide (Example 108)

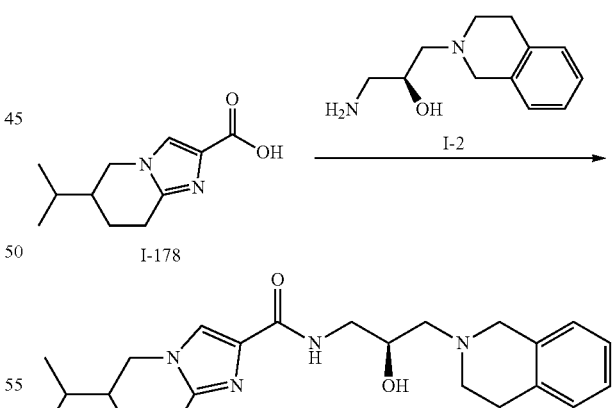

Example 108 was prepared according to method exemplified for Example 105 starting from the acid (I-178, 0.44 g, 2.12 mmol) and (I2, 0.52 g, 2.54 mmol) as an off white solid (0.125 g, 15%). ¹H NMR (400 MHz, DMSO-d₆): δ 8.64 (s, 1H), 7.82 (s, 1H), 7.32-7.22 (m, 3H), 7.18 (d, J=6.8 Hz, 1H), 4.94 (d, J=4.4 Hz, 1H), 4.60-4.46 (m, 1H), 4.42-4.28 (m, 2H), 4.26-4.14 (m, 1H), 3.78-3.62 (m, 3H), 3.42-3.24 (m, 4H), 3.22-3.10 (m, 2H), 3.02-2.92 (m, 1H), 2.86-

2.75 (m, 1H), 2.06-1.98 (m, 1H), 1.82-1.72 (m, 1H), 1.69-1.50 (m, 2H), 0.94 (d, J=6.8 Hz, 6H). MS (ESI) m/z=397.3 [M+H]⁺.

N-(3-(3,4-dihydroisoquinolin-2(1H)-yl)-2-hydroxypropyl)-7-phenyl-5,6,7,8-tetrahydroimidazo[1,2-a]pyridine-2-carboxamide (Example 109)

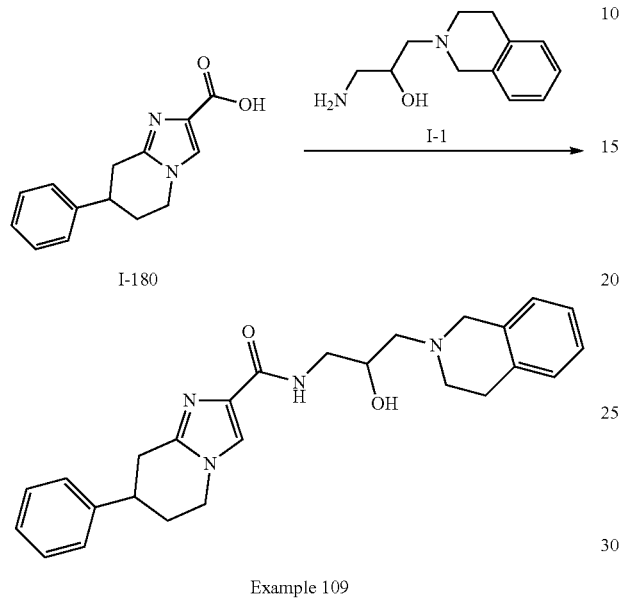

Example 109

Example 109 was prepared according to method exemplified for Example 105 starting from the acid (I-180, 0.1 g, 0.41 mmol) and (I1, 0.13 g, 0.61 mmol) as an off white solid (0.016 g, 9.5%). Compound was isolated as TFA salt since TFA was used as one of the eluent. ¹H NMR (400 MHz, DMSO-d₆): (TFA salt) δ 9.76 (bs, 1H), 8.31 (bs, 1H), 7.71 (s, 1H), 7.33-7.35 (m, 4H), 7.23-7.25 (m, 4H), 7.15-7.19 (m, 1H), 5.83 (bs, 1H), 4.32-4.36 (m, 1H), 4.13-4.18 (m, 2H), 4.03-4.074 (m, 2H), 3.26-3.45 (m, 6H), 3.07-3.11 (m, 4H), 2.92-2.95 (m, 2H). MS (ESI) m/z=431.3 [M+H]⁺.

N-(3-(3,4-dihydroisoquinolin-2(1H)-yl)-2-hydroxypropyl)-6-phenyl-5,6,7,8-tetrahydroimidazo[1,2-a]pyridine-2-carboxamide (Example 110)

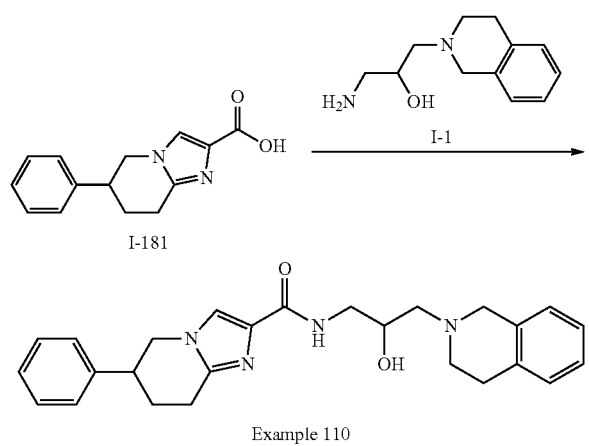

Example 110

Example 110 was prepared according to method exemplified for Example 105 starting from the acid (I-181, 0.26 g, 1.074 mmol) and (I1, 0.243 g, 1.182 mmol) as a white solid (0.225 g, 49%). ¹H NMR (400 MHz, DMSO-d₆): δ 8.60 (bs, 1H), 7.84 (s, 1H), 7.40-7.33 (m, 4H), 7.31-7.21 (m, 4H), 7.20-7.16 (m, 1H), 4.60-4.48 (m, 1H), 4.42-4.34 (m, 2H), 4.24-4.15 (m, 1H), 4.06 (t, J=12 Hz, 1H), 3.80-3.62 (m, 1H), 3.50-3.42 (m, 1H), 3.38-3.34 (m, 2H), 3.32-3.26 (m, 2H), 3.22-3.12 (m, 2H), 3.06-2.96 (m, 3H), 2.20-2.10 (m, 2H). MS (ESI) m/z=431.2 [M+H]⁺.

N-(3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 111)

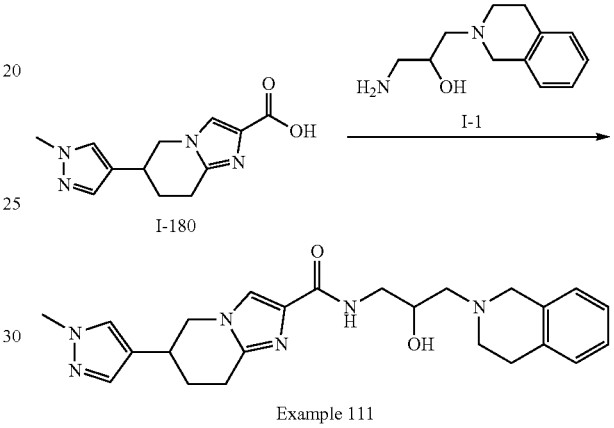

Example 111

Example 11 was prepared according to method exemplified for Example 105 starting from the acid (I-180, 0.1 g, 0.41 mmol) and (I1, 0.1 g, 0.49 mmol) as a white solid (0.044 g, 25%). ¹H NMR (400 MHz, DMSO-d₆): δ 7.78 (t, J=5.2 Hz, 1H), 7.57 (s, 1H), 7.46 (s, 1H), 7.35 (s, 1H), 7.08 (d, J=3.2 Hz, 3H), 7.02-6.98 (m, 1H), 4.86 (bs, 1H), 4.28-4.20 (m, 1H), 3.90-3.80 (m, 2H), 3.77 (s, 3H), 3.62-3.56 (m, 2H), 3.44-3.34 (m, 2H), 3.24-3.12 (m, 3H), 2.84-2.80 (m, 2H), 2.78-2.66 (m, 4H), 2.16-2.08 (m, 1H), 1.98-1.86 (m, 1H). MS (ESI) m/z=435.2 [M+H]⁺.

N—((S)-3-(3,4-dihydroisoquinolin-2(1H)-yl)-2-hydroxypropyl)-6-phenyl-5,6-dihydro-8H-imidazo[2,1-c][1,4]oxazine-2-carboxamide (Example 112)

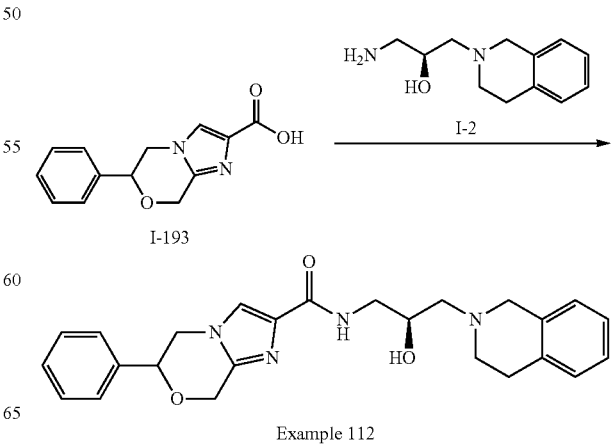

Example 112

Example 112 was prepared according to method exemplified for Example 105 starting from the acid (I-193, 0.2 g, 0.8 mmol) and (12, 0.329 g, 1.6 mmol) as a white solid (0.033 g, 9.3%). $^1$H NMR (400 MHz, DMSO-d$_6$): δ 7.86 (s, 1H), 7.58 (s, 1H), 7.46-7.42 (m, 2H), 7.39-7.35 (m, 3H), 7.07 (bs, 3H), 7.00 (bs, 1H), 5.01-4.99 (m, 1H), 4.91-4.82 (m, 3H), 4.37-4.34 (m, 1H), 3.98 (t, J=12 Hz, 1H), 3.82 (bs, 1H), 3.59 (s, 2H), 3.36-3.22 (m, 2H), 2.86-2.81 (m, 3H), 2.77-2.64 (m, 2H). MS (ESI) m/z=433.4[M+H]$^+$.

N-(3-(3,4-dihydroisoquinolin-2(1H)-yl)-2-hydroxypropyl)-7-isopropyl-5,6,7,8-tetrahydroimidazo [1,2-a] pyrazine-2-carboxamide (Example 113)

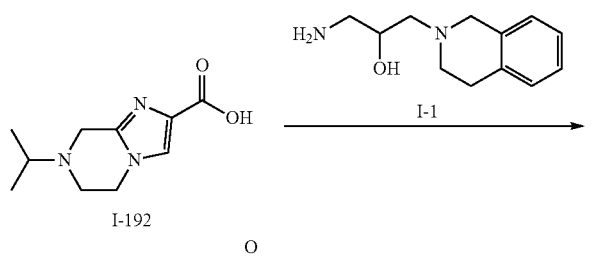

Example 113

Example 113 was prepared according to method exemplified for Example 105 starting from the acid (I-192, 0.1 g, 0.47 mmol) and (I1, 0.12 g, 0.574 mmol) as a white solid (0.02 g, 10%). $^1$H NMR, (400 MHz, CDCl$_3$): δ 7.41-7.42 (m, 2H), 7.10-7.12 (m, 3H), 6.99 (d, J=5.2 Hz, 1H), 3.79-3.82 (m, 1H), 3.75 (s, 2H), 3.59-3.67 (m, 3H), 3.40-3.47 (m, 1H), 2.89-2.96 (m, 6H), 2.73 (t, J=5.6 Hz, 1H), 2.58 (d, J=6.4 Hz, 2H), 1.13 (d, J=7.2 Hz, 6H); MS (ESI) m/z=398.0 (M+H)$^+$.

N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 114)

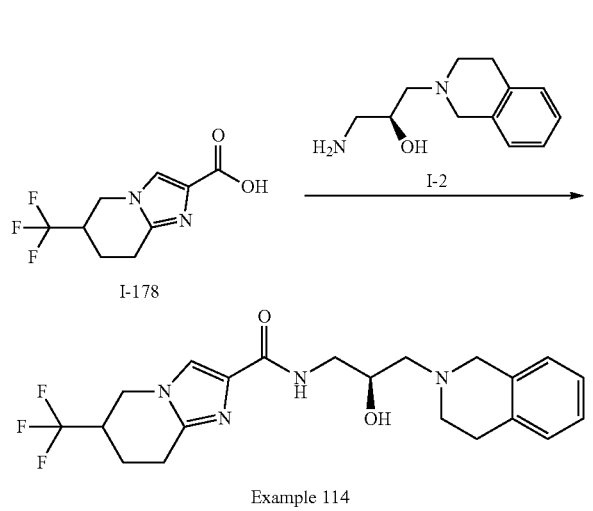

Example 114

To a stirred solution of 6-(trifluoromethyl)-5,6,7,8-tetrahydroimidazo[1,2-a]pyridine-2-carboxylic acid (I-178, 0.64 g, 2.74 mmol) in DCM (10 mL) was added (S)-1-amino-3-(3,4-dihydroisoquinolin-2(1H)-yl)propan-2-ol (I2, 0.68 g, 3.28 mmol) and triethylamine (1.14 mL, 8.21 mmol). Then reaction mixture was cooled to 0° C. and T$_3$P (2.78 mL, 4.38 mmol) was added at the same temperature. The reaction mixture was then stirred at RT for 3 h. After completion of the reaction, the reaction mixture was washed with water and brine. The organic layer was dried over anhydrous Na$_2$SO$_4$, filtered and concentrated under reduced pressure. Purification was done by Pre-HPLC in to afford Example 114 as a white solid (0.032 g, 3%). $^1$H NMR (400 MHz, DMSO-d$_6$): δ 7.8 (t, J=5.2 Hz, 1H), 7.53 (s, 1H), 7.10-6.98 (m, 4H), 4.85 (bs, 1H), 4.35-4.28 (m, 1H), 3.97 (t, J=10.4 Hz, 1H), 3.86-3.78 (m, 1H), 3.58 (s, 2H), 3.42-3.32 (m, 1H), 3.24-3.12 (m, 3H), 2.88-2.78 (m, 4H), 2.69-2.61 (m, 3H), 2.2-2.12 (m, 1H), 1.95-1.82 (m, 1H). MS (ESI) m/z=423.2 [M+H]$^+$.

N—((S)-3-(3,4-dihydroisoquinolin-2(1H)-yl)-2-hydroxypropyl)-6-(4-fluorophenyl)-5,6,7,8-tetrahydroimidazo[1,2-a]pyridine-2-carboxamide (Example 115)

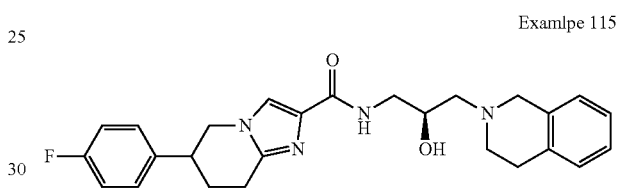

Examlpe 115

Example 15 was prepared according to method exemplified for Example 114 starting from the acid (I-89, 0.1 g, 0.39 mmol) and (12, 0.1 g, 0.46 mmol) as a white solid (0.017 g, 10%). $^1$H NMR (400 MHz, DMSO-d$_6$): δ 7.80 (t, J=5.6 Hz, 1H), 7.49 (s, 1H), 7.42-7.36 (m, 2H), 7.17 (t, J=8.8 Hz, 2H), 7.10-7.04 (m, 3H), 7.02-6.98 (m, 1H), 4.87 (d, J=3.6 Hz, 1H), 4.28-4.18 (m, 1H), 3.94 (t, J=12 Hz, 1H), 3.88-3.80 (m, 1H), 3.60 (s, 2H), 3.42-3.16 (m, 5H), 2.90-2.80 (m, 4H), 2.78-2.70 (m, 1H), 2.68-2.62 (m, 1H), 2.14-2.02 (m, 2H). MS (ESI) m/z=449.2 [M+H]$^+$.

N—((S)-3-(3,4-dihydroisoquinolin-2(1H)-yl)-2-hydroxypropyl)-6-(4-fluorophenyl)-5,6-dihydro-8H-imidazo[2,1-c][1,4]oxazine-2-carboxamide (Example 116)

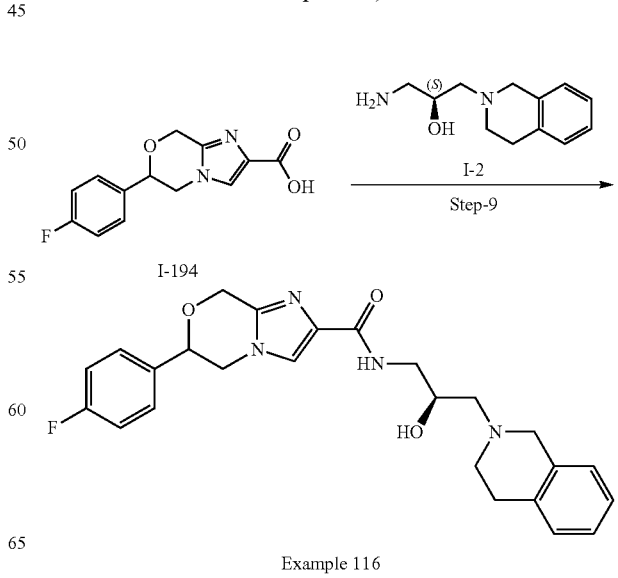

Example 116

To a stirred solution of 6-(4-fluorophenyl)-5,6-dihydro-8H-imidazo[2,1-c][1,4]oxazine-2-carboxylic acid (11, 0.3 g 1.14 mmol) in DMF (4 mL), HATU (0.652 g, 1.71 mmol) and DIPEA (0.99 mL, 5.72 mmol) were added and reaction mixture stirred at room temperature for 10 minutes. Then (S)-1-amino-3-(3,4-dihydroisoquinolin-2(1H)-yl)propan-2-ol (12, 0.353 g, 1.71 mmol) was added dissolving in DMF (2 mL) and reaction mixture stirred at room temperature for 16 h. After completion, evaporated the solvent from reaction mixture to obtain the residue. This residue diluted with water and extracted with 10% MeOH in DCM (3 times). The organic layer was separated, dried over anhydrous sodium sulphate and concentrated under reduced pressure to obtain the crude. This crude purified by combiflash using 5.0% MeOH in DCM as eluent. The desired fractions were concentrated under reduced pressure and again purified by prep HPLC to offered N—((S)-3-(3,4-dihydroisoquinolin-2(1H)-yl)-2-hydroxypropyl)-6-(4-fluorophenyl)-5,6-dihydro-8H-imidazo[2,1-c][1,4]oxazine-2-carboxamide as off white solid. Yield: 0.062 g (12%) LC-MS (ES) m/z=451.16 [M+H]⁺. 1H NMR (400 MHz, DMSO-d6) δ 8.14 (bs, 1H), 7.68 (s, 1H), 7.53 (dd, J=8.0, 5.6 Hz, 2H), 7.29-7.17 (m, 6H), 5.87 (bs, 1H), 5.06-4.92 (m, 3H), 4.59-4.51 (m, 1H), 4.42-4.32 (m, 3H), 4.17 (bs, 2H), 4.03 (t, J=11.6 Hz, 1H), 3.68 (bs, 1H), 3.32 (bs, 3H), 3.21-3.08 (m, 2H).

N-((2S,3S)-4-(3,4-dihydroisoquinolin-2(1H)-yl)-2,3-dihydroxybutyl)-6-(trifluoromethyl)-5,6,7,8-tetrahydroimidazo[1,2-a]pyridine-2-carboxamide (Example 117)

Step-1: N-(((4S,5S)-5-((3,4-dihydroisoquinolin-2(1H)-yl)methyl)-2,2-dimethyl-1,3-dioxolan-4-yl)methyl)-6-(trifluoromethyl)-5,6,7,8-tetrahydroimidazo[1,2-a]pyridine-2-carboxamide (A110)

To a stirred solution of 6-(trifluoromethyl)-5,6,7,8-tetrahydroimidazo[1,2-a]pyridine-2-carboxylic acid (I-183A, 0.4 g 1.69 mmol) in DMF (3 mL), HATU (0.966 g, 2.54 mmol) and DIPEA (0.88 mL, 5.08 mmol) were added and reaction mixture stirred at room temperature for 10 minutes. Then ((4S,5S)-5-((3,4-dihydroisoquinolin-2(1H)-yl)methyl)-2,2-dimethyl-1,3-dioxolan-4-yl)methanamine (A89, 0.467 g, 1.69 mmol) was added dissolving in DMF (2 mL) and reaction mixture stirred at room temperature for 16 h. After completion, reaction mixture quenched with water and extracted with ethyl acetate (3 times). The organic layer was separated, dried over anhydrous sodium sulphate and concentrated under reduced pressure to obtain the crude. This crude purified by combiflash using 4.5% MeOH in DCM as eluent. The desired fractions were concentrated under reduced pressure to offered N-(((4S,5S)-5-((3,4-dihydroisoquinolin-2(1H)-yl)methyl)-2,2-dimethyl-1,3-dioxolan-4-yl)methyl)-6-(trifluoromethyl)-5,6,7,8-tetrahydroimidazo[1,2-a]pyridine-2-carboxamide (A110) as brown gummy solid. Yield: 0.42 g (48%) LC-MS (ES) m/z=493.28 [M+H]⁺.

Step-2: N-((2S,3S)-4-(3,4-dihydroisoquinolin-2(1H)-yl)-2,3-dihydroxybutyl)-6-(trifluoromethyl)-5,6,7,8-tetrahydroimidazo[1,2-a]pyridine-2-carboxamide To a stirred solution of N-(((4S,5S)-5-((3,4-dihydroisoquinolin-2(1H)-yl)methyl)-2,2-dimethyl-1,3-dioxolan-4-yl)methyl)-6-(trifluoromethyl)-5,6,7,8-tetrahydroimidazo[1,2-a]pyridine-2-carboxamide (3, 0.4 g 0.81 mmol) in MeOH (3 mL) at 0° C., 4N HCl in dioxane was added and reaction mixture stirred at room temperature for 4 h. After completion, evaporated the solvent from reaction mixture to obtain the residue. This residue quenched with NaHCO₃ solution and extracted with ethyl acetate (3 times). The organic layer was separated, dried over anhydrous sodium sulphate and concentrated under reduced pressure to obtain the crude. This crude washed with diethyl ether and on high vacuum pump to offered N-((2S,3S)-4-(3,4-dihydroisoquinolin-2(1H)-yl)-2,3-dihydroxybutyl)-6-(trifluoromethyl)-5,6,7,8-tetrahydroimidazo[1,2-a]pyridine-2-carboxamide as white solid. Yield: 0.124 g (32%) LC-MS (ES) m/z=453.18 [M+H]⁺. 1H NMR (400 MHz, DMSO-d6) δ 7.76 (t, J=2.5 Hz, 1H), 7.55 (s, 1H), 7.09-7.0 (m, 4H), 4.8 (d, J=5.6 Hz, 1H), 4.53 (d, J=4.8 Hz, 1H), 4.33 (dd, J=12.0, 4.7 Hz, 1H), 3.99 (t, J=11.8 Hz, 1H), 3.64-3.56 (m, 4H), 3.43-3.4 (m, 1H), 3.21-3.19 (m, 2H), 2.91-2.84 (m, 2H), 2.78 (bs, 2H), 2.72-2.66 (m, 2H), 2.62-2.6 (m, 2H), 2.19-2.16 (m, 1H), 1.93-1.9 (m, 1H).

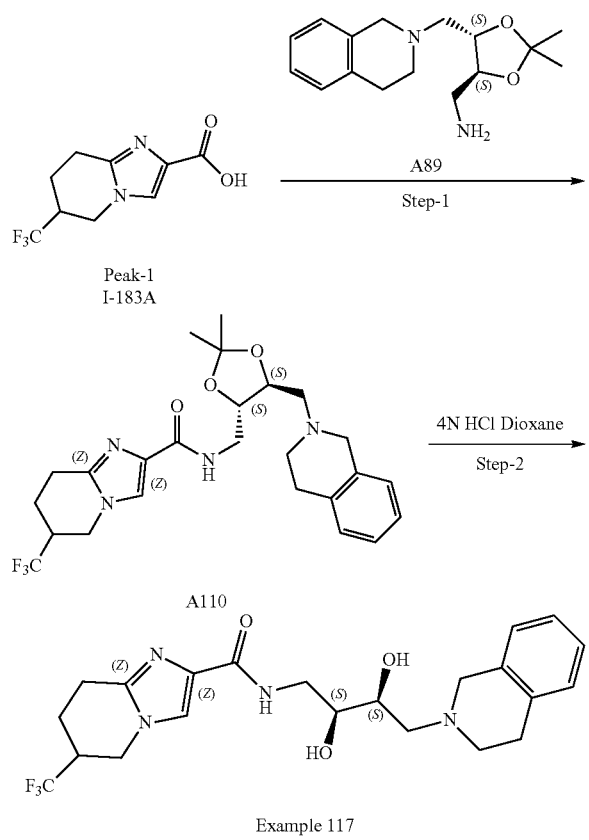

Example 117

6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide-Isomer-1 (Example 118B)
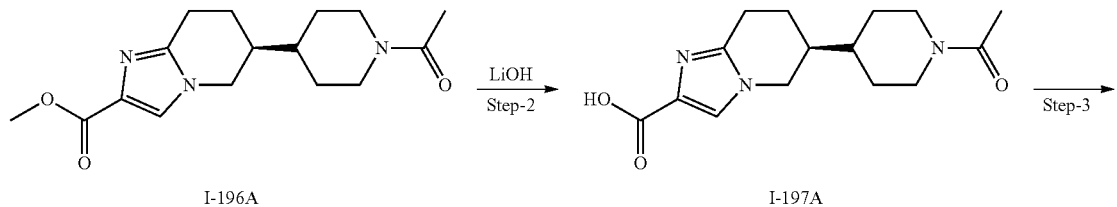
I-196A        I-197A
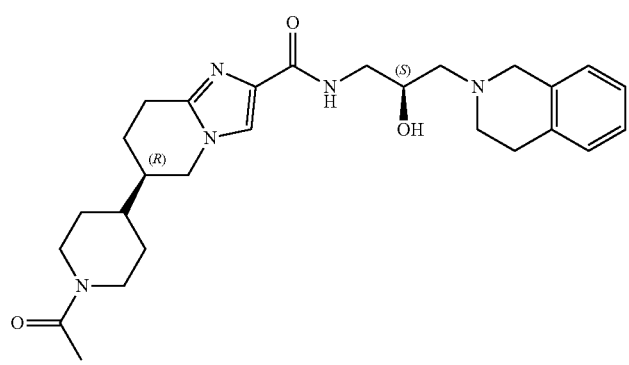
Example 118A
Isomer 1
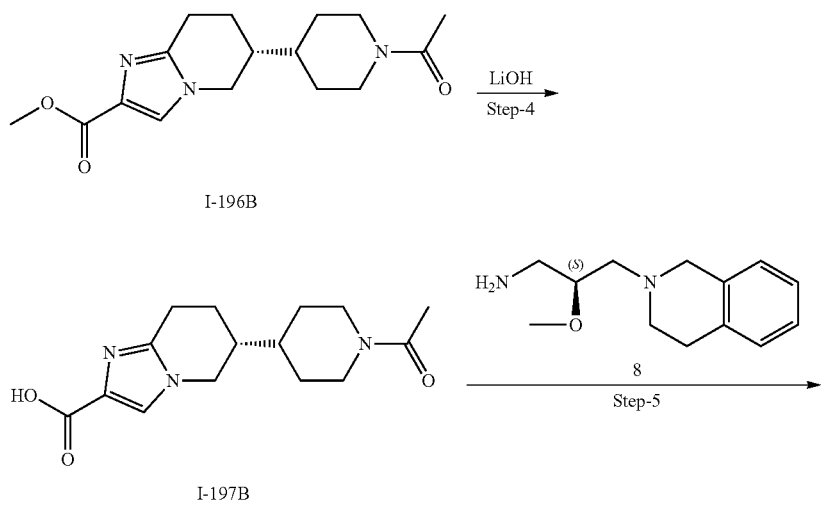
I-196B
I-197B
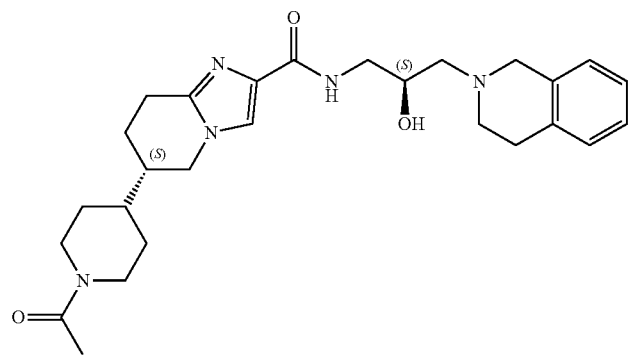
Example 118B

Step-1: methyl 6-(1-acetylpiperidin-4-yl)-5,6,7,8-tetrahydroimidazo[1,2-a]pyridine-2-carboxylate (1196A and 1196B)

To a solution of methyl 6-(piperidin-4-yl)-5,6,7,8-tetrahydroimidazo[1,2-a]pyridine-2-carboxylate (I-, 1.20 g, 4.55 mmol) in DCM (25 mL) at 0° C. was added TEA (1.90 mL, 13.67 mmol) and acetyl chloride (0.48 mL, 6.82 mmol) was added and the resulting solution was stirred at room temperature for 4 h. After completion of reaction diluted with DCM and washed with water the organic layer was dried over anhydrous sodium sulfate, filtered and concentrated under reduced pressure to get crude which was purified by prep-HPLC to afford methyl 6-(1-acetylpiperidin-4-yl)-5,6,7,8-tetrahydroimidazo[1,2-a]pyridine-2-carboxylate 6 as a white solid. Yield: 0.25 g (15%) LC-MS (ES) m/z: 306.12 [M+H]+ which was purified by chiral-HPLC to afford methyl 6-(1-acetylpiperidin-4-yl)-5,6,7,8-tetrahydroimidazo[1,2-a]pyridine-2-carboxylate 1196: 1196A and 1196B & 2 as a white solid. (Peak-1) Yield: 0.090 g and (Peak-2) Yield: 0.12 g.

Step-2: 6-(1-acetylpiperidin-4-yl)-5,6,7,8-tetrahydroimidazo[1,2-a]pyridine-2-carboxylic acid (I197A)

To a stirred solution of methyl 6-(1-acetylpiperidin-4-yl)-5,6,7,8-tetrahydroimidazo[1,2-a]pyridine-2-carboxylate (I196A, 0.09 g, 0.29 mmol) in (6 mL) of THF:MeOH:$H_2O$ (2:1:1) was added LiOH (0.022 g, 0.92 mmol). The reaction mixture was stirred for 3 h at room temp. After completion of reaction organic solvent was evaporated and the aqueous layer was acidified with 1N HCl up to pH 3 to 4 and aqueous layer was concentrated to get crude as a 6-(1-acetylpiperidin-4-yl)-5,6,7,8-tetrahydroimidazo[1,2-a]pyridine-2-carboxylic acid I197A as a white solid. Yield: 0.09 g (crude) LC-MS (ES) m/z: 292.16 [M+H]+

Step-3: 6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide

Example 118A

To a solution of 6-(1-acetylpiperidin-4-yl)-5,6,7,8-tetrahydroimidazo[1,2-a]pyridine-2-carboxylic acid (I197A, 0.09 g, 0.30 mmol) in DMF (6 mL) was added DIPEA (0.15 mL, 0.90 mmol) followed by HATU (0.12 g, 0.33 mmol). The reaction mixture was stirred for 10 min followed by addition of (S)-1-amino-3-(3,4-dihydroisoquinolin-2(1H)-yl)propan-2-ol (8, 0.092 g, 0.45 mmol). The reaction mixture was stirred at room temperature for 16 h. The reaction was monitored till the completion of starting materials (LC/MS) and then concentrated under reduced pressure. The obtained crude was purified by column chromatography using 0-10% methanol/dichloromethane as the eluent to afford 6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide 118A as white solid (0.015 g, 8%). LC-MS (ES) m/z: 480.37 [M+H]+ 1H NMR (DMSO-$d_6$, 400 MHz, ppm) δ 7.79 (bs, 1H), 7.44 (d, J=2.16 Hz, 1H), 7.08-7.02 (m, 4H), 4.89 (bs, 1H), 4.42 (d, J=Hz, 1H), 4.11-4.07 (dd, J=7.84 Hz, 1H), 3.83 (d, J=11.64 Hz, 2H), 3.71-3.65 (m, 1H), 3.59 (bs, 1H), 3.38-3.19 (m, 2H), 3.00-2.93 (m, 1H), 2.82-2.61 (m, 5H), 2.46-2.32 (m, 4H), 1.98 (s, 4H), 1.78-1.51 (m, 5H), 1.23-1.02 (m, 3H).

Step-4: 6-(1-acetylpiperidin-4-yl)-5,6,7,8-tetrahydroimidazo[1,2-a]pyridine-2-carboxylic acid (I197B)

To a stirred solution of methyl 6-(1-acetylpiperidin-4-yl)-5,6,7,8-tetrahydroimidazo[1,2-a]pyridine-2-carboxylate (I196B 0.12 g, 0.393 mmol) in (6 mL) of THF:MeOH:$H_2O$ (2:1:1) was added LiOH (0.028 g, 1.18 mmol). The reaction mixture was stirred for 3 h at room temp. After completion of reaction organic solvent was evaporated and the aqueous layer was acidified with 1N HCl up to pH 3 to 4 and aqueous layer was concentrated to get crude as a 6-(1-acetylpiperidin-4-yl)-5,6,7,8-tetrahydroimidazo[1,2-a]pyridine-2-carboxylic acid I197B as a white solid. Yield: 0.12 g (crude) LC-MS (ES) m/z: 292.16 [M+H]+.

Step-5: 6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide

Example 118B

To a solution of 6-(1-acetylpiperidin-4-yl)-5,6,7,8-tetrahydroimidazo[1,2-a]pyridine-2-carboxylic acid (I197B 0.12 g, 0.41 mmol) in DMF (6 mL) was added DIPEA (0.20 mL, 1.23 mmol) followed by HATU (0.17 g, 0.45 mmol). The reaction mixture was stirred for 10 min followed by addition of (S)-1-amino-3-(3,4-dihydroisoquinolin-2(1H)-yl)propan-2-ol (8, 0.120 g, 0.61 mmol). The reaction mixture was stirred at room temperature for 16 h. The reaction was monitored till the completion of starting materials (LC/MS) and then concentrated under reduced pressure. The obtained crude was purified by column chromatography using 0-10% methanol/dichloromethane as the eluent to afford 6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide Example 118B as white solid (0.025 g, 13%). LC-MS (ES) m/z: 480.34 [M+H]+ 1H NMR (DMSO-$d_6$, 400 MHz, ppm) δ 7.82 (bs, 1H), 7.45 (s, 1H), 7.11-7.04 (m, 4H), 4.91 (bs, 1H), 4.42 (d, J=12.20 Hz, 1H), 4.09 (d, J=7.84 Hz, 1H), 3.84 (d, J=12.72 Hz, 2H), 3.71-3.61 (m, 2H), 3.38-3.28 (m, 2H), 3.07-2.77 (m, 5H), 2.66-2.59 (m, 5H), 1.98 (m, 4H), 1.78-1.52 (m, 5H), 1.23-1.10 (m, 3H).

N-3-(3,4-dihydroisoquinolin-2(1H)-yl)-2-hydroxypropyl)-N-methyl-6-(trifluoromethyl)-5,6,7,8-tetrahydroimidazo[1,2-a]pyridine-2-carboxamide (Example-119)

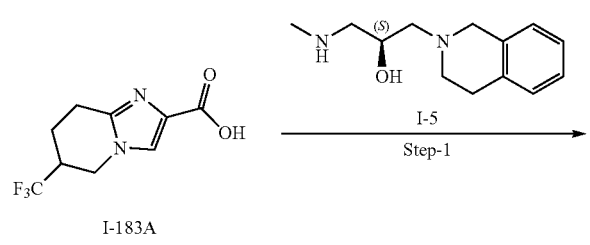

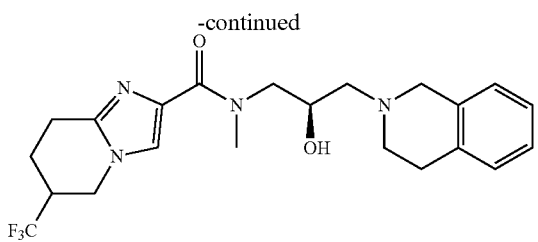

Example 119

To a stirred solution of 6-(trifluoromethyl)-5,6,7,8-tetrahydroimidazo[1,2-a]pyridine-2-carboxylic acid (I-187, 0.2 g 0.85 mmol) in DMF (3 mL), HATU (0.487 g, 1.28 mmol) and DIPEA (0.74 mL, 4.27 mmol) were added and reaction mixture stirred at room temperature for 10 minutes. Then (S)-1-(3,4-dihydroisoquinolin-2(1H)-yl)-3-(methylamino) propan-2-ol (I-5, 0.225 g, 1.02 mmol) was added dissolving in DMF (2 mL) and reaction mixture stirred at room temperature for 16 h. After completion, reaction mixture quenched with water and extracted with ethyl acetate. The organic layer was separated, dried over anhydrous sodium sulphate and concentrated under reduced pressure to obtain the crude. This crude purified by combiflash using 3.0% MeOH in DCM as eluent. The desired fractions were concentrated under reduced pressure to offered N—((R)-3-(3,4-dihydroisoquinolin-2(1H)-yl)-2-hydroxypropyl)-N-methyl-6-(trifluoromethyl)-5,6,7,8-tetrahydroimidazo[1,2-a]pyridine-2-carboxamide as white solid. Yield: 0.20 g (53%) LC-MS (ES) m/z=437.28 [M+H]$^+$. Note: compound is rotameric, two sets of peak appeared. 1H NMR (400 MHz, DMSO-d6) δ 7.52 (s, 1H), 7.09-7.01 (m, 4H), 5.56 (bs, 1H), 4.75 (bs, 1H), 4.29 (bs, 1H), 4.03 (bs, 1H), 3.93 (bs, 2H), 3.73 (bs, 1H), 3.57 (bs, 2H), 3.47 (bs, 1H), 3.13 (bs, 2H), 2.97 (s, 2H), 2.76 (bs, 4H), 2.69 (d, J=4.8 Hz, 2H), 2.44 (d, J=5.7 Hz, 3H), 2.15 (bs, 1H), 1.87 (bs, 1H). At higher temperature: 1H NMR (400 MHz, DMSO-d6) δ 7.48 (s, 1H), 7.08 (d, J=4.1 Hz, 3H), 7.01 (d, J=4.3 Hz, 1H), 4.93 (bs, 1H), 4.33-4.28 (m, 1H), 4.03-3.94 (m, 2H), 3.84 (bs, 1H), 3.62 (s, 2H), 3.53 (bs, 1H), 3.12 (bs, 2H), 2.89-2.85 (m, 1H), 2.79-2.74 (m, 5H), 2.5 (s, 3H), 2.19-2.16 (m, 1H), 1.93-1.89 (m, 1H).

(R)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 120A and 120B)

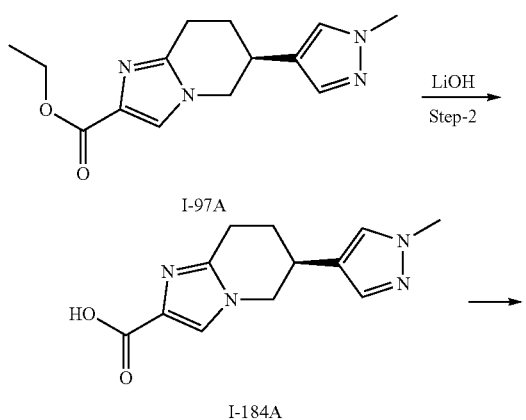

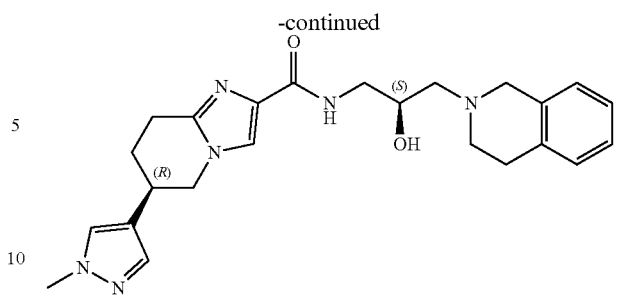

Example 120A

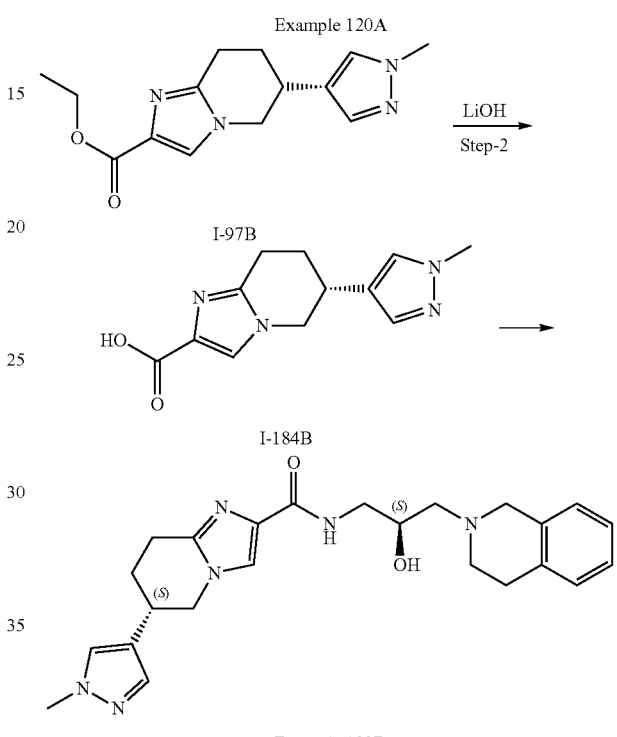

Example 120B

Step-:1 ethyl 6-(1-methyl-1H-pyrazol-4-yl)-5,6,7,8-tetrahydroimidazo[1,2-a]pyridine-2-carboxylate (2)

To a stirred solution of ethyl 6-(1-methyl-1H-pyrazol-4-yl)imidazo[1,2-a]pyridine-2-carboxylate (0.7 g, 2.58 mmol) in MeOH (25 mL) was added ammonium formate (0.48 g, 7.76 mmol), followed by 10% Pd/C (0.21 g). The reaction mixture was heated for 16 h at 100° C. after completion of reaction mixture filtered over celite bed and washed with EtOAC. The filtrate was washed with water, brine solution, dried over anhydrous Na$_2$SO$_4$ and concentrated under reduced pressure. The obtained crude was purified by chiral prep-HPLC to afford ethyl 6-(1-methyl-1H-pyrazol-4-yl)-5,6,7,8-tetrahydroimidazo[1,2-a]pyridine-2-carboxylat I97A and B as white solid Yield: I97A 0.12 g, (17%) & I97B 0.08 g, (11%). LC-MS m/z: 275.17 [M+H]$^+$.

Step-2: 6-(1-methyl-1H-pyrazol-4-yl)-5,6,7,8-tetrahydroimidazo[1,2-a]pyridine-2-carboxylic acid (I-184-A)

To a stirred solution of ethyl 6-(1-methyl-1H-pyrazol-4-yl)-5,6,7,8-tetrahydroimidazo[1,2-a]pyridine-2-carboxylate (I-197A, 0.12 g, 0.43 mmol) in (6 mL) of THF:MeOH:H$_2$O (2:1:1) was added LiOH (0.05 g, 1.31 mmol). The reaction mixture was stirred for 3 h at room temp. After completion of reaction organic solvent was evaporated and the aqueous layer was acidified with 1N HCl up to pH 3 to 4 and aqueous layer was concentrated to get crude as 6-(1-methyl-1H-pyrazol-4-yl)-5,6,7,8-tetrahydroimidazo[1,2-a]pyridine-2-carboxylic acid I-184A as off white solid. Yield: 0.12 g (crude) (91%) LC-MS (ES) m/z: 247.08 [M+H]⁺.

Step-3: (R)—N—((S)-3-(3,4-dihydroisoquinolin-2 (1H)-yl)-2-hydroxypropyl)-6-(1-methyl-1H-pyrazol-4-yl)-5,6,7,8-tetrahydroimidazo[1,2-a]pyridine-2-carboxamide (Example 120 A)

Eaxample 120 A

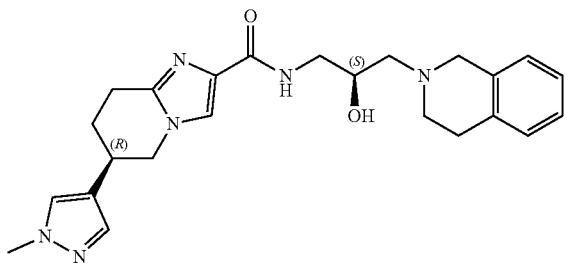

To a solution of 6-(1-methyl-1H-pyrazol-4-yl)-5,6,7,8-tetrahydroimidazo[1,2-a]pyridine-2-carboxylic acid (I-184A, 0.12 g, 0.48 mmol) in DMF (10 mL) was added DIPEA (0.25 mL, 1.46 mmol) followed by HATU (0.27 g, 0.73 mmol). The reaction mixture was stirred for 10 min followed by addition of (S)-1-amino-3-(3,4-dihydroisoquinolin-2(1H)-yl)propan-2-ol (I2, 0.12 g, 0.06 mmol). The reaction mixture was stirred at room temperature for 16 h. The reaction was monitored till the completion of starting materials and then concentrated under reduced pressure. The obtained crude was purified by Prep HPLC to afford (R)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide Example 120A as off white solid Yield: 0.009 g, (4%). LC-MS (ES) m/z: 435.35 [M+H]⁺. ¹H NMR (DMSO-d₆, 400 MHz, ppm)-δ 7.80 (dd, J=11.16 Hz, 1H), 7.58 (s, 1H), 7.47 (s, 1H), 7.36 (s, 1H), 7.09 (d, J=3.68 Hz, 3H), 7.02 (bs, 1H), 4.90 (d, J=4.60 Hz, 1H), 4.27-4.22 (dd, J=12.36 Hz, 5.12 Hz, 1H), 3.89-3.83 (m, 2H), 3.78 (s, 3H), 3.59 (s, 2H), 3.39-3.17 (m, 5H), 2.82-2.62 (m, 6H), 2.13 (d, J=11.56 Hz, 1H), 1.95-1.89 (m, 1H).

Step-2: 6-(1-methyl-1H-pyrazol-4-yl)-5,6,7,8-tetrahydroimidazo[1,2-a]pyridine-2-carboxylic acid I-184B To a stirred solution of ethyl 6-(1-methyl-1H-pyrazol-4-yl)-5,6,7,8-tetrahydroimidazo[1,2-a]pyridine-2-carboxylate (5, 0.08 g, 0.32 mmol) in (6 mL) of THF:MeOH:H₂O (2:1:1) was added LiOH (0.04 g, 0.97 mmol). The reaction mixture was stirred for 3 h at room temp. After completion of reaction organic solvent was evaporated and the aqueous layer was acidified with 1N HCl up to pH 3 to 4 and aqueous layer was concentrated to get crude as 6-(1-methyl-1H-pyrazol-4-yl)-5,6,7,8-tetrahydroimidazo[1,2-a]pyridine-2-carboxylic acid I-184B as off white solid. Yield: 0.08 g crude (93%) LC-MS (ES) m/z: 247.08 [M+H]⁺.

Step 3: (S)—N—((S)-3-(3,4-dihydroisoquinolin-2 (1H)-yl)-2-hydroxypropyl)-6-(1-methyl-1H-pyrazol-4-yl)-5,6,7,8-tetrahydroimidazo[1,2-a]pyridine-2-carboxamide (Example 120B)

Example 120B

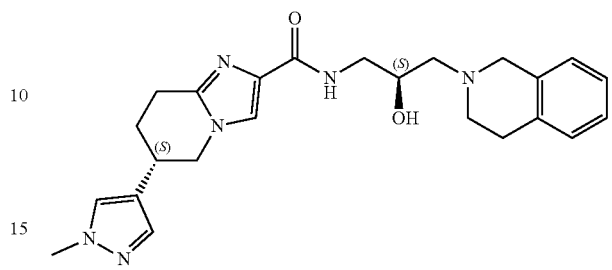

To a solution of 6-(1-methyl-1H-pyrazol-4-yl)-5,6,7,8-tetrahydroimidazo[1,2-a]pyridine-2-carboxylic acid (I-184B, 0.18 g, 0.32 mmol) in DMF (10 mL) was added DIPEA (0.17 mL, 0.97 mmol) followed by HATU (0.27 g, 0.48 mmol). The reaction mixture was stirred for 10 min followed by addition of (S)-1-amino-3-(3,4-dihydroisoquinolin-2(1H)-yl)propan-2-ol (I2, 0.08 g, 0.38 mmol). The reaction mixture was stirred at room temperature for 16 h. The reaction was monitored till the completion of starting materials and then concentrated under reduced pressure. The obtained crude was purified by Prep HPLC (S)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo [1,2-a]pyridine-2-carboxamide Example 120B as off white solid Yield: 0.019 g, (13%). LC-MS (ES) m/z: 435.40 [M+H]⁺. ¹H NMR (DMSO-d₆, 400 MHz, ppm)-δ 7.81 (dd, J=11.20 Hz, 1H), 7.58 (s, 1H), 7.47 (s, 1H), 7.36 (s, 1H), 7.09 (d, J=4.60 Hz, 3H), 7.02 (d, J=4.52 Hz, 1H), 4.90 (d, J=4.52 Hz, 1H), 4.27-4.22 (dd, J=12.36 Hz, 5.12 Hz, 1H), 3.88-3.80 (m, 2H), 3.78 (s, 3H), 3.59 (s, 2H), 3.39-3.18 (m, 3H), 2.82-2.64 (m, 6H), 2.49-2.42 (m, 2H), 2.14-2.12 (m, 1H), 1.95-1.89 (m, 1H).

(R)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121A and 121B)

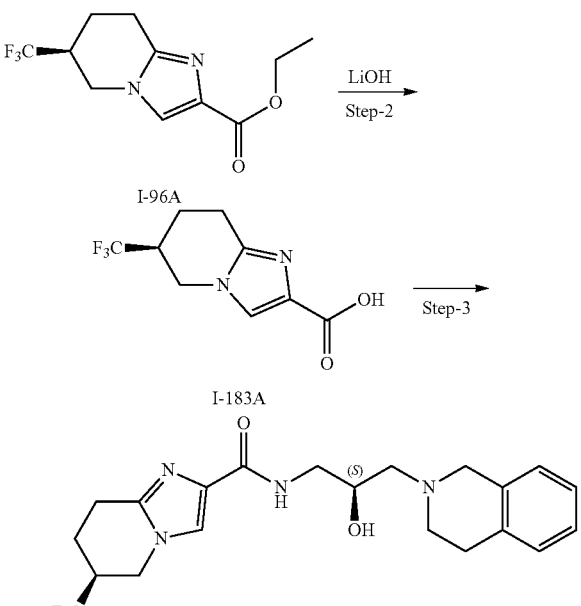

Example 121A

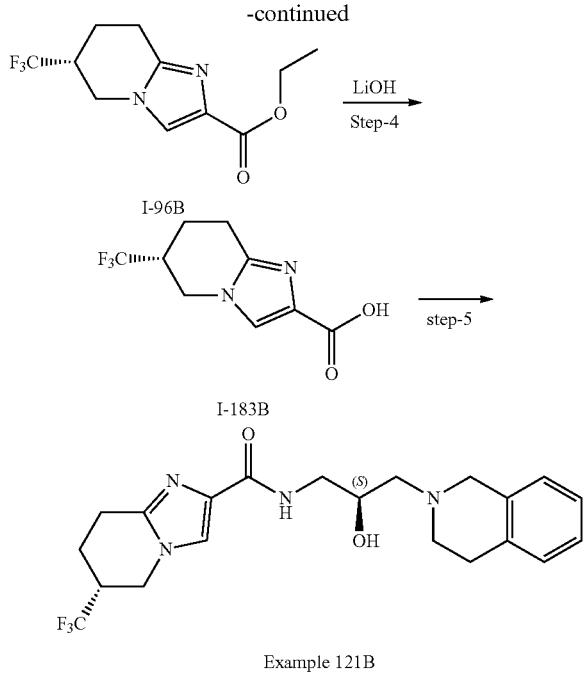

Example 121B

Step-1: ethyl (R)-6-(trifluoromethyl)-5,6,7,8-tetra-hydroimidazo[1,2-a]pyridine-2-carboxylate (I-96B) (peak1) and ethyl (S)-6-(trifluoromethyl)-5,6,7,8-tetrahydroimidazo[1,2-a]pyridine-2-carboxylate (I-96A) (peak2)

To a stirred solution of ethyl 6-(trifluoromethyl)imidazo[1,2-a]pyridine-2-carboxylate (10.0 g 38.75 mmol) in THF 200 mL, $PtO_2$ (1.4 g, 6.5 mmol) was added and reaction mixture stirred at room temperature under $H_2$ atmosphere for 48 h. After completion, reaction mixture filter through celite bed and evaporated the filtrate to obtain the crude. This crude purified by column chromatography using 30% ethyl acetate in hexane as eluent. The desired fractions were concentrated under reduced pressure to obtain the compound. This compound purified by chiral HPLC to offered ethyl (R)-6-(trifluoromethyl)-5,6,7,8-tetrahydroimidazo[1,2-a]pyridine-2-carboxylate (I-96A) as black solid. Yield: 3.2 g (31%) LC-MS (ES) m/z=263.24 [M+H]$^+$ and ethyl (S)-6-(trifluoromethyl)-5,6,7,8-tetrahydroimidazo[1,2-a]pyridine-2-carboxylate (I-96B) as black solid. Yield: 3.4 g (33.4%) LC-MS (ES) m/z=263.24 [M+H]$^+$.

Step-2: (R)-6-(trifluoromethyl)-5,6,7,8-tetrahydro-imidazo[1,2-a]pyridine-2-carboxylic acid (I-183 A)

To a stirred solution of ethyl (R)-6-(trifluoromethyl)-5,6,7,8-tetrahydroimidazo[1,2-a]pyridine-2-carboxylate (4, 3.0 g 11.45 mmol) in MeOH:THF:$H_2O$ (1:1:1) 30 mL, LiOH.$H_2O$ (0.961 g, 22.9 mmol) was added and reaction mixture stirred at room temperature for 5 h. After completion, evaporated the solvent from reaction mixture to obtain the residue. This residue diluted with water and washed with diethyl ether twice. Then aqueous layer acidified with 1N HCl and concentrated to dryness under reduced pressure to offered (R)-6-(trifluoromethyl)-5,6,7,8-tetrahydroimidazo[1,2-a]pyridine-2-carboxylic acid (I-183A) as white gummy solid. Yield: 2.3 g (79%) LC-MS (ES) m/z=235.22 [M+H]$^+$.

I-183B was prepared using a process similar for synthesizing I-183A.

Step-3: (R)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121A)

To a stirred solution of (R)-6-(trifluoromethyl)-5,6,7,8-tetrahydroimidazo[1,2-a]pyridine-2-carboxylic acid (6, 2.1 g 8.97 mmol) in DMF 15 mL, HATU (5.1 g, 13.46 mmol) and DIPEA (4.69 mL, 26.92 mmol) were added and reaction mixture stirred at room temperature for 10 minutes. Then (S)-1-amino-3-(3,4-dihydroisoquinolin-2(1H)-yl)propan-2-ol (5, 2.77 g, 13.46 mmol) was added dissolving in DMF 5 mL and reaction mixture stirred at room temperature for 16 h. After completion, evaporated the solvent from reaction mixture to obtain the residue. This residue diluted with water and extracted with 10% MeOH in DCM (3 times). The organic layer was separated, dried over anhydrous sodium sulphate and concentrated under reduced pressure to obtain the crude. This crude purified by combiflash using 5.0% MeOH in DCM as eluent. The desired fractions were concentrated under reduced pressure to offered (R)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide example 121A as white solid. Yield: 1.4 g (37%) LC-MS (ES) m/z=423.17 [M+H]$^+$. H NMR (400 MHz, DMSO-d6) δ 7.82 (t, J=5.5 Hz, 1H), 7.54 (s, 1H), 7.09-7.01 (m, 4H), 4.89 (bs, 1H), 4.32 (dd, J$_1$-3=12.4 Hz, J$_1$-2=5.2 Hz 1H), 3.98 (t, J=10.7 Hz, 1H), 3.83 (bs, 1H), 3.59 (s, 2H), 3.37 (m, 1H), 3.21 (m, 2H), 2.82-2.62 (m, 7H), 2.45 (bs, 1H), 2.16 (bs, 1H), 1.9 (m, 1H).

Similarly (S)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide Example 121B was prepared using the above protocol.

(R)-6-bromo-N-(3-(3,4-dihydroisoquinolin-2(1H)-yl)-2-hydroxypropyl)imidazo[1,2-a]pyridine-2-carboxamide (Example 122)

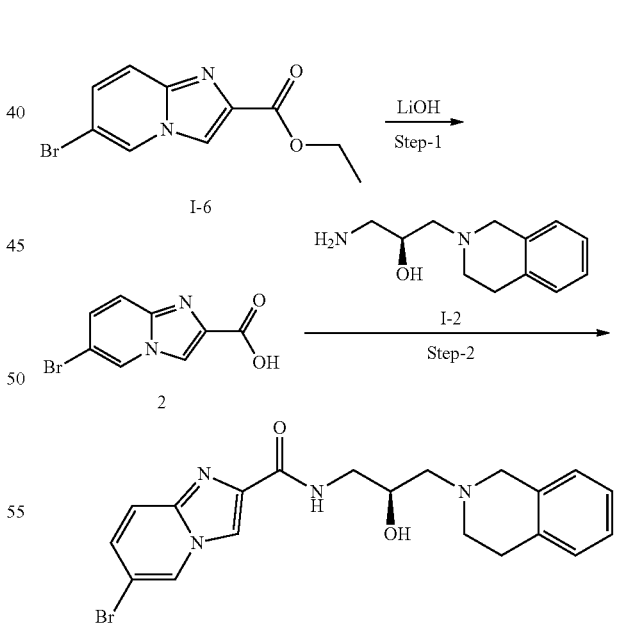

Example 122

Step-1: 6-bromoimidazo[1,2-a]pyridine-2-carboxylic acid (2)

To a stirred solution of ethyl 6-bromoimidazo[1,2-a]pyridine-2-carboxylate (I-6, 10.0 g 37.17 mmol) in (200 mL) of THF:MeOH:H$_2$O (2:1:1) was added LiOH (2.67 g, 111.52 mmol). The reaction mixture was stirred for 5 h at room temp. After completion of reaction, the organic solvent was evaporated and the aqueous layer was acidified with 1N HCl up to pH 3 to 4 and aqueous layer was concentrated to get 6-bromoimidazo[1,2-a]pyridine-2-carboxylic acid 2 as a white solid. Yield: 8.0 g (crude) LC-MS (ES) m/z: 241.05 [M+H]$^+$ Step-2: (S)-6-bromo-N-(3-(3,4-dihydroisoquinolin-2(1H)-yl)-2-hydroxypropyl)imidazo[1,2-a]pyridine-2-carboxamide (Example 122)

To a solution of 6-bromoimidazo[1,2-a]pyridine-2-carboxylic acid (2, 8.0 g, 33.33 mmol) in DMF (160 mL) was added DIPEA (16.49 mL, 99.99 mmol) followed by HATU (13.93 g, 36.66 mmol). The reaction mixture was stirred for 10 min followed by addition of (S)-1-amino-3-(3,4-dihydroisoquinolin-2(1H)-yl)propan-2-ol (I-1, 6.86 g, 33.33 mmol). The reaction mixture was stirred at room temperature for 16 h. After completion, the reaction mixture was diluted with ethyl acetate and water. The organic layer was washed with water, brine solution, dried over anhydrous Na$_2$SO$_4$ and concentrated under reduced pressure. The obtained crude was purified by column chromatography using 0-10% methanol/dichloromethane as the eluent to afford to (S)-6-bromo-N-(3-(3,4-dihydroisoquinolin-2(1H)-yl)-2-hydroxypropyl)imidazo [1,2-a]pyridine-2-carboxamide as yellow solid. Yield: 8.0 g (56%) LC-MS (ES) m/z: 430.32 [M+H]$^+$; δ 8.92 (s, 1H), 8.30 (s, 1H), 8.28 (s, 1H), 7.50-7.43 (m, 2H), 7.10-7.03 (m, 5H), 4.97 (s, 1H), 3.91 (s, 1H), 3.66 (d, J=12.24 Hz, 2H), 3.48-3.42 (m, 1H), 2.93 (s, 1H), 2.84-2.72 (m, 5H).

(S)-6-cyano-N-(3-(3,4-dihydroisoquinolin-2(1H)-yl)-2-hydroxypropyl)imidazo[1,2-a]pyridine-2-carboxamide (Example 123)

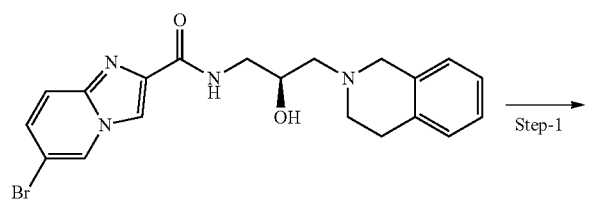

Example 122

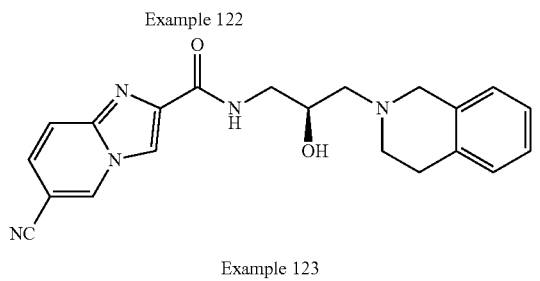

Example 123

To a solution of (S)-6-bromo-N-(3-(3,4-dihydroisoquinolin-2(1H)-yl)-2-hydroxypropyl)imidazo[1,2-a]pyridine-2-carboxamide (0.30 g, 0.692 mmol) in N,N-dimethylformamide (10 mL), zinc cyanide (0.24 g, 2.09 mmol) and zinc dust (0.0041 g, 0.034 mmol) were added at room temperature and the reaction mixture was degassed with argon for 15 min. 1,1′-Bis(diphenylphosphino)ferrocene (0.019 g, 0.034 mmol) and tris(dibenzylideneacetone)dipalladium (0.031 g, 0.034 mmol) were added to the reaction, degassed for additional 5 min and mixture was heated at 140° C. for 6 h. After completion, the reaction mass was diluted with ethyl acetate and washed with cold water. The organic layer was separated and dried over anhydrous sodium sulphate, filtered and concentrated to give crude. The crude was purified by silica gel column chromatography using 3-5% methanol in dichloromethane as eluent. The desired fractions were concentrated and further purified by prep-HPLC to afford (S)-6-cyano-N-(3-(3,4-dihydroisoquinolin-2(1H)-yl)-2-hydroxypropyl)imidazo[1,2-a]pyridine-2-carboxamide; off white solid. Yield: 0.04 g (20%). LC-MS (ES) m/z: 376.24 [M+H]$^+$, $^1$H NMR (DMSO-d$_6$, 400 MHz, ppm) δ 9.38 (s, 1H), 8.65 (dd, J=5.28 Hz, 1H), 8.45 (s, 1H), 7.77 (d, J=9.44 Hz, 1H), 7.63 (d, J=9.48 Hz, 1H), 7.29-7.17 (m, 4H), 5.90 (bs, 1H), 4.59-4.51 (m, 1H), 4.42-4.32 (m, 1H), 4.22 (bs, 1H), 3.74-3.67 (m, 2H), 3.47-3.42 (m, 2H), 3.31-3.20 (m, 2H), 3.05-2.97 (m, 2H).

(R)—N-(3-(3,4-dihydroisoquinolin-2(1H)-yl)-2-hydroxypropyl)imidazo[1,2-a]pyridine-2-carboxamide (Example 124)

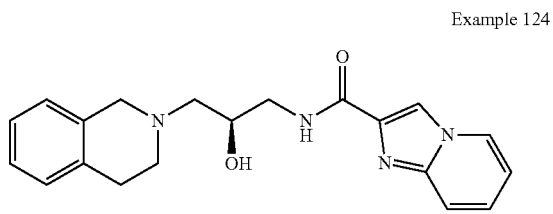 [SMILES: O=C(NC[C@@H](O)CN1CCc2ccccc2C1)c1cn2ccccc2n1]

Example 124

Example 124 was prepared according to method exemplified for Example 122. LC-MS (ES) m/z: 350.42 [M+H]$^+$ (R)—N-(3-(3,4-dihydroisoquinolin-2(1H)-yl)-2-hydroxypropyl)-6-fluoroimidazo[1,2-a]pyridine-2-carboxamide (Example 125)

Intermediate 3 was prepared as I-6, and the Example 125 was prepared according to method exemplified for Example 122

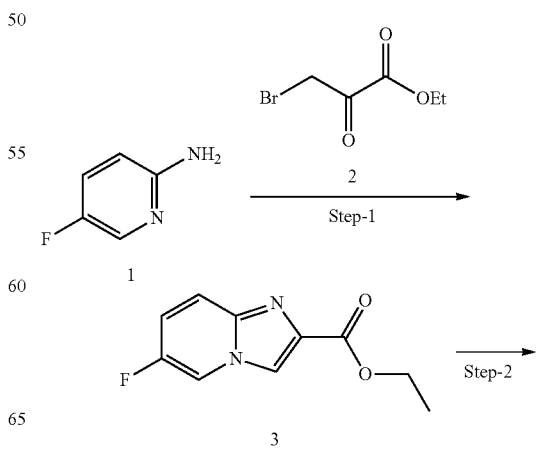

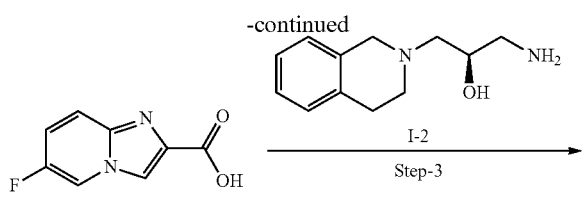

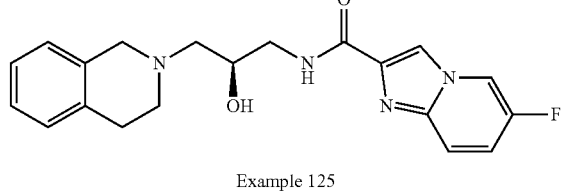

Example 125

LC-MS (ES) m/z: 368.41 [M+H]+.

(R)-2-((3-(3,4-dihydroisoquinolin-2(1H)-yl)-2-hydroxypropyl)carbamoyl)imidazo[1,2-a]pyridine-6-carboxylic acid (Example 126)

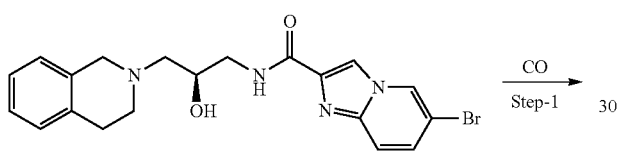

Example 122

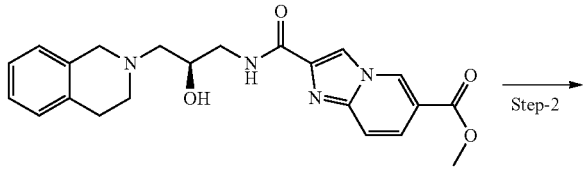

1

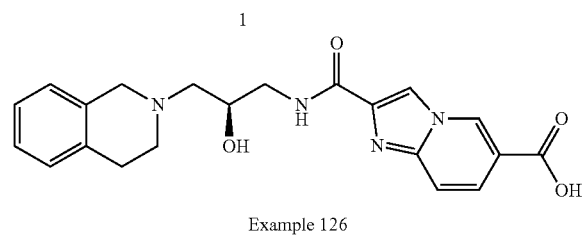

Example 126

Step-1:methyl(S)-2-((3-(3,4-dihydroisoquinolin-2(1H)-yl)-2-hydroxypropyl)carbamoyl)imidazo[1,2-a]pyridine-6-carboxylate (1)

To a stirred solution of (S)-6-bromo-N-(3-(3,4-dihydroisoquinolin-2(1H)-yl)-2-hydroxypropyl)imidazo[1,2-a]pyridine-2-carboxamide (3.0 g, 6.98 mmol) in methanol (60 mL) was added triethylamine (2.12 mL, 20.96 mmol). The reaction mixture was purged with $N_2$ gas for 20 min. To the above reaction mixture was added [1,1'-Bis(diphenylphosphino)ferrocene]dichloropalladium(II) (0.51 g, 0.698 mmol) and the resulting solution was filled with carbon monoxide (CO) at 100 psi in parr-vessel and reaction was stirred for 16 h at 80° C. The reaction mixture was filtered over celite bed and washed with ethyl acetate. The filtrate was dried over anhydrous $Na_2SO_4$, filtered and concentrated under reduced pressure. The crude was purified by column chromatography using 0-10% methanol/dichloromethane as the eluent to afford methyl(S)-2-((3-(3,4-dihydroisoquinolin-2(1H)-yl)-2-hydroxypropyl)carbamoyl) imidazo[1,2-a]pyridine-6-carboxylate 1 as off white solid. Yield: 1.51 g (53%) LC-MS (ES) m/z: 409.36 [M+H]+

Step-2: (S)-2-((3-(3,4-dihydroisoquinolin-2(1H)-yl)-2-hydroxypropyl)carbamoyl)imidazo[1,2-a]pyridine-6-carboxylic acid (Example 126)

To a stirred solution of methyl (S)-2-((3-(3,4-dihydroisoquinolin-2(1H)-yl)-2-hydroxypropyl)carbamoyl)imidazo[1,2-a]pyridine-6-carboxylate (1, 1.50 g, 3.33 mmol) in (30 mL) of THF:MeOH:$H_2O$ (2:1:1) was added LiOH (0.24 g, 9.99 mmol). The reaction mixture was stirred for 5 h at room temp. After completion of reaction, the organic solvents were evaporated and the aqueous layer was acidified with 1N HCl up to pH 3 to 4 and aqueous layer was concentrated to get (S)-2-((3-(3,4-dihydroisoquinolin-2(1H)-yl)-2-hydroxypropyl)carbamoyl)imidazo[1,2-a]pyridine-6-carboxylic acid Example 126 as a white solid. Yield: 1.40 g (crude) LC-MS (ES) m/z: 395.07 [M+H]+

(S)—N-(3-(3,4-dihydroisoquinolin-2(1H)-yl)-2-hydroxypropyl)-6-(piperidine-1-carbonyl)imidazo[1,2-a]pyridine-2-carboxamide (Example 127)

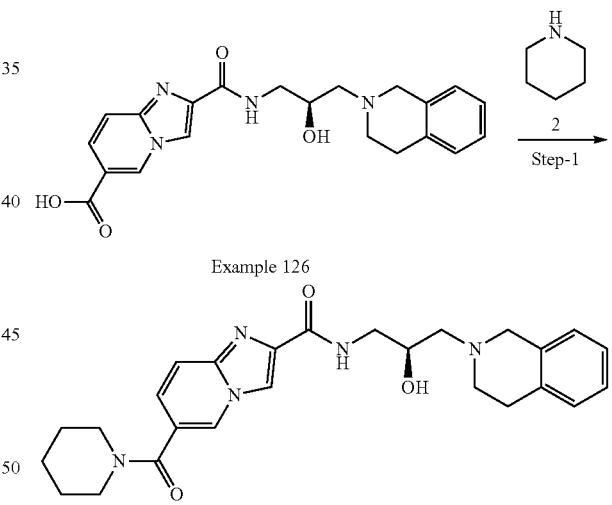

Example 126

Example 127

Step-1: To a solution of (S)-2-((3-(3,4-dihydroisoquinolin-2(1H)-yl)-2-hydroxypropyl)carbamoyl)imidazo[1,2-a]pyridine-6-carboxylic acid (0.25 g, 0.634 mmol) in DMF (6 mL) was added DIPEA (0.31 mL, 1.90 mmol) followed by HATU (0.24 g, 0.634 mmol). The reaction mixture was stirred for 10 min followed by addition of piperidine (2, 0.080 g 0.95 mmol). The reaction mixture was stirred at room temperature for 16 h. After completion, the reaction mixture was diluted with ethyl acetate and water. The organic layer was washed with water, brine solution, dried over anhydrous $Na_2SO_4$ and concentrated under reduced pressure. The obtained crude was purified by prep-HPLC to afford to (S)—N-(3-(3,4-dihydroisoquinolin-2(1H)-yl)-2-hydroxypropyl)-6-(piperidine-1-carbonyl)imidazo[1,2-a]pyridine-2-carboxamide as off white solid. Yield: 0.18 g (62%) LC-MS (ES) m/z: 395.07 [M+H]⁺; 1H NMR (DMSO-d6, 400 MHz, ppm) δ 8.74 (s, 1H), 8.38 (s, 2H), 7.56 (d, J=8.88 Hz, 1H), 7.33 (d, J=9.28 Hz, 1H), 7.13-7.07 (m, 4H), 5.02 (bs, 1H), 4.00 (m, 1H), 3.75-3.44 (m, 6H), 3.15-2.89 (m, 4H), 2.66-2.07 (m, 2H), 1.62-1.53 (m, 6H). 1.23-1.21 (m, 2H).

(S)—N6-(3,3-difluorocyclobutyl)-N2-(3-(3,4-dihydroisoquinolin-2(1H)-yl)-2-hydroxypropyl)imidazo[1,2-a]pyridine-2,6-dicarboxamide (Example 128)

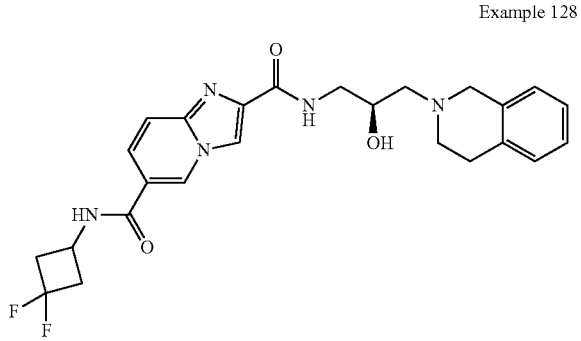 [SMILES: O=C(NC1CC(F)(F)C1)c1ccc2nc(C(=O)NC[C@H](O)CN3CCc4ccccc4C3)cn2c1]

Example 128

Example 128 was prepared according to method exemplified for Example 127. LC-MS (ES) m/z: 484.37 [M+H]⁺, 1H NMR (DMSO-d6, 400 MHz, ppm) δ 9.13 (s, 1H), 9.01 (d, J=4.96 Hz, 1H), 8.46 (s, 1H), 8.36 (dd, J=11.04 Hz, 1H), 7.71 (d, J=1.28 Hz, 1H), 7.54 (d, J=9.52 Hz, 1H), 7.10-7.06 (m, 3H), 7.01 (d, J=6.16 Hz, 1H), 4.98 (bs, 1H), 4.28 (bs, 1H), 3.93-3.90 (m, 1H), 3.66-3.58 (m, 2H), 3.49-3.43 (m, 1H), 3.33-3.27 (m, 1H), 3.00-2.96 (m, 2H), 2.84 (d, J=5.16 Hz, 2H), 2.78-2.49 (m, 6H).

(S)—N-(3-(3,4-dihydroisoquinolin-2(1H)-yl)-2-hydroxypropyl)-6-(piperazine-1-carbonyl)imidazo[1,2-a]pyridine-2-carboxamide (Example 129)

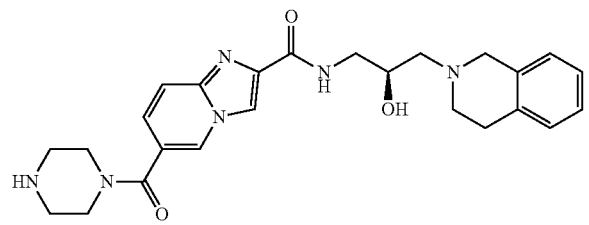

Example 129

Example 129 was prepared according to method exemplified for Example 127. LC-MS (ES) m/z: 463.46[M+H]⁺
(S)—N6-cyclohexyl-N2-(3-(3,4-dihydroisoquinolin-2(1H)-yl)-2-hydroxypropyl)imidazo[1,2-a]pyridine-2,6-dicarboxamide (Example 130)

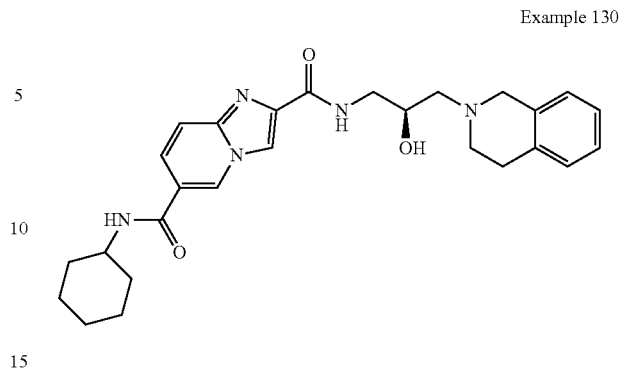

Example 130

Example 130 was prepared according to method exemplified for Example 127. LC-MS (ES) m/z: 476.40 [M+H]⁺, 1H NMR (DMSO-d6, 400 MHz, ppm) δ 9.08 (s, 1H), 8.43 (s, 1H), 8.37-8.33 (m, 2H), 7.74-7.71 (dd, J=9.56 Hz, 1.40 Hz, 1H), 7.51 (d, J=9.48 Hz, 1H), 7.10-7.06 (m, 3H), 7.02 (d, J=5.96 Hz, 1H), 4.95 (bs, 1H), 3.91 (bs, 1H), 3.78 (bs, 1H), 3.66-3.62 (m, 2H), 3.49-3.45 (m, 1H), 2.84-2.68 (m, 7H), 1.84-1.75 (m, 2H), 1.73-1.63 (m, 2H), 1.62-1.60 (m, 1H), 1.33-1.29 (m, 4H), 1.18-1.15 (m, 1H).

(R)—N-(3-(3,4-dihydroisoquinolin-2(1H)-yl)-2-hydroxypropyl)-6-(2,6-diazaspiro[3.3]heptane-2-carbonyl)imidazo[1,2-a]pyridine-2-carboxamide (Example 131)

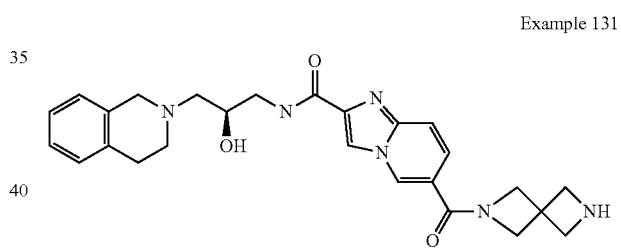

Example 131

Example 131 was prepared according to method exemplified for Example 127. LC-MS (ES) m/z: 475.24 [M+H]⁺

N—((R)-3-(3,4-dihydroisoquinolin-2(1H)-yl)-2-hydroxypropyl)-6-(octahydropyrrolo[3,4-c]pyrrole-2-carbonyl)imidazo[1,2-a]pyridine-2-carboxamide (Example 132)

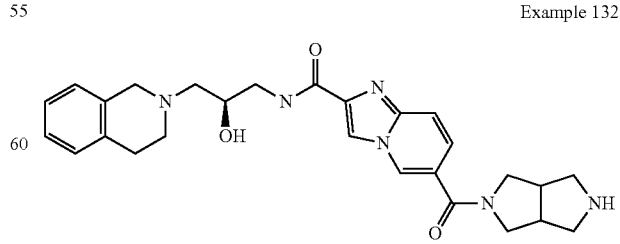

Example 132

Example 132 was prepared according to method exemplified for Example 127. LC-MS (ES) m/z: 489.25 [M+H]⁺

N—((S)-3-(3,4-dihydroisoquinolin-2(1H)-yl)-2-hydroxypropyl)-6-(piperidine-1-carbonyl)-5,6,7,8-tetrahydroimidazo[1,2-a]pyridine-2-carboxamide (Example 133)

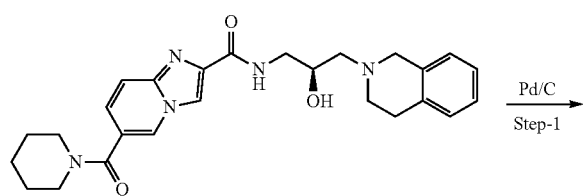

Example 127

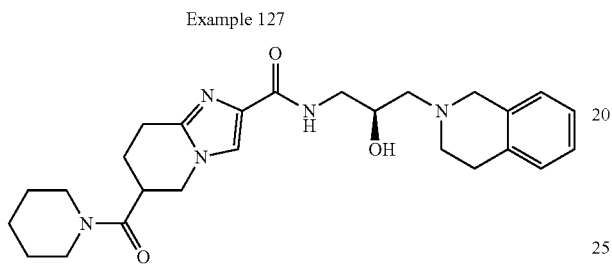

Example 133

Step-1: To a stirred solution of (S)—N-(3-(3,4-dihydroisoquinolin-2(1H)-yl)-2-hydroxypropyl)-6-(piperidine-1-carbonyl)imidazo[1,2-a]pyridine-2-carboxamide (0.10 g, 0.21 mmol) in ethanol (3 mL) was added ammonium formate (0.068 g, 1.08 mmol) and Pd/C (0.011 g, 0.10 mmol) under $N_2$ atmosphere and the reaction mixture was stirred at 80° C. for 48 h. After completion, the reaction mixture was filtered through celite and washed with EtOAc. The filtrate was concentrated to dryness. The obtained crude was submitted to prep-HPLC for purification to afford N—((S)-3-(3,4-dihydroisoquinolin-2(1H)-yl)-2-hydroxypropyl)-6-(piperidine-1-carbonyl)-5,6,7,8-tetrahydroimidazo[1,2-a]pyridine-2-carboxamide as off white solid; LC-MS (ES) m/z: 466.26 [M+H]$^+$ N6-(3,3-difluorocyclobutyl)-N2-((S)-3-(3,4-dihydroisoquinolin-2(1H)-yl)-2-hydroxypropyl)-5,6,7,8-tetrahydroimidazo[1,2-a]pyridine-2,6-dicarboxamide (Example 134)

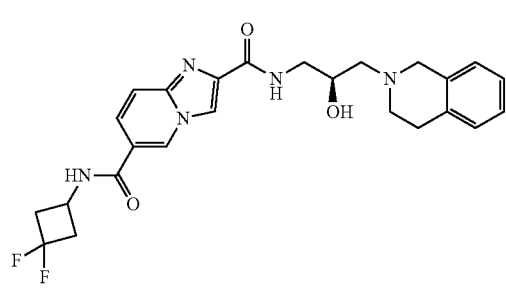

Example 128

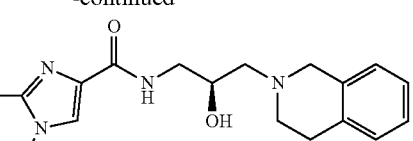

Example 134

Example 134 was prepared according to method exemplified for Example 133. LC-MS (ES) m/z: 488.24 [M+H]$^+$ N—((S)-3-(3,4-dihydroisoquinolin-2(1H)-yl)-2-hydroxypropyl)-6-(piperazine-1-carbonyl)-5,6,7,8-tetrahydroimidazo[1,2-a]pyridine-2-carboxamide (Example 135)

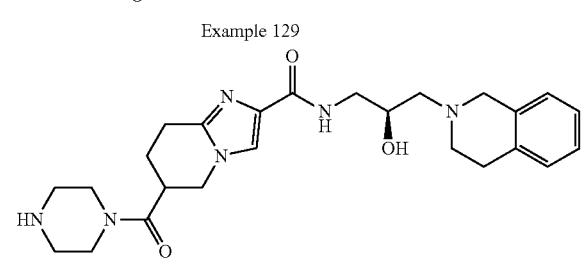

Example 129

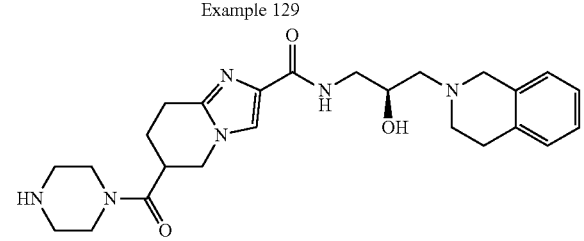

Example 135

Example 135 was prepared according to method exemplified for Example 133. LC-MS (ES) m/z: 467.27 [M+H]$^+$ N—((R)-3-(3,4-dihydroisoquinolin-2(1H)-yl)-2-hydroxypropyl)-6-(2,6-diazaspiro[3.3]heptane-2-carbonyl)-5,6,7,8-tetrahydroimidazo[1,2-a]pyridine-2-carboxamide (Example 136)

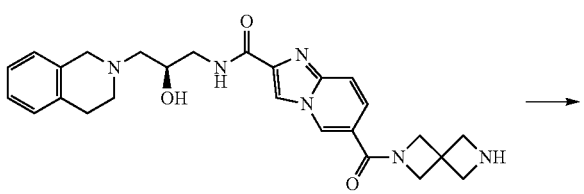

Example 131

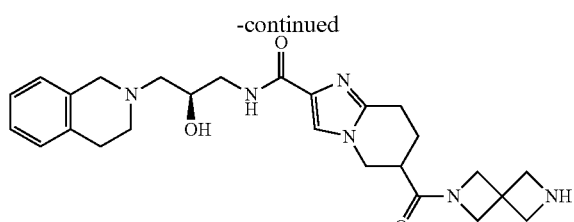

Example 136

Example 136 was prepared according to method exemplified for Example 133. LC-MS (ES) m/z: 479.27 [M+H]⁺

N—((R)-3-(3,4-dihydroisoquinolin-2(1H)-yl)-2-hydroxypropyl)-6-(octahydropyrrolo[3,4-c]pyrrole-2-carbonyl)-5,6,7,8-tetrahydroimidazo[1,2-a]pyridine-2-carboxamide (Example 137)

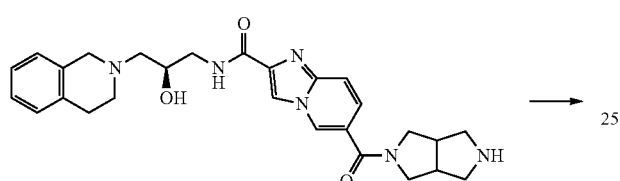

Example 132

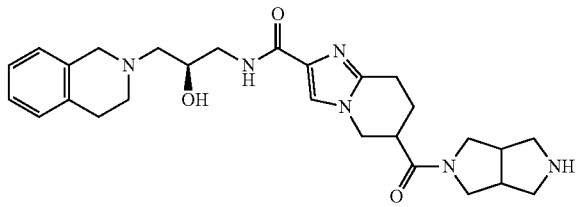

Example 137

Example 137 was prepared according to method exemplified for Example 133. LC-MS (ES) m/z: 493.62 [M+H]⁺

(S)-6-benzamido-N-(3-(3,4-dihydroisoquinolin-2(1H)-yl)-2-hydroxypropyl)imidazo[1,2-a]pyridine-2-carboxamide (Example 138)

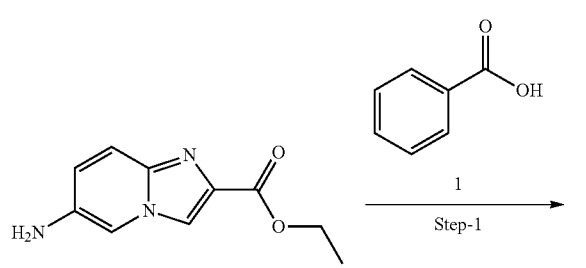

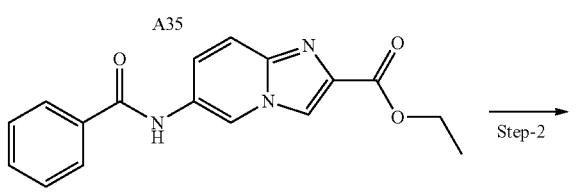

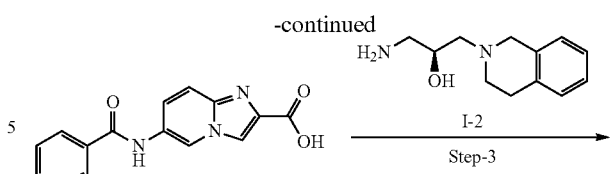

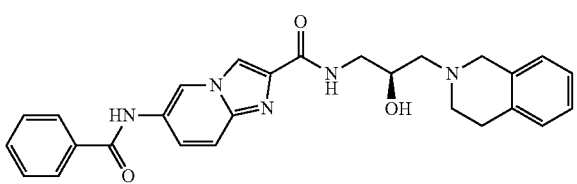

Example 138

Step-1: Ethyl 6-benzamidoimidazo[1,2-a]pyridine-2-carboxylate (2)

To a solution of benzoic acid (1, 0.35 g, 2.92 mmol) in DMF (10 mL) was added DIPEA (1.27 mL, 7.31 mmol) followed by HATU (1.01 g, 2.68 mmol). The reaction mixture was stirred for 10 min followed by addition of ethyl 6-aminoimidazo[1,2-a]pyridine-2-carboxylate (A35, 0.50 g, 2.43 mmol). The reaction mixture was stirred at room temperature for 16 h. After completion, the reaction mixture was diluted with ethyl acetate and water. The organic layer was washed with water, brine solution, dried over anhydrous Na₂SO₄ and concentrated under reduced pressure. The obtained crude was purified by column chromatography using 10% methanol in dichloromethane as eluent to afford the desired product ethyl 6-benzamidoimidazo[1,2-a]pyridine-2-carboxylate 2 as white solid. Yield: 0.44 g, (58%). LC-MS (ES) m/z: 310.10 [M+H]⁺

Step-2: 6-benzamidoimidazo[1,2-a]pyridine-2-carboxylic acid (3)

To a stirred solution of ethyl 6-benzamidoimidazo[1,2-a]pyridine-2-carboxylate (2, 0.44 g, 1.42 mmol) in (8 mL) of THF:MeOH:H₂O (2:1:1) was added LiOH (0.179 g, 4.27 mmol). The reaction mixture was stirred for 3 h at room temp. After completion, reaction mixture was evaporated and the residue was acidified with 1N HCl up to pH 3 to 4 and concentrated to get 6-acetamidoimidazo[1,2-a]pyridine-2-carboxylic acid 3 as an off white solid. Yield: 0.40 g, (crude). LC-MS (ES) m/z: 282.05 [M+H]⁺

Step-3: (S)-6-benzamido-N-(3-(3,4-dihydroisoquinolin-2(1H)-yl)-2-hydroxypropyl)imidazo[1,2-a]pyridine-2-carboxamide (Example 138)

To a solution of 6-benzamidoimidazo[1,2-a]pyridine-2-carboxylic acid (7, 0.40 g, 1.42 mmol) in DMF (10 mL) was added DIPEA (0.74 mL, 4.27 mmol) followed by HATU (0.59 g, 1.56 mmol). The reaction mixture was stirred for 10 min followed by addition of (S)-1-amino-3-(3,4-dihydroisoquinolin-2(1H)-yl)propan-2-ol (I-1, 0.35 g, 1.70 mmol). The reaction mixture was stirred at room temperature for 16 h. The reaction was monitored till the completion of starting materials (LC/MS) and then concentrated under reduced pressure. The obtained crude was purified by Prep HPLC to afford the desired product (S)-6-benzamido-N-(3-(3,4-dihydroisoquinolin-2(1H)-yl)-2-hydroxypropyl)imidazo[1,2-a]pyridine-2-carboxamide as white solid. Yield: 0.25 g, (37%). LC-MS (ES) m/z: 470.34 [M+H]$^+$, 1H NMR (DMSO-d6, 400 MHz, ppm) δ 10.41 (s, 1H). 9.40 (s, 1H), 8.45 (s, 1H), 8.25-8.22 (dd, J=5.72 Hz, 1H), 7.98 (d, H=7.2 Hz, 2H), 7.64-7.54 (m, 5H), 7.10-7.01 (m, 4H), 4.95 (d, J=4.68 Hz, 1H), 3.3-3.89 (m, 1H), 3.66-3.31 (m, 4H), 2.84 (s, 2H), 2.78-2.67 (m, 2H), 2.57-2.40 (m, 2H).

(S)—N-(3-(3,4-dihydroisoquinolin-2(1H)-yl)-2-hydroxypropyl)-6-(2-fluorobenzamido)imidazo[1,2-a]pyridine-2-carboxamide (Example 139)

Example 139

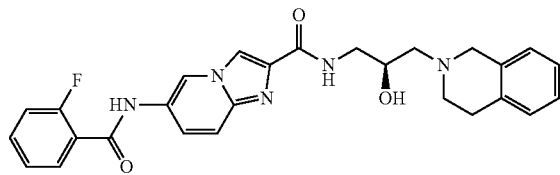

Example 139 was prepared according to method exemplified for Example 138. LC-MS (ES) m/z: 484.37 [M+H]$^+$, 1H NMR (DMSO-d6, 400 MHz, ppm) δ 10.61 (s, 1H), 9.40 (s, 1H), 8.46 (s, 1H), 8.24 (dd, J=11.36 Hz, 1H), 7.70 (dd, J=14.44 Hz, 1H), 7.62 (dd, J=13.52 Hz, 1H), 7.53 (d, J=9.68 Hz, 1H), 7.40-7.34 (m, 3H), 7.13-7.03 (m, 4H), 4.96 (d, J=4.04 Hz, 1H), 3.91 (d, J=4.68 Hz, 1H), 3.66-3.62 (m, 2H), 3.58-3.44 (m, 1H), 3.31-3.26 (m, 1H), 2.84-2.67 (m, 6H).

(S)-6-(cyclohexanecarboxamido)-N-(3-(3,4-dihydroisoquinolin-2(1H)-yl)-2-hydroxypropyl)imidazo[1,2-a]pyridine-2-carboxamide (Example 140)

Example 140

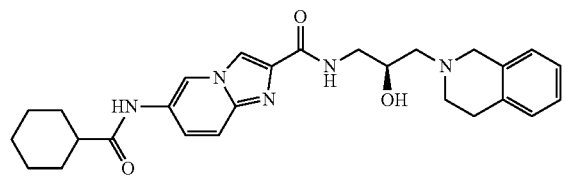

Example 140 was prepared according to method exemplified for Example 138. LC-MS (ES) m/z: 476.34 [M+H]$^+$ (S)—N-(3-(3,4-dihydroisoquinolin-2(1H)-yl)-2-hydroxypropyl)-6-(tetrahydro-2H-pyran-4-carboxamido)imidazo[1,2-a]pyridine-2-carboxamide (Example 141)

Example 141

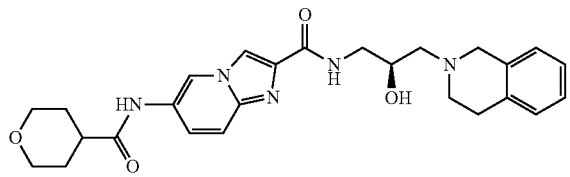

Example 141 was prepared according to method exemplified for Example 138. LC-MS (ES) m/z: 478.36 [M+H]$^+$, 1H NMR (DMSO-d6, 400 MHz, ppm) δ 10.11 (s, 1H). 9.28 (s, 1H), 8.38 (s, 1H), 8.22-8.19 (dd, J=11.24 Hz, 1H), 7.48 (d, H=9.64 Hz, 1H), 7.27-7.24 (dd, J=9.71, 1.6 Hz, 1H), 7.09-6.90 (m, 4H), 4.97 (bs, 1H), 3.91 (d, J=11.2 Hz, 3H), 3.65-3.24 (m, 7H), 2.83 (s, 2H), 2.77-2.59 (m, 4H), 1.71-1.62 (m, 4H).

(S)-6-(cyclopropanecarboxamido)-N-(3-(3,4-dihydroisoquinolin-2(1H)-yl)-2-hydroxypropyl)imidazo[1,2-a]pyridine-2-carboxamide (Example 142)

Example 142

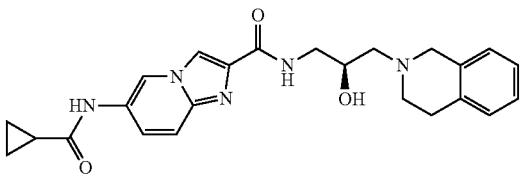

Example 142 was prepared according to method exemplified for Example 138. LC-MS (ES) m/z: 434.30 [M+H]$^+$, 1H NMR (DMSO-d6, 400 MHz, ppm) δ 10.39 (s, 1H). 9.22 (s, 1H), 8.37 (s, 1H), 8.22-8.19 (dd, J=5.68 Hz, 1H), 7.48 (d, H=9.6 Hz, 1H), 7.26 (d, J=9.64 Hz, 1H), 7.09-7.01 (m, 4H), 4.98 (bs, 1H), 3.89 (t, J=5.68 Hz, 1H), 3.65-3.26 (m, 5H), 2.83 (s, 2H), 2.77-2.66 (m, 3H), 1.80 (t, J=5.92 Hz, 1H), 0.84-0.82 (m, 4H).

(S)-6-(cyclobutanecarboxamido)-N-(3-(3,4-dihydroisoquinolin-2(1H)-yl)-2-hydroxypropyl)imidazo[1,2-a]pyridine-2-carboxamide (Example 143)

Example 143

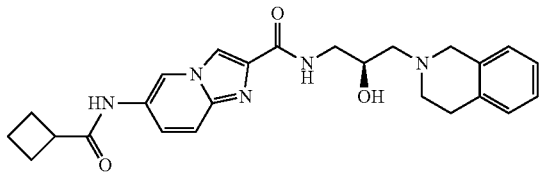

Example 143 was prepared according to method exemplified for Example 138. LC-MS (ES) m/z: 448.54 [M+H]$^+$

(S)-6-(4-cyanobenzamido)-N-(3-(3,4-dihydroisoquinolin-2(1H)-yl)-2-hydroxypropyl)imidazo[1,2-a]pyridine-2-carboxamide (Example 144)

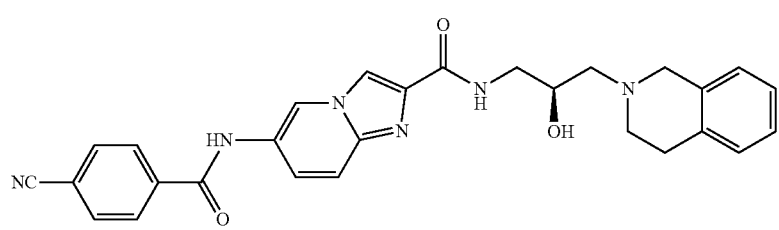

Example 144

Example 144 was prepared according to method exemplified for Example 138. LC-MS (ES) m/z: 495.21 [M+H]$^+$
Methyl 6-aminoimidazo[1,2-a]pyridine-2-carboxylate (2)

Step-1: Methyl 6-aminoimidazo[1,2-a]pyridine-2-carboxylate (2)

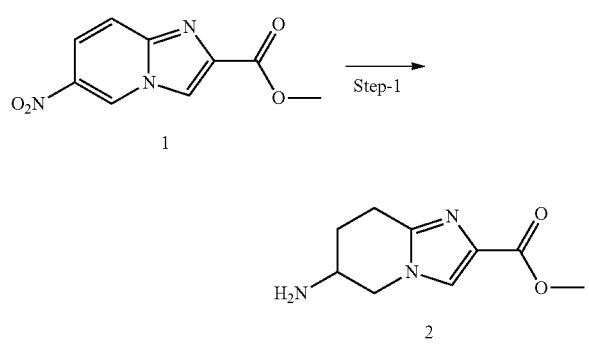

To a stirred solution of methyl 6-nitroimidazo[1,2-a]pyridine-2-carboxylate (1, 10.0 g, 42.55 mmol) in ethanol (150 mL) was added ammonium formate (13.4 g, 212.76 mmol) and Pd/C (2.25 g, 21.27 mmol) under $N_2$ atmosphere and the reaction mixture was stirred at 80° C. for 48 h. After completion, the reaction mixture was filtered through celite and washed with EtOAc. The filtrate was concentrated to dryness. The residue was washed with n-pentane dried to get compound methyl 6-amino-5,6,7,8-tetrahydroimidazo[1,2-a]pyridine-2-carboxylate 2 as a black solid. Yield: 7.50 g (84%) LC-MS (ES) m/z: 196.06 [M+H]$^+$.

6-(4-cyanobenzamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 145)

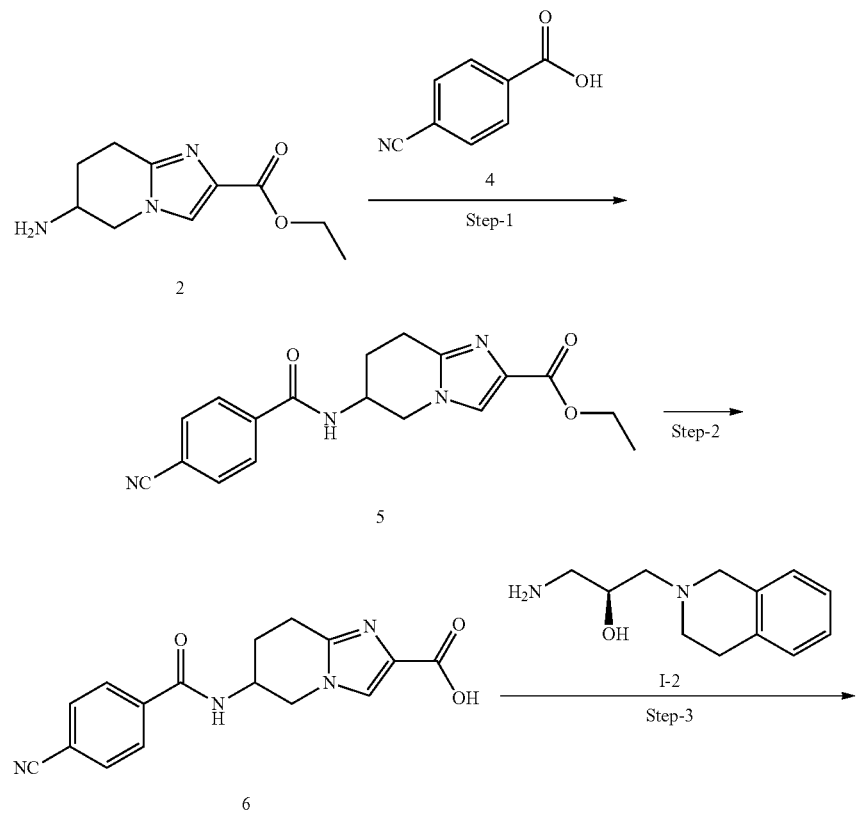

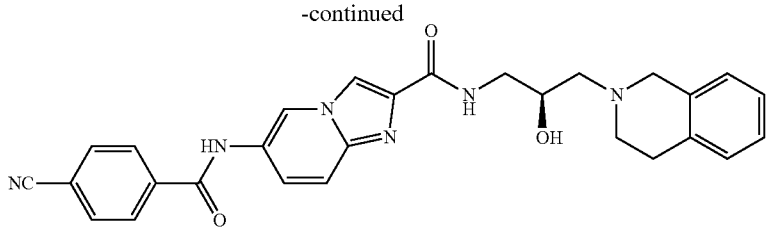

Example 145

Step-1: ethyl 6-(4-cyanobenzamido)-5,6,7,8-tetrahydroimidazo[1,2-a]pyridine-2-carboxylate (5)

To a solution of 4-cyanobenzoic acid (4, 0.42 g, 2.87 mmol) in DMF (10 mL) was added DIPEA (1.27 mL, 7.31 mmol) followed by HATU (1.01 g, 2.68 mmol). The reaction mixture was stirred for 10 min followed by addition of ethyl 6-amino-5,6,7,8-tetrahydroimidazo[1,2-a]pyridine-2-carboxylate (2, 0.50 g, 2.39 mmol). The reaction mixture was stirred at room temperature for 16 h. After completion, the reaction mixture was diluted with ethyl acetate and water. The organic layer was washed with water, brine solution, dried over anhydrous $Na_2SO_4$ and concentrated under reduced pressure. The obtained crude was purified by column chromatography using 10% methanol in dichloromethane as eluent to afford the desired product ethyl 6-(4-cyanobenzamido)-5,6,7,8-tetrahydroimidazo[1,2-a]pyridine-2-carboxylate 5 as white solid. Yield: 0.28 g, (35%). LC-MS (ES) m/z: 310.10 $[M+H]^+$ Step-2: 6-(4-cyanobenzamido)-5,6,7,8-tetrahydroimidazo[1,2-a]pyridine-2-carboxylic acid (6)

To a stirred solution of ethyl 6-(4-cyanobenzamido)-5,6,7,8-tetrahydroimidazo[1,2-a]pyridine-2-carboxylate (5, 0.28 g, 0.82 mmol) in (8 mL) of $THF:MeOH:H_2O$ (2:1:1) was added LiOH (0.10 g, 2.48 mmol). The reaction mixture was stirred for 3 h at room temp. After completion of reaction, the organic solvents were evaporated and the aqueous layer was acidified with 1N HCl up to pH 3 to 4 and aqueous layer was concentrated to get 6-(4-cyanobenzamido)-5,6,7,8-tetrahydroimidazo[1,2-a]pyridine-2-carboxylic acid 6 as an off white solid. Yield: 0.28 g, (crude). LC-MS (ES) m/z: 282.05 $[M+H]^+$ Step-3:6-(4-cyanobenzamido)-N—((S)-3-(3,4-dihydroisoquinolin-2(1H)-yl)-2-hydroxypropyl)-5,6,7,8-tetrahydroimidazo[1,2-a]pyridine-2-carboxamide Example 145

To a solution of 6-(4-cyanobenzamido)-5,6,7,8-tetrahydroimidazo[1,2-a]pyridine-2-carboxylic acid (6, 0.28 g, 0.90 mmol) in DMF (10 mL) was added DIPEA (0.47 mL, 2.70 mmol) followed by HATU (0.37 g, 0.99 mmol). The reaction mixture was stirred for 10 min followed by addition of (S)-1-amino-3-(3,4-dihydroisoquinolin-2(1H)-yl)propan-2-ol (7, 0.22 g, 1.08 mmol). The reaction mixture was stirred at room temperature for 16 h. The reaction was monitored till the completion of starting materials (LC/MS) and then concentrated under reduced pressure. The obtained crude was purified by Prep HPLC to afford 6-(4-cyanobenzamido)-N—((S)-3-(3,4-dihydroisoquinolin-2(1H)-yl)-2-hydroxypropyl)-5,6,7,8-tetrahydroimidazo[1,2-a]pyridine-2-carboxamide as white solid. Yield: 0.10 g, (22%). LC-MS (ES) m/z: 499.71 $[M+H]^+$, 1H NMR (DMSO-d6, 400 MHz, ppm) δ 8.85 (d, J=5.64 Hz, 1H), 8.01-7.95 (m, 4H), 8.83 (d, J=3.96 Hz, 1H), 7.51 (s, 1H), 7.09-7.08 (m, 3H), 7.01 (d, J=5.16 Hz, 1H), 4.89 (bs, 1H), 4.43-4.31 (m, 1H), 4.30-4.27 (m, 1H), 3.92-3.82 (m, 2H), 3.24-3.21 (m, 2H), 2.90-2.64 (m, 7H), 2.47-2.44 (m, 3H), 2.08-2.02 (m, 2H).

6-benzamido-N—((S)-3-(3,4-dihydroisoquinolin-2(1H)-yl)-2-hydroxypropyl)-5,6,7,8-tetrahydroimidazo[1,2-a]pyridine-2-carboxamide (Example 146)

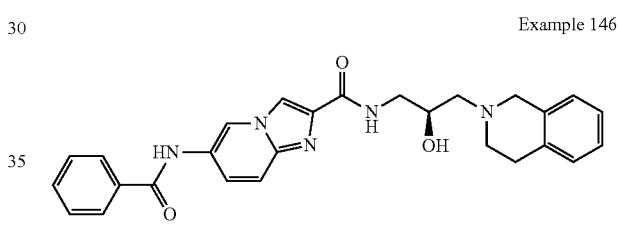

Example 146

Example 146 was prepared according to method exemplified for Example 145. LC-MS (ES) m/z: 474.38 $[M+H]^+$, 1H NMR (DMSO-d6, 400 MHz, ppm) δ 8.59 (d, J=5.44 Hz, 1H), 7.85-7.82 (m, 3H), 7.56-7.45 (m, 4H), 7.09-7.01 (m, 4H), 4.89 (t, J=4.28 Hz, 1H), 4.42 (bs, 1H), 4.30-4.26 (dd, J=12.52, 5.16 Hz, 1H), 3.90-3.81 (m, 2H), 3.60 (s, 2H), 3.41-3.33 (m, 1H), 3.27-3.25 (m, 1H), 2.92-2.63 (m, 6H), 2.47-2.42 (m, 2H), 2.07-2.01 (m, 2H).

N—((S)-3-(3,4-dihydroisoquinolin-2(1H)-yl)-2-hydroxypropyl)-6-(isonicotinamido)-5,6,7,8-tetrahydroimidazo[1,2-a]pyridine-2-carboxamide (Example 147)

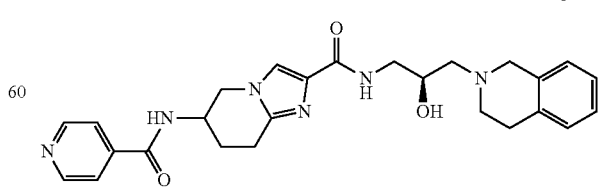

Example 147

Example 147 was prepared according to method exemplified for Example 145. LC-MS (ES) m/z: 475.24$[M+H]^+$

N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-4-carboxamide (Example 148)

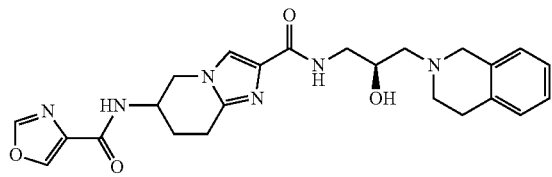

Example 148

Example 148 was prepared according to method exemplified for Example 145. LC-MS (ES) m/z: 465.24[M+H]⁺

N—((R)-3-(3,4-dihydroisoquinolin-2(1H)-yl)-2-hydroxypropyl)-6-(tetrahydro-2H-pyran-4-carboxamido)-5,6,7,8-tetrahydroimidazo[1,2-a]pyridine-2-carboxamide (Example 149)

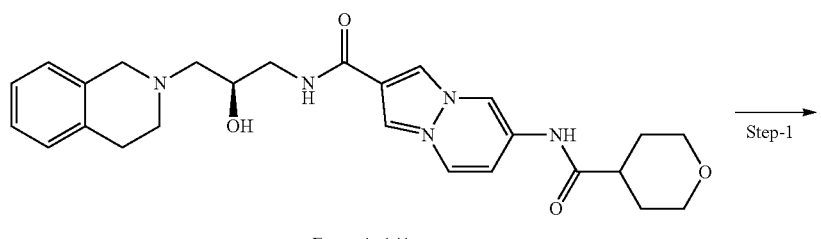

Example 141

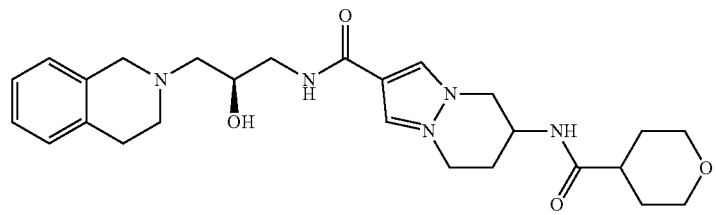

Example 149

Step-1: N—((S)-3-(3,4-dihydroisoquinolin-2(1H)-yl)-2-hydroxypropyl)-6-(tetrahydro-2H-pyran-4-carboxamido)-5,6,7,8-tetrahydroimidazo[1,2-a]pyridine-2-carboxamide (Example 149)

To a stirred solution of (S)—N-(3-(3,4-dihydroisoquinolin-2(1H)-yl)-2-hydroxypropyl)-6-(tetrahydro-2H-pyran-4-carboxamido)imidazo[1,2-a]pyridine-2-carboxamide (0.20 g, 0.41 mmol) in ethanol (5 mL) was added ammonium formate (0.13 g, 2.09 mmol) and Pd/C (0.021 g, 0.20 mmol) under N₂ atmosphere and the reaction mixture was stirred at 80° C. for 48 h. After completion, the reaction mixture was filtered through celite and washed with EtOAc. The filtrate was concentrated to dryness. The obtained crude was purified by prep-HPLC to afford N—((S)-3-(3,4-dihydroisoquinolin-2(1H)-yl)-2-hydroxypropyl)-6-(tetrahydro-2H-pyran-4-carboxamido)-5,6,7,8-tetrahydroimidazo[1,2-a]pyridine-2-carboxamide as a brown solid. Yield: 0.050 g (25%) LC-MS (ES) m/z: 482.26 [M+H]⁺

6-(cyclopentanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 150)

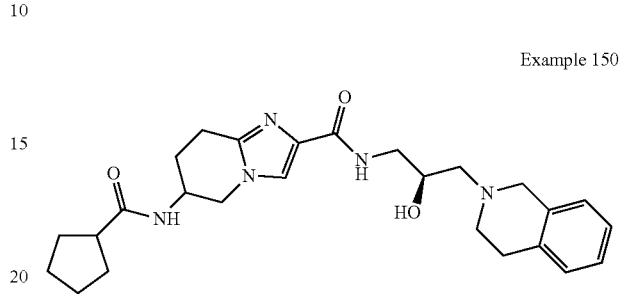

Example 150

Example 150 was prepared according to method exemplified for Example 149. LC-MS (ES) m/z: 482.26[M+H]⁺

6-(cyclopropanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 151)

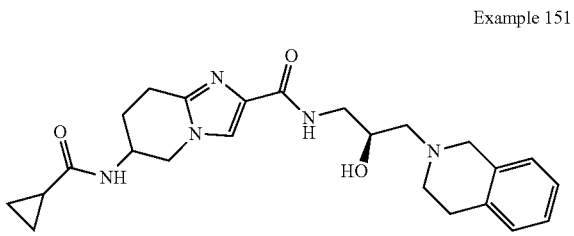 [SMILES: O=C(NC[C@H](O)CN1CCc2ccccc2C1)c1cn2c(n1)CCC(NC(=O)C1CC1)C2]

Example 151

Example 151 was prepared according to method exemplified for Example 149. LC-MS (ES) m/z: 438.26[M+H]⁺

6-(cyclohexanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 152)

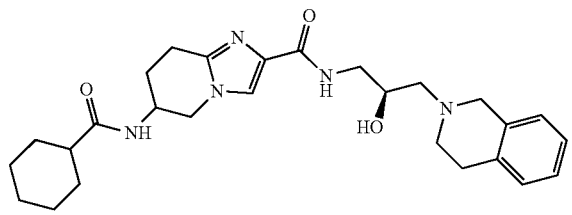

Example 152

Example 152 was prepared according to method exemplified for Example 149. LC-MS (ES) m/z: 480.30[M+H]$^+$.

6-(cyclobutanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 153)

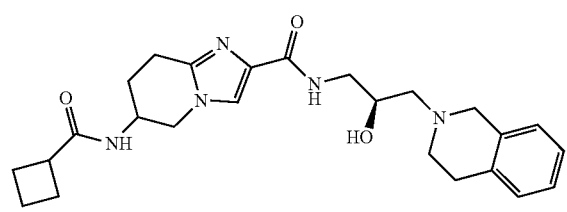

Example 153

Example 153 was prepared according to method exemplified for Example 149. LC-MS (ES) m/z: 452.57 [M+H]$^+$.

(R)—N-(3-(3,4-dihydroisoquinolin-2(1H)-yl)-2-hydroxypropyl)-6-(phenylsulfonamido)imidazo[1,2-a]pyridine-2-carboxamide (Example 154)

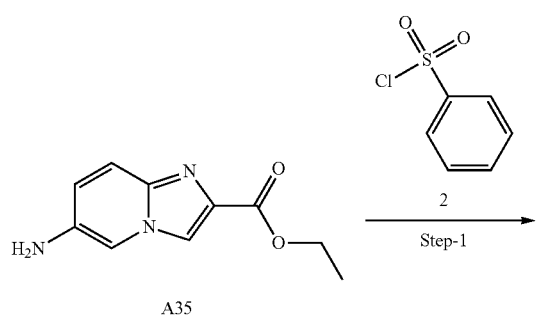

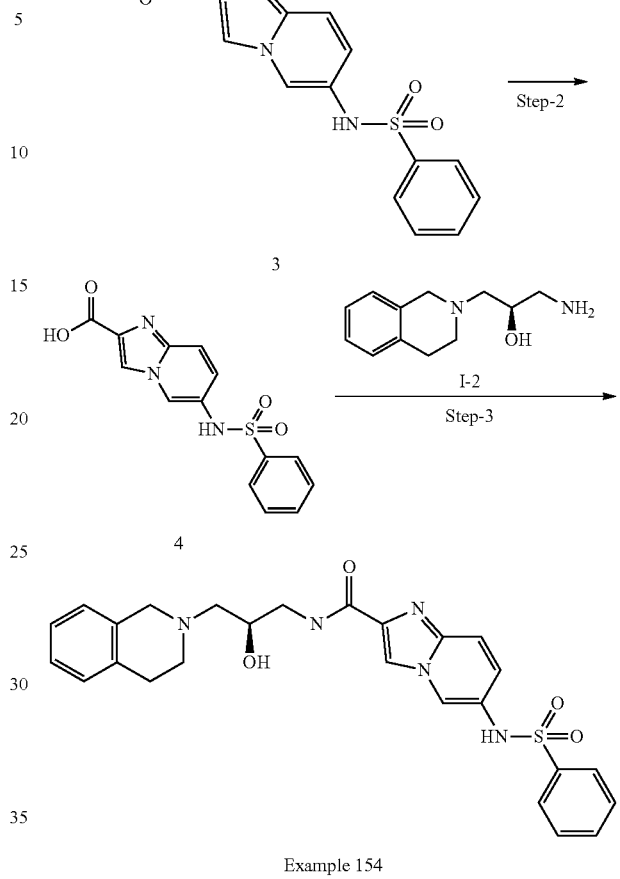

Example 154

Step-1: ethyl 6-(phenylsulfonamido)imidazo[1,2-a]pyridine-2-carboxylate (3)

To a solution of ethyl 6-aminoimidazo[1,2-a]pyridine-2-carboxylate (A35, 1.0 g, 4.87 mmol) in pyridine (10 mL), benzenesulfonyl chloride (2, 0.75 mL, 5.84 mmol) was added and the resulting solution was stirred at room temperature for 16 h. After completion, the reaction mixture was concentrated under reduced pressure to get crude. The crude was dissolved in DCM and washed with water and dried with anhydrous Na$_2$SO$_4$, filtered and concentrated under reduced pressure. The crude was purified by column chromatography using silica gel (100-200 mesh) 0-80% EtOAc/n-hexanes as the eluent to afford ethyl 6-(phenylsulfonamido)imidazo[1,2-a]pyridine-2-carboxylate 3 as a Light green solid. Yield: 1.20 g (71%) LC-MS (ES) m/z: 346.08 [M+H]$^+$.

Step-2: 6-(phenylsulfonamido)imidazo[1,2-a]pyridine-2-carboxylic acid (4)

To a stirred solution of ethyl 6-(phenylsulfonamido)imidazo[1,2-a]pyridine-2-carboxylate (3, 0.8 g, 2.31 mmol) in (16 mL) of THF:MeOH:H$_2$O (2:1:1) was added LiOH (0.29 g, 6.95 mmol). The reaction mixture was stirred for 16 h at room temp. After completion, organic solvents were evaporated and the aqueous layer was acidified with 1N HCl up to pH 3 to 4 and aqueous layer was concentrated to get crude as a 6-(phenylsulfonamido)imidazo[1,2-a]pyridine-2-carboxylic acid 4 as a white solid. Yield: 0.80 g (crude); LC-MS (ES) m/z: 318.02 [M+H]+.

Step-3: (S)—N-(3-(3,4-dihydroisoquinolin-2(1H)-yl)-2-hydroxypropyl)-6-(phenylsulfonamido)imidazo[1,2-a]pyridine-2-carboxamide (Example 154)

To a solution of 6-(phenylsulfonamido)imidazo[1,2-a]pyridine-2-carboxylic acid (4, 0.80 g, 2.52 mmol) in DMF (16 mL) was added DIPEA (1.24 mL, 7.57 mmol) followed by HATU (0.95 g, 2.52 mmol). The reaction mixture was stirred for 10 min followed by addition of (S)-1-amino-3-(3,4-dihydroisoquinolin-2(1H)-yl)propan-2-ol (I-1, 0.62 g, 3.02 mmol). The reaction mixture was stirred at room temperature for 16 h. After completion, the reaction mixture was diluted with water and extracted with EtOAc. The organic layer was dried with anhydrous Na2SO4, filtered and concentrated under reduced pressure. The crude was purified by combiflash column chromatography using 0-10% MeOH/DCM as the eluent. The desired fractions were concentrated and submitted to prep HPLC for further purification to get Example 154 as a white solid. LC-MS (ES) m/z: 506.19 [M+H]+.

N—((R)-3-(3,4-dihydroisoquinolin-2(1H)-yl)-2-hydroxypropyl)-6-(phenylsulfonamido)-5,6,7,8-tetrahydroimidazo[1,2-a]pyridine-2-carboxamide (Example 155)

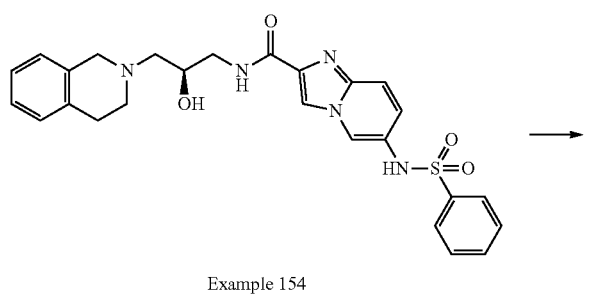

Example 154

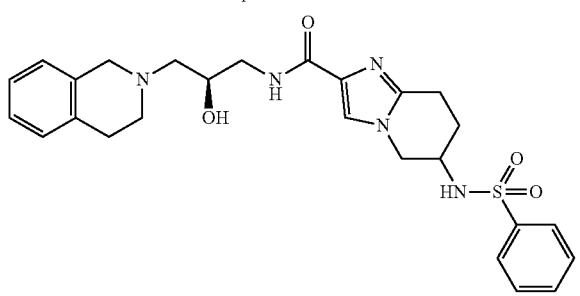

Example 155

LC-MS (ES) m/z: 510.63 [M+H]+.

rac-(R)-6-(azetidine-1-carbonyl)-N-(3-(3,4-dihydroisoquinolin-2(1H)-yl)-2-hydroxypropyl)imidazo[1,2-a]pyridine-2-carboxamide (Example 156)

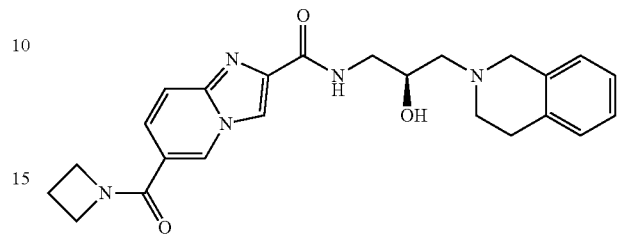

Example 156

Example 156 was prepared according to method exemplified for Example 127. LC-MS (ES) m/z: 434.51 [M+H]+.

(S)—N-(2-((3-(3,4-dihydroisoquinolin-2(1H)-yl)-2-hydroxypropyl)carbamoyl)imidazo[1,2-a]pyridin-6-yl)isoxazole-3-carboxamide (Example 157)

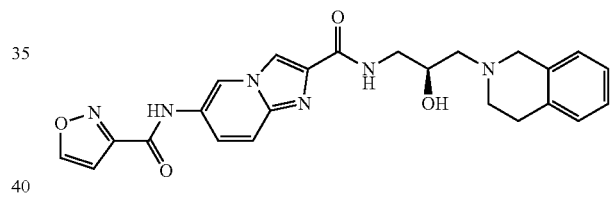

Example 157

Example 157 was prepared according to method exemplified for Example 138. LC-MS (ES) m/z: 461.49 [M+H]+.

6-(bicyclo[2.2.1]heptane-2-carboxamido)-N—((S)-3-(3,4-dihydroisoquinolin-2(1H)-yl)-2-hydroxypropyl)imidazo[1,2-a]pyridine-2-carboxamide (Example 158)

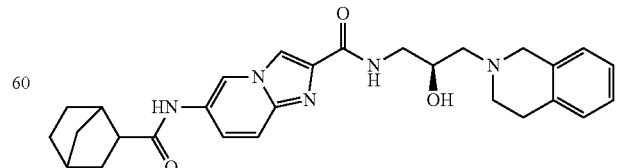

Example 158

Example 158 was prepared according to method exemplified for Example 138. LC-MS (ES) m/z: 488.60 [M+H]+.

(S)—N-(2-((3-(3,4-dihydroisoquinolin-2(1H)-yl)-2-hydroxypropyl)carbamoyl)imidazo[1,2-a]pyridin-6-yl)oxazole-2-carboxamide (Example 159)

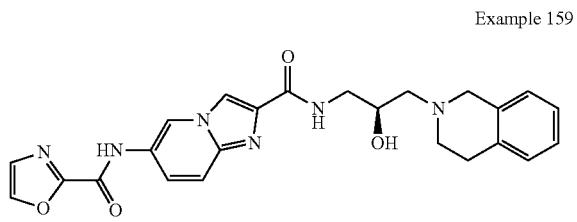 [SMILES: O=C(NC[C@H](O)CN1CCc2ccccc2C1)c1cn2cc(NC(=O)c3ncco3)ccc2n1]

Example 159

Example 159 was prepared according to method exemplified for Example 138. LC-MS (ES) m/z: 461.49 [M+H]$^+$.

(S)—N-(2-((3-(3,4-dihydroisoquinolin-2(1H)-yl)-2-hydroxypropyl)carbamoyl)imidazo[1,2-a]pyridin-6-yl)thiazole-5-carboxamide (Example 160)

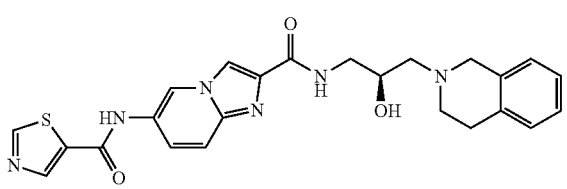

Example 160

Example 160 was prepared according to method exemplified for Example 138. LC-MS (ES) m/z: 477.56 [M+H]$^+$.

N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)isoxazole-3-carboxamide (Example 161)

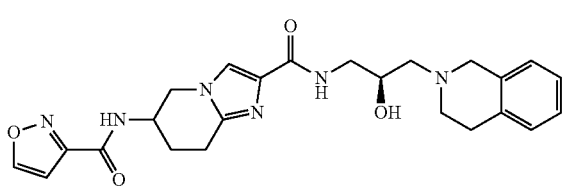

Example 161

Example 161 was prepared according to method exemplified for Example 149. LC-MS (ES) m/z: 465.53 [M+H]$^+$.

6-(bicyclo[2.2.1]heptane-2-carboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 162)

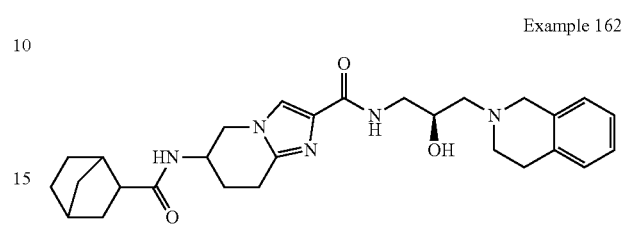

Example 162

Example 162 was prepared according to method exemplified for Example 149. LC-MS (ES) m/z: 492.64 [M+H]$^+$.

N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-2-carboxamide (Example 163)

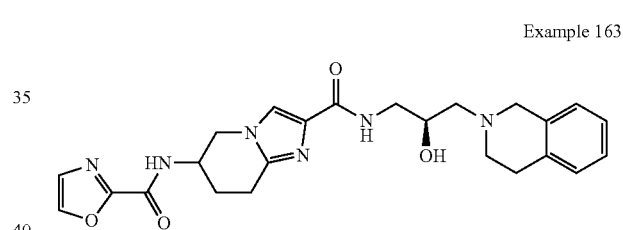

Example 163

Example 163 was prepared according to method exemplified for Example 149. LC-MS (ES) m/z: 465.53 [M+H]$^+$.

N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)thiazole-5-carboxamide (Example 164)

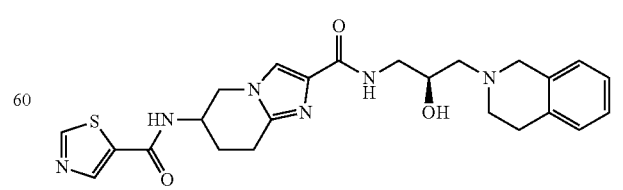

Example 164

Example 164 was prepared according to method exemplified for Example 149. LC-MS (ES) m/z: 481.59 [M+H]$^+$.

(S)—N-(3-(3,4-dihydroisoquinolin-2(1H)-yl)-2-hydroxypropyl)-6-ethylimidazo[1,2-a]pyridine-2-carboxamide (Example 165)

Example 165

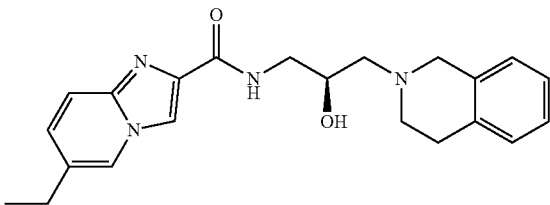

LC-MS (ES) m/z: 379.48 [M+H]+.

(S)-6-(1,1-difluoroethyl)-N-(3-(3,4-dihydroisoquinolin-2(1H)-yl)-2-hydroxypropyl)imidazo[1,2-a]pyridine-2-carboxamide (Example 166)

Example 166

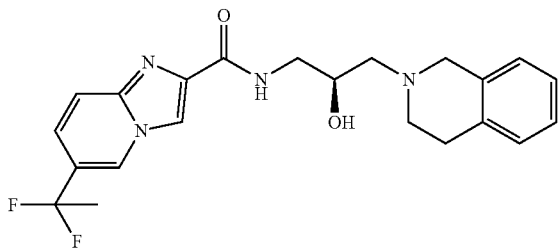

LC-MS (ES) m/z: 415.46 [M+H]+.

(S)—N-(3-(3,4-dihydroisoquinolin-2(1H)-yl)-2-hydroxypropyl)-6-(pentafluoro-I6-sulfaneyl)imidazo[1,2-a]pyridine-2-carboxamide (Example 167)

Example 167

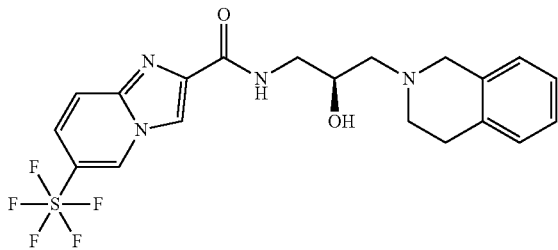

LC-MS (ES) m/z: 477.47 [M+H]+.

Biological Evaluation

Expression and Purification of PRMT5:MEP50 Complex

Full-length human PRMT5 (NP_006100) and Full-length human MEP50 (NP_077007) were synthesized at GenScript. PRMT5 subcloned into pFastBacl with an amino terminal FLAG tag (MDYKDDDDK) and MEP50 subcloned into pFastBac HT A vector introducing an amino terminal tobacco etch virus cleavable His tag (MSYYHHHHHHDYDIPTTENLYFQGA).

Protein Expression:

Recombinant baculovirus and Baculovirus-infected insect cell (BIIC) were generated according to the Bac-to-Bac® protocol (Life Technologies) and protein was expressed in baculovirus-infected Sf9 (Spodoptera frugiperda) insect cells grown in SF-900 II serum-free medium (Invitrogen) in a spinner flask. Protein overexpression was accomplished by infecting exponentially growing Sf9 cell culture at 1×106 cells/ml with a 5,000-fold dilution of PRMT5 and MEP50 (at 1:1 ratio) BIIC stock. Infections were carried out at 27° C. for 72 h, and cells were harvested by centrifugation and stored at −80° C. for purification.

Protein Purification:

Sf9 overexpressed full-length human FLAG-PRMT5-6×His-MEP50 protein complex were purified from cell paste in 2 steps: Nickel affinity chromatography followed by size exclusion chromatography. Frozen pellets were resuspended in 50 mMTris, pH 8.0, 250 mM NaCl, 5% (v/v) glycerol, 0.1% (w/v) Triton X-100, 5 mM imidazole, 1 mM TCEP and cell lysis was performed by sonication. The homogenate was clarified by centrifugation at 39,000×g for 120 min and the supernatant was filtered through 0.8 μm filter membrane (Millipore). The clarified supernatant was loaded onto a 6 ml Ni-Sepharose™ 6 fast flow beads from (GE Healthcare). The column was washed thoroughly with 12 CV of the wash buffer (50 mMTris pH 8.0, 250 mM NaCl, 50 mM Imidazole, 1 mM TCEP, Tris(2-carboxyethyl)phosphine hydrochloride and 5% (v/v) Glycerol) at a flow rate of 1 mL/min until the elute UV absorbance was approximately zero. The PRMT5:MEP50 complex was then eluted with a 50 mM to 500 mM linear gradient of Imidazole in buffer (50 mMTris-HCl pH 8.0, 250 mM NaCl, 1 mM TCEP, 500 mM Imidazole and 5% (v/v) Glycerol). Purity of the eluted fractions was examined on a 12% SDS-PAGE gel. Fractions containing protein of interest, for further purification collected from the protein elution peak and concentrated to 5 mL and injected onto a 26/60 Superdex 200 column (GE) equilibrated with 50 mMTris-HCl pH 8.0, 250 mM NaCl, 3 mM TCEP, and 20% (v/v) Glycerol. The main peak that contains PRMT5:MEP50 complex eluted around 450 kDa position. Fractions containing PRMT5:MEP50 were concentrated to 2 mg/mL for Assay. All chromatographic steps were performed at 4° C.

General Procedure for Biological Evaluation

PRMT5 Biochemical Assay

General materials like S-adenocylmethionine (SAM), S-adenosylhomocysteine (SAH), Tris-HCl, DTT, Bovine skin albumin (BSA) and Tween-20 were purchased from Sigma-Aldrich. 3H-SAM and 384-well streptavidin Flashplates were purchased from Perkin Elmer. Substrates that were used were Peptide representative of human Histone 4 residues 1-15 which was purchased from Rockland antibodies and assays. The peptide was purified to greater than 95% purity and the sequence was Ac-SGRGKGGKGLGKGGA [K-Biot]-amide.

PRMT5/MEP50 Enzyme assay on Peptide Substrates.

The assays were all performed in a buffer consisting of 50 mMTris-HCl, pH 8, 1 mM DTT, 0.01% BSA, 0.01% Tween-20, prepared on the day of use. Test compounds were diluted 3-fold in assay buffer (final DMSO concentration of 1%) and added into a 384-well OptiPlate (PerkinElmer, #6007290). A cocktail (10 μL) of PRMT5/MEP50 enzyme and the peptide was added to the wells. The compounds were allowed to incubate with PRMT5/MEP50 for 30 min at room temperature, then 5 μL of 3H-SAM was added to initiate the reaction. The final concentrations of the components were as follows: PRMT5/MEP50-10 nM, H4, 1-15aa peptide-100 nM, ³H-SAM-1 µM. The assays were stopped by the addition of 1 mM SAH. 25 µL of the reaction from the 384-well OptiPlate was then transferred to a 384-well Flashplate and the biotinylated peptides were allowed to bind to the streptavidin surface for at least 1 h, before being washed twice with 50 mMTris-HCl, pH 8, 0.1% Tween-20. The plates were then read in a PerkinElmer Topcount plate reader to measure the quantity of ³H-labeled peptide bound to the Flashplate surface measured as disintegrations per minute (dpm), also referred to as counts per minute (cpm).

$$\% \ inh = 100 - \left[\frac{cpmcmpd - cpm\min}{cpm\max - cpm\min} * 100\right]$$

The $IC_{50}$ values were calculated using a 4-parameter variable slope fit algorithm (cpm—counts per minute, cmpd—signal in assay well, and cpmmax and cpmmin mare the respective minimum and maximum signal controls).

Z-138 Methylation Assay

General reagents. Z-138 suspension cells (Cat #CRL-3001) were purchased from ATCC. Iscove's Modified Dulbecco's Medium (IMDM), Horse serum, penicillin-streptomycin, PBS and TMB-ELISA substrate solution were purchased from ThermoFisher Scientific. Symmetric di-methyl arginine antibody was purchased from Cell Signaling Technologies.Anti-SNRPD3/SmD3 antibody was purchased from Sigma-Aldrich.

ELISA for detection of Symmetric di-methyl arginine. Exponentially growing Z-138 cells were plated in 96-well plates (Costar 3596) at a density of 150,000 cells/mL, in a volume of 80 µL. A compound source plate was prepared by performing ten-point 3-fold dilution in DMSO, such that the final top concentration of the compound was 10 µM, and DMSO was 0.3%. The total volume of compounds added was 20 µL. The cells were incubated for 96 h at 37° C., 5% $CO_2$. Z-138 cells were directly lysed in media with 3× Lysis Buffer (1×: 10 mM HEPES pH7.9, 5 mM MgCl2, 1M NaCl, 0.25M Sucrose, 1% Triton X-100, 1 mM PMSF, Protease & Phosphatase inhibitors). The lysates were diluted with Tris buffer to a final salt concentration of 100 mM NaCl and appropriate amounts were added to each well of a 96-well titer plate (ThermoFisher, #3855). Plates were incubated at room temperature for a minimum of 3 h and then washed with PBS-Tween 20 (0.05%). The plates were blocked with 5% BSA at room temperature for 1 h, washed with PBS-Tween 20 and incubated with primary antibody at 4 C overnight. The next day, the plates were washed with PBST, followed by secondary antibody (anti-rabbit IgG horseradish peroxidase conjugate (CST, #7074) for 1 h at room temperature. After a final wash, TMB solution was added to the wells, and color allowed to develop in the dark at room temperature. The reaction was stopped with 1N $H_2SO_4$, and the plates were read on a PerkinElmer EnVision reader scanning at 450 nM.

Z-138 Long Term Proliferation Assays

Z-138 cells (ATCC, Cat #CRL-3001) were cultured in Iscove's Modified Dulbecco's Medium (IMDM), supplemented with horse serum to a final concentration of 10%. For the assessment of the effect of compounds on the proliferation of Z-138 cells, exponentially growing cells were plated in 96-well plates (Costar 3596) at a density of 150,000 cells/mL in a final volume of 80 µL medium. A compound source plate was prepared by performing ten-point 3-fold dilution in DMSO, such that the final top concentration of the compound was 10 µM, and DMSO was 0.3%. The total volume of compounds added was 20 µL. The cells were incubated for 96 h at 37° C., 5% $CO_2$. At this point, the DMSO-treated (Max) cells were counted and reseeded at similar seeding density. The cells were re-treated with the compounds and incubated for an additional four days. Cell viability was measured on both day 4 and day 8, by adding 25 µL of Cell Titer Glo reagent to an equal volume of cell suspension. Luminescence was read on a PerkinElmer Victor3 multiplate reader. The concentration of compound inhibiting cell viability by 50% was determined using a 4-parameter, variable slope fit of the normalized dose response curves.

Evaluation of Biological Activity:

Table 1 below displays the biochemical data for PRMT5 inhibition of compounds of Formula L. Compounds having an activity designated as "A" provided $IC_{50}$ 0.01-1 µM; compounds having an activity designated as "B" provided $IC_{50}$=1-5 µM; and compounds having an activity designated as "C" provided $IC_{50}$=>5 µM.

TABLE 1

Biochemical PRMT5 inhibiton data

| Example | PRMT5 Enzyme_$IC_{50}$_µM | PRMT5_Z138_$GI_{50}$_Day 8_µM | PRMT5_Z138_SDMA ELISA_Day 4_µM |
|---|---|---|---|
| 1 | A | A | A |
| 2 | A | A | A |
| 3 | nd | A | C |
| 4 | A | A | A |
| 5 | A | A | A |
| 6 | A | A | A |
| 7 | A | A | A |
| 8 | A | A | A |
| 9 | B | B | A |
| 10 | A | A | A |
| 11 | A | A | A |
| 12 | A | A | A |
| 13 | C | C | A |
| 14 | A | A | A |
| 15 | A | A | A |
| 16 | A | A | A |
| 17 | A | A | A |
| 18 | A | A | A |
| 19 | A | A | A |
| 20 | A | A | A |
| 21 | nd | nd | nd |

TABLE 1-continued

Biochemical PRMT5 inhibiton data

| Example | PRMT5 Enzyme_IC$_{50}$_μM | PRMT5_Z138_GI$_{50}$_Day 8_μM | PRMT5_Z138_SDMA ELISA_Day 4_μM |
|---|---|---|---|
| 22 | A | A | nd |
| 23 | A | A | A |
| 24 | A | A | nd |
| 25 | A | A | nd |
| 26 | A | A | nd |
| 27 | A | A | nd |
| 28 | A | A | nd |
| 29 | A | A | nd |
| 30 | A | A | nd |
| 31 | A | A | nd |
| 32 | A | A | nd |
| 33 | A | A | nd |
| 34 | A | A | nd |
| 35 | A | A | nd |
| 36 | A | A | A |
| 37 | A | A | nd |
| 38 | A | A | nd |
| 39 | A | B | A |
| 40 | B | C | nd |
| 41 | C | A | A |
| 42 | A | B | A |
| 43 | C | C | A |
| 44 | A | A | nd |
| 45 | A | A | A |
| 46 | A | A | nd |
| 47 | A | A | A |
| 48 | A | A | A |
| 49 | A | A | nd |
| 50 | B | B | nd |
| 51 | A | A | nd |
| 52 | A | A | nd |
| 53 | A | B | nd |
| 54 | B | B | nd |
| 55 | B | B | nd |
| 56 | B | C | nd |
| 57 | B | B | nd |
| 58 | B | B | nd |
| 59 | B | B | nd |
| 60 | B | B | nd |
| 61 | B | B | nd |
| 62 | B | B | nd |
| 63 | A | B | nd |
| 64 | A | A | nd |
| 65 | A | A | nd |
| 66 | A | A | nd |
| 67 | B | C | nd |
| 68 | C | C | nd |
| 69 | A | B | A |
| 70 | A | B | nd |
| 71 | A | B | nd |
| 72 | A | B | nd |
| 73 | B | B | A |
| 74 | A | A | nd |
| 75 | A | A | nd |
| 76 | A | A | nd |
| 77 | A | A | nd |
| 78 | A | A | nd |
| 79 | A | A | nd |
| 80 | A | A | nd |
| 81 | A | A | nd |
| 82 | B | B | nd |
| 83 | C | C | nd |
| 84 | B | B | nd |
| 85 | B | B | nd |
| 86 | nd | nd | nd |
| 87 | nd | nd | nd |
| 88 | A | A | nd |
| 89 | A | A | nd |
| 90 | B | C | nd |
| 91 | B | C | nd |
| 92 | A | B | nd |
| 93 | A | B | A |
| 94 | B | B | nd |
| 95 | A | A | nd |
| 96 | A | A | A |

TABLE 1-continued

Biochemical PRMT5 inhibiton data

| Example | PRMT5 Enzyme_IC$_{50}$_μM | PRMT5_Z138_GI$_{50}$_Day 8_μM | PRMT5_Z138_SDMA ELISA_Day 4_μM |
|---|---|---|---|
| 97 | A | A | nd |
| 98 | A | A | nd |
| 99 | A | A | nd |
| 100 | B | B | A |
| 101 | B | C | nd |
| 102 | B | A | A |
| 103 | B | A | A |
| 104 | nd | B | A |
| 105 | nd | B | A |
| 106 | A | B | A |
| 107A | C | B | A |
| 107B | nd | nd | nd |
| 108 | B | A | A |
| 109 | B | C | A |
| 110 | B | B | A |
| 111 | B | B | A |
| 112 | B | B | A |
| 113 | C | C | B |
| 114 | B | A | A |
| 115 | A | A | A |
| 116 | A | A | A |
| 117 | A | A | nd |
| 118A | A | A | nd |
| 118B | nd | nd | nd |
| 119 | A | A | nd |
| 120A | A | A | nd |
| 120B | A | B | nd |
| 121A | A | A | A |
| 121B | B | A | A |
| 122 | A | A | nd |
| 123 | A | A | nd | nd = not determined

Table 1 summarized the biological activity of the compounds. It was observed that Examples 1, 2, 4-8, 10-12, 14-20, 23, 36, 45, 47, 48, 96, 115, 116, 121A showed an IC$_{50}$ value in the range of 0.01-1 μM for all the three assays and were found to be potent for inhibiting PRMT5 enzymes.

Optimal biological activity was obtained for Examples 124-167.

What is claimed is:

1. A compound having the structure of Formula Ia

Formula Ia

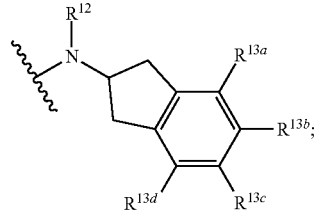

their analogs, tautomeric forms, stereoisomers, geometrical isomers, polymorphs, hydrates, solvates, pharmaceutically acceptable salts, pharmaceutical compositions, metabolites and prodrugs thereof,
wherein A is

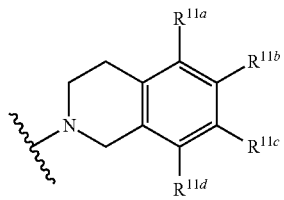

Ia

-continued

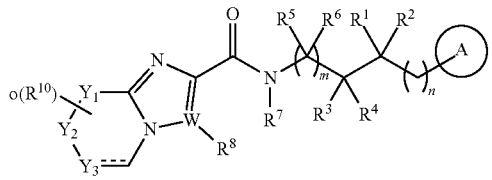

Ib

- - - - represents optional single or double bond;
n is 0 or 1;
m is 0-2;
o is 1-3;
$R^1, R^2, R^3, R^4, R^5$ and $R^6$ are independently selected from hydrogen, halogen, hydroxyl, or $C_{1-6}$ alkyl, wherein, $C_{1-6}$ alkyl is optionally substituted with one or more groups selected from hydroxyl, or halogen;
$R^7$ is selected from hydrogen, and $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl or cyano;
$R^{11a}, R^{11b}, R^{11c}$ are independently selected from hydrogen, halogen, cyano, $C_{1-6}$ alkyl, $C_{1-6}$ haloalkyl, or $C_{1-6}$ alkoxy;
$Y^1, Y^2$ and $Y^3$ are independently selected from N or CH;
W is selected from N or C;
$R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and

285

$R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, or $SO_2R_a$, wherein, $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{3-6}$ cycloalkyl, $C_{1-6}$ alkyl, $C_{1-6}$ haloalkyl, $C_{1-6}$ alkoxy, $C_{3-6}$ cycloalkyl, $C(O)R_b$, 3-6 membered saturated or unsaturated heterocyclyl or heteroaryl ring with 1-5 heteroatoms selected from N, S or O, wherein, 3-6 membered saturated or unsaturated heterocyclyl or heteroaryl ring with 1-3 heteroatoms selected from N, S or O is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

2. The compound of Formula Ia as claimed in claim 1, their analogs, tautomeric forms, stereoisomers, geometrical isomers, polymorphs, hydrates, solvates, pharmaceutically acceptable salts, pharmaceutical compositions, metabolites and prodrugs thereof, wherein, A is Ia

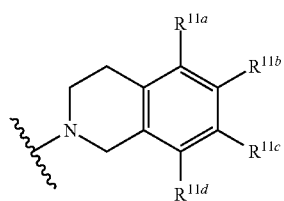

Ib

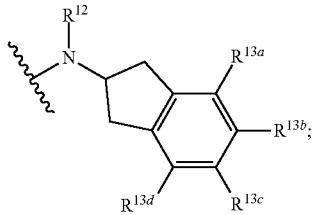

- - - - represents optional single or double bond;
n is 0 or 1;
m is 0-2;
o is 1-3;
$R^1$, $R^2$, $R^3$, $R^4$, $R^5$ and $R^6$ are independently selected from the group consisting of hydrogen, halogen, hydroxyl and $C_{1-4}$ alkyl, wherein, $C_{1-4}$ alkyl is optionally substituted with one or more groups selected from hydroxyl or halogen;
$R^7$ is selected from hydrogen and $C_{1-6}$ alkyl, wherein, $C_{1-6}$ alkyl is optionally substituted with $C_{5-6}$ aryl, wherein $C_{5-6}$ aryl is optionally substituted with one or more groups selected from the group consisting of $C_{1-6}$ alkyl, $C_{1-6}$ alkoxy, halogen, hydroxyl or cyano;

286

$R^{11a}$, $R^{11b}$, $R^{11c}$ and $R^{11d}$ are independently selected from the group consisting of hydrogen, halogen, cyano, $C_{1-6}$ alkyl, $C_{1-6}$ haloalkyl, or $C_{1-6}$ alkoxy;
$Y^1$, $Y^2$ and $Y^3$ are independently selected from N or CH;
W is selected from N or C;
$R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and
$R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein, $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, 3-6 membered saturated or unsaturated heterocyclyl or heteroaryl ring with 1-3 heteroatoms selected from N, S or O, wherein, 3-6 membered saturated or unsaturated heterocyclyl or heteroaryl ring with 1-3 heteroatoms selected from N, S or O is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

3. The compound of Formula Ia as claimed in claim 2, their analogs, tautomeric forms, stereoisomers, geometrical isomers, polymorphs, hydrates, solvates, pharmaceutically acceptable salts, pharmaceutical compositions, metabolites and prodrugs thereof, wherein, A is Ia

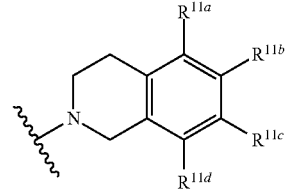

Ib

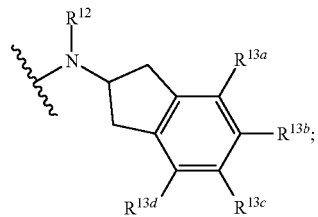

- - - - represents optional single or double bond;
n is 0 or 1;
m is 0-2;
o is 1-3;
$R^1$, $R^2$, $R^3$ $R^4$, $R^5$ and $R^6$ are independently selected from the group consisting of hydrogen, halogen, hydroxyl or $C_{1-4}$ alkyl, wherein $C_{1-4}$ alkyl is optionally substituted with one or more groups selected from hydroxyl or halogen;

$R^7$ is selected from hydrogen or $C_{1-4}$ alkyl, wherein, $C_{1-4}$ alkyl is optionally substituted with $C_6$ aryl, and wherein, $C_6$ aryl is optionally substituted with one or more groups selected from the group consisting of $C_{1-4}$ alkyl, $C_{1-4}$ alkoxy, halogen, hydroxyl or cyano;

$R^{11a}$, $R^{11b}$, $R^{11c}$ and $R^{11d}$ are independently selected from the group consisting of hydrogen, halogen, cyano, $C_{1-6}$ alkyl, $C_{1-6}$ haloalkyl, or $C_{1-6}$ alkoxy;

$Y^1$, $Y^2$ and $Y^3$ are independently selected from N or CH;

W is selected from N or C;

$R^8$ is absent or is selected from hydrogen, halogen, $C_{1-6}$ alkyl, $C_{1-6}$ alkenyl, $C_{1-6}$ alkynyl, $C_{1-6}$ haloalkyl, $C_{3-6}$ cycloalkyl, $C_{5-6}$ aryl, $C_{3-15}$ heteroaryl, and $C_{3-15}$ heterocyclyl; and $R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$ and $SO_2R_a$, wherein, $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, and wherein, 3-6 membered saturated or unsaturated heterocyclyl or heteroaryl ring with 1-3 heteroatoms selected from N, S or O is optionally substituted with $C(O)R_b$, wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

4. The compound of Formula Ia as claimed in claim 1, their analogs, tautomeric forms, stereoisomers, geometrical isomers, polymorphs, hydrates, solvates, pharmaceutically acceptable salts, pharmaceutical compositions, metabolites and prodrugs thereof, wherein, A is

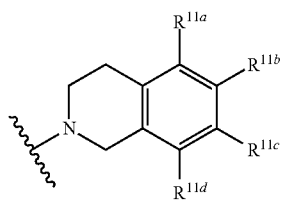

Ia

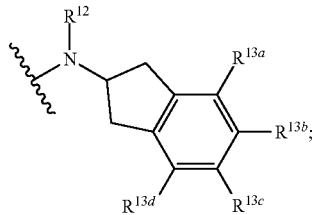

Ib

- - - - represents optional single or double bond;

n is 0 or 1;

m is 0 or 1;

o is 1-3;

$R^1$, $R^2$, $R^3$, $R^4$, $R^5$ and $R^6$ are independently selected from the group consisting of hydrogen, halogen, hydroxyl and $C_{1-4}$ alkyl, wherein, $C_{1-4}$ alkyl is optionally substituted with one or more groups selected from hydroxyl, fluoro, chloro or bromo;

$R^7$ is selected from hydrogen and $C_{1-4}$ alkyl, wherein, $C_{1-4}$ alkyl is optionally substituted with $C_6$ aryl, and wherein $C_6$ aryl is optionally substituted with one or more groups selected from the group consisting of $C_{1-4}$ alkyl, $C_{1-4}$ alkoxy, halogen, hydroxyl or cyano;

$R^{11a}$, $R^{11b}$, $R^{11c}$ and $R^{11d}$ are independently selected from the group consisting of hydrogen, halogen, cyano, $C_{1-6}$ alkyl, $C_{1-6}$ haloalkyl, or $C_{1-6}$ alkoxy;

$Y^1$, $Y^2$ and $Y^3$ are independently selected from N or CH;

W is selected from N or C;

$R^8$ is absent or is selected from hydrogen, halogen, $C_{1-4}$ alkyl, $C_{1-4}$ alkenyl, $C_{1-4}$ alkynyl, $C_{1-4}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-4}$alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SF_5$, $SONR_aR_b$, $SO_2NR_aR_b$, $OR_a$, $OR_aC(O)OR_b$, $OC(O)NR_aR_b$, $OC(O)R_a$, $OC(O)NR_aR_b$, $R_aNR_bR_c$, $R_aOR_b$, $SR_a$, $SOR_a$ and $SO_2R_a$, wherein, $C_{5-6}$ aryl, $C_{3-6}$ cycloalkyl, and 3-15 membered saturated or unsaturated heterocyclyl or heteroaryl ring are optionally substituted with one or more groups selected from the group consisting of halogen, hydroxyl, cyano, oxo, $C_{1-4}$ alkyl, $C_{1-4}$ haloalkyl, $C_{1-4}$ alkoxy, $C_{3-6}$ cycloalkyl, $C(O)R_b$, 3-6 membered saturated or unsaturated heterocyclyl or heteroaryl ring with 1-3 heteroatoms selected from N, S or O, wherein, 3-6 membered saturated or unsaturated heterocyclyl or heteroaryl ring with 1-3 heteroatoms selected from N, S or O is optionally substituted with $C(O)R_b$, and wherein, $R_a$, $R_b$ and $R_c$ are independently selected from hydrogen, $C_{1-4}$ alkyl, $C_{3-6}$ cycloalkyl, $C_{5-6}$ aryl, $C_{3-6}$ cycloalkyl, $C_{3-15}$ heterocyclyl, and $C_{3-15}$ heteroaryl, wherein, $C_{5-6}$ aryl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

5. The compound as claimed in claim 1 having the structure of Formula Ib

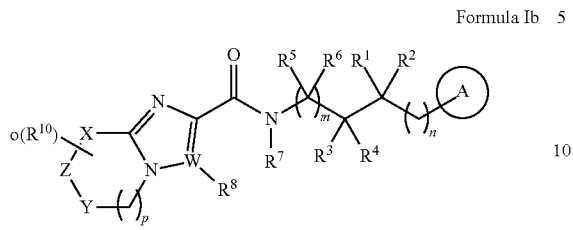

Formula Ib their analogs, tautomeric forms, stereoisomers, geometrical isomers, polymorphs, hydrates, solvates, pharmaceutically acceptable salts, pharmaceutical compositions, metabolites, and prodrugs thereof,
wherein, A is

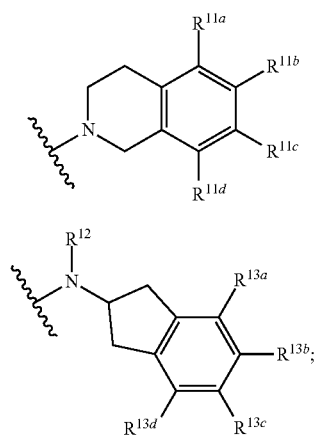

n is 0 or 1;
m is 0-2;
p is 1;
o is 1-3;
$R^1$, $R^2$, $R^3$ and $R^4$ are independently selected from hydrogen, halogen, hydroxyl or $C_{1-6}$ alkyl, wherein, $C_{1-6}$ alkyl is optionally substituted with one or more groups selected from hydroxyl or halogen;
$R^5$ and $R^6$ are independently selected from hydrogen, $C_{1-6}$ alkyl, or halogen, wherein $C_{1-6}$ alkyl is optionally substituted with one or more groups selected from hydroxyl or halogen;
$R^7$ is selected from hydrogen or $C_{1-6}$ alkyl, wherein, $C_{1-6}$ alkyl is optionally substituted with $C_{5-6}$ aryl, and wherein, $C_{5-6}$ aryl is optionally substituted with one or more groups selected from $C_{1-6}$ alkyl, $C_{1-6}$ alkoxy, halogen, hydroxyl, or cyano;
$R^{11a}$, $R^{11b}$, $R^{11c}$, and $R^{11d}$ are independently selected from hydrogen, halogen, cyano, $C_{1-6}$ alkyl, $C_{1-6}$ haloalkyl or $C_{1-6}$ alkoxy;
X, Y and Z are independently selected from $CR^{10}$, $NR^{10}$, O or S;
W is selected from N or C;
$R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, or 3-15 membered saturated or unsaturated heterocyclyl or heteroaryl ring with 1-5 heteroatoms selected from N, S or O, wherein, $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein, 3-6 membered saturated or unsaturated heterocyclyl or heteroaryl ring is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, $C_3$-6 cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

6. The compound of Formula Ib as claimed in claim 5, their analogs, tautomeric forms, stereoisomers, geometrical isomers, polymorphs, hydrates, solvates, pharmaceutically acceptable salts, pharmaceutical compositions, metabolites, and prodrugs thereof, wherein,
A is

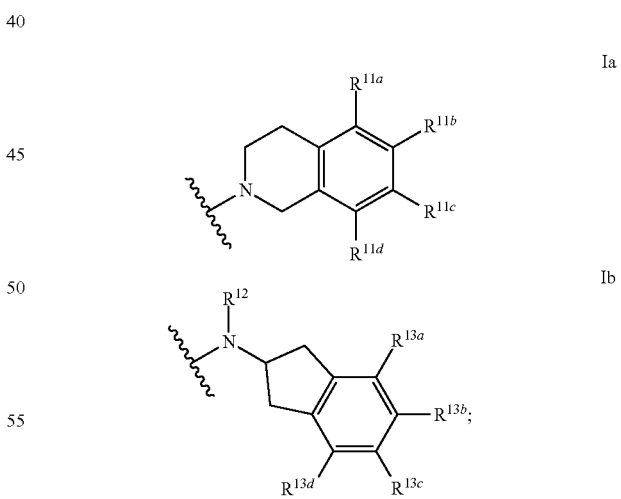

n is 0 or 1;
m is 0 or 1;
p is 1;
o is 1-3;
$R^1$, $R^2$, $R^3$ and $R^4$ are independently selected from hydrogen, halogen, hydroxyl or $C_{1-5}$ alkyl, wherein, $C_{1-5}$ alkyl is optionally substituted with one or more groups selected from hydroxyl or halogen;

$R^5$ and $R^6$ are independently selected from hydrogen, $C_{1-5}$ alkyl or halogen, wherein, $C_{1-5}$ alkyl is optionally substituted with hydroxyl and halogen;

$R^7$ is selected from hydrogen or $C_{1-6}$ alkyl, wherein, $C_{1-6}$ alkyl is optionally substituted with $C_{5-6}$ aryl, and wherein, $C_{5-6}$ aryl is optionally substituted with one or more groups selected from $C_{1-6}$ alkyl, $C_{1-6}$ alkoxy, halogen, hydroxyl or cyano;

$R^{11a}$, $R^{11b}$, $R^{11c}$ and $R^{11d}$ are independently selected from hydrogen, halogen, cyano, $C_{1-6}$ alkyl, $C_{1-6}$ haloalkyl, or $C_{1-6}$ alkoxy;

X, Y and Z are independently selected from $CR^{10}$, $NR^{10}$, O or S;

W is selected from N or C;

$R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein, $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein, 3-6 membered saturated or unsaturated heterocyclyl or heteroaryl ring is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

7. The compound of Formula Ib as claimed in claim 5, their analogs, tautomeric forms, stereoisomers, geometrical isomers, polymorphs, hydrates, solvates, pharmaceutically acceptable salts, pharmaceutical compositions, metabolites, and prodrugs thereof, wherein, A is

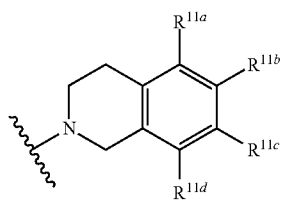

Ia

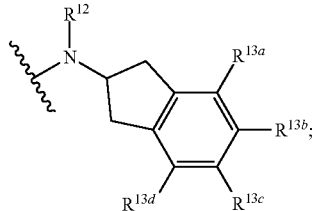

Ib n is 0 or 1;

m is 0 or 1;

p is 1;

o is 1-3;

$R^1$, $R^2$, $R^3$ and $R^4$ are independently selected from hydrogen, halogen, hydroxyl or $C_{1-4}$ alkyl, wherein, $C_{1-4}$ alkyl is optionally substituted with one or more groups selected from hydroxyl, chloro, bromo, fluoro or iodo;

$R^5$ and $R^6$ are independently selected from hydrogen, $C_{1-4}$ alkyl, or halogen, wherein, $C_{1-4}$ alkyl is optionally substituted with one or more groups selected from hydroxyl, chloro, bromo, fluoro, or iodo;

$R^7$ is selected from hydrogen or $C_{1-4}$ alkyl, wherein, $C_{1-4}$ alkyl is optionally substituted with $C_6$ aryl, and wherein, $C_6$ aryl is optionally substituted with one or more groups selected from $C_{1-4}$ alkyl, $C_{1-4}$ alkoxy, halogen, hydroxyl or cyano;

$R^{11a}$, $R^{11b}$, $R^{11c}$ and $R^{11d}$ are independently selected from hydrogen, halogen, cyano, $C_{1-6}$ alkyl, $C_{1-6}$ haloalkyl, or $C_{1-6}$ alkoxy;

X, Y and Z are independently selected from $CR^{10}$, $NR^{10}$, O or S;

W is selected from N or C;

$R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein, $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, cyano, $C_{1-6}$ alkyl, $C_{1-6}$ haloalkyl, $C_{1-6}$ alkoxy, $C_{3-6}$ cycloalkyl, $C(O)R_b$, or 3-6 membered saturated or unsaturated heterocyclyl or heteroaryl ring with 1-5 heteroatoms selected from N, S or O, wherein, 3-6 membered saturated or unsaturated heterocyclyl or heteroaryl ring is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

8. The compound of Formula Ib as claimed in claim 5, their analogs, tautomeric forms, stereoisomers, geometrical isomers, polymorphs, hydrates, solvates, pharmaceutically acceptable salts, pharmaceutical compositions, metabolites and prodrugs thereof, wherein, A is

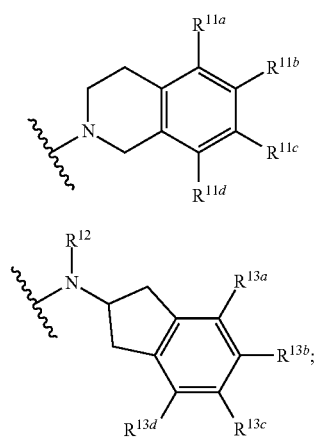

n is 0 or 1;
m is 0 or 1;
p is 1;
o is 1-3;
$R^1$, $R^2$, $R^3$ and $R^4$ are independently selected from hydrogen, halogen, hydroxyl or $C_{1-4}$ alkyl, wherein, $C_{1-4}$ alkyl is optionally substituted with one or more groups selected from hydroxyl, fluoro or chloro;
$R^5$ and $R^6$ are independently selected from hydrogen, $C_{1-4}$ alkyl or halogen, wherein, $C_{1-4}$ alkyl is optionally substituted with one or more groups selected from hydroxyl, chloro, bromo, fluoro or iodo;
$R^7$ is selected from hydrogen or $C_{1-4}$ alkyl, wherein, $C_{1-4}$ alkyl is optionally substituted with $C_6$ aryl, and wherein, $C_6$ aryl is optionally substituted with one or more groups selected from $C_{1-4}$ alkyl, $C_{1-4}$ alkoxy, halogen, hydroxyl or cyano;
$R^{11a}$, $R^{11b}$, $R^{11c}$ and $R^{11d}$ are independently selected from hydrogen, halogen, cyano, $C_{1-6}$ alkyl, $C_{1-6}$ haloalkyl or $C_{1-6}$ alkoxy;
X, Y and Z are independently selected from $CR^{10}$, $NR^{10}$, O or S;
W is selected from N or C;
$R^8$ is absent or is selected from hydrogen, halogen, $C_{1-4}$ alkyl, $C_{2-4}$ alkenyl, $C_{2-4}$ alkynyl, $C_{1-4}$ haloalkyl, $C_{3-6}$ cycloalkyl, $C_{5-6}$ aryl, $C_{3-15}$ heteroaryl or $C_{3-15}$ heterocyclyl; and
$R^{10}$ is selected from hydrogen, halogen, hydroxyl, oxo, nitro, cyano, azido, nitroso, amino, hydrazino, formyl, $C_{1-4}$ alkyl, $C_{1-4}$ haloalkyl, $C_{1-4}$ alkoxy, $C_{1-4}$ haloalkoxy, $C_{3-6}$ cycloalkyl, $C_{5-6}$ aryl, $C_{1-4}$ alkylamino, $COOR_a$, $C(O)R_b$, $C(S)R_a$, $C(O)NR_aR_b$, $C(S)NR_aR_b$, $NR_aC(O)NR_bR_c$, $NR_aC(S)NR_bR_c$, $N(R_a)SOR_b$, $N(R_a)SO_2R_b$, $NR_aC(O)OR_b$, $NR_aR_b$, $NR_aC(O)R_b$, $NR_aC(S)R_b$, $SONR_aR_b$, $SO_2NR_aR_b$, $OR_a$, $OR_aC(O)OR_b$, $OC(O)NR_bR_c$, $OC(O)R_a$, $OC(O)NR_aR_b$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein, $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, oxo, cyano, $C_{1-4}$ alkyl, $C_{1-4}$ haloalkyl, $C_{1-4}$ alkoxy, $C_{3-6}$ cycloalkyl, $C(O)R_b$, or 3-6 membered saturated or unsaturated heterocyclyl or heteroaryl ring with 1-3 heteroatoms selected from N, S or O, wherein, 3-6 membered saturated or unsaturated heterocyclyl or heteroaryl ring is optionally substituted with $C(O)R_b$, and wherein, $R_a$, $R_b$ and $R_c$ are independently selected from hydrogen, $C_{1-4}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, $C_3$-6 cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O.

9. A compound having the structure Formula Ia and Ib, their analogs, tautomeric forms, stereoisomers, geometrical isomers, polymorphs, hydrates, solvates, pharmaceutically acceptable salts, pharmaceutical compositions, metabolites and prodrugs thereof, which is selected from a group consisting of:
N-(3-(3,4-dihydroisoquinolin-2(1H)-yl)-2-hydroxypropyl)-6-(trifluoromethyl)imidazo[1,2-a]pyridine-2-carboxamide (Example 1),
N-(3-(3,4-dihydroisoquinolin-2(1H)-yl)-2-hydroxypropyl)-6-methylimidazo[1,2-a]pyridine-2-carboxamide (Example 2),
N-(2-(3,4-dihydroisoquinolin-2(1H)-yl)-1-hydroxyethyl)-7-(4-fluorophenyl) imidazo[1,2-a]pyridine-2-carboxamide (Example 3),
(S)—N-(3-(3,4-dihydroisoquinolin-2(1H)-yl)-2-hydroxypropyl)-6-(1-ethyl-1H-pyrazol-4-yl)imidazo [1,2-a] pyridine-2-carboxamide (Example 4),
(S)—N-(3-(3,4-dihydroisoquinolin-2(1H)-yl)-2-hydroxypropyl)-6-(5-propyl-1,2,4-oxadiazol-3-yl)imidazo[1,2-a]pyridine-2-carboxamide (Example 5),
(S)—N-(3-(3,4-dihydroisoquinolin-2(1H)-yl)-2-hydroxypropyl)-6-(5-methyl-1,2,4-oxadiazol-3-yl)imidazo[1,2-a]pyridine-2-carboxamide (Example 6),
(S)—N-(3-(3,4-dihydroisoquinolin-2(1H)-yl)-2-hydroxypropyl)-6-(5-(trifluoromethyl)-1,2,4-oxadiazol-3-yl) imidazo[1,2-a]pyridine-2-carboxamide (Example 7),
(S)—N-(3-(3,4-dihydroisoquinolin-2(1H)-yl)-2-hydroxypropyl)-6(trifluoromethyl) imidazo[1,2-a]pyridine-2-carboxamide (Example 8),
N-(3-(3,4-dihydroisoquinolin-2(1H)-yl)-2-hydroxypropyl)-6-methoxyimidazo [1,2a]pyridine-2-carboxamide (Example 9),
N-(3-(3,4-dihydroisoquinolin-2(1H)-yl)-2-hydroxypropyl)-6- phenylimidazo [1,2-a]pyridine-2-carboxamide (Example 10),
N-(3-(3,4-dihydroisoquinolin-2(1H)-yl)-2-hydroxypropyl)-6-(4-fluorophenyl) imidazo[1,2-a]pyridine-2-carboxamide (Example 11),
(S)—N-(3-(3,4-dihydroisoquinolin-2(1H)-yl)-2-hydroxypropyl)-6- isopropylimidazo [1,2-a]pyridine-2-carboxamide (Example 12),
(S)—N-(3-(3,4-dihydroisoquinolin-2(1H)-yl)-2-hydroxypropyl)-6-(1-methyl-1H-pyrazol-4-yl)imidazo[1,2-a]pyridine-2-carboxamide (Example 13), (S)-6-(4-cyanophenyl)-N-(3-(3,4-dihydroisoquinolin-2 (1H)-yl)-2-hydroxypropyl) imidazo[1,2-a]pyridine-2-carboxamide (Example 14), (S)—N-(3-(3,4-dihydroisoquinolin-2(1H)-yl)-2-hydroxypropyl)-6-(3,5-dimethyl isoxazol-4-yl)imidazo[1,2-a] pyridine-2-carboxamide (Example 15), (S)-6-(3,5-difluorophenyl)-N-(3-(3,4-dihydroisoquinolin-2(1H)-yl)-2-hydroxypropyl)imidazo[1,2-a]pyridine-2-carboxamide (Example 16), (S)—N-(3-(3,4-dihydroisoquinolin-2(1H)-yl)-2-hydroxypropyl)-6-(4fluorophenyl) imidazo[1,2-a]pyridine-2-carboxamide (Example 17), (S)—N-(3-(3,4-dihydroisoquinolin-2(1H)-yl)-2-hydroxypropyl)-6-(1-isobutyl-1H-pyrazol-4-yl)imidazo[1,2-a] pyridine-2-carboxamide (Example 18), (S)-6-(3,6-dihydro-2H-pyran-4-yl)-N-(3-(3,4-dihydroisoquinolin-2(1H)-yl)-2-hydroxypropyl)imidazo[1,2-a] pyridine-2-carboxamide (Example 19), N—((S)-3-(3,4-dihydroisoquinolin-2(1H)-yl)-2-hydroxypropyl)-6-(1-((R)-tetrahydrofuran-3-yl)-1H-pyrazol-4-yl)imidazo[1,2-a]pyridine-2-carboxamide (Example 20), (S)—N-(3-(3,4-dihydroisoquinolin-2(1H)-yl)-2-hydroxypropyl)-6-(1H-pyrazol-4-yl)imidazo[1,2-a]pyridine-2-carboxamide (Example 21), (S)—N-(3-(3,4-dihydroisoquinolin-2(1H)-yl)-2-hydroxypropyl)-6-(1-(oxetan-3-yl)-1H-pyrazol-4-yl)imidazo[1,2-a]pyridine-2-carboxamide (Example 22), (S)-6-(1-(1-acetylaziridine-3-yl)-1H-pyrazol-4-yl)-N-(3-(3,4-dihydroisoquinolin-2(1H)-yl)-2-hydroxypropyl) imidazo[1,2-a]pyridine-2-carboxamide (Example 23), (S)—N-(3-(3,4-dihydroisoquinolin-2(1H)-yl)-2-hydroxypropyl)-6-(5-isopropyl-1,2,4-oxadiazol-3-yl)imidazo[1,2-a]pyridine-2-carboxamide (Example 24), (S)-6-(5-cyclopropyl-1,2,4-oxadiazol-3-yl)-N-(3-(3,4-dihydroisoquinolin-2(1H)-yl)-2-hydroxypropyl)imidazo[1,2-a]pyridine-2-carboxamide (Example 25), (S)—N-(3-(3,4-dihydroisoquinolin-2(1H)-yl)-2-hydroxypropyl)-6-(tetrahydro-2H-pyran-4-yl)imidazo[1,2-a]pyridine-2-carboxamide (Example-26), (S)-6-(1-acetylpiperidin-4-yl)-N-(3-(3,4-dihydroisoquinolin-2(1H)-yl)-2-hydroxypropyl)imidazo[1,2-a]pyridine-2-carboxamide (Example 27), (S)—N-(3-(3,4-dihydroisoquinolin-2(1H)-yl)-2-hydroxypropyl)-6-(2-methylpyrimidin-5-yl)imidazo[1,2-a] pyridine-2-carboxamide (Example 28), (S)—N-(3-(3,4-dihydroisoquinolin-2(1H)-yl)-2-hydroxypropyl)-6-(6-methylpyridin-3-yl)imidazo[1,2-a]pyridine-2-carboxamide (Example 29), (S)—N-(3-(3,4-dihydroisoquinolin-2(1H)-yl)-2-hydroxypropyl)-6-(6-methylpyridazin-3-yl)imidazo[1,2-a]pyridine-2-carboxamide (Example 30), (S)—N-(3-(3,4-dihydroisoquinolin-2(1H)-yl)-2-hydroxypropyl)-6-(2-methylthiazol-5-yl)imidazo[1,2-a]pyridine-2-carboxamide (Example 31), (S)—N-(3-(3,4-dihydroisoquinolin-2(1H)-yl)-2-hydroxypropyl)-6-(4,5-dimethylthiazol-2-yl)imidazo[1,2-a]pyridine-2-carboxamide (Example 32), (S)-6-(5-chloropyridin-2-yl)-N-(3-(3,4-dihydroisoquinolin-2(1H)-yl)-2-hydroxypropyl)imidazo[1,2-a]pyridine-2-carboxamide (Example 33), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyridine-2-carboxamide (Example 34), (S)—N-(3-(3,4-dihydroisoquinolin-2(1H)-yl)-2-hydroxypropyl)-6-(1-methyl-2-oxo-1,2-dihydropyridin-4-yl)imidazo[1,2-a]pyridine-2-carboxamide (Example 35), (S)—N-(3-(3,4-dihydroisoquinolin-2(1H)-yl)-2-hydroxypropyl)-6-(1-methyl-1H-1,2,3-triazol-4-yl)imidazo[1,2-a]pyridine-2-carboxamide (Example 36), (S)—N-(3-(3,4-dihydroisoquinolin-2(1H)-yl)-2-hydroxypropyl)-6-(1-isopropyl-1H-1,2,3-triazol-4-yl)imidazo[1,2-a]pyridine-2-carboxamide (Example 37), (S)—N2-(3-(3,4-dihydroisoquinolin-2(1H)-yl)-2-hydroxypropyl)-N6-methylimidazo[1,2-a]pyridine-2,6-dicarboxamide (Example 38), (S)-6-acetamido-N-(3-(3,4-dihydroisoquinolin-2(1H)-yl)-2- hydroxypropyl)imidazo[1,2-a]pyridine-2-carboxamide (Example 39), (S)—N-(3-(3,4-dihydroisoquinolin-2(1H)-yl)-2-hydroxypropyl)-6-sulfamoylimidazo[1,2-a]pyridine-2-carboxamide (Example 40), (S)—N-(3-(3,4-dihydroisoquinolin-2(1H)-yl)-2-hydroxypropyl)-6-(methylsulfonamido)imidazo[1,2-a]pyridine-2-carboxamide (Example 41), ((S)—N-(3-(3,4-dihydroisoquinolin-2(1H)-yl)-2-hydroxypropyl)-6-(trifluoromethyl)imidazo[1,2-a]pyrimidine-2-carboxamide (Example 42), (S)—N-(3-(3,4-dihydroisoquinolin-2(1H)-yl)-2-hydroxypropyl)-6-(1-methyl-1H-pyrazol-4-yl)imidazo[1,2-a] pyrimidine-2-carboxamide (Example 43), (S)—N-(3-(3,4-dihydroisoquinolin-2(1H)-yl)-2-hydroxypropyl)-6-(1-methyl-2-oxo-1,2-dihydropyridin-4-yl) imidazo[1,2-a]pyrimidine-2-carboxamide (Example 44), (S)—N-(3-(3,4-dihydroisoquinolin-2(1H)-yl)-2-hydroxypropyl)-6-(1-methyl-1H-pyrazol-4-yl)imidazo[1,2-a] pyrazine-2-carboxamide (Example 45), (S)—N-(3-(3,4-dihydroisoquinolin-2(1H)-yl)-2-hydroxypropyl)-6-(1-methyl-2-oxo-1,2-dihydropyridin-4-yl) imidazo[1,2-a]pyrazine-2-carboxamide (Example 47), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 51), (S)-6-(1-acetylpiperidin-4-yl)-N-(3-(3,4-dihydroisoquinolin-2(1H)-yl)-2-hydroxypropyl)imidazo[1,2-a]pyrazine-2-carboxamide (Example 52), (S)—N-(3-(3,4-dihydroisoquinolin-2(1H)-yl)-2-hydroxypropyl)-6-(trifluoromethyl)imidazo[1,2-a]pyrazine-2-carboxamide (Example 53), (S)—N-(3-(3,4-dihydroisoquinolin-2(1H)-yl)-2-hydroxypropyl)-3,6-dimethylimidazo[1,2-a]pyrazine-2-carboxamide (Example 55), (S)—N-(3-(3,4-dihydroisoquinolin-2(1H)-yl)-2-hydroxypropyl)-6-(trifluoromethyl)imidazo[1,2-a]pyrazine-2-carboxamide (Example 57), (S)-6-(3,3-difluoroazetidin-1-yl)-N-(3-(3,4-dihydroisoquinolin-2(1H)-yl)-2-hydroxypropyl)imidazo[1,2-a] pyrazine-2-carboxamide (Example 58), (S)-6-(3,3-difluoroazetidin-1-yl)-N-(3-(3,4-dihydroisoquinolin-2(1H)-yl)-2-hydroxypropyl)imidazo[1,2-a] pyridine-2-carboxamide (Example 59), (S)—N-(3-(3,4-dihydroisoquinolin-2(1H)-yl)-2-hydroxypropyl)-5-(trifluoromethyl)pyrazolo[1,5-a]pyrimidine-2-carboxamide (Example 60), (S)—N-(3-(3,4-dihydroisoquinolin-2(1H)-yl)-2-hydroxypropyl)-6-(3-hydroxyoxetan-3-yl)imidazo[1,2-a]pyridine-2-carboxamide (Example 61), (S)—N-(3-(3,4-dihydroisoquinolin-2(1H)-yl)-2-hydroxypropyl)-5-(1-methyl-1H-pyrazol-4-yl)pyrazolo[1,5-a]pyrimidine-2-carboxamide (Example 62), (S)—N-(3-(3,4-dihydroisoquinolin-2(1H)-yl)-2-hydroxypropyl)-5-(1-methyl-2-oxo-1,2-dihydropyridin-4-yl)pyrazolo[1,5-a]pyrimidine-2-carboxamide (Example 63), (S)—N-(3-(3,4-dihydroisoquinolin-2(1H)-yl)-2-hydroxypropyl)-3-methyl-6-(1-methyl-1H-pyrazol-4-yl)imidazo[1,2-a]pyrazine-2-carboxamide (Example 64), (S)—N-(3-(3,4-dihydroisoquinolin-2(1H)-yl)-2-hydroxypropyl)-3-methyl-6-(1-methyl-2-oxo-1,2-dihydropyridin-4-yl)imidazo[1,2-a]pyrazine-2-carboxamide (Example 65), (S)—N-(3-(3,4-dihydroisoquinolin-2(1H)-yl)-2-hydroxypropyl)-3-methyl-6-(1-methyl-6-oxo-1,6-dihydropyridin-3-yl)imidazo[1,2-a]pyrazine-2-carboxamide (Example 66)

(S)—N-(3-(3,4-dihydroisoquinolin-2(1H)-yl)-2-hydroxypropyl)-5-methylpyrazolo[1,5-a]pyrimidine-2-carboxamide (Example 67), (S)—N-(3-(3,4-dihydroisoquinolin-2(1H)-yl)-2-hydroxypropyl)-3-fluoro-5-(trifluoromethyl)pyrazolo[1,5-a]pyrimidine-2-carboxamide (Example 68), (S)-6-(azetidin-1-yl)-N-(3-(3,4-dihydroisoquinolin-2(1H)-yl)-2-hydroxypropyl)imidazo[1,2-a]pyridine-2-carboxamide (Example 69), N—((S)-3-(3,4-dihydroisoquinolin-2(1H)-yl)-2-hydroxypropyl)-6-(3-fluoropyrrolidin-1-yl)imidazo[1,2-a]pyridine-2-carboxamide (Example 70), (S)—N-(3-(3,4-dihydroisoquinolin-2(1H)-yl)-2-hydroxypropyl)-6-(4-methylpiperazin-1-yl)imidazo[1,2-a]pyridine-2-carboxamide (Example 71), (S)—N-(3-(3,4-dihydroisoquinolin-2(1H)-yl)-2-hydroxypropyl)-6-morpholinoimidazo[1,2-a]pyridine-2-carboxamide (Example 72), N—((S)-3-(3,4-dihydroisoquinolin-2(1H)-yl)-2-hydroxypropyl)-6-(3-fluoropyrrolidin-1-yl)imidazo[1,2-a]pyrazine-2-carboxamide (Example 73), (S)-6-(4-cyanophenyl)-N-(3-(3,4-dihydroisoquinolin-2(1H)-yl)-2-hydroxypropyl)imidazo[1,2-a]pyrazine-2-carboxamide (Example 74), (S)—N-(3-(3,4-dihydroisoquinolin-2(1H)-yl)-2-hydroxypropyl)-6-(1-methyl-6-oxo-1,6-dihydropyridin-3-yl)imidazo[1,2-a]pyrazine-2-carboxamide (Example 75), N-((2S,3S)-4-(3,4-dihydroisoquinolin-2(1H)-yl)-2,3-dihydroxybutyl)-6-(trifluoromethyl)imidazo[1,2-a]pyridine-2-carboxamide (Example 76), N-((2R,3R)-4-(3,4-dihydroisoquinolin-2(1H)-yl)-2,3-dihydroxybutyl)-6-(trifluoromethyl)imidazo[1,2-a]pyridine-2-carboxamide (Example 77), N-((2S,3S)-4-(3,4-dihydroisoquinolin-2(1H)-yl)-2,3-dihydroxybutyl)-6-(5-methyl-1,2,4-oxadiazol-3-yl)imidazo[1,2-a]pyridine-2-carboxamide (Example 78), N-((2S,3S)-4-(3,4-dihydroisoquinolin-2(1H)-yl)-2,3-dihydroxybutyl)-6-(1-((R)-tetrahydrofuran-3-yl)-1H-pyrazol-4-yl)imidazo[1,2-a]pyridine-2-carboxamide (Example 79), N-((2S,3S)-4-(3,4-dihydroisoquinolin-2(1H)-yl)-2,3-dihydroxybutyl)-6-(1-methyl-2-oxo-1,2-dihydropyridin-4-yl)imidazo[1,2-a]pyridine-2-carboxamide (Example 80), N-((2S,3S)-4-(3,4-dihydroisoquinolin-2(1H)-yl)-2,3-dihydroxybutyl)-6-(1-methyl-1H-pyrazol-4-yl)imidazo[1,2-a]pyridine-2-carboxamide (Example 81), (S)—N-(3-(6-fluoro-3,4-dihydroisoquinolin-2(1H)-yl)-2-hydroxypropyl)-6-(1-methyl-1H-pyrazol-4-yl)imidazo[1,2-a]pyridine-2-carboxamide (Example 82), —(S)—N-(3-(6-fluoro-3,4-dihydroisoquinolin-2(1H)-yl)-2-hydroxypropyl)-6-(trifluoromethyl)imidazo[1,2-a]pyrazine-2-carboxamide (Example 84), (S)—N-(3-(6-fluoro-3,4-dihydroisoquinolin-2(1H)-yl)-2-hydroxypropyl)-6-(1-methyl-2-oxo-1,2-dihydropyridin-4-yl) imidazo[1,2-a]pyrazine-2-carboxamide (Example 85), (S)-6-(difluoromethyl)-N-(3-(3,4-dihydroisoquinolin-2(1H)-yl)-2-hydroxypropyl)imidazo[1,2-a]pyridine-2-carboxamide (Example 86), 6-(difluoromethyl)-N—((S)-3-(3,4-dihydroisoquinolin-2(1H)-yl)-2- hydroxypropyl)-5,6,7,8-tetrahydroimidazo[1,2-a]pyridine-2-carboxamide (Example 87), (R)—N-(3-(3,4-dihydroisoquinolin-2(1H)-yl)-2-hydroxypropyl)-N-methyl-6-(trifluoromethyl)imidazo[1,2-a]pyridine-2-carboxamide (Example 88), (R)—N-(3-(3,4-dihydroisoquinolin-2(1H)-yl)-2-hydroxypropyl)-N-methyl-6-(trifluoromethyl)imidazo[1,2-a]pyrazine-2-carboxamide (Example 89), (R)—N-(3-(3,4-dihydroisoquinolin-2(1H)-yl)-2-hydroxypropyl)-N-methyl-5-(trifluoromethyl)pyrazolo[1,5-a]pyrimidine-2-carboxamide (Example 90), —(R)—N-(3-(3,4-dihydroisoquinolin-2(1H)-yl)-2-hydroxypropyl)-N-methyl-6-(1-methyl-1H-pyrazol-4-yl) imidazo[1,2-a]pyrazine-2-carboxamide (Example 92), (R)—N-(3-(3,4-dihydroisoquinolin-2(1H)-yl)-2-hydroxypropyl)-N-methyl-6-(1-methyl-2-oxo-1,2-dihydropyridin-4-yl)imidazo[1,2-a]pyrazine-2-carboxamide (Example 93), (R)—N-(3-(3,4-dihydroisoquinolin-2(1H)-yl)-2-hydroxypropyl)-N-methyl-6-(1-methyl-6-oxo-1,6-dihydropyridin-3-yl)imidazo[1,2-a]pyrazine-2-carboxamide (Example 94), (R)-6-(4-cyanophenyl)-N-(3-(3,4-dihydroisoquinolin-2(1H)-yl)-2- hydroxypropyl)-N-methylimidazo[1,2-a]pyrazine-2-carboxamide (Example 95), N-(4-(3,4-dihydroisoquinolin-2(1H)-yl)-1-hydroxybutan-2-yl)-6-(trifluoromethyl)imidazo[1,2-a]pyridine-2-carboxamide (Example 100), N-(3-(3,4-dihydroisoquinolin-2(1H)-yl)-2-hydroxypropyl)-5,6,7,8 tetrahydroimidazo[1,2-a]pyridine-2-carboxamide (Example 101), N-(3-(3,4-dihydroisoquinolin-2(1H)-yl)-2-hydroxypropyl)-6-methyl-5,6,7,8-tetrahydroimidazo[1,2-a]pyridine-2-carboxamide (Example 102), N-(3-(3,4-dihydroisoquinolin-2(1H)-yl)-2-hydroxypropyl)-7-methyl-5,6,7,8-tetrahydroimidazo[1,2-a]pyridine-2-carboxamide (Example 103), 6-cyclopropyl-N—((S)-3-(3,4-dihydroisoquinolin-2(1H)-yl)-2-hydroxypropyl)-5,6,7,8-tetrahydroimidazo[1,2-a]pyridine-2-carboxamide (Example 104), N-(3-(3,4-dihydroisoquinolin-2(1H)-yl)-2-hydroxypropyl)-7-propyl-5,6,7,8-tetrahydroimidazo[1,2-a]pyridine-2-carboxamide (Example 105), N-(3-(3,4-dihydroisoquinolin-2(1H)-yl)-2-hydroxypropyl)-6-propyl-5,6,7,8-tetrahydroimidazo[1,2-a]pyridine-2-carboxamide (Example 106), (R)—N—((S)-3-(3,4-dihydroisoquinolin-2(1H)-yl)-2-hydroxypropyl)-6-methoxy-5,6,7,8-tetrahydroimidazo[1,2-a]pyridine-2-carboxamide (Example 107a) and (S)—N—((S)-3-(3,4-dihydroisoquinolin-2(1H)-yl)-2-hydroxypropyl)-6-methoxy-5,6,7,8-tetrahydroimidazo[1,2-a]pyridine-2-carboxamide (Example 107b) (Examples 107a and 107b), N—((S)-3-(3,4-dihydroisoquinolin-2(1H)-yl)-2-hydroxypropyl)-6- isopropyl-5,6,7,8-tetrahydroimidazo[1,2-a]pyridine-2-carboxamide (Example 108), N-(2-(3,4-dihydroisoquinolin-2(1H)-yl)-1-hydroxyethyl)-7-phenyl-5,6,7,8-tetrahydroimidazo[1,2-a]pyridine-2-carboxamide (Example 109), N-(3-(3,4-dihydroisoquinolin-2(1H)-yl)-2-hydroxypropyl)-6-phenyl-5,6,7,8-tetrahydroimidazo[1,2-a]pyridine-2-carboxamide (Example 110), N-(3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 111), N—((S)-3-(3,4-dihydroisoquinolin-2(1H)-yl)-2-hydroxypropyl)-6-phenyl-5,6-dihydro-8H-imidazo[2,1-c][1,4]oxazine-2-carboxamide (Example 112), N-(3-(3,4-dihydroisoquinolin-2(1H)-yl)-2-hydroxypropyl)-7-isopropyl-5,6,7,8-tetrahydroimidazo[1,2-a]pyrazine-2-carboxamide (Example 113), N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 114), N—((S)-3-(3,4-dihydroisoquinolin-2(1H)-yl)-2-hydroxypropyl)-6-(4-fluorophenyl)-5,6,7,8-tetrahydroimidazo[1,2-a]pyridine-2-carboxamide (Example 115), N—((S)-3-(3,4-dihydroisoquinolin-2(1H)-yl)-2-hydroxypropyl)-6-(4-fluorophenyl)-5,6-dihydro-8H-imidazo[2,1-c][1,4]oxazine-2-carboxamide (Example 116), N-((2S,3S)-4-(3,4-dihydroisoquinolin-2(1H)-yl)-2,3-dihydroxybutyl)-6-(trifluoromethyl)-5,6,7,8-tetrahydroimidazo[1,2-a]pyridine-2-carboxamide (Example 117), 6-(1-acetylpiperidin-4-yl)-N—((S)-3-(3,4-dihydroisoquinolin-2(1H)-yl)-2- hydroxypropyl)-5,6,7,8-tetrahydroimidazo[1,2-a]pyridine-2-carboxamide- Isomer-1 (Example 118A), (S)-6-(1-acetylpiperidin-4-yl)-N—((S)-3-(3,4-dihydroisoquinolin-2(1H)-yl)-2-hydroxypropyl)-5,6,7,8-tetrahydroimidazo[1,2-a]pyridine-2-carboxamide (Example 118B), N-3-(3,4-dihydroisoquinolin-2(1H)-yl)-2-hydroxypropyl)-N-methyl-6-(trifluoromethyl)-5,6,7,8-tetrahydroimidazo[1,2-a]pyridine-2-carboxamide (Example-119), R)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 120A), (S)—N—((S)-3-(3,4-dihydroisoquinolin-2(1H)-yl)-2-hydroxypropyl)-6-(1-methyl-1H-pyrazol-4-yl)-5,6,7,8-tetrahydroimidazo[1,2-a]pyridine-2-carboxamide (Example 120B), (S)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121A), (R)—N—((S)-3-(3,4-dihydroisoquinolin-2(1H)-yl)-2-hydroxypropyl)-6-(trifluoromethyl)-5,6,7,8-tetrahydroimidazo[1,2-a]pyridine-2-carboxamide (Example 121B), (R)-6-bromo-N-(3-(3,4-dihydroisoquinolin-2(1H)-yl)-2-hydroxypropyl)imidazo[1,2-a]pyridine-2-carboxamide (Example 122), (S)-6-cyano-N-(3-(3,4-dihydroisoquinolin-2(1H)-yl)-2-hydroxypropyl) imidazo[1,2-a]pyridine-2-carboxamide (Example 123), (R)—N-(3-(3,4-dihydroisoquinolin-2(1H)-yl)-2-hydroxypropyl)imidazo[1,2-a]pyridine-2-carboxamide (Example 124), (R)—N-(3-(3,4-dihydroisoquinolin-2(1H)-yl)-2-hydroxypropyl)-6-fluoroimidazo[1,2-a]pyridine-2-carboxamide (Example 125), (R)-2-((3-(3,4-dihydroisoquinolin-2(1H)-yl)-2-hydroxypropyl)carbamoyl)imidazo[1,2-a]pyridine-6-carboxylic acid (Example 126), (S)—N-(3-(3,4-dihydroisoquinolin-2(1H)-yl)-2-hydroxypropyl)-6-(piperidine-1-carbonyl)imidazo[1,2-a]pyridine-2-carboxamide (Example 127), (S)—N6-(3,3-difluorocyclobutyl)-N2-(3-(3,4-dihydroisoquinolin-2(1H)-yl)-2-hydroxypropyl)imidazo[1,2-a]pyridine-2,6-dicarboxamide (Example 128), (S)—N-(3-(3,4-dihydroisoquinolin-2(1H)-yl)-2-hydroxypropyl)-6-(piperazine-1-carbonyl)imidazo[1,2-a]pyridine-2-carboxamide (Example 129), (S)—N6-cyclohexyl-N2-(3-(3,4-dihydroisoquinolin-2(1H)-yl)-2- hydroxypropyl)imidazo[1,2-a]pyridine-2,6-dicarboxamide (Example 130), (R)—N-(3-(3,4-dihydroisoquinolin-2(1H)-yl)-2-hydroxypropyl)-6-(2,6-diazaspiro[3.3]heptane-2-carbonyl)imidazo[1,2-a]pyridine-2-carboxamide (Example 131), N—((R)-3-(3,4-dihydroisoquinolin-2(1H)-yl)-2-hydroxypropyl)-6-(octahydropyrrolo[3,4-c]pyrrole-2-carbonyl)imidazo[1,2-a]pyridine-2-carboxamide (Example 132), N—((S)-3-(3,4-dihydroisoquinolin-2(1H)-yl)-2-hydroxypropyl)-6-(piperidine-1-carbonyl)-5,6,7,8-tetrahydroimidazo[1,2-a]pyridine-2-carboxamide (Example 133), N6-(3,3-difluorocyclobutyl)-N2-((S)-3-(3,4-dihydroisoquinolin-2(1H)-yl)-2-hydroxypropyl)-5,6,7,8-tetrahydroimidazo[1,2-a]pyridine-2,6-dicarboxamide (Example 134), N—((S)-3-(3,4-dihydroisoquinolin-2(1H)-yl)-2-hydroxypropyl)-6-(piperazine-1-carbonyl)-5,6,7,8-tetrahydroimidazo[1,2-a]pyridine-2-carboxamide (Example 135), N—((R)-3-(3,4-dihydroisoquinolin-2(1H)-yl)-2-hydroxypropyl)-6-(2,6-diazaspiro[3.3]heptane-2-carbonyl)-5,6,7,8-tetrahydroimidazo[1,2-a]pyridine-2-carboxamide (Example 136), N—((R)-3-(3,4-dihydroisoquinolin-2(1H)-yl)-2-hydroxypropyl)-6-(octahydropyrrolo[3,4-c]pyrrole-2-carbonyl)-5,6,7,8-tetrahydroimidazo[1,2-a]pyridine-2-carboxamide (Example 137), (S)-6-benzamido-N-(3-(3,4-dihydroisoquinolin-2(1H)-yl)-2- hydroxypropyl)imidazo[1,2-a]pyridine-2-carboxamide (Example 138), (S)—N-(3-(3,4-dihydroisoquinolin-2(1H)-yl)-2-hydroxypropyl)-6-(2-fluorobenzamido)imidazo[1,2-a]pyridine-2-carboxamide (Example 139), (S)-6-(cyclohexanecarboxamido)-N-(3-(3,4-dihydroisoquinolin-2(1H)-yl)-2-hydroxypropyl)imidazo[1,2-a]pyridine-2-carboxamide (Example 140), (S)—N-(3-(3,4-dihydroisoquinolin-2(1H)-yl)-2-hydroxypropyl)-6-(tetrahydro-2H-pyran-4-carboxamido)imidazo[1,2-a]pyridine-2-carboxamide (Example 141), (S)-6-(cyclopropanecarboxamido)-N-(3-(3,4-dihydroisoquinolin-2(1H)-yl)-2-hydroxypropyl)imidazo[1,2-a]pyridine-2-carboxamide (Example 142), (S)-6-(cyclobutanecarboxamido)-N-(3-(3,4-dihydroisoquinolin-2(1H)-yl)-2-hydroxypropyl)imidazo[1,2-a]pyridine-2-carboxamide (Example 143), (S)-6-(4-cyanobenzamido)-N-(3-(3,4-dihydroisoquinolin-2(1H)-yl)-2-hydroxypropyl)imidazo[1,2-a]pyridine-2-carboxamide (Example 144), 6-(4-cyanobenzamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 145), 6-benzamido-N—((S)-3-(3,4-dihydroisoquinolin-2(1H)-yl)-2- hydroxypropyl)-5,6,7,8-tetrahydroimidazo[1,2-a]pyridine-2-carboxamide (Example 146), N—((S)-3-(3,4-dihydroisoquinolin-2(1H)-yl)-2-hydroxypropyl)-6-(isonicotinamido)-5,6,7,8-tetrahydroimidazo[1,2-a]pyridine-2-carboxamide (Example 147), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-4-carboxamide (Example 148), N—((R)-3-(3,4-dihydroisoquinolin-2(1H)-yl)-2-hydroxypropyl)-6-(tetrahydro-2H-pyran-4-carboxamido)-5,6,7,8-tetrahydroimidazo[1,2-a]pyridine-2-carboxamide (Example 149), 6-(cyclopentanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 150), 6-(cyclopropanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 151), 6-(cyclohexanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 152), 6-(cyclobutanecarboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 153), (R)—N-(3-(3,4-dihydroisoquinolin-2(1H)-yl)-2-hydroxypropyl)-6-(phenylsulfonamido)imidazo[1,2-a]pyridine-2-carboxamide (Example 154), N—((R)-3-(3,4-dihydroisoquinolin-2(1H)-yl)-2-hydroxypropyl)-6-(phenylsulfonamido)-5,6,7,8-tetrahydroimidazo[1,2-a]pyridine-2-carboxamide (Example 155), rac-(R)-6-(azetidine-1-carbonyl)-N-(3-(3,4-dihydroisoquinolin-2(1H)-yl)-2-hydroxypropyl)imidazo[1,2-a]pyridine-2-carboxamide (Example 156), (S)—N-(2-((3-(3,4-dihydroisoquinolin-2(1H)-yl)-2-hydroxypropyl)carbamoyl)imidazo[1,2-a]pyridin-6-yl)isoxazole-3-carboxamide (Example 157), 6-(bicyclo[2.2.1]heptane-2-carboxamido)-N—((S)-3-(3,4-dihydroisoquinolin-2(1H)-yl)-2-hydroxypropyl)imidazo[1,2-a]pyridine-2-carboxamide (Example 158), (S)—N-(2-((3-(3,4-dihydroisoquinolin-2(1H)-yl)-2-hydroxypropyl)carbamoyl)imidazo[1,2-a]pyridin-6-yl)oxazole-2-carboxamide (Example 159), (S)—N-(2-((3-(3,4-dihydroisoquinolin-2(1H)-yl)-2-hydroxypropyl)carbamoyl)imidazo[1,2-a]pyridin-6-yl)thiazole-5-carboxamide (Example 160), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)isoxazole-3-carboxamide (Example 161), 6-(bicyclo[2.2.1]heptane-2-carboxamido)-N—((S)-3-(3,4-dihydroisoquinolin-2(1H)-yl)-2-hydroxypropyl)-5,6,7,8-tetrahydroimidazo[1,2-a]pyridine-2-carboxamide (Example 162), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)oxazole-2-carboxamide (Example 163), N-(2-(((S)-3-(3,4-dihydroisoquinolin-2(1H)-yl)-2-hydroxypropyl)carbamoyl)-5,6,7,8-tetrahydroimidazo[1,2-a]pyridin-6-yl)thiazole-5-carboxamide (Example 164), (S)—N-(3-(3,4-dihydroisoquinolin-2(1H)-yl)-2-hydroxypropyl)-6-ethyl imidazo[1,2-a]pyridine-2-carboxamide (Example 165), (S)-6-(1,1-difluoroethyl)-N-(3-(3,4-dihydroisoquinolin-2(1H)-yl)-2-hydroxypropyl)imidazo[1,2-a]pyridine-2-carboxamide (Example 166), and (S)—N-(3-(3,4-dihydroisoquinolin-2(1H)-yl)-2-hydroxypropyl)-6-(pentafluoro-l6-sulfanyl)imidazo[1,2-a]pyridine-2-carboxamide (Example 167).

10. A process of preparation of compounds of Formula I, or its analogs, tautomeric forms, stereoisomers, geometrical isomers, polymorphs, hydrates, solvates, pharmaceutically acceptable salts, pharmaceutical compositions, metabolites and prodrugs thereof, the process comprising reacting Formula II and Formula III

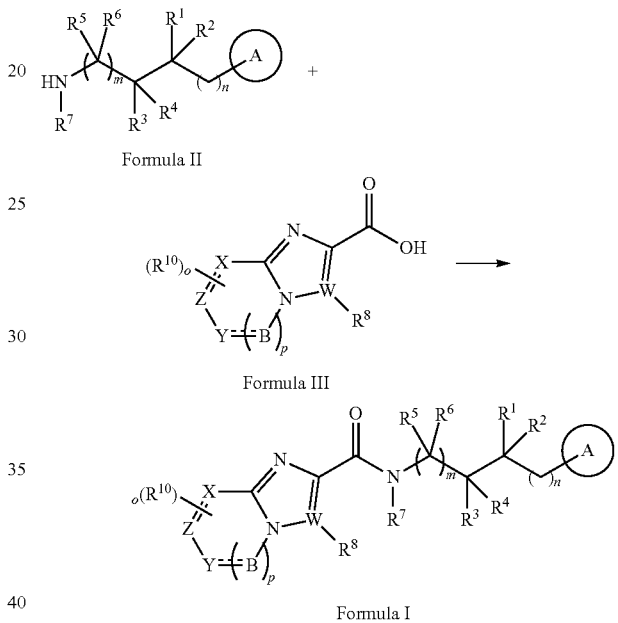

in presence of a coupling reagent and a solvent to obtain the compounds of Formula I, wherein, X, Y and Z of Formula III are independently selected from $CR^{10}$, $NR^{10}$, O or S; W is selected from N or C, B is C, p is 1 or 2; o is 1-3; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl or $C_{3-15}$ heterocyclyl, and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein $C_{5-6}$ aryl, $C_{3-6}$ cycloalkyl, and 3-15 membered saturated or unsaturated heterocyclyl or heteroaryl ring are optionally substituted with one or more groups selected from halogen, cyano, $C_{1-6}$ alkyl, $C_{1-6}$ haloalkyl, $C_{1-6}$ alkoxy or 3-15 membered saturated or unsaturated heterocyclyl or heteroaryl ring with 1-5 heteroatoms selected from N, S or O, wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, and $C_{3-15}$ heteroaryl are optionally substituted with $C_{1-6}$ alkyl; n is 0-1;

A of Formula II is

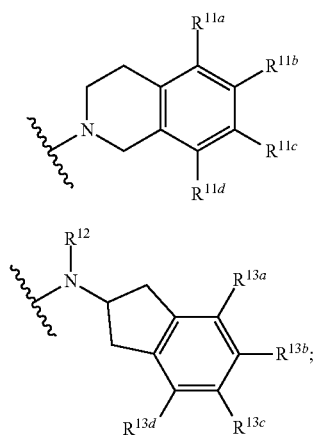

n is 0-1; m is 0-2; o is 1-3; $R^1$, $R^2$, $R^3$ and $R^4$ are independently selected from hydrogen, halogen, hydroxyl or $C_{1-6}$ alkyl, wherein, $C_{1-6}$ alkyl is optionally substituted with hydroxyl, halogen, and combinations thereof; $R^5$, and $R^6$ are independently selected from hydrogen, $C_{1-6}$ alkyl or halogen, wherein, $C_{1-6}$ alkyl is optionally substituted with hydroxyl, halogen, and combinations thereof; $R^7$ is selected from hydrogen or $C_{1-6}$ alkyl, wherein, $C_{1-6}$ alkyl is optionally substituted with $C_{5-6}$ aryl, and wherein, $C_{5-6}$ aryl is optionally substituted with one or more groups selected from $C_{1-6}$ alkyl, $C_{1-6}$ alkoxy, halogen, hydroxyl or cyano; $R^{11a}$, $R^{11b}$, $R^{11c}$ and $R^{11d}$ are independently selected from hydrogen, halogen, cyano, $C_{1-6}$ alkyl, $C_{1-6}$ haloalkyl, or $C_{1-6}$ alkoxy; A of Formula I is

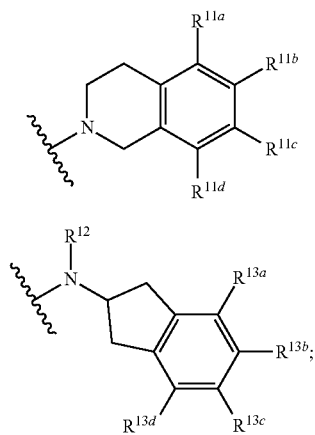

- - - - represents optional single or double bond; n is 0 or 1; m is 0-2; p is 1; o is 1-3;
$R^1$, $R^2$, $R^3$, $R^4$, $R^5$ and $R^6$ are independently selected from hydrogen, halogen, hydroxyl or $C_{1-6}$ alkyl, wherein, $C_{1-6}$ alkyl is optionally substituted with one or more groups selected from hydroxyl or halogen; $R^7$ is selected from hydrogen or $C_{1-6}$ alkyl, wherein, $C_{1-6}$ alkyl is optionally substituted with $C_{5-6}$ aryl, and wherein, $C_{5-6}$ aryl is optionally substituted with one or more groups selected from $C_{1-6}$ alkyl, $C_{1-6}$ alkoxy, halogen, hydroxyl or cyano; $R^{11a}$, $R^{11b}$, $R^{11c}$ and $R^{11d}$ are independently selected from hydrogen, halogen, cyano, $C_{1-6}$ alkyl, $C_{1-6}$ haloalkyl, or $C_{1-6}$ alkoxy; X, Y and Z are independently selected from $CR^{10}$, $NR^{10}$, O or S; W and B are independently selected from N or C; $R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and $R^{10}$ is selected from hydrogen, halogen, hydroxyl, oxo, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$ or 3-15 membered saturated or unsaturated heterocyclyl or heteroaryl ring with 1-5 heteroatoms selected from N, S or O, wherein, $C_{5-6}$ aryl, $C_{3-6}$ cycloalkyl, and 3-15 membered saturated or unsaturated heterocyclyl or heteroaryl ring are optionally substituted with one or more groups selected from halogen, hydroxyl, cyano, oxo, $C_{1-6}$ alkyl, $C_{1-6}$ haloalkyl, $C_{1-6}$ alkoxy, $C_{3-6}$ cycloalkyl, $C(O) R_b$, or 3-6 membered saturated or unsaturated heterocyclyl or heteroaryl ring with 1-3 heteroatoms selected from N, S or O, wherein, 3-6 membered saturated or unsaturated heterocyclyl or heteroaryl ring with 1-3 heteroatoms selected from N, S or O is optionally substituted with $C(O)R_b$, and wherein, $R_a$, $R_b$ and $R_c$ are independently selected from hydrogen, $C_{1-6}$ alkyl, $C_{3-6}$ cycloalkyl, $C_{5-6}$ aryl, $C_{3-15}$ heterocyclyl or $C_{3-15}$ heteroaryl, wherein, $C_{5-6}$ aryl, $C_{3-6}$ cycloalkyl, and $C_{3-15}$ heteroaryl are optionally substituted with one or more substituents selected from halogen, cyano or $C_{1-6}$ alkyl; or $R_a$ and $R_b$ can be taken together to form a 5-10 membered monocyclic or bicyclic, saturated or unsaturated heterocyclic ring with 1-3 heteroatoms selected from N, S or O, wherein compounds of Formula I, or its analogs, tautomeric forms, stereoisomers, geometrical isomers, polymorphs, hydrates, solvates, pharmaceutically acceptable salts, pharmaceutical compositions, metabolites, and prodrugs thereof comprises a compound having the structure of Formula Ia Formula Ia

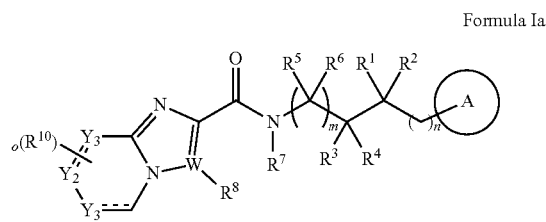

their analogs, tautomeric forms, stereoisomers, geometrical isomers, polymorphs, hydrates, solvates, pharmaceutically acceptable salts, pharmaceutical compositions, metabolites, and prodrugs thereof, wherein A is

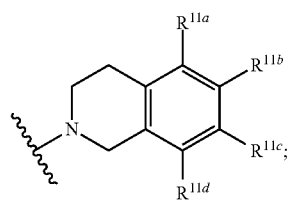

- - - - represents optional single or double bond;
n is 0 or 1;
m is 0-2;
o is 1-3;
$R^1$, $R^2$, $R^3$, $R^4$, $R^5$, and $R^6$ are independently selected from hydrogen, halogen, hydroxyl, or $C_{1-6}$ alkyl, wherein $C_{1-6}$ alkyl is optionally substituted with one or more groups selected from hydroxyl, or halogen;
$R^7$ is selected from hydrogen, and $C_{1-6}$ alkyl, wherein $C_{1-6}$ alkyl is optionally substituted with $C_{5-6}$ aryl, and wherein $C_{5-6}$ aryl is optionally substituted with one or more groups selected from $C_{1-6}$ alkyl, $C_{1-6}$ alkoxy, halogen, hydroxyl, or cyano;
$R^{11a}$, $R^{11b}$, $R^{11c}$, and $R^{11d}$ are independently selected from hydrogen, halogen, cyano, $C_{1-6}$ alkyl, $C_{1-6}$ haloalkyl, or $C_{1-6}$ alkoxy;
$Y^1$, $Y^2$, and $Y^3$ are independently selected from N or CH;
W is selected from N or C;
$R^8$ is absent or is selected from hydrogen, halogen, $C_{1-6}$ alkyl, $C_{2-6}$ alkenyl, $C_{2-6}$ alkynyl, $C_{1-6}$ haloalkyl, $C_{3-6}$ cycloalkyl, $C_{5-6}$ aryl, $C_{3-15}$ heteroaryl, or $C_{3-15}$ heterocyclyl; and
$R^{10}$ is selected from hydrogen, halogen, hydroxyl, nitro, cyano, azido, nitroso, amino, hydrazino, formyl, $C_{1-6}$ alkyl, $C_{1-6}$ haloalkyl, $C_{1-6}$ alkoxy, $C_{1-6}$ haloalkoxy, $C_{3-6}$ cycloalkyl, $C_{5-6}$ aryl, 3-15 membered saturated or unsaturated heterocyclyl or heteroaryl ring with 1-5 heteroatoms selected from N, S or O, $C_{1-6}$ alkylamino, $COOR_a$, $C(O)R_b$, $C(S)R_a$, $C(O)NR_aR_b$, $C(S)NR_aR_b$, $NR_aC(O)NR_bR_c$, $N(R_a)SOR_b$, $N(R_a)SO_2R_b$, $NR_aC(O)OR_b$, $NR_aR_b$, $NR_aC(S)NR_bR_c$, $NR_aC(O)R_b$, $NR_aC(S)R_b$, $SF_5$, $SONR_aR_b$, $SO_2NR_aR_b$, $OC(O)NR_aR_b$, $OR_aC(O)OR_b$, $OC(O)NR_aR_b$, $OC(O)R_a$, $OR_a$, $R_aNR_bR_c$, $R_aOR_b$, $SR_a$, $SOR_a$, $SO_2R_a$, wherein $C_{5-6}$ aryl, and 3-15 membered saturated or unsaturated heterocyclyl or heteroaryl ring are optionally substituted with one or more groups selected from the group consisting of halogen, hydroxyl, cyano, oxo, $C_{3-6}$ cycloalkyl, $C_{1-6}$ alkyl, $C_{1-6}$ haloalkyl, $C_{1-6}$ alkoxy, $C_{3-6}$ cycloalkyl, $C(O)R_b$, 3-6 membered saturated or unsaturated heterocyclyl or heteroaryl ring with 1-5 heteroatoms selected from N, S or O, wherein 3-6 membered saturated or unsaturated heterocyclyl or heteroaryl ring with 1-3 heteroatoms selected from N, S or O is optionally substituted with $C(O)R_b$, and wherein $R_a$, $R_b$, and $R_c$ are independently selected from hydrogen, $C_{1-6}$ alkyl, $C_{3-6}$ cycloalkyl, $C_{5-6}$ aryl, $C_{3-15}$ heterocyclyl, and $C_{3-15}$ heteroaryl, wherein $C_{5-6}$ aryl, $C_{3-6}$ cycloalkyl, and $C_{3-15}$ heteroaryl are optionally substituted with one or more substituents selected from halogen, cyano, or $C_{1-6}$ alkyl; or or $R_a$ and $R_b$ can be taken together to form a 5-10 membered monocyclic or bicyclic, saturated or unsaturated heterocyclic ring with 1-3 heteroatoms selected from N, S or O.

11. The process as claimed in claim 10, wherein, the coupling reagent is selected from the group consisting of N-(3-dimethylaminopropyl)-N'-ethylcarbodiimide hydrochloride, hydroxybenzotriazole, propane phosphonic acid anhydride, and combinations thereof.

12. The process as claimed in claim 11, wherein the solvent is a polar aprotic solvent selected from the group consisting of DMF, dioxane, acetonitrile, THF, and combinations thereof.

13. A pharmaceutical composition comprising a compound of Formula Ia or a pharmaceutically acceptable salt thereof as claimed in claim 2 together with a pharmaceutically acceptable carrier, optionally in combination with one or more other pharmaceutical compositions.

14. The pharmaceutical composition as claimed in claim 13, wherein the composition is in a form selected from the group consisting of a tablet, capsule, powder, syrup, solution, aerosol and suspension.

15. A method for inhibiting PRMT5, comprising administering to a subject suffering from a condition mediated by PRMT5, a therapeutically effective amount of the compound according to claim 1, with other clinically relevant cytotoxic agents or non-cytotoxic agents or other clinically relevant immune modulator agents to a subject in need thereof.

16. The method for inhibiting PRMT5 as claimed in claim 14, wherein, the compound is administered in a pharmaceutical composition in a form selected from the group consisting of a tablet, capsule, powder, syrup, solution, aerosol and suspension.

* * * * *